United States Patent
Kumar et al.

(10) Patent No.: US 12,421,295 B2
(45) Date of Patent: Sep. 23, 2025

(54) TGF-BETA SUPERFAMILY TYPE I AND TYPE II RECEPTOR HETEROMULTIMERS AND USES THEREOF

(71) Applicant: Acceleron Pharma Inc., Cambridge, MA (US)

(72) Inventors: Ravindra Kumar, Cambridge, MA (US); Asya Grinberg, Cambridge, MA (US); Dianne S. Sako, Cambridge, MA (US); Roselyne Castonguay, Cambridge, MA (US)

(73) Assignee: Acceleron Pharma Inc., Rahway, NJ (US)

( * ) Notice: Subject to any disclaimer, the term of this patent is extended or adjusted under 35 U.S.C. 154(b) by 306 days.

(21) Appl. No.: 17/942,695

(22) Filed: Sep. 12, 2022

(65) Prior Publication Data

US 2023/0265161 A1 Aug. 24, 2023

Related U.S. Application Data

(63) Continuation of application No. 16/340,040, filed as application No. PCT/US2017/055420 on Oct. 5, 2017, now Pat. No. 11,440,949.

(60) Provisional application No. 62/404,563, filed on Oct. 5, 2016.

(51) Int. Cl.
*C07K 14/71* (2006.01)
*A61K 38/00* (2006.01)

(52) U.S. Cl.
CPC .............. *C07K 14/71* (2013.01); *A61K 38/00* (2013.01); *C07K 2317/52* (2013.01); *C07K 2319/30* (2013.01)

(58) Field of Classification Search
None
See application file for complete search history.

(56) References Cited

U.S. PATENT DOCUMENTS

| | | |
|---|---|---|
| 10,196,434 B2 | 2/2019 | Kumar et al. |
| 10,227,392 B2 | 3/2019 | Kumar et al. |
| 10,227,393 B2 | 3/2019 | Kumar et al. |
| 10,738,098 B2 | 8/2020 | Kumar et al. |
| 10,906,958 B2 | 2/2021 | Kumar et al. |
| 11,028,145 B2 | 6/2021 | Kumar et al. |
| 11,279,746 B2 | 3/2022 | Kumar et al. |
| 2006/0223753 A1 | 10/2006 | Glass |
| 2012/0149879 A1 | 6/2012 | Brinkmann et al. |
| 2013/0171095 A1 | 7/2013 | Bernett et al. |
| 2015/0283209 A1 | 10/2015 | Sung et al. |
| 2016/0039922 A1 | 2/2016 | Attie |
| 2016/0289298 A1 | 10/2016 | Kumar et al. |
| 2016/0297867 A1 | 10/2016 | Kumar et al. |
| 2017/0306027 A1 | 10/2017 | Knopf et al. |
| 2018/0057607 A1 | 3/2018 | Igawa et al. |
| 2018/0163187 A1 | 6/2018 | Kumar et al. |
| 2019/0100570 A1 | 4/2019 | Kumar et al. |
| 2019/0218272 A1 | 7/2019 | Kumar et al. |
| 2021/0163569 A1 | 6/2021 | Kumar et al. |
| 2022/0119491 A1 | 4/2022 | Kumar et al. |
| 2022/0242927 A1 | 8/2022 | Kumar et al. |
| 2022/0396607 A1 | 12/2022 | Kumar et al. |

FOREIGN PATENT DOCUMENTS

| | | |
|---|---|---|
| CA | 2737271 A1 | 3/2010 |
| WO | WO-98/52038 A1 | 11/1998 |
| WO | WO-2012/058768 A1 | 5/2012 |
| WO | WO-2016/154601 A1 | 9/2016 |
| WO | WO-2016/159213 A1 | 10/2016 |
| WO | WO-2016/164089 A2 | 10/2016 |

OTHER PUBLICATIONS

Chen et al., Immunoregulation by members of the TGFbeta superfamily, Nat. Rev. Immunol. vol. 16(12): 723-740 (2016).
Derwall et al., "Inhibition of Bone Morphogenetic Protein Signaling Reduces Vascular Calcification and Atherosclerosis", Arteriosclerosis, Thrombosis, and Vascular Biology, vol. 32(3): 613-622 (2012).
Escobar-Cabrera, E. et al., "Asymmetric Fc Engineering for Bispecific Antibodies with Reduced Effector Function," Antibodies, vol. 6(2) 1-16 (2017).
International Search Report PCT/US2017/055420 dated Apr. 12, 2018 ; (8 pages).

(Continued)

*Primary Examiner* — Ruixiang Li
(74) *Attorney, Agent, or Firm* — Patrick Rehfuss; Alysia A. Finnegan

(57) ABSTRACT

In certain aspects, the disclosure provides soluble heteromeric polypeptide complexes comprising an extracellular domain of a type I serine/threonine kinase receptor of the TGF-beta family and an extracellular domain of a type II serine/threonine kinase receptor of the TGF-beta family. In some embodiments, the disclosure provides soluble polypeptide complexes comprising an extracellular domain of a type II receptor selected from: ActRIIA, ActRIIB, TGFBRII, BMPRII, and MISRII. In some embodiments, the disclosure provides soluble polypeptide complexes comprising an extracellular domain of a type I receptor selected from: ALK1, ALK2, ALK3, ALK4, ALK5, ALK6, and ALK7. Optionally the soluble complex is a heterodimer. In certain aspects, such soluble polypeptide complexes may be used to regulate (promote or inhibit) growth of tissues or cells including, for example, muscle, bone, cartilage, fat, neural tissue, tumors, cancerous cells, and/or cells of hematopoietic lineages, including red blood cells. In certain aspects, such soluble polypeptide complexes are can be used to improve muscle formation, bone formation, hematopoiesis, metabolic parameters, and disorders associated with these tissues, cellular networks, and endocrine systems.

11 Claims, 18 Drawing Sheets

Specification includes a Sequence Listing.

(56) References Cited

OTHER PUBLICATIONS

Koncarevic et al., "A Soluble Activin Receptor Type IIB Prevents the Effects of Androgen Deprivation on Body Composition and Bone Health", Endocrinology, vol. 151(9): 4289-4300 (2010).

Lavery et al., "BMP-2/4 and BMP-6/7 Differentially Utilize Cell Surface Receptors to Induce Osteoblastic Differentiation of Human Bone Marrow-derived Mesenchymal Stem Cells," Journal of Biological Chemistry, vol. 283(30): 20948-20958 (2008).

Qin et al., "A novel highly potent trivalent TGF-? receptor trap inhibits early-stage tumorigenesis and tumor cell invasion in murine Pten-deficient prostate glands," Oncotarget, Advance Publications: vol. 7(52): 86087-86102 (2016).

Sako et al., "Characterization of the Ligand Binding Functionality of the Extracellular Domain of Activin Receptor Type IIB", Journal of Biological Chemistry, American Society for Biochemistry and Molecular Biology, US, vol. 285(27): p. 21037-21048 (2010).

Supplementary European Search Report, EP 17 85 9218, dated Sep. 15, 2020 (9 pages).

Yamawaki et al., "The soluble form of BMPRIB is a novel therapeutic candidate for treating bone related disorders," Scientific Reports, vol. 6(18849); 10 pages (2016).

U.S. Appl. No. 16/340,040, filed Apr. 5, 2019.

Del Re, Elisabetta et al., In the Absence of Type III Receptor, the Transforming Growth Factor (TGF)-β Type II-B Receptor Requires the Type I Receptor to Bind TGF-β2, The Journal of Biological Chemistry, vol. 279, No. 21, 22765-22772, 2004.

```
ActRIIa    LLGRSETQEC LFFNANWEKD RTNQTGVEPC YGDKDKRRHC FATWKNISGS
ActRIIb    GRGEAETREC IYYNANWELE RTNQSGLERC EGEQDKRLHC YASWRNSSGT

IEIVKQGCWL DDINCYDRTD CVEKKDSPEV YFCCCEGNMC NEKFSYFPEM
           IELVKKGCWL DDFNCYDRQE CVATEENPQV YFCCCEGNFC NERFTHLPEA

EVTQPTSNPV TPKPPT
           GGPEVTYEPP PTAPT
```

FIGURE 3

```
IgG1    --------THTCPPCPAPELLGGPSVFLFPPKPKDTLMISRTPEVTCVVVDVSHEDPEVKF  53
IgG4    ----ESKYGPPCPSCPAPEFLGGPSVFLFPPKPKDTLMISRTPEVTCVVVDVSQEDPEVQF  57
IgG2    --------VECPPCPAPPVAG-PSVFLFPPKPKDTLMISRTPEVTCVVVDVSHEDPEVQF  51
IgG3    EPKSCDTPPPCPRCPAPELLGGPSVFLFPPKPKDTLMISRTPEVTCVVVDVSHEDPEVQF  60
               ** ****  . * ******************************:*****:*

IgG1    NWYVDGVEVHNAKTKPREEQYNSTYRVVSVLTVLHQDWLNGKEYKCKVSNKALPAPIEKT  113
IgG4    NWYVDGVEVHNAKTKPREEQFNSTYRVVSVLTVLHQDWLNGKEYKCKVSNKGLPSSIEKT  117
IgG2    NWYVDGVEVHNAKTKPREEQFNSTFRVVSVLTVVHQDWLNGKEYKCKVSNKGLPAPIEKT  111
IgG3    KWYVDGVEVHNAKTKPREEQYNSTFRVVSVLTVLHQDWLNGKEYKCKVSNKALPAPIEKT  120
        :***********************:***:******:*************.**:.****

IgG1    ISKAKGQPREPQVYTLPPSREEMTKNQVSLTCLVKGFYPSDIAVEWESNGQPENNYKTTP  173
IgG4    ISKAKGQPREPQVYTLPPSQEEMTKNQVSLTCLVKGFYPSDIAVEWESNGQPENNYKTTP  177
IgG2    ISKTKGQPREPQVYTLPPSREEMTKNQVSLTCLVKGFYPSDIAVEWESNGQPENNYKTTP  171
IgG3    ISKTKGQPREPQVYTLPPSREEMTKNQVSLTCLVKGFYPSDIAVEWESSGQPENNYNTTP  180
        ***:***************:****************************.*******:***

IgG1    PVLDSDGSFFLYSKLTVDKSRWQQGNVFSCSVMHEALHNHYTQKSLSLSPGK  225
IgG4    PVLDSDGSFFLYSRLTVDKSRWQEGNVFSCSVMHEALHNHYTQKSLSLSLGK  229
IgG2    PMLDSDGSFFLYSKLTVDKSRWQQGNVFSCSVMHEALHNHYTQKSLSLSPGK  223
IgG3    PMLDSDGSFFLYSKLTVDKSRWQQGNIFSCSVMHEALHNRFTQKSLSLSPGK  232
        *:***********:*********:**:***********:*******  **
```

FIGURE 5

TGF-BETA SUPERFAMILY TYPE I AND TYPE II RECEPTOR HETEROMULTIMERS AND USES THEREOF

CROSS-REFERENCE TO RELATED APPLICATIONS

This application is a continuation of U.S. application Ser. No. 16/340,040, filed Apr. 5, 2019 (now U.S. Pat. No. 11,440,949), which is a national stage filing under 35 U.S.C. § 371 of International Application No. PCT/US2017/055420, filed on Oct. 5, 2017, which claims the benefit of priority from U.S. Provisional Application No. 62/404,563, filed Oct. 5, 2016. The specifications of each of the foregoing applications are incorporated herein by reference in their entirety.

SEQUENCE LISTING

The instant application contains a Sequence Listing which has been submitted via EFS-Web and is hereby incorporated by reference in its entirety. Said XML copy, created on Feb. 13, 2023, is named 1848179-0002-118-302.XML and is 981,734 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general phylogenetic clades: the more recently evolved members of the superfamily, which includes TGF-betas, Activins, and nodal and the clade of more distantly related proteins of the superfamily, which includes a number of BMPs and GDFs. Hinck (2012) FEBS Letters 586:1860-1870. TGF-beta family members have diverse, often complementary biological effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al. (1997) Nat Genet., 17(1):71-4. Furthermore, in humans, inactive alleles of GDF8 are associated with increased muscle mass and, reportedly, exceptional strength. Schuelke et al. (2004) N Engl J Med, 350:2682-8.

Changes in muscle, bone, fat, red blood cells, and other tissues may be achieved by enhancing or inhibiting signaling (e.g., SMAD 1, 2, 3, 5, and/or 8) that is mediated by ligands of the TGF-beta family. Thus, there is a need for agents that regulate the activity of various ligands of the TGF-beta superfamily.

SUMMARY OF THE INVENTION

In part, the disclosure provides heteromultimers comprising at least one TGF-beta superfamily type I serine/threonine kinase receptor polypeptide (e.g., an ALK1, ALK2, ALK3, ALK4, ALK5, ALK6, and ALK7 polypeptide), including fragments and variants thereof, and at least one TGF-beta superfamily type II serine/threonine kinase receptor polypeptide (e.g., ActRIIA, ActRIIB, TGFBRII, BMPRII, and MISRII), including fragments and variants thereof. In other aspects, the disclosure provides heteromultimers comprising at least two different TGF-beta superfamily type I serine/threonine kinase receptor polypeptide (e.g., an ALK1, ALK2, ALK3, ALK4, ALK5, ALK6, and ALK7 polypeptide), including fragments and variants thereof. In still other aspects, the disclosure provides heteromultimers comprising at least two different TGF-beta superfamily type II serine/threonine kinase receptor polypeptide (e.g., ActRIIA, ActRIIB, TGFBRII, BMPRII, and MISRII), including fragments and variants thereof. Optionally, heteromultimerics disclosed herein (e.g., an ActRIIB:ALK4 heterodimer) have different ligand binding specificities/profiles compared to their corresponding homomultimers (e.g., an ActRIIB homodimer and ALK4 homodimer). Novel properties, including novel ligand binding attributes, are exhibited by heteromultimeric polypeptide complexes comprising type I and type II receptor polypeptides of the TGF-beta superfamily, as shown by Examples herein.

Heteromultimeric structures include, for example, heterodimers, heterotrimers, and higher order complexes. See, e.g., FIGS. 1, 2, and 15. In some embodiments heteromultimers of the disclosure are heterodimers. Preferably, TGF-beta superfamily type I and type II receptor polypeptides as described herein comprise a ligand-binding domain of the receptor, for example, an extracellular domain of a TGF-beta superfamily type I or type II receptor. Accordingly, in certain aspects, protein complexes described herein comprise an extracellular domain of a type II TGF-beta superfamily receptor selected from: ActRIIA, ActRIIB, TGFBRII, BMPRII, and MISRII, as well as truncations and variants thereof, and an extracellular domain of a type I TGF-beta superfamily receptor selected from: ALK1, ALK2, ALK3, ALK4, ALK5, ALK6, and ALK7, as well as truncations and variants thereof. Preferably, TGF-beta superfamily type I and type II polypeptides as described herein, as well as protein complexes comprising the same, are soluble. In certain aspects, heteromultimers of the disclosure bind to one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, Müllerian-inhibiting substance (MIS), and Lefty). Optionally, protein complexes of the disclosure bind to one or more of these ligands with a $K_D$ of greater than or equal to $10^{-8}$, $10^{-9}$, $10^{-10}$, $10^{-11}$, or $10^{-12}$. In general, heteromultimers of the disclosure antagonize (inhibit) one or more activities of at least one TGF-beta superfamily ligand, and such alterations in activity may be measured using various assays known in the art, including, for example, a cell-based assay as described herein. Preferably heteromultimers of the disclosure exhibit a serum half-life of at least 4, 6, 12, 24, 36, 48, or 72 hours in a mammal (e.g., a mouse or a human). Optionally, heteromultimers of the disclosure may exhibit a serum half-life of at least 6, 8, 10, 12, 14, 20, 25, or 30 days in a mammal (e.g., a mouse or a human).

T-beta superfamily type I receptor polypeptide and the amino acid sequence of a first member of an interaction pair and the second polypeptide comprises the amino acid sequence of a TGF-beta superfamily type II receptor polypeptide and the amino acid sequence of a second member of the interaction pair. In other aspects, heteromultimers described herein comprise a first polypeptide covalently or non-covalently associated with a second polypeptide wherein the first polypeptide comprises the amino acid sequence of a TGF-beta superfamily type I receptor polypeptide and the amino acid sequence of a first member of an interaction pair and the second polypeptide comprises the amino acid sequence of a different TGF-beta superfamily type I receptor polypeptide and the amino acid sequence of a second member of the interaction pair. In still other aspects, heteromultimers described herein comprise a first polypeptide covalently or non-covalently associated with a second polypeptide wherein the first polypeptide comprises the amino acid sequence of a TGF-beta superfamily type II receptor polypeptide and the amino acid sequence of a first member of an interaction pair and the second polypeptide comprises the amino acid sequence of a different TGF-beta superfamily type II receptor polypeptide and the amino acid sequence of a second member of the interaction pair. Optionally, the TGF-beta superfamily type I receptor polypeptide is connected directly to the first member of the interaction pair, or an intervening sequence, such as a linker, may be positioned between the amino acid sequence of the TGF-beta superfamily type I receptor polypeptide and the amino acid sequence of the first member of the interaction pair. Similarly, the TGF-beta superfamily type II receptor polypeptide may be connected directly to the second member of the interaction pair, or an intervening sequence, such as a linker, may be positioned between the amino acid sequence of the TGF-beta superfamily type II receptor polypeptide and the amino acid sequence of the second member of the interaction pair. Linkers may correspond to the roughly 15 amino acid unstructured region at the C-terminal end of the extracellular domain of ActRIIB or ALK4 (the "tail"), or it may be an artificial sequence of between 5 and 15, 20, 30, 50, 100 or more amino acids that are relatively free of secondary structure. A linker may be rich in glycine and proline residues and may, for example, contain repeating sequences of threonine/serine and glycines. Examples of linkers include, but are not limited to, the sequences TGGG (SEQ ID NO: 62), TGGGG (SEQ ID NO: 60), SGGGG (SEQ ID NO: 61), GGGG (SEQ ID NO: 59), and GGG (SEQ ID NO: 58).

Interaction pairs described herein are designed to promote dimerization or form higher order multimers. In some embodiments, the interaction pair may be any two polypeptide sequences that interact to form a complex, particularly a heterodimeric complex although operative embodiments may also employ an interaction pair that forms a homodimeric sequence. The first and second members of the interaction pair may be an asymmetric pair, meaning that the members of the pair preferentially associate with each other rather than self-associate. Accordingly, first and second members of an asymmetric interaction pair may associate to form a heterodimeric complex. Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer complex or a heterodimeric complex. Optionally, the first member of the interaction action pair (e.g., an asymmetric pair or an unguided interaction pair) associates covalently with the second member of the interaction pair. Optionally, the first member of the interaction action pair (e.g., an asymmetric pair or an unguided interaction pair) associates non-covalently with the second member of the interaction pair. Optionally, the first member of the interaction pair (e.g., an asymmetrical or an unguided interaction pair) associates through both covalent and non-covalent mechanisms with the second member of the interaction pair.

In certain aspects, type I and/or type II polypeptides may be fusion proteins. For example, in some embodiments, an type I polypeptide may be a fusion protein comprising an type I polypeptide domain and one or more heterologous (non-type I) polypeptide domains (e.g., type I-Fc fusion proteins). Similarly, in some embodiments, an type II polypeptide may be a fusion protein comprising an type II polypeptide domain and one or more heterologous (non-type II) polypeptide domains (type II-Fc fusion proteins).

In some embodiments, type I polypeptides are fusion proteins that comprise an Fc domain of an immunoglobulin. Similarly, in some embodiments, type II polypeptides are fusion proteins that comprise an Fc domain of an immunoglobulin. Traditional Fc fusion proteins and antibodies are examples of unguided interaction pairs, whereas a variety of engineered Fc domains have been designed as asymmetric interaction pairs [Spiess et al (2015) Molecular Immunology 67(2A): 95-106]. Therefore, a first member and/or a second member of an interaction pair described herein may comprise a constant domain of an immunoglobulin, including, for example, the Fc portion of an immunoglobulin. For example, a first member of an interaction pair may comprise an amino acid sequence that is derived from an Fc domain of an IgG (IgG1, IgG2, IgG3, or IgG4), IgA (IgA1 or IgA2), IgE, or IgM immunoglobulin. Such immunoglobulin domains may comprise one or more amino acid modifications (e.g., deletions, additions, and/or substitutions) that promote type I:type I, type II:type II, and/or type I:type II heteromultimer formation. Similarly, a second member of an interaction pair may comprise an amino acid sequence that is derived from an Fc domain of an IgG (IgG1, IgG2, IgG3, or IgG4), IgA (IgA1 or IgA2), IgE, or IgM. Such immunoglobulin domains may comprise one or more amino acid modifications (e.g., deletions, additions, and/or substitutions) that promote type I:type II heteromultimer formation. For example, the second member of an interaction pair may comprise, consist essentially of, or consist of an amino acid sequence that is at least 70%, 75%, 80%, 85%, 90%, 91%, 92%, 93%, 94%, 95%, 96%, 97%, 98%, 99% or 100% identical to any one of SEQ ID NOs: 200-207, 3100, 3200, 3300, 3400 and 3500. In some embodiments, a first member and a second member of an interaction pair comprise Fc domains derived from the same immunoglobulin class and subtype. In other embodiments, a first member and a second member of an interaction pair comprise Fc domains derived from different immunoglobulin classes or subtypes.

In certain aspects, the disclosure relates to type I:type II heteromultimers comprising at least one type I-Fc fusion protein and at least one type II-Fc fusion protein wherein the type I-Fc fusion protein comprises one or more amino acid modifications (e.g., amino acid substitution, cationization, deamination, carboxyl-terminal amino acid heterogeneity, phosphorylation, and glycosylation) that alter the isoelectric point (pI) of the type I-Fc fusion protein and/or the type II-Fc fusion protein comprises one or more amino acid modifications that alter the pI of the type II-Fc fusion protein. In some embodiments, the one or more amino acid modifications in the type I-Fc fusion protein confers increased difference in pIs between the type I-Fc fusion protein and the type II-Fc fusion protein. In other embodiments, the one or more amino acid modifications in the type II-Fc fusion protein confers increased difference in pIs between the type II-Fc fusion protein and the type I-Fc fusion protein. In still other embodiments the one or more amino acid modifications in the type I-Fc fusion protein confers increased difference in pIs between the type I-Fc fusion protein and the type II-Fc fusion protein, and the one or more amino acid modifications in the type II-Fc fusion protein confers increased difference in pIs between the type II-Fc fusion protein and the type I-Fc fusion protein. In some embodiments, the type I-Fc fusion protein comprises one or more amino acid modifications that alter pI by at least 0.1 (e.g., by at least 0.1, 0.2, 0.3, 0.4, 0.5, 0.7, 0.8, 0.9, 1.0, 1.3, 1.5, 1.7, 2.0, 2.3, 2.5, 2.7, 3.0, 3.3, 3.5, 3.7, or at least by 4.0). In some embodiments, the type II-Fc fusion protein comprises one or more amino acid modifications that alter pI by at least 0.1 (e.g., by at least 0.1, 0.2, 0.3, 0.4, 0.5, 0.7, 0.8, 0.9, 1.0, 1.3, 1.5, 1.7, 2.0, 2.3, 2.5, 2.7, 3.0, 3.3, 3.5, 3.7, or at least by 4.0). In some embodiments, the type I-Fc fusion protein comprises one or more amino acid modifications that alter pI by at least 0.1 (e.g., by at least 0.1, 0.2, 0.3, 0.4, 0.5, 0.7, 0.8, 0.9, 1.0, 1.3, 1.5, 1.7, 2.0, 2.3, 2.5, 2.7, 3.0, 3.3, 3.5, 3.7, or at least by 4.0) and the type II-Fc fusion protein comprises one or more amino acid modifications that alter pI by at least 0.1 (e.g., by at least 0.1, 0.2, 0.3, 0.4, 0.5, 0.7, 0.8, 0.9, 1.0, 1.3, 1.5, 1.7, 2.0, 2.3, 2.5, 2.7, 3.0, 3.3, 3.5, 3.7, or at least by 4.0). In some embodiments, the type I-Fc fusion protein and the type II-Fc fusion protein have at least a 0.7 difference in pI (e.g., at least 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or at least 4.0 or more difference in pI).

In certain aspects, an type I:type II heteromultimer of the disclosure comprises an type I-Fc fusion protein comprising one or more amino acid modifications that increase the pI of the type I-Fc fusion protein; and an type II-Fc fusion protein comprising one or more amino acid modifications that decrease the pI of the type II-Fc fusion protein. For example, an type I-Fc fusion protein may be modified by substituting one or more neutral or negatively charged amino acids with one or more positively charged amino acids [e.g., an arginine (R), lysine (K), or histidine (H)]. Similarly, an type II-Fc fusion protein may be modified by substituting one or more neutral or positively charged amino acids with one or more negatively charged amino acids [e.g., aspartic acid (E) or glutamic acid (D)]. In some embodiments, the type I-Fc fusion protein Fc domain is an IgG1 Fc domain that comprises one or more amino acid modifications that alter the pI of the type I-Fc fusion protein. In some embodiments, the type I-Fc fusion protein IgG1 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the type I-Fc fusion protein IgG1 Fc domain comprises one or more amino acid substitutions selected from: a) an amino acid substitution at the position corresponding to N162 of SEQ ID NO: 3100; b) an amino acid substitution at the position corresponding to D179 of SEQ ID NO: 3100; and c) an amino acid substitution at the position corresponding to N162 of SEQ ID NO: 3100 and an amino acid substitution at the position corresponding to D179 of SEQ ID NO: 3100. In some embodiments, the type I-Fc fusion protein IgG1 Fc domain comprises one or more amino acid substitutions selected from: a) an arginine, lysine, or histidine substitution at the position corresponding to N162 of SEQ ID NO: 3100 (N162R, N162K, or N162H); b) an arginine, lysine, or histidine substitution at the position corresponding to D179 of SEQ ID NO: 3100 (D179R, D179K, or D179H); and c) an arginine, lysine, or histidine substitution at the position corresponding to N162 of SEQ ID NO: 3100 (N162R, N162K. or N162H) and an arginine, lysine, or histidine substitution at the position corresponding to D179 of SEQ ID NO: 3100 (D179R, D179K. or D179H). In some embodiments, the type I-Fc fusion protein IgG1 Fc domain comprises one or more amino acid substitutions selected from: a) an arginine substitution at the position corresponding to N162 of SEQ ID NO: 3100 (N162R); b) an arginine substitution at the position corresponding to D179 of SEQ ID NO: 3100 (D179R); and c) an arginine substitution at the position corresponding to N162 of SEQ ID NO: 3100 (N162R) and an arginine substitution at the position corresponding to D179 of SEQ ID NO: 3100 (D179R). In some embodiments, the type I-Fc fusion protein Fc domain is an IgG2 Fc domain that comprises one or more amino acid modifications that alter the pI of the type I-Fc fusion protein. In some embodiments, the type I-Fc fusion protein IgG2 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the type I-Fc fusion protein IgG2 Fc domain comprises one or more amino acid substitutions selected from: a) an amino acid substitution at the position corresponding to N160 of SEQ ID NO: 3200; b) an amino acid substitution at the position corresponding to D177 of SEQ ID NO: 3200; and c) an amino acid substitution at the position corresponding to N160 of SEQ ID NO: 3200 and an amino acid substitution at the position corresponding to D177 of SEQ ID NO: 3200. In some embodiments, the type I-Fc fusion protein IgG2 Fc domain comprises one or more amino acid substitutions selected from: a) an arginine, lysine, or histidine substitution at the position corresponding to N160 of SEQ ID NO: 3200 (N160R, N160K, or N160H); b) an arginine, lysine, or histidine substitution at the position corresponding to D177 of SEQ ID NO: 3200 (D177R, D177K, or D177H); and c) an arginine, lysine, or histidine substitution at the position corresponding to N160 of SEQ ID NO: 3200 (N160R, N160K, or N160H) and an arginine, lysine, or histidine substitution at the position corresponding to D177 of SEQ ID NO: 3200 (D177R, D177K. or D177H). In some embodiments, the type I-Fc fusion protein Fc domain is an IgG3 Fc domain that comprises one or more amino acid modifications that alter the pI of the type I-Fc fusion protein. In some embodiments, the type I-Fc fusion protein IgG3 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3300. In some embodiments, the type I-Fc fusion protein IgG3 Fc domain comprises one or more amino acid substitutions selected from: a) an amino acid substitution at the position corresponding to S169 of SEQ ID NO: 3300; b) an amino acid substitution at the position corresponding to D186 of SEQ ID NO: 3300; and c) an amino acid substitution at the position corresponding to S169 of SEQ ID NO: 3300 and an amino acid substitution at the position corresponding to D186 of SEQ ID NO: 3300. In some embodiments, the type I-Fc fusion protein IgG3 Fc domain comprises one or more amino acid substitutions selected from: a) an arginine, lysine, or histidine substitution at the position corresponding to S169 of SEQ ID NO: 3300 (S169R, S169K, or S169H); b) an arginine, lysine, or histidine substitution at the position corresponding to D186 of SEQ ID NO: 3300 (D186R, D186K, or D186H); and c) an arginine, lysine, or histidine substitution at the position corresponding to S169 of SEQ ID NO: 3300 (S169R, S169K, or S169H) and an arginine, lysine, or histidine substitution at the position corresponding to D186 of SEQ ID NO: 3300 (D186R, D186K, or D186H). In some embodiments, the type I-Fc fusion protein Fc domain is an IgG4 Fc domain that comprises one or more amino acid modifications that alter the pI of the type I-Fc fusion protein. In some embodiments, the type I-Fc fusion protein IgG4 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the type I-Fc fusion protein IgG4 Fc domain comprises one or more amino acid substitutions selected from: a) an amino acid substitution at the position corresponding to N166 of SEQ ID NO: 3500; b) an amino acid substitution at the position corresponding to D183 of SEQ ID NO: 3500; and c) an amino acid substitution at the position corresponding to N166 of SEQ ID NO: 3500 and an amino acid substitution at the position corresponding to D183 of SEQ ID NO: 3500. In some embodiments, the type I-Fc fusion protein IgG4 Fc domain comprises one or more amino acid substitutions selected from: a) an arginine, lysine, or histidine substitution at the position corresponding to N166 of SEQ ID NO: 3500 (N166R, N166K, or N166H); b) an arginine, lysine, or histidine substitution at the position corresponding to D183 of SEQ ID NO: 3500 (D183R, D183K, or D183H); and c) an arginine, lysine, or histidine substitution at the position corresponding to N166 of SEQ ID NO: 3500 (N166R, N166K, or N166H) and an arginine, lysine, or histidine substitution at the position corresponding to D183 of SEQ ID NO: 3500 (D183R, D183K. or D183H). In some embodiments, the type II-Fc fusion protein Fc domain is an IgG1 Fc domain that comprises one or more amino acid modifications that alter the pI of the type II-Fc fusion protein. In some embodiments, the type II-Fc fusion protein IgG1 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the type II-Fc fusion protein IgG1 Fc domain comprises one or more amino acid substitutions selected from: a) an amino acid substitution at the position corresponding to K138 of SEQ ID NO: 3100; b) an amino acid substitution at the position corresponding to K217 of SEQ ID NO: 3100; and c) an amino acid substitution at the position corresponding to K138 of SEQ ID NO: 3100 and an amino acid substitution at the position corresponding to K217 of SEQ ID NO: 3100. In some embodiments, the type II-Fc fusion protein IgG1 Fc domain comprises one or more amino acid substitutions selected from: a) an aspartic acid or glutamic acid substitution at the position corresponding to K138 of SEQ ID NO: 3100 (K138E or K138D); b) an aspartic acid or glutamic acid substitution at the position corresponding to K217 of SEQ ID NO: 3100 (K217E or K217D); and c) an aspartic acid or glutamic acid substitution at the position corresponding to K138 of SEQ ID NO: 3100 (K138E or K138D) and an aspartic acid or glutamic acid substitution at the position corresponding to K217 of SEQ ID NO: 3100 (K217E or K217D). In some embodiments, the type II-Fc fusion protein IgG1 Fc domain comprises one or more amino acid substitutions selected from: a) a glutamic acid substitution at the position corresponding to K138 of SEQ ID NO: 3100 (K138E); b) an aspartic acid substitution at the position corresponding to K217 of SEQ ID NO: 3100 (K217D); and c) a glutamic acid substitution at the position corresponding to K138 of SEQ ID NO: 3100 (K138E) and an aspartic acid substitution at the position corresponding to K217 of SEQ ID NO: 3100 (K217D). In some embodiments, the type II-Fc fusion protein Fc domain is an IgG2 Fc domain that comprises one or more amino acid modifications that alter the pI of the type II-Fc fusion protein. In some embodiments, the type II-Fc fusion protein IgG2 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the type II-Fc fusion protein IgG2 fusion Fc domain comprises one or more amino acid substitutions selected from: a) an amino acid substitution at the position corresponding to K136 of SEQ ID NO: 3200; b) an amino acid substitution at the position corresponding to K215 of SEQ ID NO: 3200; and c) an amino acid substitution at the position corresponding to K136 of SEQ ID NO: 3200 and an amino acid substitution at the position corresponding to K215 of SEQ ID NO: 3200. In some embodiments, the type II-Fc fusion protein IgG2 Fc domain comprises one or more amino acid substitutions selected from: a) an aspartic acid or glutamic acid substitution at the position corresponding to K136 of SEQ ID NO: 3200 (K136E or K136D); b) an aspartic acid or glutamic acid substitution at the position corresponding to K215 of SEQ ID NO: 3200 (K215E or K215D); and c) an aspartic acid or glutamic acid substitution at the position corresponding to K136 of SEQ ID NO: 3200 (K136E or K136D) and an aspartic acid or glutamic acid substitution at the position corresponding to K215 of SEQ ID NO: 3200 (K215E or K215D). In some embodiments, the type II-Fc fusion protein Fc domain is an IgG3 Fc domain that comprises one or more amino acid modifications that alter the pI of the type II-Fc fusion protein. In some embodiments, the type II-Fc fusion protein IgG3 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3300. In some embodiments, the type II-Fc fusion protein IgG3 fusion Fc domain comprises one or more amino acid substitutions selected from: a) an amino acid substitution at the position corresponding to K145 of SEQ ID NO: 3300; b) an amino acid substitution at the position corresponding to K224 of SEQ ID NO: 3300; and c) an amino acid substitution at the position corresponding to K145 of SEQ ID NO: 3300 and an amino acid substitution at the position corresponding to K224 of SEQ ID NO: 3300. In some embodiments, the modified type II-Fc fusion protein IgG3 Fc domain comprises one or more amino acid substitutions selected from: a) an aspartic acid or glutamic acid substitution at the position corresponding to K145 of SEQ ID NO: 3300 (K145E or K145D); b) an aspartic acid or glutamic acid substitution at the position corresponding to K224 of SEQ ID NO: 3300 (K224E or K224D); and c) an aspartic acid or glutamic acid substitution at the position corresponding to K145 of SEQ ID NO: 3300 (K145E or K145D) and an aspartic acid or glutamic acid substitution at the position corresponding to K224 of SEQ ID NO: 3300 (K224E or K224D). In some embodiments, the type II-Fc fusion protein Fc domain is an IgG4 Fc domain that comprises one or more amino acid modifications that alter the pI of the type II-Fc fusion protein. In some embodiments, the type II-Fc fusion protein IgG4 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the type II-Fc fusion protein IgG4 fusion Fc domain comprises one or more amino acid substitutions selected from: a) an amino acid substitution at the position corresponding to K142 of SEQ ID NO: 3500; b) an amino acid substitution at the position corresponding to K221 of SEQ ID NO: 3500; and c) an amino acid substitution at the position corresponding to K142 of SEQ ID NO: 3500 and an amino acid substitution at the position corresponding to K221 of SEQ ID NO: 3500. In some embodiments, the type II-Fc fusion protein IgG4 Fc domain comprises one or more amino acid substitutions selected from: a) an aspartic acid or glutamic acid substitution at the position corresponding to K142 of SEQ ID NO: 3500 (K142E or K142D); b) an aspartic acid or glutamic acid substitution at the position corresponding to K221 of SEQ ID NO: 3500 (K221E or K221D); and c) an aspartic acid or glutamic acid substitution at the position corresponding to K142 of SEQ ID NO: 3500 (K142E or K142D) and an aspartic acid or glutamic acid substitution at the position corresponding to K221 of SEQ ID NO: 3500 (K221E or K221D).

In certain aspects, an type I:type II heteromultimer of the disclosure comprises an type II-Fc fusion protein comprising one or more amino acid modifications that increase the pI of the type II-Fc fusion protein; and an type I-Fc fusion protein comprising one or more amino acid modifications that decrease the pI of the type I-Fc fusion protein. For example, an type II-Fc fusion protein may be modified by substituting one or more neutral or negatively charged amino acids with one or more positively charged amino acids [e.g., an arginine (R), lysine (K), or histidine (H)]. Similarly, an type I-Fc fusion protein may be modified by substituting one or more neutral or positively charged amino acids with one or more negatively charged amino acids [e.g., aspartic acid (E) or glutamic acid (D)]. In some embodiments, the type II-Fc fusion protein Fc domain is an IgG1 Fc domain that comprises one or more amino acid modifications that alter the pI of the type II-Fc fusion protein. In some embodiments, the type II-Fc fusion protein IgG1 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the type II-Fc fusion protein IgG1 Fc domain comprises one or more amino acid substitutions selected from: a) an amino acid substitution at the position corresponding to N162 of SEQ ID NO: 3100; b) an amino acid substitution at the position corresponding to D179 of SEQ ID NO: 3100; and c) an amino acid substitution at the position corresponding to N162 of SEQ ID NO: 3100 and an amino acid substitution at the position corresponding to D179 of SEQ ID NO: 3100. In some embodiments, the type II-Fc fusion protein IgG1 Fc domain comprises one or more amino acid substitutions selected from: a) an arginine, lysine, or histidine substitution at the position corresponding to N162 of SEQ ID NO: 3100 (N162R, N162K, or N162H); b) an arginine, lysine, or histidine substitution at the position corresponding to D179 of SEQ ID NO: 3100 (D179R, D179K, or D179H); and c) an arginine, lysine, or histidine substitution at the position corresponding to N162 of SEQ ID NO: 3100 (N162R, N162K. or N162H) and an arginine, lysine, or histidine substitution at the position corresponding to D179 of SEQ ID NO: 3100 (D179R, D179K. or D179H). In some embodiments, the type II-Fc fusion protein IgG1 Fc domain comprises one or more amino acid substitutions selected from: a) an arginine substitution at the position corresponding to N162 of SEQ ID NO: 3100 (N162R); b) an arginine substitution at the position corresponding to D179 of SEQ ID NO: 3100 (D179R); and c) an arginine substitution at the position corresponding to N162 of SEQ ID NO: 3100 (N162R) and an arginine substitution at the position corresponding to D179 of SEQ ID NO: 3100 (D179R). In some embodiments, the type II-Fc fusion protein Fc domain is an IgG2 Fc domain that comprises one or more amino acid modifications that alter the pI of the type II-Fc fusion protein. In some embodiments, the type II-Fc fusion protein IgG2 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the type II-Fc fusion protein IgG2 Fc domain comprises one or more amino acid substitutions selected from: a) an amino acid substitution at the position corresponding to N160 of SEQ ID NO: 3200; b) an amino acid substitution at the position corresponding to D177 of SEQ ID NO: 3200; and c) an amino acid substitution at the position corresponding to N160 of SEQ ID NO: 3200 and an amino acid substitution at the position corresponding to D177 of SEQ ID NO: 3200. In some embodiments, the type II-Fc fusion protein IgG2 Fc domain comprises one or more amino acid substitutions selected from: a) an arginine, lysine, or histidine substitution at the position corresponding to N160 of SEQ ID NO: 3200 (N160R, N160K, or N160H); b) an arginine, lysine, or histidine substitution at the position corresponding to D177 of SEQ ID NO: 3200 (D177R, D177K, or D177H); and c) an arginine, lysine, or histidine substitution at the position corresponding to N160 of SEQ ID NO: 3200 (N160R, N160K, or N160H) and an arginine, lysine, or histidine substitution at the position corresponding to D177 of SEQ ID NO: 3200 (D177R, D177K. or D177H). In some embodiments, the type II-Fc fusion protein Fc domain is an IgG3 Fc domain that comprises one or more amino acid modifications that alter the pI of the type II-Fc fusion protein. In some embodiments, the type II-Fc fusion protein IgG3 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3300. In some embodiments, the type II-Fc fusion protein IgG3 Fc domain comprises one or more amino acid substitutions selected from: a) an amino acid substitution at the position corresponding to S169 of SEQ ID NO: 3300; b) an amino acid substitution at the position corresponding to D186 of SEQ ID NO: 3300; and c) an amino acid substitution at the position corresponding to S169 of SEQ ID NO: 3300 and an amino acid substitution at the position corresponding to D186 of SEQ ID NO: 3300. In some embodiments, the type II-Fc fusion protein IgG3 Fc domain comprises one or more amino acid substitutions selected from: a) an arginine, lysine, or histidine substitution at the position corresponding to S169 of SEQ ID NO: 3300 (S169R, S169K, or S169H); b) an arginine, lysine, or histidine substitution at the position corresponding to D186 of SEQ ID NO: 3300 (D186R, D186K, or D186H); and c) an arginine, lysine, or histidine substitution at the position corresponding to S169 of SEQ ID NO: 3300 (S169R, S169K, or S169H) and an arginine, lysine, or histidine substitution at the position corresponding to D186 of SEQ ID NO: 3300 (D186R, D186K, or D186H). In some embodiments, the type II-Fc fusion protein Fc domain is an IgG4 Fc domain that comprises one or more amino acid modifications that alter the pI of the type II-Fc fusion protein. In some embodiments, the type II-Fc fusion protein IgG4 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the type II-Fc fusion protein IgG4 Fc domain comprises one or more amino acid substitutions selected from: a) an amino acid substitution at the position corresponding to N166 of SEQ ID NO: 3500; b)

an amino acid substitution at the position corresponding to D183 of SEQ ID NO: 3500; and c) an amino acid substitution at the position corresponding to N166 of SEQ ID NO: 3500 and an amino acid substitution at the position corresponding to D183 of SEQ ID NO: 3500. In some embodiments, the type II-Fc fusion protein IgG4 Fc domain comprises one or more amino acid substitutions selected from: a) an arginine, lysine, or histidine substitution at the position corresponding to N166 of SEQ ID NO: 3500 (N166R, N166K, or N166H); b) an arginine, lysine, or histidine substitution at the position corresponding to D183 of SEQ ID NO: 3500 (D183R, D183K, or D183H); and c) an arginine, lysine, or histidine substitution at the position corresponding to N166 of SEQ ID NO: 3500 (N166R, N166K, or N166H) and an arginine, lysine, or histidine substitution at the position corresponding to D183 of SEQ ID NO: 3500 (D183R, D183K. or D183H). In some embodiments, the type I-Fc fusion protein Fc domain is an IgG1 Fc domain that comprises one or more amino acid modifications that alter the pI of the type I-Fc fusion protein. In some embodiments, the type I-Fc fusion protein IgG1 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the type I-Fc fusion protein IgG1 Fc domain comprises one or more amino acid substitutions selected from: a) an amino acid substitution at the position corresponding to K138 of SEQ ID NO: 3100; b) an amino acid substitution at the position corresponding to K217 of SEQ ID NO: 3100; and c) an amino acid substitution at the position corresponding to K138 of SEQ ID NO: 3100 and an amino acid substitution at the position corresponding to K217 of SEQ ID NO: 3100. In some embodiments, the type I-Fc fusion protein IgG1 Fc domain comprises one or more amino acid substitutions selected from: a) an aspartic acid or glutamic acid substitution at the position corresponding to K138 of SEQ ID NO: 3100 (K138E or K138D); b) an aspartic acid or glutamic acid substitution at the position corresponding to K217 of SEQ ID NO: 3100 (K217E or K217D); and c) an aspartic acid or glutamic acid substitution at the position corresponding to K138 of SEQ ID NO: 3100 (K138E or K138D) and an aspartic acid or glutamic acid substitution at the position corresponding to K217 of SEQ ID NO: 3100 (K217E or K217D). In some embodiments, the type I-Fc fusion protein IgG1 Fc domain comprises one or more amino acid substitutions selected from: a) a glutamic acid substitution at the position corresponding to K138 of SEQ ID NO: 3100 (K138E); b) an aspartic acid substitution at the position corresponding to K217 of SEQ ID NO: 3100 (K217D); and c) a glutamic acid substitution at the position corresponding to K138 of SEQ ID NO: 3100 (K138E) and an aspartic acid substitution at the position corresponding to K217 of SEQ ID NO: 3100 (K217D). In some embodiments, the type I-Fc fusion protein Fc domain is an IgG2 Fc domain that comprises one or more amino acid modifications that alter the pI of the type I-Fc fusion protein. In some embodiments, the type I-Fc fusion protein IgG2 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the type I-Fc fusion protein IgG2 fusion Fc domain comprises one or more amino acid substitutions selected from: a) an amino acid substitution at the position corresponding to K136 of SEQ ID NO: 3200; b) an amino acid substitution at the position corresponding to K215 of SEQ ID NO: 3200; and c) an amino acid substitution at the position corresponding to K136 of SEQ ID NO: 3200 and an amino acid substitution at the position corresponding to K215 of SEQ ID NO: 3200. In some embodiments, the type I-Fc fusion protein IgG2 Fc domain comprises one or more amino acid substitutions selected from: a) an aspartic acid or glutamic acid substitution at the position corresponding to K136 of SEQ ID NO: 3200 (K136E or K136D); b) an aspartic acid or glutamic acid substitution at the position corresponding to K215 of SEQ ID NO: 3200 (K215E or K215D); and c) an aspartic acid or glutamic acid substitution at the position corresponding to K136 of SEQ ID NO: 3200 (K136E or K136D) and an aspartic acid or glutamic acid substitution at the position corresponding to K215 of SEQ ID NO: 3200 (K215E or K215D). In some embodiments, the type I-Fc fusion protein Fc domain is an IgG3 Fc domain that comprises one or more amino acid modifications that alter the pI of the type I-Fc fusion protein. In some embodiments, the type I-Fc fusion protein IgG3 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3300. In some embodiments, the type I-Fc fusion protein IgG3 fusion Fc domain comprises one or more amino acid substitutions selected from: a) an amino acid substitution at the position corresponding to K145 of SEQ ID NO: 3300; b) an amino acid substitution at the position corresponding to K224 of SEQ ID NO: 3300; and c) an amino acid substitution at the position corresponding to K145 of SEQ ID NO: 3300 and an amino acid substitution at the position corresponding to K224 of SEQ ID NO: 3300. In some embodiments, the modified type I-Fc fusion protein IgG3 Fc domain comprises one or more amino acid substitutions selected from: a) an aspartic acid or glutamic acid substitution at the position corresponding to K145 of SEQ ID NO: 3300 (K145E or K145D); b) an aspartic acid or glutamic acid substitution at the position corresponding to K224 of SEQ ID NO: 3300 (K224E or K224D); and c) an aspartic acid or glutamic acid substitution at the position corresponding to K145 of SEQ ID NO: 3300 (K145E or K145D) and an aspartic acid or glutamic acid substitution at the position corresponding to K224 of SEQ ID NO: 3300 (K224E or K224D). In some embodiments, the type I-Fc fusion protein Fc domain is an IgG4 Fc domain that comprises one or more amino acid modifications that alter the pI of the type I-Fc fusion protein. In some embodiments, the type I-Fc fusion protein IgG4 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the type I-Fc fusion protein IgG4 fusion Fc domain comprises one or more amino acid substitutions selected from: a) an amino acid substitution at the position corresponding to K142 of SEQ ID NO: 3500; b) an amino acid substitution at the position corresponding to K221 of SEQ ID NO: 3500; and c) an amino acid substitution at the position corresponding to K142 of SEQ ID NO: 3500 and an amino acid substitution at the position corresponding to K221 of SEQ ID NO: 3500. In some embodiments, the type I-Fc fusion protein IgG4 Fc domain comprises one or more amino acid substitutions selected from: a) an aspartic acid or glutamic acid substitution at the position corresponding to K142 of SEQ ID NO: 3500 (K142E or K142D); b) an aspartic acid or glutamic acid substitution at the position corresponding to K221 of SEQ ID NO: 3500 (K221E or K221D); and c) an aspartic acid or glutamic acid substitution at the position corresponding to K142 of SEQ ID NO: 3500 (K142E or K142D) and an aspartic acid or glutamic acid substitution at the position corresponding to K221 of SEQ ID NO: 3500 (K221E or K221D).

In certain aspects, a type I:type II heteromultimer of the disclosure comprises an first type I-Fc fusion protein comprising one or more amino acid modifications that increase the pI of the first type I-Fc fusion protein; and a second type I-Fc fusion protein comprising one or more amino acid modifications that decrease the pI of the second type I-Fc fusion protein, wherein the first type I-Fc fusion protein and second type I-Fc fusion protein are different TGFβ superfamily type I receptor polypeptides. For example, a first type I-Fc fusion protein may be modified by substituting one or more neutral or negatively charged amino acids with one or more positively charged amino acids [e.g., an arginine (R), lysine (K), or histidine (H)]. Similarly, a second type I-Fc fusion protein may be modified by substituting one or more neutral or positively charged amino acids with one or more negatively charged amino acids [e.g., aspartic acid (E) or glutamic acid (D)]. In some embodiments, the first type I-Fc fusion protein Fc domain is an IgG1 Fc domain that comprises one or more amino acid modifications that alter the pI of the first type I-Fc fusion protein. In some embodiments, the first type I-Fc fusion protein IgG1 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the first type I-Fc fusion protein IgG1 Fc domain comprises one or more amino acid substitutions selected from: a) an amino acid substitution at the position corresponding to N162 of SEQ ID NO: 3100; b) an amino acid substitution at the position corresponding to D179 of SEQ ID NO: 3100; and c) an amino acid substitution at the position corresponding to N162 of SEQ ID NO: 3100 and an amino acid substitution at the position corresponding to D179 of SEQ ID NO: 3100. In some embodiments, the first type I-Fc fusion protein IgG1 Fc domain comprises one or more amino acid substitutions selected from: a) an arginine, lysine, or histidine substitution at the position corresponding to N162 of SEQ ID NO: 3100 (N162R, N162K, or N162H); b) an arginine, lysine, or histidine substitution at the position corresponding to D179 of SEQ ID NO: 3100 (D179R, D179K, or D179H); and c) an arginine, lysine, or histidine substitution at the position corresponding to N162 of SEQ ID NO: 3100 (N162R, N162K. or N162H) and an arginine, lysine, or histidine substitution at the position corresponding to D179 of SEQ ID NO: 3100 (D179R, D179K. or D179H). In some embodiments, the first type I-Fc fusion protein IgG1 Fc domain comprises one or more amino acid substitutions selected from: a) an arginine substitution at the position corresponding to N162 of SEQ ID NO: 3100 (N162R); b) an arginine substitution at the position corresponding to D179 of SEQ ID NO: 3100 (D179R); and c) an arginine substitution at the position corresponding to N162 of SEQ ID NO: 3100 (N162R) and an arginine substitution at the position corresponding to D179 of SEQ ID NO: 3100 (D179R). In some embodiments, the first type I-Fc fusion protein Fc domain is an IgG2 Fc domain that comprises one or more amino acid modifications that alter the pI of the first type I-Fc fusion protein. In some embodiments, the first type I-Fc fusion protein IgG2 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the first type I-Fc fusion protein IgG2 Fc domain comprises one or more amino acid substitutions selected from: a) an amino acid substitution at the position corresponding to N160 of SEQ ID NO: 3200; b) an amino acid substitution at the position corresponding to D177 of SEQ ID NO: 3200; and c) an amino acid substitution at the position corresponding to N160 of SEQ ID NO: 3200 and an amino acid substitution at the position corresponding to D177 of SEQ ID NO: 3200. In some embodiments, the first type I-Fc fusion protein IgG2 Fc domain comprises one or more amino acid substitutions selected from: a) an arginine, lysine, or histidine substitution at the position corresponding to N160 of SEQ ID NO: 3200 (N160R, N160K, or N160H); b) an arginine, lysine, or histidine substitution at the position corresponding to D177 of SEQ ID NO: 3200 (D177R, D177K, or D177H); and c) an arginine, lysine, or histidine substitution at the position corresponding to N160 of SEQ ID NO: 3200 (N160R, N160K, or N160H) and an arginine, lysine, or histidine substitution at the position corresponding to D177 of SEQ ID NO: 3200 (D177R, D177K. or D177H). In some embodiments, the first type I-Fc fusion protein Fc domain is an IgG3 Fc domain that comprises one or more amino acid modifications that alter the pI of the first type I-Fc fusion protein. In some embodiments, the first type I-Fc fusion protein IgG3 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3300. In some embodiments, the first type I-Fc fusion protein IgG3 Fc domain comprises one or more amino acid substitutions selected from: a) an amino acid substitution at the position corresponding to S169 of SEQ ID NO: 3300; b) an amino acid substitution at the position corresponding to D186 of SEQ ID NO: 3300; and c) an amino acid substitution at the position corresponding to S169 of SEQ ID NO: 3300 and an amino acid substitution at the position corresponding to D186 of SEQ ID NO: 3300. In some embodiments, the first type I-Fc fusion protein IgG3 Fc domain comprises one or more amino acid substitutions selected from: a) an arginine, lysine, or histidine substitution at the position corresponding to S169 of SEQ ID NO: 3300 (S169R, S169K, or S169H); b) an arginine, lysine, or histidine substitution at the position corresponding to D186 of SEQ ID NO: 3300 (D186R, D186K, or D186H); and c) an arginine, lysine, or histidine substitution at the position corresponding to S169 of SEQ ID NO: 3300 (S169R, S169K, or S169H) and an arginine, lysine, or histidine substitution at the position corresponding to D186 of SEQ ID NO: 3300 (D186R, D186K, or D186H). In some embodiments, the first type I-Fc fusion protein Fc domain is an IgG4 Fc domain that comprises one or more amino acid modifications that alter the pI of the first type I-Fc fusion protein. In some embodiments, the first type I-Fc fusion protein IgG4 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the first type I-Fc fusion protein IgG4 Fc domain comprises one or more amino acid substitutions selected from: a) an amino acid substitution at the position corresponding to N166 of SEQ ID NO: 3500; b) an amino acid substitution at the position corresponding to D183 of SEQ ID NO: 3500; and c) an amino acid substitution at the position corresponding to N166 of SEQ ID NO: 3500 and an amino acid substitution at the position corresponding to D183 of SEQ ID NO: 3500. In some embodiments, the first type I-Fc fusion protein IgG4 Fc domain comprises one or more amino acid substitutions selected from: a) an arginine, lysine, or histidine substitution at the position corresponding to N166 of SEQ ID NO: 3500 (N166R, N166K, or N166H);

b) an arginine, lysine, or histidine substitution at the position corresponding to D183 of SEQ ID NO: 3500 (D183R, D183K, or D183H); and c) an arginine, lysine, or histidine substitution at the position corresponding to N166 of SEQ ID NO: 3500 (N166R, N166K, or N166H) and an arginine, lysine, or histidine substitution at the position corresponding to D183 of SEQ ID NO: 3500 (D183R, D183K. or D183H). In some embodiments, the second type I-Fc fusion protein Fc domain is an IgG1 Fc domain that comprises one or more amino acid modifications that alter the pI of the second type I-Fc fusion protein. In some embodiments, the second type I-Fc fusion protein IgG1 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the second type I-Fc fusion protein IgG1 Fc domain comprises one or more amino acid substitutions selected from: a) an amino acid substitution at the position corresponding to K138 of SEQ ID NO: 3100; b) an amino acid substitution at the position corresponding to K217 of SEQ ID NO: 3100; and c) an amino acid substitution at the position corresponding to K138 of SEQ ID NO: 3100 and an amino acid substitution at the position corresponding to K217 of SEQ ID NO: 3100. In some embodiments, the second type I-Fc fusion protein IgG1 Fc domain comprises one or more amino acid substitutions selected from: a) an aspartic acid or glutamic acid substitution at the position corresponding to K138 of SEQ ID NO: 3100 (K138E or K138D); b) an aspartic acid or glutamic acid substitution at the position corresponding to K217 of SEQ ID NO: 3100 (K217E or K217D); and c) an aspartic acid or glutamic acid substitution at the position corresponding to K138 of SEQ ID NO: 3100 (K138E or K138D) and an aspartic acid or glutamic acid substitution at the position corresponding to K217 of SEQ ID NO: 3100 (K217E or K217D). In some embodiments, the second type I-Fc fusion protein IgG1 Fc domain comprises one or more amino acid substitutions selected from: a) a glutamic acid substitution at the position corresponding to K138 of SEQ ID NO: 3100 (K138E); b) an aspartic acid substitution at the position corresponding to K217 of SEQ ID NO: 3100 (K217D); and c) a glutamic acid substitution at the position corresponding to K138 of SEQ ID NO: 3100 (K138E) and an aspartic acid substitution at the position corresponding to K217 of SEQ ID NO: 3100 (K217D). In some embodiments, the second type I-Fc fusion protein Fc domain is an IgG2 Fc domain that comprises one or more amino acid modifications that alter the pI of the second type I-Fc fusion protein. In some embodiments, the second type I-Fc fusion protein IgG2 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the second type I-Fc fusion protein IgG2 fusion Fc domain comprises one or more amino acid substitutions selected from: a) an amino acid substitution at the position corresponding to K136 of SEQ ID NO: 3200; b) an amino acid substitution at the position corresponding to K215 of SEQ ID NO: 3200; and c) an amino acid substitution at the position corresponding to K136 of SEQ ID NO: 3200 and an amino acid substitution at the position corresponding to K215 of SEQ ID NO: 3200. In some embodiments, the second type I-Fc fusion protein IgG2 Fc domain comprises one or more amino acid substitutions selected from: a) an aspartic acid or glutamic acid substitution at the position corresponding to K136 of SEQ ID NO: 3200 (K136E or K136D); b) an aspartic acid or glutamic acid substitution at the position corresponding to K215 of SEQ ID NO: 3200 (K215E or K215D); and c) an aspartic acid or glutamic acid substitution at the position corresponding to K136 of SEQ ID NO: 3200 (K136E or K136D) and an aspartic acid or glutamic acid substitution at the position corresponding to K215 of SEQ ID NO: 3200 (K215E or K215D). In some embodiments, the second type I-Fc fusion protein Fc domain is an IgG3 Fc domain that comprises one or more amino acid modifications that alter the pI of the second type I-Fc fusion protein. In some embodiments, the second type I-Fc fusion protein IgG3 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3300. In some embodiments, the second type I-Fc fusion protein IgG3 fusion Fc domain comprises one or more amino acid substitutions selected from: a) an amino acid substitution at the position corresponding to K145 of SEQ ID NO: 3300; b) an amino acid substitution at the position corresponding to K224 of SEQ ID NO: 3300; and c) an amino acid substitution at the position corresponding to K145 of SEQ ID NO: 3300 and an amino acid substitution at the position corresponding to K224 of SEQ ID NO: 3300. In some embodiments, the second type I-Fc fusion protein IgG3 Fc domain comprises one or more amino acid substitutions selected from: a) an aspartic acid or glutamic acid substitution at the position corresponding to K145 of SEQ ID NO: 3300 (K145E or K145D); b) an aspartic acid or glutamic acid substitution at the position corresponding to K224 of SEQ ID NO: 3300 (K224E or K224D); and c) an aspartic acid or glutamic acid substitution at the position corresponding to K145 of SEQ ID NO: 3300 (K145E or K145D) and an aspartic acid or glutamic acid substitution at the position corresponding to K224 of SEQ ID NO: 3300 (K224E or K224D). In some embodiments, the second type I-Fc fusion protein Fc domain is an IgG4 Fc domain that comprises one or more amino acid modifications that alter the pI of the second type I-Fc fusion protein. In some embodiments, the second type I-Fc fusion protein IgG4 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the second type I-Fc fusion protein IgG4 fusion Fc domain comprises one or more amino acid substitutions selected from: a) an amino acid substitution at the position corresponding to K142 of SEQ ID NO: 3500; b) an amino acid substitution at the position corresponding to K221 of SEQ ID NO: 3500; and c) an amino acid substitution at the position corresponding to K142 of SEQ ID NO: 3500 and an amino acid substitution at the position corresponding to K221 of SEQ ID NO: 3500. In some embodiments, the second type I-Fc fusion protein IgG4 Fc domain comprises one or more amino acid substitutions selected from: a) an aspartic acid or glutamic acid substitution at the position corresponding to K142 of SEQ ID NO: 3500 (K142E or K142D); b) an aspartic acid or glutamic acid substitution at the position corresponding to K221 of SEQ ID NO: 3500 (K221E or K221D); and c) an aspartic acid or glutamic acid substitution at the position corresponding to K142 of SEQ ID NO: 3500 (K142E or K142D) and an aspartic acid or glutamic acid substitution at the position corresponding to K221 of SEQ ID NO: 3500 (K221E or K221D).

In certain aspects, a type II:type II heteromultimer of the disclosure comprises an first type II-Fc fusion protein comprising one or more amino acid modifications that increase the pI of the first type II-Fc fusion protein; and a second type II-Fc fusion protein comprising one or more amino acid modifications that decrease the pI of the second type II-Fc fusion protein, wherein the first type II-Fc fusion protein and second type II-Fc fusion protein are different TGFβ superfamily type II receptor polypeptides. For example, a first type II-Fc fusion protein may be modified by substituting one or more neutral or negatively charged amino acids with one or more positively charged amino acids [e.g., an arginine (R), lysine (K), or histidine (H)]. Similarly, a second type II-Fc fusion protein may be modified by substituting one or more neutral or positively charged amino acids with one or more negatively charged amino acids [e.g., aspartic acid (E) or glutamic acid (D)]. In some embodiments, the first type II-Fc fusion protein Fc domain is an IgG1 Fc domain that comprises one or more amino acid modifications that alter the pI of the first type II-Fc fusion protein. In some embodiments, the first type II-Fc fusion protein IgG1 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the first type II-Fc fusion protein IgG1 Fc domain comprises one or more amino acid substitutions selected from: a) an amino acid substitution at the position corresponding to N162 of SEQ ID NO: 3100; b) an amino acid substitution at the position corresponding to D179 of SEQ ID NO: 3100; and c) an amino acid substitution at the position corresponding to N162 of SEQ ID NO: 3100 and an amino acid substitution at the position corresponding to D179 of SEQ ID NO: 3100. In some embodiments, the first type II-Fc fusion protein IgG1 Fc domain comprises one or more amino acid substitutions selected from: a) an arginine, lysine, or histidine substitution at the position corresponding to N162 of SEQ ID NO: 3100 (N162R, N162K, or N162H); b) an arginine, lysine, or histidine substitution at the position corresponding to D179 of SEQ ID NO: 3100 (D179R, D179K, or D179H); and c) an arginine, lysine, or histidine substitution at the position corresponding to N162 of SEQ ID NO: 3100 (N162R, N162K. or N162H) and an arginine, lysine, or histidine substitution at the position corresponding to D179 of SEQ ID NO: 3100 (D179R, D179K. or D179H). In some embodiments, the first type II-Fc fusion protein IgG1 Fc domain comprises one or more amino acid substitutions selected from: a) an arginine substitution at the position corresponding to N162 of SEQ ID NO: 3100 (N162R); b) an arginine substitution at the position corresponding to D179 of SEQ ID NO: 3100 (D179R); and c) an arginine substitution at the position corresponding to N162 of SEQ ID NO: 3100 (N162R) and an arginine substitution at the position corresponding to D179 of SEQ ID NO: 3100 (D179R). In some embodiments, the first type II-Fc fusion protein Fc domain is an IgG2 Fc domain that comprises one or more amino acid modifications that alter the pI of the first type II-Fc fusion protein. In some embodiments, the first type II-Fc fusion protein IgG2 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the first type II-Fc fusion protein IgG2 Fc domain comprises one or more amino acid substitutions selected from: a) an amino acid substitution at the position corresponding to N160 of SEQ ID NO: 3200; b) an amino acid substitution at the position corresponding to D177 of SEQ ID NO: 3200; and c) an amino acid substitution at the position corresponding to N160 of SEQ ID NO: 3200 and an amino acid substitution at the position corresponding to D177 of SEQ ID NO: 3200. In some embodiments, the first type II-Fc fusion protein IgG2 Fc domain comprises one or more amino acid substitutions selected from: a) an arginine, lysine, or histidine substitution at the position corresponding to N160 of SEQ ID NO: 3200 (N160R, N160K, or N160H); b) an arginine, lysine, or histidine substitution at the position corresponding to D177 of SEQ ID NO: 3200 (D177R, D177K, or D177H); and c) an arginine, lysine, or histidine substitution at the position corresponding to N160 of SEQ ID NO: 3200 (N160R, N160K, or N160H) and an arginine, lysine, or histidine substitution at the position corresponding to D177 of SEQ ID NO: 3200 (D177R, D177K. or D177H). In some embodiments, the first type II-Fc fusion protein Fc domain is an IgG3 Fc domain that comprises one or more amino acid modifications that alter the pI of the first type II-Fc fusion protein. In some embodiments, the first type II-Fc fusion protein IgG3 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3300. In some embodiments, the first type II-Fc fusion protein IgG3 Fc domain comprises one or more amino acid substitutions selected from: a) an amino acid substitution at the position corresponding to 5169 of SEQ ID NO: 3300; b) an amino acid substitution at the position corresponding to D186 of SEQ ID NO: 3300; and c) an amino acid substitution at the position corresponding to S169 of SEQ ID NO: 3300 and an amino acid substitution at the position corresponding to D186 of SEQ ID NO: 3300. In some embodiments, the first type II-Fc fusion protein IgG3 Fc domain comprises one or more amino acid substitutions selected from: a) an arginine, lysine, or histidine substitution at the position corresponding to S169 of SEQ ID NO: 3300 (S169R, S169K, or S169H); b) an arginine, lysine, or histidine substitution at the position corresponding to D186 of SEQ ID NO: 3300 (D186R, D186K, or D186H); and c) an arginine, lysine, or histidine substitution at the position corresponding to S169 of SEQ ID NO: 3300 (S169R, S169K, or S169H) and an arginine, lysine, or histidine substitution at the position corresponding to D186 of SEQ ID NO: 3300 (D186R, D186K, or D186H). In some embodiments, the first type II-Fc fusion protein Fc domain is an IgG4 Fc domain that comprises one or more amino acid modifications that alter the pI of the first type II-Fc fusion protein. In some embodiments, the first type II-Fc fusion protein IgG4 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the first type II-Fc fusion protein IgG4 Fc domain comprises one or more amino acid substitutions selected from: a) an amino acid substitution at the position corresponding to N166 of SEQ ID NO: 3500; b) an amino acid substitution at the position corresponding to D183 of SEQ ID NO: 3500; and c) an amino acid substitution at the position corresponding to N166 of SEQ ID NO: 3500 and an amino acid substitution at the position corresponding to D183 of SEQ ID NO: 3500. In some embodiments, the first type II-Fc fusion protein IgG4 Fc domain comprises one or more amino acid substitutions selected from: a) an arginine, lysine, or histidine substitution at the position corresponding to N166 of SEQ ID NO: 3500 (N166R, N166K, or N166H); b) an arginine, lysine, or histidine substitution at the position corresponding to D183 of SEQ ID NO: 3500 (D183R, D183K, or D183H); and c) an arginine, lysine, or histidine substitution at the position corresponding to N166 of SEQ ID NO: 3500 (N166R, N166K, or N166H) and an arginine, lysine, or histidine substitution at the position corresponding to D183 of SEQ ID NO: 3500 (D183R, D183K. or D183H). In some embodiments, the second type II-Fc fusion protein Fc domain is an IgG1 Fc domain that comprises one or more amino acid modifications that alter the pI of the second type II-Fc fusion protein. In some embodiments, the second type II-Fc fusion protein IgG1 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the second type II-Fc fusion protein IgG1 Fc domain comprises one or more amino acid substitutions selected from: a) an amino acid substitution at the position corresponding to K138 of SEQ ID NO: 3100; b) an amino acid substitution at the position corresponding to K217 of SEQ ID NO: 3100; and c) an amino acid substitution at the position corresponding to K138 of SEQ ID NO: 3100 and an amino acid substitution at the position corresponding to K217 of SEQ ID NO: 3100. In some embodiments, the second type II-Fc fusion protein IgG1 Fc domain comprises one or more amino acid substitutions selected from: a) an aspartic acid or glutamic acid substitution at the position corresponding to K138 of SEQ ID NO: 3100 (K138E or K138D); b) an aspartic acid or glutamic acid substitution at the position corresponding to K217 of SEQ ID NO: 3100 (K217E or K217D); and c) an aspartic acid or glutamic acid substitution at the position corresponding to K138 of SEQ ID NO: 3100 (K138E or K138D) and an aspartic acid or glutamic acid substitution at the position corresponding to K217 of SEQ ID NO: 3100 (K217E or K217D). In some embodiments, the second type II-Fc fusion protein IgG1 Fc domain comprises one or more amino acid substitutions selected from: a) a glutamic acid substitution at the position corresponding to K138 of SEQ ID NO: 3100 (K138E); b) an aspartic acid substitution at the position corresponding to K217 of SEQ ID NO: 3100 (K217D); and c) a glutamic acid substitution at the position corresponding to K138 of SEQ ID NO: 3100 (K138E) and an aspartic acid substitution at the position corresponding to K217 of SEQ ID NO: 3100 (K217D). In some embodiments, the second type II-Fc fusion protein Fc domain is an IgG2 Fc domain that comprises one or more amino acid modifications that alter the pI of the second type II-Fc fusion protein. In some embodiments, the second type II-Fc fusion protein IgG2 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the second type I-Fc fusion protein IgG2 fusion Fc domain comprises one or more amino acid substitutions selected from: a) an amino acid substitution at the position corresponding to K136 of SEQ ID NO: 3200; b) an amino acid substitution at the position corresponding to K215 of SEQ ID NO: 3200; and c) an amino acid substitution at the position corresponding to K136 of SEQ ID NO: 3200 and an amino acid substitution at the position corresponding to K215 of SEQ ID NO: 3200. In some embodiments, the second type II-Fc fusion protein IgG2 Fc domain comprises one or more amino acid substitutions selected from: a) an aspartic acid or glutamic acid substitution at the position corresponding to K136 of SEQ ID NO: 3200 (K136E or K136D); b) an aspartic acid or glutamic acid substitution at the position corresponding to K215 of SEQ ID NO: 3200 (K215E or K215D); and c) an aspartic acid or glutamic acid substitution at the position corresponding to K136 of SEQ ID NO: 3200 (K136E or K136D) and an aspartic acid or glutamic acid substitution at the position corresponding to K215 of SEQ ID NO: 3200 (K215E or K215D). In some embodiments, the second type II-Fc fusion protein Fc domain is an IgG3 Fc domain that comprises one or more amino acid modifications that alter the pI of the second type II-Fc fusion protein. In some embodiments, the second type II-Fc fusion protein IgG3 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3300. In some embodiments, the second type II-Fc fusion protein IgG3 fusion Fc domain comprises one or more amino acid substitutions selected from: a) an amino acid substitution at the position corresponding to K145 of SEQ ID NO: 3300; b) an amino acid substitution at the position corresponding to K224 of SEQ ID NO: 3300; and c) an amino acid substitution at the position corresponding to K145 of SEQ ID NO: 3300 and an amino acid substitution at the position corresponding to K224 of SEQ ID NO: 3300. In some embodiments, the second type II-Fc fusion protein IgG3 Fc domain comprises one or more amino acid substitutions selected from: a) an aspartic acid or glutamic acid substitution at the position corresponding to K145 of SEQ ID NO: 3300 (K145E or K145D); b) an aspartic acid or glutamic acid substitution at the position corresponding to K224 of SEQ ID NO: 3300 (K224E or K224D); and c) an aspartic acid or glutamic acid substitution at the position corresponding to K145 of SEQ ID NO: 3300 (K145E or K145D) and an aspartic acid or glutamic acid substitution at the position corresponding to K224 of SEQ ID NO: 3300 (K224E or K224D). In some embodiments, the second type II-Fc fusion protein Fc domain is an IgG4 Fc domain that comprises one or more amino acid modifications that alter the pI of the second type II-Fc fusion protein. In some embodiments, the second type II-Fc fusion protein IgG4 Fc domain comprises an amino acid sequence that is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the second type II-Fc fusion protein IgG4 fusion Fc domain comprises one or more amino acid substitutions selected from: a) an amino acid substitution at the position corresponding to K142 of SEQ ID NO: 3500; b) an amino acid substitution at the position corresponding to K221 of SEQ ID NO: 3500; and c) an amino acid substitution at the position corresponding to K142 of SEQ ID NO: 3500 and an amino acid substitution at the position corresponding to K221 of SEQ ID NO: 3500. In some embodiments, the second type II-Fc fusion protein IgG4 Fc domain comprises one or more amino acid substitutions selected from: a) an aspartic acid or glutamic acid substitution at the position corresponding to K142 of SEQ ID NO: 3500 (K142E or K142D); b) an aspartic acid or glutamic acid substitution at the position corresponding to K221 of SEQ ID NO: 3500 (K221E or K221D); and c) an aspartic acid or glutamic acid substitution at the position corresponding to K142 of SEQ ID NO: 3500 (K142E or K142D) and an aspartic acid or glutamic acid substitution at the position corresponding to K221 of SEQ ID NO: 3500 (K221E or K221D).

As described herein, type I-Fc fusion proteins and/or type II-Fc fusion proteins may comprise one or more modifications that promote heteromultimer formation (e.g., type I-Fc:type II-Fc heterodimerization). Similarly, type I-Fc fusion proteins and/or type II-Fc fusion proteins may comprise one or more modifications that inhibit homomultimer formation (e.g., type I-Fc and/or type II-Fc homodimerization). In some embodiments, type I-Fc fusion proteins and/or type II-Fc fusion proteins may comprise one or more modifications that promote heteromultimer formation and comprise one or more modifications that inhibit homomultimer formation.

For example, in some embodiments, an type I:type II heteromultimer comprises: a) a type I-Fc fusion protein having an IgG1 Fc domain comprising a cysteine substitution at position S132 of SEQ ID NO: 3100 (S132C) and a tryptophan substitution at position T144 of SEQ ID NO: 3100 (T144W); and b) an type II-Fc fusion protein having an IgG1 Fc domain comprising a cysteine substitution at position Y127 of SEQ ID NO: 3100 (Y127C), a serine substitution at position T144 of SEQ ID NO: 3100 (T144S), an alanine substitution at position L146 of SEQ ID NO: 3100 (L146A), and a valine substitution at position Y185 of SEQ ID NO: 3100 (Y185V). In some embodiments, an type I:type II heteromultimer comprises: a) an type II-Fc fusion protein having an IgG1 Fc domain comprising a cysteine substitution at position S132 of SEQ ID NO: 3100 (S132C) and a tryptophan substitution at position T144 of SEQ ID NO: 3100 (T144W); and b) an type I-Fc fusion protein having an IgG1 Fc domain comprising a cysteine substitution at position Y127 of SEQ ID NO: 3100 (Y127C), a serine substitution at position T144 of SEQ ID NO: 3100 (T144S), an alanine substitution at position L146 of SEQ ID NO: 3100 (L146A), and a valine substitution at position Y185 of SEQ ID NO: 3100 (Y185V). In some embodiments, a type I:type II heteromultimer comprises: a) an type I-Fc fusion protein having an IgG2 Fc domain comprising a cysteine substitution at position S130 of SEQ ID NO: 3200 (S130C) and a tryptophan substitution at position T142 of SEQ ID NO: 3200 (T142W); and b) an type II-Fc fusion protein having an IgG2 Fc domain comprising a cysteine substitution at position Y125 of SEQ ID NO: 3200 (Y125C), a serine substitution at position T142 of SEQ ID NO: 3200 (T142S), an alanine substitution at position L144 of SEQ ID NO: 3200 (L144A), and a valine substitution at position Y183 of SEQ ID NO: 3200 (Y183V). In some embodiments, an type I:type II heteromultimer comprises: a) an type II-Fc fusion protein having an IgG2 Fc domain comprising a cysteine substitution at position S130 of SEQ ID NO: 3200 (S130C) and a tryptophan substitution at position T142 of SEQ ID NO: 3200 (T142W); and b) an type I-Fc fusion protein having an IgG2 Fc domain comprising a cysteine substitution at position Y125 of SEQ ID NO: 3200 (Y125C), a serine substitution at position T142 of SEQ ID NO: 3200 (T142S), an alanine substitution at position L144 of SEQ ID NO: 3200 (L144A), and a valine substitution at position Y183 of SEQ ID NO: 3200 (Y183V). In some embodiments, an type I:type II heteromultimer comprises: a) an type I-Fc fusion protein having an IgG3 Fc domain comprising a cysteine substitution at position S139 of SEQ ID NO: 3300 (S139C) and a tryptophan substitution at position T151 of SEQ ID NO: 3300 (T151W); and b) the type II-Fc fusion protein having an IgG3 Fc domain comprising a cysteine substitution at position Y134 of SEQ ID NO: 3300 (Y134C), a serine substitution at position T151 of SEQ ID NO: 3300 (T151S), an alanine substitution at position L153 of SEQ ID NO: 3300 (L153A), and a valine substitution at position Y192 of SEQ ID NO: 3300 (Y192V). In some embodiments, an type I:type II heteromultimer comprises: a) an type II-Fc fusion protein having an IgG3 Fc domain comprising a cysteine substitution at position S139 of SEQ ID NO: 3300 (S139C) and a tryptophan substitution at position T151 of SEQ ID NO: 3300 (T151W); and b) an type I-Fc fusion protein having an IgG3 Fc domain comprising a cysteine substitution at position Y134 of SEQ ID NO: 3300 (Y134C), a serine substitution at position T151 of SEQ ID NO: 3300 (T151S), an alanine substitution at position L153 of SEQ ID NO: 3300 (L153A), and a valine substitution at position Y192 of SEQ ID NO: 3300 (Y192V). In some embodiments, an type I:type II heteromultimer comprises: a) an type I-Fc fusion protein having an IgG4 Fc domain comprises a cysteine substitution at position S136 of SEQ ID NO: 3500 (S136C) and a tryptophan substitution at position T148 of SEQ ID NO: 3500 (T148W); and b) an typeII-Fc fusion protein having an IgG4 Fc domain comprises a cysteine substitution at position Y131 of SEQ ID NO: 3500 (Y131C), a serine substitution at position T148 of SEQ ID NO: 3500 (T148S), an alanine substitution at position L150 of SEQ ID NO: 3500 (L150A), and a valine substitution at position Y189 of SEQ ID NO: 3500 (Y189V). In some embodiments, an type I:type II heteromultimer comprises: a) an type II-Fc fusion protein having an IgG4 Fc domain comprising a cysteine substitution at position S136 of SEQ ID NO: 3500 (S136C) and a tryptophan substitution at position T148 of SEQ ID NO: 3500 (T148W); and b) an type I-Fc fusion protein having an IgG4 Fc domain comprising a cysteine substitution at position Y131 of SEQ ID NO: 3500 (Y131C), a serine substitution at position T148 of SEQ ID NO: 3500 (T148S), an alanine substitution at position L150 of SEQ ID NO: 3500 (L150A), and a valine substitution at position Y189 of SEQ ID NO: 3500 (Y189V).

In some embodiments, an type I:type I heteromultimer comprises: a) a first type I-Fc fusion protein having an IgG1 Fc domain comprising a cysteine substitution at position S132 of SEQ ID NO: 3100 (S132C) and a tryptophan substitution at position T144 of SEQ ID NO: 3100 (T144W); and b) an second type I-Fc fusion protein having an IgG1 Fc domain comprising a cysteine substitution at position Y127 of SEQ ID NO: 3100 (Y127C), a serine substitution at position T144 of SEQ ID NO: 3100 (T144S), an alanine substitution at position L146 of SEQ ID NO: 3100 (L146A), and a valine substitution at position Y185 of SEQ ID NO: 3100 (Y185V). In some embodiments, a type I:type I heteromultimer comprises: a) an first type I-Fc fusion protein having an IgG2 Fc domain comprising a cysteine substitution at position S130 of SEQ ID NO: 3200 (S130C) and a tryptophan substitution at position T142 of SEQ ID NO: 3200 (T142W); and b) a second type I-Fc fusion protein having an IgG2 Fc domain comprising a cysteine substitution at position Y125 of SEQ ID NO: 3200 (Y125C), a serine substitution at position T142 of SEQ ID NO: 3200 (T142S), an alanine substitution at position L144 of SEQ ID NO: 3200 (L144A), and a valine substitution at position Y183 of SEQ ID NO: 3200 (Y183V). In some embodiments, a type I:type I heteromultimer comprises: a) a first type I-Fc fusion protein having an IgG3 Fc domain comprising a cysteine substitution at position S139 of SEQ ID NO: 3300 (S139C) and a tryptophan substitution at position T151 of SEQ ID NO: 3300 (T151W); and b) a second type I-Fc fusion protein having an IgG3 Fc domain comprising a cysteine substitution at position Y134 of SEQ ID NO: 3300 (Y134C), a serine substitution at position T151 of SEQ ID NO: 3300 (T151S), an alanine substitution at position L153 of SEQ ID NO: 3300 (L153A), and a valine substitution at position Y192 of SEQ ID NO: 3300 (Y192V). In some embodiments, a type I:type I heteromultimer comprises: a) a first type I-Fc fusion protein having an IgG4 Fc domain comprises a cysteine substitution at position S136 of SEQ ID NO: 3500 (S136C) and a tryptophan substitution at position T148 of SEQ ID NO: 3500 (T148W); and b) a second type I-Fc fusion protein having an IgG4 Fc domain comprises a cysteine substitution at position Y131 of SEQ ID NO: 3500 (Y131C), a serine substitution at position T148 of SEQ ID NO: 3500 (T148S), an alanine substitution at position L150 of SEQ ID NO: 3500 (L150A), and a valine substitution at position Y189 of SEQ ID NO: 3500 (Y189V).

In some embodiments, a type II:type II heteromultimer comprises: a) a first type II-Fc fusion protein having an IgG1 Fc domain comprising a cysteine substitution at position S132 of SEQ ID NO: 3100 (S132C) and a tryptophan substitution at position T144 of SEQ ID NO: 3100 (T144W); and b) an second type II-Fc fusion protein having an IgG1 Fc domain comprising a cysteine substitution at position Y127 of SEQ ID NO: 3100 (Y127C), a serine substitution at position T144 of SEQ ID NO: 3100 (T144S), an alanine substitution at position L146 of SEQ ID NO: 3100 (L146A), and a valine substitution at position Y185 of SEQ ID NO: 3100 (Y185V). In some embodiments, a type II:type II heteromultimer comprises: a) an first type II-Fc fusion protein having an IgG2 Fc domain comprising a cysteine substitution at position S130 of SEQ ID NO: 3200 (S130C) and a tryptophan substitution at position T142 of SEQ ID NO: 3200 (T142W); and b) a second type II-Fc fusion protein having an IgG2 Fc domain comprising a cysteine substitution at position Y125 of SEQ ID NO: 3200 (Y125C), a serine substitution at position T142 of SEQ ID NO: 3200 (T142S), an alanine substitution at position L144 of SEQ ID NO: 3200 (L144A), and a valine substitution at position Y183 of SEQ ID NO: 3200 (Y183V). In some embodiments, a type I:type I heteromultimer comprises: a) a first type II-Fc fusion protein having an IgG3 Fc domain comprising a cysteine substitution at position S139 of SEQ ID NO: 3300 (S139C) and a tryptophan substitution at position T151 of SEQ ID NO: 3300 (T151W); and b) a second type II-Fc fusion protein having an IgG3 Fc domain comprising a cysteine substitution at position Y134 of SEQ ID NO: 3300 (Y134C), a serine substitution at position T151 of SEQ ID NO: 3300 (T151S), an alanine substitution at position L153 of SEQ ID NO: 3300 (L153A), and a valine substitution at position Y192 of SEQ ID NO: 3300 (Y192V). In some embodiments, a type II:type II heteromultimer comprises: a) a first type II-Fc fusion protein having an IgG4 Fc domain comprises a cysteine substitution at position S136 of SEQ ID NO: 3500 (S136C) and a tryptophan substitution at position T148 of SEQ ID NO: 3500 (T148W); and b) a second type II-Fc fusion protein having an IgG4 Fc domain comprises a cysteine substitution at position Y131 of SEQ ID NO: 3500 (Y131C), a serine substitution at position T148 of SEQ ID NO: 3500 (T148S), an alanine substitution at position L150 of SEQ ID NO: 3500 (L150A), and a valine substitution at position Y189 of SEQ ID NO: 3500 (Y189V).

In certain aspects, a type I:type II heteromultimer of the disclosure comprises: a) an type I-Fc fusion protein having an Fc domain that is at least 75%, 80%, 85%, 90%, 91%, 92%, 93%, 94%, 95%, 96%, 97%, 98%, 99%, or 100% identical to the amino acid sequence of SEQ ID NO: 660; and b) a type II-Fc fusion protein having an Fc domain that is at least 75%, 80%, 85%, 90%, 91%, 92%, 93%, 94%, 95%, 96%, 97%, 98%, 99%, or 100% identical to the amino acid sequence of SEQ ID NO: 670. In some embodiments, the type I-Fc fusion protein Fc domain comprises one or more amino acid substitutions selected from: a) a glutamic acid at the position corresponding to 138 of SEQ ID NO: 660; b) an aspartic acid at the position corresponding to 217 of SEQ ID NO: 660; and c) a glutamic acid at the position corresponding to 138 of SEQ ID NO: 660 and an aspartic acid at the position corresponding to 217 of SEQ ID NO: 660. Optionally, the type I-Fc fusion protein Fc domain further comprises a cysteine at the position corresponding to 132 of SEQ ID NO: 660 and a tryptophan at the position corresponding to 144 of SEQ ID NO: 660. In some embodiments, the type II-Fc fusion protein Fc domain comprises one or more amino acid substitutions selected from: a) an arginine at the position corresponding to 162 of SEQ ID NO: 670; b) an arginine at the position corresponding to 179 of SEQ ID NO: 670; and c) an arginine at the position corresponding to 162 of SEQ ID NO: 670 and an arginine at the position corresponding to 179 of SEQ ID NO: 670. Optionally, the type II-Fc fusion protein Fc domain further comprises a cysteine at the position corresponding to 127 of SEQ ID NO: 670, a serine at the position corresponding to 144 of SEQ ID NO: 670, an alanine at the position corresponding to 146 of SEQ ID NO: 670, and a valine at the position corresponding to 185 of SEQ ID NO: 670.

In certain aspects, a type I:type II heteromultimer of the disclosure comprises: a) a type II-Fc fusion protein having an Fc domain that is at least 75%, 80%, 85%, 90%, 91%, 92%, 93%, 94%, 95%, 96%, 97%, 98%, 99%, or 100% identical to the amino acid sequence of SEQ ID NO: 660; and b) a type I-Fc fusion protein having an Fc domain that is at least 75%, 80%, 85%, 90%, 91%, 92%, 93%, 94%, 95%, 96%, 97%, 98%, 99%, or 100% identical to the amino acid sequence of SEQ ID NO: 670. In some embodiments, the type II-Fc fusion protein Fc domain comprises one or more amino acid substitutions selected from: a) a glutamic acid at the position corresponding to 138 of SEQ ID NO: 660; b) an aspartic acid at the position corresponding to 217 of SEQ ID NO: 660; and c) a glutamic acid at the position corresponding to 138 of SEQ ID NO: 660 and an aspartic acid at the position corresponding to 217 of SEQ ID NO: 660. Optionally, the type II-Fc fusion protein Fc domain further comprises a cysteine at the position corresponding to 132 of SEQ ID NO: 660 and a tryptophan at the position corresponding to 144 of SEQ ID NO: 660. In some embodiments, the type I-Fc fusion protein Fc domain comprises one or more amino acid substitutions selected from: a) an arginine at the position corresponding to 162 of SEQ ID NO: 670; b) an arginine at the position corresponding to 179 of SEQ ID NO: 670; and c) an arginine at the position corresponding to 162 of SEQ ID NO: 670 and an arginine at the position corresponding to 179 of SEQ ID NO: 670. Optionally, the type I-Fc fusion protein Fc domain further comprises a cysteine at the position corresponding to 127 of SEQ ID NO: 670, a serine at the position corresponding to 144 of SEQ ID NO: 670, an alanine at the position corresponding to 146 of SEQ ID NO: 670, and a valine at the position corresponding to 185 of SEQ ID NO: 670.

In certain aspects, a type I:type I heteromultimer of the disclosure comprises: a) a first type I-Fc fusion protein having an Fc domain that is at least 75%, 80%, 85%, 90%, 91%, 92%, 93%, 94%, 95%, 96%, 97%, 98%, 99%, or 100% identical to the amino acid sequence of SEQ ID NO: 660; and b) a second type I-Fc fusion protein having an Fc domain that is at least 75%, 80%, 85%, 90%, 91%, 92%, 93%, 94%, 95%, 96%, 97%, 98%, 99%, or 100% identical to the amino acid sequence of SEQ ID NO: 670. In some embodiments, the first type I-Fc fusion protein Fc domain comprises one or more amino acid substitutions selected from: a) a glutamic acid at the position corresponding to 138 of SEQ ID NO: 660; b) an aspartic acid at the position corresponding to 217 of SEQ ID NO: 660; and c) a glutamic acid at the position corresponding to 138 of SEQ ID NO: 660 and an aspartic acid at the position corresponding to 217 of SEQ ID NO: 660. Optionally, the first type I-Fc fusion protein Fc domain further comprises a cysteine at the position corresponding to 132 of SEQ ID NO: 660 and a tryptophan at the position corresponding to 144 of SEQ ID NO: 660. In some embodiments, the second type I-Fc fusion protein Fc domain comprises one or more amino acid substitutions selected from: a) an arginine at the position corresponding to 162 of SEQ ID NO: 670; b) an arginine at the position corresponding to 179 of SEQ ID NO: 670; and c) an arginine at the position corresponding to 162 of SEQ ID NO: 670 and an arginine at the position corresponding to 179 of SEQ ID NO: 670. Optionally, the second type I-Fc fusion protein Fc domain further comprises a cysteine at the position corresponding to 127 of SEQ ID NO: 670, a serine at the position corresponding to 144 of SEQ ID NO: 670, an alanine at the position corresponding to 146 of SEQ ID NO: 670, and a valine at the position corresponding to 185 of SEQ ID NO: 670.

In certain aspects, a type II:type II heteromultimer of the disclosure comprises: a) a first type II-Fc fusion protein having an Fc domain that is at least 75%, 80%, 85%, 90%, 91%, 92%, 93%, 94%, 95%, 96%, 97%, 98%, 99%, or 100% identical to the amino acid sequence of SEQ ID NO: 660; and b) a second type II-Fc fusion protein having an Fc domain that is at least 75%, 80%, 85%, 90%, 91%, 92%, 93%, 94%, 95%, 96%, 97%, 98%, 99%, or 100% identical to the amino acid sequence of SEQ ID NO: 670. In some embodiments, the first type II-Fc fusion protein Fc domain comprises one or more amino acid substitutions selected from: a) a glutamic acid at the position corresponding to 138 of SEQ ID NO: 660; b) an aspartic acid at the position corresponding to 217 of SEQ ID NO: 660; and c) a glutamic acid at the position corresponding to 138 of SEQ ID NO: 660 and an aspartic acid at the position corresponding to 217 of SEQ ID NO: 660. Optionally, the first type II-Fc fusion protein Fc domain further comprises a cysteine at the position corresponding to 132 of SEQ ID NO: 660 and a tryptophan at the position corresponding to 144 of SEQ ID NO: 660. In some embodiments, the second type II-Fc fusion protein Fc domain comprises one or more amino acid substitutions selected from: a) an arginine at the position corresponding to 162 of SEQ ID NO: 670; b) an arginine at the position corresponding to 179 of SEQ ID NO: 670; and c) an arginine at the position corresponding to 162 of SEQ ID NO: 670 and an arginine at the position corresponding to 179 of SEQ ID NO: 670. Optionally, the second type II-Fc fusion protein Fc domain further comprises a cysteine at the position corresponding to 127 of SEQ ID NO: 670, a serine at the position corresponding to 144 of SEQ ID NO: 670, an alanine at the position corresponding to 146 of SEQ ID NO: 670, and a valine at the position corresponding to 185 of SEQ ID NO: 670.

In certain aspects, the disclosure relates to a recombinant type I:type II heteromultimer comprising at least one type I-Fc fusion protein and at least one type II-Fc fusion protein, wherein: a) the type I-Fc fusion protein comprises an IgG1 Fc domain comprising a cysteine at the position corresponding to S132 of SEQ ID NO: 3100 (S132C), a tryptophan at the position corresponding to T144 of SEQ ID NO: 3100 (T144W), and an acidic amino acid at the position corresponding to H213 of SEQ ID NO: 3100; and b) the type II-Fc fusion protein comprises an IgG1 Fc domain comprising a cysteine at the position corresponding to Y127 of SEQ ID NO: 3100 (Y127C), a serine at the position corresponding to T144 of SEQ ID NO: 3100 (T144S), an alanine at the position corresponding to L146 of SEQ ID NO: 3100 (L146A), and a valine at the position corresponding to Y185 of SEQ ID NO: 3100 (Y185V). In some embodiments, wherein the acidic amino acid at the position corresponding to H213 of SEQ ID NO: 3100 is an aspartic acid. In some embodiments, the acidic amino acid at the position corresponding to H213 of SEQ ID NO: 3100 is a glutamic acid. In some embodiments, the type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100.

In certain aspects, the disclosure relates to a recombinant type I:type I heteromultimer comprising at least a first type I-Fc fusion protein and a second type I-Fc fusion protein, wherein: a) the first type I-Fc fusion protein comprises an IgG1 Fc domain comprising a cysteine at the position corresponding to S132 of SEQ ID NO: 3100 (S132C), a tryptophan at the position corresponding to T144 of SEQ ID NO: 3100 (T144W), and an acidic amino acid at the position corresponding to H213 of SEQ ID NO: 3100; and b) the second type I-Fc fusion protein comprises an IgG1 Fc domain comprising a cysteine at the position corresponding to Y127 of SEQ ID NO: 3100 (Y127C), a serine at the position corresponding to T144 of SEQ ID NO: 3100 (T144S), an alanine at the position corresponding to L146 of SEQ ID NO: 3100 (L146A), and a valine at the position corresponding to Y185 of SEQ ID NO: 3100 (Y185V). In some embodiments, wherein the acidic amino acid at the position corresponding to H213 of SEQ ID NO: 3100 is an aspartic acid. In some embodiments, the acidic amino acid at the position corresponding to H213 of SEQ ID NO: 3100 is a glutamic acid. In some embodiments, the first type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the second type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100.

In certain aspects, the disclosure relates to a recombinant type II:type II heteromultimer comprising at least a first type II-Fc fusion protein and a second type II-Fc fusion protein, wherein: a) the first type II-Fc fusion protein comprises an IgG1 Fc domain comprising a cysteine at the position corresponding to S132 of SEQ ID NO: 3100 (S132C), a tryptophan at the position corresponding to T144 of SEQ ID NO: 3100 (T144W), and an acidic amino acid at the position corresponding to H213 of SEQ ID NO: 3100; and b) the second type II-Fc fusion protein comprises an IgG1 Fc domain comprising a cysteine at the position corresponding to Y127 of SEQ ID NO: 3100 (Y127C), a serine at the position corresponding to T144 of SEQ ID NO: 3100 (T144S), an alanine at the position corresponding to L146 of SEQ ID NO: 3100 (L146A), and a valine at the position corresponding to Y185 of SEQ ID NO: 3100 (Y185V). In some embodiments, wherein the acidic amino acid at the position corresponding to H213 of SEQ ID NO: 3100 is an aspartic acid. In some embodiments, the acidic amino acid at the position corresponding to H213 of SEQ ID NO: 3100 is a glutamic acid. In some embodiments, the first type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the second type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100.

In certain aspects, the disclosure relates to a recombinant type I:type II heteromultimer comprising at least one type I-Fc fusion protein and at least one type II-Fc fusion protein, wherein: a) the type I-Fc fusion protein comprises an IgG1 Fc domain comprising a cysteine at the position corresponding to S132 of SEQ ID NO: 3100 (S132C), and a tryptophan at the position corresponding to T144 of SEQ ID NO: 3100 (T144W); and b) the type II-Fc fusion protein comprises an IgG1 Fc domain comprising a cysteine at the position corresponding to Y127 of SEQ ID NO: 3100 (Y127C), a serine at the position corresponding to T144 of SEQ ID NO: 3100 (T144S), an alanine at the position corresponding to L146 of SEQ ID NO: 3100 (L146A), a valine at the position corresponding to Y185 of SEQ ID NO: 3100 (Y185V), and an acidic amino acid at the position corresponding to H213 of SEQ ID NO: 3100. In some embodiments, wherein the acidic amino acid at the position corresponding to H213 of SEQ ID NO: 3100 is an aspartic acid. In some embodiments, the acidic amino acid at the position corresponding to H213 of SEQ ID NO: 3100 is a glutamic acid. In some embodiments, the type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100.

In certain aspects, the disclosure relates to a recombinant type I:type II heteromultimer comprising at least one type I-Fc fusion protein and at least one type II-Fc fusion protein, wherein: a) the type II-Fc fusion protein comprises an IgG1 Fc domain comprising a cysteine at the position corresponding to S132 of SEQ ID NO: 3100 (S132C), and a tryptophan at the position corresponding to T144 of SEQ ID NO: 3100 (T144W); and b) the type I-Fc fusion protein comprises an IgG1 Fc domain comprising a cysteine at the position corresponding to Y127 of SEQ ID NO: 3100 (Y127C), a serine at the position corresponding to T144 of SEQ ID NO: 3100 (T144S), an alanine at the position corresponding to L146 of SEQ ID NO: 3100 (L146A), and a valine at the position corresponding to Y185 of SEQ ID NO: 3100 (Y185V), and an acidic amino acid at the position corresponding to H213 of SEQ ID NO: 3100. In some embodiments, wherein the acidic amino acid at the position corresponding to H213 of SEQ ID NO: 3100 is an aspartic acid. In some embodiments, the acidic amino acid at the position corresponding to H213 of SEQ ID NO: 3100 is a glutamic acid. In some embodiments, the type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100.

In certain aspects, the disclosure relates to a recombinant type I:type I heteromultimer comprising at least one first type I-Fc fusion protein and a second type I-Fc fusion protein, wherein: a) the first type I-Fc fusion protein comprises an IgG1 Fc domain comprising a cysteine at the position corresponding to S132 of SEQ ID NO: 3100 (S132C), and a tryptophan at the position corresponding to T144 of SEQ ID NO: 3100 (T144W); and b) the second type I-Fc fusion protein comprises an IgG1 Fc domain comprising a cysteine at the position corresponding to Y127 of SEQ ID NO: 3100 (Y127C), a serine at the position corresponding to T144 of SEQ ID NO: 3100 (T144S), an alanine at the position corresponding to L146 of SEQ ID NO: 3100 (L146A), a valine at the position corresponding to Y185 of SEQ ID NO: 3100 (Y185V), and an acidic amino acid at the position corresponding to H213 of SEQ ID NO: 3100. In some embodiments, wherein the acidic amino acid at the position corresponding to H213 of SEQ ID NO: 3100 is an aspartic acid. In some embodiments, the acidic amino acid at the position corresponding to H213 of SEQ ID NO: 3100 is a glutamic acid. In some embodiments, the first type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100. In some embodiments, the second type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100.

In certain aspects, the disclosure relates to a recombinant type II:type II heteromultimer comprising at least one first type II-Fc fusion protein and a second type II-Fc fusion protein, wherein: a) the first type II-Fc fusion protein comprises an IgG1 Fc domain comprising a cysteine at the position corresponding to S132 of SEQ ID NO: 3100 (S132C), and a tryptophan at the position corresponding to T144 of SEQ ID NO: 3100 (T144W); and b) the second type II-Fc fusion protein comprises an IgG1 Fc domain comprising a cysteine at the position corresponding to Y127 of SEQ ID NO: 3100 (Y127C), a serine at the position corresponding to T144 of SEQ ID NO: 3100 (T144S), an alanine at the position corresponding to L146 of SEQ ID NO: 3100 (L146A), a valine at the position corresponding to Y185 of SEQ ID NO: 3100 (Y185V), and an acidic amino acid at the position corresponding to H213 of SEQ ID NO: 3100. In some embodiments, wherein the acidic amino acid at the position corresponding to H213 of SEQ ID NO: 3100 is an aspartic acid. In some embodiments, the acidic amino acid at the position corresponding to H213 of SEQ ID NO: 3100 is a glutamic acid. In some embodiments, the first type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100.

In some embodiments, the second type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3100.

In certain aspects, the disclosure relates to a recombinant type I:type II heteromultimer comprising at least one type I-Fc fusion protein and at least one type II-Fc fusion protein, wherein: a) the type I-Fc fusion protein comprises an IgG2 Fc domain comprising a cysteine at the position corresponding to S130 of SEQ ID NO: 3200 (S130C), a tryptophan at the position corresponding to T142 of SEQ ID NO: 3200 (T142W), and an acidic amino acid at the position corresponding to H211 of SEQ ID NO: 3200; and b) the type II-Fc fusion protein comprises an IgG2 Fc domain comprising a cysteine at the position corresponding to Y125 of SEQ ID NO: 3200 (Y125C), a serine at the position corresponding to T142 of SEQ ID NO: 3200 (T142S), an alanine at the position corresponding to L144 of SEQ ID NO: 3200 (L144A), and a valine at the position corresponding to Y183 of SEQ ID NO: 3200 (Y183V). In some embodiments, wherein the acidic amino acid at the position corresponding to H211 of SEQ ID NO: 3200 is an aspartic acid. In some embodiments, the acidic amino acid at the position corresponding to H211 of SEQ ID NO: 3200 is a glutamic acid. In some embodiments, the type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200.

In certain aspects, the disclosure relates to a recombinant type I:type II heteromultimer comprising at least one type I-Fc fusion protein and at least one type II-Fc fusion protein, wherein: a) the type II-Fc fusion protein comprises an IgG2 Fc domain comprising a cysteine at the position corresponding to S130 of SEQ ID NO: 3200 (S130C), a tryptophan at the position corresponding to T142 of SEQ ID NO: 3200 (T142W), and an acidic amino acid at the position corresponding to H211 of SEQ ID NO: 3200; and b) the type I-Fc fusion protein comprises an IgG2 Fc domain comprising a cysteine at the position corresponding to Y125 of SEQ ID NO: 3200 (Y125C), a serine at the position corresponding to T142 of SEQ ID NO: 3200 (T142S), an alanine at the position corresponding to L144 of SEQ ID NO: 3200 (L144A), and a valine at the position corresponding to Y183 of SEQ ID NO: 3200 (Y183V). In some embodiments, wherein the acidic amino acid at the position corresponding to H211 of SEQ ID NO: 3200 is an aspartic acid. In some embodiments, the acidic amino acid at the position corresponding to H211 of SEQ ID NO: 3200 is a glutamic acid. In some embodiments, the type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200.

In certain aspects, the disclosure relates to a recombinant type I:type I heteromultimer comprising at first type I-Fc fusion protein and a second type I-Fc fusion protein, wherein: a) the first type I-Fc fusion protein comprises an IgG2 Fc domain comprising a cysteine at the position corresponding to S130 of SEQ ID NO: 3200 (S130C), a tryptophan at the position corresponding to T142 of SEQ ID NO: 3200 (T142W), and an acidic amino acid at the position corresponding to H211 of SEQ ID NO: 3200; and b) the second type I-Fc fusion protein comprises an IgG2 Fc domain comprising a cysteine at the position corresponding to Y125 of SEQ ID NO: 3200 (Y125C), a serine at the position corresponding to T142 of SEQ ID NO: 3200 (T142S), an alanine at the position corresponding to L144 of SEQ ID NO: 3200 (L144A), and a valine at the position corresponding to Y183 of SEQ ID NO: 3200 (Y183V). In some embodiments, wherein the acidic amino acid at the position corresponding to H211 of SEQ ID NO: 3200 is an aspartic acid. In some embodiments, the acidic amino acid at the position corresponding to H211 of SEQ ID NO: 3200 is a glutamic acid. In some embodiments, the first type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the second type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200.

In certain aspects, the disclosure relates to a recombinant type II:type II heteromultimer comprising at first type II-Fc fusion protein and a second type II-Fc fusion protein, wherein: a) the first type II-Fc fusion protein comprises an IgG2 Fc domain comprising a cysteine at the position corresponding to S130 of SEQ ID NO: 3200 (S130C), a tryptophan at the position corresponding to T142 of SEQ ID NO: 3200 (T142W), and an acidic amino acid at the position corresponding to H211 of SEQ ID NO: 3200; and b) the second type II-Fc fusion protein comprises an IgG2 Fc domain comprising a cysteine at the position corresponding to Y125 of SEQ ID NO: 3200 (Y125C), a serine at the position corresponding to T142 of SEQ ID NO: 3200 (T142S), an alanine at the position corresponding to L144 of SEQ ID NO: 3200 (L144A), and a valine at the position corresponding to Y183 of SEQ ID NO: 3200 (Y183V). In some embodiments, wherein the acidic amino acid at the position corresponding to H211 of SEQ ID NO: 3200 is an aspartic acid. In some embodiments, the acidic amino acid at the position corresponding to H211 of SEQ ID NO: 3200 is a glutamic acid. In some embodiments, the first type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the second type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200.

In certain aspects, the disclosure relates to a recombinant type I:type II heteromultimer comprising at least one type I-Fc fusion protein and at least one type II-Fc fusion protein, wherein: a) the type I-Fc fusion protein comprises an IgG2 Fc domain comprising a cysteine at the position corresponding to S130 of SEQ ID NO: 3200 (S130C), and a tryptophan at the position corresponding to T142 of SEQ ID NO: 3200 (T142W); and b) the type II-Fc fusion protein comprises an IgG2 Fc domain comprising a cysteine at the position corresponding to Y125 of SEQ ID NO: 3200 (Y125C), a serine at the position corresponding to T142 of SEQ ID NO: 3200 (T142S), an alanine at the position corresponding to L144 of SEQ ID NO: 3200 (L144A), a valine at the position corresponding to Y183 of SEQ ID NO: 3200 (Y183V), and an acidic amino acid at the position corresponding to H211 of SEQ ID NO: 3200. In some embodiments, wherein the acidic amino acid at the position corresponding to H211 of SEQ ID NO: 3200 is an aspartic acid. In some embodiments, the acidic amino acid at the position corresponding to H211 of SEQ ID NO: 3200 is a glutamic acid. In some embodiments, the type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200.

In certain aspects, the disclosure relates to a recombinant type I:type II heteromultimer comprising at least one type I-Fc fusion protein and at least one type II-Fc fusion protein, wherein: a) the type II-Fc fusion protein comprises an IgG2 Fc domain comprising a cysteine at the position corresponding to S130 of SEQ ID NO: 3200 (S130C), and a tryptophan at the position corresponding to T142 of SEQ ID NO: 3200 (T142W); and b) the type I-Fc fusion protein comprises an IgG2 Fc domain comprising a cysteine at the position corresponding to Y125 of SEQ ID NO: 3200 (Y125C), a serine at the position corresponding to T142 of SEQ ID NO: 3200 (T142S), an alanine at the position corresponding to L144 of SEQ ID NO: 3200 (L144A), a valine at the position corresponding to Y183 of SEQ ID NO: 3200 (Y183V), and an acidic amino acid at the position corresponding to H211 of SEQ ID NO: 3200. In some embodiments, wherein the acidic amino acid at the position corresponding to H211 of SEQ ID NO: 3200 is an aspartic acid. In some embodiments, the acidic amino acid at the position corresponding to H211 of SEQ ID NO: 3200 is a glutamic acid. In some embodiments, the type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200.

In certain aspects, the disclosure relates to a recombinant type I:type I heteromultimer comprising a first type I-Fc fusion protein and a second type I-Fc fusion protein, wherein: a) the first type I-Fc fusion protein comprises an IgG2 Fc domain comprising a cysteine at the position corresponding to S130 of SEQ ID NO: 3200 (S130C), and a tryptophan at the position corresponding to T142 of SEQ ID NO: 3200 (T142W); and b) the second type I-Fc fusion protein comprises an IgG2 Fc domain comprising a cysteine at the position corresponding to Y125 of SEQ ID NO: 3200 (Y125C), a serine at the position corresponding to T142 of SEQ ID NO: 3200 (T142S), an alanine at the position corresponding to L144 of SEQ ID NO: 3200 (L144A), a valine at the position corresponding to Y183 of SEQ ID NO: 3200 (Y183V), and an acidic amino acid at the position corresponding to H211 of SEQ ID NO: 3200. In some embodiments, wherein the acidic amino acid at the position corresponding to H211 of SEQ ID NO: 3200 is an aspartic acid. In some embodiments, the acidic amino acid at the position corresponding to H211 of SEQ ID NO: 3200 is a glutamic acid. In some embodiments, the first type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the second type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200.

In certain aspects, the disclosure relates to a recombinant type II:type II heteromultimer comprising a first type II-Fc fusion protein and a second type II-Fc fusion protein, wherein: a) the first type II-Fc fusion protein comprises an IgG2 Fc domain comprising a cysteine at the position corresponding to S130 of SEQ ID NO: 3200 (S130C), and a tryptophan at the position corresponding to T142 of SEQ ID NO: 3200 (T142W); and b) the second type II-Fc fusion protein comprises an IgG2 Fc domain comprising a cysteine at the position corresponding to Y125 of SEQ ID NO: 3200 (Y125C), a serine at the position corresponding to T142 of SEQ ID NO: 3200 (T142S), an alanine at the position corresponding to L144 of SEQ ID NO: 3200 (L144A), a valine at the position corresponding to Y183 of SEQ ID NO: 3200 (Y183V), and an acidic amino acid at the position corresponding to H211 of SEQ ID NO: 3200. In some embodiments, wherein the acidic amino acid at the position corresponding to H211 of SEQ ID NO: 3200 is an aspartic acid. In some embodiments, the acidic amino acid at the position corresponding to H211 of SEQ ID NO: 3200 is a glutamic acid. In some embodiments, the first type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200. In some embodiments, the second type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3200.

In certain aspects, the disclosure relates to a recombinant type I:type II heteromultimer comprising at least one type I-Fc fusion protein and at least one type II-Fc fusion protein, wherein: a) the type I-Fc fusion protein comprises an IgG4 Fc domain comprising a cysteine at the position corresponding to S136 of SEQ ID NO: 3500 (S136C), a tryptophan at the position corresponding to T148 of SEQ ID NO: 3500 (T148W), and an acidic amino acid at the position corresponding to H217 of SEQ ID NO: 3500; and b) the type II-Fc fusion protein comprises an IgG4 Fc domain comprising a cysteine at the position corresponding to Y131 of SEQ ID NO: 3500 (Y131C), a serine at the position corresponding to T148 of SEQ ID NO: 3500 (T148S), an alanine at the position corresponding to L150 of SEQ ID NO: 3500 (L150A), and a valine at the position corresponding to Y189 of SEQ ID NO: 3500 (Y189V). In some embodiments, wherein the acidic amino acid at the position corresponding to H217 of SEQ ID NO: 3500 is an aspartic acid. In some embodiments, the acidic amino acid at the position corresponding to H217 of SEQ ID NO: 3500 is a glutamic acid. In some embodiments, the type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500.

In certain aspects, the disclosure relates to a recombinant type I:type II heteromultimer comprising at least one type I-Fc fusion protein and at least one type II-Fc fusion protein, wherein: a) the type II-Fc fusion protein comprises an IgG4 Fc domain comprising a cysteine at the position corresponding to S136 of SEQ ID NO: 3500 (S136C), a tryptophan at the position corresponding to T148 of SEQ ID NO: 3500 (T148W), and an acidic amino acid at the position corresponding to H217 of SEQ ID NO: 3500; and b) the type I-Fc fusion protein comprises an IgG4 Fc domain comprising a cysteine at the position corresponding to Y131 of SEQ ID NO: 3500 (Y131C), a serine at the position corresponding to T148 of SEQ ID NO: 3500 (T148S), an alanine at the position corresponding to L150 of SEQ ID NO: 3500 (L150A), and a valine at the position corresponding to Y189 of SEQ ID NO: 3500 (Y189V). In some embodiments, wherein the acidic amino acid at the position corresponding to H217 of SEQ ID NO: 3500 is an aspartic acid. In some embodiments, the acidic amino acid at the position corresponding to H217 of SEQ ID NO: 3500 is a glutamic acid. In some embodiments, the type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500.

In certain aspects, the disclosure relates to a recombinant type I:type I heteromultimer comprising a first type I-Fc fusion protein and a second type I-Fc fusion protein, wherein: a) the first type I-Fc fusion protein comprises an IgG4 Fc domain comprising a cysteine at the position corresponding to S136 of SEQ ID NO: 3500 (S136C), a tryptophan at the position corresponding to T148 of SEQ ID NO: 3500 (T148W), and an acidic amino acid at the position corresponding to H217 of SEQ ID NO: 3500; and b) the second type I-Fc fusion protein comprises an IgG4 Fc domain comprising a cysteine at the position corresponding to Y131 of SEQ ID NO: 3500 (Y131C), a serine at the position corresponding to T148 of SEQ ID NO: 3500 (T148S), an alanine at the position corresponding to L150 of SEQ ID NO: 3500 (L150A), and a valine at the position corresponding to Y189 of SEQ ID NO: 3500 (Y189V). In some embodiments, wherein the acidic amino acid at the position corresponding to H217 of SEQ ID NO: 3500 is an aspartic acid. In some embodiments, the acidic amino acid at the position corresponding to H217 of SEQ ID NO: 3500 is a glutamic acid. In some embodiments, the first type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the second type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500.

In certain aspects, the disclosure relates to a recombinant type II:type II heteromultimer comprising a first type II-Fc fusion protein and a second type II-Fc fusion protein, wherein: a) the first type II-Fc fusion protein comprises an IgG4 Fc domain comprising a cysteine at the position corresponding to S136 of SEQ ID NO: 3500 (S136C), a tryptophan at the position corresponding to T148 of SEQ ID NO: 3500 (T148W), and an acidic amino acid at the position corresponding to H217 of SEQ ID NO: 3500; and b) the second type II-Fc fusion protein comprises an IgG4 Fc domain comprising a cysteine at the position corresponding to Y131 of SEQ ID NO: 3500 (Y131C), a serine at the position corresponding to T148 of SEQ ID NO: 3500 (T148S), an alanine at the position corresponding to L150 of SEQ ID NO: 3500 (L150A), and a valine at the position corresponding to Y189 of SEQ ID NO: 3500 (Y189V). In some embodiments, wherein the acidic amino acid at the position corresponding to H217 of SEQ ID NO: 3500 is an aspartic acid. In some embodiments, the acidic amino acid at the position corresponding to H217 of SEQ ID NO: 3500 is a glutamic acid. In some embodiments, the first type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the second type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500.

In certain aspects, the disclosure relates to recombinant type I:type II heteromultimer comprising at least one type I-Fc fusion protein and at least one type II-Fc fusion protein, wherein: a) the type I-Fc fusion protein comprises an IgG4 Fc domain comprising a cysteine at the position corresponding to S136 of SEQ ID NO: 3500 (S136C), and a tryptophan at the position corresponding to T148 of SEQ ID NO: 3500 (T148W); and b) the type II-Fc fusion protein comprises an IgG4 Fc domain comprising a cysteine at the position corresponding to Y131 of SEQ ID NO: 3500 (Y131C), a serine at the position corresponding to T148 of SEQ ID NO: 3500 (T148S), an alanine at the position corresponding to L150 of SEQ ID NO: 3500 (L150A), a valine at the position corresponding to Y189 of SEQ ID NO: 3500 (Y189V), and an acidic amino acid at the position corresponding to H217 of SEQ ID NO: 3500. In some embodiments, wherein the acidic amino acid at the position corresponding to H217 of SEQ ID NO: 3500 is an aspartic acid. In some embodiments, the acidic amino acid at the position corresponding to H217 of SEQ ID NO: 3500 is a glutamic acid. In some embodiments, the type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500.

In certain aspects, the disclosure relates to recombinant type I:type II heteromultimer comprising at least one type I-Fc fusion protein and at least one type II-Fc fusion protein, wherein: a) the type II-Fc fusion protein comprises an IgG4 Fc domain comprising a cysteine at the position corresponding to S136 of SEQ ID NO: 3500 (S136C), and a tryptophan at the position corresponding to T148 of SEQ ID NO: 3500 (T148W); and b) the type I-Fc fusion protein comprises an IgG4 Fc domain comprising a cysteine at the position corresponding to Y131 of SEQ ID NO: 3500 (Y131C), a serine at the position corresponding to T148 of SEQ ID NO: 3500 (T148S), an alanine at the position corresponding to L150 of SEQ ID NO: 3500 (L150A), a valine at the position corresponding to Y189 of SEQ ID NO: 3500 (Y189V), and an acidic amino acid at the position corresponding to H217 of SEQ ID NO: 3500. In some embodiments, wherein the acidic amino acid at the position corresponding to H217 of SEQ ID NO: 3500 is an aspartic acid. In some embodiments, the acidic amino acid at the position corresponding to H217 of SEQ ID NO: 3500 is a glutamic acid. In some embodiments, the type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500.

In certain aspects, the disclosure relates to recombinant type I:type I heteromultimer comprising a first type I-Fc fusion protein and a second type I-Fc fusion protein, wherein: a) the first type I-Fc fusion protein comprises an IgG4 Fc domain comprising a cysteine at the position corresponding to S136 of SEQ ID NO: 3500 (S136C), and a tryptophan at the position corresponding to T148 of SEQ ID NO: 3500 (T148W); and b) the second type I-Fc fusion protein comprises an IgG4 Fc domain comprising a cysteine at the position corresponding to Y131 of SEQ ID NO: 3500 (Y131C), a serine at the position corresponding to T148 of SEQ ID NO: 3500 (T148S), an alanine at the position corresponding to L150 of SEQ ID NO: 3500 (L150A), a valine at the position corresponding to Y189 of SEQ ID NO: 3500 (Y189V), and an acidic amino acid at the position corresponding to H217 of SEQ ID NO: 3500. In some embodiments, wherein the acidic amino acid at the position corresponding to H217 of SEQ ID NO: 3500 is an aspartic acid. In some embodiments, the acidic amino acid at the position corresponding to H217 of SEQ ID NO: 3500 is a glutamic acid. In some embodiments, the first type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the second type I-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500.

In certain aspects, the disclosure relates to recombinant type II:type II heteromultimer comprising a first type II-Fc fusion protein and a second type II-Fc fusion protein, wherein: a) the first type II-Fc fusion protein comprises an IgG4 Fc domain comprising a cysteine at the position corresponding to S136 of SEQ ID NO: 3500 (S136C), and a tryptophan at the position corresponding to T148 of SEQ ID NO: 3500 (T148W); and b) the second type II-Fc fusion protein comprises an IgG4 Fc domain comprising a cysteine at the position corresponding to Y131 of SEQ ID NO: 3500 (Y131C), a serine at the position corresponding to T148 of SEQ ID NO: 3500 (T148S), an alanine at the position corresponding to L150 of SEQ ID NO: 3500 (L150A), a valine at the position corresponding to Y189 of SEQ ID NO: 3500 (Y189V), and an acidic amino acid at the position corresponding to H217 of SEQ ID NO: 3500. In some embodiments, wherein the acidic amino acid at the position corresponding to H217 of SEQ ID NO: 3500 is an aspartic acid. In some embodiments, the acidic amino acid at the position corresponding to H217 of SEQ ID NO: 3500 is a glutamic acid. In some embodiments, the first type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500. In some embodiments, the second type II-Fc fusion protein Fc domain is at least 75%, 80%, 85%, 90%, 91%, 92%, 93%, 94%, 95%, 96%, 97%, 98%, 99%, or more identical to the amino acid sequence of SEQ ID NO: 3500.

In certain aspects embodiments, the disclosure relates to a heteromultimer comprising at least one ALK1-Fc fusion protein and at least one ActRIIA-Fc fusion protein. In some embodiments, an ALK1-Fc:ActRIIA-Fc heteromultimers binds to one or more TGF-beta superfamily ligands such as those described herein. In some embodiments, an ALK1-Fc:ActRIIA-Fc heteromultimers inhibit signaling of one or more TGF-beta superfamily ligands such as those described herein. In some embodiments, an ALK1-Fc:ActRIIA-Fc heteromultimers is a heterodimer.

In certain aspects embodiments, the disclosure relates to a heteromultimer comprising at least one ALK2-Fc fusion protein and at least one ActRIIA-Fc fusion protein. In some embodiments, an ALK2-Fc:ActRIIA-Fc heteromultimers binds to one or more TGF-beta superfamily ligands such as those described herein. In some embodiments, an ALK2-Fc:ActRIIA-Fc heteromultimers inhibit signaling of one or more TGF-beta superfamily ligands such as those described herein. In some embodiments, an ALK2-Fc:ActRIIA-Fc heteromultimers is a heterodimer.

In certain aspects embodiments, the disclosure relates to a heteromultimer comprising at least one ALK3-Fc fusion protein and at least one ActRIIA-Fc fusion protein. In some embodiments, an ALK3-Fc:ActRIIA-Fc heteromultimers binds to one or more TGF-beta superfamily ligands such as those described herein. In some embodiments, an ALK3-Fc:ActRIIA-Fc heteromultimers inhibit signaling of one or more TGF-beta superfamily ligands such as those described herein. In some embodiments, an ALK3-Fc:ActRIIA-Fc heteromultimers is a heterodimer.

In certain aspects embodiments, the disclosure relates to a heteromultimer comprising at least one ALK4-Fc fusion protein and at least one ActRIIA-Fc fusion protein. In some embodiments, an ALK4-Fc:ActRIIA-Fc heteromultimers binds to one or more TGF-beta superfamily ligands such as those described herein. In some embodiments, an ALK4-Fc:ActRIIA-Fc heteromultimers inhibit signaling of one or more TGF-beta superfamily ligands such as those described herein. In some embodiments, an ALK4-Fc:ActRIIA-Fc heteromultimers is a heterodimer.

In certain aspects embodiments, the disclosure relates to a heteromultimer comprising at least one ALK5-Fc fusion protein and at least one ActRIIA-Fc fusion protein. In some embodiments, an ALK5-Fc:ActRIIA-Fc heteromultimers binds to one or more TGF-beta superfamily ligands such as those described herein. In some embodiments, an ALK5-Fc:ActRIIA-Fc heteromultimers inhibit signaling of one or more TGF-beta superfamily ligands such as those described herein. In some embodiments, an ALK5-Fc:ActRIIA-Fc heteromultimers is a heterodimer.

In certain aspects embodiments, the disclosure relates to a heteromultimer comprising at least one ALK6-Fc fusion protein and at least one ActRIIA-Fc fusion protein. In some embodiments, an ALK6-Fc:ActRIIA-Fc heteromultimers binds to one or more TGF-beta superfamily ligands such as those described herein. In some embodiments, an ALK6-Fc:ActRIIA-Fc heteromultimers inhibit signaling of one or more TGF-beta superfamily ligands such as those described herein. In some embodiments, an ALK6-Fc:ActRIIA-Fc heteromultimers is a heterodimer.

In certain aspects embodiments, the disclosure relates to a heteromultimer comprising at least one ALK7-Fc fusion protein and at least one ActRIIA-Fc fusion protein. In some embodiments, an ALK7-Fc:ActRIIA-Fc heteromultimers binds to one or more TGF-beta superfamily ligands such as those described herein. In some embodiments, an ALK7-Fc:ActRIIA-Fc heteromultimers inhibit signaling of one or more TGF-beta superfamily ligands such as those described herein. In some embodiments, an ALK7-Fc:ActRIIA-Fc heteromultimers is a heterodimer.

In certain aspects embodiments, the disclosure relates to a heteromultimer comprising at least one ALKT-Fc fusion protein and at least one ActRIIB-Fc fusion protein. In some embodiments, an ALK1-Fc:ActRIIB-Fc heteromultimers binds to one or more TGF-beta superfamily ligands such as those described herein. In some embodiments, an ALK1-Fc:ActRIIB-Fc heteromultimers inhibit signaling of one or more TGF-beta superfamily ligands such as those described herein. In some embodiments, an ALKT-Fc:ActRIIB-Fc heteromultimers is a heterodimer.

In certain aspects embodiments, the disclosure relates to a heteromultimer comprising at least one ALK2-Fc fusion protein and at least one ActRIIB-Fc fusion protein. In some embodiments, an ALK2-Fc:ActRIIB-Fc heteromultimers binds to one or more TGF-beta superfamily ligands such as those described herein. In some embodiments, an ALK2-Fc:ActRIIB-Fc heteromultimers inhibit signaling of one or more TGF-beta superfamily ligands such as those described herein. In some embodiments, an ALK2-Fc:ActRIIB-Fc heteromultimers is a heterodimer.

In certain aspects embodiments, the disclosure relates to a heteromultimer comprising at least one ALK3-Fc fusion protein and at least one ActRIIB-Fc fusion protein. In some embodiments, an ALK3-Fc:ActRIIB-Fc heteromultimers binds to one or more TGF-beta superfamily ligands such as those described herein. In some embodiments, an ALK3-Fc:ActRIIB-Fc heteromultimers inhibit signaling of one or more TGF-beta superfamily ligands such as those described herein. In some embodiments, an ALK3-Fc:ActRIIB-Fc heteromultimers is a heterodimer.

In certain aspects embodiments, the disclosure relates to a heteromultimer comprising at least one ALK4-Fc fusion protein and at least one ActRIIB-Fc fusion protein. In some embodiments, an ALK4-Fc:ActRIIB-Fc heteromultimers binds to one or more TGF-beta superfamily ligands such as those described herein. In some embodiments, an ALK4-Fc:ActRIIB-Fc heteromultimers inhibit signaling of one or more TGF-beta superfamily ligands such as those described herein. In some embodiments, an ALK4-Fc:ActRIIB-Fc heteromultimers is a heterodimer.

In certain aspects embodiments, the disclosure relates to a heteromultimer comprising at least one ALK5-Fc fusion protein and at least one ActRIIB-Fc fusion protein. In some embodiments, an ALK5-Fc:ActRIIB-Fc heteromultimers binds to one or more TGF-beta superfamily ligands such as those described herein. In some embodiments, an ALK5-Fc:ActRIIB-Fc heteromultimers inhibit signaling of one or more TGF-beta superfamily ligands such as those described herein. In some embodiments, an ALK5-Fc:ActRIIB-Fc heteromultimers is a heterodimer.

In certain aspects embodiments, the disclosure relates to a heteromultimer comprising at least one ALK6-Fc fusion protein and at least one ActRIIB-Fc fusion protein. In some embodiments, an ALK6-Fc:ActRIIB-Fc heteromultimers binds to one or more TGF-beta superfamily ligands such as those described herein. In some embodiments, an ALK6-Fc:ActRIIB-Fc heteromultimers inhibit signaling of one or more TGF-beta superfamily ligands such as those described herein. In some embodiments, an ALK6-Fc:ActRIIB-Fc heteromultimers is a heterodimer.

In certain aspects embodiments, the disclosure relates to a heteromultimer comprising at least one ALK7-Fc fusion protein and at least one ActRIIB-Fc fusion protein. In some embodiments, an ALK7-Fc:ActRIIB-Fc heteromultimers binds to one or more TGF-beta superfamily ligands such as those described herein. In some embodiments, an ALK7-Fc:ActRIIB-Fc heteromultimers inhibit signaling of one or more TGF-beta superfamily ligands such as those described herein. In some embodiments, an ALK7-Fc:ActRIIB-Fc heteromultimers is a heterodimer.

In certain aspects embodiments, the disclosure relates to a heteromultimer comprising at least one ALK1-Fc fusion protein and at least one BMPRII-Fc fusion protein. In some embodiments, an ALK1-Fc:BMPRII-Fc heteromultimers binds to one or more TGF-beta superfamily ligands such as those described herein. In some embodiments, an ALK1-Fc:BMPRII-Fc heteromultimers inhibit signaling of one or more TGF-beta superfamily ligands such as those described herein. In some embodiments, an ALK1-Fc:BMPRII-Fc heteromultimers is a heterodimer.

In certain aspects embodiments, the disclosure relates to a heteromultimer comprising at least one ALK2-Fc fusion protein and at least one BMPRII-Fc fusion protein. In some embodiments, an ALK2-Fc:BMPRII-Fc heteromultimers binds to one or more TGF-beta superfamily ligands such as those described herein. In some embodiments, an ALK2-Fc:BMPRII-Fc heteromultimers inhibit signaling of one or more TGF-beta superfamily ligands such as those described herein. In some embodiments, an ALK2-Fc:BMPRII-Fc heteromultimers is a heterodimer.

In certain aspects embodiments, the disclosure relates to a heteromultimer comprising at least one ALK3-Fc fusion protein and at least one BMPRII-Fc fusion protein. In some embodiments, an ALK3-Fc:BMPRII-Fc heteromultimers binds to one or more TGF-beta superfamily ligands such as those described herein. In some embodiments, an ALK3-Fc:BMPRII-Fc heteromultimers inhibit signaling of one or more TGF-beta superfamily ligands such as those described herein. In some embodiments, an ALK3-Fc:BMPRII-Fc heteromultimers is a heterodimer.

In certain aspects embodiments, the disclosure relates to a heteromultimer comprising at least one ALK4-Fc fusion protein and at least one BMPRII-Fc fusion protein. In some embodiments, an ALK4-Fc:BMPRII-Fc heteromultimers binds to one or more TGF-beta superfamily ligands such as those described herein. In some embodiments, an ALK4-Fc:BMPRII-Fc heteromultimers inhibit signaling of one or more TGF-beta superfamily ligands such as those described herein. In some embodiments, an ALK4-Fc:BMPRII-Fc heteromultimers is a heterodimer.

In certain aspects embodiments, the disclosure relates to a heteromultimer comprising at least one ALK5-Fc fusion protein and at least one BMPRII-Fc fusion protein. In some embodiments, an ALK5-Fc:BMPRII-Fc heteromultimers binds to one or more TGF-beta superfamily ligands such as those described herein. In some embodiments, an ALK5-Fc:BMPRII-Fc heteromultimers inhibit signaling of one or more TGF-beta superfamily ligands such as those described herein. In some embodiments, an ALK5-Fc:BMPRII-Fc heteromultimers is a heterodimer.

In certain aspects embodiments, the disclosure relates to a heteromultimer comprising at least one ALK6-Fc fusion protein and at least one BMPRII-Fc fusion protein. In some embodiments, an ALK6-Fc:BMPRII-Fc heteromultimers binds to one or more TGF-beta superfamily ligands such as those described herein. In some embodiments, an ALK6-Fc:BMPRII-Fc heteromultimers inhibit signaling of one or more TGF-beta superfamily ligands such as those described herein. In some embodiments, an ALK6-Fc:BMPRII-Fc heteromultimers is a heterodimer.

In certain aspects embodiments, the disclosure relates to a heteromultimer comprising at least one ALK7-Fc fusion protein and at least one BMPRII-Fc fusion protein. In some embodiments, an ALK7-Fc:BMPRII-Fc heteromultimers binds to one or more TGF-beta superfamily ligands such as those described herein. In some embodiments, an ALK7-Fc:BMPRII-Fc heteromultimers inhibit signaling of one or more TGF-beta superfamily ligands such as those described herein. In some embodiments, an ALK7-Fc:BMPRII-Fc heteromultimers is a heterodimer.

In certain aspects embodiments, the disclosure relates to a heteromultimer comprising at least one ALKT-Fc fusion protein and at least one TGFBRII-Fc fusion protein. In some embodiments, an ALK1-Fc:TGFBRII-Fc heteromultimers binds to one or more TGF-beta superfamily ligands such as those described herein. In some embodiments, an ALK1-Fc:TGFBRII-Fc heteromultimers inhibit signaling of one or more TGF-beta superfamily ligands such as those described herein. In some embodiments, an ALKT-Fc:TGFBRII-Fc heteromultimers is a heterodimer.

In certain aspects embodiments, the disclosure relates to a heteromultimer comprising at least one ALK2-Fc fusion protein and at least one TGFRII-Fc fusion protein. In some embodiments, an ALK2-Fc:TGFBRII-Fc heteromultimers binds to one or more TGF-beta superfamily ligands such as those described herein. In some embodiments, an ALK2-Fc:TGFBRII-Fc heteromultimers inhibit signaling of one or more TGF-beta superfamily ligands such as those described herein. In some embodiments, an ALK2-Fc:TGFBRII-Fc heteromultimers is a heterodimer.

In certain aspects embodiments, the disclosure relates to a heteromultimer comprising at least one ALK3-Fc fusion protein and at least one TGFBRII-Fc fusion protein. In some embodiments, an ALK3-Fc:TGFBRII-Fc heteromultimers binds to one or more TGF-beta superfamily ligands such as those described herein. In some embodiments, an ALK3-Fc:TGFBRII-Fc heteromultimers inhibit signaling of one or more TGF-beta superfamily ligands such as those described herein. In some embodiments, an ALK3-Fc:TGFBRII-Fc heteromultimers is a heterodimer.

In certain aspects embodiments, the disclosure relates to a heteromultimer comprising at least one ALK4-Fc fusion protein and at least one TGFBRII-Fc fusion protein. In some embodiments, an ALK4-Fc:TGFBRII-Fc heteromultimers binds to one or more TGF-beta superfamily ligands such as those described herein. In some embodiments, an ALK4-Fc:TGFBRII-Fc heteromultimers inhibit signaling of one or more TGF-beta superfamily ligands such as those described herein. In some embodiments, an ALK4-Fc:TGFBRII-Fc heteromultimers is a heterodimer.

In certain aspects embodiments, the disclosure relates to a heteromultimer comprising at least one ALK5-Fc fusion protein and at least one TGFBRII-Fc fusion protein. In some embodiments, an ALK5-Fc:TGFBRII-Fc heteromultimers binds to one or more TGF-beta superfamily ligands such as those described herein. In some embodiments, an ALK5-Fc:TGFBRII-Fc heteromultimers inhibit signaling of one or more TGF-beta superfamily ligands such as those described herein. In some embodiments, an ALK5-Fc:TGFBRII-Fc heteromultimers is a heterodimer.

In certain aspects embodiments, the disclosure relates to a heteromultimer comprising at least one ALK6-Fc fusion protein and at least one TGFBRII-Fc fusion protein. In some embodiments, an ALK6-Fc:TGFBRII-Fc heteromultimers binds to one or more TGF-beta superfamily ligands such as those described herein. In some embodiments, an ALK6-Fc:TGFBRII-Fc heteromultimers inhibit signaling of one or more TGF-beta superfamily ligands such as those described herein. In some embodiments, an ALK6-Fc:TGFBRII-Fc heteromultimers is a heterodimer.

In certain aspects embodiments, the disclosure relates to a heteromultimer comprising at least one ALK7-Fc fusion protein and at least one TGFBRII-Fc fusion protein. In some embodiments, an ALK7-Fc:TGFBRII-Fc heteromultimers binds to one or more TGF-beta superfamily ligands such as those described herein. In some embodiments, an ALK7-Fc:TGFBRII-Fc heteromultimers inhibit signaling of one or more TGF-beta superfamily ligands such as those described herein. In some embodiments, an ALK7-Fc:TGFBRII-Fc heteromultimers is a heterodimer.

In certain aspects embodiments, the disclosure relates to a heteromultimer comprising at least one ALKT-Fc fusion protein and at least one MISRII-Fc fusion protein. In some embodiments, an ALK1-Fc:MISRII-Fc heteromultimers binds to one or more TGF-beta superfamily ligands such as those described herein. In some embodiments, an ALK1-Fc:MISRII-Fc heteromultimers inhibit signaling of one or more TGF-beta superfamily ligands such as those described herein. In some embodiments, an ALK1-Fc:MISRII-Fc heteromultimers is a heterodimer.

In certain aspects embodiments, the disclosure relates to a heteromultimer comprising at least one ALK2-Fc fusion protein and at least one MISRII-Fc fusion protein. In some embodiments, an ALK2-Fc:MISRII-Fc heteromultimers binds to one or more TGF-beta superfamily ligands such as those described herein. In some embodiments, an ALK2-Fc:MISRII-Fc heteromultimers inhibit signaling of one or more TGF-beta superfamily ligands such as those described herein. In some embodiments, an ALK2-Fc:MISRII-Fc heteromultimers is a heterodimer.

In certain aspects embodiments, the disclosure relates to a heteromultimer comprising at least one ALK3-Fc fusion protein and at least one MISRII-Fc fusion protein. In some embodiments, an ALK3-Fc:MISRII-Fc heteromultimers binds to one or more TGF-beta superfamily ligands such as those described herein. In some embodiments, an ALK3-Fc:MISRII-Fc heteromultimers inhibit signaling of one or more TGF-beta superfamily ligands such as those described herein. In some embodiments, an ALK3-Fc:MISRII-Fc heteromultimers is a heterodimer.

In certain aspects embodiments, the disclosure relates to a heteromultimer comprising at least one ALK4-Fc fusion protein and at least one MISRII-Fc fusion protein. In some embodiments, an ALK4-Fc:MISRII-Fc heteromultimers binds to one or more TGF-beta superfamily ligands such as those described herein. In some embodiments, an ALK4-Fc:MISRII-Fc heteromultimers inhibit signaling of one or more TGF-beta superfamily ligands such as those described herein. In some embodiments, an ALK4-Fc:MISRII-Fc heteromultimers is a heterodimer.

In certain aspects embodiments, the disclosure relates to a heteromultimer comprising at least one ALK5-Fc fusion protein and at least one MISRII-Fc fusion protein. In some embodiments, an ALK5-Fc:MISRII-Fc heteromultimers binds to one or more TGF-beta superfamily ligands such as those described herein. In some embodiments, an ALK5-Fc:MISRII-Fc heteromultimers inhibit signaling of one or more TGF-beta superfamily ligands such as those described herein. In some embodiments, an ALK5-Fc:MISRII-Fc heteromultimers is a heterodimer.

In certain aspects embodiments, the disclosure relates to a heteromultimer comprising at least one ALK6-Fc fusion protein and at least one MISRII-Fc fusion protein. In some embodiments, an ALK6-Fc:MISRII-Fc heteromultimers binds to one or more TGF-beta superfamily ligands such as those described herein. In some embodiments, an ALK6-Fc:MISRII-Fc heteromultimers inhibit signaling of one or more TGF-beta superfamily ligands such as those described herein. In some embodiments, an ALK6-Fc:MISRII-Fc heteromultimers is a heterodimer.

In certain aspects embodiments, the disclosure relates to a heteromultimer comprising at least one ALK7-Fc fusion protein and at least one MISRII-Fc fusion protein. In some embodiments, an ALK7-Fc:MISRII-Fc heteromultimers binds to one or more TGF-beta superfamily ligands such as those described herein. In some embodiments, an ALK7-Fc:MISRII-Fc heteromultimers inhibit signaling of one or more TGF-beta superfamily ligands such as those described herein. In some embodiments, an ALK7-Fc:MISRII-Fc heteromultimers is a heterodimer.

In certain aspects embodiments, the disclosure relates to a heteromultimer comprising at least one ALK1-Fc fusion protein and at least one ALK2-Fc fusion protein. In some embodiments, an ALK1-Fc:ALK2-Fc heteromultimers binds to one or more TGF-beta superfamily ligands such as those described herein. In some embodiments, an ALK1-Fc:ALK2-Fc heteromultimers inhibit signaling of one or more TGF-beta superfamily ligands such as those described herein. In some embodiments, an ALK1-Fc:ALK2-Fc heteromultimers is a heterodimer.

In certain aspects embodiments, the disclosure relates to a heteromultimer comprising at least one ALK1-Fc fusion protein and at least one ALK3-Fc fusion protein. In some embodiments, an ALK1-Fc:ALK3-Fc heteromultimers binds to one or more TGF-beta superfamily ligands such as those described herein. In some embodiments, an ALK1-Fc:ALK3-Fc heteromultimers inhibit signaling of one or more TGF-beta superfamily ligands such as those described herein. In some embodiments, an ALK1-Fc:ALK3-Fc heteromultimers is a heterodimer.

In certain aspects embodiments, the disclosure relates to a heteromultimer comprising at least one ALKT-Fc fusion protein and at least one ALK4-Fc fusion protein. In some embodiments, an ALKT-Fc:ALK4-Fc heteromultimers binds to one or more TGF-beta superfamily ligands such as those described herein. In some embodiments, an ALK1-Fc:ALK4-Fc heteromultimers inhibit signaling of one or more TGF-beta superfamily ligands such as those described herein. In some embodiments, an ALKT-Fc:ALK4-Fc heteromultimers is a heterodimer.

In certain aspects embodiments, the disclosure relates to a heteromultimer comprising at least one ALKT-Fc fusion protein and at least one ALK5-Fc fusion protein. In some embodiments, an ALKT-Fc:ALK5-Fc heteromultimers binds to one or more TGF-beta superfamily ligands such as those described herein. In some embodiments, an ALK1-Fc:ALK5-Fc heteromultimers inhibit signaling of one or more TGF-beta superfamily ligands such as those described herein. In some embodiments, an ALKT-Fc:ALK5-Fc heteromultimers is a heterodimer.

In certain aspects embodiments, the disclosure relates to a heteromultimer comprising at least one ALKT-Fc fusion protein and at least one ALK6-Fc fusion protein. In some embodiments, an ALKT-Fc:ALK6-Fc heteromultimers binds to one or more TGF-beta superfamily ligands such as those described herein. In some embodiments, an ALK1-Fc:ALK6-Fc heteromultimers inhibit signaling of one or more TGF-beta superfamily ligands such as those described herein. In some embodiments, an ALKT-Fc:ALK6-Fc heteromultimers is a heterodimer.

In certain aspects embodiments, the disclosure relates to a heteromultimer comprising at least one ALKT-Fc fusion protein and at least one ALK7-Fc fusion protein. In some embodiments, an ALKT-Fc:ALK7-Fc heteromultimers binds to one or more TGF-beta superfamily ligands such as those described herein. In some embodiments, an ALK1-Fc:ALK7-Fc heteromultimers inhibit signaling of one or more TGF-beta superfamily ligands such as those described herein. In some embodiments, an ALKT-Fc:ALK7-Fc heteromultimers is a heterodimer.

In certain aspects embodiments, the disclosure relates to a heteromultimer comprising at least one ALK2-Fc fusion protein and at least one ALK3-Fc fusion protein. In some embodiments, an ALK2-Fc:ALK3-Fc heteromultimers binds to one or more TGF-beta superfamily ligands such as those described herein. In some embodiments, an ALK2-Fc:ALK3-Fc heteromultimers inhibit signaling of one or more TGF-beta superfamily ligands such as those described herein. In some embodiments, an ALK2-Fc:ALK3-Fc heteromultimers is a heterodimer.

In certain aspects embodiments, the disclosure relates to a heteromultimer comprising at least one ALK2-Fc fusion protein and at least one ALK4-Fc fusion protein. In some embodiments, an ALK2-Fc:ALK4-Fc heteromultimers binds to one or more TGF-beta superfamily ligands such as those described herein. In some embodiments, an ALK2-Fc:ALK4-Fc heteromultimers inhibit signaling of one or more TGF-beta superfamily ligands such as those described herein. In some embodiments, an ALK2-Fc:ALK4-Fc heteromultimers is a heterodimer.

In certain aspects embodiments, the disclosure relates to a heteromultimer comprising at least one ALK2-Fc fusion protein and at least one ALK5-Fc fusion protein. In some embodiments, an ALK2-Fc:ALK5-Fc heteromultimers binds to one or more TGF-beta superfamily ligands such as those described herein. In some embodiments, an ALK2-Fc:ALK5-Fc heteromultimers inhibit signaling of one or more TGF-beta superfamily ligands such as those described herein. In some embodiments, an ALK2-Fc:ALK5-Fc heteromultimers is a heterodimer.

In certain aspects embodiments, the disclosure relates to a heteromultimer comprising at least one ALK2-Fc fusion protein and at least one ALK6-Fc fusion protein. In some embodiments, an ALK2-Fc:ALK6-Fc heteromultimers binds to one or more TGF-beta superfamily ligands such as those described herein. In some embodiments, an ALK2-Fc:ALK6-Fc heteromultimers inhibit signaling of one or more TGF-beta superfamily ligands such as those described herein. In some embodiments, an ALK2-Fc:ALK6-Fc heteromultimers is a heterodimer.

In certain aspects embodiments, the disclosure relates to a heteromultimer comprising at least one ALK2-Fc fusion protein and at least one ALK7-Fc fusion protein. In some embodiments, an ALK2-Fc:ALK7-Fc heteromultimers binds to one or more TGF-beta superfamily ligands such as those described herein. In some embodiments, an ALK2-Fc:ALK7-Fc heteromultimers inhibit signaling of one or more TGF-beta superfamily ligands such as those described herein. In some embodiments, an ALK2-Fc:ALK7-Fc heteromultimers is a heterodimer.

In certain aspects embodiments, the disclosure relates to a heteromultimer comprising at least one ALK3-Fc fusion protein and at least one ALK4-Fc fusion protein. In some embodiments, an ALK3-Fc:ALK4-Fc heteromultimers binds to one or more TGF-beta superfamily ligands such as those described herein. In some embodiments, an ALK3-Fc:ALK4-Fc heteromultimers inhibit signaling of one or more TGF-beta superfamily ligands such as those described herein. In some embodiments, an ALK3-Fc:ALK4-Fc heteromultimers is a heterodimer.

In certain aspects embodiments, the disclosure relates to a heteromultimer comprising at least one ALK3-Fc fusion protein and at least one ALK5-Fc fusion protein. In some embodiments, an ALK3-Fc:ALK5-Fc heteromultimers binds to one or more TGF-beta superfamily ligands such as those described herein. In some embodiments, an ALK3-Fc:ALK5-Fc heteromultimers inhibit signaling of one or more TGF-beta superfamily ligands such as those described herein. In some embodiments, an ALK3-Fc:ALK5-Fc heteromultimers is a heterodimer.

In certain aspects embodiments, the disclosure relates to a heteromultimer comprising at least one ALK3-Fc fusion protein and at least one ALK6-Fc fusion protein. In some embodiments, an ALK3-Fc:ALK6-Fc heteromultimers binds to one or more TGF-beta superfamily ligands such as those described herein. In some embodiments, an ALK3-Fc:ALK6-Fc heteromultimers inhibit signaling of one or more TGF-beta superfamily ligands such as those described herein. In some embodiments, an ALK3-Fc:ALK6-Fc heteromultimers is a heterodimer.

In certain aspects embodiments, the disclosure relates to a heteromultimer comprising at least one ALK3-Fc fusion protein and at least one ALK7-Fc fusion protein. In some embodiments, an ALK3-Fc:ALK7-Fc heteromultimers binds to one or more TGF-beta superfamily ligands such as those described herein. In some embodiments, an ALK3-Fc:ALK7-Fc heteromultimers inhibit signaling of one or more TGF-beta superfamily ligands such as those described herein. In some embodiments, an ALK3-Fc:ALK7-Fc heteromultimers is a heterodimer.

In certain aspects embodiments, the disclosure relates to a heteromultimer comprising at least one ALK4-Fc fusion protein and at least one ALK5-Fc fusion protein. In some embodiments, an ALK4-Fc:ALK5-Fc heteromultimers binds to one or more TGF-beta superfamily ligands such as those described herein. In some embodiments, an ALK4-Fc:ALK5-Fc heteromultimers inhibit signaling of one or more TGF-beta superfamily ligands such as those described herein. In some embodiments, an ALK4-Fc:ALK5-Fc heteromultimers is a heterodimer.

In certain aspects embodiments, the disclosure relates to a heteromultimer comprising at least one ALK4-Fc fusion protein and at least one ALK6-Fc fusion protein. In some embodiments, an ALK4-Fc:ALK6-Fc heteromultimers binds to one or more TGF-beta superfamily ligands such as those described herein. In some embodiments, an ALK4-Fc:ALK6-Fc heteromultimers inhibit signaling of one or more TGF-beta superfamily ligands such as those described herein. In some embodiments, an ALK4-Fc:ALK6-Fc heteromultimers is a heterodimer.

In certain aspects embodiments, the disclosure relates to a heteromultimer comprising at least one ALK4-Fc fusion protein and at least one ALK7-Fc fusion protein. In some embodiments, an ALK4-Fc:ALK7-Fc heteromultimers binds to one or more TGF-beta superfamily ligands such as those described herein. In some embodiments, an ALK4-Fc:ALK7-Fc heteromultimers inhibit signaling of one or more TGF-beta superfamily ligands such as those described herein. In some embodiments, an ALK4-Fc:ALK7-Fc heteromultimers is a heterodimer.

In certain aspects embodiments, the disclosure relates to a heteromultimer comprising at least one ALK5-Fc fusion protein and at least one ALK6-Fc fusion protein. In some embodiments, an ALK5-Fc:ALK6-Fc heteromultimers binds to one or more TGF-beta superfamily ligands such as those described herein. In some embodiments, an ALK5-Fc:ALK6-Fc heteromultimers inhibit signaling of one or more TGF-beta superfamily ligands such as those described herein. In some embodiments, an ALK5-Fc:ALK6-Fc heteromultimers is a heterodimer.

In certain aspects embodiments, the disclosure relates to a heteromultimer comprising at least one ALK5-Fc fusion protein and at least one ALK7-Fc fusion protein. In some embodiments, an ALK5-Fc:ALK7-Fc heteromultimers binds to one or more TGF-beta superfamily ligands such as those described herein. In some embodiments, an ALK5-Fc:ALK7-Fc heteromultimers inhibit signaling of one or more TGF-beta superfamily ligands such as those described herein. In some embodiments, an ALK5-Fc:ALK7-Fc heteromultimers is a heterodimer.

In certain aspects embodiments, the disclosure relates to a heteromultimer comprising at least one ALK6-Fc fusion protein and at least one ALK7-Fc fusion protein. In some embodiments, an ALK6-Fc:ALK7-Fc heteromultimers binds to one or more TGF-beta superfamily ligands such as those described herein. In some embodiments, an ALK6-Fc:ALK7-Fc heteromultimers inhibit signaling of one or more TGF-beta superfamily ligands such as those described herein. In some embodiments, an ALK6-Fc:ALK7-Fc heteromultimers is a heterodimer.

In certain aspects embodiments, the disclosure relates to a heteromultimer comprising at least one ActRIIA-Fc fusion protein and at least one ActRIIB-Fc fusion protein. In some embodiments, an ActRIIA-Fc:ActRIIB-Fc heteromultimers binds to one or more TGF-beta superfamily ligands such as those described herein. In some embodiments, an ActRIIA-Fc:ActRIIB-Fc heteromultimers inhibit signaling of one or more TGF-beta superfamily ligands such as those described herein. In some embodiments, an ActRIIA-Fc:ActRIIB-Fc heteromultimers is a heterodimer.

In certain aspects embodiments, the disclosure relates to a heteromultimer comprising at least one ActRIIA-Fc fusion protein and at least one BMPRII-Fc fusion protein. In some embodiments, an ActRIIA-Fc:BMPRII-Fc heteromultimers binds to one or more TGF-beta superfamily ligands such as those described herein. In some embodiments, an ActRIIA-Fc:BMPRII-Fc heteromultimers inhibit signaling of one or more TGF-beta superfamily ligands such as those described herein. In some embodiments, an ActRIIA-Fc:BMPRII-Fc heteromultimers is a heterodimer.

In certain aspects embodiments, the disclosure relates to a heteromultimer comprising at least one ActRIIA-Fc fusion protein and at least one TGFBRII-Fc fusion protein. In some embodiments, an ActRIIA-Fc:TGFBRII-Fc heteromultimers binds to one or more TGF-beta superfamily ligands such as those described herein. In some embodiments, an ActRIIA-Fc:TGFBRII-Fc heteromultimers inhibit signaling of one or more TGF-beta superfamily ligands such as those described herein. In some embodiments, an ActRIIA-Fc:TGFBRII-Fc heteromultimers is a heterodimer.

In certain aspects embodiments, the disclosure relates to a heteromultimer comprising at least one ActRIIA-Fc fusion protein and at least one MISRII-Fc fusion protein. In some embodiments, an ActRIIA-Fc:MISRII-Fc heteromultimers binds to one or more TGF-beta superfamily ligands such as those described herein. In some embodiments, an ActRIIA-Fc:MISRII-Fc heteromultimers inhibit signaling of one or more TGF-beta superfamily ligands such as those described herein. In some embodiments, an ActRIIA-Fc:MISRII-Fc heteromultimers is a heterodimer.

In certain aspects embodiments, the disclosure relates to a heteromultimer comprising at least one ActRIIB-Fc fusion protein and at least one BMPRII-Fc fusion protein. In some embodiments, an ActRIIB-Fc:BMPRII-Fc heteromultimers binds to one or more TGF-beta superfamily ligands such as those described herein. In some embodiments, an ActRIIB-Fc:BMPRII-Fc heteromultimers inhibit signaling of one or more TGF-beta superfamily ligands such as those described herein. In some embodiments, an ActRIIB-Fc:BMPRII-Fc heteromultimers is a heterodimer.

In certain aspects embodiments, the disclosure relates to a heteromultimer comprising at least one ActRIIB-Fc fusion protein and at least one TGFBRII-Fc fusion protein. In some embodiments, an ActRIIB-Fc:TGFBRII-Fc heteromultimers binds to one or more TGF-beta superfamily ligands such as those described herein. In some embodiments, an ActRIIB-Fc:TGFBRII-Fc heteromultimers inhibit signaling of one or more TGF-beta superfamily ligands such as those described herein. In some embodiments, an ActRIIB-Fc:TGFBRII-Fc heteromultimers is a heterodimer.

In certain aspects, the disclosure relates to a heteromultimer comprising at least one ActRIIB-Fc fusion protein and at least one MISRII-Fc fusion protein. In some embodiments, an ActRIIB-Fc:MISRII-Fc heteromultimers binds to one or more TGF-beta superfamily ligands such as those described herein. In some embodiments, an ActRIIB-Fc:MISRII-Fc heteromultimers inhibit signaling of one or more TGF-beta superfamily ligands such as those described herein. In some embodiments, an ActRIIB-Fc:MISRII-Fc heteromultimers is a heterodimer.

In certain aspects embodiments, the disclosure relates to a heteromultimer comprising at least one BMPRII-Fc fusion protein and at least one TGFBRII-Fc fusion protein. In some embodiments, an BMPRII-Fc:TGFBRII-Fc heteromultimers binds to one or more TGF-beta superfamily ligands such as those described herein. In some embodiments, an BMPRII-Fc:TGFBRII-Fc heteromultimers inhibit signaling of one or more TGF-beta superfamily ligands such as those described herein. In some embodiments, an BMPRII-Fc:TGFBRII-Fc heteromultimers is a heterodimer.

In certain aspects embodiments, the disclosure relates to a heteromultimer comprising at least one BMPRII-Fc fusion protein and at least one MISRII-Fc fusion protein. In some embodiments, an BMPRII-Fc:MISRII-Fc heteromultimers binds to one or more TGF-beta superfamily ligands such as those described herein. In some embodiments, an BMPRII-Fc:MISRII-Fc heteromultimers inhibit signaling of one or more TGF-beta superfamily ligands such as those described herein. In some embodiments, an BMPRII-Fc:MISRII-Fc heteromultimers is a heterodimer.

In certain aspects embodiments, the disclosure relates to a heteromultimer comprising at least one TGFBRII-Fc fusion protein and at least one TGFBRII-Fc fusion protein. In some embodiments, an TGFBRII-Fc:MISRII-Fc heteromultimers binds to one or more TGF-beta superfamily ligands such as those described herein. In some embodiments, an TGFBRII-Fc:MISRII-Fc heteromultimers inhibit signaling of one or more TGF-beta superfamily ligands such as those described herein. In some embodiments, an TGFBRII-Fc:MISRII-Fc heteromultimers is a heterodimer.

In certain aspects, the disclosure relates to a heteromultimer that comprises an ALK1-Fc fusion protein. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids of 22-34 (e.g., amino acid residues 22, 23, 24, 25, 26, 27, 28, 29, 30, 31, 32, 33, and 34) SEQ ID NO: 14, ends at any one of amino acids 95-118 (e.g., amino acid residues 95, 96, 97, 98, 99, 100, 101, 102, 103, 104, 105, 106, 107, 108, 109, 110, 111, 112, 113, 114, 115, 116, 117, and 118) of SEQ ID NO: 14. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 22-118 of SEQ ID NO: 14. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-95 of SEQ ID NO: 14. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 14, 15, 124, 126, 413, and 414.

In certain aspects, the disclosure relates to a heteromultimer that comprises an ALK2-Fc fusion protein. In some embodiments, the ALK2-Fc fusion protein comprises an ALK2 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21-35 (e.g., amino acid residues 21, 22, 23, 24, 25, 26, 27, 28, 29, 30, 31, 32, 33, 34, and 35) SEQ ID NO: 18, and ends at any one of amino acids 99-123 (e.g., amino acid residues 99, 100, 101, 102, 103, 104, 105, 106, 107, 108, 109, 110, 111, 112, 113, 114, 115, 116, 117, 118, 119, 120, 121, 122, and 123) of SEQ ID NO: 18. In some embodiments, the ALK2-Fc fusion protein comprises an ALK2 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 35-99 of SEQ ID NO: 18. In some embodiments, the ALK2-Fc fusion protein comprises an ALK2 domain comprising an amino acid sequence that is at least 70%, 75%, 80%, 85%, 86%, 87%, 88%, 89%0, 90%, 91%, 92%, 93%, 94%, 95%, 96%, 97%, 98%, 99%, or 100% identical to amino acids 21-123 of SEQ ID NO: 18. In some embodiments, the ALK2-Fc fusion protein comprises an ALK2 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID Nos: 18, 19, 136, 138, 421, and 422.

In certain aspects, the disclosure relates to a heteromultimer that comprises an ALK3-Fc fusion protein. In some embodiments, the ALK3-Fc fusion protein comprises an ALK3 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 24-61 (e.g., amino acid residues 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, and 61) SEQ ID NO: 22, and ends at any one of amino acids 130-152 (e.g., amino acid residues 130, 131, 132, 133, 134, 135, 136, 137, 138, 139, 140, 141, 142, 143, 144, 145, 146, 147, 148, 149, 150, 151, and 152) of SEQ ID NO: 22. In some embodiments, the ALK3-Fc fusion protein comprises an ALK3 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 61-130 of SEQ ID NO: 22. In some embodiments, the ALK3-Fc fusion protein comprises an ALK3 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 24-152 of SEQ ID NO: 22. In some embodiments, the ALK3-Fc fusion protein comprises an ALK3 domain comprising an amino acid sequence that is at least 70%, 75%, 80%, 85%, 86%, 87%, 88%, 89%0, 90%, 91%, 92%, 93%, 94%, 95%, 96%, 97%, 98%, 99%, or 100% identical to the amino acid sequence of any one of SEQ ID Nos: 22, 23, 115, 117, 407, and 408.

In certain aspects, the disclosure relates to a heteromultimer that comprises an ALK4-Fc fusion protein. In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 23-34 (e.g., amino acid residues 23, 24, 25, 26, 27, 28, 29, 30, 31, 32, 33, 34) SEQ ID NO: 26 or 83, and ends at any one of amino acids 101-126 (e.g., amino acid residues 101, 102, 103, 104, 105, 106, 107, 108, 109, 110, 111, 112, 113, 114, 115, 116, 117, 118, 119, 120, 121, 122, 123, 124, 125, and 126) of SEQ ID NO: 26 or 83. In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-101 of SEQ ID NOs: 26 or 83. In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 23-126 of SEQ ID Nos: 26 or 83. In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 26, 27, 83, 84, 104, 106, 403, and 404.

In certain aspects, the disclosure relates to a heteromultimer that comprises an ALK5-Fc fusion protein. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 25-36 (e.g., amino acid residues 25, 26, 27, 28, 29, 30, 31, 32, 33, 34, 35, and 36) SEQ ID NO: 30 or 87, and ends at any one of amino acids 106-126 (e.g., amino acid residues 106, 107, 108, 109, 110, 111, 112, 113, 114, 115, 116, 117, 118, 119, 120, 121, 122, 123, 124, 125, and 126) of SEQ ID NO: 30 or 87. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 36-106 of SEQ ID NOs: 30 or 87. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 25-126 of SEQ ID NOs: 30 or 87. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 30, 31, 87, 88, 139, 141, 423, and 424.

In certain aspects, the disclosure relates to a heteromultimer that comprises an ALK6-Fc fusion protein. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 14-32 (e.g., amino acid residues 14, 15, 16, 17, 18, 19, 20, 21, 22, 23, 24, 25, 26, 27, 28, 29, 30, 31, and 32) SEQ ID NO: 34, and ends at any one of amino acids 102-126 (e.g., amino acid residues 102, 103, 104, 105, 106, 107, 108, 109, 110, 111, 112, 113, 114, 115, 116, 117, 118, 119, 120, 121, 122, 123, 124, 125, and 126) of SEQ ID NO: 34. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 32-102 of SEQ ID NO: 34. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 14-126 of SEQ ID NO: 34. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 34, 35, 91, 92, 142, 144, 425, and 426. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 26-62 (e.g., amino acid residues 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, and 62) SEQ ID NO: 91, and ends at any one of amino acids 132-156 (e.g., amino acid residues 132, 133, 134, 135, 136, 137, 138, 139, 140, 141, 142, 143, 144, 145, 146, 147, 148, 149, 150, 151, 152, 153, 154, 155, and 156) of SEQ ID NO: 91. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 62-132 of SEQ ID NO: 91. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 26-156 of SEQ ID NO: 91. In certain aspects, the disclosure relates to a heteromultimer that comprises an ALK7-Fc fusion protein. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21-28 (e.g., amino acid residues 21, 22, 23, 24, 25, 26, 27, and 28) SEQ ID NO: 38, 305, or 309, and ends at any one of amino acids 92-113 (e.g., amino acid residues 92, 93, 94, 95, 96, 97, 98, 99, 100, 101, 102, 103, 104, 105, 106, 107, 108, 109, 110, 111, 112, and 113) of SEQ ID NO: 38, 305, or 309. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 28-92 of SEQ ID NOs: 38, 305, or 309. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 21-113 of SEQ ID NOs: 38, 305, or 309. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 38, 39, 301, 302, 305, 306, 309, 310, 313, 112, 114, 405, and 406.

In certain aspects, the disclosure relates to a heteromultimer that comprises an ActRIIA-Fc fusion protein. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21-30 (e.g., amino acid residues 21, 22, 23, 24, 25, 26, 27, 28, 29, or 30) SEQ ID NO: 9, and ends at any one of amino acids 110-135 (e.g., 110, 111, 112, 113, 114, 115, 116, 117, 118, 119, 120, 121, 122, 123, 124, 125, 126, 127, 128, 129, 130, 131, 132, 133, 134 or 135) of SEQ ID NO: 9. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 9. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 21-135 of SEQ ID NO: 9. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 9, 10, 11, 118, 120, 409, and 410.

In certain aspects, the disclosure relates to a heteromultimer that comprises an ActRIIB-Fc fusion protein. In some embodiments, the ActRIIB-Fc fusion protein comprises an ActRIIB domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 20-29 (e.g., amino acid residues 20, 21, 22, 23, 24, 25, 26, 27, 28, or 29) SEQ ID NO: 1, and ends at any one of amino acids 109-134 (e.g., amino acid residues 109, 110, 111, 112, 113, 114, 115, 116, 117, 118, 119, 120, 121, 122, 123, 124, 125, 126, 127, 128, 129, 130, 131, 132, 133, or 134 of SEQ ID NO: 1. In some embodiments, the ActRIIB-Fc fusion protein comprises an ActRIIB domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 29-109 of SEQ ID NO: 1. In some embodiments, the ActRIIB-Fc fusion protein comprises an ActRIIB domain comprising an amino acid sequence that is at least 70%, 75%, 80%, 85%, 86%, 87%, 88%, 89%⁰, 90%, 91%, 92%, 93%, 94%, 95%, 96%, 97%, 98%, 99%, or 100% identical to amino acids 20-134 of SEQ ID NO: 1. In some embodiments, the ActRIIB-Fc fusion protein comprises an ActRIIB domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 1, 2, 3, 4, 5, 6, 100, 102, 401, and 402.

In certain aspects, the disclosure relates to a heteromultimer that comprises an BMPRII-Fc fusion protein. In some embodiments, the BMPRII-Fc fusion protein comprises an BMPRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 27-34 (e.g., amino acid residues 27, 28, 29, 30, 31, 32, 33, and 34) SEQ ID NO: 46 or 71, and ends at any one of amino acids 123-150 (e.g., amino acid residues 123, 124, 125, 126, 127, 128, 129, 130, 131, 132, 133, 134, 135, 136, 137, 138, 139, 140, 141, 142, 143, 144, 145, 146, 147, 148, 149, and 150) of SEQ ID NO: 46 or 71. In some embodiments, the BMPRII-Fc fusion protein comprises an BMPRII domain comprising an amino acid sequence that is at least 70%, 75%, 80%, 85%, 86%, 87%, 88%, 89%0, 90%, 91%, 92%, 93%, 94%, 95%, 96%, 97%, 98%, 99%, or 100% identical to amino acids 34-123 of SEQ ID NO: 46 or 71. In some embodiments, the BMPRII-Fc fusion protein comprises an BMPRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 27-150 of SEQ ID NO: 46 or 71. In some embodiments, the BMPRII-Fc fusion protein comprises an BMPRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 46, 47, 71, 72, 121, 123, 411, and 412.

In certain aspects, the disclosure relates to a heteromultimer that comprises an TGFBII-Fc fusion protein. In some embodiments, the TGFBII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 23-44 (e.g., 23, 24, 25, 26, 27, 28, 29, 30, 31, 32, 33, 34, 35, 36, 37, 38, 39, 40, 41, 42, 43 or 44) of SEQ ID NO: 67, and ends at any one of amino acids 168-191 (e.g., 168, 169, 170, 171, 172, 173, 174, 175, 176, 177, 178, 179, 180, 181, 182, 183, 184, 185, 186, 187, 188, 189, 190 or 191) of SEQ ID NO: 67. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 44-168 of SEQ ID NO: 67. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%9, 92%, 93%, 94%, 95%, 96%, 97%, 98%, 99%, or 100% identical to amino acids 23-191 of SEQ ID NO: 67. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 42, 43, 67, 68, 127, 129, 130, 132, 415, 416, 417, and 418. In some embodiments, the TGFBII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 23-51 (e.g., 23, 24, 25, 26, 27, 28, 29, 30, 31, 32, 33, 34, 35, 36, 37, 38, 39, 40, 41, 42, 43, 44, 45, 46, 47, 48, 49, 50, and 51) of SEQ ID NO: 42, and ends at any one of amino acids 143-166 (e.g., 143, 144, 145, 146, 147, 148, 149, 150, 151, 152, 153, 154, 155, 156, 157, 158, 159, 160, 161, 162, 163, 164, 165, and 166) of SEQ ID NO: 42. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 51-143 of SEQ ID NO: 42. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 23-166 of SEQ ID NO: 42.

In certain aspects, the disclosure relates to a heteromultimer that comprises an MISRII-Fc fusion protein. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 17-24 (e.g., amino acid residues 17, 18, 19, 20, 21, 22, 23, and 24) SEQ ID NO: 50, 75, or 79, and ends at any one of amino acids 116-149 (e.g., amino acid residues 116, 117, 118, 119, 120, 121, 122 123, 124, 125, 126, 127, 128, 129, 130, 131, 132, 133, 134, 135, 136, 137, 138, 139, 140, 141, 142, 143, 144, 145, 146, 147, 148, and 149) of SEQ ID NO: 50, 75, or 79. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 24-116 of SEQ ID NO: 50, 75, or 79. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 17-149 of SEQ ID NO: 50, 75, or 79. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 50, 51, 75, 76, 79, and 80.

In some embodiments, the TGF-beta superfamily type I and/or type II receptor polypeptides disclosed herein comprise one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. In some embodiments, the TGF-beta superfamily type I and/or type II polypeptides described herein are glycosylated and have a glycosylation pattern obtainable from the expression of the polypeptides in a mammalian cell, including, for example, a CHO cell.

In certain aspects the disclosure provides nucleic acids encoding any of the TGF-beta superfamily type I and/or type II polypeptides described herein. Nucleic acids disclosed herein may be operably linked to a promoter for expression, and the disclosure further provides cells transformed with such recombinant polynucleotides. In some embodiments the cell is a mammalian cell such as a COS cell or a CHO cell.

In certain aspects, the disclosure provides methods for making any of the TGF-beta superfamily type I and/or type II polypeptides described herein as well as protein complexes comprising such polypeptides. Such a method may include expressing any of the nucleic acids disclosed herein in a suitable cell (e.g., CHO cell or a COS cell). Such a method may comprise: a) culturing a cell under conditions suitable for expression of the TGF-beta superfamily type I or type II polypeptides described herein, wherein said cell is transformed with a type I or type II polypeptide expression construct; and b) recovering the type I or type II polypeptides so expressed. TGF-beta superfamily type I and/or type II polypeptides described herein, as well as protein complexes of the same, may be recovered as crude, partially purified, or highly purified fractions using any of the well-known techniques for obtaining protein from cell cultures.

In certain aspects, the disclosure provides methods for making any of the heteromultimeric complexes disclosed herein. Such a method may include expressing any of the nucleic acids disclosed herein in a suitable cell (e.g., CHO cell or a COS cell). Such a method may comprise: a) obtaining a cell that comprises a nucleic acid comprising the coding sequence for a TGF-beta superfamily type I receptor polypeptide disclosed herein and a nucleic acid comprising the coding sequence for a TGF-beta superfamily type II receptor polypeptide disclosed herein; (b) culturing such cell under conditions suitable for expression of the TGF-beta superfamily type I and type II polypeptides described herein; and c) recovering the heteromeric complex comprising such type I and type II polypeptides so expressed. Heteromultimeric complexes disclosed herein as crude, partially purified, or highly purified fractions using any of the well-known techniques for obtaining protein from cell cultures.

Any of the protein complexes described herein may be incorporated into a pharmaceutical preparation. Optionally, such pharmaceutical preparations are at least 80%, 85%, 90%, 95%, 97%, 98% or 99% pure with respect to other polypeptide components. Optionally, pharmaceutical preparations disclosed herein may comprise one or more additional active agents. In some embodiments, heteromultimers of the disclosure comprise less than 10%, 9%, 8%, 7%, 5%, 4%, 3%, 2%, or less than 1% type I receptor polypeptide homomultimers. In some embodiments, heteromultimers of the disclosure comprise less than 10%, 9%, 8%, 7%, 5%, 4%, 3%, 2%, or less than 1% type II receptor polypeptide homomultimers. In some embodiments, heteromultimers of the disclosure comprise less than 10%, 9%, 8%, 7%, 5%, 4%, 3%, 2%, or less than 1% type I receptor polypeptide homomultimers and less than 10%, 9%, 8%, 7%, 5%, 4%, 3%, 2%, or less than 1% type II receptor polypeptide homomultimers.

The disclosure further provides methods and heteromultimers for use in the treatment or prevention of various disease and disorders associated with, for example, muscle, bone, fat, red blood cells, and other tissues that are affected by one or more ligands of the TGF-beta superfamily. Such disease and disorders include, but are not limited to, disorders associated with muscle loss or insufficient muscle growth (e.g., muscle atrophy; muscular dystrophy, including Duchenne muscular dystrophy, Becker muscular dystrophy, and facioscapulohumeral muscular dystrophy; amyotrophic lateral sclerosis; and cachexia) and disorders associated with undesirable weight gain (e.g., obesity, type 2 diabetes or non-insulin dependent diabetes mellitus (NIDDM), cardiovascular disease, hypertension, osteoarthritis, stroke, respiratory problems, and gall bladder disease). In some embodiments, heteromultimeric complexes disclosed herein may be used to decrease body fat content or reduce the rate of increase in body fat content in a subject in need thereof. In some embodiments, heteromultimeric complexes disclosed herein may be used to reduce cholesterol and/or triglyceride levels in a patient.

In some embodiments, heteromeric complexes disclosed herein may be used to treat anemia. In some embodiments, heteromeric complexes disclosed herein may be used to treat thalassemia. In some embodiments, heteromeric complexes disclosed herein may be used to treat myelodysplastinc syndrome. In some embodiments, heteromeric complexes disclosed herein may be used to treat myelofibrosis. In some embodiments, heteromeric complexes disclosed herein may be used to treat a hemoglobinopathy. In some embodiments, heteromeric complexes disclosed herein may be used to treat sickle cell disease. In some embodiments, heteromeric complexes disclosed herein may be used to reduce transfusion burden in a patient in need thereof. In some embodiments, heteromeric complexes disclosed herein may be used to treat a patient with endogenously high erythropoietin levels relative to the erythropoietin levels of one or more healthy patients of similar age and sex. In some embodiments, heteromeric complexes disclosed herein may be used to treat a patient that has anemia and is non-responsive or intolerate to treatment with EPO (or derivative thereof or an EPO receptor agonist).

BRIEF DESCRIPTION OF THE DRAWINGS

FIG. 1A depicts a heterodimeric protein complex comprising one type I receptor fusion polypeptide and one type II receptor fusion polypeptide, which can be assembled covalently or noncovalently via a multimerization domain contained within each polypeptide chain. Two assembled multimerization domains constitute an interaction pair, which can be either guided or unguided. FIG. 1B depicts a heterotetrameric protein complex comprising two heterodimeric complexes as in FIG. 1A. Complexes of higher order can be envisioned.

FIG. 3 shows an alignment of extracellular domains of human ActRIIA (SEQ ID NO: 500) and human ActRIIB (SEQ ID NO: 2) with the residues that are deduced herein, based on composite analysis of multiple ActRIIB and ActRIIA crystal structures, to directly contact ligand indicated with boxes.

FIG. 5 shows multiple sequence alignment of Fc domains from human IgG isotypes using Clustal 2.1. Hinge regions are indicated by dotted underline. Double underline indicates examples of positions engineered in IgG1 Fc to promote asymmetric chain pairing and the corresponding positions with respect to other isotypes IgG2, IgG3 and IgG4.

DETAILED DESCRIPTION OF THE INVENTION

1. Overview

Figure 1A:
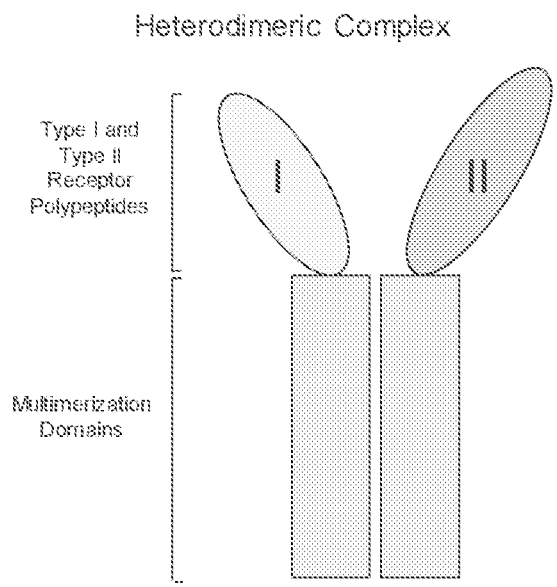
FIGS. 1A and 1B show two schematic examples of heteromeric protein complexes comprising type I receptor and type II receptor polypeptides.

In part, the present disclosure relates to heteromultimers comprising an extracellular domain of a TGFβ superfamily type I receptor polypeptide and an extracellular domain of a TGFβ superfamily type II receptor polypeptide, heteromultimers comprising an extracellular domain of at least two different TGFβ superfamily type I receptor polypeptides, heteromultimers comprising an extracellular domain of at least two different TGFβ superfamily type II receptor polypeptides, methods of making such heteromultimers, and uses thereof. As described herein, in some embodiments, heteromultimers may comprise an extracellular domain of a TGFβ superfamily type I receptor polypeptide selected from: ALK1, ALK2, ALK3, ALK4, ALK5, ALK6, and ALK7. Similarly, in some embodiments, these heteromultimers may comprise an extracellular domain of a TGFβ superfamily type II receptor polypeptide selected from: ActRIIA, ActRIIB, TGFBRII, BMPRII, and MISRII. In certain preferred embodiments, heteromultimers of the disclosure have an altered TGFβ superfamily ligand binding specificity/profile relative to a corresponding sample of a homomultimer (e.g., an ActRIIB:ALK4 heterodimer compared to an ActRIIB:ActRIIB homodimer or an ALK4:ALK4 homodimer).

The TGF-β superfamily is comprised of over 30 secreted factors including TGF-betas, activins, nodals, bone morphogenetic proteins (BMPs), growth and differentiation factors (GDFs), and anti-Mullerian hormone (AMH). See, e.g., Weiss et al. (2013) Developmental Biology, 2(1): 47-63. Members of the superfamily, which are found in both vertebrates and invertebrates, are ubiquitously expressed in diverse tissues and function during the earliest stages of development throughout the lifetime of an animal. Indeed, TGF-β superfamily proteins are key mediators of stem cell self-renewal, gastrulation, differentiation, organ morphogenesis, and adult tissue homeostasis. Consistent with this ubiquitous activity, aberrant TGF-beta superfamily signaling is associated with a wide range of human pathologies including, for example, autoimmune disease, cardiovascular disease, fibrotic disease, and cancer.

Ligands of the TGF-beta superfamily share the same dimeric structure in which the central 3½ turn helix of one monomer packs against the concave surface formed by the beta-strands of the other monomer. The majority of TGF-beta family members are further stabilized by an intermolecular disulfide bonds. This disulfide bond traverses through a ring formed by two other disulfide bonds generating what has been termed a 'cysteine knot' motif. See, e.g., Lin et al., (2006) Reproduction 132: 179-190 and Hinck et al. (2012) FEBS Letters 586: 1860-1870.

TGF-beta superfamily signaling is mediated by heteromeric complexes of type I and type II serine/threonine kinase receptors, which phosphorylate and activate downstream SMAD proteins (e.g., SMAD proteins 1, 2, 3, 5, and 8) upon ligand stimulation. See, e.g., Massague (2000) Nat. Rev. Mol. Cell Biol. 1:169-178. These type I and type II receptors are transmembrane proteins, composed of a ligand-binding extracellular domain with cysteine-rich region, a transmembrane domain, and a cytoplasmic domain with predicted serine/threonine kinase specificity. In general, type I receptors mediate intracellular signaling while the type II receptors are required for binding TGF-beta superfamily ligands. Type I and II receptors form a stable complex after ligand binding, resulting in phosphorylation of type I receptors by type II receptors.

The TGF-beta family can be divided into two phylogenetic branches based on the type I receptors they bind and the Smad proteins they activate. One is the more recently evolved branch, which includes, e.g., the TGF-betas, activins, GDF8, GDF9, GDF11, BMP3 and nodal, which signal through type I receptors that activate Smads 2 and 3 [Hinck (2012) FEBS Letters 586:1860-1870]. The other branch comprises the more distantly related proteins of the superfamily and includes, e.g., BMP2, BMP4, BMP5, BMP6, BMP7, BMP8a, BMP8b, BMP9, BMP10, GDF1, GDF5, GDF6, and GDF7, which signal through Smads 1, 5, and 8.

TGF-beta isoforms are the founding members of the TGF-beta superfamily, of which there are 3 known isoforms in mammals designated as TGF-beta1, TGF-beta2 and TGF-beta3. Mature bioactive TGF-beta ligands function as homodimers and predominantly signal through the type I receptor ALK5, but have also been found to additionally signal through ALK1 in endothelial cells. See, e.g., Goumans et al. (2003) Mol Cell 12(4): 817-828. TGF-beta1 is the most abundant and ubiquitously expressed isoform. TGF-beta1 is known to have an important role in wound healing, and mice expressing a constitutively active TGF-beta1 transgene develop fibrosis. See e.g., Clouthier et al., (1997) J Clin. Invest. 100(11): 2697-2713. TGF-beta1 is also involved in T cell activation and maintenance of T regulatory cells. See, e.g., Li et al., (2006) Immunity 25(3): 455-471. TGF-beta2 expression was first described in human glioblastoma cells, and is occurs in neurons and astroglial cells of the embryonic nervous system. TGF-beta2 is known to suppress interleukin-2-dependent growth of T lymphocytes. TGF-beta3 was initially isolated from a human rhabdomyosarcoma cell line and since has been found in lung adenocarcinoma and kidney carcinoma cell lines. TGF-beta3 is known to be important for palate and lung morphogenesis. See, e.g., Kubiczkova et al., (2012) Journal of Translational Medicine 10:183.

Activins are members of the TGF-beta superfamily and were initially discovered as regulators of secretion of follicle-stimulating hormone, but subsequently various reproductive and non-reproductive roles have been characterized. There are three principal activin forms (A, B, and AB) that are homo/heterodimers of two closely related β subunits ($β_Aβ_A$, $β_Bβ_B$, and $β_Aβ_B$, respectively). The human genome also encodes an activin C and an activin E, which are primarily expressed in the liver, and heterodimeric forms containing Pc or E are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos. See, e.g., DePaolo et al. (1991) Proc Soc Ep Biol Med. 198:500-512; Dyson et al. (1997) Curr Biol. 7:81-84; and Woodruff (1998) Biochem Pharmacol. 55:953-963. In several tissues, activin signaling is antagonized by its related heterodimer, inhibin. For example, in the regulation of follicle-stimulating hormone (FSH) secretion from the pituitary, activin promotes FSH synthesis and secretion, while inhibin reduces FSH synthesis and secretion. Other proteins that may regulate activin bioactivity and/or bind to activin include follistatin (FS), follistatin-related protein (FSRP, also known as FLRG or FSTL3), and $α_2$-macroglobulin.

As described herein, agents that bind to "activin A" are agents that specifically bind to the $β_A$ subunit, whether in the context of an isolated $β_A$ subunit or as a dimeric complex (e.g., a $β_Aβ_A$ homodimer or a $β_Aβ_B$ heterodimer). In the case of a heterodimer complex (e.g., a $β_Aβ_B$ heterodimer), agents that bind to "activin A" are specific for epitopes present within the $β_A$ subunit, but do not bind to epitopes present within the non-PA subunit of the complex (e.g., the $β_B$ subunit of the complex). Similarly, agents disclosed herein that antagonize (inhibit) "activin A" are agents that inhibit one or more activities as mediated by a $β_A$ subunit, whether in the context of an isolated $β_A$ subunit or as a dimeric complex (e.g., a $β_Aβ_A$ homodimer or a $β_Aβ_B$ heterodimer). In the case of $β_Aβ_B$ heterodimers, agents that inhibit "activin A" are agents that specifically inhibit one or more activities of the $β_A$ subunit, but do not inhibit the activity of the non-$β_A$ subunit of the complex (e.g., the $β_B$ subunit of the complex). This principle applies also to agents that bind to and/or inhibit "activin B", "activin C", and "activin E". Agents disclosed herein that antagonize "activin AB", "activin AC", "activin AE", "activin BC", or "activin BE" are agents that inhibit one or more activities as mediated by the $\beta_A$ subunit and one or more activities as mediated by the $\beta_B$ subunit. The same principle applies to agents that bind to and/or inhibit "activin AC", "activin AE", "activin BC", or "activin BE".

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as SMAD proteins. Studies support the idea that ActRIIA and ActRIIB serve as type II receptors for nodal. See, e.g., Sakuma et al. (2002) Genes Cells. 2002, 7:401-12. It is suggested that Nodal ligands interact with their co-factors (e.g., Cripto or Cryptic) to activate activin type I and type II receptors, which phosphorylate SMAD2. Nodal proteins are implicated in many events critical to the early vertebrate embryo, including mesoderm formation, anterior patterning, and left-right axis specification. Experimental evidence has demonstrated that nodal signaling activates pAR3-Lux, a luciferase reporter previously shown to respond specifically to activin and TGF-beta. However, nodal is unable to induce pTlx2-Lux, a reporter specifically responsive to bone morphogenetic proteins. Recent results provide direct biochemical evidence that nodal signaling is mediated by SMAD2 and SMAD3, which also mediate signaling by TGF-betas and activins. Further evidence has shown that the extracellular protein Cripto or Cryptic is required for nodal signaling, making it distinct from activin or TGF-beta signaling.

The BMPs and GDFs together form a family of cysteine-knot cytokines sharing the characteristic fold of the TGF-beta superfamily. See, e.g., Rider et al. (2010) Biochem J., 429(1):1-12. This family includes, for example, BMP2, BMP4, BMP6, BMP7, BMP2a, BMP3, BMP3b (also known as GDF10), BMP4, BMP5, BMP6, BMP7, BMP8, BMP8a, BMP8b, BMP9 (also known as GDF2), BMP10, BMP11 (also known as GDF11), BMP12 (also known as GDF7), BMP13 (also known as GDF6), BMP14 (also known as GDF5), BMP15, GDF1, GDF3 (also known as VGR2), GDF8 (also known as myostatin), GDF9, GDF15, and decapentaplegic. Besides the ability to induce bone formation, which gave the BMPs their name, the BMP/GDFs display morphogenetic activities in the development of a wide range of tissues. BMP/GDF homo- and hetero-dimers interact with combinations of type I and type II receptor dimers to produce multiple possible signaling complexes, leading to the activation of one of two competing sets of SMAD transcription factors. BMP/GDFs have highly specific and localized functions. These are regulated in a number of ways, including the developmental restriction of BMP/GDF expression and through the secretion of several specific BMP antagonist proteins that bind with high affinity to the cytokines. Curiously, a number of these antagonists resemble TGF-beta superfamily ligands.

Growth and differentiation factor-8 (GDF8) is also known as myostatin. GDF8 is a negative regulator of skeletal muscle mass and is highly expressed in developing and adult skeletal muscle. The GDF8 null mutation in transgenic mice is characterized by a marked hypertrophy and hyperplasia of skeletal muscle. See, e.g., McPherron et al., Nature (1997) 387:83-90. Similar increases in skeletal muscle mass are evident in naturally occurring mutations of GDF8 in cattle and, strikingly, in humans. See, e.g., Ashmore et al. (1974) Growth, 38:501-507; Swatland and Kieffer, J. Anim. Sci. (1994) 38:752-757; McPherron and Lee, Proc. Natl. Acad. Sci. USA (1997) 94:12457-12461; Kambadur et al., Genome Res. (1997) 7:910-915; and Schuelke et al. (2004) N Engl J Med, 350:2682-8. Studies have also shown that muscle wasting associated with HIV-infection in humans is accompanied by increases in GDF8 protein expression. See, e.g., Gonzalez-Cadavid et al., PNAS (1998) 95:14938-43. In addition, GDF8 can modulate the production of muscle-specific enzymes (e.g., creatine kinase) and modulate myoblast cell proliferation. See, e.g., International Patent Application Publication No. WO 00/43781). The GDF8 propeptide can noncovalently bind to the mature GDF8 domain dimer, inactivating its biological activity. See, e.g., Miyazono et al. (1988) J. Biol. Chem., 263: 6407-6415; Wakefield et al. (1988) J. Biol. Chem., 263; 7646-7654; and Brown et al. (1990) Growth Factors, 3: 35-43. Other proteins which bind to GDF8 or structurally related proteins and inhibit their biological activity include follistatin, and potentially, follistatin-related proteins. See, e.g., Gamer et al. (1999) Dev. Biol., 208: 222-232.

GDF11, also known as BMP11, is a secreted protein that is expressed in the tail bud, limb bud, maxillary and mandibular arches, and dorsal root ganglia during mouse development. See, e.g., McPherron et al. (1999) Nat. Genet., 22: 260-264; and Nakashima et al. (1999) Mech. Dev., 80: 185-189. GDF11 plays a unique role in patterning both mesodermal and neural tissues. See, e.g., Gamer et al. (1999) Dev Biol., 208:222-32. GDF11 was shown to be a negative regulator of chondrogenesis and myogenesis in developing chick limb. See, e.g., Gamer et al. (2001) Dev Biol., 229:407-20. The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium. See, e.g., Wu et al. (2003) Neuron., 37:197-207. Hence, GDF11 may have in vitro and in vivo applications in the treatment of diseases such as muscle diseases and neurodegenerative diseases (e.g., amyotrophic lateral sclerosis).

BMP7, also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in calcium regulation and bone homeostasis. Like activin, BMP7 binds to type II receptors, ActRIIA and ActRIIB. However, BMP7 and activin recruit distinct type I receptors into heteromeric receptor complexes. The major BMP7 type I receptor observed was ALK2, while activin bound exclusively to ALK4 (ActRIIB). BMP7 and activin elicited distinct biological responses and activated different SMAD pathways. See, e.g., Macias-Silva et al. (1998) J Biol Chem. 273:25628-36.

Anti-Mullerian hormone (AMH), also known as Mullerian-inhibiting substance (MIS), is a TGF-beta family glycoprotein. One AMH-associated type II receptor has been identified and is designated as AMHRII, or alternatively MISRII. AMH induces regression of the Mullerian ducts in the human male embryo. AMH is expressed in reproductive age women and does not fluctuate with cycle or pregnancy, but was found to gradual decrease as both oocyte quantity and quality decrease, suggesting AMH could serve as a biomarker for ovarian physiology. See e.g. Zec et al., (2011) Biochemia Medica 21(3): 219-30.

Activin receptor-like kinase-1 (ALK1), the product of the ACVRL1 gene known alternatively as ACVRLK1, is a type I receptor whose expression is predominantly restricted to endothelial cells. See, e.g., OMIM entry 601284. ALK1 is activated by the binding of TGF-beta family ligands such as BMP9 and BMP10, and ALK1 signaling is critical in the regulation of both developmental and pathological blood vessel formation. ALK1 expression overlaps with sites of vasculogenesis and angiogenesis in early mouse development, and ALK1 knockout mice die around embryonic day 11.5 because of severe vascular abnormalities (see e.g., Cunha and Pietras (2011) Blood 117(26):6999-7006.) ALK1 expression has also been described in other cell types such as hepatic stellate cells and chondrocytes. Additionally, ALK1 along with activin receptor-like kinase-2 (ALK2) have been found to be important for BMP9-induced osteogenic signaling in mesenchymal stem cells. See e.g., Cunha and Pietras (2011) Blood 117(26):6999-7006.

ALK2, the product of the ACVR1 gene known alternatively as ActRIA or ACVRLK2, is a type I receptor that has been shown to bind activins and BMPs. ALK2 is critical for embryogenesis as ALK2 knockout mice die soon after gastrulation. See, e.g., Mishina et al. (1999) Dev Biol. 213: 314-326 and OMIM entry 102576. Constitutively active mutations in ALK2 are associated with fibrodysplasia ossificans progressiva (FOP). FOP is rare genetic disorder that causes fibrous tissue, including muscle, tendon and ligament, to be ossified spontaneously or when damaged. An arginine to histidine mutation in codon 206 of ALK2 is naturally occurring mutation associated with FOP in humans. This mutation induces BMP-specific signaling via ALK2 without the binding of ligand. See, e.g., Fukuda et al., (2009) J Biol Chem. 284(11):7149-7156 and Kaplan et al., (2011) Ann N.Y. Acad Sci. 1237: 5-10.

Activin receptor-like kinase-3 (ALK3), the product of the BMPR1A gene known alternatively as ACVRLK3, is a type I receptor mediating effects of multiple ligands in the BMP family. Unlike several type I receptors with ubiquitous tissue expression, ALK3 displays a restricted pattern of expression consistent with more specialized functionality. See, e.g., ten Dijke (1993) Oncogene, 8: 2879-2887 and OMIM entry 601299. ALK3 is generally recognized as a high affinity receptor for BMP2, BMP4, BMP7 and other members of the BMP family. BMP2 and BMP7 are potent stimulators of osteoblastic differentiation, and are now used clinically to induce bone formation in spine fusions and certain non-union fractures. ALK3 is regarded as a key receptor in mediating BMP2 and BMP4 signaling in osteoblasts. See, e.g., Lavery et al. (2008) J. Biol. Chem. 283: 20948-20958. A homozygous ALK3 knockout mouse dies early in embryogenesis (~day 9.5), however, adult mice carrying a conditional disruption of ALK3 in osteoblasts have been recently reported to exhibit increased bone mass, although the newly formed bone showed evidence of disorganization. See, e.g., Kamiya (2008) J. Bone Miner. Res., 23:2007-2017; and Kamiya (2008) Development 135: 3801-3811. This finding is in startling contrast to the effectiveness of BMP2 and BMP7 (ligands for ALK3) as bone building agents in clinical use.

Activin receptor-like kinase-4 (ALK4), the product of the ACVR1B gene alternatively known as ACVRLK4, is a type I receptor that transduces signaling for a number of TGF-beta family ligands including activins, nodal and GDFs. ALK4 mutations are associated with pancreatic cancer and expression of dominant negative truncated ALK4 isoforms are highly expressed in human pituitary tumors. See, e.g., Tsuchida et al., (2008) Endocrine Journal 55(1):11-21 and OMIM entry 601300.

Activin receptor-like kinase-5 (ALK5), the product of the TGFBR1 gene, is widely expressed in most cell types. Several TGF-beta superfamily ligands, including TGF-betas, activin, and GDF-8, signal via ALK5 and activate downstream Smad 2 and Smad 3. Mice deficient in ALK5 exhibit severe defects in the vascular development of the yolk sac and placenta, lack circulating red blood cells, and die mid-gestation. It was found that these embryos had normal hematopoietic potential, but enhanced proliferation and improper migration of endothelial cells. Thus, ALK5-dependent signaling is important for angiogenesis, but not for the development of hematopoietic progenitor cells and functional hematopoiesis. See, e.g. Larsson et al., (2001) The EMBO Journal, 20(7): 1663-1673 and OMIM entry 190181. In endothelial cells, ALK5 acts cooperatively and opposite to ALK1 signaling. ALK5 inhibits cell migration and proliferation, notably the opposite effect of ALK1. See, e.g., Goumans et al. (2003) Mol Cell 12(4): 817-828. Additionally, ALK5 is believed to negatively regulate muscle growth. Knockdown of ALK5 in the muscle a mouse model of muscular dystrophy was found to decrease fibrosis and increase expression of genes associate with muscle growth. See, e.g. Kemaladewi et al., (2014) Mol Ther Nucleic Acids 3, e156.

Activin receptor-like kinase-6 (ALK6) is the product of the BMPR1B gene, whose deficiency is associated with chrondodysplasia and limb defects in both humans and mice. See, e.g., Demirhan et al., (2005) J Med Genet. 42:314-317. ALK6 is widely expressed throughout the developing skeleton, and is required for chondrogenesis in mice. See, e.g., Yi et al., (2000) Development 127:621-630 and OMIM entry 603248.

Activin receptor-like kinase-7 (ALK7) is the product of the ACVR1C gene. ALK7 null mice are viable, fertile, and display no skeletal or limb malformations. GDF3 signaling through ALK7 appears to play a role in insulin sensitivity and obesity. This is supported by results that Alk7 null mice show reduced fat accumulation and resistance to diet-induced obesity. See, e.g., Andersson et al., (2008) PNAS 105(20): 7252-7256. ALK7-mediated Nodal signaling has been implicated to have both tumor promoting and tumor suppressing effects in a variety of different cancer cell lines. See, e.g., De Silva et al., (2012) Frontiers in Endocrinology 3:59 and OMIM entry 608981.

As used herein the term "ActRII" refers to the family of type II activin receptors. This family includes both the activin receptor type IIA (ActRIIA), encoded by the ACVR2A gene, and the activin receptor type IIB (ActRIIB), encoded by the ACVR2B gene. ActRII receptors are TGF-beta superfamily type II receptors that bind a variety of TGF-beta superfamily ligands including activins, GDF8 (myostatin), GDF11, and a subset of BMPs, notably BMP6 and BMP7. ActRII receptors are implicated in a variety of biological disorders including muscle and neuromuscular disorders (e.g., muscular dystrophy, amyotrophic lateral sclerosis (ALS), and muscle atrophy), undesired bone/cartilage growth, adipose tissue disorders (e.g., obesity), metabolic disorders (e.g., type 2 diabetes), and neurodegenerative disorders. See, e.g., Tsuchida et al., (2008) Endocrine Journal 55(1):11-21, Knopf et al., U.S. Pat. No. 8,252,900, and OMIM entries 102581 and 602730.

Transforming growth factor beta receptor II (TGFBRII), encoded by the TGFBR2 gene, is a type II receptor that is known to bind TGF-beta ligands and activate downstream Smad 2 and Smad 3 effectors. See, e.g., Hinck (2012) FEBS Letters 586: 1860-1870 and OMIM entry 190182. TGF-beta signaling through TGFBRII is critical in T-cell proliferation, maintenance of T regulatory cells and proliferation of pre-cartilaginous stem cells. See, e.g., Li et al., (2006) Immunity 25(3): 455-471 and Cheng et al., Int. J. Mol. Sci. 2014, 15, 12665-12676.

Bone morphogenetic protein receptor II (BMPRII), encoded by the BMPR2 gene, is a type II receptor that is thought to bind certain BMP ligands. In some instances, efficient ligand binding to BMPRII is dependent on the presence of the appropriate TGFBR type I receptors. See, e.g., Rosenzweig et al., (1995) PNAS 92:7632-7636. Mutations in BMPRII are associated pulmonary hypertension in humans. See OMIM entry 600799.

Müllerian-inhibiting substance receptor II (MISRII), the product of the AMHR2 gene known alternatively as anti-Müllerian hormone type II receptor, is a type II TGF-beta receptor. MISRII binds the MIS ligand, but requires the presence of an appropriate type I receptor, such as ALK3 or ALK6, for signal transduction. See, e.g., Hinck (2012) FEBS Letters 586:1860-1870 and OMIM entry 600956. MISRII is involved in sex differentiation in humans and is required for Müllerian regression in the human male. AMH is expressed in reproductive age women and does not fluctuate with cycle or pregnancy, but was found to gradual decrease as both oocyte quantity and quality decrease, suggesting AMH could serve as a biomarker of ovarian physiology. See, e.g., Zec et al., (2011) Biochemia Medica 21(3): 219-30 and OMIM entry 600956.

In certain aspects, the present disclosure relates to the use of a) heteromultimers comprising an extracellular domain of a TGFβ superfamily type I receptor polypeptide (e.g., ALK1, ALK2, ALK3, ALK4, ALK5, ALK6, and ALK7) and an extracellular domain of a TGFβ superfamily type II receptor polypeptide (e.g., ActRIIA, ActRIIB, TGFBRII, BMPRII, and MISRII) b) heteromultimers comprising an extracellular domain of at least two TGFβ superfamily type I receptor polypeptide (e.g., ALK1, ALK2, ALK3, ALK4, ALK5, ALK6, and ALK7), and heteromultimers comprising an extracellular domain of at least two TGFβ superfamily type II receptor polypeptide (e.g., ActRIIA, ActRIIB, TGFBRII, BMPRII, and MISRII), preferably soluble heteromultimers, to antagonize intracellular signaling transduction (e.g., Smad 2/3 and/or Smad 1/5/8 signaling) initiated by one or more TGFβ superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-01, TGF-02, TGF-03, activin A, activin B, activin C, activin E, activin AB, activin AC, activin AE, activin BC, activin BE, nodal, glial cell-derived neurotrophic factor (GDNF), neurturin, artemin, persephin, Müllerian-inhibiting substance (MIS), and Lefty). As described herein, such antagonist heteromultimer complexes may be useful in the treatment or prevention of various disorders/conditions associated with, e.g., muscle loss, insufficient muscle growth, neurodegeneration, bone loss, reduced bone density and/or mineralization, insufficient bone growth, metabolic disorders such as obesity and red blood cell disorders such as anemia.

In particular, the data of the present disclosure demonstrates that heteromultimers comprising an extracellular domain of a TGFβ superfamily type I receptor polypeptide and an extracellular domain of a TGFβ superfamily type II receptor polypeptide have different ligand binding specificities/profiles in comparison to their corresponding homomultimer complexes.

The terms used in this specification generally have their ordinary meanings in the art, within the context of this disclosure and in the specific context where each term is used. Certain terms are discussed below or elsewhere in the specification to provide additional guidance to the practitioner in describing the compositions and methods of the disclosure and how to make and use them. The scope or meaning of any use of a term will be apparent from the specific context in which it is used.

The terms "heteromer" or "heteromultimer" is a complex comprising at least a first polypeptide and a second polypeptide, wherein the second polypeptide differs in amino acid sequence from the first polypeptide by at least one amino acid residue. The heteromer can comprise a "heterodimer" formed by the first and second polypeptide or can form higher order structures where polypeptides in addition to the first and second polypeptide are present. Exemplary structures for the heteromultimer include, for example, heterodimers, heterotrimers, heterotetramers and further oligomeric structures. Heterodimers are designated herein as X:Y or equivalently as X-Y, where X represents a first polypeptide and Y represents a second polypeptide. In certain embodiments a heteromultimer is recombinant (e.g., one or more polypeptide components may be a recombinant protein), isolated and/or purified protein complex.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. However, in common usage and in the instant application, the term "homologous," when modified with an adverb such as "highly," may refer to sequence similarity and may or may not relate to a common evolutionary origin.

The term "sequence similarity," in all its grammatical forms, refers to the degree of identity or correspondence between nucleic acid or amino acid sequences that may or may not share a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity. The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Figure 1B:
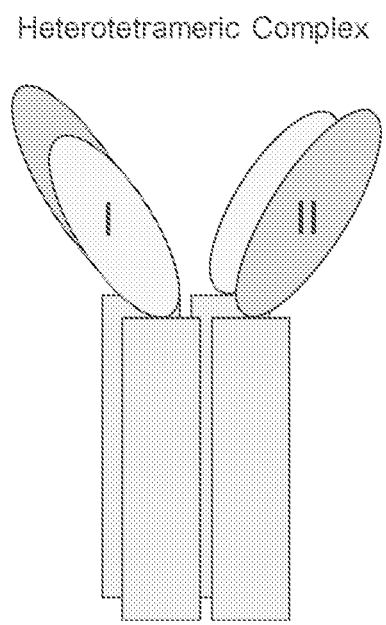
Figure 2:
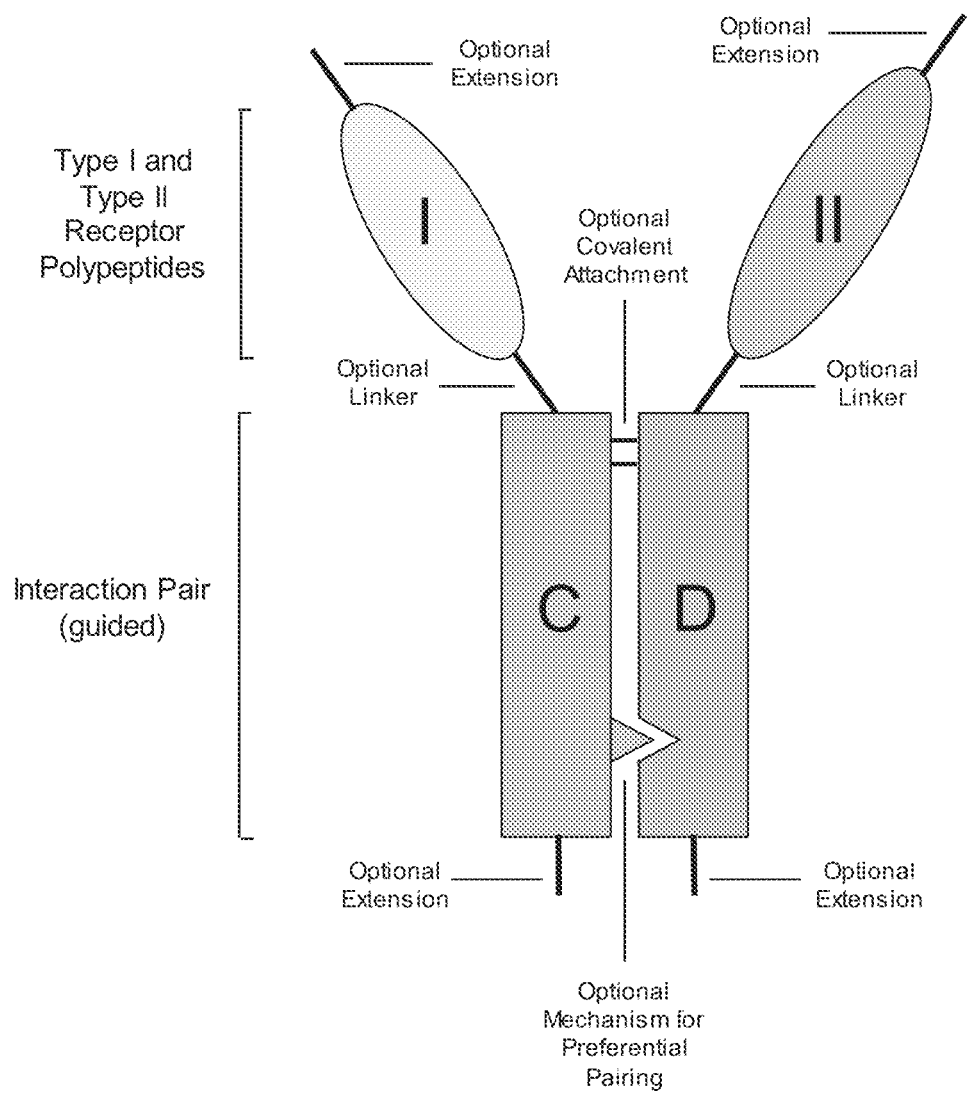
FIG. 2 shows a schematic example of a heteromeric protein complex comprising a type I receptor polypeptide (indicated as "I") (e.g. a polypeptide that is at least 80%, 85%, 90%, 95%, 97%, 98%, 99% or 100% identical to an extracellular domain of an ALK1, ALK2, ALK3, ALK4, ALK5, ALK6 or ALK7 protein from humans or other species such as those described herein, e.g., SEQ ID Nos: 14, 15, 124, 126, 413, 414, 18, 19, 136, 138, 421, 422, 22, 23, 115, 117, 407, 408, 26, 27, 83, 84, 104, 106, 403, 404, 30, 31, 87, 88, 139, 141, 423, 424, 34, 35, 91, 92, 142, 144, 425, 426, 38, 39, 301, 302, 305, 306, 309, 310, 313, 112, 114, 405, and 406) and a type II receptor polypeptide (indicated as "II") (e.g. a polypeptide that is at least 80%, 85%, 90%, 95%, 97%, 98%, 99% or 100% identical to an extracellular domain of an ActRIIA, ActRIIB, MISRII, BMPRII, or TGFBRII protein from humans or other species such as those described herein, e.g., 9, 10, 11, 118, 120, 409, 410, 1, 2, 3, 4, 5, 6, 100, 102, 401, 402, 46, 47, 71, 72, 121, 123, 411, 412, 50, 51, 75, 76, 79, 80, 42, 43, 67, 68, 127, 129, 130, 132, 415, 416, 417, and 418). In the illustrated embodiment, the type I receptor polypeptide is part of a fusion polypeptide that comprises a first member of an interaction pair ("C"), and the type II receptor polypeptide is part of a fusion polypeptide that comprises a second member of an interaction pair ("D"). In each fusion polypeptide, a linker may be positioned between the type I or type II receptor polypeptide and the corresponding member of the interaction pair. The first and second members of the interaction pair (C, D) may be a guided (asymmetric) pair, meaning that the members of the pair associate preferentially with each other rather than self-associate, or the interaction pair may be unguided, meaning that the members of the pair may associate with each other or self-associate without substantial preference and may have the same or different amino acid sequences. Traditional Fc fusion proteins and antibodies are examples of unguided interaction pairs, whereas a variety of engineered Fc domains have been designed as guided (asymmetric) interaction pairs [e.g., Spiess et al (2015) Molecular Immunology 67(2A): 95-106].

2. TGF-beta Superfamily Type I Receptor and Type II Receptor Polypeptides and Heteromultimers Thereof In certain aspects, the present disclosure relates to heteromultimers comprising one or more TGF-beta superfamily type I receptor polypeptides (e.g., ALK1, ALK2, ALK3, ALK4, ALK5, ALK6, and ALK7 proteins from humans or other species such as those described herein, e.g., SEQ ID NOs: 14, 15, 124, 126, 413, 414, 18, 19, 136, 138, 421, 422, 22, 23, 115, 117, 407, 408, 26, 27, 83, 84, 104, 106, 403, 404, 30, 31, 87, 88, 139, 141, 423, 424, 34, 35, 91, 92, 142, 144, 425, 426, 38, 39, 301, 302, 305, 306, 309, 310, 313, 112, 114, 405, and 406) and one or more TGF-beta superfamily type II receptor polypeptides (e.g., ActRIIA, ActRIIB, TGFBRII, BMPRII, and MISRII proteins from humans or other species such as those described herein, e.g., SEQ ID NOs: 9, 10, 11, 118, 120, 409, 410, 1, 2, 3, 4, 5, 6, 100, 102, 401, 402, 46, 47, 71, 72, 121, 123, 411, 412, 50, 51, 75, 76, 79, 80, 42, 43, 67, 68, 127, 129, 130, 132, 415, 416, 417, and 418); heteromultimers comprising at least two different TGF-beta superfamily type I receptor polypeptides (e.g., ALK1, ALK2, ALK3, ALK4, ALK5, ALK6, and ALK7 proteins from humans or other species such as those described herein, e.g., SEQ ID NOs: 14, 15, 124, 126, 413, 414, 18, 19, 136, 138, 421, 422, 22, 23, 115, 117, 407, 408, 26, 27, 83, 84, 104, 106, 403, 404, 30, 31, 87, 88, 139, 141, 423, 424, 34, 35, 91, 92, 142, 144, 425, 426, 38, 39, 301, 302, 305, 306, 309, 310, 313, 112, 114, 405, and 406); and heteromultimer complexes comprising at least two different TGF-beta superfamily type II receptor polypeptides (e.g., ActRIIA, ActRIIB, TGFBRII, BMPRII, and MISRII proteins from humans or other species such as those described herein, e.g., SEQ ID NOs: 9, 10, 11, 118, 120, 409, 410, 1, 2, 3, 4, 5, 6, 100, 102, 401, 402, 46, 47, 71, 72, 121, 123, 411, 412, 50, 51, 75, 76, 79, 80, 42, 43, 67, 68, 127, 129, 130, 132, 415, 416, 417, and 418), which are generally referred to herein as "heteromers", "heteromultimer complexes" or "heteromultimers". Preferably, heteromultimers are soluble, e.g., a heteromultimer comprises a soluble portion (domain) of at least one TGFβ superfamily type I receptor polypeptide and a soluble portion of at least one TGFβ superfamily type II receptor polypeptide. In general, the extracellular domains of TGFβ superfamily type I and type II receptors correspond to a soluble portion of the type I and type II receptor. Therefore, in some embodiments, heteromultimers of the disclosure comprise an extracellular domain of a TGFβ superfamily type I receptor polypeptide (e.g., one or more ALK1, ALK2, ALK3, ALK4, ALK5, ALK6, and/or ALK7 receptor extracellular domains) and/or an extracellular domain of a TGFβ superfamily type II receptor polypeptide (e.g., one or more ActRIIA, ActRIIB, TGFBRII, BMPRII, and/or MISRII receptor extracellular domains). Exemplary extracellular domains of ALK1, ALK2, ALK3, ALK4, ALK5, ALK6, ALK7, ActRIIA, ActRIIB, TGFBRII, BMPRII, and MISRII are disclosed herein and such sequences, as well as fragments, functional variants, and modified forms thereof, may be used in accordance with the inventions of the present disclosure (e.g., heteromultimers compositions and uses thereof). Heteromultimers of the disclosure include, e.g., heterodimers, heterotrimers, heterotetramers, and higher order oligomeric structures. See, e.g., FIGS. 1, 2, and 15. In certain preferred embodiments, heteromultimers of the disclosure are heterodimers.

A defining structural motif known as a three-finger toxin fold is important for ligand binding by type I and type II receptors and is formed by 10, 12, or 14 conserved cysteine residues located at varying positions within the extracellular domain of each monomeric receptor. See, e.g., Greenwald et al. (1999) Nat Struct Biol 6:18-22; Hinck (2012) FEBS Lett 586:1860-1870. The core ligand-binding domains of TGFβ superfamily receptors, as demarcated by the outermost of these conserved cysteines, corresponds to positions 29-109 of SEQ ID NO: 1 (ActRIIB precursor); positions 30-110 of SEQ ID NO: 9 (ActRIIA precursor); positions 34-95 of SEQ ID NO: 14 (ALK1 precursor); positions 35-99 of SEQ ID NO: 18 (ALK2 precursor); positions 61-130 of SEQ ID NO: 22 (ALK3 precursor); positions 34-101 of SEQ ID NOs: 26 and 83 (ALK4 precursors); positions 36-106 of SEQ ID NOs: 30 and 87 (ALK5 precursors); positions 32-102 of SEQ ID NO: 34 (ALK6 isoform B precursor); positions 28-92 of SEQ ID NOs: 38, 305, and 309 (ALK7 precursors); positions 51-143 of SEQ ID NO: 42 (TGFBRII isoform B precursor); positions 34-123 of SEQ ID NO: 46 and 71 (BMPRII precursors); positions 24-116 of SEQ ID NO: 50, 75, and 79 (MISRII precursors); positions 44-168 of SEQ ID NO: 67 (TGFBRII isoform A precursor); and positions 62-132 of SEQ ID NO: 91 (ALK6 isoform A precursor). The structurally less-ordered amino acids flanking these cysteine-demarcated core sequences can be truncated on either terminus without necessarily altering ligand binding. Exemplary extracellular domains for N-terminal and/or C-terminal truncation include SEQ ID NOs: 2, 3, 5, 6, 10, 11, 15, 19, 23, 27, 31, 35, 39, 43, 47, 51, 68, 72, 76, 80, 84, 88, 92, 302, 306, 310, and 313.

In preferred embodiments, heteromultimers of the disclosure bind to and/or inhibit (antagonize) activity of one or more TGF-beta superfamily ligands including, but not limited to, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty. In particular, heteromultimers of the disclosure may be used to antagonize signaling transduction (e.g., Smad 2/3 and/or Smad 1/5/8 signaling) initiated by one or more TGFβ superfamily ligands, which may be determined, for example, using a cell-based assay such as those described herein. As described herein, such antagonist heteromultimers may be useful in the treatment or prevention of various disorders/conditions associated with, e.g., muscle loss, insufficient muscle growth, neurodegeneration, bone loss, reduced bone density and/or mineralization, insufficient bone growth, and/or obesity. In some embodiments, heteromultimers of the disclosure have different ligand binding specificities/profiles in comparison to their corresponding homomultimer complex (e.g., an ALK4:ActRIIB heterodimer vs. a corresponding ActRIIB or ALK4 homodimer).

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. Examples of such variant ActRIIB polypeptides are provided throughout the present disclosure as well as in International Patent Application Publication Nos. WO 2006/012627, WO 2008/097541, and Wo 2010/151426, which are incorporated herein by reference in their entirety.

A human ActRIIB precursor protein sequence is as follows:

(SEQ ID NO: 1)
```
  1 MTAPWVALAL LWGSLCAGSG RGEAETRECI YYNANWELER TNQSGLERCE
 51 GEQDKRLHCY ASWRNSSGTI ELVKKGCWLD DFNCYDRQEC VATEENPQVY
101 FCCCEGNFCN ERFTHLPEAG GPEVTYEPPP TAPTLLTVLA YSLLPIGGLS
151 LIVLLAFWMY RHRKPPYGHV DIHEDPGPPP PSPLVGLKPL QLLEIKARGR
201 FGCVWKAQLM NDFVAVKIFP LQDKQSWQSE REIFSTPGMK HENLLQFIAA
251 EKRGSNLEVE LWLITAFHDK GSLTDYLKGN IITWNELCHV AETMSRGLSY
301 LHEDVPWCRG EGHKPSIAHR DFKSKNVLLK SDLTAVLADF GLAVRFEPGK
351 PPGDTHGQVG TRRYMAPEVL EGAINFQRDA FLRIDMYAMG LVLWELVSRC
401 KAADGPVDEY MLPFEEEIGQ HPSLEELQEV VVHKKMRPTI KDHWLKHPGL
451 AQLCVTIEEC WDHDAEARLS AGCVEERVSL IRRSVNGTTS DCLVSLVTSV
501 TNVDLPPKES SI
```

The signal peptide is indicated with a single underline; an extracellular domain is indicated in bold font; and the potential, endogenous N-linked glycosylation sites are indicated with a double underline.

A processed extracellular ActRIIB polypeptide sequence is as follows:

(SEQ ID NO: 2)
GRGEAETRECIYYNANWELERTNQSGLERCEGEQDKRLHCYASWRNSSG
TIELVKKGCWLDDFNCYDRQECVATEENPQVYFCCCEGNFCNERFTHLP
EAGGPEVTYEPPPTAPT.

In some embodiments, the protein may be produced with an "SGR . . . " sequence at the N-terminus. The C-terminal "tail" of the extracellular domain is indicated by a single underline. The sequence with the "tail" deleted (a Δ15 sequence) is as follows:

(SEQ ID NO: 3)
GRGEAETRECIYYNANWELERTNQSGLERCEGEQDKRLHCYASWRNSSG
TIELVKKGCWLDDFNCYDRQECVATEENPQVYFCCCEGNFCNERFTHLP
EA.

A form of ActRIIB with an alanine at position 64 of SEQ ID NO: 1 (A64) is also reported in the literature. See, e.g., Hilden et al. (1994) Blood, 83(8): 2163-2170. Applicants have ascertained that an ActRIIB-Fc fusion protein comprising an extracellular domain of ActRIIB with the A64 substitution has a relatively low affinity for activin and GDF11. By contrast, the same ActRIIB-Fc fusion protein with an arginine at position 64 (R64) has an affinity for activin and GDF11 in the low nanomolar to high picomolar range. Therefore, sequences with an R64 are used as the "wild-type" reference sequence for human ActRIIB in this disclosure.

A form of ActRIIB with an alanine at position 64 is as follows:

(SEQ ID NO: 4)
```
  1 MTAPWVALAL LWGSLCAGSG RGEAETRECI YYNANWELER TNQSGLERCE

51 GEQDKRLHCY ASWANSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI
```

The signal peptide is indicated by single underline and the extracellular domain is indicated by bold font.

A processed extracellular ActRIIB polypeptide sequence of the alternative A64 form is as follows:

(SEQ ID NO: 5)
GRGEAETRECIYYNANWELERTNQSGLERCEGEQDKRLHCYASWANSSG

TIELVKKGCWLDDFNCYDRQECVATEENPQVYFCCCEGNFCNERFTHLP

EAGGPEVTYEPPPTAPT

In some embodiments, the protein may be produced with an "SGR . . . " sequence at the N-terminus. The C-terminal "tail" of the extracellular domain is indicated by single underline. The sequence with the "tail" deleted (a A15 sequence) is as follows:

(SEQ ID NO: 6)
GRGEAETRECIYYNANWELERTNQSGLERCEGEQDKRLHCYASWANSSG

TIELVKKGCWLDDFNCYDRQECVATEENPQVYFCCCEGNFCNERFTHLP

EA

A nucleic acid sequence encoding the human ActRIIB precursor protein is shown in SEQ ID NO: 7, representing nucleotides 25-1560 of Genbank Reference Sequence NM_001106.3, which encode amino acids 1-513 of the ActRIIB precursor. The sequence as shown in SEQ ID NO: 7 provides an arginine at position 64 and may be modified to provide an alanine instead. A nucleic acid sequence encoding a processed extracellular human ActRIIB polypeptide is shown in SEQ ID NO: 8. The sequence of SEQ ID NO: 8 provides an arginine at position 64, and may be modified to provide an alanine instead.

An alignment of the amino acid sequences of human ActRIIB extracellular domain and human ActRIIA extracellular domain are illustrated in FIG. 3. This alignment indicates amino acid residues within both receptors that are believed to directly contact ActRII ligands. For example, the composite ActRII structures indicated that the ActRIIB-ligand binding pocket is defined, in part, by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated.

Figure 4:
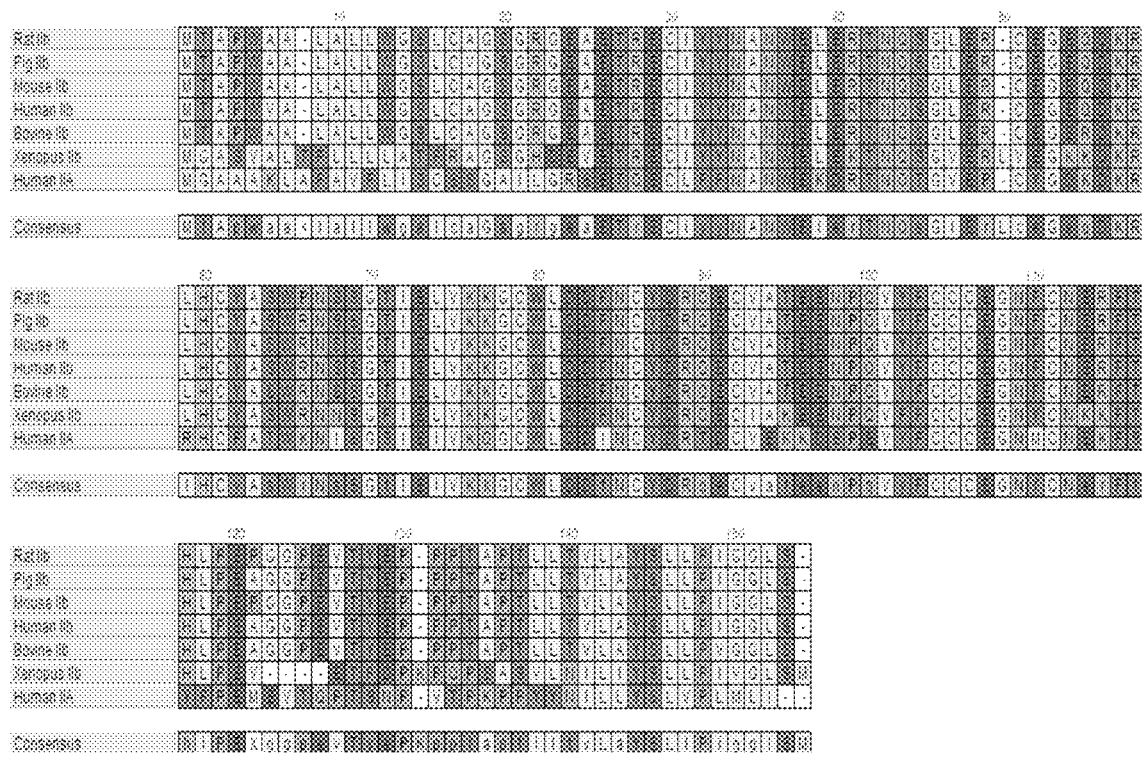
FIG. 4 shows a multiple sequence alignment of various vertebrate ActRIIB precursor proteins without their intracellular domains (SEQ ID NOs: 501, 502, 503, 504, 505, and 506, respectively), human ActRIIA precursor protein without its intracellular domain (SEQ ID NO: 507), and a consensus ActRII precursor protein (SEQ ID NO: 508).

In addition, ActRIIB is well-conserved among vertebrates, with large stretches of the extracellular domain completely conserved. For example, FIG. 4 depicts a multi-sequence alignment of a human ActRIIB extracellular domain compared to various ActRIIB orthologs. Many of the ligands that bind to ActRIIB are also highly conserved. Accordingly, from these alignments, it is possible to predict key amino acid positions within the ligand-binding domain that are important for normal ActRIIB-ligand binding activities as well as to predict amino acid positions that are likely to be tolerant of substitution without significantly altering normal ActRIIB-ligand binding activities. Therefore, an active, human ActRIIB variant polypeptide useful in accordance with the presently disclosed methods may include one or more amino acids at corresponding positions from the sequence of another vertebrate ActRIIB, or may include a residue that is similar to that in the human or other vertebrate sequences. Without meaning to be limiting, the following examples illustrate this approach to defining an active ActRIIB variant. L46 in the human extracellular domain (SEQ ID NO: 2) is a valine in *Xenopus* ActRIIB (SEQ ID NO: 506), and so this position may be altered, and optionally may be altered to another hydrophobic residue, such as V, I or F, or a non-polar residue such as A. E52 in the human extracellular domain is a K in *Xenopus*, indicating that this site may be tolerant of a wide variety of changes, including polar residues, such as E, D, K, R, H, S, T, P, G, Y and probably A. T93 in the human extracellular domain is a K in *Xenopus*, indicating that a wide structural variation is tolerated at this position, with polar residues favored, such as S, K, R, E, D, H, G, P, G and Y. F108 in the human extracellular domain is a Y in *Xenopus*, and therefore Y or other hydrophobic group, such as I, V or L should be tolerated. E111 in the human extracellular domain is K in *Xenopus*, indicating that charged residues will be tolerated at this position, including D, R, K and H, as well as Q and N. R112 in the human extracellular domain is K in *Xenopus*, indicating that basic residues are tolerated at this position, including R and H. A at position 119 in the human extracellular domain is relatively poorly conserved, and appears as P in rodents and V in *Xenopus*, thus essentially any amino acid should be tolerated at this position.

Moreover, ActRII proteins have been characterized in the art in terms of structural and functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709,605, 7,612,041, and 7,842,663]. In addition to the teachings herein, these references provide amply guidance for how to generate ActRIIB variants that retain one or more normal activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRIIB, as demarcated by the outermost of these conserved cysteines, corresponds to positions 29-109 of SEQ ID NO: 1 (ActRIIB precursor). Thus, the structurally less-ordered amino acids flanking these cysteine-demarcated core sequences can be truncated by about 1, 2, 3, 4, 5, 6, 7, 8, 9, 10, 11, 12, 13, 14, 15, 16, 17, 18, 19, 20, 21, 22, 23, 24, 25, 26, 27, or 28 residues at the N-terminus and/or by about 1, 2, 3, 4, 5, 6, 7, 8, 9, 10, 11, 12, 13, 14, 15, 16, 17, 18, 19, 20, 21, 22, 23, 24, or 25 residues a the C-terminus without necessarily altering ligand binding. Exemplary ActRIIB extracellular domains for N-terminal and/or C-terminal truncation include SEQ ID NOs: 2, 3, 5, and 6.

Attisano et al. showed that a deletion of the proline knot at the C-terminus of the extracellular domain of ActRIIB reduced the affinity of the receptor for activin. An ActRIIB-Fc fusion protein containing amino acids 20-119 of present SEQ ID NO: 1, "ActRIIB(20-119)-Fc", has reduced binding to GDF11 and activin relative to an ActRIIB(20-134)-Fc, which includes the proline knot region and the complete juxtamembrane domain (see, e.g., U.S. Pat. No. 7,842,663). However, an ActRIIB(20-129)-Fc protein retains similar, but somewhat reduced activity, relative to the wild-type, even though the proline knot region is disrupted.

Thus, ActRIIB extracellular domains that stop at amino acid 134, 133, 132, 131, 130 and 129 (with respect to SEQ ID NO: 1) are all expected to be active, but constructs stopping at 134 or 133 may be most active. Similarly, mutations at any of residues 129-134 (with respect to SEQ ID NO: 1) are not expected to alter ligand-binding affinity by large margins. In support of this, it is known in the art that mutations of P129 and P130 (with respect to SEQ ID NO: 1) do not substantially decrease ligand binding. Therefore, an ActRIIB polypeptide of the present disclosure may end as early as amino acid 109 (the final cysteine), however, forms ending at or between 109 and 119 (e.g., 109, 110, 111, 112, 113, 114, 115, 116, 117, 118, or 119) are expected to have reduced ligand binding. Amino acid 119 (with respect to present SEQ ID NO: 1) is poorly conserved and so is readily altered or truncated. ActRIIB polypeptides ending at 128 (with respect to SEQ ID NO: 1) or later should retain ligand-binding activity. ActRIIB polypeptides ending at or between 119 and 127 (e.g., 119, 120, 121, 122, 123, 124, 125, 126, or 127), with respect to SEQ ID NO: 1, will have an intermediate binding ability. Any of these forms may be desirable to use, depending on the clinical or experimental setting.

At the N-terminus of ActRIIB, it is expected that a protein beginning at amino acid 29 or before (with respect to SEQ ID NO: 1) will retain ligand-binding activity. Amino acid 29 represents the initial cysteine. An alanine-to-asparagine mutation at position 24 (with respect to SEQ ID NO: 1) introduces an N-linked glycosylation sequence without substantially affecting ligand binding [U.S. Pat. No. 7,842,663]. This confirms that mutations in the region between the signal cleavage peptide and the cysteine cross-linked region, corresponding to amino acids 20-29, are well tolerated. In particular, ActRIIB polypeptides beginning at position 20, 21, 22, 23, and 24 (with respect to SEQ ID NO: 1) should retain general ligand-biding activity, and ActRIIB polypeptides beginning at positions 25, 26, 27, 28, and 29 (with respect to SEQ ID NO: 1) are also expected to retain ligand-biding activity. It has been demonstrated, e.g., U.S. Pat. No. 7,842,663, that, surprisingly, an ActRIIB construct beginning at 22, 23, 24, or 25 will have the most activity.

Taken together, a general formula for an active portion (e.g., ligand-binding portion) of ActRIIB comprises amino acids 29-109 of SEQ ID NO: 1. Therefore ActRIIB polypeptides may, for example, comprise an amino acid sequence that is at least 70%, 75%, 80%, 85%, 86%, 87%, 88%, 89%9, 90%, 91%, 92%, 93%, 94%, 95%, 96%, 97%, 98%, 99%, or 100% identical to a portion of ActRIIB beginning at a residue corresponding to any one of amino acids 20-29 (e.g., beginning at any one of amino acids 20, 21, 22, 23, 24, 25, 26, 27, 28, or 29) of SEQ ID NO: 1 and ending at a position corresponding to any one amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. Other examples include polypeptides that begin at a position from 20-29 (e.g., any one of positions 20, 21, 22, 23, 24, 25, 26, 27, 28, or 29) or 21-29 (e.g., any one of positions 21, 22, 23, 24, 25, 26, 27, 28, or 29) of SEQ ID NO: 1 and end at a position from 119-134 (e.g., any one of positions 119, 120, 121, 122, 123, 124, 125, 126, 127, 128, 129, 130, 131, 132, 133, or 134), 119-133 (e.g., any one of positions 119, 120, 121, 122, 123, 124, 125, 126, 127, 128, 129, 130, 131, 132, or 133), 129-134 (e.g., any one of positions 129, 130, 131, 132, 133, or 134), or 129-133 (e.g., any one of positions 129, 130, 131, 132, or 133) of SEQ ID NO: 1. Other examples include constructs that begin at a position from 20-24 (e.g., any one of positions 20, 21, 22, 23, or 24), 21-24 (e.g., any one of positions 21, 22, 23, or 24), or 22-25 (e.g., any one of positions 22, 22, 23, or 25) of SEQ ID NO: 1 and end at a position from 109-134 (e.g., any one of positions 109, 110, 111, 112, 113, 114, 115, 116, 117, 118, 119, 120, 121, 122, 123, 124, 125, 126, 127, 128, 129, 130, 131, 132, 133, or 134), 119-134 (e.g., any one of positions 119, 120, 121, 122, 123, 124, 125, 126, 127, 128, 129, 130, 131, 132, 133, or 134) or 129-134 (e.g., any one of positions 129, 130, 131, 132, 133, or 134) of SEQ ID NO: 1. Variants within these ranges are also contemplated, particularly those having at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 1.

The variations described herein may be combined in various ways. In some embodiments, ActRIIB variants comprise no more than 1, 2, 5, 6, 7, 8, 9, 10 or 15 conservative amino acid changes in the ligand-binding pocket, and zero, one, or more non-conservative alterations at positions 40, 53, 55, 74, 79 and/or 82 in the ligand-binding pocket. Sites outside the binding pocket, at which variability may be particularly well tolerated, include the amino and carboxy termini of the extracellular domain (as noted above), and positions 42-46 and 65-73 (with respect to SEQ ID NO: 1). An asparagine-to-alanine alteration at position 65 (N65A) actually improves ligand binding in the A64 background, and is thus expected to have no detrimental effect on ligand binding in the R64 background [U.S. Pat. No. 7,842,663]. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64 [U.S. Pat. No. 7,842,663]. Additionally, the results of the mutagenesis program described in the art indicate that there are amino acid positions in ActRIIB that are often beneficial to conserve. With respect to SEQ ID NO: 1, these include position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, the disclosure provides a framework of amino acids that may be conserved in ActRIIB polypeptides. Other positions that may be desirable to conserve are as follows: position 52 (acidic amino acid), position 55 (basic amino acid), position 81 (acidic), 98 (polar or charged, particularly E, D, R or K), all with respect to SEQ ID NO: 1.

In certain embodiments, the disclosure relates to heteromultimers that comprise at least one ActRIIB polypeptide, which includes fragments, functional variants, and modified forms thereof. Preferably, ActRIIB polypeptides for use in accordance with the disclosure are soluble (e.g., an extracellular domain of ActRIIB). In other preferred embodiments, ActRIIB polypeptides for use in accordance with the disclosure bind to one or more TGF-beta superfamily ligands. Therefore, in some embodiments, ActRIIB polypeptides for use in accordance with the disclosure inhibit (antagonize) activity (e.g., inhibition of Smad signaling) of one or more TGF-beta superfamily ligands. In some embodiments, heteromultimers of the disclosure comprise at least one ActRIIB polypeptide that comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to amino acids 20-29 (e.g., beginning at any one of amino acids 20, 21, 22, 23, 24, 25, 26, 27, 28, or 29) of SEQ ID NO: 1 and ending at a position corresponding to amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. In certain preferred embodiments, heteromultimers of the disclosure comprise at least one ActRIIB polypeptide that comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 29-109 of SEQ ID NO: 1 In other preferred embodiments, heteromultimers of the disclosure comprise at least one ActRIIB polypeptide that comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 25-131 of SEQ ID NO: 1 In some embodiments, heteromultimers of the disclosure comprise at least one ActRIIB polypeptide that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 4, 5, 6, 100, 102, 401, and 402. In certain embodiments, heteromultimers of the disclosure comprise at least one ActRIIB polypeptide wherein the amino acid position corresponding to L79 of SEQ ID NO: 1 is not an acidic amino acid (i.e., is not a naturally occurring D or E amino acid residue or artificial acidic amino acid).

In certain embodiments, the present disclosure relates to a protein complex comprising an ActRIIA polypeptide. As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety.

The human ActRIIA precursor protein sequence is as follows:

```
                                                          (SEQ ID NO: 9)
  1 MGAAAKLAFA VFLISCSSGA ILGRSETQEC LFFNANWEED RTNQTGVEPC

51 YGDKDKRRHC FATWKNISGS IEIVKQGCWL DDINCYDRTD CVEKKDSPEV

101 YFCCCEGNMC NEKFSYFPEM EVTQPTSNPV TPKPPYYNIL LYSLVPLMLI

151 AGIVICAFWV YRHHKMAYPP VLVPTQDPGP PPPSPLLGLK PLQLLEVKAR

201 GRFGCVWKAQ LLNEYVAVKI FPIQDKQSWQ NEYEVYSLPG MKHENILQFI

251 GAEKRGTSVD VDLWLITAFH EKGSLSDFLK ANVVSWNELC HIAETMARGL

301 AYLHEDIPGL KDGHKPAISH RDIKSKNVLL KNNLTACIAD FGLALKFEAG

351 KSAGDTHGQV GTRRYMAPEV LEGAINFQRD AFLRIDMYAM GLVLWELASR

401 CTAADGPVDE YMLPFEEEIG QHPSLEDMQE VVVHKKKRPV LRDYWQKHAG

451 MAMLCETIEE CWDHDAEARL SAGCVGERIT QMQRLTNIIT TEDIVTVVTM

501 VTNVDFPPKE SSL
```

The signal peptide is indicated by a single underline; the extracellular domain is indicated in bold font; and the potential, endogenous N-linked glycosylation sites are indicated by a double underline.

The processed extracellular human ActRIIA polypeptide sequence is as follows:

(SEQ ID NO: 10)
ILGRSETQECLFFNANWEKDRTNQTGVEPCYGDKDKRRHCFATWKNISG

SIEIVKQGCWLDDINCYDRTDCVEKKDSPEVYFCCCEGNMCNEKFSYFP

EMEVTQPTSNPVTPKPP

The C-terminal "tail" of the extracellular domain is indicated by a single underline. The sequence with the "tail" deleted (a A15 sequence) is as follows:

(SEQ ID NO: 11)
ILGRSETQECLFFNANWEKDRTNQTGVEPCYGDKDKRRHCFATWKNISG

SIEIVKQGCWLDDINCYDRTDCVEKKDSPEVYFCCCEGNMCNEKFSYFP

EM

A nucleic acid sequence encoding the human ActRIIA precursor protein is shown in SEQ ID NO: 12, corresponding to nucleotides 159-1700 of Genbank Reference Sequence NM_001616.4. A nucleic acid sequence encoding a processed extracellular ActRIIA polypeptide is as shown in SEQ ID NO: 13.

A general formula for an active (e.g., ligand binding) ActRIIA polypeptide is one that comprises a polypeptide that starts at amino acid 30 and ends at amino acid 110 of SEQ ID NO: 9. Accordingly, ActRIIA polypeptides of the present disclosure may comprise a polypeptide that is at least 80%, 85%, 90%, 95%, 96%, 97%, 98%, 99%, or 100% identical to amino acids 30-110 of SEQ ID NO: 9. Optionally, ActRIIA polypeptides of the present disclosure comprise a polypeptide that is at least 80%, 85%, 90%, 95%, 96%, 97%, 98%, 99%, or 100% identical to amino acids amino acids 12-82 of SEQ ID NO: 9 optionally beginning at a position ranging from 1-5 (e.g., 1, 2, 3, 4, or 5) or 3-5 (e.g., 3, 4, or 5) and ending at a position ranging from 110-116 (e.g., 110, 111, 112, 113, 114, 115, or 116) or 110-115 (e.g., 110, 111, 112, 113, 114, or 115), respectively, and comprising no more than 1, 2, 5, 10 or 15 conservative amino acid changes in the ligand binding pocket, and zero, one or more non-conservative alterations at positions 40, 53, 55, 74, 79 and/or 82 in the ligand-binding pocket with respect to SEQ ID NO: 9.

In certain embodiments, the disclosure relates to heteromultimers that comprise at least one ActRIIA polypeptide, which includes fragments, functional variants, and modified forms thereof. Preferably, ActRIIA polypeptides for use in accordance with inventions of the disclosure (e.g., heteromultimers comprising an ActRIIA polypeptide and uses thereof) are soluble (e.g., an extracellular domain of ActRIIA). In other preferred embodiments, ActRIIA polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ActRIIA polypeptide that is at least 70%, 75%, 80%, 85%, 90%, 95%, 97%, 98%, 99%, or 100% identical to the amino acid sequence of any one of SEQ ID NOs: 9, 10, 11, 118, 120, 409, or 410. In some embodiments, heteromultimers of the disclosure comprise at least one ActRIIA polypeptide that is at least 70%, 75%, 80%, 85%, 90%, 95%, 97%, 98%, 99%, or 100% identical to the amino acid sequence of any one of SEQ ID NOs: 9, 10, 11, 118, 120, 409, or 410.

In certain aspects, the present disclosure relates to protein complexes that comprise a TGFBRII polypeptide. As used herein, the term "TGFBRII" refers to a family of transforming growth factor-beta receptor II (TGFBRII) proteins from any species and variants derived from such proteins by mutagenesis or other modification. Reference to TGFBRII herein is understood to be a reference to any one of the currently identified forms. Members of the TGFBRII family are generally transmembrane proteins, composed of a ligand-binding extracellular domain with a cysteine-rich region, a transmembrane domain, and a cytoplasmic domain with predicted serine/threonine kinase activity.

The term "TGFBRII polypeptide" includes polypeptides comprising any naturally occurring polypeptide of a TGFBRII family member as well as any variants thereof (including mutants, fragments, fusions, and peptidomimetic forms) that retain a useful activity.

A human TGFBRII precursor protein sequence (NCBI Ref Seq NP_003233.4) is as follows:

(SEQ ID NO: 42)
```
  1 MGRGLLRGLW PLHIVLWTRI ASTIPPHVQK SVNNDMIVTD NNGAVKFPQL

51 CKFCDVRFST CDNQKSCMSN CSITSICEKP QEVCVAVWRK NDENITLETV

101 CHDPKLPYHD FILEDAASPK CIMKEKKKPG ETFFMCSCSS DECNDNIIFS

151 EEYNTSNPDL LLVIFQVTGI SLLPPLGVAI SVIIIFYCYR VNRQQKLSST

201 WETGKTRKLM EFSEHCAIIL EDDRSDISST CANNINHNTE LLPIELDTLV

251 GKGRFAEVYK AKLKQNTSEQ FETVAVKIFP YEEYASWKTE KDIFSDINLK

301 HENILQFLTA EERKTELGKQ YWLITAFHAK GNLQEYLTRH VISWEDLRKL

351 GSSLARGIAH LHSDHTPCGR PKMPIVHRDL KSSNILVKND LTCCLCDFGL

401 SLRLDPTLSV DDLANSGQVG TARYMAPEVL ESRMNLENVE SFKQTDVYSM

451 ALVLWEMTSR CNAVGEVKDY EPPFGSKVRE HPCVESMKDN VLRDRGRPEI

501 PSFWLNHQGI QMVCETLTEC WDHDPEARLT AQCVAERFSE LEHLDRLSGR

551 SCSEEKIPED GSLNTTK
```

The signal peptide is indicated by a single underline and the extracellular domain is indicated in bold font.

A processed extracellular TGFBRII polypeptide sequence is as follows:

```
                                            (SEQ ID NO: 43)
TIPPHVQKSVNNDMIVTDNNGAVKFPQLCKFCDVRFSTCDNQKSCMSNC

SITSICEKPQEVCVAVWRKNDENITLETVCHDPKLPYHDFILEDAASPK

CIMKEKKKPGETFFMCSCSSDECNDNIIFSEEYNTSNPDLLLVIFQ
```

A nucleic acid sequence encoding TGFBRII precursor protein is shown in SEQ ID NO:44, corresponding to nucleotides 383-2083 of Genbank Reference Sequence NM_003242.5. A nucleic acid sequence encoding a processed extracellular TGFBRII polypeptide is shown in SEQ ID NO: 45.

An alternative isoform of TGFBRII, isoform A (NP_001020018.1), is as follows:

```
                                             (SEQ ID NO: 67)
  1  MGRGLLRGLW  PLHIVLWTRI  ASTIPPHVQK  SDVEMEAQKD  EIICPSCNRT

51  AHPLRHINND  MIVTDNNGAV  KFPQLCKFCD  VRFSTCDNQK  SCMSNCSITS

101  ICEKPQEVCV  AVWRKNDENI  TLETVCHDPK  LPYHDFILED  AASPKCIMEE

151  KKKPGETFFM  CSCSSDECND  NIIFSEEYNT  SNPDLLLVIF  QVTGISLLPP

201  LGVAISVIII  FYCYRVNRQQ  KLSSTWETGK  TRKLMEFSEH  CAIILEDDRS

251  DISSTCANNI  NHNTELLPIE  LDTLVGKGRF  AEVYKAKLKQ  NTSEQFETVA

301  VKIFPYEEYA  SWKTEKDIFS  DINLKHENIL  QFLTAEERKT  ELGKQYWLIT

351  AFHAKGNLQE  YLTRHVISWE  DLRKLGSSLA  RGIAHLHSDH  TPCGRPKMPI

401  VHRDLKSSNI  LVKNDLTCCL  CDFGLSLRLD  PTLSVDDLAN  SGQVGTARYM

451  APEVLESRMN  LENVESFKQT  DVYSMALVLW  EMTSRCNAVG  EVKDYEPPFG

501  SKVREHPCVE  SMKDNVLRDR  GRPEIPSFWL  NHQGIQMVCE  TLTECWDHDP

551  EARLTAQCVA  ERFSELEHLD  RLSGRSCSEE  KIPEDGSLNT  TK
```

The signal peptide is indicated by a single underline and the extracellular domain is indicated in bold font.

A processed extracellular TGFBRII polypeptide sequence (isoform A) is as follows:

```
                                            (SEQ ID NO: 68)
TIPPHVQKSDVEMEAQKDEIICPSCNRTAHPLRHINNDMIVTDNNGAVK

FPQLCKFCDVRFSTCDNQKSCMSNCSITSICEKPQEVCVAVWRKNDENI

TLETVCHDPKLPYHDFILEDAASPKCIMKEKKKPGETFFMCSCSSDECN

DNIIFSEEYNTSNPDLLLVIFQ
```

A nucleic acid sequence encoding the TGFBRII precursor protein (isoform A) is shown in SEQ ID NO: 69, corresponding to nucleotides 383-2158 of Genbank Reference Sequence NM_001024847.2. A nucleic acid sequence encoding the processed extracellular TGFBRII polypeptide (isoform A) is shown in SEQ ID NO: 70.

Either of the foregoing TGFBRII isoforms (SEQ ID NOs: 42, 43, 67, and 68) could incorporate an insertion of 36 amino acids (SEQ ID NO: 95) between the pair of glutamate residues (positions 151 and 152 of SEQ ID NO: 42; positions 129 and 130 of SEQ ID NO: 43; positions 176 and 177 of SEQ ID NO: 67; or positions 154 and 155 of SEQ ID NO: 68) located near the C-terminus of the TGFβRII ECD, as occurs naturally in the TGFβRII isoform C (Konrad et al., BMC Genomics 8:318, 2007).

```
                                            (SEQ ID NO: 95)
   GRCKIRHIGS  NNRLQRSTCQ  NTGWESAHVM  KTPGFR
```

In certain embodiments, the disclosure relates to heteromultimers that comprise at least one TGFBRII polypeptide, which includes fragments, functional variants, and modified forms thereof. Preferably, TGFBRII polypeptides for use in accordance with inventions of the disclosure (e.g., heteromultimers comprising a TGFBRII polypeptide and uses thereof) are soluble (e.g., an extracellular domain of TGFBRII). In other preferred embodiments, TGFBRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one TGFBRII polypeptide that is at least 70%, 75%, 80%, 85%, 90%, 95%, 97%, 98%, 99%, or 100% identical to the amino acid sequence of SEQ ID NOs: 42, 43, 67, or 68, with or without insertion of SEQ ID NO: 95 as described above. In some embodiments, heteromultimer complexes of the disclosure consist or consist essentially of at least one TGFBRII polypeptide that is at least 70%, 75%, 80%, 85%, 90%, 95%, 97%, 98%, 99%, or 100% identical to the amino acid sequence of SEQ ID NOs: 42, 43, 67, or 68, with or without insertion of SEQ ID NO: 95.

In certain aspects, the present disclosure relates to protein complexes that comprise a BMPRII polypeptide. As used herein, the term "BMPRII" refers to a family of bone morphogenetic protein receptor type II (BMPRII) proteins from any species and variants derived from such BMPRII proteins by mutagenesis or other modification. Reference to BMPRII herein is understood to be a reference to any one of the currently identified forms. Members of the BMPRII family are generally transmembrane proteins, composed of a ligand-binding extracellular domain with a cysteine-rich region, a transmembrane domain, and a cytoplasmic domain with predicted serine/threonine kinase activity.

The term "BMPRII polypeptide" includes polypeptides comprising any naturally occurring polypeptide of a BMPRII family member as well as any variants thereof (including mutants, fragments, fusions, and peptidomimetic forms) that retain a useful activity.

A human BMPRII precursor protein sequence (NCBI Ref Seq NP_001195.2) is as follows:

(SEQ ID NO: 46)

```
  1 MTSSLQRPWR VPWLPWTILL VSTAAASQNQ ERLCAFKDPY QQDLGIGESR

51 ISHENGTILC SKGSTCYGLW EKSKGDINLV KQGCWSHIGD PQECHYEECV

101 VTTTPPSIQN GTYRFCCCST DLCNVNFTEN FPPPDTTPLS PPHSFNRDET

151 IIIALASVSV LAVLIVALCF GYRMLTGDRK QGLHSMNMME AAASEPSLDL

201 DNLKLLELIG RGRYGAVYKG SLDERPVAVK VFSFANRQNF INEKNIYRVP

251 LMEHDNIARF IVGDERVTAD GRMEYLLVME YYPNGSLCKY LSLHTSDWVS

301 SCRLAHSVTR GLAYLHTELP RGDHYKPAIS HRDLNSRNVL VKNDGTCVIS

351 DFGLSMRLTG NRLVRPGEED NAAISEVGTI RYMAPEVLEG AVNLRDCESA

401 LKQVDMYALG LIYWEIFMRC TDLFPGESVP EYQMAFQTEV GNHPTFEDMQ

451 VLVSREKQRP KFPEAWKENS LAVRSLKETI EDCWDQDAEA RLTAQCAEER

501 MAELMMIWER NKSVSPTVNP MSTAMQNERN LSHNRRVPKI GPYPDYSSSS

551 YIEDSIHHTD SIVKNISSEH SMSSTPLTIG EKNRNSINYE RQQAQARIPS

601 PETSVTSLST NTTTTNTTGL TPSTGMTTIS EMPYPDETNL HTTNVAQSIG

651 PTPVCLQLTE EDLETNKLDP KEVDKNLKES SDENLMEHSL KQFSGPDPLS

701 STSSSLLYPL IKLAVEATGQ QDFTQTANGQ ACLIPDVLPT QIYPLPKQQN

751 LPKRPTSLPL NTKNSTKEPR LKFGSKHKSN LKQVETGVAK MNTINAAEPH

801 VVTVTMNGVA GRNHSVNSHA ATTQYANGTV LSGQTTNIVT HRAQEMLQNQ

851 FIGEDTRLNI NSSPDEHEPL LRREQQAGHD EGVLDRLVDR RERPLEGGRT

901 NSNNNNSNPC SEQDVLAQGV PSTAADPGPS KPRRAQRPNS LDLSATNVLD

951 GSSIQIGEST QDGKSGSGEK IKKRVKTPYS LKRWRPSTWV ISTESLDCEV

1001 NNNGSNRAVH SKSSTAVYLA EGGTATTMVS KDIGMNCL
```

The signal peptide is indicated by a single underline and an extracellular domain is indicated in bold font.

A processed extracellular BMPRII polypeptide sequence is as follows:

(SEQ ID NO: 47)
SQNQERLCAFKDPYQQDLGIGESRISHENGTILCSKGSTCYGLWEKSKG

DINLVKQGCWSHIGDPQECHYEECVVTTTPPSIQNGTYRFCCCSTDLCN

VNFTENFPPPDTTPLSPPHSFNRDET

A nucleic acid sequence encoding BMPRII precursor protein is shown in SEQ ID NO: 48, as follows nucleotides 1149-4262 of Genbank Reference Sequence NM_001204.6. A nucleic acid sequence encoding an extracellular BMPRII polypeptide is shown in SEQ ID NO: 49.

An alternative isoform of BMPRII, isoform 2 (GenBank: AAA86519.1) is as follows:

(SEQ ID NO: 71)

```
  1 MTSSLQRPWR VPWLPWTILL VSTAAASQNQ ERLCAFKDPY QQDLGIGESR

51 ISHENGTILC SKGSTCYGLW EKSKGDINLV KQGCWSHIGD PQECHYEECV

101 VTTTPPSIQN GTYRFCCCST DLCNVNFTEN FPPPDTTPLS PPHSFNRDET
```

```
151 IIIALASVSV LAVLIVALCF GYRMLTGDRK QGLHSMNMME AAASEPSLDL

201 DNLKLLELIG RGRYGAVYKG SLDERPVAVK VFSFANRQNF INEKNIYRVP

251 LMEHDNIARF IVGDERVTAD GRMEYLLVME YYPNGSLCKY LSLHTSDWVS

301 SCRLAHSVTR GLAYLHTELP RGDHYKPAIS HRDLNSRNVL VKNDGTCVIS

351 DFGLSMRLTG NRLVRPGEED NAAISEVGTI RYMAPEVLEG AVNLRDCESA

401 LKQVDMYALG LIYWEIFMRC TDLFPGESVP EYQMAFQTEV GNHPTFEDMQ

451 VLVSREKQRP KFPEAWKENS LAVRSLKETI EDCWDQDAEA RLTAQCAEER

501 MAELMMIWER NKSVSPTVNP MSTAMQNERR
```

The signal peptide is indicated by a single underline and the extracellular domain is indicated in bold font.

A processed extracellular BMPRII polypeptide sequence (isoform 2) is as follows:

```
                                              (SEQ ID NO: 72)
SQNQERLCAFKDPYQQDLGIGESRISHENGTILCSKGSTCYGLWEKSKG

DINLVKQGCWSHIGDPQECHYEECVVTTTPPSIQNGTYRFCCCSTDLCN

VNFTENFPPPDTTPLSPPHSFNRDET
```

A nucleic acid sequence encoding human BMPRII precursor protein (isoform 2) is shown in SEQ ID NO:73, corresponding to nucleotides 163-1752 of Genbank Reference Sequence U25110.1. The signal sequence is underlined. A nucleic acid sequence encoding an extracellular BMPRII polypeptide (isoform 2) is shown in SEQ ID NO: 74

In certain embodiments, the disclosure relates to heteromultimers that comprise at least one BMPRII polypeptide, which includes fragments, functional variants, and modified forms thereof. Preferably, BMPRII polypeptides for use in accordance with inventions of the disclosure (e.g., heteromultimers comprising a BMPRII polypeptide and uses thereof) are soluble (e.g., an extracellular domain of BMPRII). In other preferred embodiments, BMPRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one BMPRII polypeptide that is at least 70%, 75%, 80%, 85%, 90%, 95%, 97%, 98%, 99%, or 100% identical to the amino acid sequence of SEQ ID NO: 46, 47, 71, 72, 121, 123, 411, or 412. In some embodiments, heteromultimer complexes of the disclosure consist or consist essentially of at least one BMPRII polypeptide that is at least 70%, 75%, 80%, 85%, 90%, 95%, 97%, 98%, 99%, or 100% identical to the amino acid sequence of SEQ ID NO: 46, 47, 71, 72, 121, 123, 411, or 412.

In certain aspects, the present disclosure relates to protein complexes that comprise an MISRII polypeptide. As used herein, the term "MISRII" refers to a family of Müllerian inhibiting substance receptor type II (MISRII) proteins from any species and variants derived from such MISRII proteins by mutagenesis or other modification. Reference to MISRII herein is understood to be a reference to any one of the currently identified forms. Members of the MISRII family are generally transmembrane proteins, composed of a ligand-binding extracellular domain with a cysteine-rich region, a transmembrane domain, and a cytoplasmic domain with predicted serine/threonine kinase activity.

The term "MISRII polypeptide" includes polypeptides comprising any naturally occurring polypeptide of an MIS-RII family member as well as any variants thereof (including mutants, fragments, fusions, and peptidomimetic forms) that retain a useful activity.

A human MISRII precursor protein sequence (NCBI Ref Seq NP 065434.1) is as follows:

```
                                                      (SEQ ID NO: 50)
  1 MLGSLGLWAL LPTAVEAPPN RRTCVFFEAP GVRGSTKTLG ELLDTGTELP

51 RAIRCLYSRC CFGIWNLTQD RAQVEMQGCR DSDEPGCESL HCDPSPRAHP

101 SPGSTLFTCS CGTDFCNANY SHLPPPGSPG TPGSQGPQAA PGESIWMALV

151 LLGLFLLLLL LLGSIILALL QRKNYRVRGE PVPEPRPDSG RDWSVELQEL

201 PELCFSQVIR EGGHAVVWAG QLQGKLVAIK AFPPRSVAQF QAERALYELP

251 GLQHDHIVRF ITASRGGPGR LLSGPLLVLE LHPKGSLCHY LTQYTSDWGS

301 SLRMALSLAQ GLAFLHEERW QNGQYKPGIA HRDLSSQNVL IREDGSCAIG
```

```
351 DLGLALVLPG LTQPPAWTPT QPQGPAAIME AGTQRYMAPE LLDKTLDLQD

401 WGMALRRADI YSLALLLWEI LSRCPDLRPD SSPPPFQLAY EAELGNTPTS

451 DELWALAVQE RRRPYIPSTW RCFATDPDGL RELLEDCWDA DPEARLTAEC

501 VQQRLAALAH PQESHPFPES CPRGCPPLCP EDCTSIPAPT ILPCRPQRSA

551 CHFSVQQGPC SRNPQPACTL SPV
```

The signal peptide is indicated by a single underline and an extracellular domain is indicated in bold font.

A processed extracellular MISRII polypeptide sequence is as follows:

```
                                                      (SEQ ID NO: 51)
PPNRRTCVFFEAPGVRGSTKTLGELLDTGTELPRAIRCLYSRCCFGIWN

LTQDRAQVEMQGCRDSDEPGCESLHCDPSPRAHPSPGSTLFTCSCGTDF

CNANYSHLPPPGSPGTPGSQGPQAAPGESIWMAL
```

A nucleic acid sequence encoding the MISRII precursor protein is shown in SEQ ID NO: 52, corresponding to nucleotides 81-1799 of Genbank Reference Sequence NM_020547.2. A nucleic acid sequence encoding the extracellular human MISRII polypeptide is shown in SEQ ID NO: 53.

An alternative isoform of the human MISRII precursor protein sequence, isoform 2 (NCBI Ref Seq NP_001158162.1), is as follows:

```
                                                      (SEQ ID NO: 75)
  1 MLGSLGLWAL LPTAVEAPPN RRTCVFFEAP GVRGSTKTLG ELLDTGTELP

051 RAIRCLYSRC CFGIWNLTQD RAQVEMQGCR DSDEPGCESL HCDPSPRAHP

101 SPGSTLFTCS CGTDFCNANY SHLPPPGSPG TPGSQGPQAA PGESIWMALV

151 LLGLFLLLLL LLGSIILALL QRKNYRVRGE PVPEPRPDSG RDWSVELQEL

201 PELCFSQVIR EGGHAVVWAG QLQGKLVAIK AFPPRSVAQF QAERALYELP

251 GLQHDHIVRF ITASRGGPGR LLSGPLLVLE LHPKGSLCHY LTQYTSDWGS

301 SLRMALSLAQ GLAFLHEERW QNGQYKPGIA HRDLSSQNVL IREDGSCAIG

351 DLGLALVLPG LTQPPAWTPT QPQGPAAIME AGTQRYMAPE LLDKTLDLQD

401 WGMALRRADI YSLALLLWEI LSRCPDLRPA VHHPSNWPMR QNWAIPLPLM

451

SYGPWQCRRG GVPTSHPPGA ALPQTLMG
```

The signal peptide is indicated by a single underline and the extracellular domain is indicated in bold font.

A processed extracellular MISRII polypeptide sequence (isoform 2) is as follows:

```
                                                      (SEQ ID NO: 76)
PPNRRTCVFFEAPGVRGSTKTLGELLDTGTELPRAIRCLYSRCCFGIWN

LTQDRAQVEMQGCRDSDEPGCESLHCDPSPRAHPSPGSTLFTCSCGTDF

CNANYSHLPPPGSPGTPGSQGPQAAPGESIWMAL
```

A nucleic acid sequence encoding the MISRII precursor protein (isoform 2) is shown in SEQ ID NO: 77, corresponding to nucleotides 81-1514 of Genbank Reference Sequence NM_001164690.1. A nucleic acid sequence encoding processed soluble (extracellular) human MISRII polypeptide (isoform 2) is shown in SEQ ID NO: 78.

An alternative isoform of the human MISRII precursor protein sequence, isoform 3 (NCBI Ref Seq NP_001158163.1), is as follows:

```
                                                           (SEQ ID NO: 79)
  1 MLGSLGLWAL LPTAVEAPPN RRTCVFFEAP GVRGSTKTLG ELLDTGTELP

51 RAIRCLYSRC CFGIWNLTQD RAQVEMQGCR DSDEPGCESL HCDPSPRAHP

101 SPGSTLFTCS CGTDFCNANY SHLPPPGSPG TPGSQGPQAA PGESIWNALV

151 LLGLFLLLLL LLGSIILALL QRKNYRVRGE PVPEPRPDSG RDWSVELQEL

201 PELCFSQVIR EGGHAVVWAG QLQGKLVAIK AFPPRSVAQF QAERALYELP

251 GLQHDHIVRF ITASRGGPGR LLSGPLLVLE LHPKGSLCHY LTQYTSDWGS

301 SLRMALSLAQ GLAFLHEERW QNGQYKPGIA HRDLSSQNVL IREDGSCAIG

351 DLGLALVLPG LTQPPAWTPT QPQGPAAIME DPDGLRELLE DCWDADPEAR

401 LTAECVQQRL AALAHPQESH PFPESCPRGC PPLCPEDCTS IPAPTILPCR

451 PQRSACHFSV QQGPCSRNPQ PACTLSPV
```

The signal peptide is indicated by a single underline and the extracellular domain is indicated in bold font.

A processed extracellular MISRII polypeptide sequence (isoform 3) is as follows:

```
                                                (SEQ ID NO: 80)
PPNRRTCVFFEAPGVRGSTKTLGELLDTGTELPRAIRCLYSRCCFGIWN

LTQDRAQVEMQGCRDSDEPGCESLHCDPSPRAHPSPGSTLFTCSCGTDF

CNANYSHLPPPGSPGTPGSQGPQAAPGESIWMAL
```

A nucleic acid sequence encoding human MISRII precursor protein (isoform 3) is shown in SEQ ID NO: 81, corresponding to nucleotides 81-1514 of Genbank Reference Sequence NM_001164691.1. A nucleic acid sequence encoding a processed soluble (extracellular) human MISRII polypeptide (isoform 3) is shown in SEQ ID NO: 82.

In certain embodiments, the disclosure relates to heteromultimers that comprise at least one MISRII polypeptide, which includes fragments, functional variants, and modified forms thereof. Preferably, MISRII polypeptides for use in accordance with inventions of the disclosure (e.g., heteromultimers comprising a MISRII polypeptide and uses thereof) are soluble (e.g., an extracellular domain of MISRII). In other preferred embodiments, MISRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one MISRII polypeptide that is at least 70%, 75%, 80%, 85%, 90%, 95%, 97%, 98%, 99%, or 100% identical to the amino acid sequence of SEQ ID NOs: 50, 51, 75, 76, 79, or 80. In some embodiments, heteromultimers of the disclosure consist or consist essentially of at least one MISRII polypeptide that is at least 70%, 75%, 80%, 85%, 90%, 95%, 97%, 98%, 99%, or 100% identical to the amino acid sequence of SEQ ID NOs: 50, 51, 75, 76, 79, or 80.

In certain aspects, the present disclosure relates to protein complexes that comprise an ALK1 polypeptide. As used herein, the term "ALK1" refers to a family of activin receptor-like kinase-1 proteins from any species and variants derived from such ALK1 proteins by mutagenesis or other modification. Reference to ALK1 herein is understood to be a reference to any one of the currently identified forms. Members of the ALK1 family are generally transmembrane proteins, composed of a ligand-binding extracellular domain with a cysteine-rich region, a transmembrane domain, and a cytoplasmic domain with predicted serine/threonine kinase activity.

The term "ALK1 polypeptide" includes polypeptides comprising any naturally occurring polypeptide of an ALK1 family member as well as any variants thereof (including mutants, fragments, fusions, and peptidomimetic forms) that retain a useful activity.

The human ALK1 precursor protein sequence (NCBI Ref Seq NP_000011.2) is as follows:

```
                                                           (SEQ ID NO: 14)
  1 MTLGSPRKGL LMLLMALVTQ GDPVKPSRGP LVTCTCESPH CKGPTCRGAW

51 CTVVLVREEG RHPQEHRGCG NLHRELCRGR PTEFVNHYCC DSHLCNHNVS

101 LVIEATQPPS EQPGTDGQLA LILGPVLALL ALVALGVLGL WHVRRRQEKQ

151 RGLHSELGES SLILKASEQG DSMLGDLLDS DCTTGSGSGL PFLVQRTVAR

201 QVALVECVGK GRYGEVWRGL WHGESVAVKI FSSRDEQSWF RETEIYNTVL

251 LRHDNILGFI ASDMTSRNSS TQLWLITHYH EHGSLYDFLQ RQTLEPHLAL

301 RLAVSAACGL AHLHVEIFGT QGKPAIAHRD FKSRNVLVKS NLQCCIADLG

351 LAVMHSQGSD YLDIGNNPRV GTKRYMAPEV LDEQIRTDCF ESYKWTDIWA
```

```
401 FGLVLWEIAR RTIVNGIVED YRPPFYDVVP NDPSFEDMKK VVCVDQQTPT

451 IPNRLAADPV LSGLAQMMRE CWYPNPSARL TALRIKKTLQ KISNSPEKPK

501 VIQ
```

The signal peptide is indicated by a single underline and the extracellular domain is indicated in bold font.

A processed extracellular ALK1 polypeptide sequence is as follows:

```
                                              (SEQ ID NO: 15)
DPVKPSRGPLVTCTCESPHCKGPTCRGAWCTVVLVREEGRHPQEHRGCG

NLHRELCRGRPTEFVNHYCCDSHLCNHNVSLVLEATQPPSEQPGTDGQ
```

A nucleic acid sequence encoding human ALK1 precursor protein is shown in SEQ ID NO: 16, corresponding to nucleotides 284-1792 of Genbank Reference Sequence NM_000020.2. A nucleic acid sequence encoding a processed extracellular ALK1 polypeptide is in SEQ ID NO: 17.

In certain embodiments, the disclosure relates to heteromultimers that comprise at least one ALK1 polypeptide, which includes fragments, functional variants, and modified forms thereof. Preferably, ALK1 polypeptides for use in accordance with inventions of the disclosure (e.g., heteromultimers comprising an ALK1 polypeptide and uses thereof) are soluble (e.g., an extracellular domain of ALK1). In other preferred embodiments, ALK1 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK1 polypeptide that is at least 70%, 75%, 80%, 85%, 90%, 95%, 97%, 98%, 99%, or 100% identical to the amino acid sequence of SEQ ID NO: 14, 15, 124, 126, 413, or 414. In some embodiments, heteromultimers of the disclosure consist or consist essentially of at least one ALK1 polypeptide that is at least 70%, 75%, 80%, 85%, 90%, 95%, 97%, 98%, 99% or 100% identical to the amino acid sequence of SEQ ID NO: 14, 15, 124, 126, 413, or 414.

In certain aspects, the present disclosure relates to protein complexes that comprise an ALK2 polypeptide. As used herein, the term "ALK2" refers to a family of activin receptor-like kinase-2 proteins from any species and variants derived from such ALK2 proteins by mutagenesis or other modification. Reference to ALK2 herein is understood to be a reference to any one of the currently identified forms. Members of the ALK2 family are generally transmembrane proteins, composed of a ligand-binding extracellular domain with a cysteine-rich region, a transmembrane domain, and a cytoplasmic domain with predicted serine/threonine kinase activity.

The term "ALK2 polypeptide" includes polypeptides comprising any naturally occurring polypeptide of an ALK2 family member as well as any variants thereof (including mutants, fragments, fusions, and peptidomimetic forms) that retain a useful activity.

A human ALK2 precursor protein sequence (NCBI Ref Seq NP_001096.1) is as follows:

```
                                              (SEQ ID NO: 18)
  1 MVDGVMILPV LIMIALPSPS MEDEKPKVNP KLYMCVCEGL SCGNEDHCEG

51 QQCFSSLSIN DGFHVYQKGC FQVYEQGKMT CKTPPSPGQA VECCQGDWCN

101 RNITAQLPTK GKSFPGTQNF HLEVGLIILS VVFAVCLLAC LLGVALRKFK

151 RRNQERLNPR DVEYGTIEGL ITTNVGDSTL ADLLDHSCTS GSGSGLPFLV

201 QRTVARQITL LECVGKGRYG EVWRGSWQGE NVAVKIFSSR DEKSWFRETE

251 LYNTVMLRHE NILGFIASDM TSRHSSTQLW LITHYHEMGS LYDYLQLTTL

301 DTVSCLRIVL SIASGLAHLH IEIFGTQGKP AIAHRDLKSK NILVKKNGQC

351 CIADLGLAVM HSQSTNQLDV GNNPRVGTKR YMAPEVLDET IQVDCFDSYK

401 RVDIWAFGLV LWEVARRMVS NGIVEDYKPP FYDVVPNDPS FEDMRKVVCV

451 DQQRPNIPNR WFSDPTLTSL AKLMKECWYQ NPSARLTALR IKKTLTKIDN

501 SLDKLKTDC
```

The signal peptide is indicated by a single underline and the extracellular domain is indicated in bold font.

A processed extracellular ALK2 polypeptide sequence is as follows:

```
                                              (SEQ ID NO: 19)
MEDEKPKVNPKLYMCVCEGLSCGNEDHCEGQQCFSSLSINDGFHVYQKG

CFQVYEQGKMTCKTPPSPGQAVECCQGDWCNRNITAQLPTKGKSFPGTQ

NFHLE
```

A nucleic acid sequence encoding human ALK2 precursor protein is shown in SEQ ID NO: 20, corresponding to nucleotides 431-1957 of Genbank Reference Sequence NM_001105.4. A nucleic acid sequence encoding the extracellular ALK2 polypeptide is as in SEQ ID NO: 21.

In certain embodiments, the disclosure relates to heteromultimers that comprise at least one ALK2 polypeptide, which includes fragments, functional variants, and modified forms thereof. Preferably, ALK2 polypeptides for use in accordance with inventions of the disclosure (e.g., heteromultimers comprising an ALK2 polypeptide and uses thereof) are soluble (e.g., an extracellular domain of ALK2). In other preferred embodiments, ALK2 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK2 polypeptide that is at least 70%, 75%, 80%, 85%, 90%, 95%, 97%, 98%, 99%, or 100% identical to the amino acid sequence of SEQ ID NO: 18 or 19. In some embodiments, heteromultimer complexes of the disclosure consist or consist essentially of at least one ALK2 polypeptide that is at least 70%, 75%, 80%, 85%, 90%, 95%, 97%, 98%, 99%, or 100% identical to the amino acid sequence of SEQ ID NO: 18 or 19.

In certain aspects, the present disclosure relates to protein complexes that comprise an ALK3 polypeptide. As used herein, the term "ALK3" refers to a family of activin receptor-like kinase-3 proteins from any species and variants derived from such ALK3 proteins by mutagenesis or other modification. Reference to ALK3 herein is understood to be a reference to any one of the currently identified forms. Members of the ALK3 family are generally transmembrane proteins, composed of a ligand-binding extracellular domain with a cysteine-rich region, a transmembrane domain, and a cytoplasmic domain with predicted serine/threonine kinase activity.

The term "ALK3 polypeptide" includes polypeptides comprising any naturally occurring polypeptide of an ALK3 family member as well as any variants thereof (including mutants, fragments, fusions, and peptidomimetic forms) that retain a useful activity.

A human ALK3 precursor protein sequence (NCBI Ref Seq NP_004320.2) is as follows:

NM_004329.2. The signal sequence is underlined and the extracellular domain is indicated in bold font. A nucleic acid sequence encoding the extracellular human ALK3 polypeptide is shown in SEQ ID NO: 25.

A general formula for an active (e.g., ligand binding) ALK3 polypeptide is one that comprises a polypeptide that begins at any amino acid position 25-31 (i.e., position 25, 26, 27, 28, 29, 30, or 31) of SEQ ID NO: 22 and ends at any amino acid position 140-152 of SEQ ID NO: 22 (i.e., 140, 141, 142, 143, 144, 145, 146, 147, 148, 149, 150, 151, or 152). See U.S. Pat. No. 8,338,377, the teachings of which are incorporated herein by reference in their entirety.

In certain embodiments, the disclosure relates to heteromultimers that comprise at least one ALK3 polypeptide, which includes fragments, functional variants, and modified forms thereof. Preferably, ALK3 polypeptides for use in accordance with inventions of the disclosure (e.g., heteromultimers comprising an ALK3 polypeptide and uses thereof) are soluble (e.g., an extracellular domain of ALK3). In other preferred embodiments, ALK3 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK3 polypeptide that comprises an amino acid beginning at any amino acid position 25-31 (i.e., position 25, 26, 27, 28, 29, 30, or 31) of SEQ ID NO: 22 and ending at any amino acid position 140-153 of SEQ ID NO: 22 (i.e., 140, 141, 142, 143, 144, 145, 146, 147, 148, 149, 150, 151, or 152) of SEQ ID NO: 22. In some embodiments, heteromultimer complexes of the disclosure comprise at least one ALK3 polypeptide that is at least 70%, 75%, 80%, 85%, 90%, 95%, 97%, 98%, 99%, or

```
                                                              (SEQ ID NO: 22)
  1 MPQLYIYIRL LGAYLFIISR VQGQNLDSML HGTGMKSDSD QKKSENGVTL APEDTLPFLK

61 CYCSGHCPDD AINNTCITNG HCFAIIEEDD QGETTLASGC MKYEGSDFQC KDSPKAQLRR

121 TIECCRTNLC NQYLQPTLPP VVIGPFFDGS IRWLVLLISM AVCIIAMIIF SSCFCYKHYC

181 KSISSRRRYN RDLEQDEAFI PVGESLKDLI DQSQSSGSGS GLPLLVQRTI AKQIQMVRQV

241 GKGRYGEVWM GKWRGEKVAV KVFFTTEEAS WFRETEIYQT VLMRHENILG FIAADIKGTG

301 SWTQLYLITD YHENGSLYDF LKCATLDTRA LLKLAYSAAC GLCHLHTEIY GTQGKPAIAH

361 RDLKSKNILI KKNGSCCIAD LGLAVKFNSD TNEVDVPLNT RVGTKRYMAP EVLDESLNKN

421 HFQPYIMADI YSFGLIIWEM ARRCITGGIV EEYQLPYYNM VPSDPSYEDM REVVCVKRLR

481 PIVSNRWNSD ECLRAVLKLM SECWAHNPAS RLTALRIKKT LAKMVESQDV KI
```

The signal peptide is indicated by a single underline and the extracellular domain is indicated in bold font.

A processed extracellular ALK3 polypeptide sequence is as follows:

100% identical to the amino acid sequence of SEQ ID NO: 22, 23, 115, 117, 407, or 408. In some embodiments, heteromultimer complexes of the disclosure consist or consist essentially of at least one ALK3 polypeptide that is at

```
                                                              (SEQ ID NO: 23)
  1 QNLDSMLHGT GMKSDSDQKK SENGVTLAPE DTLPFLKCYC SGHCPDDAIN NTCITNGHCF

61 AIIEEDDQGE TTLASGCMKY EGSDFQCKDS PKAQLRRTIE CCRTNLCNQY LQPTLPPVVI

121 GPFFDGSIR
```

A nucleic acid sequence encoding human ALK3 precursor protein is shown in SEQ ID NO: 24, corresponding to nucleotides 549-2144 of Genbank Reference Sequence least 70%, 75%, 80%, 85%, 90%, 95%, 97%, 98%, or 99% identical to the amino acid sequence of SEQ ID NO: 22, 23, 115, 117, 407, or 408.

In certain aspects, the present disclosure relates to protein complexes that comprise an ALK4 polypeptide. As used herein, the term "ALK4" refers to a family of activin receptor-like kinase-4 proteins from any species and variants derived from such ALK4 proteins by mutagenesis or other modification. Reference to ALK4 herein is understood to be a reference to any one of the currently identified forms. Members of the ALK4 family are generally transmembrane proteins, composed of a ligand-binding extracellular domain with a cysteine-rich region, a transmembrane domain, and a cytoplasmic domain with predicted serine/threonine kinase activity.

The term "ALK4 polypeptide" includes polypeptides comprising any naturally occurring polypeptide of an ALK4 family member as well as any variants thereof (including mutants, fragments, fusions, and peptidomimetic forms) that retain a useful activity.

A human ALK4 precursor protein sequence (NCBI Ref Seq NP_004293) is as follows:

```
                                                      (SEQ ID NO: 26)
  1 MAESAGASSF FPLVVLLLAG SGGSGPRGVQ ALLCACTSCL QANYTCETDG ACMVSIFNLD

61 GMEHHVRTCI PKVELVPAGK PFYCLSSEDL RNTHCCYTDY CNRIDLRVPS GHLKEPEHPS

121 MWGPVELVGI LAGPVFLLFL IIIIVFLVIN YHQRVYHNRQ RLDMEDPSCE MCLSKDKTLQ

181 DLVYDLSTSG SGSGLPLFVQ RTVARTIVLQ EIIGKGRFGE VWRGRWRGGD VAVKIFSSRE

241 ERSWFREAEI YQTVMLRHEN ILGFIAADNK DNGTWTQLWL VSDYHEGSL  FDYLNRYTVT

301 IEGMIKLALS AASGLAHLHM EIVGTQGKPG IAHRDLKSKN ILVKKNGMCA LADLGLAVRH

361 DAVTDTIDIA PNQRVGTKRY MAPEVLDETI NMKHFDSFKC ADIYALGLVY WEIARRCNSG

421 GVHEEYQLPY YDLVPSDPSI EEMRKVVCDQ KLRPNIPNWW QSYEALRVMG KMMRECWYAN

481 GAARLTALRI KKTLSQLSVQ EDVKI
```

The signal peptide is indicated by a single underline and the extracellular domain is indicated in bold font.

A processed extracellular human ALK4 polypeptide sequence is as follows:

```
                                                      (SEQ ID NO: 27)
SGPRGVQALLCACTSCLQANYTCETDGACMVSIFNLDGMEHHVRTCIPK

VELVPAGKPFYCLSSEDLRNTHCCYTDYCNRIDLRVPSGHLKEPEHPSM

WGPVE
```

A nucleic acid sequence encoding an ALK4 precursor protein is shown in SEQ ID NO: 28), corresponding to nucleotides 78-1592 of Genbank Reference Sequence NM_004302.4. A nucleic acid sequence encoding the extracellular ALK4 polypeptide is shown in SEQ ID NO: 28

An alternative isoform of human ALK4 precursor protein sequence, isoform C (NCBI Ref Seq NP_064733.3), is as follows:

```
                                                      (SEQ ID NO: 83)
  1 MAESAGASSF FPLVVLLLAG SGGSGPRGVQ ALLCACTSCL QANYTCETDG ACMVSIFNLD

61 GMEHHVRTCI PKVELVPAGK PFYCLSSEDL RNTHCCYTDY CNRIDLRVPS GHLKEPEHPS

121 MWGPVELVGI IAGPVFLLFL IIIIVFLVIN YHQRVYHNRQ RLDMEDPSCE MCLSKDKTLQ

181 DLVYDLSTSG SGSGLPLFVQ RTVARTIVLQ EIIGKGRFGE VWRGRWRGGD VAVKIFSSRE

241 ERSWFREAEI YQTVMLRHEN ILGFIAADNK ADCSFLTLPW EVVMVSAAPK LRSLRLQYKG

301 GRGRARFLFP LNNGTWTQLW LVSDYHEGS  LFDYLNRYTV TIEGMIKLAL SAASGLAHLH

361 MEIVGTQGKP GIAHRDLKSK NILVKKNGMC AIADLGLAVR HDAVTDTIDI APNQRVGTKR

421 YMAPEVLDET INMKHFDSFK CADIYALGLV YWEIARRCNS GGVHEEYQLP YYDLVPSDPS

481 IEEMRKVVCD QKLRPNIPNW WQSYEALRVM GKMMRECWYA NGAARLTALR IKKTLSQLSV

541 QEDVKI
```

The signal peptide is indicated by a single underline and the extracellular domain is indicated in bold font.

A processed extracellular ALK4 polypeptide sequence (isoform C) is as follows:

(SEQ ID NO: 84)
SGPRGVQALLCACTSCLQANYTCETDGACMVSIFNLDGMEHHVRTCIPK

VELVPAGKPFYCLSSEDLRNTHCCYTDYCNRIDLRVPSGHLKEPEHPSM

WGPVE

A nucleic acid sequence encoding an ALK4 precursor protein (isoform C) is shown in SEQ ID NO: 85, corresponding to nucleotides 78-1715 of Genbank Reference Sequence NM_020328.3. A nucleic acid sequence encoding the extracellular ALK4 polypeptide (isoform C) is shown in SEQ ID NO: 86.

In certain embodiments, the disclosure relates to heteromultimers that comprise at least one ALK4 polypeptide, which includes fragments, functional variants, and modified forms thereof. Preferably, ALK4 polypeptides for use in accordance with inventions of the disclosure (e.g., heteromultimers comprising an ALK4 polypeptide and uses thereof) are soluble (e.g., an extracellular domain of ALK4). In other preferred embodiments, ALK4 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK4 polypeptide that is at least 70%, 75%, 80%, 85%, 90%, 95%, 97%, 98%, 99%, or 100% identical to the amino acid sequence of SEQ ID NO: 26, 27, 83, 84, 104, 106, 403, or 404. In some embodiments, heteromultimers of the disclosure consist or consist essentially of at least one ALK4 polypeptide that is at least 70%, 75%, 80%, 85%, 90%, 95%, 97%, 98%, 99%, or 100% identical to the amino acid sequence of SEQ ID NO: 26, 27, 83, 84, 104, 106, 403, or 404.

In certain aspects, the present disclosure relates to protein complexes that comprise an ALK5 polypeptide. As used herein, the term "ALK5" refers to a family of activin receptor-like kinase-5 proteins from any species and variants derived from such ALK4 proteins by mutagenesis or other modification. Reference to ALK5 herein is understood to be a reference to any one of the currently identified forms. Members of the ALK5 family are generally transmembrane proteins, composed of a ligand-binding extracellular domain with a cysteine-rich region, a transmembrane domain, and a cytoplasmic domain with predicted serine/threonine kinase activity.

The term "ALK5 polypeptide" includes polypeptides comprising any naturally occurring polypeptide of an ALK5 family member as well as any variants thereof (including mutants, fragments, fusions, and peptidomimetic forms) that retain a useful activity.

A human ALK5 precursor protein sequence (NCBI Ref Seq NP_004603.1) is as follows:

(SEQ ID NO: 30)
```
  1 MEAAVAAPRP RLLLLVLAAA AAAAAALLPG ATALQCFCHL CTKDNFTCVT DGLCFVSVME

61 TTDKVIHNSM CIAEIDLIPR DRPFVCAPSS KTGSVTTTYC CNQDHCNKIE LPTTVKSSPG

121 LGPVELAAVI AGPVCFVCIS LMLMVYICHN RTVIHHRVPN EEDPSLDRPF ISEGTTLKDL

181 IYDMTTSGSG SGLPLLVQRT IARTIVLQES IGKGRFGEVW RGKWRGEEVA VKIFSSREER

241 SWFREAEIYQ TVMLRHENIL GFIAADNKDN GTWTQLWLVS DYHEHGSLFD YLNRYTVTVE

301 GMIKLALSTA SGLAHLHMEI VGTQGKPAIA HRDLKSKNIL VKKNGTCCIA DLGLAVRHDS

361 ATDTIDIAPN HRVGTKRYMA PEVLDDSINM KHFESFKRAD IYAMGLVFWE IARRCSIGGI

421 HEDYQLPYYD LVPSDPSVEE MRKVVCEQKL RPNIPNRWQS CEALRVMAKI MRECWYANGA

481 ARLTALRIKK TLSQLSQQEG IKM
```

The signal peptide is indicated by a single underline and the extracellular domain is indicated in bold font.

A processed extracellular ALK5 polypeptide sequence is as follows:

(SEQ ID NO: 31)
AALLPGATALQCFCHLCTKDNFTCVTDGLCFVSVTETTDKVIHNSMCIA

EIDLIPRDRPFVCAPSSKTGSVTTTYCCNQDHCNKIELPTTVKSSPGLG

PVEL

A nucleic acid sequence encoding the ALK5 precursor protein is shown in SEQ ID NO: 32, corresponding to nucleotides 77-1585 of Genbank Reference Sequence NM_004612.2. A nucleic acid sequence encoding an extracellular human ALK5 polypeptide is shown in SEQ ID NO: 33.

An alternative isoform of the human ALK5 precursor protein sequence, isoform 2 (NCBI Ref Seq XP_005252207.1), is as follows:

(SEQ ID NO: 87)
```
  1 MEAAVAAPRP RLLLLVLAAA AAAAAALLPG ATALQCFCHL CTKDNFTCVT DGLCFVSVME

61 TTDKVIHNSM CIAEIDLIPR DRPFVCAPSS KTGSVTTTYC CNQDHCNKIE LPTTGPFSVK

121 SSPGLGPVEL AAVIAGPVCF VCISLMLMVY ICHNRTVIHH RVPNEEDPSL DRPFISEGTT
```

```
181 LKDLIYDMTT SGSGSGLPLL VQRTIARTIV LQESIGKGRF GEVWRGKWRG EEVAVKIFSS

241 REERSWFREA EIYQTVMLRH ENILGFIAAD NKDNGTWTQL WLVSDYHEHG SLFDYLNRYT

301 VTVEGMIKLA LSTASGLAHL HMEIVGTQGK PAIAHRDLKS KNILVKKNGT CCIADLGLAV

361 RHDSATDTID LAPNHRVGTK RYMAPEVLDD SINMKHFESF KRADIYAMGL VFWEIARRCS

421 IGGIHEDYQL PYYDLVPSDP SVEEMRKVVC EQKLRPNIPN RWQSCEALRV MAKIMRECWY

481 ANGAARLTAL RIKKTLSQLS QQEGIKM
```

The signal peptide is indicated by a single underline and the extracellular domain is indicated in bold font.

A processed extracellular ALK5 polypeptide sequence (isoform 2) is as follows:

```
                                              (SEQ ID NO: 88)
AALLPGATALQCFCHLCTKDNFTCVTDGLCFVSVTETTDKVIHNSMCIA

EIDLIPRDRPFVCAPSSKTGSVTTTYCCNQDHCNKIELPTTGPFSVKSS

PGLGPVEL
```

A nucleic acid sequence encoding human ALK5 precursor protein (isoform 2) is shown in SEQ ID NO: 89, corresponding to nucleotides 77-1597 of Genbank Reference Sequence XM_005252150.1. A nucleic acid sequence encoding a processed extracellular ALK5 polypeptide is shown in SEQ ID NO: 90.

In certain embodiments, the disclosure relates to heteromultimers that comprise at least one ALK5 polypeptide, which includes fragments, functional variants, and modified forms thereof. Preferably, ALK5 polypeptides for use in accordance with inventions of the disclosure (e.g., heteromultimers comprising an ALK5 polypeptide and uses thereof) are soluble (e.g., an extracellular domain of ALK5). In other preferred embodiments, ALK5 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK5 polypeptide that is at least 70%, 75%, 80%, 85%, 90%, 95%, 97%, 98%, 99%, or 100% identical to the amino acid sequence of SEQ ID NO: 30, 31, 87, or 88. In some embodiments, heteromultimer complexes of the disclosure consist or consist essentially of at least one ALK5 polypeptide that is at least 70%, 75%, 80%, 85%, 90%, 95%, 97%, 98%, 99%, or 100% identical to the amino acid sequence of SEQ ID NO: 30, 31, 87, or 88.

In certain aspects, the present disclosure relates to protein complexes that comprise an ALK6 polypeptide. As used herein, the term "ALK6" refers to a family of activin receptor-like kinase-6 proteins from any species and variants derived from such ALK6 proteins by mutagenesis or other modification. Reference to ALK6 herein is understood to be a reference to any one of the currently identified forms. Members of the ALK6 family are generally transmembrane proteins, composed of a ligand-binding extracellular domain with a cysteine-rich region, a transmembrane domain, and a cytoplasmic domain with predicted serine/threonine kinase activity.

The term "ALK6 polypeptide" includes polypeptides comprising any naturally occurring polypeptide of an ALK6 family member as well as any variants thereof (including mutants, fragments, fusions, and peptidomimetic forms) that retain a useful activity.

A human ALK6 precursor protein sequence (NCBI Ref Seq NP_001194.1) is as follows:

```
                                                              (SEQ ID NO: 34)
  1 MLLRSAGKLN VGTKKEDGES TAPTPRPKVL RCKCHHHCPE DSVNNICSTD GYCFTMIEED

61 DSGLPVVTSG CLGLEGSDFQ CRDTPIPHQR RSIECCTERN ECNKDLHPTL PPLKNRDFVD

121 GPIHHRALLI SVTVCSLLLV LIILFCYFRY KRQETRPRYS IGLEQDETYI PPGESLRDLI

181 EQSQSSGSGS GLPLLVQRTI AKQIQMVKQI GKGRYGEVWM GKWRGEKVAV KVFFTTEEAS

241 WFRETEIYQT VLMRHENILG FIAADIKGTG SWTQLYLITD YHENGSLYDY LKSTTLDAKS

301 MLKLAYSSVS GLCHLHTEIF STQGKPAIAH RDLKSKNILV KKNGTCCIAD LGLAVKFISD

361 TNEVDIPPNT RVGTKRYMPP EVLDESLNRN HFQSYIMADM YSFGLILWEV ARRCVSGGIV

421 EEYQLPYHDL VPSDPSYEDM REIVCIKKLR PSFPNRWSSD ECLRQMGKLM TECWAHNPAS

481 RLTALRVKKT LAKMSESQDI KL
```

The signal peptide is indicated by a single underline and the extracellular domain is indicated in bold font.

The processed extracellular ALK6 polypeptide sequence is as follows:

```
                                              (SEQ ID NO: 35)
KKEDGESTAPTPRPKVLRCKCHHHCPEDSVNNICSTDGYCFTMIEEDDS

GLPVVTSGCLGLEGSDFQCRDTPIPHQRRSIECCTERNECNKDLHPTLP

PLKNRDFVDGPIHHR
```

A nucleic acid sequence encoding the ALK6 precursor protein is shown in SEQ ID NO: 36, corresponding to nucleotides 275-1780 of Genbank Reference Sequence NM_001203.2. A nucleic acid sequence encoding processed extracellular ALK6 polypeptide is shown in SEQ ID NO: 37.

An alternative isoform of human ALK6 precursor protein sequence, isoform 2 (NCBI Ref Seq NP_001243722.1) is as follows:

(SEQ ID NO: 91)

```
  1 MGWLEELNWQ LHIFLLILLS MHTRANFLDN MLLRSAGKLN VGTKKEDGES TAPTPRPKVL

61 RCKCHHHCPE DSVNNICSTD GYCFTMIEED DSGLPVVTSG CLGLEGSDFQ CRDTPIPHQR

121 RSIECCTERN ECNKDLHPTL PPLKNRDFVD GPIHHRALLI SVTVCSLLLV LIILFCYFRY

181 KRQETRPRYS IGLEQDETYI PPGESLRDLI EQSQSSGSGS GLPLLVQRTI AKQIQMVKQI

241 GKGRYGEVWM GKWRGEKVAV KVFFTTEEAS WFRETEIYQT VLMRHENILG FIAADIKGTG

301 SWTQLYLITD YHENGSLYDY LKSTTLDAKS MLKLAYSSVS GLCHLHTEIF STQGKPAIAH

361 RDLKSKNILV KKNGTCCIAD LGLAVKFISD TNEVDIPPNT RVGTKRYMPP EVLDESLNRN

421 HFQSYIMADM YSFGLILWEV ARRCVSGGIV EEYQLPYHDL VPSDPSYEDM REIVCIKKLR

481 PSFPNRWSSD ECLRQMGKLM TECWAHNPAS RLTALRVKKT LAKMSESQDI KL
```

The signal peptide is indicated by a single underline and the extracellular domain is indicated in bold font.

A processed extracellular ALK6 polypeptide sequence (isoform 2) is as follows:

(SEQ ID NO: 92)

NFLDNMLLRSAGKLNVGTKKEDGESTAPTPRPKVLRCKCHHHCPEDSVN
NICSTDGYCFTMIEEDDSGLPVVTSGCLGLEGSDFQCRDTPIPHQRRSI
ECCTERNECNKDLHPTLPPLKNRDFVDGPIHHR

A nucleic acid sequence encoding human ALK6 precursor protein (isoform 2) is shown in SEQ ID NO: 93, corresponding to nucleotides 22-1617 of Genbank Reference Sequence NM_001256793.1. A nucleic acid sequence encoding a processed extracellular ALK6 polypeptide is shown in SEQ ID NO: 94.

In certain embodiments, the disclosure relates to heteromultimers that comprise at least one ALK6 polypeptide, which includes fragments, functional variants, and modified forms thereof. Preferably, ALK6 polypeptides for use in accordance with inventions of the disclosure (e.g., heteromultimers comprising an ALK6 polypeptide and uses thereof) are soluble (e.g., an extracellular domain of ALK6). In other preferred embodiments, ALK6 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK6 polypeptide that is at least 70%, 75%, 80%, 85%, 90%, 95%, 97%, 98%, 99%, or 100% identical to the amino acid sequence of SEQ ID NO: 34, 35, 91, or 92. In some embodiments, heteromultimers of the disclosure consist or consist essentially of at least one ALK6 polypeptide that is at least 70%, 75%, 80%, 85%, 90%, 95%, 97%, 98%, 99%, or 100% identical to the amino acid sequence of SEQ ID NO: 34, 35, 91, or 92.

In certain aspects, the present disclosure relates to protein complexes that comprise an ALK7 polypeptide. As used herein, the term "ALK7" refers to a family of activin receptor-like kinase-7 proteins from any species and variants derived from such ALK7 proteins by mutagenesis or other modification. Reference to ALK7 herein is understood to be a reference to any one of the currently identified forms. Members of the ALK7 family are generally transmembrane proteins, composed of a ligand-binding extracellular domain with a cysteine-rich region, a transmembrane domain, and a cytoplasmic domain with predicted serine/threonine kinase activity.

The term "ALK7 polypeptide" includes polypeptides comprising any naturally occurring polypeptide of an ALK7 family member as well as any variants thereof (including mutants, fragments, fusions, and peptidomimetic forms) that retain a useful activity.

Four naturally occurring isoforms of human ALK7 have been described. The sequence of human ALK7 isoform 1 precursor protein (NCBI Ref Seq NP_660302.2) is as follows:

(SEQ ID NO: 38)

```
  1 MTRALCSALR QALLLLAAAA ELSPGLKCVC LLCDSSNFTC QTEGACWASV MLTNGKEQVI

61 KSCVSLPELN AQVFCHSSNN VTKTECCFTD FCNNITLHLP TASPNAPKLG PMELAIIITV

121 PVCLLSIAAM LTVWACQGRQ CSYRKKKRPN VEEPLSECNL VNAGKTLKDL IYDVTASGSG

181 SGLPLLVQRT IARTIVLQEI VGKGRFGEVW HGRWCGEDVA VKIFSSRDER SWFREAEIYQ

241 TVMLRHENIL GFIAADNKDN GTWTQLWLVS EYHEQGSLYD YLNRNIVTVA GMIKLALSIA

301 SGLAHLHMEI VGTQGKPAIA HRDIKSKNIL VKKCETCAIA DLGLAVKHDS ILNTIDIPQN

361 PKVGTKRYMA PEMLDDTMNV NIFESFKRAD IYSVGLVYWE IARRCSVGGI VEEYQLPYYD

421 MVPSDPSIEE MRKVVCDQKF RPSIPNQWQS CEALRVMGRI MRECWYANGA ARLTALRIKK

481 TISQLCVKED CKA
```

The signal peptide is indicated by a single underline and the extracellular domain is indicated in bold font.

A processed extracellular ALK7 isoform 1 polypeptide sequence is as follows:

(SEQ ID NO: 39)
ELSPGLKCVCLLCDSSNFTCQTEGACWASVMLTNGKEQVIKSCVSLPEL

NAQVFCHSSNNVTKTECCFTDFCNNITLHLPTASPNAPKLGPME

A nucleic acid sequence encoding human ALK7 isoform 1 precursor protein is shown below in SEQ ID NO: 40, corresponding to nucleotides 244-1722 of Genbank Reference Sequence NM_145259.2. A nucleic acid sequence encoding the processed extracellular ALK7 polypeptide (isoform 1) is show in in SEQ ID NO: 41.

An amino acid sequence of an alternative isoform of human ALK7, isoform 2 (NCBI Ref Seq NP_001104501.1), is shown in its processed form as follows (SEQ ID NO: 301), where the extracellular domain is indicated in bold font.

(SEQ ID NO: 301)

```
  1 MLTNGKEQVI KSCVSLPELN AQVFCHSSNN VTKTECCFTD FCNNITLHLP TASPNAPKLG

61 PMELAIIITV PVCLLSIAAM LTVWACQGRQ CSYRKKKRPN VEEPLSECNL VNAGKTLKDL

121 IYDVTASGSG SGLPLLVQRT IARTIVLQEI VGKGRFGEVW HGRWCGEDVA VKIFSSRDER

181 SWFREAEIYQ TVMLRHENIL GFIAADNKDN GTWTQLWLVS EYHEQGSLYD YLNRNIVTVA

241 GMIKLALSIA SGLAHLHMEI VGTQGKPAIA HRDIKSKNIL VKKCETCAIA DLGLAVKHDS

301 ILNTIDIPQN PKVGTKRYMA PEMLDDTMNV NIFESFKRAD IYSVGLVYWE IARRCSVGGI

361 VEEYQLPYYD MVPSDPSIEE MRKVVCDQKF RPSIPNQWQS CEALRVMGRI MRECWYANGA

421 ARLTALRIKK TISQLCVKED CKA
```

An amino acid sequence of the extracellular ALK7 polypeptide (isoform 2) is as follows:

(SEQ ID NO: 302)
MLTNGKEQVIKSCVSLPELNAQVFCHSSNNVTKTECCFTDFCNNITLHL

PTASPNAPKLGPME.

A nucleic acid sequence encoding the processed ALK7 polypeptide (isoform 2) is shown below in SEQ ID NO: 303, corresponding to nucleotides 279-1607 of NCBI Reference Sequence NM_001111031.1.

A nucleic acid sequence encoding an extracellular ALK7 polypeptide (isoform 2) is shown in SEQ ID NO: 304.

An amino acid sequence of an alternative human ALK7 precursor protein, isoform 3 (NCBI Ref Seq NP_001104502.1), is shown as follows (SEQ ID NO: 305), where the signal peptide is indicated by a single underline.

(SEQ ID NO: 305)

```
  1 MTRALCSALR QALLLLAAAA ELSPGLKCVC LLCDSSNFTC QTEGACWASV MLTNGKEQVI

61 KSCVSLPELN AQVFCHSSNN VTKTECCFTD FCNNITLHLP TGLPLLVQRT IARTIVLQEI

121 VGKGRFGEVW HGRWCGEDVA VKIFSSRDER SWFREAEIYQ TVMLRHENIL GFIAADNKDN

181 GTWTQLWLVS EYHEQGSLYD YLNRNIVTVA GMIKLALSIA SGLAHLHMEI VGTQGKPAIA

241 HRDIKSKNIL VKKCETCAIA DLGLAVKHDS ILNTIDIPQN PKVGTKRYMA PEMLDDTMNV

301 NIFESFKRAD IYSVGLVYWE IARRCSVGGI VEEYQLPYYD MVPSDPSIEE MRKVVCDQKF

361 RPSIPNQWQS CEALRVMGRI MRECWYANGA ARLTALRIKK TISQLCVKED CKA
```

The amino acid sequence of a processed ALK7 polypeptide (isoform 3) is as follows (SEQ ID NO: 306). This isoform lacks a transmembrane domain and is therefore proposed to be soluble in its entirety (Roberts et al., 2003, Biol Reprod 68:1719-1726). N-terminal variants of SEQ ID NO: 306 are predicted as described below.

```
                                                               (SEQ ID NO: 306)
  1 ELSPGLKCVC LLCDSSNFTC QTEGACWASV MLTNGKEQVI KSCVSLPELN AQVFCHSSNN

61 VTKTECCFTD FCNNITLHLP TGLPLLVQRT IARTIVLQEI VGKGRFGEVW HGRWCGEDVA

121 VKIFSSRDER SWFREAEIYQ TVMLRHENIL GFIAADNKDN GTWTQLWLVS EYHEQGSLYD

181 YLNRNIVTVA GMIKLALSIA SGLAHLHMEI VGTQGKPAIA HRDIKSKNIL VKKCETCAIA

241 DLGLAVKHDS ILNTIDIPQN PKVGTKRYMA PEMLDDTMNV NIFESFKRAD IYSVGLVYWE

301 IARRCSVGGI VEEYQLPYYD MVPSDPSIEE MRKVVCDQKF RPSIPNQWQS CEALRVMGRI

361 MRECWYANGA ARLTALRIKK TISQLCVKED CKA
```

A nucleic acid sequence encoding an unprocessed ALK7 polypeptide precursor protein (isoform 3) is shown in SEQ ID NO: 307, corresponding to nucleotides 244-1482 of NCBI Reference Sequence NM_001111032.1. A nucleic acid sequence encoding a processed ALK7 polypeptide (isoform 3) is shown in SEQ ID NO: 308.

An amino acid sequence of an alternative human ALK7 precursor protein, isoform 4 (NCBI Ref Seq NP_001104503.1), is shown as follows (SEQ ID NO: 309), where the signal peptide is indicated by a single underline.

```
                                                               (SEQ ID NO: 309)
  1 MTRALCSALR QALLLLAAAA ELSPGLKCVC LLCDSSNFTC QTEGACWASV MLTNGKEQVI

61 KSCVSLPELN AQVFCHSSNN VTKTECCFTD FCNNITLHLP TDNGTWTQLW LVSEYHEQGS

121 LYDYLNRNIV TVAGMIKLAL SIASGLAHLH MEIVGTQGKP AIAHRDIKSK NILVKKCETC

181 AIADLGLAVK HDSILNTIDI PQNPKVGTKR YMAPEMLDDT MNVNIFESFK RADIYSVGLV

241 YWEIARRCSV GGIVEEYQLP YYDMVPSDPS IEEMRKVVCD QKFRPSIPNQ WQSCEALRVM

301 GRIMRECWYA NGAARLTALR IKKTISQLCV KEDCKA
```

An amino acid sequence of a processed ALK7 polypeptide (isoform 4) is as follows (SEQ ID NO: 310). Like ALK7 isoform 3, isoform 4 lacks a transmembrane domain and is therefore proposed to be soluble in its entirety (Roberts et al., 2003, Biol Reprod 68:1719-1726). N-terminal variants of SEQ ID NO: 310 are predicted as described below.

```
                                                               (SEQ ID NO: 310)
  1 ELSPGLKCVC LLCDSSNFTC QTEGACWASV MLTNGKEQVI KSCVSLPELN AQVFCHSSNN

61 VTKTECCFTD FCNNITLHLP TDNGTWTQLW LVSEYHEQGS LYDYLNRNIV TVAGMIKLAL

121 SIASGLAHLH MEIVGTQGKP AIAHRDIKSK NILVKKCETC AIADLGLAVK HDSILNTIDI

181 PQNPKVGTKR YMAPEMLDDT MNVNIFESFK RADIYSVGLV YWEIARRCSV GGIVEEYQLP

240 YYDMVPSDPS IEEMRKVVCD QKFRPSIPNQ WQSCEALRVM GRIMRECWYA NGAARLTALR

301 IKKTISQLCV KEDCKA
```

A nucleic acid sequence encoding the unprocessed ALK7 polypeptide precursor protein (isoform 4) is shown in SEQ ID NO: 311, corresponding to nucleotides 244-1244 of NCBI Reference Sequence NM_001111033.1. A nucleic acid sequence encoding the processed ALK7 polypeptide (isoform 4) is shown in SEQ ID NO: 312.

Based on the signal sequence of full-length ALK7 (isoform 1) in the rat (see NCBI Reference Sequence NP_620790.1) and on the high degree of sequence identity between human and rat ALK7, it is predicted that a processed form of human ALK7 isoform 1 is as follows (SEQ ID NO: 313).

(SEQ ID NO: 313)
```
  1 LKCVCLLCDS SNFTCQTEGA CWASVMLTNG KEQVIKSCVS LPELNAQVFC HSSNNVTKTE
 61 CCFTDFCNNI TLHLPTASPN APKLGPME
```

Active variants of processed ALK7 isoform 1 are predicted in which SEQ ID NO: 39 is truncated by 1, 2, 3, 4, 5, 6, or 7 amino acids at the N-terminus and SEQ ID NO: 313 is truncated by 1 or 2 amino acids at the N-terminus. Consistent with SEQ ID NO: 313, it is further expected that leucine is the N-terminal amino acid in the processed forms of human ALK7 isoform 3 (SEQ ID NO: 306) and human ALK7 isoform 4 (SEQ ID NO: 310).

In certain embodiments, the disclosure relates to heteromultimers that comprise at least one ALK7 polypeptide, which includes fragments, functional variants, and modified forms thereof. Preferably, ALK7 polypeptides for use in accordance with inventions of the disclosure (e.g., heteromultimers comprising an ALK7 polypeptide and uses thereof) are soluble (e.g., an extracellular domain of ALK7). In other preferred embodiments, ALK7 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK7 polypeptide that is at least 70%, 75%, 80%, 85%, 90%, 95%, 97%, 98%, 99%, or 100% identical to the amino acid sequence of SEQ ID NO: 38, 39, 112, 114, 301, 302, 305, 306, 309, 310, 313, 405, or 406. In some embodiments, heteromultimers of the disclosure consist or consist essentially of at least one ALK7 polypeptide that is at least 70%, 75%, 80%, 85%, 90%, 95%, 97%, 98%, 99%, or 100% identical to the amino acid sequence of SEQ ID NO: 38, 39, 112, 114, 301, 302, 305, 306, 309, 310, 313, 405, or 406.

In some embodiments, the present disclosure contemplates making functional variants by modifying the structure of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) for such purposes as enhancing therapeutic efficacy or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more TGF-beta superfamily ligands including, for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty.

In some embodiments, the present disclosure contemplates making functional variants by modifying the structure of the TGF-beta superfamily type I receptor polypeptide and/or TGF-beta superfamily type II receptor polypeptide for such purposes as enhancing therapeutic efficacy or stability (e.g., increased shelf-life and/or increased resistance to proteolytic degradation).

In certain embodiments, the present disclosure contemplates specific mutations of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) receptor of the disclosure so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, TGF-beta superfamily type I and II receptor complexes of the present disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) disclosed herein, as well as truncation mutants. Pools of combinatorial mutants are especially useful for identifying functionally active (e.g., ligand binding) TGF-beta superfamily type I and/or TGF-beta superfamily type II receptor sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, TGF-beta superfamily type I and II receptor complex variants may be screened for ability to bind to a TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-01, TGF-02, TGF-03, activin A, activin B, activin C, activin E, activin AB, activin AC, activin AE, activin BC, activin BE, nodal, glial cell-derived neurotrophic factor (GDNF), neurturin, artemin, persephin, MIS, and Lefty), to prevent binding of a TGF-beta superfamily ligand to a TGF-beta superfamily receptor, and/or to interfere with signaling caused by an TGF-beta superfamily ligand.

The activity of a TGF-beta superfamily heteromultimer of the disclosure also may be tested, for example in a cell-based or in vivo assay. For example, the effect of a heteromultimer complex on the expression of genes or the activity of proteins involved in muscle production in a muscle cell may be assessed. This may, as needed, be performed in the presence of one or more recombinant TGF-beta superfamily ligand proteins (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-03, activin A, activin B, activin C, activin E, activin AB, activin AC, activin AE, activin BC, activin BE, nodal, glial cell-derived neurotrophic factor (GDNF), neurturin, artemin, persephin, MIS, and Lefty), and cells may be transfected so as to produce a TGF-beta superfamily type I and II receptor complex, and optionally, a TGF-beta superfamily ligand. Likewise, a heteromultimer complex of the disclosure may be administered to a mouse or other animal, and one or more measurements, such as muscle formation and strength may be assessed using art-recognized methods. Similarly, the activity of a heteromultimer, or variants thereof, may be tested in osteoblasts, adipocytes, and/or neuronal cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference TGF-beta superfamily heteromultimer. Such variants, when expressed from recombinant DNA constructs, can be used in gene therapy protocols. Likewise, mutagenesis can give rise to variants which have intracellular half-lives dramatically different than the corresponding unmodified TGF-beta superfamily heteromultimer. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter one or more activities of the TGF-beta superfamily heteromultimer complex including, for example, immunogenicity, half-life, and solubility.

A combinatorial library may be produced by way of a degenerate library of genes encoding a library of polypeptides which each include at least a portion of potential TGF-beta superfamily type I and/or II receptor sequences. For instance, a mixture of synthetic oligonucleotides can be enzymatically ligated into gene sequences such that the degenerate set of potential TGF-beta superfamily type I and/or II receptor encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art. See, e.g., Narang, S A (1983) Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins. See, e.g., Scott et al., (1990) Science 249:386-390; Roberts et al. (1992) PNAS USA 89:2429-2433; Devlin et al. (1990) Science 249: 404-406; Cwirla et al., (1990) PNAS USA 87: 6378-6382; as well as U.S. Pat. Nos. 5,223,409, 5,198,346, and 5,096,815.

Alternatively, other forms of mutagenesis can be utilized to generate a combinatorial library. For example, TGF-beta superfamily heteromultimers of the disclosure can be generated and isolated from a library by screening using, for example, alanine scanning mutagenesis [see, e.g., Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218: 597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis [see, e.g., Gustin et al. (1993) Virology 193:653-660; and Brown et al. (1992) Mol. Cell Biol. 12:2644-2652; McKnight et al. (1982) Science 232: 316], by saturation mutagenesis [see, e.g., Meyers et al., (1986) Science 232:613]; by PCR mutagenesis [see, e.g., Leung et al. (1989) Method Cell Mol Biol 1:11-19]; or by random mutagenesis, including chemical mutagenesis [see, e.g., Miller et al. (1992) A Short Course in Bacterial Genetics, CSHL Press, Cold Spring Harbor, NY; and Greener et al. (1994) Strategies in Mol Biol 7:32-34]. Linker scanning mutagenesis, particularly in a combinatorial setting, is an attractive method for identifying truncated (bioactive) forms of TGF-beta superfamily type I and/or II receptor polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of TGF-beta superfamily heteromultimers of the disclosure. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-01, TGF-02, TGF-03, activin A, activin B, activin C, activin E, activin AB, activin AC, activin AE, activin BC, activin BE, nodal, glial cell-derived neurotrophic factor (GDNF), neurturin, artemin, persephin, MIS, and Lefty) binding assays and/or TGF-beta superfamily ligand-mediated cell signaling assays.

In certain embodiments, TGF-beta superfamily type I and II heteromultimers of the disclosure may further comprise post-translational modifications in addition to any that are naturally present in the TGF-beta superfamily type I and/or II receptor polypeptide. Such modifications include, but are not limited to, acetylation, carboxylation, glycosylation, phosphorylation, lipidation, and acylation. As a result, the TGF-beta superfamily type I and II heteromultimer may comprise non-amino acid elements, such as polyethylene glycols, lipids, polysaccharide or monosaccharide, and phosphates. Effects of such non-amino acid elements on the functionality of a heteromultimer complex may be tested as described herein for other heteromultimer complex variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, WI38, NIH-3T3 or HEK293) have specific cellular machinery and characteristic mechanisms for such post-translational activities and may be chosen to ensure the correct modification and processing of the TGF-beta superfamily type I and/or type II receptor polypeptides as well as heteromultimers comprising the same.

In certain aspects, the polypeptides disclosed herein may form protein complexes comprising at least one TGF-beta superfamily type I polypeptide associated, covalently or non-covalently, with at least one type II receptor polypeptide. Preferably, polypeptides disclosed herein form heterodimers, although higher order heteromultimers are also included such as, but not limited to, heterotrimers, heterotetramers, and further oligomeric structures (see, e.g., FIGS. 1, 2, and 15). In some embodiments, TGF-beta superfamily type I and/or type II receptor polypeptides of the present disclosure comprise at least one multimerization domain. As disclosed herein, the term "multimerization domain" refers to an amino acid or sequence of amino acids that promote covalent or non-covalent interaction between at least a first polypeptide and at least a second polypeptide. Polypeptides disclosed herein may be joined covalently or non-covalently to a multimerization domain. Preferably, a multimerization domain promotes interaction between a first polypeptide (e.g., TGF-beta superfamily type I polypeptide) and a second polypeptide (e.g., TGF-beta superfamily type II polypeptide) to promote heteromultimer formation (e.g., heterodimer formation), and optionally hinders or otherwise disfavors homomultimer formation (e.g., homodimer formation), thereby increasing the yield of desired heteromultimer (see, e.g., FIG. 1, 2, or 15).

Many methods known in the art can be used to generate TGF-beta superfamily heteromultimers of the disclosure. For example, non-naturally occurring disulfide bonds may be constructed by replacing on a first polypeptide (e.g., TGF-beta superfamily type I polypeptide) a naturally occurring amino acid with a free thiol-containing residue, such as cysteine, such that the free thiol interacts with another free thiol-containing residue on a second polypeptide (e.g., TGF-beta superfamily type II polypeptide) such that a disulfide bond is formed between the first and second polypeptides. Additional examples of interactions to promote heteromultimer formation include, but are not limited to, ionic interactions such as described in Kjaergaard et al., WO2007147901; electrostatic steering effects such as described in Kannan et al., U.S. Pat. No. 8,592,562; coiled-coil interactions such as described in Christensen et al., U.S.20120302737; leucine zippers such as described in Pack & Plueckthun, (1992) Biochemistry 31: 1579-1584; and helix-turn-helix motifs such as described in Pack et al., (1993) Bio/Technology 11: 1271-1277. Linkage of the various segments may be obtained via, e.g., covalent binding such as by chemical cross-linking, peptide linkers, disulfide bridges, etc., or affinity interactions such as by avidin-biotin or leucine zipper technology.

In certain aspects, a multimerization domain may comprise one component of an interaction pair. In some embodiments, the polypeptides disclosed herein may form protein complexes comprising a first polypeptide covalently or non-covalently associated with a second polypeptide, wherein the first polypeptide comprises the amino acid sequence of a TGF-beta superfamily type I polypeptide and the amino acid sequence of a first member of an interaction pair; and the second polypeptide comprises the amino acid sequence of a TGF-beta superfamily type II polypeptide and the amino acid sequence of a second member of an interaction pair. The interaction pair may be any two polypeptide sequences that interact to form a complex, particularly a heterodimeric complex although operative embodiments may also employ an interaction pair that can form a homodimeric complex. One member of the interaction pair may be fused to a TGF-beta superfamily type I or type II polypeptide as described herein, including for example, a polypeptide sequence comprising, consisting essentially of, or consisting of an amino acid sequence that is at least 80%, 85%, 90%, 95%, 96%, 97%, 98%, 99%, or 100% identical to the sequence of any one of SEQ ID NOs: 14, 15, 124, 126, 413, 414, 18, 19, 136, 138, 421, 422, 22, 23, 115, 117, 407, 408, 26, 27, 83, 84, 104, 106, 403, 404, 30, 31, 87, 88, 139, 141, 423, 424, 34, 35, 91, 92, 142, 144, 425, 426, 38, 39, 301, 302, 305, 306, 309, 310, 313, 112, 114, 405, 406, 9, 10, 11, 118, 120, 409, 410, 1, 2, 3, 4, 5, 6, 100, 102, 401, 402, 46, 47, 71, 72, 121, 123, 411, 412, 50, 51, 75, 76, 79, 80, 42, 43, 67, 68, 127, 129, 130, 132, 415, 416, 417, and 418. An interaction pair may be selected to confer an improved property/activity such as increased serum half-life, or to act as an adaptor on to which another moiety is attached to provide an improved property/activity. For example, a polyethylene glycol moiety may be attached to one or both components of an interaction pair to provide an improved property/activity such as improved serum half-life.

The first and second members of the interaction pair may be an asymmetric pair, meaning that the members of the pair preferentially associate with each other rather than self-associate. Accordingly, first and second members of an asymmetric interaction pair may associate to form a heterodimeric complex (see, e.g., FIGS. 2 and 15). Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer complex or a heterodimeric complex. Optionally, the first member of the interaction pair (e.g., an asymmetric pair or an unguided interaction pair) associates covalently with the second member of the interaction pair. Optionally, the first member of the interaction pair (e.g., an asymmetric pair or an unguided interaction pair) associates non-covalently with the second member of the interaction pair.

As specific examples, the present disclosure provides fusion proteins comprising TGF-beta superfamily type I or type II polypeptides fused to a polypeptide comprising a constant domain of an immunoglobulin, such as a CH1, CH2, or CH3 domain of an immunoglobulin or an Fc domain. Fc domains derived from human IgG1, IgG2, IgG3, and IgG4 are provided herein. Other mutations are known that decrease either CDC or ADCC activity, and collectively, any of these variants are included in the disclosure and may be used as advantageous components of a heteromultimeric complex of the disclosure. Optionally, the IgG1 Fc domain of SEQ ID NO: 208 has one or more mutations at residues such as Asp-265, Lys-322, and Asn-434 (numbered in accordance with the corresponding full-length IgG1). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

An example of a native amino acid sequence that may be used for the Fc portion of human IgG1 (G1Fc) is shown below (SEQ ID NO: 3100). Dotted underline indicates the hinge region, and solid underline indicates positions with naturally occurring variants. In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 3100. Naturally occurring variants in G1Fc would include E134D and M136L according to the numbering system used in SEQ ID NO: 3100 (see Uniprot P01857).

```
                                          (SEQ ID NO: 3100)
  1    THTCPPCPAP ELLGGPSVFL FPPKPKDTLM

ISRTPEVTCV VVDVSHEDPE

51    VKFNWYVDGV EVHNAKTKPR EEQYNSTYRV

VSVLTVLHQD WLNGKEYKCK

101    VSNKALPAPI EKTISKAKGQ PREPQVYTLP

PSREEMTKNQ VSLTCLVKGF
```

```
151    YPSDIAVEWE SNGQPENNYK TTPPVLDSDG

SFFLYSKLTV DKSRWQQGNV

201    FSCSVMHEAL HNHYTQKSLS LSPGK
```

An example of a native amino acid sequence that may be used for the Fc portion of human IgG2 (G2Fc) is shown below (SEQ ID NO: 3200). Dotted underline indicates the hinge region and double underline indicates positions where there are data base conflicts in the sequence (according to UniProt P01859). In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 3200.

```
                                          (SEQ ID NO: 3200)
  1    VECPPCPAPP VAGPSVFLFP PKPKDTLMIS

RTPEVTCVVV DVSHEDPEVQ

51    FNWYVDGVEV HNAKTKPREE QFNSTFRVVS

VLTVVHQDWL NGKEYKCKVS

101    NKGLPAPIEK TISKTKGQPR EPQVYTLPPS

REEMTKNQVS LTCLVKGFYP

151    SDIAVEWESN GQPENNYKTT PPMLDSDGSF

FLYSKLTVDK SRWQQGNVFS

201    CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 3300) contains a short hinge region consisting of a single 15-residue segment, whereas the second G3Fc sequence (SEQ ID NO: 3400) contains a full-length hinge region. In each case, dotted underline indicates the hinge region, and solid underline indicates positions with naturally occurring variants according to UniProt P01859. In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NOs: 3300 and 3400.

```
                                          (SEQ ID NO: 3300)
  1    EPKSCDTPPP CPRCPAPELL GGPSVFLFPP

KPKDTLMISR TPEVTCVVVD

51    VSHEDPEVQF KWYVDGVEVH NAKTKPREEQ

YNSTFRVVSV LTVLHQDWLN

101    GKEYKCKVSN KALPAPIEKT ISKTKGQPRE

PQVYTLPPSR EEMTKNQVSL

151    TCLVKGFYPS DIAVEWESSG QPENNYNTTP

PMLDSDGSFF LYSKLTVDKS
```

```
201    RWQQGNIFSC SVMHEALHNR FTQKSLSLSP GK (SEQ ID NO: 3400)
  1    ELKTPLGDTT HTCPRCPEPK SCDTPPPCPR

CPEPKSCDTP PPCPRCPEPK

51    SCDTPPPCPR CPAPELLGGP SVFLFPPKPK

DTLMISRTPE VTCVVVDSH

101    EDPEVQFKWY VDGVEVHNAK TKPREEQYNS

TFRVVSVLTV LHQDWLNGKE

151    YKCKVSNKAL PAPIEKTISK TKGQPREPQV

YTLPPSREEM TKNQVSLTCL

201    VKGFYPSDIA VEWESSGQPE NNYNTTPPML

DSDGSFFLYS KLTVDKSRWQ

251    QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 3300, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 3500). Dotted underline indicates the hinge region. In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 3500.

```
                                    (SEQ ID NO: 3500)
  1    ESKYGPPCPS CPAPEFLGGP SVFLFPPKPK

DTLMISRTPE VTCVVVDVSQ

51    EDPEVQFNWY VDGVEVHNAK TKPREEQFNS

TYRVVSVLTV LHQDWLNGKE

101    YKCKVSNKGL PSSIEKTISK AKGQPREPQV

YTLPPSQEEM TKNQVSLTCL

151    VKGFYPSDIA VEWESNGQPE NNYKTTPPVL

DSDGSFFLYS RLTVDKSRWQ

201    EGNVFSCSVM HEALHNHYTQ KSLSLSLGK
```

A variety of engineered mutations in the Fc domain are presented herein with respect to the G1Fc sequence (SEQ ID NO: 3100), and analogous mutations in G2Fc, G3Fc, and G4Fc can be derived from their alignment with G1Fc in FIG. 5. Due to unequal hinge lengths, analogous Fc positions based on isotype alignment (FIG. 5) possess different amino acid numbers in SEQ ID NOs: 3100, 3200, 3300, and 3500. It can also be appreciated that a given amino acid position in an immunoglobulin sequence consisting of hinge, $C_H2$, and $C_H3$ regions (e.g., SEQ ID NOs: 3100, 3200, 3300, and 3500) will be identified by a different number than the same position when numbering encompasses the entire IgG1 heavy-chain constant domain (consisting of the $C_H1$, hinge, $C_H2$, and $C_H3$ regions) as in the Uniprot database. For example, correspondence between selected $C_H3$ positions in a human G1Fc sequence (SEQ ID NO: 3100), the human IgG1 heavy chain constant domain (Uniprot P01857), and the human IgG1 heavy chain is as follows.

| Correspondence of $C_H3$ Positions in Different Numbering Systems | | |
|---|---|---|
| G1Fc (Numbering begins at first threonine in hinge region) | IgG1 heavy chain constant domain (Numbering begins at $C_H1$) | IgG1 heavy chain (EU numbering scheme of Kabat et al., 1991*) |
| Y127 | Y232 | Y349 |
| S132 | S237 | S354 |
| E134 | E239 | E356 |
| K138 | K243 | K360 |
| T144 | T249 | T366 |
| L146 | L251 | L368 |
| N162 | N267 | N384 |
| K170 | K275 | K392 |
| D177 | D282 | D399 |
| D179 | D284 | D401 |
| Y185 | Y290 | Y407 |
| K187 | K292 | K409 |
| H213 | H318 | H435 |
| K217 | K322 | K439 |

*Kabat et al. (eds) 1991; pp. 688-696 in Sequences of Proteins of Immunological Interest, 5th ed., Vol. 1, NIH, Bethesda, MD.

A problem that arises in large-scale production of asymmetric immunoglobulin-based proteins from a single cell line is known as the "chain association issue". As confronted prominently in the production of bispecific antibodies, the chain association issue concerns the challenge of efficiently producing a desired multichain protein from among the multiple combinations that inherently result when different heavy chains and/or light chains are produced in a single cell line [see, for example, Klein et al (2012) mAbs 4:653-663]. This problem is most acute when two different heavy chains and two different light chains are produced in the same cell, in which case there are a total of 16 possible chain combinations (although some of these are identical) when only one is typically desired. Nevertheless, the same principle accounts for diminished yield of a desired multichain fusion protein that incorporates only two different (asymmetric) heavy chains.

Various methods are known in the art that increase desired pairing of Fc-containing fusion polypeptide chains in a single cell line to produce a preferred asymmetric fusion protein at acceptable yields [see, for example, Klein et al (2012) mAbs 4:653-663; and Spiess et al (2015) Molecular Immunology 67(2A): 95-106]. Methods to obtain desired pairing of Fc-containing chains include, but are not limited to, charge-based pairing (electrostatic steering), "knobs-into-holes" steric pairing, SEEDbody pairing, and leucine zipper-based pairing. See, for example, Ridgway et al (1996) Protein Eng 9:617-621; Merchant et al (1998) Nat Biotech 16:677-681; Davis et al (2010) Protein Eng Des Sel 23:195-202; Gunasekaran et al (2010); 285:19637-19646; Wranik et al (2012) J Biol Chem 287:43331-43339; U.S. Pat. No. 5,932,448; WO 1993/011162; WO 2009/089004, and WO 2011/034605. As described herein, these methods may be used to generate heterodimers comprising TGF-beta superfamily type I and type II receptor polypeptides, at least two different TGF-beta superfamily type I receptor polypeptides, and at least two different TGF-beta superfamily type II receptor polypeptides. See FIG. 15.

For example, one means by which interaction between specific polypeptides may be promoted is by engineering protuberance-into-cavity (knob-into-holes) complementary regions such as described in Arathoon et al., U.S. Pat. No. 7,183,076 and Carter et al., U.S. Pat. No. 5,731,168. "Protuberances" are constructed by replacing small amino acid side chains from the interface of the first polypeptide (e.g., a first interaction pair) with larger side chains (e.g., tyrosine or tryptophan). Complementary "cavities" of identical or similar size to the protuberances are optionally created on the interface of the second polypeptide (e.g., a second interaction pair) by replacing large amino acid side chains with smaller ones (e.g., alanine or threonine). Where a suitably positioned and dimensioned protuberance or cavity exists at the interface of either the first or second polypeptide, it is only necessary to engineer a corresponding cavity or protuberance, respectively, at the adjacent interface.

At neutral pH (7.0), aspartic acid and glutamic acid are negatively charged and lysine, arginine, and histidine are positively charged. These charged residues can be used to promote heterodimer formation and at the same time hinder homodimer formation. Attractive interactions take place between opposite charges and repulsive interactions occur between like charges. In part, protein complexes disclosed herein make use of the attractive interactions for promoting heteromultimer formation (e.g., heterodimer formation), and optionally repulsive interactions for hindering homodimer formation (e.g., homodimer formation) by carrying out site directed mutagenesis of charged interface residues.

For example, the IgG1 CH3 domain interface comprises four unique charge residue pairs involved in domain-domain interactions: Asp356-Lys439', Glu357-Lys370', Lys392-Asp399', and Asp399-Lys409' [residue numbering in the second chain is indicated by (')]. It should be noted that the numbering scheme used here to designate residues in the IgG1 CH3 domain conforms to the EU numbering scheme of Kabat. Due to the 2-fold symmetry present in the CH3-CH3 domain interactions, each unique interaction will represented twice in the structure (e.g., Asp-399-Lys409' and Lys409-Asp399'). In the wild-type sequence, K409-D399' favors both heterodimer and homodimer formation. A single mutation switching the charge polarity (e.g., K409E; positive to negative charge) in the first chain leads to unfavorable interactions for the formation of the first chain homodimer. The unfavorable interactions arise due to the repulsive interactions occurring between the same charges (negative-negative; K409E-D399' and D399-K409E'). A similar mutation switching the charge polarity (D399K'; negative to positive) in the second chain leads to unfavorable interactions (K409'-D399K' and D399K-K409') for the second chain homodimer formation. But, at the same time, these two mutations (K409E and D399K') lead to favorable interactions (K409E-D399K' and D399-K409') for the heterodimer formation.

The electrostatic steering effect on heterodimer formation and homodimer discouragement can be further enhanced by mutation of additional charge residues which may or may not be paired with an oppositely charged residue in the second chain including, for example, Arg355 and Lys360. The table below lists possible charge change mutations that can be used, alone or in combination, to enhance heteromultimer formation of the polypeptide complexes disclosed herein.

Examples of Pair-Wise Charged Residue Mutations to Enhance Heterodimer Formation

| Position in first chain | Mutation in first chain | Interacting position in second chain | Corresponding mutation in second chain |
| --- | --- | --- | --- |
| Lys409 | Asp or Glu | Asp399' | Lys, Arg, or His |
| Lys392 | Asp or Glu | Asp399' | Lys, Arg, or His |
| Lys439 | Asp or Glu | Asp356' | Lys, Arg, or His |
| Lys370 | Asp or Glu | Glu357' | Lys, Arg, or His |
| Asp399 | Lys, Arg, or His | Lys409' | Asp or Glu |
| Asp399 | Lys, Arg, or His | Lys392' | Asp or Glu |
| Asp356 | Lys, Arg, or His | Lys439' | Asp or Glu |
| Glu357 | Lys, Arg, or His | Lys370' | Asp or Glu |

In some embodiments, one or more residues that make up the CH3-CH3 interface in a fusion protein of the instant application are replaced with a charged amino acid such that the interaction becomes electrostatically unfavorable. For example, a positive-charged amino acid in the interface (e.g., a lysine, arginine, or histidine) is replaced with a negatively charged amino acid (e.g., aspartic acid or glutamic acid). Alternatively, or in combination with the forgoing substitution, a negative-charged amino acid in the interface is replaced with a positive-charged amino acid. In certain embodiments, the amino acid is replaced with a non-naturally occurring amino acid having the desired charge characteristic. It should be noted that mutating negatively charged residues (Asp or Glu) to His will lead to increase in side chain volume, which may cause steric issues. Furthermore, His proton donor- and acceptor-form depends on the localized environment. These issues should be taken into consideration with the design strategy. Because the interface residues are highly conserved in human and mouse IgG subclasses, electrostatic steering effects disclosed herein can be applied to human and mouse IgG1, IgG2, IgG3, and IgG4. This strategy can also be extended to modifying uncharged residues to charged residues at the CH3 domain interface.

In part, the disclosure provides desired pairing of asymmetric Fc-containing polypeptide chains using Fc sequences engineered to be complementary on the basis of charge pairing (electrostatic steering). One of a pair of Fc sequences with electrostatic complementarity can be arbitrarily fused to the TGF-beta superfamily type I or type II receptor polypeptide of the construct, with or without an optional linker, to generate a TGF-beta superfamily type I or type II receptor fusion polypeptide This single chain can be coexpressed in a cell of choice along with the Fc sequence complementary to the first Fc to favor generation of the desired multichain construct (e.g., a TGF-beta superfamily heteromeric complex). In this example based on electrostatic steering, SEQ ID NO: 200 [human G1Fc(E134K/D177K)] and SEQ ID NO: 201 [human G1Fc(K170D/K187D)] are examples of complementary Fc sequences in which the engineered amino acid substitutions are double underlined, and the TGF-beta superfamily type I or type II receptor polypeptide of the construct can be fused to either SEQ ID NO: 200 or SEQ ID NO: 201, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 200 and 201).

```
                                                           (SEQ ID NO: 200)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSRKEMTKNQ VSLTCLVKGF

151 YPSDIAVEWE SNGQPENNYK TTPPVLKSDG SFFLYSKLTV DKSRWQQGNV

201 FSCSVMHEAL HNHYTQKSLS LSPGK
                                                           (SEQ ID NO: 201)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYD TTPPVLDSDG SFFLYSDLTV DKSRWQQGNV

201 FSCSVMHEAL HNHYTQKSLS LSPGK
```

In part, the disclosure provides desired pairing of asymmetric Fc-containing polypeptide chains using Fc sequences engineered for steric complementarity. In part, the disclosure provides knobs-into-holes pairing as an example of steric complementarity. One of a pair of Fc sequences with steric complementarity can be arbitrarily fused to the TGF-beta superfamily type I or type II polypeptide of the construct, with or without an optional linker, to generate a TGF-beta superfamily type I or type II fusion polypeptide. This single chain can be coexpressed in a cell of choice along with the Fc sequence complementary to the first Fc to favor generation of the desired multichain construct. In this example based on knobs-into-holes pairing, SEQ ID NO: 202 [human G1Fc(T144Y)] and SEQ ID NO: 203 [human G1Fc(Y185T)] are examples of complementary Fc sequences in which the engineered amino acid substitutions are double underlined, and the TGF-beta superfamily type I or type II polypeptide of the construct can be fused to either SEQ ID NO: 202 or SEQ ID NO: 203, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 202 and 203).

```
                                                           (SEQ ID NO: 202)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLYCLVKGF

151 YPSDIAVEWE SNGQPENNYK TTPPVLDSDG SFFLYSKLTV DKSRWQQGNV

201 FSCSVMHEAL HNHYTQKSLS LSPGK
                                                           (SEQ ID NO: 203)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLTSKLTV DKSRWQQGNV

201 FSCSVMHEAL HNHYTQKSLS LSPGK
```

An example of Fc complementarity based on knobs-into-holes pairing combined with an engineered disulfide bond is disclosed in SEQ ID NO: 204 [hG1Fc(S132C/T144W)] and SEQ ID NO: 205 [hG1Fc(Y127C/T144S/L146A/Y185V)]. The engineered amino acid substitutions in these sequences are double underlined, and the TGF-beta superfamily type I or type II polypeptide of the construct can be fused to either SEQ ID NO: 204 or SEQ ID NO: 205, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 204 and 205).

```
                                                        (SEQ ID NO: 204)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PCREEMTKNQ VSLWCLVKGF

151 YPSDIAVEWE SNGQPENNYK TTPPVLDSDG SFFLYSKLTV DKSRWQQGNV

201 FSCSVMHEAL HNHYTQKSLS LSPGK (SEQ ID NO: 205)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVCTLP PSREEMTKNQ VSLSCAVKGF

151 YPSDIAVEWE SNGQPENNYK TTPPVLDSDG SFFLVSKLTV DKSRWQQGNV

201 FSCSVMHEAL HNHYTQKSLS LSPGK
```

In part, the disclosure provides desired pairing of asymmetric Fc-containing polypeptide chains using Fc sequences engineered to generate interdigitating β-strand segments of human IgG and IgA $C_H3$ domains. Such methods include the use of strand-exchange engineered domain (SEED) $C_H3$ heterodimers allowing the formation of SEEDbody fusion proteins [see, for example, Davis et al (2010) Protein Eng Design Sel 23:195-202]. One of a pair of Fc sequences with SEEDbody complementarity can be arbitrarily fused to the TGF-beta superfamily type I or type II polypeptide of the construct, with or without an optional linker, to generate a TGF-beta superfamily type I or type II fusion polypeptide. This single chain can be coexpressed in a cell of choice along with the Fc sequence complementary to the first Fc to favor generation of the desired multichain construct. In this example based on SEEDbody (Sb) pairing, SEQ ID NO: 206 [hG1Fc(Sb$_{AG}$)] and SEQ ID NO: 207 [hG1Fc(Sb$_{GA}$)] are examples of complementary IgG Fc sequences in which the engineered amino acid substitutions from IgA Fc are double underlined, and the TGF-beta superfamily type I or type II polypeptide of the construct can be fused to either SEQ ID NO: 206 or SEQ ID NO: 207, but not both. Given the high degree of amino acid sequence identity between native hG1Fc, native hG2Fc, native hG3Fc, and native hG4Fc, it can be appreciated that amino acid substitutions at corresponding positions in hG1Fc, hG2Fc, hG3Fc, or hG4Fc (see FIG. 5) will generate an Fc monomer which may be used in the complementary IgG-IgA pair below (SEQ ID NOs: 206 and 207).

```
                                                        (SEQ ID NO: 206)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PFRPEVHLLP PSREEMTKNQ VSLTCLARGF

151 YPKDIAVEWE SNGQPENNYK TTPSRQEPSQ GTTTFAVTSK LTVDKSRWQQ

201 GNVFSCSVMH EALHNHYTQK TISLSPGK (SEQ ID NO: 207)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PPSEELALNE LVTLTCLVKG

151 FYPSDIAVEW ESNGQELPRE KYLTWAPVLD SDGSFFLYSI LRVAAEDWKK

201 GDTFSCSVMH EALHNHYTQK SLDRSPGK
```

In part, the disclosure provides desired pairing of asymmetric Fc-containing polypeptide chains with a cleavable leucine zipper domain attached at the C-terminus of the Fc $C_H3$ domains. Attachment of a leucine zipper is sufficient to cause preferential assembly of heterodimeric antibody heavy chains. See, e.g., Wranik et al (2012) J Biol Chem 287:43331-43339. As disclosed herein, one of a pair of Fc sequences attached to a leucine zipper-forming strand can be arbitrarily fused to the TGF-beta superfamily type I or type II polypeptide of the construct, with or without an optional linker, to generate a TGF-beta superfamily type I or type II fusion polypeptide. This single chain can be coexpressed in a cell of choice along with the Fc sequence attached to a complementary leucine zipper-forming strand to favor generation of the desired multichain construct. Proteolytic digestion of the construct with the bacterial endoproteinase Lys-C post purification can release the leucine zipper domain, resulting in an Fc construct whose structure is identical to that of native Fc. In this example based on leucine zipper pairing, SEQ ID NO: 213 [hG1Fc-Ap1

(acidic)] and SEQ ID NO: 214 [hG1Fc-Bp1 (basic)] are examples of complementary IgG Fc sequences in which the engineered complimentary leucine zipper sequences are underlined, and the TGF-beta superfamily type I or type II polypeptide of the construct can be fused to either SEQ ID NO: 213 or SEQ ID NO: 214, but not both. Given the high degree of amino acid sequence identity between native hG1Fc, native hG2Fc, native hG3Fc, and native hG4Fc, it can be appreciated that leucine zipper-forming sequences attached, with or without an optional linker, to hG1Fc, hG2Fc, hG3Fc, or hG4Fc (see FIG. 5) will generate an Fc monomer which may be used in the complementary leucine zipper-forming pair below (SEQ ID NOs: 213 and 214).

pI marker standards (e.g., Amersham, pI range 3-10, 8 .mu.L) are used to determine relative pI for the proteins. Electrophoresis is performed, for example, at 1500 V, 50 mA for 105 minutes. The gel is fixed using, for example, a Sigma fixing solution (5×) diluted with purified water to 1× Staining is performed, for example, overnight at room temperature using Simply Blue stain (Invitrogen). Destaining is carried out, for example, with a solution that consisted of 25% ethanol, 8% acetic acid and 67% purified water. Isoelectric points are determined using, for example, a Bio-Rad Densitometer relative to calibration curves of the standards. The one or more metrics may further include metrics characterizing stability of the domain under one or more different

```
                                                              (SEQ ID NO: 213)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGKGGSAQ LEKELQALEK ENAQLEWELQ

251 ALEKELAQGA T (SEQ ID NO: 214)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEALHNHYTQKSLS LSPGKGGSAQ LKKKLQALKK KNAQLKWKLQ

251 ALKKKLAQGAT
```

In certain aspects, the disclosure relates to type I receptor polypeptides (e.g., type I-Fc fusion proteins) comprising one or more amino acid modifications that alter the isoelectric point (pI) of the type I receptor polypeptide and/or type II receptor polypeptides (e.g., type II-Fc fusion proteins) comprising one or more amino acid modifications that alter the isoelectric point of the type II receptor polypeptide. In some embodiments, one or more candidate domains that have a pI value higher than about 5.0, 5.5, 6.0, 6.5, 7.0, 7.5, 8.0, 8.5, or 9.0 are selected for construction of the full multidomain protein. In other embodiments, one or more candidate domains that have a pI value less than about 9.0, 8.5, 8.0, 7.5, 7.0, 6.5, 6.0, 5.5, or 5.0 are selected for construction of the full multidomain protein. It will be understood by one skilled in the art that a single protein will have multiple charge forms. Without wishing to be bound by any particular theory, the charge of a protein can be modified by a number of different mechanisms including but not limited to, amino acid substitution, cationization, deamination, carboxyl-terminal amino acid heterogeneity, phosphorylation and glycosylation.

The pI of a protein may be determined by a variety of methods including but not limited to, isoelectric focusing and various computer algorithms (see for example Bjellqvist et al., 1993, Electrophoresis 14:1023). In one embodiment, pI is determined using a Pharmacia Biotech Multiphor 2 electrophoresis system with a multi temp refrigerated bath recirculation unit and an EPS 3501 XL power supply. Pre-cast ampholine gels (e.g., Amersham Biosciences, pI range 2.5-10) are loaded with protein samples. Broad range conditions selected from the group consisting of different pH values, different temperatures, different shear stresses, and different freeze/thaw cycles.

In part, the disclosure provides desired pairing of asymmetric Fc-containing polypeptide chains by methods described above in combination with additional mutations in the Fc domain that facilitate purification of the desired heteromeric species. An example is complementarity of Fc domains based on knobs-into-holes pairing combined with an engineered disulfide bond, as disclosed above, plus additional substitution of two negatively charged amino acids (aspartic acid or glutamic acid) in one Fc-containing polypeptide chain and two positively charged amino acids (e.g., arginine) in the complementary Fc-containing polypeptide chain (SEQ ID NOs: 660 and 670). These four amino acid substitutions facilitate selective purification of the desired heteromeric fusion protein from a heterogeneous polypeptide mixture based on differences in isoelectric point. The engineered amino acid substitutions in these sequences are double underlined below, and the ALK4 or ActRIIB polypeptide of the construct can be fused to either SEQ ID NO: 660 or SEQ ID NO: 670, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 660 and 670).

```
                                                    (SEQ ID NO: 660)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PCREEMTENQ VSLWCLVKGF

151 YPSDIAVEWE SNGQPENNYK TTPPVLDSDG SFFLYSKLTV DKSRWQQGNV

201 FSCSVMHEAL HNHYTQDSLS LSPGK (SEQ ID NO: 670)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVCTLP PSREEMTKNQ VSLSCAVKGF

151 YPSDIAVEWE SRGQPENNYK TTPPVLDSRG SFFLVSKLTV DKSRWQQGNV

201 FSCSVMHEAL HNHYTQKSLS LSPGK
```

Another example involves complementarity of Fc domains based on knobs-into-holes pairing combined with an engineered disulfide bond, as disclosed above, plus a histidine-to-arginine substitution at position 213 in one Fc-containing polypeptide chain (SEQ ID NO: 680). This substitution (denoted H435R in the numbering system of Kabat et al.) facilitates separation of desired heteromer from undesirable homodimer based on differences in affinity for protein A. The engineered amino acid substitution is indicated by double underline, and the ALK4 or ActRIIB polypeptide of the construct can be fused to either SEQ ID NO: 680 or SEQ ID NO: 205, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair of SEQ ID NO: 680 (below) and SEQ ID NO: 205.

Correspondence between $C_H3$ Positions for Human Fc Isotypes*

| IgG1 SEQ ID NO: 3100 Numbering begins at THT... | IgG4 SEQ ID NO: 3500 Numbering begins at ESK... | IgG2 SEQ ID NO: 3200 Numbering begins at VEC... | IgG3 SEQ ID NO: 3300 Numbering begins at EPK... |
|---|---|---|---|
| Y127 | Y131 | Y125 | Y134 |
| S132 | S136 | S130 | S139 |
| E134 | E138 | E132 | E141 |
| K138 | K142 | K136 | K145 |
| T144 | T148 | T142 | T151 |
| L146 | L150 | L144 | L153 |
| N162 | N166 | N160 | S169 |
| K170 | K174 | K168 | N177 |
| D177 | D181 | D175 | D184 |
| D179 | D183 | D177 | D186 |
| Y185 | Y189 | Y183 | Y192 |
| K187 | R191 | K185 | K194 |

```
                                                    (SEQ ID NO: 680)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PCREEMTKNQ VSLWCLVKGF

151 YPSDIAVEWE SNGQPENNYK TTPPVLDSDG SFFLYSKLTV DKSRWQQGNV

201 FSCSVMHEAL HNRYTQKSLS LSPGK
```

A variety of engineered mutations in the Fc domain are presented above with respect to the G1Fc sequence (SEQ ID NO: 3100). Analogous mutations in G2Fc, G3Fc, and G4Fc can be derived from their alignment with G1Fc in FIG. 5. Due to unequal hinge lengths, analogous Fc positions based on isotype alignment (FIG. 5) possess different amino acid numbers in SEQ ID NOs: 3100, 3200, 3300, 3400, and 3500 as summarized in the following table.

-continued

Correspondence between $C_H3$ Positions for Human Fc Isotypes*

| IgG1 SEQ ID NO: 3100 Numbering begins at THT... | IgG4 SEQ ID NO: 3500 Numbering begins at ESK... | IgG2 SEQ ID NO: 3200 Numbering begins at VEC... | IgG3 SEQ ID NO: 3300 Numbering begins at EPK... |
|---|---|---|---|
| H213 | H217 | H211 | R220 |
| K217 | K221 | K215 | K224 |

*Numbering based on multiple sequence alignment shown in FIG. 5

It is understood that different elements of the fusion proteins (e.g., immunoglobulin Fc fusion proteins) may be arranged in any manner that is consistent with desired functionality. For example, a TGF-beta superfamily type I and/or type II receptor polypeptide domain may be placed C-terminal to a heterologous domain, or alternatively, a heterologous domain may be placed C-terminal to a TGF-beta superfamily type I and/or type II receptor polypeptide domain. The TGF-beta superfamily type I and/or type II receptor polypeptide domain and the heterologous domain need not be adjacent in a fusion protein, and additional domains or amino acid sequences may be included C- or N-terminal to either domain or between the domains.

For example, a TGF-beta superfamily type I and/or type II receptor fusion protein may comprise an amino acid sequence as set forth in the formula A-B-C. The B portion corresponds to a TGF-beta superfamily type I and/or type II receptor polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10, 2-5, 2-4, 2-3 glycine residues) or glycine and proline residues and may, for example, contain a single sequence of threonine/serine and glycines or repeating sequences of threonine/serine and/or glycines, e.g., GGG (SEQ ID NO: 58), GGGG (SEQ ID NO: 59), TGGGG (SEQ ID NO: 60), SGGGG (SEQ ID NO: 61), TGGG (SEQ ID NO: 62), or SGGG (SEQ ID NO: 63) singlets, or repeats. In certain embodiments, a TGF-beta superfamily type I and/or type II receptor fusion protein comprises an amino acid sequence as set forth in the formula A-B-C, wherein A is a leader (signal) sequence, B consists of a TGF-beta superfamily type I and/or type II receptor polypeptide domain, and C is a polypeptide portion that enhances one or more of in vivo stability, in vivo half-life, uptake/administration, tissue localization or distribution, formation of protein complexes, and/or purification. In certain embodiments, a TGF-beta superfamily type I and/or type II receptor fusion protein comprises an amino acid sequence as set forth in the formula A-B-C, wherein A is a TPA leader sequence, B consists of a TGF-beta superfamily type I and/or type II receptor polypeptide domain, and C is an immunoglobulin Fc domain. Preferred fusion proteins comprise the amino acid sequence set forth in any one of SEQ ID NOs: 100, 102, 104, 106, 112, 114, 115, 117, 118, 120, 121, 123, 124, 126, 127, 129, 401, 402, 403, 404, 405, 406, 407, 408, 409, 410, 411, 412, 413, 414, 415, and 416.

In some embodiments, TGF-beta superfamily receptor heteromultimers of the present disclosure further comprise one or more heterologous portions (domains) so as to confer a desired property. For example, some fusion domains are particularly useful for isolation of the fusion proteins by affinity chromatography. Well-known examples of such fusion domains include, but are not limited to, polyhistidine, Glu-Glu, glutathione S-transferase (GST), thioredoxin, protein A, protein G, an immunoglobulin heavy-chain constant region (Fc), maltose binding protein (MBP), or human serum albumin. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the ligand trap polypeptides. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for factor Xa or thrombin, which allows the relevant protease to partially digest the fusion proteins and thereby liberate the recombinant proteins therefrom. The liberated proteins can then be isolated from the fusion domain by subsequent chromatographic separation.

In certain embodiments, TGF-beta superfamily type I and/or type II receptor polypeptides of the present disclosure comprise one or more modifications that are capable of stabilizing the polypeptides. For example, such modifications enhance the in vitro half-life of the polypeptides, enhance circulatory half-life of the polypeptides, and/or reduce proteolytic degradation of the polypeptides. Such stabilizing modifications include, but are not limited to, fusion proteins (including, for example, fusion proteins comprising a TGF-beta superfamily type I and/or type II receptor polypeptide domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion proteins, but also includes nonproteinaceous modifications such as a carbohydrate moiety, or nonproteinaceous moiety, such as polyethylene glycol.

In preferred embodiments, TGF-beta superfamily heteromultimers to be used in accordance with the methods described herein are isolated polypeptide complexes. As used herein, an isolated protein (or protein complex) or polypeptide (or polypeptide complex) is one which has been separated from a component of its natural environment. In some embodiments, a heteromultimer complex of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of antibody purity are well known in the art [See, e.g., Flatman et al., (2007) J. Chromatogr. B 848:79-87]. In some embodiments, heteromultimer preparations of the disclosure are substantially free of TGF-beta superfamily type I receptor polypeptide homomultimers and/or TGF-beta superfamily type II receptor polypeptide homomultimers. For example, in some embodiments, heteromultimer preparations comprise less than about 10%, 9%, 8%, 7%, 5%, 4%, 3%, 2%, or less than 1% of TGF-beta superfamily type I receptor polypeptide homomultimers. In some embodiments, heteromultimer preparations comprise less than about 10%, 9%, 8%, 7%, 5%, 4%, 3%, 2%, or less than 1% of TGF-beta superfamily type II receptor polypeptide homomultimers. In some embodiments, heteromultimer preparations comprise less than about 10%, 9%, 8%, 7%, 5%, 4%, 3%, 2%, or less than 1% of TGF-beta superfamily type I receptor polypeptide homomultimers and less than about 10%, 9%, 8%, 7%, 5%, 4%, 3%, 2%, or less than 1% of TGF-beta superfamily type II receptor polypeptide homomultimers.

In certain embodiments, TGFβ superfamily type I and/or type II receptor polypeptides, as well as heteromultimers thereof, of the disclosure can be produced by a variety of art-known techniques. For example, polypeptides of the disclosure can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (see, e.g., Advanced ChemTech Model 396; Milligen/Biosearch 9600). Alternatively, the polypeptides and complexes of the disclosure, including fragments or variants thereof, may be recombinantly produced using various expression systems [e.g., *E. coli*, Chinese Hamster Ovary (CHO) cells, COS cells, baculovirus] as is well known in the art. In a further embodiment, the modified or unmodified polypeptides of the disclosure may be produced by digestion of recombinantly produced full-length TGFβ superfamily type I and/or type II receptor polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites.

With respect to antibodies that bind to and antagonize ligands that bind to TGF-beta type I receptor polypeptide: TGF-beta type II receptor polypeptide heteromultimers of the disclosure (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty) it is contemplated that an antibody may be designed as a bispecific antibody comprising a first portion that binds to an epitope of such ligand, such that the first portion of the antibody competes for binding with a type I receptor and comprising a second portion that binds to an epitope of such ligand, such that the second portion of the antibody competes for binding with a type II receptor. In this manner, a bispecific antibody targeting a single ligand can be designed to mimic the dual type I-type II receptor binding blockade that may be conferred by an ALK7:ActRIIB heteromultimer. Similarly it is contemplated that the same effect could be achieved using a combination of two or more antibodies wherein at least a first antibody binds to an epitope of such ligand, such that the first antibody competes for binding with a type I receptor and at least a second antibody binds to an epitope of such ligand, such that the second antibody competes for binding with a type II receptor.

3. Nucleic Acids Encoding TGFβ Superfamily Type I and/or Type II Receptor Polypeptides In certain embodiments, the present disclosure provides isolated and/or recombinant nucleic acids encoding TGFβ superfamily type I and/or type II receptors (including fragments, functional variants, and fusion proteins thereof) disclosed herein. For example, SEQ ID NO: 12 encodes the naturally occurring human ActRIIA precursor polypeptide, while SEQ ID NO: 13 encodes the mature, extracellular domain of ActRIIA. The subject nucleic acids may be single-stranded or double stranded. Such nucleic acids may be DNA or RNA molecules. These nucleic acids may be used, for example, in methods for making TGF-beta superfamily heteromultimer complexes of the present disclosure.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding TGFβ superfamily type I and/or type II receptor polypeptides of the present disclosure are understood to include nucleic acids that are variants of any one of SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143. Variant nucleotide sequences include sequences that differ by one or more nucleotide substitutions, additions, or deletions including allelic variants, and therefore, will include coding sequences that differ from the nucleotide sequence designated in any one of SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143.

In certain embodiments, TGFβ superfamily type I and/or type II receptor polypeptides of the present disclosure are encoded by isolated or recombinant nucleic acid sequences that are at least 80%, 85%, 90%, 95%, 96%, 97%, 98%, 99%, or 100% identical to SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143. One of ordinary skill in the art will appreciate that nucleic acid sequences that are at least 80%, 85%, 90%, 95%, 96%, 97%, 98%, or 99% identical to the sequences complementary to SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143 are also within the scope of the present disclosure. In further embodiments, the nucleic acid sequences of the disclosure can be isolated, recombinant, and/or fused with a heterologous nucleotide sequence or in a DNA library.

In other embodiments, nucleic acids of the present disclosure also include nucleotide sequences that hybridize under highly stringent conditions to the nucleotide sequence designated in SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143, the complement sequence of SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143, or fragments thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the present disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

In certain aspects of the present disclosure, the subject nucleic acid is provided in an expression vector comprising a nucleotide sequence encoding a TGFβ superfamily type I and/or type II receptor polypeptide and operably linked to at least one regulatory sequence. Regulatory sequences are art-recognized and are selected to direct expression of the TGFβ superfamily type I and/or type II receptor polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, CA (1990). For instance, any of a wide variety of expression control sequences that control the expression of a DNA sequence when operatively linked to it may be used in these vectors to express DNA sequences encoding a TGFβ superfamily type I and/or type II receptor polypeptides. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant TGFβ superfamily type I and/or type II receptor polypeptide include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as *E. coli.*

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see, e.g., Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject TGFβ superfamily type I and/or type II receptor polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wisc.). As will be apparent, the subject gene constructs can be used to cause expression of the subject TGFβ superfamily type I and/or type II receptor polypeptide in cells propagated in culture, e.g., to produce proteins, including fusion proteins or variant proteins, for purification.

This disclosure also pertains to a host cell transfected with a recombinant gene including a coding sequence for one or more of the subject TGFβ superfamily type I and/or type II receptor polypeptides. The host cell may be any prokaryotic or eukaryotic cell. For example, a TGFβ superfamily type I and/or type II receptor polypeptide of the disclosure may be expressed in bacterial cells such as E. coli, insect cells (e.g., using a baculovirus expression system), yeast, or mammalian cells [e.g. a Chinese hamster ovary (CHO) cell line]. Other suitable host cells are known to those skilled in the art.

Accordingly, the present disclosure further pertains to methods of producing the subject TGFβ superfamily type I and/or type II receptor polypeptides. For example, a host cell transfected with an expression vector encoding a TGFβ superfamily type I and/or type II receptor polypeptide can be cultured under appropriate conditions to allow expression of the TGFβ superfamily type I and/or type II receptor polypeptide to occur. The polypeptide may be secreted and isolated from a mixture of cells and medium containing the polypeptide. Alternatively, the TGFβ superfamily type I and/or type II receptor polypeptide may be isolated from a cytoplasmic or membrane fraction obtained from harvested and lysed cells. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the TGFβ superfamily type I and/or type II receptor polypeptides and affinity purification with an agent that binds to a domain fused to TGFβ superfamily type I and/or type II receptor polypeptide (e.g., a protein A column may be used to purify a TGFβ superfamily type I receptor-Fc and/or type II receptor-Fc fusion protein). In some embodiments, the TGFβ superfamily type I and/or type II receptor polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. A TGFβ superfamily type I receptor-Fc and/or type II receptor-Fc fusion protein may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant TGFβ superfamily type I and/or type II receptor polypeptide, can allow purification of the expressed fusion protein by affinity chromatography using a $Ni^{2+}$ metal resin. The purification leader sequence can then be subsequently removed by treatment with enterokinase to provide the purified TGFβ superfamily type I and/or type II receptor polypeptide. See, e.g., Hochuli et al. (1987) J. Chromatography 411:177; and Janknecht et al. (1991) PNAS USA 88:8972.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

4. Screening Assays

In certain aspects, the present disclosure relates to the use of TGFβ superfamily type I and type II receptor heteromultimers to identify compounds (agents) which are agonists or antagonists of TGFβ superfamily receptors. Compounds identified through this screening can be tested to assess their ability to modulate tissues such as bone, cartilage, muscle, fat, and/or neurons, to assess their ability to modulate tissue growth in vivo or in vitro. These compounds can be tested, for example, in animal models.

There are numerous approaches to screening for therapeutic agents for modulating tissue growth by targeting TGFβ superfamily ligand signaling (e.g., SMAD 2/3 and/or SMAD 1/5/8 signaling). In certain embodiments, high-throughput screening of compounds can be carried out to identify agents that perturb TGFβ superfamily receptor-mediated effects on a selected cell line. In certain embodiments, the assay is carried out to screen and identify compounds that specifically inhibit or reduce binding of a TGF-beta superfamily heteromultimer to its binding partner, such as a TGFβ superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-01, TGF-02, TGF-03, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). Alternatively, the assay can be used to identify compounds that enhance binding of a TGF-beta superfamily heteromultimer to its binding partner such as a TGFβ superfamily ligand. In a further embodiment, the compounds can be identified by their ability to interact with a TGF-beta superfamily heteromultimer of the disclosure.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro.

Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In certain embodiments, the test agent is a small organic molecule having a molecular weight of less than about 2,000 Daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S-transferase (GST), photoactivatible crosslinkers or any combinations thereof.

In many drug-screening programs which test libraries of compounds and natural extracts, high-throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a TGF-beta superfamily heteromultimer and its binding partner (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-03, activin A, activin B, activin C, activin E, activin AB, activin AC, activin AE, activin BC, activin BE, nodal, glial cell-derived neurotrophic factor (GDNF), neurturin, artemin, persephin, MIS, and Lefty).

Merely to illustrate, in an exemplary screening assay of the present disclosure, the compound of interest is contacted with an isolated and purified TGF-beta superfamily heteromultimer which is ordinarily capable of binding to a TGF-beta superfamily ligand, as appropriate for the intention of the assay. To the mixture of the compound and TGF-beta superfamily heteromultimer is then added to a composition containing the appropriate TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-01, TGF-02, TGF-03, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). Detection and quantification of heteromultimer-superfamily ligand provides a means for determining the compound's efficacy at inhibiting (or potentiating) complex formation between the TGF-beta superfamily heteromultimer and its binding protein. The efficacy of the compound can be assessed by generating dose-response curves from data obtained using various concentrations of the test compound. Moreover, a control assay can also be performed to provide a baseline for comparison. For example, in a control assay, isolated and purified TGF-beta superfamily ligand is added to a composition containing the TGF-beta superfamily heteromultimer, and the formation of heteromultimer-ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Binding of a TGF-beta superfamily heteromultimer to another protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled TGF-beta superfamily heteromultimer and/or its binding protein, by immunoassay, or by chromatographic detection.

In certain embodiments, the present disclosure contemplates the use of fluorescence polarization assays and fluorescence resonance energy transfer (FRET) assays in measuring, either directly or indirectly, the degree of interaction between a TGF-beta superfamily heteromultimer and its binding protein. Further, other modes of detection, such as those based on optical waveguides (see, e.g., PCT Publication WO 96/26432 and U.S. Pat. No. 5,677,196), surface plasmon resonance (SPR), surface charge sensors, and surface force sensors, are compatible with many embodiments of the disclosure.

Moreover, the present disclosure contemplates the use of an interaction trap assay, also known as the "two-hybrid assay," for identifying agents that disrupt or potentiate interaction between a TGF-beta superfamily heteromultimer and its binding partner. See, e.g., U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present disclosure contemplates the use of reverse two-hybrid systems to identify compounds (e.g., small molecules or peptides) that dissociate interactions between a TGF-beta superfamily heteromultimer and its binding protein [see, e.g., Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368].

In certain embodiments, the subject compounds are identified by their ability to interact with a TGF-beta superfamily heteromultimer of the disclosure. The interaction between the compound and the TGF-beta superfamily heteromultimer may be covalent or non-covalent. For example, such interaction can be identified at the protein level using in vitro biochemical methods, including photo-crosslinking, radiolabeled ligand binding, and affinity chromatography. See, e.g., Jakoby W B et al. (1974) Methods in Enzymology 46:1. In certain cases, the compounds may be screened in a mechanism-based assay, such as an assay to detect compounds which bind to a TGF-beta superfamily heteromultimer. This may include a solid-phase or fluid-phase binding event. Alternatively, the gene encoding a TGF-beta superfamily heteromultimer can be transfected with a reporter system (e.g., 0-galactosidase, luciferase, or green fluorescent protein) into a cell and screened against the library preferably by high-throughput screening or with individual members of the library. Other mechanism-based binding assays may be used; for example, binding assays which detect changes in free energy. Binding assays can be performed with the target fixed to a well, bead or chip or captured by an immobilized antibody or resolved by capillary electrophoresis. The bound compounds may be detected usually using colorimetric endpoints or fluorescence or surface plasmon resonance.

5. Exemplary Therapeutic Uses

In certain embodiments, a TGF-beta superfamily heteromultimer, or combinations of TGF-beta superfamily heteromultimers, of the present disclosure can be used to treat or prevent a disease or condition that is associated with abnormal activity of a TGFβ superfamily receptor (e.g., ALK1, ALK2, ALK3, ALK4, ALK5, ALK6, ALK7, ActRIIA, ActRIIB, BMPRII, TGFBRII, and MISRII) and/or a TGFβ superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-03, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). These diseases, disorders or conditions are generally referred to herein as "TGFβ superfamily-associated conditions" or "TGFβ superfamily-associated disorders." In certain embodiments, the present invention provides methods of treating or preventing an individual in need thereof through administering to the individual a therapeutically effective amount of a TGF-beta superfamily heteromultimer, or combinations of TGF-beta superfamily heteromultimers, as described herein. Any of the TGF-beta superfamily heteromultimer complexes of the present disclosure can potentially be employed individually or in combination for therapeutic uses disclosed herein. These methods are particularly aimed at therapeutic and prophylactic treatments of mammals including, for example, rodents, primates, and humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes amelioration or elimination of the condition once it has been established. In either case, prevention or treatment may be discerned in the diagnosis provided by a physician or other health care provider and the intended result of administration of the therapeutic agent.

TGFβ superfamily receptor-ligand complexes play essential roles in tissue growth as well as early developmental processes such as the correct formation of various structures or in one or more post-developmental capacities including sexual development, pituitary hormone production, and creation of bone and cartilage. Thus, TGFβ superfamily-associated conditions/disorders include abnormal tissue growth and developmental defects. In addition, TGFβ superfamily-associated conditions include, but are not limited to, disorders of cell growth and differentiation such as inflammation, allergy, autoimmune diseases, infectious diseases, and tumors.

Exemplary TGFβ superfamily-associated conditions include neuromuscular disorders (e.g., muscular dystrophy and muscle atrophy), congestive obstructive pulmonary disease (and muscle wasting associated with COPD), muscle wasting syndrome, sarcopenia, cachexia, adipose tissue disorders (e.g., obesity), type 2 diabetes (NIDDM, adult-onset diabetes), and bone degenerative disease (e.g., osteoporosis). Other exemplary TGFβ superfamily-associated conditions include musculodegenerative and neuromuscular disorders, tissue repair (e.g., wound healing), neurodegenerative diseases (e.g., amyotrophic lateral sclerosis), and immunologic disorders (e.g., disorders related to abnormal proliferation or function of lymphocytes).

In certain embodiments, a TGF-beta superfamily heteromultimer, or combinations of TGF-beta superfamily heteromultimers, of the disclosure are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject TGF-beta superfamily heteromultimer complexes include: Duchenne muscular dystrophy (DMD), Becker muscular dystrophy (BMD), Emery-Dreifuss muscular dystrophy (EDMD), limb-girdle muscular dystrophy (LGMD), facioscapulohumeral muscular dystrophy (FSH or FSHD) (also known as Landouzy-Dejerine), myotonic dystrophy (MMD; also known as Steinert's Disease), oculopharyngeal muscular dystrophy (OPMD), distal muscular dystrophy (DD), congenital muscular dystrophy (CMD).

Duchenne muscular dystrophy (DMD) was first described by the French neurologist Guillaume Benjamin Amand Duchenne in the 1860s. Becker muscular dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is defective. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either of insufficient quantity or poor quality. The presence of some dystrophin protects the muscles of patients with BMD from degenerating as severely or as quickly as those of patients with DMD.

Studies in animals indicate that inhibition of the GDF8 signaling pathway may effectively treat various aspects of disease in DMD and BMD patients (Bogdanovich et al., 2002, Nature 420:418-421; Pistilli et al., 2011, Am J Pathol 178:1287-1297). Thus, TGF-beta superfamily heteromultimer complexes of the disclosure may act as GDF8 inhibitors (antagonists), and constitute an alternative means of blocking signaling by GDF8 and/or related TGFβ superfamily ligands in vivo in DMD and BMD patients.

Similarly, TGF-beta superfamily heteromultimers of the disclosure may provide an effective means to increase muscle mass in other disease conditions that are in need of muscle growth. For example, amyotrophic lateral sclerosis (ALS), also called Lou Gehrig's disease or motor neuron disease, is a chronic, progressive, and incurable CNS disorder that attacks motor neurons, which are components of the central nervous system required for initiation of skeletal muscle contraction. In ALS, motor neurons deteriorate and eventually die, and though a person's brain normally remains fully functioning and alert, initiation of muscle contraction is blocked at the spinal level. Individuals who develop ALS are typically between 40 and 70 years old, and the first motor neurons to degenerate are those innervating the arms or legs. Patients with ALS may have trouble walking, may drop things, fall, slur their speech, and laugh or cry uncontrollably. As the disease progresses, muscles in the limbs begin to atrophy from disuse. Muscle weakness becomes debilitating, and patients eventually require a wheel chair or become confined to bed. Most ALS patients die from respiratory failure or from complications of ventilator assistance like pneumonia 3-5 years from disease onset.

Promotion of increased muscle mass by TGF-beta superfamily heteromultimers might also benefit those suffering from muscle wasting diseases. Gonzalez-Cadavid et al. (supra) reported that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

Since loss of GDF8 function is also associated with fat loss without diminution of nutrient intake (Zimmers et al., supra; McPherron and Lee, supra), the subject TGF-beta superfamily heteromultimers may further be used as a therapeutic agent for slowing or preventing the development of obesity and type 2 diabetes.

Cancer anorexia-cachexia syndrome is among the most debilitating and life-threatening aspects of cancer. This syndrome is a common feature of many types of cancer—present in approximately 80% of cancer patients at death—and is responsible not only for a poor quality of life and poor response to chemotherapy but also a shorter survival time than is found in patients with comparable tumors but without weight loss. Cachexia is typically suspected in patients with cancer if an involuntary weight loss of greater than five percent of premorbid weight occurs within a six-month period. Associated with anorexia, wasting of fat and muscle tissue, and psychological distress, cachexia arises from a complex interaction between the cancer and the host. Cancer cachexia affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Currently, there is no treatment to control or reverse the cachexic process. Since systemic overexpression of GDF8 in adult mice was found to induce profound muscle and fat loss analogous to that seen in human cachexia syndromes (Zimmers et al., supra), the subject TGF-beta superfamily heteromultimer complex pharmaceutical compositions may be beneficially used to prevent, treat, or alleviate the symptoms of the cachexia syndrome, where muscle growth is desired. An example of a heteromultimer useful for preventing, treating, or alleviating muscle loss as described above is ActRIIB-Fc:ALK4-Fc.

In certain embodiments, a TGF-beta superfamily heteromultimer, or combinations of TGF-beta superfamily heteromultimers, of the present disclosure may be used in methods of inducing bone and/or cartilage formation, preventing bone loss, increasing bone mineralization, preventing the demineralization of bone, and/or increasing bone density. TGF-beta superfamily heteromultimer complexes may be useful in patients who are diagnosed with subclinical low bone density, as a protective measure against the development of osteoporosis.

In some embodiments, a TGF-beta superfamily heteromultimer, or combinations of TGF-beta superfamily heteromultimers, of the present disclosure may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent is useful for repair of craniofacial defects that are congenital, trauma-induced, or caused by oncologic resection, and is also useful in cosmetic plastic surgery. Further, methods and compositions of the invention may be used in the treatment of periodontal disease and in other tooth repair processes. In certain cases, a TGF-beta superfamily heteromultimer, or combinations of TGF-beta superfamily heteromultimers, may provide an environment to attract bone-forming cells, stimulate growth of bone-forming cells, or induce differentiation of progenitors of bone-forming cells. TGF-beta superfamily heteromultimers of the disclosure may also be useful in the treatment of osteoporosis. Further, TGF-beta superfamily heteromultimers may be used in repair of cartilage defects and prevention/reversal of osteoarthritis. Examples of heteromultimers useful for inducing bone formation, preventing bone loss, increasing bone mineralization, preventing the demineralization of bone, and/or increasing bone density as described above are ActRIIB-Fc:ALK3-Fc and ActRIIB-Fc:ALK4-Fc.

Methods and compositions of the invention can be applied to conditions characterized by or causing bone loss, such as osteoporosis (including secondary osteoporosis), hyperparathyroidism, chronic kidney disease mineral bone disorder, sex hormone deprivation or ablation (e.g. androgen and/or estrogen), glucocorticoid treatment, rheumatoid arthritis, severe burns, hyperparathyroidism, hypercalcemia, hypocalcemia, hypophosphatemia, osteomalacia (including tumor-induced osteomalacia), hyperphosphatemia, vitamin D deficiency, hyperparathyroidism (including familial hyperparathyroidism) and pseudohypoparathyroidism, tumor metastases to bone, bone loss as a consequence of a tumor or chemotherapy, tumors of the bone and bone marrow (e.g., multiple myeloma), ischemic bone disorders, periodontal disease and oral bone loss, Cushing's disease, Paget's disease, thyrotoxicosis, chronic diarrheal state or malabsorption, renal tubular acidosis, or anorexia nervosa. Methods and compositions of the invention may also be applied to conditions characterized by a failure of bone formation or healing, including non-union fractures, fractures that are otherwise slow to heal, fetal and neonatal bone dysplasias (e.g., hypocalcemia, hypercalcemia, calcium receptor defects and vitamin D deficiency), osteonecrosis (including osteonecrosis of the jaw) and osteogenesis imperfecta. Additionally, the anabolic effects will cause such antagonists to diminish bone pain associated with bone damage or erosion. As a consequence of the anti-resorptive effects, such antagonists may be useful to treat disorders of abnormal bone formation, such as osteoblastic tumor metastases (e.g., associated with primary prostate or breast cancer), osteogenic osteosarcoma, osteopetrosis, progressive diaphyseal dysplasia, endosteal hyperostosis, osteopoikilosis, and melorheostosis. Other disorders that may be treated include fibrous dysplasia and chondrodysplasias.

In another specific embodiment, the disclosure provides a therapeutic method and composition for repairing fractures and other conditions related to cartilage and/or bone defects or periodontal diseases. The invention further provides therapeutic methods and compositions for wound healing and tissue repair. The types of wounds include, but are not limited to, burns, incisions and ulcers. See, e.g., PCT Publication No. WO 84/01106. Such compositions comprise a therapeutically effective amount of at least one of the TGF-beta superfamily heteromultimer complexes of the disclosure in admixture with a pharmaceutically acceptable vehicle, carrier, or matrix.

In some embodiments, a TGF-beta superfamily heteromultimer, or combinations of TGF-beta superfamily heteromultimers, of the disclosure can be applied to conditions causing bone loss such as osteoporosis, hyperparathyroidism, Cushing's disease, thyrotoxicosis, chronic diarrheal state or malabsorption, renal tubular acidosis, or anorexia nervosa. It is commonly appreciated that being female, having a low body weight, and leading a sedentary lifestyle are risk factors for osteoporosis (loss of bone mineral density, leading to fracture risk). However, osteoporosis can also result from the long-term use of certain medications. Osteoporosis resulting from drugs or another medical condition is known as secondary osteoporosis. In Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenytoin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Bone loss resulting from cancer therapy is widely recognized and termed cancer therapy-induced bone loss (CTIBL). Bone metastases can create cavities in the bone that may be corrected by treatment with a TGF-beta superfamily heteromultimer. Bone loss can also be caused by gum disease, a chronic infection in which bacteria located in gum recesses produce toxins and harmful enzymes.

In a further embodiment, the present disclosure provides methods and therapeutic agents for treating diseases or disorders associated with abnormal or unwanted bone growth. For example, patients with the congenital disorder fibrodysplasia ossificans progressiva (FOP) are afflicted by progressive ectopic bone growth in soft tissues spontaneously or in response to tissue trauma, with a major impact on quality of life. Additionally, abnormal bone growth can occur after hip replacement surgery and thus ruin the surgical outcome. This is a more common example of pathological bone growth and a situation in which the subject methods and compositions may be therapeutically useful. The same methods and compositions may also be useful for treating other forms of abnormal bone growth (e.g., pathological growth of bone following trauma, burns or spinal cord injury), and for treating or preventing the undesirable conditions associated with the abnormal bone growth seen in connection with metastatic prostate cancer or osteosarcoma.

In certain embodiments, a TGF-beta superfamily heteromultimer, or combinations of TGF-beta superfamily heteromultimers, of the disclosure may be used to promote bone formation in patients with cancer. Patients having certain tumors (e.g. prostate, breast, multiple myeloma or any tumor causing hyperparathyroidism) are at high risk for bone loss due to tumor-induced bone loss, bone metastases, and therapeutic agents. Such patients may be treated with a TGF-beta superfamily heteromultimer, or a combination of heteromultimers, even in the absence of evidence of bone loss or bone metastases. Patients may also be monitored for evidence of bone loss or bone metastases, and may be treated with a TGF-beta superfamily heteromultimer in the event that indicators suggest an increased risk. Generally, DEXA scans are employed to assess changes in bone density, while indicators of bone remodeling may be used to assess the likelihood of bone metastases. Serum markers may be monitored. Bone specific alkaline phosphatase (BSAP) is an enzyme that is present in osteoblasts. Blood levels of BSAP are increased in patients with bone metastasis and other conditions that result in increased bone remodeling. Osteocalcin and procollagen peptides are also associated with bone formation and bone metastases. Increases in BSAP have been detected in patients with bone metastasis caused by prostate cancer, and to a lesser degree, in bone metastases from breast cancer. BMP7 levels are high in prostate cancer that has metastasized to bone, but not in bone metastases due to bladder, skin, liver, or lung cancer. Type I carboxyterminal telopeptide (ICTP) is a crosslink found in collagen that is formed during to the resorption of bone. Since bone is constantly being broken down and reformed, ICTP will be found throughout the body. However, at the site of bone metastasis, the level will be significantly higher than in an area of normal bone. ICTP has been found in high levels in bone metastasis due to prostate, lung, and breast cancer. Another collagen crosslink, Type I N-terminal telopeptide (NTx), is produced along with ICTP during bone turnover. The amount of NTx is increased in bone metastasis caused by many different types of cancer including lung, prostate, and breast cancer. Also, the levels of NTx increase with the progression of the bone metastasis. Therefore, this marker can be used to both detect metastasis as well as measure the extent of the disease. Other markers of resorption include pyridinoline and deoxypyridinoline. Any increase in resorption markers or markers of bone metastases indicate the need for therapy with a TGF-beta superfamily heteromultimer complex, or combinations of TGF-beta superfamily heteromultimer complexes, in a patient.

A TGF-beta superfamily heteromultimer, or combinations of TGF-beta superfamily heteromultimers, of the disclosure may be conjointly administered with other bone-active pharmaceutical agents. Conjoint administration may be accomplished by administration of a single co-formulation, by simultaneous administration, or by administration at separate times. TGF-beta superfamily heteromultimers may be particularly advantageous if administered with other bone-active agents. A patient may benefit from conjointly receiving a TGF-beta superfamily heteromultimer and taking calcium supplements, vitamin D, appropriate exercise and/ or, in some cases, other medication. Examples of other medications include, bisphosphonates (alendronate, ibandronate and risedronate), calcitonin, estrogens, parathyroid hormone and raloxifene. The bisphosphonates (alendronate, ibandronate and risedronate), calcitonin, estrogens and raloxifene affect the bone remodeling cycle and are classified as anti-resorptive medications. Bone remodeling consists of two distinct stages: bone resorption and bone formation. Anti-resorptive medications slow or stop the bone-resorbing portion of the bone-remodeling cycle but do not slow the bone-forming portion of the cycle. As a result, new formation continues at a greater rate than bone resorption, and bone density may increase over time. Teriparatide, a form of parathyroid hormone, increases the rate of bone formation in the bone remodeling cycle. Alendronate is approved for both the prevention (5 mg per day or 35 mg once a week) and treatment (10 mg per day or 70 mg once a week) of postmenopausal osteoporosis. Alendronate reduces bone loss, increases bone density and reduces the risk of spine, wrist and hip fractures. Alendronate also is approved for treatment of glucocorticoid-induced osteoporosis in men and women as a result of long-term use of these medications (i.e., prednisone and cortisone) and for the treatment of osteoporosis in men. Alendronate plus vitamin D is approved for the treatment of osteoporosis in postmenopausal women (70 mg once a week plus vitamin D), and for treatment to improve bone mass in men with osteoporosis. Ibandronate is approved for the prevention and treatment of postmenopausal osteoporosis. Taken as a once-a-month pill (150 mg), ibandronate should be taken on the same day each month. Ibandronate reduces bone loss, increases bone density and reduces the risk of spine fractures. Risedronate is approved for the prevention and treatment of postmenopausal osteoporosis. Taken daily (5 mg dose) or weekly (35 mg dose or 35 mg dose with calcium), risedronate slows bone loss, increases bone density and reduces the risk of spine and non-spine fractures. Risedronate also is approved for use by men and women to prevent and/or treat glucocorticoid-induced osteoporosis that results from long-term use of these medications (i.e., prednisone or cortisone). Calcitonin is a naturally occurring hormone involved in calcium regulation and bone metabolism. In women who are more than 5 years beyond menopause, calcitonin slows bone loss, increases spinal bone density, and may relieve the pain associated with bone fractures. Calcitonin reduces the risk of spinal fractures. Calcitonin is available as an injection (50-100 IU daily) or nasal spray (200 IU daily).

A patient may also benefit from conjointly receiving a TGF-beta superfamily heteromultimer, or combinations of TGF-beta superfamily heteromultimers, and additional bone-active medications. Estrogen therapy (ET)/hormone therapy (HT) is approved for the prevention of osteoporosis. ET has been shown to reduce bone loss, increase bone density in both the spine and hip, and reduce the risk of hip and spinal fractures in postmenopausal women. ET is administered most commonly in the form of a pill or skin patch that delivers a low dose of approximately 0.3 mg daily or a standard dose of approximately 0.625 mg daily and is effective even when started after age 70. When estrogen is taken alone, it can increase a woman's risk of developing cancer of the uterine lining (endometrial cancer). To eliminate this risk, healthcare providers prescribe the hormone progestin in combination with estrogen (hormone replacement therapy or HT) for those women who have an intact uterus. ET/HT relieves menopause symptoms and has been shown to have a beneficial effect on bone health. Side effects may include vaginal bleeding, breast tenderness, mood disturbances and gallbladder disease. Raloxifene, 60 mg a day, is approved for the prevention and treatment of postmenopausal osteoporosis. It is from a class of drugs called Selective Estrogen Receptor Modulators (SERMs) that have been developed to provide the beneficial effects of estrogens without their potential disadvantages. Raloxifene increases bone mass and reduces the risk of spine fractures. Data are not yet available to demonstrate that raloxifene can reduce the risk of hip and other non-spine fractures. Teriparatide, a form of parathyroid hormone, is approved for the treatment of osteoporosis in postmenopausal women and men who are at high risk for a fracture. This medication stimulates new bone formation and significantly increases bone mineral density. In postmenopausal women, fracture reduction was noted in the spine, hip, foot, ribs and wrist. In men, fracture reduction was noted in the spine, but there were insufficient data to evaluate fracture reduction at other sites. Teriparatide is self-administered as a daily injection for up to 24 months.

In other embodiments, a TGF-beta superfamily heteromultimer, or combinations of TGF-beta superfamily heteromultimers can be used for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present disclosure relates to regulating body weight by administering to an animal (e.g., a human) in need thereof a TGF-beta superfamily heteromultimer, or combinations of TGF-beta superfamily heteromultimers, of the disclosure.

In some embodiments, a TGF-beta superfamily heteromultimer, or combinations of TGF-beta superfamily heteromultimers, of the present disclosure can be used for reducing body weight and/or reducing weight gain in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass. In addition, disorders of high cholesterol (e.g., hypercholesterolemia or dislipidemia) may be treated with a TGF-beta superfamily heteromultimer, or combinations of TGF-beta superfamily heteromultimers, of the disclosure.

In certain aspects, a TGF-beta superfamily heteromultimer, or a combination of TGF-beta superfamily heteromultimers, of the present disclosure can be used to increase red blood cell levels, treat or prevent an anemia, and/or treat or prevent ineffective erythropoiesis in a subject in need thereof. In certain aspects, a TGF-beta superfamily heteromultimer, or a combination of TGF-beta superfamily heteromultimers, of the present disclosure may be used in combination with conventional therapeutic approaches for increasing red blood cell levels, particularly those used to treat anemias of multifactorial origin. Conventional therapeutic approaches for increasing red blood cell levels include, for example, red blood cell transfusion, administration of one or more EPO receptor activators, hematopoietic stem cell transplantation, immunosuppressive biologics and drugs (e.g., corticosteroids). In certain embodiments, the patient has an anemia and is non-responsive or intolerate to treatment with EPO (or a derivative thereof or an EPO receptor agonist) In certain embodiments, a TGF-beta superfamily heteromultimer, or a combination of TGF-beta superfamily heteromultimers, of the present disclosure can be used to treat or prevent ineffective erythropoiesis and/or the disorders associated with ineffective erythropoiesis in a subject in need thereof. In certain aspects, a TGF-beta superfamily heteromultimer, or a combination of TGF-beta superfamily heteromultimers, of the present disclosure can be used in combination with conventional therapeutic approaches for treating or preventing an anemia or ineffective erythropoiesis disorder, particularly those used to treat anemias of multifactorial origin.

In general, treatment or prevention of a disease or condition as described in the present disclosure is achieved by administering a TGF-beta superfamily heteromultimer, or a combination of TGF-beta superfamily heteromultimers, of the present disclosure in an "effective amount". An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

In certain embodiments, a TGF-beta superfamily heteromultimer, or a combination of TGF-beta superfamily heteromultimers, optionally combined with an EPO receptor activator, may be used to increase red blood cell, hemoglobin, or reticulocyte levels in healthy individuals and selected patient populations. Examples of appropriate patient populations include those with undesirably low red blood cell or hemoglobin levels, such as patients having an anemia, and those that are at risk for developing undesirably low red blood cell or hemoglobin levels, such as those patients who are about to undergo major surgery or other procedures that may result in substantial blood loss. In one embodiment, a patient with adequate red blood cell levels is treated with a TGF-beta superfamily heteromultimer, or a combination of TGF-beta superfamily heteromultimers, to increase red blood cell levels, and then blood is drawn and stored for later use in transfusions.

One or more TGF-beta superfamily heteromultimers of the disclosure, optionally combined with an EPO receptor activator, may be used to increase red blood cell levels, hemoglobin levels, and/or hematocrit levels in a patient having an anemia. When observing hemoglobin and/or hematocrit levels in humans, a level of less than normal for the appropriate age and gender category may be indicative of anemia, although individual variations are taken into account. For example, a hemoglobin level from 10-12.5 g/dl, and typically about 11.0 g/dl is considered to be within the normal range in health adults, although, in terms of therapy, a lower target level may cause fewer cardiovascular side effects [see, e.g., Jacobs et al. (2000) Nephrol Dial Transplant 15, 15-19]. Alternatively, hematocrit levels (percentage of the volume of a blood sample occupied by the cells) can be used as a measure for anemia. Hematocrit levels for healthy individuals range from about 41-51% for adult males and from 35-45% for adult females. In certain embodiments, a patient may be treated with a dosing regimen intended to restore the patient to a target level of red blood cells, hemoglobin, and/or hematocrit. As hemoglobin and hematocrit levels vary from person to person, optimally, the target hemoglobin and/or hematocrit level can be individualized for each patient.

Anemia is frequently observed in patients having a tissue injury, an infection, and/or a chronic disease, particularly cancer. In some subjects, anemia is distinguished by low erythropoietin levels and/or an inadequate response to erythropoietin in the bone marrow [see, e.g., Adamson (2008) Harrison's Principles of Internal Medicine, 17th ed.; McGraw Hill, New York, pp 628-634]. Potential causes of anemia include, for example, blood loss, nutritional deficits (e.g. reduced dietary intake of protein), medication reaction, various problems associated with the bone marrow, and many diseases. More particularly, anemia has been associated with a variety of disorders and conditions that include, for example, bone marrow transplantation; solid tumors (e.g., breast cancer, lung cancer, and colon cancer); tumors of the lymphatic system (e.g., chronic lymphocyte leukemia, non-Hodgkins lymphoma, and Hodgkins lymphoma); tumors of the hematopoietic system (e.g., leukemia, a myelodysplastic syndrome and multiple myeloma); radiation therapy; chemotherapy (e.g., platinum containing regimens); inflammatory and autoimmune diseases, including, but not limited to, rheumatoid arthritis, other inflammatory arthritides, systemic lupus erythematosis (SLE), acute or chronic skin diseases (e.g., psoriasis), inflammatory bowel disease (e.g., Crohn's disease and ulcerative colitis); acute or chronic renal disease or failure, including idiopathic or congenital conditions; acute or chronic liver disease; acute or chronic bleeding; situations where transfusion of red blood cells is not possible due to patient allo- or auto-antibodies and/or for religious reasons (e.g., some Jehovah's Witnesses); infections (e.g., malaria and osteomyelitis); hemoglobinopathies including, for example, sickle cell disease (anemia), thalassemias; drug use or abuse (e.g., alcohol misuse); pediatric patients with anemia from any cause to avoid transfusion; and elderly patients or patients with underlying cardiopulmonary disease with anemia who cannot receive transfusions due to concerns about circulatory overload [see, e.g., Adamson (2008) Harrison's Principles of Internal Medicine, 17th ed.; McGraw Hill, New York, pp 628-634]. In some embodiments, one or more TGF-beta superfamily heteromultimers of the disclosure could be used to treat or prevent anemia associated with one or more of the disorders or conditions disclosed herein.

Many factors can contribute to cancer-related anemia. Some are associated with the disease process itself and the generation of inflammatory cytokines such as interleukin-1, interferon-gamma, and tumor necrosis factor [Bron et al. (2001) Semin Oncol 28(Suppl 8):1-6]. Among its effects, inflammation induces the key iron-regulatory peptide hepcidin, thereby inhibiting iron export from macrophages and generally limiting iron availability for erythropoiesis [see, e.g., Ganz (2007) J Am Soc Nephrol 18:394-400]. Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality. In some embodiments, one or more TGF-beta superfamily heteromultimers of the disclosure, optionally combined with an EPO receptor activator, could be used to treat a cancer-related anemia.

A hypoproliferative anemia can result from primary dysfunction or failure of the bone marrow. Hypoproliferative anemias include: anemia of chronic disease, anemia of kidney disease, anemia associated with hypometabolic states, and anemia associated with cancer. In each of these types, endogenous erythropoietin levels are inappropriately low for the degree of anemia observed. Other hypoproliferative anemias include: early-stage iron-deficient anemia, and anemia caused by damage to the bone marrow. In these types, endogenous erythropoietin levels are appropriately elevated for the degree of anemia observed. Prominent examples would be myelosuppression caused by cancer and/or chemotherapeutic drugs or cancer radiation therapy. A broad review of clinical trials found that mild anemia can occur in 100% of patients after chemotherapy, while more severe anemia can occur in up to 80% of such patients [see, e.g., Groopman et al. (1999) J Natl Cancer Inst 91:1616-1634]. Myelosuppressive drugs include, for example: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibiotics such as anthracyclines (e.g., doxorubicin); 4) kinase inhibitors (e.g., gefitinib); 5) mitotic inhibitors such as taxanes (e.g., paclitaxel) and *vinca* alkaloids (e.g., vinorelbine); 6) monoclonal antibodies (e.g., rituximab); and 7) topoisomerase inhibitors (e.g., topotecan and etoposide). In addition, conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. In some embodiments, one or more TGF-beta superfamily heteromultimer complexes of the disclosure, optionally combined with an EPO receptor activator, could be used to treat a hyperproliferative anemia.

Chronic kidney disease is sometimes associated with hypoproliferative anemia, and the degree of the anemia varies in severity with the level of renal impairment. Such anemia is primarily due to inadequate production of erythropoietin and reduced survival of red blood cells. Chronic kidney disease usually proceeds gradually over a period of years or decades to end-stage (Stage 5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function [see, e.g., Levin et al. (1999) Am J Kidney Dis 27:347-354; Nissenson (1992) Am J Kidney Dis 20(Suppl 1):21-24; Revicki et al. (1995) Am J Kidney Dis 25:548-554; Gafter et al., (1994) Kidney Int 45:224-231]. In some embodiments, one or more TGF-beta superfamily heteromultimer complexes of the disclosure, optionally combined with an EPO receptor activator, could be used to treat anemia associated with acute or chronic renal disease or failure.

Anemia resulting from acute blood loss of sufficient volume, such as from trauma or postpartum hemorrhage, is known as acute post-hemorrhagic anemia. Acute blood loss initially causes hypovolemia without anemia since there is proportional depletion of RBCs along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency. In some embodiments, one or more TGF-beta superfamily heteromultimers of the disclosure, optionally combined with an EPO receptor activator, could be used to treat anemia resulting from acute blood loss.

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs [see, e.g., Adamson (2008) Harrison's Principles of Internal Medicine, 17th ed.; McGraw Hill, New York, pp 628-634]. Appropriate therapy for iron-deficiency anemia depends on its cause and severity, with oral iron preparations, parenteral iron formulations, and RBC transfusion as major conventional options. In some embodiments, one or more TGF-beta superfamily heteromultimers of the disclosure, optionally combined with an EPO receptor activator, could be used to treat a chronic iron-deficiency.

Myelodysplastic syndrome (MDS) is a diverse collection of hematological conditions characterized by ineffective production of myeloid blood cells and risk of transformation to acute myelogenous leukemia. In MDS patients, blood stem cells do not mature into healthy red blood cells, white blood cells, or platelets. MDS disorders include, for example, refractory anemia, refractory anemia with ringed sideroblasts, refractory anemia with excess blasts, refractory anemia with excess blasts in transformation, refractory cytopenia with multilineage dysplasia, and myelodysplastic syndrome associated with an isolated 5q chromosome abnormality. As these disorders manifest as irreversible defects in both quantity and quality of hematopoietic cells, most MDS patients are afflicted with chronic anemia. Therefore, MDS patients eventually require blood transfusions and/or treatment with growth factors (e.g., erythropoietin or G-CSF) to increase red blood cell levels. However, many MDS patients develop side-effects due to frequency of such therapies. For example, patients who receive frequent red blood cell transfusion can exhibit tissue and organ damage from the buildup of extra iron. Accordingly, one or more TGF-beta superfamily heteromultimers of the disclosure, may be used to treat patients having MDS. In certain embodiments, patients suffering from MDS may be treated using one or more TGF-beta superfamily heteromultimers of the disclosure, optionally in combination with an EPO receptor activator. In other embodiments, patients suffering from MDS may be treated using a combination of one or more TGF-beta superfamily heteromultimers of the disclosure and one or more additional therapeutic agents for treating MDS including, for example, thalidomide, lenalidomide, azacitadine, decitabine, erythropoietins, deferoxamine, antithymocyte globulin, and filgrastrim (G-CSF).

Originally distinguished from aplastic anemia, hemorrhage, or peripheral hemolysis on the basis of ferrokinetic studies [see, e.g., Ricketts et al. (1978) Clin Nucl Med 3:159-164], ineffective erythropoiesis describes a diverse group of anemias in which production of mature RBCs is less than would be expected given the number of erythroid precursors (erythroblasts) present in the bone marrow

[Tanno et al. (2010) Adv Hematol 2010:358283]. In such anemias, tissue hypoxia persists despite elevated erythropoietin levels due to ineffective production of mature RBCs. A vicious cycle eventually develops in which elevated erythropoietin levels drive massive expansion of erythroblasts, potentially leading to splenomegaly (spleen enlargement) due to extramedullary erythropoiesis [see, e.g., Aizawa et al. (2003) Am J Hematol 74:68-72], erythroblast-induced bone pathology [see, e.g., Di Matteo et al. (2008) J Biol Regul Homeost Agents 22:211-216], and tissue iron overload, even in the absence of therapeutic RBC transfusions [see, e.g., Pippard et al. (1979) Lancet 2:819-821]. Thus, by boosting erythropoietic effectiveness, one or more TGF-beta superfamily heteromultimer complexes of the present disclosure may break the aforementioned cycle and thus alleviate not only the underlying anemia but also the associated complications of elevated erythropoietin levels, splenomegaly, bone pathology, and tissue iron overload. In some embodiments, one or more TGF-beta superfamily heteromultimers of the present disclosure can be used to treat or prevent ineffective erythropoiesis, including anemia and elevated EPO levels as well as complications such as splenomegaly, erythroblast-induced bone pathology, iron overload, and their attendant pathologies. In some embodiments, the elevated EPO levels are relative to one or more healthy control patients of similar age and/or the same sex. With splenomegaly, such pathologies include thoracic or abdominal pain and reticuloendothelial hyperplasia. Extramedullary hematopoiesis can occur not only in the spleen but potentially in other tissues in the form of extramedullary hematopoietic pseudotumors [see, e.g., Musallam et al. (2012) Cold Spring Harb Perspect Med 2:a013482]. With erythroblast-induced bone pathology, attendant pathologies include low bone mineral density, osteoporosis, and bone pain [see, e.g., Haidar et al. (2011) Bone 48:425-432]. With iron overload, attendant pathologies include hepcidin suppression and hyperabsorption of dietary iron [see, e.g., Musallam et al. (2012) Blood Rev 26(Suppl 1):S16-S19], multiple endocrinopathies and liver fibrosis/cirrhosis [see, e.g., Galanello et al. (2010) Orphanet J Rare Dis 5:11], and iron-overload cardiomyopathy [Lekawanvijit et al., 2009, Can J Cardiol 25:213-218].

The most common causes of ineffective erythropoiesis are the thalassemia syndromes, hereditary hemoglobinopathies in which imbalances in the production of intact alpha- and beta-hemoglobin chains lead to increased apoptosis during erythroblast maturation [see, e.g., Schrier (2002) Curr Opin Hematol 9:123-126]. Thalassemias are collectively among the most frequent genetic disorders worldwide, with changing epidemiologic patterns predicted to contribute to a growing public health problem in both the U.S. and globally [Vichinsky (2005) Ann NY Acad Sci 1054:18-24]. Thalassemia syndromes are named according to their severity. Thus, α-thalassemias include α-thalassemia minor (also known as α-thalassemia trait; two affected α-globin genes), hemoglobin H disease (three affected α-globin genes), and α-thalassemia major (also known as hydrops fetalis; four affected α-globin genes). β-Thalassemias include β-thalassemia minor (also known as β-thalassemia trait; one affected β-globin gene), β-thalassemia intermedia (two affected β-globin genes), hemoglobin E thalassemia (two affected β-globin genes), and β-thalassemia major (also known as Cooley's anemia; two affected β-globin genes resulting in a complete absence of β-globin protein). β-Thalassemia impacts multiple organs, is associated with considerable morbidity and mortality, and currently requires life-long care. Although life expectancy in patients with β-thalassemia has increased in recent years due to use of regular blood transfusions in combination with iron chelation, iron overload resulting both from transfusions and from excessive gastrointestinal absorption of iron can cause serious complications such as heart disease, thrombosis, hypogonadism, hypothyroidism, diabetes, osteoporosis, and osteopenia [see, e.g., Rund et al. (2005) N Engl J Med 353:1135-1146]. In certain embodiments, one or more TGF-beta superfamily heteromultimers of the disclosure, optionally combined with an EPO receptor activator, can be used to treat or prevent a thalassemia syndrome.

In some embodiments, one or more TGF-beta superfamily heteromultimers of the disclosure, optionally combined with an EPO receptor activator, can be used for treating disorders of ineffective erythropoiesis besides thalassemia syndromes. Such disorders include sideroblastic anemia (inherited or acquired); dyserythropoietic anemia (types I and II); sickle cell anemia; hereditary spherocytosis; pyruvate kinase deficiency; megaloblastic anemias, potentially caused by conditions such as folate deficiency (due to congenital diseases, decreased intake, or increased requirements), cobalamin deficiency (due to congenital diseases, pernicious anemia, impaired absorption, pancreatic insufficiency, or decreased intake), certain drugs, or unexplained causes (congenital dyserythropoietic anemia, refractory megaloblastic anemia, or erythroleukemia); myelophthisic anemias including, for example, myelofibrosis (myeloid metaplasia) and myelophthisis; congenital erythropoietic porphyria; and lead poisoning.

In certain embodiments, one or more TGF-beta superfamily heteromultimers of the disclosure may be used in combination with supportive therapies for ineffective erythropoiesis. Such therapies include transfusion with either red blood cells or whole blood to treat anemia. In chronic or hereditary anemias, normal mechanisms for iron homeostasis are overwhelmed by repeated transfusions, eventually leading to toxic and potentially fatal accumulation of iron in vital tissues such as heart, liver, and endocrine glands. Thus, supportive therapies for patients chronically afflicted with ineffective erythropoiesis also include treatment with one or more iron-chelating molecules to promote iron excretion in the urine and/or stool and thereby prevent, or reverse, tissue iron overload [see, e.g., Hershko (2006) Haematologica 91:1307-1312; Cao et al. (2011), Pediatr Rep 3(2):e17]. Effective iron-chelating agents should be able to selectively bind and neutralize ferric iron, the oxidized form of non-transferrin bound iron which likely accounts for most iron toxicity through catalytic production of hydroxyl radicals and oxidation products [see, e.g., Esposito et al. (2003) Blood 102:2670-2677]. These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) [Kalinowski et al. (2005) Pharmacol Rev 57:547-583]. In general, effective iron-chelating agents also are relatively low molecular weight (e.g., less than 700 daltons), with solubility in both water and lipids to enable access to affected tissues. Specific examples of iron-chelating molecules include deferoxamine, a hexadentate agent of bacterial origin requiring daily parenteral administration, and the orally active synthetic agents deferiprone (bidentate) and deferasirox (tridentate). Combination therapy consisting of same-day administration of two iron-chelating agents shows promise in patients unresponsive to chelation monotherapy and also in overcoming issues of poor patient compliance with dereroxamine alone [Cao et al. (2011) Pediatr Rep 3(2):e17; Galanello et al. (2010) Ann NY Acad Sci 1202:79-86].

In certain aspects, one or more TGF-beta superfamily heteromultimers of the disclosure may be used to decrease blood cell transfusion burden in a patient. For example, a TGF-beta superfamily heteromultimer may be used to decrease blood cell transfusion by greater than about 30%, 40%, 50%, 60%, 70%, 80%, 90%, or 100% for 4 to 8 weeks relative to the equal time prior to the start of the TGF-beta superfamily heteromultimer treatment. In some embodiments, a TGF-beta superfamily heteromultimer may be used to decrease blood cell transfusion by greater than about 50% for 4 to 8 weeks relative to the equal time prior to the start of the TGF-beta superfamily heteromultimer treatment in a patient. In certain embodiments, a patient may be treated with a dosing regimen intended to restore the patient to a target level of red blood cells, hemoglobin, and/or hematocrit or allow the reduction or elimination of red blood cell transfusions (reduce transfusion burden) while maintaining an acceptable level of red blood cells, hemoglobin and/or hematocrit. As hemoglobin and hematocrit levels vary from person to person, optimally, the target hemoglobin and/or hematocrit level can be individualized for each patient.

As used herein, "in combination with" or "conjoint administration" refers to any form of administration such that the second therapy is still effective in the body (e.g., the two compounds are simultaneously effective in the patient, which may include synergistic effects of the two compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more TGF-beta superfamily heteromultimers of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired therapeutic effect to be achieved.

In certain embodiments, one or more TGF-beta superfamily heteromultimers of the disclosure may be used in combination with hepcidin or a hepcidin agonist for ineffective erythropoiesis. A circulating polypeptide produced mainly in the liver, hepcidin is considered a master regulator of iron metabolism by virtue of its ability to induce the degradation of ferroportin, an iron-export protein localized on absorptive enterocytes, hepatocytes, and macrophages. Broadly speaking, hepcidin reduces availability of extracellular iron, so hepcidin agonists may be beneficial in the treatment of ineffective erythropoiesis [see, e.g., Nemeth (2010) Adv Hematol 2010:750643]. This view is supported by beneficial effects of increased hepcidin expression in a mouse model of 3-thalassemia [Gardenghi et al. (2010) J Clin Invest 120:4466-4477].

One or more TGF-beta superfamily heteromultimers of the disclosure, optionally combined with an EPO receptor activator, would also be appropriate for treating anemias of disordered RBC maturation, which are characterized in part by undersized (microcytic), oversized (macrocytic), misshapen, or abnormally colored (hypochromic) RBCs.

In certain embodiments, the present disclosure provides methods of treating or preventing anemia in an individual in need thereof by administering to the individual a therapeutically effective amount of one or more TGF-beta superfamily heteromultimers of the disclosure and a EPO receptor activator. In certain embodiments, one or more TGF-beta superfamily heteromultimers of the disclosure may be used in combination with EPO receptor activators to reduce the required dose of these activators in patients that are susceptible to adverse effects of EPO. These methods may be used for therapeutic and prophylactic treatments of a patient.

One or more TGF-beta superfamily heteromultimers of the disclosure may be used in combination with EPO receptor activators to achieve an increase in red blood cells, particularly at lower dose ranges of EPO receptor activators. This may be beneficial in reducing the known off-target effects and risks associated with high doses of EPO receptor activators. The primary adverse effects of EPO include, for example, an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which relate to hypertension, are headaches, influenza-like syndrome, obstruction of shunts, myocardial infarctions and cerebral convulsions due to thrombosis, hypertensive encephalopathy, and red cell blood cell aplasia. See, e.g., Singibarti (1994) J. Clin Investig 72(suppl 6), S36-S43; Horl et al. (2000) Nephrol Dial Transplant 15(suppl 4), 51-56; Delanty et al. (1997) Neurology 49, 686-689; and Bunn (2002) N Engl J Med 346(7), 522-523).

Provided that TGF-beta superfamily heteromultimers of the present disclosure act by a different mechanism than EPO, these antagonists may be useful for increasing red blood cell and hemoglobin levels in patients that do not respond well to EPO. For example, a TGF-beta superfamily heteromultimer of the present disclosure may be beneficial for a patient in which administration of a normal-to-increased dose of EPO (>300 IU/kg/week) does not result in the increase of hemoglobin level up to the target level. Patients with an inadequate EPO response are found in all types of anemia, but higher numbers of non-responders have been observed particularly frequently in patients with cancers and patients with end-stage renal disease. An inadequate response to EPO can be either constitutive (observed upon the first treatment with EPO) or acquired (observed upon repeated treatment with EPO).

In certain embodiments, the present disclosure provides methods for managing a patient that has been treated with, or is a candidate to be treated with, one or more TGF-beta superfamily heteromultimers of the disclosure by measuring one or more hematologic parameters in the patient. The hematologic parameters may be used to evaluate appropriate dosing for a patient who is a candidate to be treated with the antagonist of the present disclosure, to monitor the hematologic parameters during treatment, to evaluate whether to adjust the dosage during treatment with one or more antagonist of the disclosure, and/or to evaluate an appropriate maintenance dose of one or more antagonists of the disclosure. If one or more of the hematologic parameters are outside the normal level, dosing with one or more TGF-beta superfamily heteromultimers of the disclosure may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art-recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range or on the high side of normal in a patient who is a candidate to be treated with one or more TGF-beta superfamily heteromultimers of the disclosure, then onset of administration of the one or more TGF-beta superfamily heteromultimers of the disclosure may be delayed until the hematologic parameters have returned to a normal or acceptable level either naturally or via therapeutic intervention. For example, if a candidate patient is hypertensive or pre-hypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the one or more TGF-beta superfamily heteromultimers of the disclosure may be delayed until the levels have returned to a normal or acceptable level.

In certain embodiments, if one or more hematologic parameters are outside the normal range or on the high side of normal in a patient who is a candidate to be treated with one or more TGF-beta superfamily heteromultimers of the disclosure, then the onset of administration may not be delayed. However, the dosage amount or frequency of dosing of the one or more TGF-beta superfamily heteromultimers of the disclosure may be set at an amount that would reduce the risk of an unacceptable increase in the hematologic parameters arising upon administration of the one or more TGF-beta superfamily heteromultimers of the disclosure. Alternatively, a therapeutic regimen may be developed for the patient that combines one or more TGF-beta superfamily heteromultimers of the disclosure with a therapeutic agent that addresses the undesirable level of the hematologic parameter. For example, if the patient has elevated blood pressure, then a therapeutic regimen involving administration of one or more TGF-beta superfamily heteromultimers of the disclosure and a blood pressure-lowering agent may be designed. For a patient having lower than desired iron stores, a therapeutic regimen of one or more TGF-beta superfamily heteromultimers of the disclosure and iron supplementation may be developed.

In one embodiment, baseline parameter(s) for one or more hematologic parameters may be established for a patient who is a candidate to be treated with one or more TGF-beta superfamily heteromultimers of the disclosure and an appropriate dosing regimen established for that patient based on the baseline value(s). Alternatively, established baseline parameters based on a patient's medical history could be used to inform an appropriate dosing regimen for a patient. For example, if a healthy patient has an established baseline blood pressure reading that is above the defined normal range it may not be necessary to bring the patient's blood pressure into the range that is considered normal for the general population prior to treatment with the one or more TGF-beta superfamily heteromultimers of the disclosure. A patient's baseline values for one or more hematologic parameters prior to treatment with one or more TGF-beta superfamily heteromultimers of the disclosure may also be used as the relevant comparative values for monitoring any changes to the hematologic parameters during treatment with the one or more TGF-beta superfamily heteromultimers of the disclosure.

In certain embodiments, one or more hematologic parameters are measured in patients who are being treated with a one or more TGF-beta superfamily heteromultimers of the disclosure. The hematologic parameters may be used to monitor the patient during treatment and permit adjustment or termination of the dosing with the one or more TGF-beta superfamily heteromultimers of the disclosure or additional dosing with another therapeutic agent. For example, if administration of one or more TGF-beta superfamily heteromultimers of the disclosure of the disclosure results in an increase in blood pressure, red blood cell level, or hemoglobin level, or a reduction in iron stores, then the dose of the one or more TGF-beta superfamily heteromultimers of the disclosure may be reduced in amount or frequency in order to decrease the effects of the one or more TGF-beta superfamily heteromultimers of the disclosure on the one or more hematologic parameters. If administration of one or more TGF-beta superfamily heteromultimers of the disclosure results in a change in one or more hematologic parameters that is adverse to the patient, then the dosing of the one or more TGF-beta superfamily heteromultimers of the disclosure may be terminated either temporarily, until the hematologic parameter(s) return to an acceptable level, or permanently. Similarly, if one or more hematologic parameters are not brought within an acceptable range after reducing the dose or frequency of administration of the one or more TGF-beta superfamily heteromultimers of the disclosure, then the dosing may be terminated. As an alternative, or in addition to, reducing or terminating the dosing with the one or more TGF-beta superfamily heteromultimers of the disclosure, the patient may be dosed with an additional therapeutic agent that addresses the undesirable level in the hematologic parameter(s), such as, for example, a blood pressure-lowering agent or an iron supplement. For example, if a patient being treated with one or more TGF-beta superfamily heteromultimers of the disclosure has elevated blood pressure, then dosing with the one or more TGF-beta superfamily heteromultimers of the disclosure may continue at the same level and a blood pressure-lowering agent is added to the treatment regimen, dosing with the one or more TGF-beta superfamily heteromultimers of the disclosure may be reduced (e.g., in amount and/or frequency) and a blood pressure-lowering agent is added to the treatment regimen, or dosing with the one or more TGF-beta superfamily heteromultimers of the disclosure may be terminated and the patient may be treated with a blood pressure-lowering agent.

6. Pharmaceutical Compositions

In certain aspects, TGF-beta superfamily heteromultimers of the present disclosure can be administered alone or as a component of a pharmaceutical formulation (also referred to as a therapeutic composition or pharmaceutical composition). A pharmaceutical formation refers to a preparation which is in such form as to permit the biological activity of an active ingredient (e.g., an agent of the present disclosure)

contained therein to be effective and which contains no additional components which are unacceptably toxic to a subject to which the formulation would be administered. The subject compounds may be formulated for administration in any convenient way for use in human or veterinary medicine. For example, one or more agents of the present disclosure may be formulated with a pharmaceutically acceptable carrier. A pharmaceutically acceptable carrier refers to an ingredient in a pharmaceutical formulation, other than an active ingredient, which is generally nontoxic to a subject. A pharmaceutically acceptable carrier includes, but is not limited to, a buffer, excipient, stabilizer, and/or preservative. In some embodiments, pharmaceutical formulations for use in the present disclosure are in a pyrogen-free, physiologically-acceptable form when administered to a subject. Therapeutically useful agents other than those described herein, which may optionally be included in the formulation as described above, may be administered in combination with the subject agents in the methods of the present disclosure.

In certain embodiments, compositions will be administered parenterally [e.g., by intravenous (I.V.) injection, intraarterial injection, intraosseous injection, intramuscular injection, intrathecal injection, subcutaneous injection, or intradermal injection]. Pharmaceutical compositions suitable for parenteral administration may comprise one or more agents of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use. Injectable solutions or dispersions may contain antioxidants, buffers, bacteriostats, suspending agents, thickening agents, or solutes which render the formulation isotonic with the blood of the intended recipient. Examples of suitable aqueous and nonaqueous carriers which may be employed in the pharmaceutical formulations of the present disclosure include water, ethanol, polyols (e.g., glycerol, propylene glycol, polyethylene glycol, etc.), vegetable oils (e.g., olive oil), injectable organic esters (e.g., ethyl oleate), and suitable mixtures thereof. Proper fluidity can be maintained, for example, by the use of coating materials (e.g., lecithin), by the maintenance of the required particle size in the case of dispersions, and by the use of surfactants.

In some embodiments, a therapeutic method of the present disclosure includes administering the pharmaceutical composition systemically, or locally, from an implant or device. Further, the pharmaceutical composition may be encapsulated or injected in a form for delivery to a target tissue site (e.g., bone marrow or muscle). In certain embodiments, compositions of the present disclosure may include a matrix capable of delivering one or more of the agents of the present disclosure to a target tissue site (e.g., bone marrow or muscle), providing a structure for the developing tissue and optimally capable of being resorbed into the body. For example, the matrix may provide slow release of one or more agents of the present disclosure. Such matrices may be formed of materials presently in use for other implanted medical applications.

The choice of matrix material may be based on one or more of: biocompatibility, biodegradability, mechanical properties, cosmetic appearance, and interface properties. The particular application of the subject compositions will define the appropriate formulation. Potential matrices for the compositions may be biodegradable and chemically defined calcium sulfate, tricalciumphosphate, hydroxyapatite, polylactic acid, and polyanhydrides. Other potential materials are biodegradable and biologically well-defined including, for example, bone or dermal collagen. Further matrices are comprised of pure proteins or extracellular matrix components. Other potential matrices are non-biodegradable and chemically defined including, for example, sintered hydroxyapatite, bioglass, aluminates, or other ceramics. Matrices may be comprised of combinations of any of the above mentioned types of material including, for example, polylactic acid and hydroxyapatite or collagen and tricalciumphosphate. The bioceramics may be altered in composition (e.g., calcium-aluminate-phosphate) and processing to alter one or more of pore size, particle size, particle shape, and biodegradability.

In certain embodiments, pharmaceutical compositions of present disclosure can be administered topically. "Topical application" or "topically" means contact of the pharmaceutical composition with body surfaces including, for example, the skin, wound sites, and mucous membranes. The topical pharmaceutical compositions can have various application forms and typically comprises a drug-containing layer, which is adapted to be placed near to or in direct contact with the tissue upon topically administering the composition. Pharmaceutical compositions suitable for topical administration may comprise one or more one or more TGFβ superfamily type I and/or type II receptor polypeptide heteromultimers of the disclosure in combination formulated as a liquid, a gel, a cream, a lotion, an ointment, a foam, a paste, a putty, a semi-solid, or a solid. Compositions in the liquid, gel, cream, lotion, ointment, foam, paste, or putty form can be applied by spreading, spraying, smearing, dabbing or rolling the composition on the target tissue. The compositions also may be impregnated into sterile dressings, transdermal patches, plasters, and bandages. Compositions of the putty, semi-solid or solid forms may be deformable. They may be elastic or non-elastic (e.g., flexible or rigid). In certain aspects, the composition forms part of a composite and can include fibers, particulates, or multiple layers with the same or different compositions.

Topical compositions in the liquid form may include pharmaceutically acceptable solutions, emulsions, microemulsions, and suspensions. In addition to the active ingredient(s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof].

Topical gel, cream, lotion, ointment, semi-solid or solid compositions may include one or more thickening agents, such as a polysaccharide, synthetic polymer or protein-based polymer. In one embodiment of the invention, the gelling agent herein is one that is suitably nontoxic and gives the desired viscosity. The thickening agents may include polymers, copolymers, and monomers of: vinylpyrrolidones, methacrylamides, acrylamides N-vinylimidazoles, carboxy vinyls, vinyl esters, vinyl ethers, silicones, polyethyleneoxides, polyethyleneglycols, vinylalcohols, sodium acrylates, acrylates, maleic acids, NN-dimethylacrylamides, diacetone acrylamides, acrylamides, acryloyl morpholine, pluronic, collagens, polyacrylamides, polyacrylates, polyvinyl alcohols, polyvinylenes, polyvinyl silicates, polyacrylates substituted with a sugar (e.g., sucrose, glucose, glucosamines, galactose, trehalose, mannose, or lactose), acylamidopropane sulfonic acids, tetramethoxyorthosilicates, methyltrimethoxyorthosilicates, tetraalkoxyorthosilicates, trialkoxyorthosilicates, glycols, propylene glycol, glycerine, polysaccharides, alginates, dextrans, cyclodextrin, celluloses, modified celluloses, oxidized celluloses, chitosans, chitins, guars, carrageenans, hyaluronic acids, inulin, starches, modified starches, agarose, methylcelluloses, plant gums, hylaronans, hydrogels, gelatins, glycosaminoglycans, carboxymethyl celluloses, hydroxyethyl celluloses, hydroxy propyl methyl celluloses, pectins, low-methoxy pectins, cross-linked dextrans, starch-acrylonitrile graft copolymers, starch sodium polyacrylate, hydroxyethyl methacrylates, hydroxyl ethyl acrylates, polyvinylene, polyethylvinylethers, polymethyl methacrylates, polystyrenes, polyurethanes, polyalkanoates, polylactic acids, polylactates, poly (3-hydroxybutyrate), sulfonated hydrogels, AMPS (2-acrylamido-2-methyl-1-propanesulfonic acid), SEM (sulfoethylmethacrylate), SPM (sulfopropyl methacrylate), SPA (sulfopropyl acrylate), N,N-dimethyl-N-methacryloxyethyl-N-(3-sulfopropyl)ammonium betaine, methacryllic acid amidopropyl-dimethyl ammonium sulfobetaine, SPI (itaconic acid-bis(1-propyl sulfonizacid-3) ester di-potassium salt), itaconic acids, AMBC (3-acrylamido-3-methylbutanoic acid), beta-carboxyethyl acrylate (acrylic acid dimers), and maleic anhydride-methylvinyl ether polymers, derivatives thereof, salts thereof, acids thereof, and combinations thereof. In certain embodiments, pharmaceutical compositions of present disclosure can be administered orally, for example, in the form of capsules, cachets, pills, tablets, lozenges (using a flavored basis such as sucrose and acacia or tragacanth), powders, granules, a solution or a suspension in an aqueous or non-aqueous liquid, an oil-in-water or water-in-oil liquid emulsion, or an elixir or syrup, or pastille (using an inert base, such as gelatin and glycerin, or sucrose and acacia), and/or a mouth wash, each containing a predetermined amount of a compound of the present disclosure and optionally one or more other active ingredients. A compound of the present disclosure and optionally one or more other active ingredients may also be administered as a bolus, electuary, or paste.

In solid dosage forms for oral administration (e.g., capsules, tablets, pills, dragees, powders, and granules), one or more compounds of the present disclosure may be mixed with one or more pharmaceutically acceptable carriers including, for example, sodium citrate, dicalcium phosphate, a filler or extender (e.g., a starch, lactose, sucrose, glucose, mannitol, and silicic acid), a binder (e.g. carboxymethylcellulose, an alginate, gelatin, polyvinyl pyrrolidone, sucrose, and acacia), a humectant (e.g., glycerol), a disintegrating agent (e.g., agar-agar, calcium carbonate, potato or tapioca starch, alginic acid, a silicate, and sodium carbonate), a solution retarding agent (e.g. paraffin), an absorption accelerator (e.g. a quaternary ammonium compound), a wetting agent (e.g., cetyl alcohol and glycerol monostearate), an absorbent (e.g., kaolin and bentonite clay), a lubricant (e.g., a talc, calcium stearate, magnesium stearate, solid polyethylene glycols, sodium lauryl sulfate), a coloring agent, and mixtures thereof. In the case of capsules, tablets, and pills, the pharmaceutical formulation (composition) may also comprise a buffering agent. Solid compositions of a similar type may also be employed as fillers in soft and hard-filled gelatin capsules using one or more excipients including, e.g., lactose or a milk sugar as well as a high molecular-weight polyethylene glycol.

Liquid dosage forms for oral administration of the pharmaceutical composition may include pharmaceutically acceptable emulsions, microemulsions, solutions, suspensions, syrups, and elixirs. In addition to the active ingredient(s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof]. Besides inert diluents, the oral formulation can also include an adjuvant including, for example, a wetting agent, an emulsifying and suspending agent, a sweetening agent, a flavoring agent, a coloring agent, a perfuming agent, a preservative agent, and combinations thereof.

Suspensions, in addition to the active compounds, may contain suspending agents including, for example, an ethoxylated isostearyl alcohol, polyoxyethylene sorbitol, a sorbitan ester, microcrystalline cellulose, aluminum metahydroxide, bentonite, agar-agar, tragacanth, and combinations thereof.

Prevention of the action and/or growth of microorganisms may be ensured by the inclusion of various antibacterial and antifungal agents including, for example, paraben, chlorobutanol, and phenol sorbic acid.

In certain embodiments, it may be desirable to include an isotonic agent including, for example, a sugar or sodium chloride into the compositions. In addition, prolonged absorption of an injectable pharmaceutical form may be brought about by the inclusion of an agent that delay absorption including, for example, aluminum monostearate and gelatin.

It is understood that the dosage regimen will be determined by the attending physician considering various factors which modify the action of the one or more of the agents of the present disclosure. In the case of a TGF-beta superfamily heteromultimer that promotes red blood cell formation, various factors may include, but are not limited to, the patient's red blood cell count, hemoglobin level, the desired target red blood cell count, the patient's age, the patient's sex, the patient's diet, the severity of any disease that may be contributing to a depressed red blood cell level, the time of administration, and other clinical factors. The addition of other known active agents to the final composition may also affect the dosage. Progress can be monitored by periodic assessment of one or more of red blood cell levels, hemoglobin levels, reticulocyte levels, and other indicators of the hematopoietic process.

In certain embodiments, the present disclosure also provides gene therapy for the in vivo production of one or more of the agents of the present disclosure. Such therapy would achieve its therapeutic effect by introduction of the agent sequences into cells or tissues having one or more of the disorders as listed above. Delivery of the agent sequences can be achieved, for example, by using a recombinant expression vector such as a chimeric virus or a colloidal dispersion system. Preferred therapeutic delivery of one or more of agent sequences of the disclosure is the use of targeted liposomes.

Various viral vectors which can be utilized for gene therapy as taught herein include adenovirus, herpes virus, vaccinia, or an RNA virus (e.g., a retrovirus). The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing one or more of the agents of the present disclosure.

Alternatively, tissue culture cells can be directly transfected with plasmids encoding the retroviral structural genes (gag, pol, and env), by conventional calcium phosphate transfection. These cells are then transfected with the vector plasmid containing the genes of interest. The resulting cells release the retroviral vector into the culture medium.

Another targeted delivery system for one or more of the agents of the present disclosure is a colloidal dispersion system. Colloidal dispersion systems include, for example, macromolecule complexes, nanocapsules, microspheres, beads, and lipid-based systems including oil-in-water emulsions, micelles, mixed micelles, and liposomes. In certain embodiments, the preferred colloidal system of this disclosure is a liposome. Liposomes are artificial membrane vesicles which are useful as delivery vehicles in vitro and in vivo. RNA, DNA, and intact virions can be encapsulated within the aqueous interior and be delivered to cells in a biologically active form. See, e.g., Fraley, et al. (1981) Trends Biochem. Sci., 6:77. Methods for efficient gene transfer using a liposome vehicle are known in the art. See, e.g., Mannino, et al. (1988) Biotechniques, 6:682, 1988.

The composition of the liposome is usually a combination of phospholipids, which may include a steroid (e.g. cholesterol). The physical characteristics of liposomes depend on pH, ionic strength, and the presence of divalent cations. Other phospholipids or other lipids may also be used including, for example a phosphatidyl compound (e.g., phosphatidylglycerol, phosphatidylcholine, phosphatidylserine, phosphatidylethanolamine, a sphingolipid, a cerebroside, and a ganglioside), egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1. Generation of an ActRIIB-Fc:ALK4-Fc Heterodimer

Applicants constructed a soluble ActRIIB-Fc:ALK4-Fc heteromultimer comprising the extracellular domains of human ActRIIB and human ALK4, which are each separately fused to an Fc domain with a linker positioned between the extracellular domain and the Fc domain. The individual constructs are referred to as ActRIIB-Fc fusion polypeptide and ALK4-Fc fusion polypeptide, respectively, and the sequences for each are provided below.

A methodology for promoting formation of ActRIIB-Fc: ALK4-Fc heteromultimers, as opposed to the ActRIIB-Fc or ALK4-Fc homomultimer, is to introduce alterations in the amino acid sequence of the Fc domains to guide the formation of asymmetric heteromeric complexes. Many different approaches to making asymmetric interaction pairs using Fc domains are described in this disclosure.

In one approach, illustrated in the ActRIIB-Fc and ALK4-Fc polypeptide sequences of SEQ ID NOs: 100-102 and 104-106, respectively, one Fc domain is altered to introduce cationic amino acids at the interaction face, while the other Fc domain is altered to introduce anionic amino acids at the interaction face. The ActRIIB-Fc fusion polypeptide and ALK4-Fc fusion polypeptide each employ the tissue plasminogen activator (TPA) leader:

```
                                          (SEQ ID NO: 98)
               MDAMKRGLCCVLLLCGAVFVSP.
```

The ActRIIB-Fc polypeptide sequence (SEQ ID NO: 100) is shown below:

```
                                                          (SEQ ID NO: 100)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSRKEMT KNQVSLTCLV KGFYPSDIAV

301 EWESNGQPEN NYKTTPPVLK SDGSFFLYSK LTVDKSRWQQ GNVFSCSVMH

351 EALHNHYTQK SLSLSPGK
```

The leader (signal) sequence and linker are underlined. To promote formation of the ActRIIB-Fc:ALK4-Fc heterodimer rather than either of the possible homodimeric complexes, two amino acid substitutions (replacing acidic amino acids with lysine) can be introduced into the Fc domain of the ActRIIB fusion protein as indicated by double underline above. The amino acid sequence of SEQ ID NO: 100 may optionally be provided with lysine (K) removed from the C-terminus.

This ActRIIB-Fc fusion protein is encoded by the following nucleic acid sequence (SEQ ID NO: 101):

```
                                                    (SEQ ID NO: 101)
   1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGCTAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCCGAGAACC

801 ACAGGTGTAC ACCCTGCCCC CATCCCGGAA GGAGATGACC AAGAACCAGG

851 TCAGCCTGAC CTGCCTGGTC AAAGGCTTCT ATCCCAGCGA CATCGCCGTG

901 GAGTGGGAGA GCAATGGGCA GCCGGAGAAC AACTACAAGA CCACGCCTCC

951 CGTGCTGAAG TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCACTA CACGCAGAAG AGCCTCTCCC TGTCTCCGGG

1101 TAAA
```

The mature ActRIIB-Fc fusion polypeptide (SEQ ID NO: 102) is as follows, and may optionally be provided with lysine removed from the C-terminus.

```
                                                    (SEQ ID NO: 102)
   1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 RKEMTKNQVS LTCLVKGFYP SDIAVEWESN GQPENNYKTT PPVLKSDGSF

301 FLYSKLTVDK SRWQQGNVFS CSVMHEALHN HYTQKSLSLS PGK
```

The complementary form of ALK4-Fc fusion polypeptide (SEQ ID NO: 104) is as follows:

```
                                                    (SEQ ID NO: 104)
   1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD
```

-continued

```
101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSREEMTKN QVSLTCLVKG FYPSDIAVEW ESNGQPENNY

301 DTTPPVLDSD GSFFLYSDLT VDKSRWQQGN VFSCSVMHEA LHNHYTQKSL

351 SLSPG
```

The leader sequence and linker sequence are underlined. To guide heterodimer formation with the ActRIIB-Fc fusion polypeptide of SEQ ID NOs: 100 and 102 above, two amino acid substitutions (replacing lysines with aspartic acids) can be introduced into the Fc domain of the ALK4-Fc fusion polypeptide as indicated by double underline above. The amino acid sequence of SEQ ID NO: 104 may optionally be provided with lysine added at the C-terminus.

This ALK4-Fc fusion protein is encoded by the following nucleic acid (SEQ ID NO: 105):

```
                                              (SEQ ID NO: 105)
   1 ATGGATGCAA TGAAGAGAGG GCTCTGCTGT GTGCTGCTGC TGTGTGGAGC

51 AGTCTTCGTT TCGCCCGGCG CCTCCGGGCC CCGGGGGGTC CAGGCTCTGC

101 TGTGTGCGTG CACCAGCTGC CTCCAGGCCA ACTACACGTG TGAGACAGAT

151 GGGGCCTGCA TGGTTTCCAT TTTCAATCTG GATGGGATGG AGCACCATGT

201 GCGCACCTGC ATCCCCAAAG TGGAGCTGGT CCCTGCCGGG AAGCCCTTCT

251 ACTGCCTGAG CTCGGAGGAC CTGCGCAACA CCCACTGCTG CTACACTGAC

301 TACTGCAACA GGATCGACTT GAGGGTGCCC AGTGGTCACC TCAAGGAGCC

351 TGAGCACCCG TCCATGTGGG GCCCGGTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG

751 CAGCCCCGAG AACCACAGGT GTACACCCTG CCCCCATCCC GGGAGGAGAT

801 GACCAAGAAC CAGGTCAGCC TGACCTGCCT GGTCAAAGGC TTCTATCCCA

851 GCGACATCGC CGTGGAGTGG GAGAGCAATG GGCAGCCGGA GAACAACTAC

901 GACACCACGC CTCCCGTGCT GGACTCCGAC GGCTCCTTCT TCCTCTATAG

951 CGACCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGT
```

The mature ALK4-Fc fusion protein sequence (SEQ ID NO: 106) is as follows and may optionally be provided with lysine added at the C-terminus.

```
                                                          (SEQ ID NO: 106)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPSR EEMTKNQVSL

251 TCLVKGFYPS DIAVEWESNG QPENNYDTTP PVLDSDGSFF LYSDLTVDKS

301 RWQQGNVFSC SVMHEALHNH YTQKSLSLSP G
```

The ActRIIB-Fc and ALK4-Fc proteins of SEQ ID NO: 102 and SEQ ID NO: 106, respectively, may be co-expressed and purified from a CHO cell line, to give rise to a heteromeric complex comprising ActRIIB-Fc:ALK4-Fc.

In another approach to promote the formation of heteromultimer complexes using asymmetric Fc fusion proteins the Fc domains are altered to introduce complementary hydrophobic interactions and an additional intermolecular disulfide bond as illustrated in the ActRIIB-Fc and ALK4-Fc polypeptide sequences of SEQ ID NOs: 401-402 and 403-404, respectively. The ActRIIB-Fc fusion polypeptide and ALK4-Fc fusion polypeptide each employ the tissue plasminogen activator (TPA) leader: MDAMKRGLCCVLLLCGAVFVSP (SEQ ID NO: 98).

The ActRIIB-Fc polypeptide sequence (SEQ ID NO: 401) is shown below:

```
                                                          (SEQ ID NO: 401)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPCREEMT KNQVSLWCLV KGFYPSDIAV

301 EWESNGQPEN NYKTTPPVLD SDGSFFLYSK LTVDKSRWQQ GNVFSCSVMH

351 EALHNHYTQK SLSLSPGK
```

The leader (signal) sequence and linker sequence are underlined. To promote formation of the ActRIIB-Fc:ALK4-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 401 may optionally be provided with lysine removed from the C-terminus.

The mature ActRIIB-Fc fusion polypeptide is as follows:

```
                                                          (SEQ ID NO: 402)
  1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPC

251 REEMTKNQVS LWCLVKGFYP SDIAVEWESN GQPENNYKTT PPVLDSDGSF

301 FLYSKLTVDK SRWQQGNVFS CSVMHEALHN HYTQKSLSLS PGK
```

The complementary form of ALK4-Fc fusion polypeptide (SEQ ID NO: 403) is as follows and may optionally be provided with lysine removed from the C-terminus.

(SEQ ID NO: 403)
```
  1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVCTL PPSREEMTKN QVSLSCAVKG FYPSDIAVEW ESNGQPENNY

301 KTTPPVLDSD GSFFLVSKLT VDKSRWQQGN VFSCSVMHEA LHNHYTQKSL

351 SLSPGK
```

The leader sequence and the linker are underlined. To guide heterodimer formation with the ActRIIB-Fc fusion polypeptide of SEQ ID NOs: 401 and 402 above, four amino acid substitutions can be introduced into the Fc domain of the ALK4 fusion polypeptide as indicated by double underline above. The amino acid sequence of SEQ ID NO: 403 may optionally be provided with lysine removed from the C-terminus.

The mature ALK4-Fc fusion protein sequence is as follows and may optionally be provided with lysine removed from the C-terminus.

(SEQ ID NO: 404)
```
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVCTLPPSR EEMTKNQVSL

251 SCAVKGFYPS DIAVEWESNG QPENNYKTTP PVLDSDGSFF LVSKLTVDKS

301 RWQQGNVFSC SVMHEALHNH YTQKSLSLSP GK
```

The ActRIIB-Fc and ALK4-Fc proteins of SEQ ID NO: 402 and SEQ ID NO: 404, respectively, may be co-expressed and purified from a CHO cell line, to give rise to a heteromeric complex comprising ActRIIB-Fc:ALK4-Fc.

Purification of various ActRIIB-Fc:ALK4-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In another approach to promote the formation of heteromultimer complexes using asymmetric Fc fusion proteins, the Fc domains are altered to introduce complementary hydrophobic interactions, an additional intermolecular disulfide bond, and electrostatic differences for facilitating purification, as illustrated in the ActRIIB-Fc and ALK4-Fc polypeptide sequences of SEQ ID NOs: 700-730 and 740-770, respectively. The ActRIIB-Fc fusion polypeptide and ALK4-Fc fusion polypeptide each employ the tissue plasminogen activator (TPA) leader.

The ActRIIB-Fc polypeptide sequence (SEQ ID NO: 700) is shown below:

(SEQ ID NO: 700)
```
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP
```

```
251 APIEKTISKA KGQPREPQVY TLPPCREEMT ENQVSLWCLV KGFYPSDIAV

301 EWESNGQPEN NYKTTPPVLD SDGSFFLYSK LTVDKSRWQQ GNVFSCSVMH

351 EALHNHYTQD SLSLSPG
```

The leader sequence and linker are underlined. To promote formation of the ALK4-Fc:ActRIIB-Fc heterodimer rather than either of the possible homodimeric complexes, two amino acid substitutions (replacing a serine with a cysteine and a threonine with a trytophan) can be introduced into the Fc domain of the fusion protein as indicated by double underline above. To facilitate purification of the ALK4-Fc:ActRIIB-Fc heterodimer, two amino acid substitutions (replacing lysines with acidic amino acids) can also be introduced into the Fc domain of the fusion protein as indicated by double underline above. The amino acid sequence of SEQ ID NO: 700 may optionally be provided with a lysine added at the C-terminus.

This ActRIIB-Fc fusion protein is encoded by the following nucleic acid (SEQ ID NO: 710):

```
                                                    (SEQ ID NO: 710)
   1 ATGGATGCAA TGAAGAGAGG GCTCTGCTGT GTGCTGCTGC TGTGTGGAGC

51 AGTCTTCGTT TCGCCCGGCG CCCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGCTAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCCGAGAACC

801 ACAGGTGTAC ACCCTGCCCC CATGCCGGGA GGAGATGACC GAGAACCAGG

851 TCAGCCTGTG GTGCCTGGTC AAAGGCTTCT ATCCCAGCGA CATCGCCGTG

901 GAGTGGGAGA GCAATGGGCA GCCGGAGAAC AACTACAAGA CCACGCCTCC

951 CGTGCTGGAC TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCACTA CACGCAGGAC AGCCTCTCCC TGTCTCCGGG

1101 T
```

The mature ActRIIB-Fc fusion polypeptide is as follows (SEQ ID NO: 720) and may optionally be provided with a lysine added to the C-terminus.

```
                                                    (SEQ ID NO: 720)
   1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPp PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS
```

```
-continued
201 VLTVLHQDWL NGKEYKCKVS NKALPAPIEK TISKAKGQPR EPQVYTLPPC

251 REEMTENQVS LWCLVKGFYP SDIAVEWESN GQPENNYKTT PPVLDSDGSF

301 FLYSKLTVDK SRWQQGNVFS CSVMHEALHN HYTQDSLSLS PG
```

This ActRIIB-Fc fusion polypeptide is encoded by the following nucleic acid (SEQ ID NO: 730):

```
                                                   (SEQ ID NO: 730)
   1 GGGCGTGGGG AGGCTGAGAC ACGGGAGTGC ATCTACTACA ACGCCAACTG

51 GGAGCTGGAG CGCACCAACC AGAGCGGCCT GGAGCGCTGC GAAGGCGAGC

101 AGGACAAGCG GCTGCACTGC TACGCCTCCT GGCGCAACAG CTCTGGCACC

151 ATCGAGCTCG TGAAGAAGGG CTGCTGGCTA GATGACTTCA ACTGCTACGA

201 TAGGCAGGAG TGTGTGGCCA CTGAGGAGAA CCCCCAGGTG TACTTCTGCT

251 GCTGTGAAGG CAACTTCTGC AACGAGCGCT TCACTCATTT GCCAGAGGCT

301 GGGGGCCCGG AAGTCACGTA CGAGCCACCC CCGACAGCCC CCACCGGTGG

351 TGGAACTCAC ACATGCCCAC CGTGCCCAGC ACCTGAACTC CTGGGGGGAC

401 CGTCAGTCTT CCTCTTCCCC CCAAAACCCA AGGACACCCT CATGATCTCC

451 CGGACCCCTG AGGTCACATG CGTGGTGGTG GACGTGAGCC ACGAAGACCC

501 TGAGGTCAAG TTCAACTGGT ACGTGGACGG CGTGGAGGTG CATAATGCCA

551 AGACAAAGCC GCGGGAGGAG CAGTACAACA GCACGTACCG TGTGGTCAGC

601 GTCCTCACCG TCCTGCACCA GGACTGGCTG AATGGCAAGG AGTACAAGTG

651 CAAGGTCTCC AACAAAGCCC TCCCAGCCCC CATCGAGAAA ACCATCTCCA

701 AAGCCAAAGG GCAGCCCCGA GAACCACAGG TGTACACCCT GCCCCCATGC

751 CGGGAGGAGA TGACCGAGAA CCAGGTCAGC CTGTGGTGCC TGGTCAAAGG

801 CTTCTATCCC AGCGACATCG CCGTGGAGTG GGAGAGCAAT GGGCAGCCGG

851 AGAACAACTA CAAGACCACG CCTCCCGTGC TGGACTCCGA CGGCTCCTTC

901 TTCCTCTATA GCAAGCTCAC CGTGGACAAG AGCAGGTGGC AGCAGGGGAA

951 CGTCTTCTCA TGCTCCGTGA TGCATGAGGC TCTGCACAAC CACTACACGC

1001 AGGACAGCCT CTCCCTGTCT CCGGGT
```

The complementary form of ALK4-Fc fusion polypeptide (SEQ ID NO: 740) is as follows and may optionally be provided with lysine removed from the C-terminus.

```
                                                   (SEQ ID NO: 740)
   1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVCTL PPSREEMTKN QVSLSCAVKG FYPSDIAVEW ESRGQPENNY

301 KTTPPVLDSR GSFFLVSKLT VDKSRWQQGN VFSCSVMHEA LHNHYTQKSL

351 SLSPGK
```

The leader sequence and the linker are underlined. To guide heterodimer formation with the ActRIIB-Fc fusion polypeptide of SEQ ID NOs: 700 and 720 above, four amino acid substitutions (replacing a tyrosine with a cysteine, a threonine with a serine, a leucine with an alanine, and a tyrosine with a valine) can be introduced into the Fc domain of the ALK4 fusion polypeptide as indicated by double underline above. To facilitate purification of the ALK4-Fc: ActRIIB-Fc heterodimer, two amino acid substitutions (replacing an asparagine with an arginine and an aspartate with an arginine) can also be introduced into the Fc domain of the ALK4-Fc fusion polypeptide as indicated by double underline above. The amino acid sequence of SEQ ID NO: 740 may optionally be provided with lysine removed from the C-terminus.

This ALK4-Fc fusion polypeptide is encoded by the following nucleic acid (SEQ ID NO: 750):

```
                                                 (SEQ ID NO: 750)
   1 ATGGATGCAA TGAAGAGAGG GCTCTGCTGT GTGCTGCTGC TGTGTGGAGC

51 AGTCTTCGTT TCGCCCGGCG CCTCCGGGCC CCGGGGGGTC CAGGCTCTGC

101 TGTGTGCGTG CACCAGCTGC CTCCAGGCCA ACTACACGTG TGAGACAGAT

151 GGGGCCTGCA TGGTTTCCAT TTTCAATCTG GATGGGATGG AGCACCATGT

201 GCGCACCTGC ATCCCCAAAG TGGAGCTGGT CCCTGCCGGG AAGCCCTTCT

251 ACTGCCTGAG CTCGGAGGAC CTGCGCAACA CCCACTGCTG CTACACTGAC

301 TACTGCAACA GGATCGACTT GAGGGTGCCC AGTGGTCACC TCAAGGAGCC

351 TGAGCACCCG TCCATGTGGG GCCCGGTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG

751 CAGCCCCGAG AACCACAGGT GTGCACCCTG CCCCCATCCC GGGAGGAGAT

801 GACCAAGAAC CAGGTCAGCC TGTCCTGCGC CGTCAAAGGC TTCTATCCCA

851 GCGACATCGC CGTGGAGTGG GAGAGCCGCG GGCAGCCGGA GAACAACTAC

901 AAGACCACGC CTCCCGTGCT GGACTCCCGC GGCTCCTTCT TCCTCGTGAG

951 CAAGCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGTAAA
```

The mature ALK4-Fc fusion polypeptide sequence is as follows (SEQ ID NO: 760) and may optionally be provided with lysine removed from the C-terminus.

```
                                                 (SEQ ID NO: 760)
   1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVCTLPPSR EEMTKNQVSL

251 SCAVKGFYPS DIAVEWESRG QPENNYKTTP PVLDSRGSFF LVSKLTVDKS

301 RWQQGNVFSC SVMHEALHNH YTQKSLSLSP GK
```

This ALK4-Fc fusion polypeptide is encoded by the following nucleic acid (SEQ ID NO: 770):

(SEQ ID NO: 770)
```
  1 TCCGGGCCCC GGGGGGTCCA GGCTCTGCTG TGTGCGTGCA CCAGCTGCCT

51 CCAGGCCAAC TACACGTGTG AGACAGATGG GGCCTGCATG GTTTCCATTT

101 TCAATCTGGA TGGGATGGAG CACCATGTGC GCACCTGCAT CCCCAAAGTG

151 GAGCTGGTCC CTGCCGGGAA GCCCTTCTAC TGCCTGAGCT CGGAGGACCT

201 GCGCAACACC CACTGCTGCT ACACTGACTA CTGCAACAGG ATCGACTTGA

251 GGGTGCCCAG TGGTCACCTC AAGGAGCCTG AGCACCCGTC CATGTGGGGC

301 CCGGTGGAGA CCGGTGGTGG AACTCACACA TGCCCACCGT GCCCAGCACC

351 TGAACTCCTG GGGGGACCGT CAGTCTTCCT CTTCCCCCCA AAACCCAAGG

401 ACACCCTCAT GATCTCCCGG ACCCCTGAGG TCACATGCGT GGTGGTGGAC

451 GTGAGCCACG AAGACCCTGA GGTCAAGTTC AACTGGTACG TGGACGGCGT

501 GGAGGTGCAT AATGCCAAGA CAAAGCCGCG GGAGGAGCAG TACAACAGCA

551 CGTACCGTGT GGTCAGCGTC CTCACCGTCC TGCACCAGGA CTGGCTGAAT

601 GGCAAGGAGT ACAAGTGCAA GGTCTCCAAC AAAGCCCTCC CAGCCCCCAT

651 CGAGAAAACC ATCTCCAAAG CCAAAGGGCA GCCCCGAGAA CCACAGGTGT

701 GCACCCTGCC CCCATCCCGG GAGGAGATGA CCAAGAACCA GGTCAGCCTG

751 TCCTGCGCCG TCAAAGGCTT CTATCCCAGC GACATCGCCG TGGAGTGGGA

801 GAGCCGCGGG CAGCCGGAGA ACAACTACAA GACCACGCCT CCCGTGCTGG

851 ACTCCCGCGG CTCCTTCTTC CTCGTGAGCA AGCTCACCGT GGACAAGAGC

901 AGGTGGCAGC AGGGGAACGT CTTCTCATGC TCCGTGATGC ATGAGGCTCT

951 GCACAACCAC TACACGCAGA AGAGCCTCTC CCTGTCTCCG GGTAAA
```

ActRIIB-Fc and ALK4-Fc proteins of SEQ ID NO: 720 and SEQ ID NO: 760, respectively, may be co-expressed and purified from a CHO cell line, to give rise to a heteromeric complex comprising ALK4-Fc:ActRIIB-Fc.

In another approach to promote the formation of heteromultimer complexes using asymmetric Fc fusion proteins, the Fc domains are altered to introduce complementary hydrophobic interactions, an additional intermolecular disulfide bond, and an arginine substitution specifically in the ActRIIB-Fc polypeptide chain for facilitating purification, as illustrated in the ActRIIB-Fc polypeptide sequences of SEQ ID NOs: 780, 790, 800 and 810 and the ALK4-Fc polypeptide sequences of SEQ ID NOs: 480, 820, and 830. The ActRIIB-Fc fusion polypeptide and ALK4-Fc fusion polypeptide each employ the tissue plasminogen activator (TPA) leader.j The ActRIIB-Fc polypeptide sequence (SEQ ID NO: 780) is shown below:

(SEQ ID NO: 780)
```
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPCREEMT KNQVSLWCLV KGFYPSDIAV

301 EWESNGQPEN NYKTTPPVLD SDGSFFLYSK LTVDKSRWQQ GNVFSCSVMH

351 EALHNRYTQK SLSLSPGK
```

The leader sequence and linker are underlined. To promote formation of the ALK4-Fc:ActRIIB-Fc heterodimer rather than either of the possible homodimeric complexes, two amino acid substitutions (replacing a serine with a cysteine and a threonine with a trytophan) can be introduced into the Fc domain of the ActRIIB-Fc fusion polypeptide as indicated by double underline above. Another amino acid substitution (replacing histidine with arginine) can also be introduced into the Fc domain of the fusion protein as indicated by double underline above to facilitate purification of the ALK4-Fc:ActRIIB-Fc heterodimer. The amino acid sequence of SEQ ID NO: 780 may optionally be provided with lysine removed from the C-terminus.

This ActRIIB-Fc fusion protein is encoded by the following nucleic acid (SEQ ID NO: 790):

```
                                                      (SEQ ID NO: 790)
   1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGCTAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCGAGAACC

801 ACAGGTGTAC ACCCTGCCCC CATGCCGGGA GGAGATGACC AAGAACCAGG

851 TCAGCCTGTG GTGCCTGGTC AAAGGCTTCT ATCCCAGCGA CATCGCCGTG

901 GAGTGGGAGA GCAATGGGCA GCCGGAGAAC AACTACAAGA CCACGCCTCC

951 CGTGCTGGAC TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCGCTA CACGCAGAAG AGCCTCTCCC TGTCTCCGGG

1101 TAAA
```

The mature ActRIIB-Fc fusion polypeptide is as follows (SEQ ID NO: 800) and may optionally be provided with lysine removed from the C-terminus.

```
                                                      (SEQ ID NO: 800)
   1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPC

251 REEMTKNQVS LWCLVKGFYP SDIAVEWESN GQPENNYKTT PPVLDSDGSF

301 FLYSKLTVDK SRWQQGNVFS CSVMHEALHN RYTQKSLSLS PGK
```

This ActRIIB-Fc fusion polypeptide is encoded by the following nucleic acid (SEQ ID NO: 810):

```
                                                         (SEQ ID NO: 810)
   1 GGGCGTGGGG AGGCTGAGAC ACGGGAGTGC ATCTACTACA ACGCCAACTG

51 GGAGCTGGAG CGCACCAACC AGAGCGGCCT GGAGCGCTGC GAAGGCGAGC

101 AGGACAAGCG GCTGCACTGC TACGCCTCCT GGCGCAACAG CTCTGGCACC

151 ATCGAGCTCG TGAAGAAGGG CTGCTGGCTA GATGACTTCA ACTGCTACGA

201 TAGGCAGGAG TGTGTGGCCA CTGAGGAGAA CCCCCAGGTG TACTTCTGCT

251 GCTGTGAAGG CAACTTCTGC AACGAGCGCT TCACTCATTT GCCAGAGGCT

301 GGGGGCCCGG AAGTCACGTA CGAGCCACCC CCGACAGCCC CCACCGGTGG

351 TGGAACTCAC ACATGCCCAC CGTGCCCAGC ACCTGAACTC CTGGGGGGAC

401 CGTCAGTCTT CCTCTTCCCC CCAAAACCCA AGGACACCCT CATGATCTCC

451 CGGACCCCTG AGGTCACATG CGTGGTGGTG GACGTGAGCC ACGAAGACCC

501 TGAGGTCAAG TTCAACTGGT ACGTGGACGG CGTGGAGGTG CATAATGCCA

551 AGACAAAGCC GCGGGAGGAG CAGTACAACA GCACGTACCG TGTGGTCAGC

601 GTCCTCACCG TCCTGCACCA GGACTGGCTG AATGGCAAGG AGTACAAGTG

651 CAAGGTCTCC AACAAAGCCC TCCCAGCCCC CATCGAGAAA ACCATCTCCA

701 AAGCCAAAGG GCAGCCCCGA GAACCACAGG TGTACACCCT GCCCCCATGC

751 CGGGAGGAGA TGACCAAGAA CCAGGTCAGC CTGTGGTGCC TGGTCAAAGG

801 CTTCTATCCC AGCGACATCG CCGTGGAGTG GGAGAGCAAT GGGCAGCCGG

851 AGAACAACTA CAAGACCACG CCTCCCGTGC TGGACTCCGA CGGCTCCTTC

901 TTCCTCTATA GCAAGCTCAC CGTGGACAAG AGCAGGTGGC AGCAGGGGAA

951 CGTCTTCTCA TGCTCCGTGA TGCATGAGGC TCTGCACAAC CGCTACACGC

1001 AGAAGAGCCT CTCCCTGTCT CCGGGTAAA
```

The complementary form of ALK4-Fc fusion polypeptide is SEQ ID NO: 403 (shown above), which contains four amino acid substitutions to guide heterodimer formation with the ActRIIB-Fc fusion polypeptide of SEQ ID NOs: 780 and 800 and may optionally be provided with lysine removed from the C-terminus.

This ALK4-Fc fusion polypeptide is encoded by the following nucleic acid (SEQ ID NO: 820):

```
                                                         (SEQ ID NO: 820)
   1 ATGGATGCAA TGAAGAGAGG GCTCTGCTGT GTGCTGCTGC TGTGTGGAGC

51 AGTCTTCGTT TCGCCCGGCG CCTCCGGGCC CCGGGGGGTC CAGGCTCTGC

101 TGTGTGCGTG CACCAGCTGC CTCCAGGCCA ACTACACGTG TGAGACAGAT

151 GGGGCCTGCA TGGTTTCCAT TTTCAATCTG GATGGGATGG AGCACCATGT

201 GCGCACCTGC ATCCCCAAAG TGGAGCTGGT CCCTGCCGGG AAGCCCTTCT

251 ACTGCCTGAG CTCGGAGGAC CTGCGCAACA CCCACTGCTG CTACACTGAC

301 TACTGCAACA GGATCGACTT GAGGGTGCCC AGTGGTCACC TCAAGGAGCC

351 TGAGCACCCG TCCATGTGGG GCCCGGTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT
```

```
-continued
651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG

751 CAGCCCCGAG AACCACAGGT GTGCACCCTG CCCCCATCCC GGGAGGAGAT

801 GACCAAGAAC CAGGTCAGCC TGTCCTGCGC CGTCAAAGGC TTCTATCCCA

851 GCGACATCGC CGTGGAGTGG GAGAGCAATG GGCAGCCGGA GAACAACTAC

901 AAGACCACGC CTCCCGTGCT GGACTCCGAC GGCTCCTTCT TCCTCGTGAG

951 CAAGCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGTAAA
```

The mature ALK4-Fc fusion polypeptide sequence is SEQ ID NO: 404 (shown above) and may optionally be provided with lysine removed from the C-terminus.

This ALK4-Fc fusion polypeptide is encoded by the following nucleic acid (SEQ ID NO: 830):

```
                                              (SEQ ID NO: 830)
  1 TCCGGGCCCC GGGGGGTCCA GGCTCTGCTG TGTGCGTGCA CCAGCTGCCT

51 CCAGGCCAAC TACACGTGTG AGACAGATGG GGCCTGCATG GTTTCCATTT

101 TCAATCTGGA TGGGATGGAG CACCATGTGC GCACCTGCAT CCCCAAAGTG

151 GAGCTGGTCC CTGCCGGGAA GCCCTTCTAC TGCCTGAGCT CGGAGGACCT

201 GCGCAACACC CACTGCTGCT ACACTGACTA CTGCAACAGG ATCGACTTGA

251 GGGTGCCCAG TGGTCACCTC AAGGAGCCTG AGCACCCGTC CATGTGGGGC

301 CCGGTGGAGA CCGGTGGTGG AACTCACACA TGCCCACCGT GCCCAGCACC

351 TGAACTCCTG GGGGGACCGT CAGTCTTCCT CTTCCCCCCA AAACCCAAGG

401 ACACCCTCAT GATCTCCCGG ACCCCTGAGG TCACATGCGT GGTGGTGGAC

451 GTGAGCCACG AAGACCCTGA GGTCAAGTTC AACTGGTACG TGGACGGCGT

501 GGAGGTGCAT AATGCCAAGA CAAAGCCGCG GGAGGAGCAG TACAACAGCA

551 CGTACCGTGT GGTCAGCGTC CTCACCGTCC TGCACCAGGA CTGGCTGAAT

601 GGCAAGGAGT ACAAGTGCAA GGTCTCCAAC AAAGCCCTCC CAGCCCCCAT

651 CGAGAAAACC ATCTCCAAAG CCAAAGGGCA GCCCCGAGAA CCACAGGTGT

701 GCACCCTGCC CCCATCCCGG GAGGAGATGA CCAAGAACCA GGTCAGCCTG

751 TCCTGCGCCG TCAAAGGCTT CTATCCCAGC GACATCGCCG TGGAGTGGGA

801 GAGCAATGGG CAGCCGGAGA ACAACTACAA GACCACGCCT CCCGTGCTGG

851 ACTCCGACGG CTCCTTCTTC CTCGTGAGCA AGCTCACCGT GGACAAGAGC

901 AGGTGGCAGC AGGGGAACGT CTTCTCATGC TCCGTGATGC ATGAGGCTCT

951 GCACAACCAC TACACGCAGA AGAGCCTCTC CCTGTCTCCG GGTAAA
```

ActRIIB-Fc and ALK4-Fc proteins of SEQ ID NO: 800 and SEQ ID NO: 404, respectively, may be co-expressed and purified from a CHO cell line, to give rise to a heteromeric complex comprising ALK4-Fc:ActRIIB-Fc.

Purification of various ALK4-Fc:ActRIIB-Fc complexes could be achieved by a series of column chromatography steps, including, for example, three or more of the following, in any order: protein A chromatography, Q sepharose chromatography, phenylsepharose chromatography, size exclusion chromatography and epitope-based affinity chromatography (e.g., with an antibody or functionally equivalent ligand directed against an epitope on ALK4 or ActRIIB), and multimodal chromatography (e.g., with resin containing both electrostatic and hydrophobic ligands). The purification could be completed with viral filtration and buffer exchange.

Example 2. Ligand Binding Profile of ActRIIB-Fc:ALK4-Fc Heterodimer Compared to ActRIIB-Fc Homodimer and ALK4-Fc Homodimer A Biacore™-based binding assay was used to compare ligand binding selectivity of the ActRIIB-Fc:ALK4-Fc heterodimeric complex described above with that of ActRIIB-Fc and ALK4-Fc homodimeric complexes. The ActRIIB-Fc:ALK4-Fc heterodimer, ActRIIB-Fc homodimer, and ALK4-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand off-rate is a particularly significant parameter to evaluate for ligand traps. Soluble receptor-Fc proteins administered in vivo are in constant competition with native receptors for ligands. When endogenous ligands of the TGFbeta superfamily typically bind to cognate receptors at the cell surface, a multi-step signal transduction process is triggered that is relatively slow on a molecular time scale. Native receptors dissociate from ligand slowly in part because significant time is required to generate an intracellular signal from a ligand binding event. For a soluble receptor-Fc protein to compete effectively for ligand, the off-rate for its complex with the ligand needs to be similar to, or slower than, the off-rate for a ligand complex with native receptor. Ligand binding is a dynamic process and some fraction of ligands will always be in unbound form, so it is important therapeutically for a dose of receptor-Fc protein to capture target ligand for as long as possible. One way to shift the binding equilibrium in favor of more captured ligand is to increase the concentration (dose level) of inhibitor, however this can generate off-target effects that reduce tolerability and safety. A preferable approach is to use an inhibitor with a slower ligand off-rate (longer capture time) combined with ligand binding selectivity to achieve an effective level of ligand antagonism at a lower concentration of inhibitor.

Fc homodimer in certain applications where such selective antagonism is advantageous. Examples include therapeutic applications where it is desirable to retain antagonism of one or more of activin A, activin B, activin AC, GDF8, and GDF11 but minimize antagonism of one or more of BMP9, BMP10, and BMP6.

Example 3. Activity Profile of ActRIIB-Fc:ALK4-Fc Heterodimer in Mice Compared to ActRIIB-Fc Homodimer Homodimeric and heterodimeric complexes were tested in mice to investigate differences in their activity profiles in vivo. Wild-type C57BL/6 mice were dosed subcutaneously with an ActRIIB-Fc homodimer (10 mg/kg), an ActRIIB-Fc:ALK4-Fc heterodimer (3 or 10 mg/kg), or vehicle (phosphate-buffered saline, PBS) twice per week for 4 weeks beginning at approximately 10 weeks of age (n=9 mice per group). ALK4-Fc homodimer was not tested in vivo due to its inability to bind ligands with high affinity under cell-free conditions as determined by surface plasmon resonance. Study endpoints included: body weight; total lean mass and total adipose mass as determined by nuclear magnetic resonance (NMR) at baseline and study completion (4 weeks); total bone mineral density as determined by dual energy x-ray absorptiometry (DEXA) at baseline and 4 weeks; and weights of the gastrocnemius, rectus femoris, and pectoralis muscles determined at 4 weeks.

| | Ligand binding profile of ActRIIB-Fc:ALK4-Fc heterodimer compared to ActRIIB-Fc homodimer and ALK4-Fc homodimer | | | | | | | | |
|---|---|---|---|---|---|---|---|---|---|
| | ActRIIB-Fc homodimer | | | ALK4-Fc homodimer | | | ActRIIB-Fc:ALK4-Fc heterodimer | | |
| Ligand | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.2 \times 10^7$ | $2.3 \times 10^{-4}$ | 19 | $5.8 \times 10^5$ | $1.2 \times 10^{-2}$ | 20000 | $1.3 \times 10^7$ | $1.5 \times 10^{-4}$ | 12 |
| Activin B | $5.1 \times 10^6$ | $1.0 \times 10^{-4}$ | 20 | | No binding | | $7.1 \times 10^6$ | $4.0 \times 10^{-5}$ | 6 |
| BMP6 | $3.2 \times 10^7$ | $6.8 \times 10^{-3}$ | 190 | | — | | $2.0 \times 10^6$ | $5.5 \times 10^{-3}$ | 2700 |
| BMP9 | $1.4 \times 10^7$ | $1.1 \times 10^{-3}$ | 77 | | — | | | Transient* | 3400 |
| BMP10 | $2.3 \times 10^7$ | $2.6 \times 10^{-4}$ | 11 | | — | | $5.6 \times 10^7$ | $4.1 \times 10^{-3}$ | 74 |
| GDF3 | $1.4 \times 10^6$ | $2.2 \times 10^{-3}$ | 1500 | | — | | $3.4 \times 10^6$ | $1.7 \times 10^{-2}$ | 4900 |
| GDF8 | $8.3 \times 10^5$ | $2.3 \times 10^{-4}$ | 280 | $1.3 \times 10^5$ | $1.9 \times 10^{-3}$ | 15000† | $3.9 \times 10^5$ | $2.1 \times 10^{-4}$ | 550 |
| GDF11 | $5.0 \times 10^7$ | $1.1 \times 10^{-4}$ | 2 | $5.0 \times 10^6$ | $4.8 \times 10^{-3}$ | 270† | $3.8 \times 10^7$ | $1.1 \times 10^{-4}$ | 3 |

Figure 6:
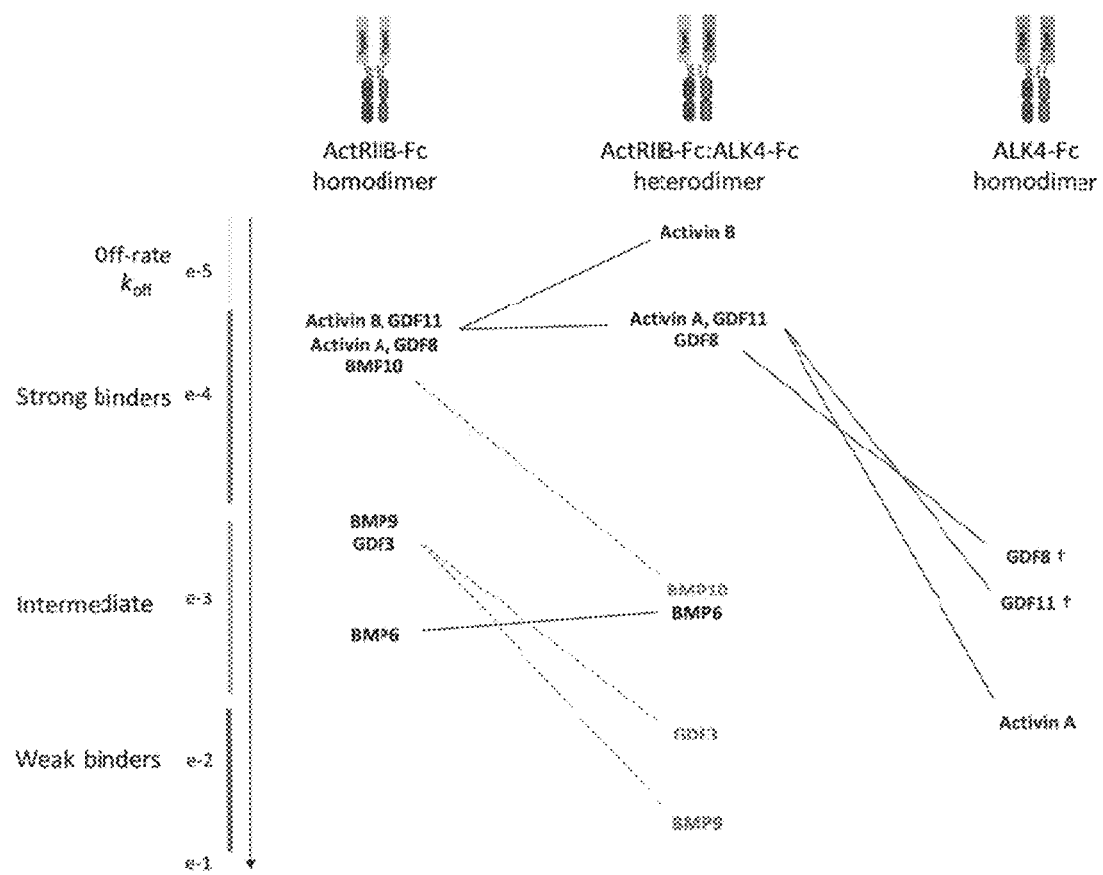
FIG. 6 shows ligand binding data for an ActRIIB-Fc: ALK4-Fc heterodimeric protein complex as compared to ActRIIB-Fc homodimer and ALK4-Fc homodimer. For each protein complex, ligands are ranked by $k_{off}$, a kinetic constant that correlates well with ligand signaling inhibition, and listed in descending order of binding affinity (ligands bound most tightly are listed at the top). At left, yellow, red, green, and blue lines indicate magnitude of the off-rate constant. Solid black lines indicate ligands whose binding to heterodimer is enhanced or unchanged compared with homodimer, whereas dashed red lines indicate substantially reduced binding compared with homodimer. As shown, the ActRIIB-Fc:ALK4-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. Like ActRIIB-Fc homodimer, the heterodimer retains intermediate-level binding to BMP6.

*Indeterminate due to transient nature of interaction
†Very low signal
— Not tested These comparative binding data demonstrate that the ActRIIB-Fc:ALK4-Fc heterodimer has an altered binding profile/selectivity relative to either the ActRIIB-Fc or ALK4-Fc homodimers. The ActRIIB-Fc:ALK4-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. In particular, BMP9 displays low or no observable affinity for the ActRIIB-Fc:ALK4-Fc heterodimer, whereas this ligand binds strongly to ActRIIB-Fc homodimer. Like ActRIIB-Fc homodimer, the heterodimer retains intermediate-level binding to BMP6. See FIG. 6.

These results therefore demonstrate that the ActRIIB-Fc:ALK4-Fc heterodimer is a more selective antagonist of activin A, activin B, GDF8, and GDF11 compared to a ActRIIB-Fc homodimer. Accordingly, an ActRIIB-Fc:ALK4-Fc heterodimer will be more useful than an ActRIIB-

| Activity of ActRIIB-Fc and ALK4-Fc Complexes in Wild-Type Mice | | | | |
|---|---|---|---|---|
| | | ActRIIB-Fc homodimer | ActRIIB-Fc: ALK4-Fc heterodimer | |
| Endpoint | | | | |
| (4 wk) | Vehicle | 10 mg/kg | 10 mg/kg | 3 mg/kg |
| Change in body weight from baseline | ↑ 15% | ↑ 38% ** | ↑ 41% ** | ↑ 33% ** |
| Change in total lean mass from baseline | ↓ 1% | ↑ 5% ** | ↑ 5% ** | ↑ 5% ** |
| Change in total adipose mass from baseline | ↑ 5% | ↓ 36% ** | ↓ 35% ** | ↓ 35% ** |
| Change in total bone mineral density from baseline | ↑ 8% | ↑ 14% * | ↑ 12% * | ↑ 11% |

Activity of ActRIIB-Fc and ALK4-Fc
Complexes in Wild-Type Mice

| Endpoint (4 wk) | Vehicle | ActRIIB-Fc homodimer 10 mg/kg | ActRIIB-Fc: ALK4-Fc heterodimer 10 mg/kg | 3 mg/kg |
| --- | --- | --- | --- | --- |
| Gastrocnemius weight † | 23 | 36 ** | 35 ** | 30 ** |
| Femoris weight † | 11.5 | 17 ** | 16 ** | 14 ** |
| Pectoralis weight† | 15 | 23 ** | 28 ** | 23 ** |

\* P < 0.05 vs. vehicle
\*\* P < 0.01 vs. vehicle
† Combined left and right muscle weights normalized to femur length (mg/mm) to control for body size Study results are summarized in the table above. As expected, ActRIIB-Fc homodimer caused marked changes in body composition, many consistent with known effects of GDF8 and activin inhibition. Treatment of wild-type mice with ActRIIB-Fc homodimer more than doubled body weight gain over the course of the study compared to vehicle-treated controls. Accompanying this net weight gain were significant increases in total lean mass and total bone mineral density, as well as a significant reduction in total adipose mass, compared to vehicle. It should be recognized that normalized (percentage-based) changes in lean and adipose tissues differ in their correspondence to absolute changes because lean mass (typically about 70% of body weight in a mouse) is much larger than adipose mass (typically about 10% of body weight). Individual skeletal muscles examined, including the gastrocnemius, femoris, and pectoralis all increased significantly in weight compared to vehicle controls over the course of treatment with ActRIIB-Fc homodimer.

The ActRIIB-Fc:ALK4-Fc heterodimer produced certain effects strikingly similar to those of the ActRIIB-Fc homodimer despite differential ligand selectivity of the two complexes. As shown in the table above, treatment of mice with the ActRIIB-Fc:ALK4-Fc heterodimer at a dose level of 10 mg/kg matched, nearly matched, or exceeded the effects of ActRIIB-Fc homodimer at the same dose level for all endpoints listed. Effects of the ActRIIB-Fc:ALK4-Fc heterodimer at 3 mg/kg were mildly attenuated for several endpoints compared to 10 mg/kg, thus providing evidence for a dose-effect relationship.

Thus, an ActRIIB-Fc:ALK4-Fc heterodimer exerts beneficial anabolic effects on skeletal muscle and bone, and catabolic effects on adipose tissue, very similar to those of ActRIIB-Fc homodimer. However, unlike ActRIIB homodimer, an ActRIIB-Fc:ALK4-Fc heterodimer exhibits only low-affinity or transient binding to BMP9 and BMP10 and so will not concurrently inhibit processes mediated by those ligands, such as angiogenesis. This novel selectivity will be useful, for example, in treating patients in need of stimulatory effects on muscle and bone, and inhibitory effects on fat, but not in need of altered angiogenesis.

Example 4. Generation of an ActRIIB-Fc:ALK3-Fc Heterodimer

Applicants constructed a soluble ActRIIB-Fc:ALK3-Fc heteromeric complex comprising the extracellular domains of human ActRIIB and human ALK3, which are each fused to an Fc domain with a linker positioned between the extracellular domain and the Fc domain. The individual constructs are referred to as ActRIIB-Fc and ALK3-Fc, respectively.

Formation of heteromeric ActRIIB-Fc:ALK3-Fc may be guided by approaches similar to those described in Example 1.

In a first approach, the polypeptide sequence of the ActRIIB-Fc fusion protein and a nucleic acid sequence encoding it are provided above in Example 1 as SEQ ID NOs: 100-102.

The complementary ALK3-Fc fusion protein employs the TPA leader and is as follows:

(SEQ ID NO: 115)

```
  1 MDAMKRGLCC VLLLCGAVFV SPGAQNLDSM LHGTGMKSDS DQKKSENGVT

51 LAPEDTLPFL KCYCSGHCPD DAINNTCITN GHCFAIIEED DQGETTLASG

101 CMKYEGSDFQ CKDSPKAQLR RTIECCRTNL CNQYLQPTLP PVVIGPFFDG

151 SIRTGGGTHT CPPCPAPELL GGPSVFLFPP KPKDTLMISR TPEVTCVVVD

201 VSHEDPEVKF NWYVDGVEVH NAKTKPREEQ YNSTYRVVSV LTVLHQDWLN

251 GKEYKCKVSN KALPAPIEKT ISKAKGQPRE PQVYTLPPSR EEMTKNQVSL

301 TCLVKGFYPS DIAVEWESNG QPENNYDTTP PVLDSDGSFF LYSDLTVDKS

351 RWQQGNVFSC SVMHEALHNH YTQKSLSLSP G
```

The leader and linker sequences are underlined. To promote formation of the ActRIIB-Fc:ALK3-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 115 may optionally be provided with a lysine added at the C-terminus.

This ALK3-Fc fusion protein is encoded by the following nucleic acid (SEQ ID NO: 116).

```
                                                     (SEQ ID NO: 116)
   1 ATGGATGCAA TGAAGAGAGG GCTCTGCTGT GTGCTGCTGC TGTGTGGAGC

51 AGTCTTCGTT TCGCCCGGCG CCCAGAATCT GGATAGTATG CTTCATGGCA

101 CTGGGATGAA ATCAGACTCC GACCAGAAAA AGTCAGAAAA TGGAGTAACC

151 TTAGCACCAG AGGATACCTT GCCTTTTTTA AAGTGCTATT GCTCAGGGCA

201 CTGTCCAGAT GATGCTATTA ATAACACATG CATAACTAAT GGACATTGCT

251 TTGCCATCAT AGAAGAAGAT GACCAGGGAG AAACCACATT AGCTTCAGGG

301 TGTATGAAAT ATGAAGGATC TGATTTTCAG TGCAAAGATT CTCCAAAAGC

351 CCAGCTACGC CGGACAATAG AATGTTGTCG GACCAATTTA TGTAACCAGT

401 ATTTGCAACC CACACTGCCC CCTGTTGTCA TAGGTCCGTT TTTTGATGGC

451 AGCATTCGAA CCGGTGGTGG AACTCACACA TGCCCACCGT GCCCAGCACC

501 TGAACTCCTG GGGGGACCGT CAGTCTTCCT CTTCCCCCCA AAACCCAAGG

551 ACACCCTCAT GATCTCCCGG ACCCCTGAGG TCACATGCGT GGTGGTGGAC

601 GTGAGCCACG AAGACCCTGA GGTCAAGTTC AACTGGTACG TGGACGGCGT

651 GGAGGTGCAT AATGCCAAGA CAAAGCCGCG GGAGGAGCAG TACAACAGCA

701 CGTACCGTGT GGTCAGCGTC CTCACCGTCC TGCACCAGGA CTGGCTGAAT

751 GGCAAGGAGT ACAAGTGCAA GGTCTCCAAC AAAGCCCTCC CAGCCCCCAT

801 CGAGAAAACC ATCTCCAAAG CCAAAGGGCA GCCCCGAGAA CCACAGGTGT

851 ACACCCTGCC CCCATCCCGG GAGGAGATGA CCAAGAACCA GGTCAGCCTG

901 ACCTGCCTGG TCAAAGGCTT CTATCCCAGC GACATCGCCG TGGAGTGGGA

951 GAGCAATGGG CAGCCGGAGA ACAACTACGA CACCACGCCT CCCGTGCTGG

1001 ACTCCGACGG CTCCTTCTTC CTCTATAGCG ACCTCACCGT GGACAAGAGC

1051 AGGTGGCAGC AGGGGAACGT CTTCTCATGC TCCGTGATGC ATGAGGCTCT

1101 GCACAACCAC TACACGCAGA AGAGCCTCTC CCTGTCTCCG GGT
```

The mature ALK3-Fc fusion protein sequence is as follows (SEQ ID NO: 117) and may optionally be provided with a lysine added at the C-terminus.

```
                                                     (SEQ ID NO: 117)
  1 GAQNLDSMLH GTGMKSDSDQ KKSENGVTLA PEDTLPFLKC YCSGHCPDDA

51 INNTCITNGH CFAIIEEDDQ GETTLASGCM KYEGSDFQCK DSPKAQLRRT

101 IECCRTNLCN QYLQPTLPPV VIGPFFDGSI RTGGGTHTCP PCPAPELLGG

151 PSVFLFPPKP KDTLMISRTP EVTCVVVDVS HEDPEVKFNW YVDGVEVHNA

201 KTKPREEQYN STYRVVSVLT VLHQDWLNGK EYKCKVSNKA LPAPIEKTIS

251 KAKGQPREPQ VYTLPPSREE MTKNQVSLTC LVKGFYPSDI AVEWESNGQP

301 ENNYDTTPPV LDSDGSFFLY SDLTVDKSRW QQGNVFSCSV MHEALHNHYT

351 QKSLSLSPG
```

The ActRIIB-Fc and ALK3-Fc fusion proteins of SEQ ID NO: 102 and SEQ ID NO: 117, respectively, may be co-expressed and purified from a CHO cell line to give rise to a heteromeric complex comprising ActRIIB-Fc:ALK3-Fc.

In another approach to promoting the formation of heteromultimer complexes using asymmetric Fc fusion proteins, illustrated in the ActRIIB-Fc and ALK3-Fc polypeptide sequences of SEQ ID NOs: 401-402 and 407-408, respectively, the Fc domains are altered to introduce complementary hydrophobic interactions and an additional intermolecular disulfide bond. The ActRIIB-Fc fusion polypeptide sequences are discussed in Example 1.

The complementary form of ALK3-Fc fusion polypeptide (SEQ ID NO: 407) is as follows:

```
                                              (SEQ ID NO: 407)
  1 MDAMKRGLCC VLLLCGAVFV SPGAQNLDSM LHGTGMKSDS DQKKSENGVT

51 LAPEDTLPFL KCYCSGHCPD DAINNTCITN GHCFAIIEED DQGETTLASG

101 CMKYEGSDFQ CKDSPKAQLR RTIECCRTNL CNQYLQPTLP PVVIGPFFDG

151 SIRTGGGTHT CPPCPAPELL GGPSVFLFPP KPKDTLMISR TPEVTCVVVD

201 VSHEDPEVKF NWYVDGVEVH NAKTKPREEQ YNSTYRVVSV LTVLHQDWLN

251 GKEYKCKVSN KALPAPIEKT ISKAKGQPRE PQVCTLPPSR EEMTKNQVSL

301 SCAVKGFYPS DIAVEWESNG QPENNYKTTP PVLDSDGSFF LVSKLTVDKS

351 RWQQGNVFSC SVMHEALHNH YTQKSLSLSP GK
```

The leader sequence and linker are underlined. To guide heterodimer formation with the ActRIIB-Fc fusion polypeptide of SEQ ID NOs 401 and 402 above, four amino acid substitutions can be introduced into the Fc domain of the ALK3 fusion polypeptide as indicated by double underline above. The amino acid sequence of SEQ ID NO: 407 may optionally be provided with the lysine removed from the C-terminus.

The mature ALK3-Fc fusion protein sequence (SEQ ID NO: 408) is as follows and may optionally be provided with the lysine (K) removed from the C-terminus.

```
                                              (SEQ ID NO: 408)
  1 GAQNLDSMLH GTGMKSDSDQ KKSENGVTLA PEDTLPFLKC YCSGHCPDDA

51 INNTCITNGH CFAIIEEDDQ GETTLASGCM KYEGSDFQCK DSPKAQLRRT

101 IECCRTNLCN QYLQPTLPPV VIGPFFDGSI RTGGGTHTCP PCPAPELLGG

151 PSVFLFPPKP KDTLMISRTP EVTCVVVDVS HEDPEVKFNW YVDGVEVHNA

201 KTKPREEQYN STYRVVSVLT VLHQDWLNGK EYKCKVSNKA LPAPIEKTIS

251 KAKGQPREPQ VCTLPPSREE MTKNQVSLSC AVKGFYPSDI AVEWESNGQP

301 ENNYKTTPPV LDSDGSFFLV SKLTVDKSRW QQGNVFSCSV MHEALHNHYT

351 QKSLSLSPGK
```

The ActRIIB-Fc and ALK3-Fc proteins of SEQ ID NO: 402 and SEQ ID NO: 408, respectively, may be co-expressed and purified from a CHO cell line, to give rise to a heteromeric complex comprising ActRIIB-Fc:ALK3-Fc.

Purification of various ActRIIB-Fc:ALK3-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 5. Ligand Binding Profile of ActRIIB-Fc:ALK3-Fc Heterodimer Compared to ActRIIB-Fc Homodimer and ALK3-Fc Homodimer A Biacore™-based binding assay was used to compare ligand binding selectivity of the ActRIIB-Fc:ALK3-Fc heterodimeric complex described above with that of ActRIIB-Fc and ALK3-Fc homodimeric complexes. The ActRIIB-Fc:ALK3-Fc heterodimer, ActRIIB-Fc homodimer, and ALK3-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profile of ActRIIB-Fc:ALK3-Fc heterodimer compared to ActRIIB-Fc homodimer and ALK3-Fc homodimer

| | ActRIIB-Fc homodimer | | | ALK3-Fc homodimer | | | ActRIIB-Fc:ALK3-Fc heterodimer | | |
|---|---|---|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.3 \times 10^7$ | $\mathbf{1.4 \times 10^{-4}}$ | 11 | No binding | | | $3.4 \times 10^7$ | $5.0 \times 10^{-3}$ | 150 |
| Activin B | $5.1 \times 10^6$ | $\mathbf{1.0 \times 10^{-4}}$ | 20 | No binding | | | $2.8 \times 10^6$ | $\mathbf{5.7 \times 10^{-4}}$ | 200 |
| BMP2 | Transient* | | >66000 | $6.8 \times 10^5$ | $\mathbf{8.9 \times 10^{-5}}$ | 130 | $8.0 \times 10^6$ | $\mathbf{1.1 \times 10^{-5}}$ | 1 |
| BMP4 | — | | | $3.0 \times 10^5$ | $\mathbf{5.3 \times 10^{-5}}$ | 180 | $2.6 \times 10^6$ | $\mathbf{6.5 \times 10^{-6}}$ | 3 |
| BMP5 | $2.6 \times 10^7$ | $7.5 \times 10^{-2}$ | 2900 | $2.9 \times 10^4$ | $2.0 \times 10^{-3}$ | 70000 | $9.0 \times 10^5$ | $\mathbf{5.8 \times 10^{-4}}$ | 640 |
| BMP6 | $3.5 \times 10^7$ | $6.8 \times 10^{-3}$ | 190 | $1.4 \times 10^5$ | $4.9 \times 10^{-3}$ | 35000 | $2.0 \times 10^7$ | $\mathbf{2.9 \times 10^{-4}}$ | 15 |

-continued

Ligand binding profile of ActRIIB-Fc:ALK3-Fc heterodimer
compared to ActRIIB-Fc homodimer and ALK3-Fc homodimer

| Ligand | ActRIIB-Fc homodimer | | | ALK3-Fc homodimer | | | ActRIIB-Fc:ALK3-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| BMP7 | $8.8 \times 10^6$ | $1.4 \times 10^{-2}$ | 1600 | $1.2 \times 10^6$ | $1.8 \times 10^{-2}$ | 15000 | $8.2 \times 10^5$ | $1.5 \times 10^{-3}$ | 1900 |
| BMP9 | $3.9 \times 10^7$ | $1.3 \times 10^{-3}$ | 34 | | No binding | | Transient* | | >33000 |
| BMP10 | $5.9 \times 10^7$ | $2.0 \times 10^{-4}$ | 4 | | No binding | | $3.0 \times 10^7$ | $9.4 \times 10^{-4}$ | 31 |
| GDF3 | $1.6 \times 10^6$ | $2.3 \times 10^{-3}$ | 1400 | | No binding | | $1.4 \times 10^7$ | $8.2 \times 10^{-2}$ | 5900 |
| GDF5 | Transient* | | >9600 | $4.8 \times 10^5$ | $1.1 \times 10^{-2}$ | 22000 | $1.2 \times 10^7$ | $8.3 \times 10^{-4}$ | 70 |
| GDF6 | — | | | $3.4 \times 10^4$ | $1.3 \times 10^{-3}$ | 40000 | $2.8 \times 10^5$ | $4.5 \times 10^{-4}$ | 1600 |
| GDF7 | Transient* | | >12000 | $2.2 \times 10^5$ | $2.7 \times 10^{-2}$ | 12000 | $7.5 \times 10^6$ | $4.0 \times 10^{-4}$ | 52 |
| GDF8 | $8.3 \times 10^5$ | $2.3 \times 10^{-4}$ | 280 | | No binding | | $3.0 \times 10^6$ | $9.2 \times 10^{-4}$ | 310 |
| GDF11 | $5.0 \times 10^7$ | $1.1 \times 10^{-4}$ | 2 | | No binding | | $1.6 \times 10^7$ | $1.1 \times 10^{-3}$ | 66 |

*Indeterminate due to transient nature of interaction
— Not tested

Figure 7:
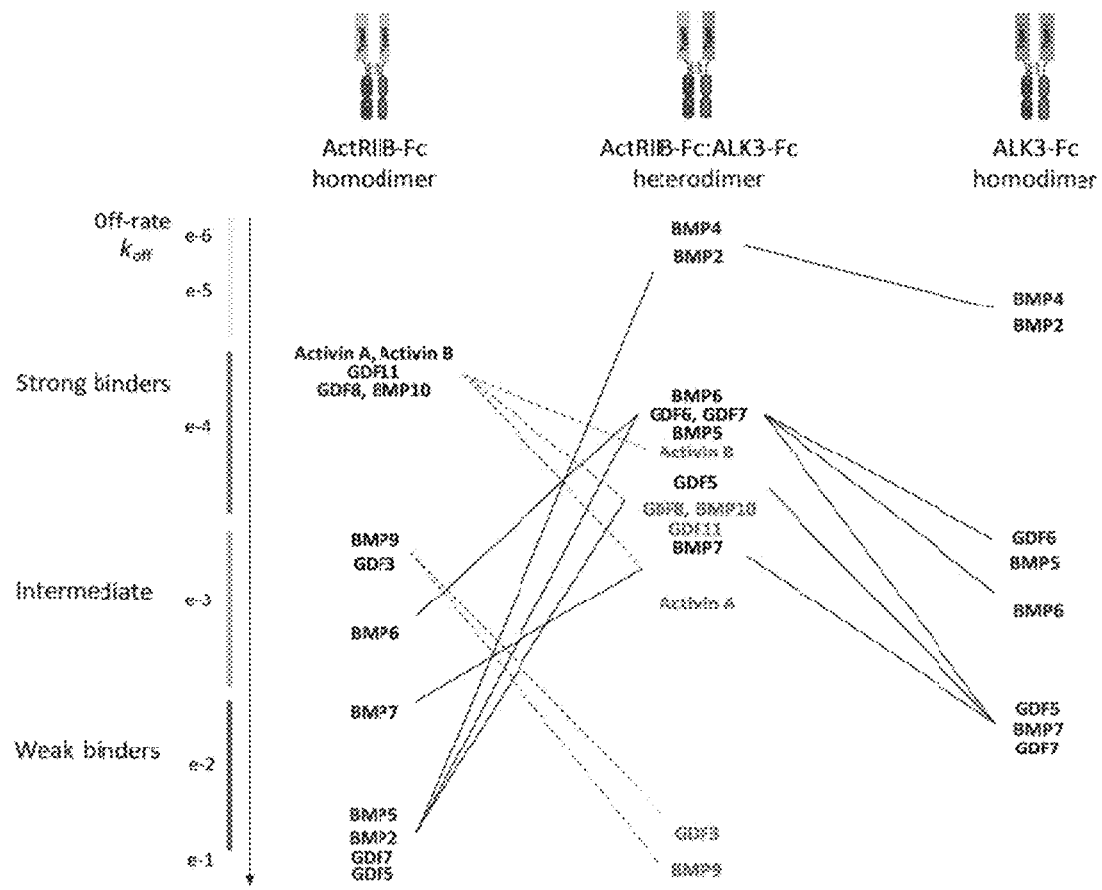
FIG. 7 shows ligand binding data for an ActRIIB-Fc: ALK3-Fc heterodimeric protein complex as compared to ActRIIB-Fc homodimer and ALK3-Fc homodimer. Format is the same as in FIG. 6. As shown, the ActRIIB-Fc:ALK3-Fc heterodimer binds BMP2 and BMP4 with exceptionally high affinity and displays greatly enhanced binding to BMP5, BMP6, BMP7, GDF5, GDF6, and GDF7 compared with either homodimer. Compared to ActRIIB homodimer, the ActRIIB-Fc:ALK3-Fc heterodimer displays reduced binding to activin A, activin B, BMP10, GDF8, and GDF11 and also discriminates among these ligands to a greater degree, particularly between activin A and activin B. In addition, the ability of ActRIIB-Fc homodimer to bind BMP9 and GDF3 with high affinity is absent for ActRIIB-Fc:ALK3-Fc heterodimer.

These comparative binding data demonstrate that the ActRIIB-Fc:ALK3-Fc heterodimer has an altered binding profile/selectivity relative to either the ActRIIB-Fc homodimer or ALK3-Fc homodimer. The ActRIIB-Fc:ALK3-Fc heterodimer binds BMP2 and BMP4 with exceptionally high affinity and displays greatly enhanced binding to BMP5, BMP6, BMP7, GDF5, GDF6, and GDF7 compared with either homodimer. Compared to ActRIIB homodimer, the ActRIIB-Fc:ALK3-Fc heterodimer displays reduced binding to activin A, activin B, BMP10, GDF8, and GDF11 and also discriminates among these ligands to a greater degree, particularly between activin A and activin B. In addition, the ability of ActRIIB-Fc homodimer to bind BMP9 and GDF3 with high affinity is absent for ActRIIB-Fc:ALK3-Fc heterodimer. See FIG. 7.

These results therefore demonstrate that the ActRIIB-Fc:ALK3-Fc heterodimer is a selective inhibitor of activin B, the GDF5/GDF6/GDF7 ligand subfamily, and several key BMP ligands excluding most notably BMP9. Accordingly, an ActRIIB-Fc:ALK3-Fc heterodimer will be more useful than either an ActRIIB-Fc homodimer or an ALK3-Fc homodimer in certain applications where such selective antagonism is advantageous. Examples include therapeutic applications where it is desirable to retain antagonism of BMP2, BMP4, BMP5, and BMP6 or activin B but minimize antagonism of one or more ligands with anabolic muscle effects (e.g., activin A and GDF8) or ligands with angiogenic effects (e.g., BMP9 and BMP10).

Example 6. Activity Profile of ActRIIB-Fc:ALK3-Fc Heterodimer in Mice Compared to ActRIIB-Fc Homodimer and ALK3-Fc Homodimer Homodimeric and heterodimeric complexes were tested in mice to investigate differences in their activity profiles in vivo. Wild-type C57BL/6 mice were dosed intraperitoneally with ActRIIB-Fc homodimer (10 mg/kg), ALK3-Fc homodimer (10 mg/kg), ActRIIB-Fc:ALK4-Fc heterodimer (3 or 10 mg/kg), or vehicle (phosphate-buffered saline, PBS) twice per week for 6.5 weeks (46 days) beginning at 10 weeks of age (n=5 mice per group). Study endpoints included body weight, total adipose mass as determined by nuclear magnetic resonance (NMR) at baseline and study completion (6.5 weeks), and total bone mineral density as determined by dual energy x-ray absorptiometry (DEXA) at baseline and 6.5 weeks.

| | Activity of ActRIIB-Fc and ALK3-Fc Complexes in Wild-Type Mice Compared to Vehicle | | | |
|---|---|---|---|---|
| Endpoint | ActRIIB-Fc homodimer | ALK3-FC homodimer | ActRIIB-Fc: ALK3-Fc heterodimer | |
| 6.5 wk | 10 mg/kg | 10 mg/kg | 10 mg/kg | 3 mg/kg |
| Body weight | ↑ 23% * | ↓ 3% | ↓ 0.5% | ↓ 1% |
| Total adipose mass | ↓ 41% * | ↓ 12% | ↓ 14% * | ↓ 18% * |
| Total bone mineral density | ↑ 8% * | ↑ 6% * | ↑ 9% * | ↑ 10% * |

* $P < 0.05$ vs. vehicle

Study results are summarized in the table above. As expected, the ActRIIB-Fc homodimer significantly increased body weight and total bone mineral density, and significantly reduced total adipose mass, all compared to vehicle. Also as expected, the ALK3-Fc homodimer significantly increased total bone mineral density compared to vehicle but unlike the ActRIIB-Fc homodimer did not significantly alter either body weight or total adipose mass. The ActRIIB-Fc:ALK3-Fc heterodimer notably displayed an activity profile different from either the ActRIIB-Fc homodimer or the ALK3-Fc homodimer. Treatment of mice with the ActRIIB-Fc:ALK4-Fc heterodimer at either dose level significantly increased bone mineral density at least as well either homodimer. However, unlike ALK3-Fc homodimer, the ActRIIB-Fc:ALK3-Fc heterodimer significantly reduced adipose mass, and unlike ActRIIB-Fc homodimer, the ActRIIB-Fc:ALK3-Fc heterodimer significantly reduced adipose mass without altering body weight. Thus, an ActRIIB-Fc:ALK3-Fc heterodimer exerts beneficial effects on bone together with potentially beneficial effects on adipose tissue. This novel selectivity will be useful, for example, in treating patients in need of stimulatory effects on bone and inhibitory effects on fat but not in need of altered body weight.

Example 7. Generation of an ActRIIB-Fc:ALK7-Fc Heterodimer

Applicants constructed a soluble ActRIIB-Fc:ALK7-Fc heteromeric complex comprising the extracellular domains of human ActRIIB and human ALK7, which are each fused to an Fc domain with a linker positioned between the extracellular domain and the Fc domain. The individual constructs are referred to as ActRIIB-Fc and ALK7-Fc, respectively.

Formation of heteromeric ALK7-Fc:ActRIIB-Fc may be guided by approaches similar to those described in Example 1.

In a first approach, the polypeptide sequence of the ActRIIB-Fc fusion protein and a nucleic acid sequence encoding it are provided above in Example 1 as SEQ ID NOs: 100-102.

The complementary ALK7-Fc fusion protein employs the TPA leader and is as follows (SEQ ID NO: 112):

```
                                                    (SEQ ID NO: 112)
  1 MDAMKRGLCC VLLLCGAVFV SPGAGLKCVC LLCDSSNFTC QTEGACWASV

51 MLTNGKEQVI KSCVSLPELN AQVFCHSSNN VTKTECCFTD FCNNITLHLP

101 TASPNAPKLG PMETGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVYTLPPSR

251 EEMTKNQVSL TCLVKGFYPS DIAVEWESNG QPENNYDTTP PVLDSDGSFF

301 LYSDLTVDKS RWQQGNVFSC SVMHEALHNH YTQKSLSLSP G
```

The signal sequence and linker sequence are underlined. To promote formation of the ActRIIB-Fc:ALK7-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 112 may optionally be provided with a lysine added at the C-terminus.

This ALK7-Fc fusion protein is encoded by the following nucleic acid (SEQ ID NO: 113):

```
                                                    (SEQ ID NO: 113)
   1 ATGGATGCAA TGAAGAGAGG GCTCTGCTGT GTGCTGCTGC TGTGTGGAGC

51 AGTCTTCGTT TCGCCCGGCG CCGGACTGAA GTGTGTATGT CTTTTGTGTG

101 ATTCTTCAAA CTTTACCTGC CAAACAGAAG GAGCATGTTG GGCATCAGTC

151 ATGCTAACCA ATGGAAAAGA GCAGGTGATC AAATCCTGTG TCTCCCTTCC

201 AGAACTGAAT GCTCAAGTCT TCTGTCATAG TTCCAACAAT GTTACCAAAA

251 CCGAATGCTG CTTCACAGAT TTTTGCAACA ACATAACACT GCACCTTCCA

301 ACAGCATCAC CAAATGCCCC AAAACTTGGA CCCATGGAGA CCGGTGGTGG

351 AACTCACACA TGCCCACCGT GCCCAGCACC TGAACTCCTG GGGGGACCGT

401 CAGTCTTCCT CTTCCCCCCA AAACCCAAGG ACACCCTCAT GATCTCCCGG

451 ACCCCTGAGG TCACATGCGT GGTGGTGGAC GTGAGCCACG AAGACCCTGA

501 GGTCAAGTTC AACTGGTACG TGGACGGCGT GGAGGTGCAT AATGCCAAGA

551 CAAAGCCGCG GGAGGAGCAG TACAACAGCA CGTACCGTGT GGTCAGCGTC

601 CTCACCGTCC TGCACCAGGA CTGGCTGAAT GGCAAGGAGT ACAAGTGCAA

651 GGTCTCCAAC AAAGCCCTCC CAGCCCCCAT CGAGAAAACC ATCTCCAAAG

701 CCAAAGGGCA GCCCCGAGAA CCACAGGTGT ACACCCTGCC CCCATCCCGG

751 GAGGAGATGA CCAAGAACCA GGTCAGCCTG ACCTGCCTGG TCAAAGGCTT

801 CTATCCCAGC GACATCGCCG TGGAGTGGGA GAGCAATGGG CAGCCGGAGA

851 ACAACTACGA CACCACGCCT CCCGTGCTGG ACTCCGACGG CTCCTTCTTC

901 CTCTATAGCG ACCTCACCGT GGACAAGAGC AGGTGGCAGC AGGGGAACGT

951 CTTCTCATGC TCCGTGATGC ATGAGGCTCT GCACAACCAC TACACGCAGA

1001 AGAGCCTCTC CCTGTCTCCG GGT
```

The mature ALK7-Fc fusion protein sequence (SEQ ID NO: 114) is expected to be as follows and may optionally be provided with a lysine added at the C-terminus.

```
                                                         (SEQ ID NO: 114)
  1 GLKCVCLLCD SSNFTCQTEG ACWASVMLTN GKEQVIKSCV SLPELNAQVF

51 CHSSNNVTKT ECCFTDFCNN ITLHLPTASP NAPKLGPMET GGGTHTCPPC

101 PAPELLGGPS VFLFPPKPKD TLMISRTPEV TCVVVDVSHE DPEVKFNWYV

151 DGVEVHNAKT KPREEQYNST YRVVSVLTVL HQDWLNGKEY KCKVSNKALP

201 APIEKTISKA KGQPREPQVY TLPPSREEMT KNQVSLTCLV KGFYPSDIAV

251 EWESNGQPEN NYDTTPPVLD SDGSFFLYSD LTVDKSRWQQ GNVFSCSVMH

301 EALHNHYTQK SLSLSPG
```

The ActRIIB-Fc and ALK7-Fc fusion proteins of SEQ ID NO: 102 and SEQ ID NO: 114, respectively, may be co-expressed and purified from a CHO cell line to give rise to a heteromeric complex comprising ActRIIB-Fc:ALK7-Fc.

In another approach to promoting the formation of heteromultimer complexes using asymmetric Fc fusion proteins, illustrated in the ActRIIB-Fc and ALK7-Fc polypeptide sequences of SEQ ID NOs: 401-402 and 405-406, respectively, the Fc domains are altered to introduce complementary hydrophobic interactions and an additional intermolecular disulfide bond. The ActRIIB-Fc fusion polypeptide sequences are discussed in Example 1.

The complementary form of ALK7-Fc fusion polypeptide (SEQ ID NO: 405) is as follows:

```
                                                         (SEQ ID NO: 405)
  1 MDAMKRGLCC VLLLCGAVFV SPGAGLKCVC LLCDSSNFTC QTEGACWASV

51 MLTNGKEQVI KSCVSLPELN AQVFCHSSNN VTKTECCFTD FCNNITLHLP

101 TASPNAPKLG PMETGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVCTLPPSR

251 EEMTKNQVSL SCAVKGFYPS DIAVEWESNG QPENNYKTTP PVLDSDGSFF

301 LVSKLTVDKS RWQQGNVFSC SVMHEALHNH YTQKSLSLSP GK
```

The leader sequence and linker sequence are underlined. To guide heterodimer formation with the ActRIIB-Fc fusion polypeptide of SEQ ID NOs 401 and 402 above, four amino acid substitutions can be introduced into the Fc domain of the ALK7 fusion polypeptide as indicated by double underline above. Furthermore, the C-terminal lysine residue of the Fc domain can be deleted. The amino acid sequence of SEQ ID NO: 405 may optionally be provided with the lysine removed from the C-terminus.

The mature ALK7-Fc fusion protein sequence (SEQ ID NO: 406) is expected to be as follows and may optionally be provided with the lysine removed from the C-terminus.

```
                                                         (SEQ ID NO: 406)
  1 GLKCVCLLCD SSNFTCQTEG ACWASVMLTN GKEQVIKSCV SLPELNAQVF

51 CHSSNNVTKT ECCFTDFCNN ITLHLPTASP NAPKLGPMET GGGTHTCPPC

101 PAPELLGGPS VFLFPPKPKD TLMISRTPEV TCVVVDVSHE DPEVKFNWYV

151 DGVEVHNAKT KPREEQYNST YRVVSVLTVL HQDWLNGKEY KCKVSNKALP

201 APIEKTISKA KGQPREPQVC TLPPSREEMT KNQVSLSCAV KGFYPSDIAV

251 EWESNGQPEN NYKTTPPVLD SDGSFFLVSK LTVDKSRWQQ GNVFSCSVMH

301 EALHNHYTQK SLSLSPGK
```

The ActRIIB-Fc and ALK7-Fc proteins of SEQ ID NO: 402 and SEQ ID NO: 406, respectively, may be co-expressed and purified from a CHO cell line, to give rise to a heteromeric complex comprising ActRIIB-Fc:ALK7-Fc.

Purification of various ActRIIB-Fc:ALK7-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 8. Ligand Binding Profile of ActRIIB-Fc:ALK7-Fc Heterodimer Compared to ActRIIB-Fc Homodimer and ALK7-Fc Homodimer A Biacore™-based binding assay was used to compare ligand binding selectivity of the ActRIIB-Fc:ALK7-Fc heterodimeric complex described above with that of ActRIIB-Fc and ALK7-Fc homodimeric complexes. The ActRIIB-Fc:ALK7-Fc heterodimer, ActRIIB-Fc homodimer, and ALK7-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Figure 8:
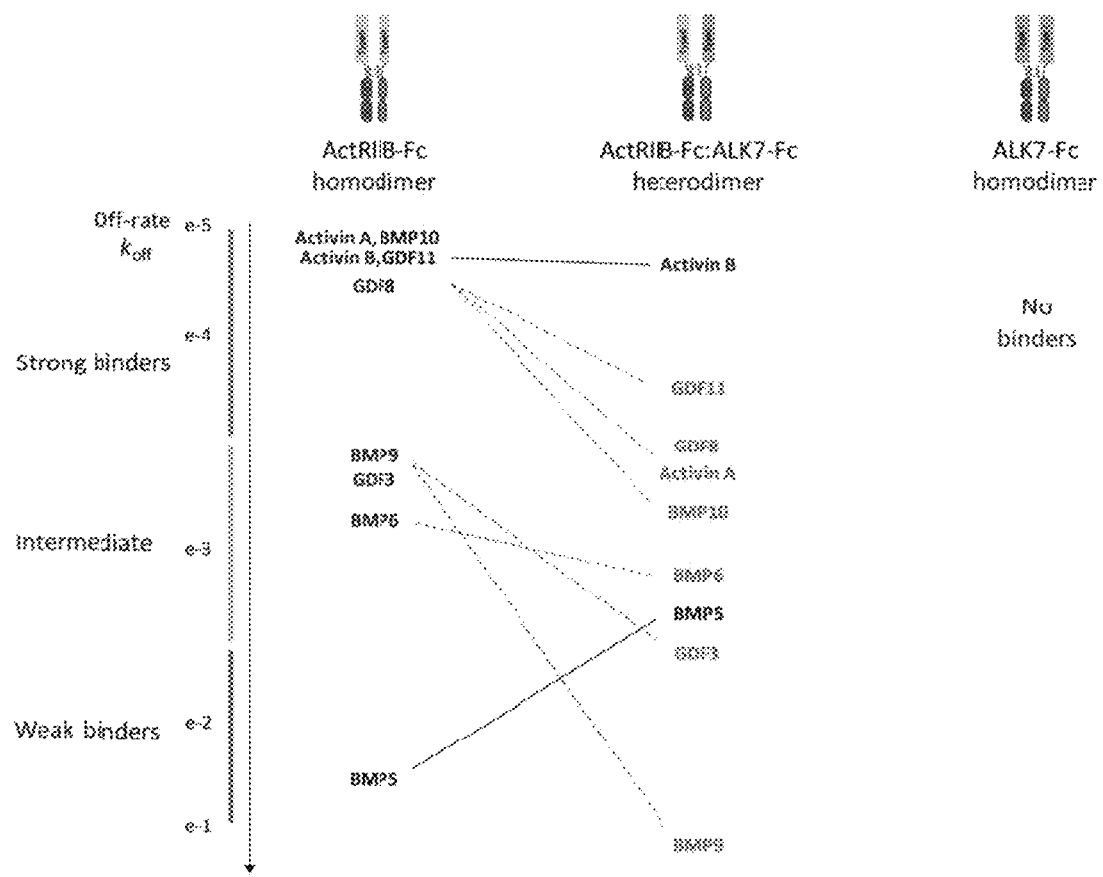
FIG. 8 shows ligand binding data for an ActRIIB-Fc: ALK7-Fc heterodimeric protein complex as compared to ActRIIB-Fc homodimer and ALK7-Fc homodimer. Format is the same as in FIG. 6. As shown, four of the five ligands with strong binding to ActRIIB-Fc homodimer (activin A, BMP10, GDF8, and GDF11) exhibit reduced binding to the ActRIIB-Fc:ALK7-Fc heterodimer, the exception being activin B which retains tight binding to the heterodimer. In addition, three ligands with intermediate binding to ActRIIB-Fc homodimer (GDF3, BMP6, and particularly BMP9) exhibit reduced binding to the ActRIIB-Fc:ALK7-Fc heterodimer. In contrast, BMP5 binds the ActRIIB-Fc:ALK7 heterodimer with intermediate strength despite only weak binding to ActRIIB-Fc homodimer. No ligands tested bind to ALK7-Fc homodimer.

ActRIIB-Fc homodimer (GDF3, BMP6, and particularly BMP9) exhibit reduced binding to the ActRIIB-Fc:ALK7-Fc heterodimer. In contrast, BMP5 binds the ActRIIB-Fc:ALK7 heterodimer with intermediate strength despite only weak binding to ActRIIB-Fc homodimer. No ligands tested bind to ALK7-Fc homodimer. See FIG. 8.

These results therefore demonstrate that the ActRIIB-Fc:ALK7-Fc heterodimer is a more selective antagonist of activin B in comparison to a ActRIIB-Fc homodimer. Accordingly, an ActRIIB-Fc:ALK7-Fc heterodimer will be more useful than an ActRIIB-Fc homodimer in certain applications where such selective antagonism is advantageous. Examples include therapeutic applications where it is desirable to retain antagonism of activin B but minimize antagonism of one or more of activin A, GDF3, GDF8, GDF11, BMP9, or BMP10.

Example 9. Generation of an ActRIIB-Fc:ALK2-Fc Heterodimer

Applicants constructed a soluble ActRIIB-Fc:ALK2-Fc heteromeric complex comprising the extracellular domains of human ActRIIB and human ALK2, which are each fused to an Fc domain with a linker positioned between the extracellular domain and the Fc domain. The individual constructs are referred to as ActRIIB-Fc and ALK2-Fc, respectively.

Ligand binding profile of ActRIIB-Fc:ALK7-Fc heterodimer compared to ActRIIB-Fc homodimer and ALK7-Fc homodimer

| Ligand | ActRIIB-Fc homodimer | | | ALK7-FC homodimer | | | ActRIIB-Fc:ALK7-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.3 \times 10^7$ | $\mathbf{1.4 \times 10^{-4}}$ | 11 | No binding | | | $4.4 \times 10^7$ | $1.9 \times 10^{-3}$ | 43 |
| Activin B | $1.5 \times 10^7$ | $\mathbf{1.6 \times 10^{-4}}$ | 8 | No binding | | | $1.2 \times 10^7$ | $\mathbf{2.0 \times 10^{-4}}$ | 17 |
| BMP5 | $2.6 \times 10^7$ | $7.5 \times 10^{-2}$ | 2900 | No binding | | | $1.5 \times 10^5$ | $8.5 \times 10^{-3}$ | 57000 |
| BMP6 | $2.4 \times 10^7$ | $3.9 \times 10^{-3}$ | 160 | No binding | | | $1.2 \times 10^6$ | $6.3 \times 10^{-3}$ | 5300 |
| BMP9 | $1.2 \times 10^8$ | $1.2 \times 10^{-3}$ | 10 | No binding | | | Transient* | | >1400 |
| BMP10 | $5.9 \times 10^6$ | $\mathbf{1.5 \times 10^{-4}}$ | 25 | No binding | | | $1.5 \times 10^7$ | $2.8 \times 10^{-3}$ | 190 |
| GDF3 | $1.4 \times 10^6$ | $2.2 \times 10^{-3}$ | 1500 | No binding | | | $2.3 \times 10^6$ | $1.0 \times 10^{-2}$ | 4500 |
| GDF8 | $3.5 \times 10^6$ | $\mathbf{2.4 \times 10^{-4}}$ | 69 | No binding | | | $3.7 \times 10^6$ | $1.0 \times 10^{-3}$ | 270 |
| GDF11 | $9.6 \times 10^7$ | $\mathbf{1.5 \times 10^{-4}}$ | 2 | No binding | | | $9.5 \times 10^7$ | $\mathbf{7.5 \times 10^{-4}}$ | 8 |

*Indeterminate due to transient nature of interaction

These comparative binding data demonstrate that the ActRIIB-Fc:ALK7-Fc heterodimer has a different binding profile compared to either the ActRIIB-Fc homodimer or ALK7-Fc homodimer. Interestingly, four of the five ligands with strong binding to ActRIIB-Fc homodimer (activin A, BMP10, GDF8, and GDF11) exhibit reduced binding to the ActRIIB-Fc:ALK7-Fc heterodimer, the exception being activin B which retains tight binding to the heterodimer. In addition, three ligands with intermediate binding to Formation of heteromeric ActRIIB-Fc:ALK2-Fc may be guided by approaches similar to those described in Example 1.

In a first approach, the polypeptide sequence of the ActRIIB-Fc fusion protein and a nucleic acid sequence encoding it are provided in Example 1 as SEQ ID NOs: 100-102.

The complementary ALK2-Fc fusion protein employs the TPA leader and is as follows (SEQ ID NO: 136):

```
                                                    (SEQ ID NO: 136)
  1 MDAMKRGLCC VLLLCGAVFV SPGAMEDEKP KVNPKLYMCV CEGLSCGNED

51 HCEGQQCFSS LSINDGFHVY QKGCFQVYEQ GKMTCKTPPS PGQAVECCQG

101 DWCNRNITAQ LPTKGKSFPG TQNFHLETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSREEMTKN QVSLTCLVKG FYPSDIAVEW ESNGQPENNY

301 DTTPPVLDSD GSFFLYSDLT VDKSRWQQGN VFSCSVMHEA LHNHYTQKSL

351 SLSPG
```

The signal sequence and linker sequence are underlined. To promote formation of the ActRIIB-Fc:ALK2-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 136 may optionally be provided with a lysine added at the C-terminus.

This ALK2-Fc fusion protein is encoded by the following nucleic acid (SEQ ID NO: 137):

```
                                                    (SEQ ID NO: 137)
   1 ATGGATGCAA TGAAGAGAGG GCTCTGCTGT GTGCTGCTGC TGTGTGGAGC

51 AGTCTTCGTT TCGCCCGGCG CCATGGAAGA TGAGAAGCCC AAGGTCAACC

101 CCAAACTCTA CATGTGTGTG TGTGAAGGTC TCTCCTGCGG TAATGAGGAC

151 CACTGTGAAG GCCAGCAGTG CTTTTCCTCA CTGAGCATCA ACGATGGCTT

201 CCACGTCTAC CAGAAAGGCT GCTTCCAGGT TTATGAGCAG GGAAAGATGA

251 CCTGTAAGAC CCCGCCGTCC CCTGGCCAAG CTGTGGAGTG CTGCCAAGGG

301 GACTGGTGTA ACAGGAACAT CACGGCCCAG CTGCCCACTA AGGAAAATC

351 CTTCCCTGGA ACACAGAATT TCCACTTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG

751 CAGCCCCGAG AACCACAGGT GTACACCCTG CCCCCATCCC GGGAGGAGAT

801 GACCAAGAAC CAGGTCAGCC TGACCTGCCT GGTCAAAGGC TTCTATCCCA

851 GCGACATCGC CGTGGAGTGG GAGAGCAATG GGCAGCCGGA GAACAACTAC

901 GACACCACGC CTCCCGTGCT GGACTCCGAC GGCTCCTTCT TCCTCTATAG

951 CGACCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGT
```

The mature ALK2-Fc fusion protein sequence (SEQ ID NO: 138) is as follows and may optionally be provided with a lysine added at the C-terminus.

```
                                                          (SEQ ID NO: 138)
  1 MEDEKPKVNP KLYMCVCEGL SCGNEDHCEG QQCFSSLSIN DGFHVYQKGC

51 FQVYEQGKMT CKTPPSPGQA VECCQGDWCN RNITAQLPTK GKSFPGTQNF

101 HLETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPSR EEMTKNQVSL

251 TCLVKGFYPS DIAVEWESNG QPENNYDTTP PVLDSDGSFF LYSDLTVDKS

301 RWQQGNVFSC SVMHEALHNH YTQKSLSLSP G
```

The ActRIIB-Fc and ALK2-Fc fusion proteins of SEQ ID NO: 102 and SEQ ID NO: 138, respectively, may be co-expressed and purified from a CHO cell line to give rise to a heteromeric complex comprising ActRIIB-Fc:ALK2-Fc.

In another approach to promoting the formation of heteromultimer complexes using asymmetric Fc fusion proteins, illustrated in the ActRIIB-Fc and ALK2-Fc polypeptide sequences of SEQ ID NOs: 401-402 and 421-422, respectively, the Fc domains are altered to introduce complementary hydrophobic interactions and an additional intermolecular disulfide bond. The ActRIIB-Fc fusion polypeptide sequences are discussed in Example 1.

The complementary form of ALK2-Fc fusion polypeptide (SEQ ID NO: 421) is as follows:

```
                                                          (SEQ ID NO: 421)
  1 MDAMKRGLCC VLLLCGAVFV SPGAMEDEKP KVNPKLYMCV CEGLSCGNED

51 HCEGQQCFSS LSINDGFHVY QKGCFQVYEQ GKMTCKTPPS PGQAVECCQG

101 DWCNRNITAQ LPTKGKSFPG TQNFHLETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVCTL PPSREEMTKN QVSLSCAVKG FYPSDIAVEW ESNGQPENNY

301 KTTPPVLDSD GSFFLVSKLT VDKSRWQQGN VFSCSVMHEA LHNHYTQKSL

351 SLSPGK
```

The leader sequence and linker sequence are underlined. To guide heterodimer formation with the ActRIIB-Fc fusion polypeptide of SEQ ID NOs 401 and 402 above, four amino acid substitutions can be introduced into the Fc domain of the ALK2 fusion polypeptide as indicated by double underline above. Furthermore, the C-terminal lysine residue of the Fc domain can be deleted. The amino acid sequence of SEQ ID NO: 421 may optionally be provided with the lysine removed from the C-terminus.

The mature ALK2-Fc fusion protein sequence (SEQ ID NO: 422) is as follows and may optionally be provided with the lysine removed from the C-terminus.

```
                                                          (SEQ ID NO: 422)
  1 MEDEKPKVNP KLYMCVCEGL SCGNEDHCEG QQCFSSLSIN DGFHVYQKGC

51 FQVYEQGKMT CKTPPSPGQA VECCQGDWCN RNITAQLPTK GKSFPGTQNF

101 HLETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVCTLPPSR EEMTKNQVSL
```

```
251 SCAVKGFYPS DIAVEWESNG QPENNYKTTP PVLDSDGSFF LVSKLTVDKS

301 RWQQGNVFSC SVMHEALHNH YTQKSLSLSP GK
```

The ActRIIB-Fc and ALK2-Fc proteins of SEQ ID NO: 402 and SEQ ID NO: 422, respectively, may be co-expressed and purified from a CHO cell line, to give rise to a heteromeric complex comprising ActRIIB-Fc:ALK2-Fc.

Purification of various ActRIIB-Fc:ALK2-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Figure 9:
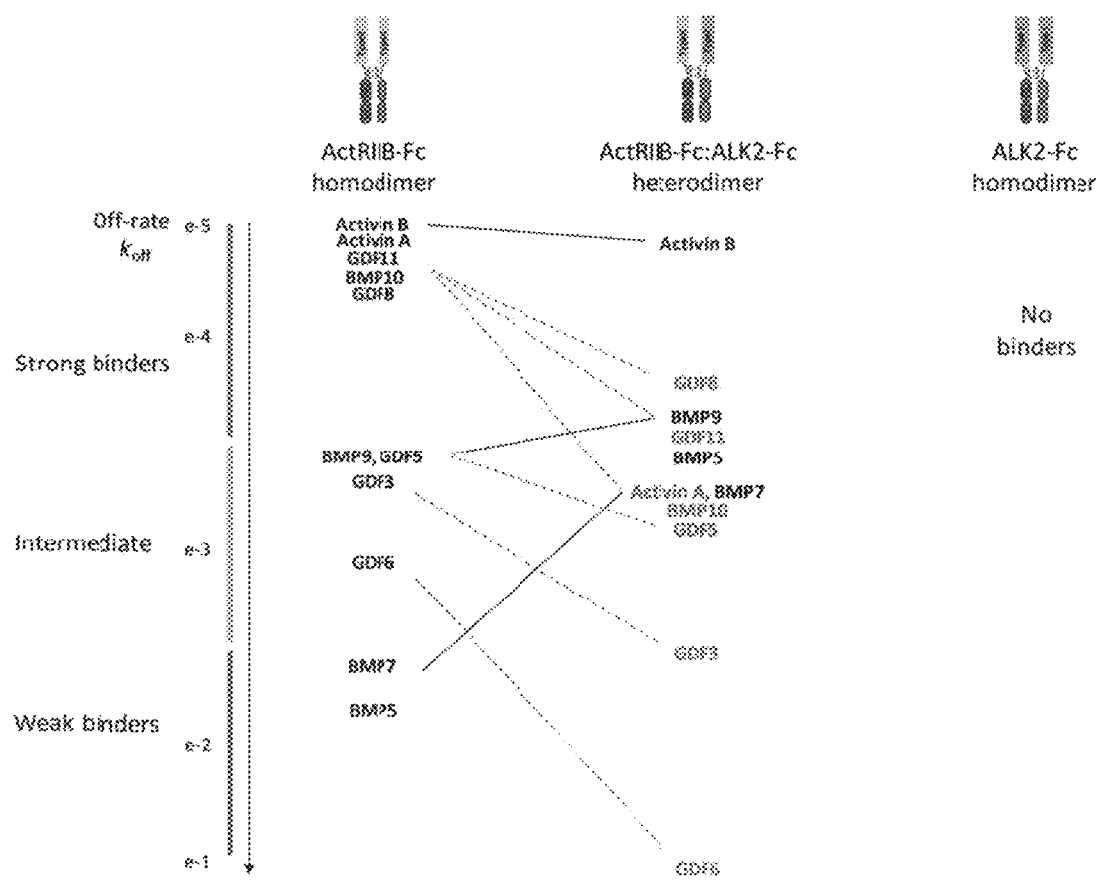
FIG. 9 shows ligand binding data for an ActRIIB-Fc:ALK2-Fc heterodimeric protein complex as compared to ActRIIB-Fc homodimer and ALK2-Fc homodimer. Format is the same as in FIG. 6. As shown, the ActRIIB-Fc:ALK2-Fc heterodimer exhibits preferential and strong binding to activin B, thus resembling ActRIIB-Fc:ALK7-Fc heterodimer (FIG. 8). However, ActRIIB-Fc:ALK2-Fc heterodimer differs from ActRIIB-Fc:ALK7-Fc in part by retaining the tight binding to BMP9 characteristic of ActRIIB-Fc homodimer. No ligands tested bind to ALK2-Fc homodimer.

Example 10. Ligand Binding Profile of ActRIIB-Fc:ALK2-Fc Heterodimer Compared to ActRIIB-Fc Homodimer and ALK2-Fc Homodimer A Biacore™-based binding assay was used to compare ligand binding selectivity of the ActRIIB-Fc:ALK2-Fc heterodimeric complex described above with that of ActRIIB-Fc and ALK2-Fc homodimeric complexes. The ActRIIB-Fc:ALK2-Fc heterodimer, ActRIIB-Fc homodimer, and ALK2-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

differs from ActRIIB-Fc:ALK7-Fc in part by retaining the tight binding to BMP9 characteristic of ActRIIB-Fc homodimer, whereas ActRIIB-Fc:ALK7-Fc binds BMP9 very weakly, if at all. No ligands tested bind to ALK2-Fc homodimer. See FIG. 9.

These results demonstrate that the ActRIIB-Fc:ALK2-Fc heterodimer is a more selective antagonist of activin B compared to ActRIIB-Fc homodimer. Accordingly, an ActRIIB-Fc:ALK2-Fc heterodimer will be useful in certain applications where such selective antagonism is advantageous. Examples include therapeutic applications where it is desirable to retain antagonism primarily of activin B and to supplement that with antagonism secondarily of BMP9, GDF8, and GDF11.

Example 11. Generation of an ActRIIB-Fc:ALK5-Fc Heterodimer

Applicants constructed a soluble ActRIIB-Fc:ALK5-Fc heteromeric complex comprising the extracellular domains of human ActRIIB and human ALK5, which are each fused to an Fc domain with a linker positioned between the extracellular domain and the Fc domain. The individual constructs are referred to as ActRIIB-Fc and ALK5-Fc, respectively.

Ligand binding profile of ActRIIB-Fc:ALK2-Fc heterodimer compared to ActRIIB-Fc homodimer and ALK2-Fc homodimer

| Ligand | ActRIIB-Fc Homodimer | | | ALK2-Fc Homodimer | | | ActRIIB-Fc:ALK2-Fc Heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.2 \times 10^7$ | $1.7 \times 10^{-4}$ | 15 | No binding | | | $3.4 \times 10^7$ | $2.6 \times 10^{-3}$ | 76 |
| Activin B | $3.8 \times 10^6$ | $1.1 \times 10^{-4}$ | 28 | No binding | | | $3.2 \times 10^6$ | $1.5 \times 10^{-4}$ | 47 |
| BMP5 | $3.8 \times 10^6$ | $3.7 \times 10^{-2}$ | 9700 | No binding | | | $1.2 \times 10^6$ | $1.4 \times 10^{-3}$ | 1200 |
| BMP7 | $8.8 \times 10^6$ | $1.4 \times 10^{-2}$ | 1600 | No binding | | | $1.5 \times 10^7$ | $2.6 \times 10^{-3}$ | 170 |
| BMP9 | $3.9 \times 10^7$ | $1.3 \times 10^{-3}$ | 34 | No binding | | | $3.2 \times 10^6$ | $8.9 \times 10^{-4}$ | 280 |
| BMP10 | $5.4 \times 10^7$ | $2.8 \times 10^{-4}$ | 5 | No binding | | | $5.5 \times 10^7$ | $2.9 \times 10^{-3}$ | 53 |
| GDF3 | $1.2 \times 10^6$ | $2.0 \times 10^{-3}$ | 1700 | No binding | | | $1.8 \times 10^6$ | $1.2 \times 10^{-2}$ | 6500 |
| GDF5 | $1.2 \times 10^6$ | $1.4 \times 10^{-3}$ | 1100 | No binding | | | $8.8 \times 10^5$ | $4.4 \times 10^{-3}$ | 5000 |
| GDF6 | $1.5 \times 10^5$ | $5.7 \times 10^{-3}$ | 39000 | No binding | | | Transient* | | >240000 |
| GDF8 | $2.5 \times 10^6$ | $3.2 \times 10^{-4}$ | 130 | No binding | | | $2.1 \times 10^6$ | $7.3 \times 10^{-4}$ | 360 |
| GDF11 | $2.0 \times 10^6$ | $2.2 \times 10^{-4}$ | 110 | No binding | | | $1.6 \times 10^6$ | $9.3 \times 10^{-4}$ | 600 |

*Indeterminate due to transient nature of interaction

These comparative binding data demonstrate that the ActRIIB-Fc:ALK2-Fc heterodimer exhibits a ligand binding profile different from either the ActRIIB-Fc homodimer or the ALK2-Fc homodimer. ActRIIB-Fc:ALK2-Fc heterodimer exhibits preferential and strong binding to activin B, thus resembling ActRIIB-Fc:ALK7-Fc heterodimer (see Example 8). However, ActRIIB-Fc:ALK2-Fc heterodimer Formation of heteromeric ActRIIB-Fc: ALK5-Fc may be guided by approaches similar to those described in Example 1.

In a first approach, the polypeptide sequence of the ActRIIB-Fc fusion protein and a nucleic acid sequence encoding it are provided in Example 1 as SEQ ID NOs: 100-102.

The complementary ALK5-Fc fusion protein employs the TPA leader and is as follows (SEQ ID NO: 139):

(SEQ ID NO: 139)

```
  1 MDAMKRGLCC VLLLCGAVFV SPGAALLPGA TALQCFCHLC TKDNFTCVTD

51 GLCFVSVTET TDKVIHNSMC IAEIDLIPRD RPFVCAPSSK TGSVTTTYCC

101 NQDHCNKIEL PTTVKSSPGL GPVETGGGTH TCPPCPAPEL LGGPSVFLFP

151 PKPKDTLMIS RTPEVTCVVV DVSHEDPEVK FNWYVDGVEV HNAKTKPREE

201 QYNSTYRVVS VLTVLHQDWL NGKEYKCKVS NKALPAPIEK TISKAKGQPR

251 EPQVYTLPPS REEMTKNQVS LTCLVKGFYP SDIAVEWESN GQPENNYDTT

301 PPVLDSDGSF FLYSDLTVDK SRWQQGNVFS CSVMHEALHN HYTQKSLSLS

351 PG
```

The signal sequence and linker sequence are underlined. To promote formation of the ActRIIB-Fc:ALK5-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 139 may optionally be provided with a lysine added at the C-terminus.

This ALK5-Fc fusion protein is encoded by the following nucleic acid (SEQ ID NO: 140):

(SEQ ID NO: 140)

```
   1 ATGGATGCAA TGAAGAGAGG GCTCTGCTGT GTGCTGCTGC TGTGTGGAGC

51 AGTCTTCGTT TCGCCCGGCG CCGCGCTGCT CCCGGGGGCG ACGGCGTTAC

101 AGTGTTTCTG CCACCTCTGT ACAAAAGACA ATTTTACTTG TGTGACAGAT

151 GGGCTCTGCT TTGTCTCTGT CACAGAGACC ACAGACAAAG TTATACACAA

201 CAGCATGTGT ATAGCTGAAA TTGACTTAAT TCCTCGAGAT AGGCCGTTTG

251 TATGTGCACC CTCTTCAAAA ACTGGGTCTG TGACTACAAC ATATTGCTGC

301 AATCAGGACC ATTGCAATAA AATAGAACTT CCAACTACTG TAAAGTCATC

351 ACCTGGCCTT GGTCCTGTGG AAACCGGTGG TGGAACTCAC ACATGCCCAC

401 CGTGCCCAGC ACCTGAACTC CTGGGGGGAC CGTCAGTCTT CCTCTTCCCC

451 CCAAAACCCA AGGACACCCT CATGATCTCC CGGACCCCTG AGGTCACATG

501 CGTGGTGGTG GACGTGAGCC ACGAAGACCC TGAGGTCAAG TTCAACTGGT

551 ACGTGGACGG CGTGGAGGTG CATAATGCCA AGACAAAGCC GCGGGAGGAG

601 CAGTACAACA GCACGTACCG TGTGGTCAGC GTCCTCACCG TCCTGCACCA

651 GGACTGGCTG AATGGCAAGG AGTACAAGTG CAAGGTCTCC AACAAAGCCC

701 TCCCAGCCCC CATCGAGAAA ACCATCTCCA AAGCCAAAGG GCAGCCCCGA

751 GAACCACAGG TGTACACCCT GCCCCCATCC CGGGAGGAGA TGACCAAGAA

801 CCAGGTCAGC CTGACCTGCC TGGTCAAAGG CTTCTATCCC AGCGACATCG

851 CCGTGGAGTG GGAGAGCAAT GGGCAGCCGG AGAACAACTA CGACACCACG

901 CCTCCCGTGC TGGACTCCGA CGGCTCCTTC TTCCTCTATA GCGACCTCAC

951 CGTGGACAAG AGCAGGTGGC AGCAGGGGAA CGTCTTCTCA TGCTCCGTGA

1001 TGCATGAGGC TCTGCACAAC CACTACACGC AGAAGAGCCT CTCCCTGTCT

1051 CCGGGT
```

The mature ALK5-Fc fusion protein sequence (SEQ ID NO: 141) is as follows and may optionally be provided with a lysine added at the C-terminus.

```
                                                              (SEQ ID NO: 141)
  1 ALLPGATALQ CFCHLCTKDN FTCVTDGLCF VSVTETTDKV IHNSMCIAEI

51 DLIPRDRPPV CAPSSKTGSV TTTYCCNQDH CNKIELPTTV KSSPGLGPVE

101 TGGGTHTCPP CPAPELLGGP SVFLFPPKPK DTLMISRTPE VTCVVVDVSH

151 EDPEVKFNWY VDGVEVHNAK TKPREEQYNS TYRVVSVLTV LHQDWLNGKE

201 YKCKVSNKAL PAPIEKTISK AKGQPREPQV YTLPPSREEM TKNQVSLTCL

251 VKGFYPSDIA VEWESNGQPE NNYDTTPPVL DSDGSFFLYS DLTVDKSRWQ

301 QGNVFSCSVM HEALHNHYTQ KSLSLSPG
```

The ActRIIB-Fc and ALK5-Fc fusion proteins of SEQ ID NO: 102 and SEQ ID NO: 141, respectively, may be co-expressed and purified from a CHO cell line to give rise to a heteromeric complex comprising ActRIIB-Fc:ALK5-Fc.

In another approach to promoting the formation of heteromultimer complexes using asymmetric Fc fusion proteins, illustrated in the ActRIIB-Fc and ALK5-Fc polypeptide sequences of SEQ ID NOs: 401-402 and 423-424, respectively, the Fc domains are altered to introduce complementary hydrophobic interactions and an additional intermolecular disulfide bond. The ActRIIB-Fc fusion polypeptide sequences are discussed in Example 1.

The complementary form of ALK5-Fc fusion polypeptide (SEQ ID NO: 423) is as follows:

```
                                                              (SEQ ID NO: 423)
  1 MDAMKRGLCC VLLLCGAVFV SPGAALLPGA TALQCFCHLC TKDNFTCVTD

51 GLCFVSVTET TDKVIHNSMC IAEIDLIPRD RPFVCAPSSK TGSVTTTYCC

101 NQDHCNKIEL PTTVKSSPGL GPVETGGGTH TCPPCPAPEL LGGPSVFLFP

151 PKPKDTLMIS RTPEVTCVVV DVSHEDPEVK FNWYVDGVEV HNAKTKPREE

201 QYNSTYRVVS VLTVLHQDWL NGKEYKCKVS NKALPAPIEK TISKAKGQPR

251 EPQVCTLPPS REEMTKNQVS LSCAVKGFYP SDIAVEWESN GQPENNYKTT

301 PPVLDSDGSF FLVSKLTVDK SRWQQGNVFS CSVMHEALHN HYTQKSLSLS

351 PGK
```

The leader sequence and linker sequence are underlined. To guide heterodimer formation with the ActRIIB-Fc fusion polypeptide of SEQ ID NOs 401 and 402 above, four amino acid substitutions can be introduced into the Fc domain of the ALK5 fusion polypeptide as indicated by double underline above. Furthermore, the C-terminal lysine residue of the Fc domain can be deleted. The amino acid sequence of SEQ ID NO: 423 may optionally be provided with the lysine removed from the C-terminus.

The mature ALK5-Fc fusion protein sequence (SEQ ID NO: 424) is as follows and may optionally be provided with the lysine removed from the C-terminus.

```
                                                              (SEQ ID NO: 424)
  1 ALLPGATALQ CFCHLCTKDN FTCVTDGLCF VSVTETTDKV IHNSMCIAEI

51 DLIPRDRPPV CAPSSKTGSV TTTYCCNQDH CNKIELPTTV KSSPGLGPVE

101 TGGGTHTCPP CPAPELLGGP SVFLFPPKPK DTLMISRTPE VTCVVVDVSH

151 EDPEVKFNWY VDGVEVHNAK TKPREEQYNS TYRVVSVLTV LHQDWLNGKE

201 YKCKVSNKAL PAPIEKTISK AKGQPREPQV CTLPPSREEM TKNQVSLSCA
```

```
251 VKGFYPSDIA VEWESNGQPE NNYKTTPPVL DSDGSFFLVS KLTVDKSRWQ

301 QGNVFSCSVM HEALHNHYTQ KSLSLSPGK
```

The ActRIIB-Fc and ALK5-Fc proteins of SEQ ID NO: 402 and SEQ ID NO: 424, respectively, may be co-expressed and purified from a CHO cell line, to give rise to a heteromeric complex comprising ActRIIB-Fc:ALK5-Fc.

Purification of various ActRIIB-Fc:ALK5-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 12. Ligand Binding Profile of ActRIIB-Fc:ALK5-Fc Heterodimer Compared to ActRIIB-Fc Homodimer and ALK5-Fc Homodimer A Biacore™-based binding assay was used to compare ligand binding selectivity of the ActRIIB-Fc:ALK5-Fc heterodimeric complex described above with that of ActRIIB-Fc and ALK5-Fc homodimeric complexes. The ActRIIB-Fc:ALK5-Fc heterodimer, ActRIIB-Fc homodimer, and ALK5-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profile of ActRIIB-Fc:ALK5-Fc heterodimer compared to ActRIIB-Fc homodimer and ALK5-Fc homodimer

| Ligand | ActRIIB-Fc Homodimer | | | ALK5-Fc Homodimer | | | ActRIIB-Fc:ALK5-Fc Heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.2 \times 10^7$ | $\mathbf{2.3 \times 10^{-4}}$ | 19 | No binding | | | $3.6 \times 10^7$ | $1.6 \times 10^{-3}$ | 46 |
| Activin B | $5.1 \times 10^6$ | $\mathbf{1.0 \times 10^{-4}}$ | 20 | No binding | | | $3.9 \times 10^6$ | $\mathbf{3.1 \times 10^{-4}}$ | 79 |
| BMP6 | $6.4 \times 10^6$ | $7.0 \times 10^{-3}$ | 1100 | No binding | | | $9.3 \times 10^6$ | $1.5 \times 10^{-2}$ | 1700 |
| BMP9 | $3.9 \times 10^7$ | $1.3 \times 10^{-3}$ | 34 | No binding | | | Transient* | | >6600 |
| BMP10 | $2.1 \times 10^7$ | $\mathbf{3.8 \times 10^{-4}}$ | 18 | No binding | | | $2.3 \times 10^7$ | $2.2 \times 10^{-3}$ | 150 |
| GDF3 | $4.7 \times 10^5$ | $1.8 \times 10^{-3}$ | 3900 | No binding | | | $1.1 \times 10^5$ | $9.7 \times 10^{-3}$ | 8500 |
| GDF8 | $1.2 \times 10^6$ | $\mathbf{1.9 \times 10^{-4}}$ | 160 | No binding | | | $1.1 \times 10^6$ | $\mathbf{5.2 \times 10^{-4}}$ | 490 |
| GDF11 | $1.9 \times 10^6$ | $\mathbf{1.4 \times 10^{-4}}$ | 74 | No binding | | | $2.3 \times 10^6$ | $\mathbf{4.6 \times 10^{-4}}$ | 600 |

*Indeterminate due to transient nature of interaction

Example 13. Generation of an ActRIIB-Fc:ALK6-Fc Heterodimer

A soluble ActRIIB-Fc:ALK6-Fc heteromeric complex can be generated comprising the extracellular domains of human ActRIIB and human ALK6, which can each be fused to an Fc domain with a linker positioned between the extracellular domain and the Fc domain. The individual constructs are referred to as ActRIIB-Fc and ALK6-Fc, respectively.

Formation of heteromeric ActRIIB-Fc: ALK6-Fc may be guided by approaches similar to those described in Example 1.

In a first approach, the polypeptide sequence of the ActRIIB-Fc fusion protein and a nucleic acid sequence encoding it are provided above in Example 1 as SEQ ID NOs: 100-102.

The complementary ALK6-Fc fusion protein employs the TPA leader and is as follows (SEQ ID NO: 142):

```
                                              (SEQ ID NO: 142)
  1 MDAMKRGLCC VLLLCGAVFV SPGAKKEDGE STAPTPRPKV LRCKCHHHCP

51 EDSVNNICST DGYCFTMIEE DDSGLPVVTS GCLGLEGSDF QCRDTPIPHQ

101 RRSIECCTER NECNKDLHPT LPPLKNRDFV DGPIHHRTGG GTHTCPPCPA

151 PELLGGPSVF LFPPKPKDTL MISRTPEVTC VVVDVSHEDP EVKFNWYVDG
```

```
-continued
201 VEVHNAKTKP REEQYNSTYR VVSVLTVLHQ DWLNGKEYKC KVSNKALPAP

251 IEKTISKAKG QPREPQVYTL PPSREEMTKN QVSLTCLVKG FYPSDIAVEW

301 ESNGQPENNY DTTPPVLDSD GSFFLYSDLT VDKSRWQQGN VFSCSVMHEA

351 LHNHYTQKSL SLSPG
```

The signal sequence and linker sequence are underlined. To promote formation of the ActRIIB-Fc:ALK6-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 142 may optionally be provided with a lysine added at the C-terminus.

This ALK6-Fc fusion protein is encoded by the following nucleic acid (SEQ ID NO: 143):

```
                                                    (SEQ ID NO: 143)
   1 ATGGATGCAA TGAAGAGAGG GCTCTGCTGT GTGCTGCTGC TGTGTGGAGC

51 AGTCTTCGTT TCGCCCGGCG CCAAGAAAGA GGATGGTGAG AGTACAGCCC

101 CCACCCCCCG TCCAAAGGTC TTGCGTTGTA AATGCCACCA CCATTGTCCA

151 GAAGACTCAG TCAACAATAT TTGCAGCACA GACGGATATT GTTTCACGAT

201 GATAGAAGAG GATGACTCTG GGTTGCCTGT GGTCACTTCT GGTTGCCTAG

251 GACTAGAAGG CTCAGATTTT CAGTGTCGGG ACACTCCCAT TCCTCATCAA

301 AGAAGATCAA TTGAATGCTG CACAGAAAGG AACGAATGTA ATAAAGACCT

351 ACACCCTACA CTGCCTCCAT TGAAAAACAG AGATTTTGTT GATGGACCTA

401 TACACCACAG GACCGGTGGT GGAACTCACA CATGCCCACC GTGCCCAGCA

451 CCTGAACTCC TGGGGGGACC GTCAGTCTTC CTCTTCCCCC CAAAACCCAA

501 GGACACCCTC ATGATCTCCC GGACCCCTGA GGTCACATGC GTGGTGGTGG

551 ACGTGAGCCA CGAAGACCCT GAGGTCAAGT TCAACTGGTA CGTGGACGGC

601 GTGGAGGTGC ATAATGCCAA GACAAAGCCG CGGGAGGAGC AGTACAACAC

651 CACGTACCGT GTGGTCAGCG TCCTCACCGT CCTGCACCAG GACTGGCTGA

701 ATGGCAAGGA GTACAAGTGC AAGGTCTCCA ACAAAGCCCT CCCAGCCCCC

751 ATCGAGAAAA CCATCTCCAA AGCCAAAGGG CAGCCCCGAG AACCACAGGT

801 GTACACCCTG CCCCCATCCC GGGAGGAGAT GACCAAGAAC CAGGTCAGCC

851 TGACCTGCCT GGTCAAAGGC TTCTATCCCA GCGACATCGC CGTGGAGTGG

901 GAGAGCAATG GGCAGCCGGA GAACAACTAC GACACCACGC CTCCCGTGCT

951 GGACTCCGAC GGCTCCTTCT TCCTCTATAG CGACCTCACC GTGGACAAGA

1001 GCAGGTGGCA GCAGGGGAAC GTCTTCTCAT GCTCCGTGAT GCATGAGGCT

1051 CTGCACAACC ACTACACGCA GAAGAGCCTC TCCCTGTCTC CGGGT
```

The mature ALK6-Fc fusion protein sequence (SEQ ID NO: 144) is as follows and may optionally be provided with a lysine added at the C-terminus.

```
                                                    (SEQ ID NO: 144)
   1 KKEDGESTAP TPRPKVLRCK CHHHCPEDSV NNICSTDGYC FTMIEEDDSG

51 LPVVTSGCLG LEGSDFQCRD TPIPHQRRSI ECCTERNECN KDLHPTLPPL

101 KNRDFVDGPI HHRTGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVYTLPPSR
```

-continued

```
251 EEMTKNQVSL TCLVKGFYPS DIAVEWESNG QPENNYDTTP PVLDSDGSFF

301 LYSDLTVDKS RWQQGNVFSC SVMHEALHNH YTQKSLSLSP G
```

The ActRIIB-Fc and ALK6-Fc fusion proteins of SEQ ID NO: 102 and SEQ ID NO: 144, respectively, may be co-expressed and purified from a CHO cell line to give rise to a heteromeric complex comprising ActRIIB-Fc:ALK6-Fc.

In another approach to promoting the formation of heteromultimer complexes using asymmetric Fc fusion proteins, illustrated in the ActRIIB-Fc and ALK6-Fc polypeptide sequences of SEQ ID NOs: 401-402 and 425-426, respectively, the Fc domains can be altered to introduce complementary hydrophobic interactions and an additional intermolecular disulfide bond. The ActRIIB-Fc fusion polypeptide sequences are discussed in Example 1.

The complementary form of ALK6-Fc fusion polypeptide (SEQ ID NO: 425) is as follows:

The ActRIIB-Fc and ALK6-Fc proteins of SEQ ID NO: 402 and SEQ ID NO: 426, respectively, may be co-expressed and purified from a CHO cell line, to give rise to a heteromeric complex comprising ActRIIB-Fc:ALK6-Fc.

Purification of various ActRIIB-Fc:ALK6-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

```
                                                   (SEQ ID NO: 425)
  1 MDAMKRGLCC VLLLCGAVFV SPGAKKEDGE STAPTPRPKV LRCKCHHHCP

51 EDSVNNICST DGYCFTMIEE DDSGLPVVTS GCLGLEGSDF QCRDTPIPHQ

101 RRSIECCTER NECNKDLHPT LPPLKNRDFV DGPIHHRTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVCTL PPSREEMTKN QVSLSCAVKG FYPSDIAVEW

301 ESNGQPENNY KTTPPVLDSD GSFFLVSKLT VDKSRWQQGN VFSCSVMHEA

351 LHNHYTQKSL SLSPGK
```

The leader sequence and linker sequence are underlined. To guide heterodimer formation with the ActRIIB-Fc fusion polypeptide of SEQ ID NOs 401 and 402 above, four amino acid substitutions can be introduced into the Fc domain of the ALK6 fusion polypeptide as indicated by double underline above. Furthermore, the C-terminal lysine residue of the Fc domain can be deleted. The amino acid sequence of SEQ ID NO: 425 may optionally be provided with the lysine removed from the C-terminus.

The mature ALK6-Fc fusion protein sequence (SEQ ID NO: 426) can be as follows and may optionally be provided with the lysine removed from the C-terminus.

Example 14. Generation of an ActRIIA-Fc:ALK4-Fc Heterodimer

Applicants constructed a soluble ActRIIA-Fc:ALK4-Fc heteromeric complex comprising the extracellular domains of human ActRIIA and human ALK4, which are each separately fused to an Fc domain with a linker positioned between the extracellular domain and the Fc domain. The individual constructs are referred to as ActRIIA-Fc fusion polypeptide and ALK4-Fc fusion polypeptide, respectively.

Formation of heteromeric ActRIIA-Fc:ALK4-Fc may be guided by approaches similar to those described in Example

```
                                                   (SEQ ID NO: 426)
  1 KKEDGESTAP TPRPKVLRCK CHHHCPEDSV NNICSTDGYC FTMIEEDDSG

51 LPVVTSGCLG LEGSDFQCRD TPIPHQRRSI ECCTERNECN KDLHPTLPPL

101 KNRDFVDGPI HHRTGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVCTLPPSR

251 EEMTKNQVSL SCAVKGFYPS DIAVEWESNG QPENNYKTTP PVLDSDGSFF

301 LVSKLTVDKS RWQQGNVFSC SVMHEALHNH YTQKSLSLSP GK
```

1. In a first approach, one Fc domain is altered to introduce cationic amino acids at the interaction face, while the other Fc domain is altered to introduce anionic amino acids at the interaction face.

The ActRIIA-Fc polypeptide sequence (SEQ ID NO: 118) is shown below:

```
                                                        (SEQ ID NO: 118)
  1 MDAMKRGLCC VLLLCGAVFV SPGAAILGRS ETQECLFFNA NWEKDRTNQT

51 GVEPCYGDKD KRRHCFATWK NISGSIEIVK QGCWLDDINC YDRTDCVEKK

101 DSPEVYFCCC EGNMCNEKFS YFPEMEVTQP TSNPVTPKPP TGGGTHTCPP

151 CPAPELLGGP SVFLFPPKPK DTLMISRTPE VTCVVVDVSH EDPEVKFNWY

201 VDGVEVHNAK TKPREEQYNS TYRVVSVLTV LHQDWLNGKE YKCKVSNKAL

251 PAPIEKTISK AKGQPREPQV YTLPPSRKEM TKNQVSLTCL VKGFYPSDIA

301 VEWESNGQPE NNYKTTPPVL KSDGSFFLYS KLTVDKSRWQ QGNVFSCSVM

351 HEALHNHYTQ KSLSLSPGK
```

The leader sequence and linker sequence are underlined. To promote formation of the ActRIIA-Fc:ALK4-Fc heterodimer rather than either of the possible homodimeric complexes, two amino acid substitutions (replacing acidic amino acids with lysine) can be introduced into the Fc domain of the ActRIIA fusion protein as indicated by double underline above. The amino acid sequence of SEQ ID NO: 118 may optionally be provided with the lysine removed from the C-terminus.

This ActRIIA-Fc fusion protein is encoded by the following nucleic acid sequence (SEQ ID NO: 119):

```
                                                        (SEQ ID NO: 119)
   1 ATGGATGCAA TGAAGAGAGG GCTCTGCTGT GTGCTGCTGC TGTGTGGAGC

51 AGTCTTCGTT TCGCCCGGCG CCGCTATACT TGGTAGATCA GAAACTCAGG

101 AGTGTCTTTT CTTTAATGCT AATTGGGAAA AAGACAGAAC CAATCAAACT

151 GGTGTTGAAC CGTGTTATGG TGACAAAGAT AAACGGCGGC ATTGTTTTGC

201 TACCTGGAAG AATATTTCTG GTTCCATTGA AATAGTGAAA CAAGGTTGTT

251 GGCTGGATGA TATCAACTGC TATGACAGGA CTGATTGTGT AGAAAAAAAA

301 GACAGCCCTG AAGTATATTT CTGTTGCTGT GAGGGCAATA TGTGTAATGA

351 AAAGTTTTCT TATTTTCCGG AGATGGAAGT CACACAGCCC ACTTCAAATC

401 CAGTTACACC TAAGCCACCC ACCGGTGGTG GAACTCACAC ATGCCCACCG

451 TGCCCAGCAC CTGAACTCCT GGGGGGACCG TCAGTCTTCC TCTTCCCCCC

501 AAAACCCAAG GACACCCTCA TGATCTCCCG GACCCCTGAG GTCACATGCG

551 TGGTGGTGGA CGTGAGCCAC GAAGACCCTG AGGTCAAGTT CAACTGGTAC

601 GTGGACGGCG TGGAGGTGCA TAATGCCAAG ACAAAGCCGC GGGAGGAGCA

651 GTACAACAGC ACGTACCGTG TGGTCAGCGT CCTCACCGTC CTGCACCAGG

701 ACTGGCTGAA TGGCAAGGAG TACAAGTGCA AGGTCTCCAA CAAAGCCCTC

751 CCAGCCCCCA TCGAGAAAAC CATCTCCAAA GCCAAAGGGC AGCCCCGAGA

801 ACCACAGGTG TACACCCTGC CCCCATCCCG GAAGGAGATG ACCAAGAACC

851 AGGTCAGCCT GACCTGCCTG GTCAAAGGCT TCTATCCCAG CGACATCGCC

901 GTGGAGTGGG AGAGCAATGG GCAGCCGGAG AACAACTACA AGACCACGCC

951 TCCCGTGCTG AAGTCCGACG GCTCCTTCTT CCTCTATAGC AAGCTCACCG

1001 TGGACAAGAG CAGGTGGCAG CAGGGGAACG TCTTCTCATG CTCCGTGATG

1051 CATGAGGCTC TGCACAACCA CTACACGCAG AAGAGCCTCT CCCTGTCTCC

1101 GGGTAAA
```

The mature ActRIIA-Fc fusion polypeptide (SEQ ID NO: 120) is as follows and may optionally be provided with the lysine removed from the C-terminus.

```
                                                         (SEQ ID NO: 120)
  1 ILGRSETQEC LFFNANWEKD RTNQTGVEPC YGDKDKRRHC FATWKNISGS

51 IEIVKQGCWL DDINCYDRTD CVEKKDSPEV YFCCCEGNMC NEKFSYFPEM

101 EVTQPTSNPV TPKPPTGGGT HTCPPCPAPE LLGGPSVFLF PPKPKDTLMI

151 SRTPEVTCVV VDVSHEDPEV KFNWYVDGVE VHNAKTKPRE EQYNSTYRVV

201 SVLTVLHQDW LNGKEYKCKV SNKALPAPIE KTISKAKGQP REPQVYTLPP

251 SREKMTKNQV SLTCLVKGFY PSDIAVEWES NGQPENNYKT TPPVLKSDGS

301 FFLYSKLTVD KSRWQQGNVF SCSVMHEALH NHYTQKSLSL SPGK
```

In this first approach, the polypeptide sequence of the complementary ALK4-Fc fusion protein and a nucleic acid sequence encoding it are provided above in Example 1 as SEQ ID NOs: 104-106.

The ActRIIA-Fc and ALK4-Fc proteins of SEQ ID NO: 120 and SEQ ID NO: 106, respectively, may be co-expressed and purified from a CHO cell line, to give rise to a heteromeric complex comprising ActRIIA-Fc:ALK4-Fc.

In a second approach to promote the formation of heteromultimer complexes using asymmetric Fc fusion proteins, the Fc domains are altered to introduce complementary hydrophobic interactions and an additional intermolecular disulfide bond.

The ActRIIA-Fc polypeptide sequence (SEQ ID NO: 409) is shown below:

```
                                                         (SEQ ID NO: 409)
  1 MDAMKRGLCC VLLLCGAVFV SPGAAILGRS ETQECLFFNA NWEKDRTNQT

51 GVEPCYGDKD KRRHCFATWK NISGSIEIVK QGCWLDDINC YDRTDCVEKK

101 DSPEVYFCCC EGNMCNEKFS YFPEMEVTQP TSNPVTPKPP TGGGTHTCPP

151 CPAPELLGGP SVFLFPPKPK DTLMISRTPE VTCVVVDVSH EDPEVKFNWY

201 VDGVEVHNAK TKPREEQYNS TYRVVSVLTV LHQDWLNGKE YKCKVSNKAL

251 PAPIEKTISK AKGQPREPQV YTLPPCREEM TKNQVSLWCL VKGFYPSDIA

301 VEWESNGQPE NNYKTTPPVL DSDGSFFLYS KLTVDKSRWQ QGNVFSCSVM

351 HEALHNHYTQ KSLSLSPGK
```

The leader sequence and linker sequence are underlined. To promote formation of the ActRIIA-Fc:ALK4-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 409 may optionally be provided with the lysine removed from the C-terminus.

The mature ActRIIA-Fc fusion polypeptide (SEQ ID NO: 410) is as follows and may optionally be provided with the lysine removed from the C-terminus.

```
                                                         (SEQ ID NO: 410)
  1 ILGRSETQEC LFFNANWEKD RTNQTGVEPC YGDKDKRRHC FATWKNISGS

51 IEIVKQGCWL DDINCYDRTD CVEKKDSPEV YFCCCEGNMC NEKFSYFPEM

101 EVTQPTSNPV TPKPPTGGGT HTCPPCPAPE LLGGPSVFLF PPKPKDTLMI
```

```
151 SRTPEVTCVV VDVSHEDPEV KFNWYVDGVE VHNAKTKPRE EQYNSTYRVV

201 SVLTVLHQDW LNGKEYKCKV SNKALPAPIE KTISKAKGQP REPQVYTLPP

251 CREEMTKNQV SLWCLVKGFY PSDIAVEWES NGQPENNYKT TPPVLDSDGS

301 FFLYSKLTVD KSRWQQGNVF SCSVMHEALH NHYTQKSLSL SPGK
```

In this second approach, the polypeptide sequence of the complementary ALK4-Fc fusion protein and a nucleic acid sequence encoding it are provided above in Example 1 as SEQ ID NOs: 403-404.

The ActRIIA-Fc and ALK4-Fc proteins of SEQ ID NO: 410 and SEQ ID NO: 404, respectively, may be co-expressed and purified from a CHO cell line, to give rise to a heteromeric complex comprising ActRIIA-Fc:ALK4-Fc.

Purification of various ActRIIA-Fc:ALK4-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 15. Ligand Binding Profile of ActRIIA-Fc:ALK4-Fc Heterodimer Compared to ActRIIA-Fc Homodimer and ALK4-Fc Homodimer A Biacore™-based binding assay was used to compare ligand binding selectivity of the ActRIIA-Fc:ALK4-Fc heterodimeric complex described above with that of ActRIIA-Fc and ALK4-Fc homodimeric complexes. The ActRIIA-Fc:ALK4-Fc heterodimer, ActRIIA-Fc homodimer, and ALK4-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Figure 10:
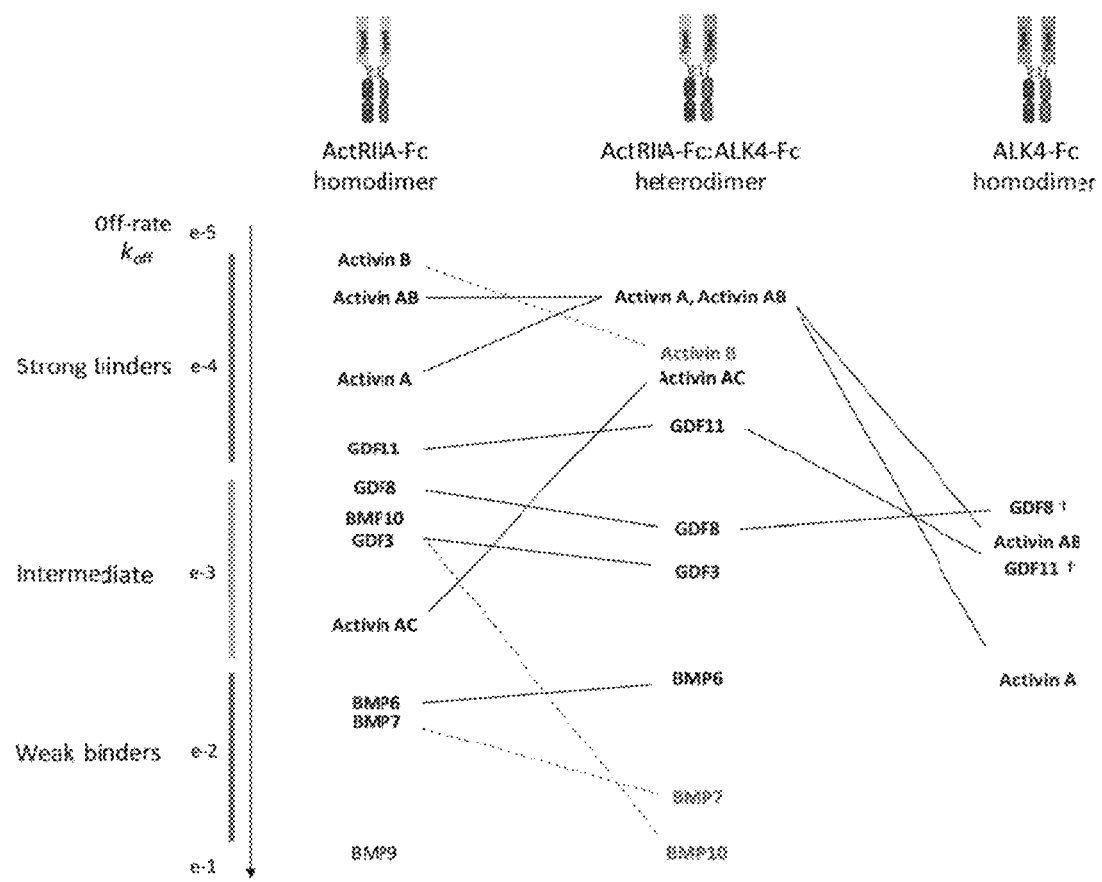
FIG. 10 shows ligand binding data for an ActRIIA-Fc:ALK4-Fc heterodimeric protein complex as compared to ActRIIA-Fc homodimer and ALK4-Fc homodimer. Format is the same as in FIG. 6. As shown, the ActRIIA-Fc:ALK4-Fc heterodimer exhibits enhanced binding to activin A, and particularly enhanced binding to activin AC, compared to ActRIIA-Fc homodimer, while retaining strong binding to activin AB and GDF11. In addition, the ligand with highest affinity for ActRIIA-Fc homodimer, activin B, displays reduced affinity (albeit still within the high-affinity range) for the ActRIIA-Fc:ALK4-Fc heterodimer. The ActRIIA-Fc:ALK4-Fc heterodimer also exhibits markedly reduced binding to BMP10 compared to ActRIIA-Fc homodimer.

ALK4-Fc homodimers. For example, the ActRIIA-Fc:ALK4-Fc heterodimer exhibits enhanced binding to activin A, and particularly enhanced binding to activin AC, compared to ActRIIA-Fc homodimer, while retaining strong binding to activin AB and GDF11. In addition, the ligand with highest affinity for ActRIIA-Fc homodimer, activin B, displays reduced affinity (albeit still within the high-affinity range) for the ActRIIA-Fc:ALK4-Fc heterodimer. The ActRIIA-Fc:ALK4-Fc heterodimer also exhibits markedly reduced binding to BMP10 compared to ActRIIA-Fc homodimer. See FIG. 10.

These results demonstrate that the ActRIIA-Fc:ALK4-Fc heterodimer is a more selective antagonist of activin A and activin AB over activin B than is ActRIIA-Fc homodimer. In addition, the ActRIIA-Fc:ALK4-Fc heterodimer has substantially increased affinity for activin AC and greatly reduced affinity for BMP10 compared to ActRIIA-Fc homodimer. Accordingly, an ActRIIA-Fc:ALK4-Fc heterodimer will be more useful than ActRIIA-Fc homodimer in certain applications where such selective antagonism is advantageous. Examples include therapeutic applications where it is desirable to antagonize activin A and/or activin AB preferentially over activin B, and to obtain strong inhibition of activin AC, while avoiding inhibition of BMP10.

Example 16. Generation of a BMPRII-Fc:ALK1-Fc Heterodimer

Applicants constructed a soluble BMPRII-Fc:ALK1-Fc heteromeric complex comprising the extracellular domains of human BMPRII and human ALK1, which are each separately fused to an Fc domain with a linker positioned between the extracellular domain and the Fc domain. The individual constructs are referred to as BMPRII-Fc fusion Ligand binding profile of ActRIIA-Fc:ALK4-Fc heterodimer compared to ActRIIA-Fc homodimer and ALK4-Fc homodimer

| Ligand | ActRIIA-Fc homodimer | | | ALK4-Fc homodimer | | | ActRIIA-Fc:ALK4-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.4 \times 10^7$ | $\mathbf{6.2 \times 10^{-4}}$ | 45 | $5.8 \times 10^5$ | $1.2 \times 10^{-2}$ | 20000 | $7.4 \times 10^6$ | $\mathbf{2.4 \times 10^{-4}}$ | 32 |
| Activin B | $1.1 \times 10^7$ | $\mathbf{1.1 \times 10^{-4}}$ | 10 | | No binding | | $9.5 \times 10^6$ | $\mathbf{4.8 \times 10^{-4}}$ | 50 |
| Activin AB | $2.8 \times 10^7$ | $\mathbf{2.6 \times 10^{-4}}$ | 9 | $1.8 \times 10^6$ | $3.6 \times 10^{-3}$ | 2000 | $1.8 \times 10^7$ | $\mathbf{2.3 \times 10^{-4}}$ | 13 |
| Activin AC | $2.2 \times 10^7$ | $7.9 \times 10^{-3}$ | 360 | | No binding | | $3.2 \times 10^6$ | $\mathbf{5.4 \times 10^{-4}}$ | 170 |
| BMP6 | $2.7 \times 10^8$ | $2.2 \times 10^{-2}$ | 800 | | No binding | | $5.4 \times 10^6$ | $1.2 \times 10^{-2}$ | 2200 |
| BMP7 | $8.9 \times 10^6$ | $3.3 \times 10^{-2}$ | 3700 | | No binding | | $2.0 \times 10^7$ | $7.2 \times 10^{-2}$ | 3500 |
| BMP9 | Transient* | | >10000 | — | | | No binding | | |
| BMP10 | $2.9 \times 10^7$ | $2.5 \times 10^{-3}$ | 85 | | No binding | | Transient* | | >6000 |
| GDF3 | $1.5 \times 10^6$ | $3.6 \times 10^{-3}$ | 2400 | | — | | $4.9 \times 10^7$ | $4.8 \times 10^{-3}$ | 9800 |
| GDF8 | $1.4 \times 10^6$ | $1.4 \times 10^{-3}$ | 99 | $1.3 \times 10^5$ | $1.9 \times 10^{-3}$ | 15000† | $1.8 \times 10^7$ | $2.8 \times 10^{-3}$ | 150 |
| GDF11 | $7.3 \times 10^7$ | $\mathbf{9.2 \times 10^{-4}}$ | 13 | $5.0 \times 10^6$ | $4.8 \times 10^{-3}$ | 970† | $3.0 \times 10^7$ | $\mathbf{6.5 \times 10^{-4}}$ | 22 |

*Indeterminate due to transient nature of interaction
†Very low signal
— Not tested These comparative binding data demonstrate that the ActRIIA-Fc:ALK4-Fc heterodimer has an altered binding profile/selectivity relative to either the ActRIIA-Fc or polypeptide and ALK1-Fc fusion polypeptide, respectively, and the sequences for each are provided below.

Formation of heteromeric BMPRII-Fc:ALK1-Fc may be guided by approaches similar to those described in Example 1. In a first approach, one Fc domain is altered to introduce cationic amino acids at the interaction face, while the other Fc domain is altered to introduce anionic amino acids at the interaction face.

The BMPRII-Fc polypeptide sequence (SEQ ID NO: 121) is shown below:

```
                                                         (SEQ ID NO: 121)
  1 MDAMKRGLCC VLLLCGAVFV SPGASQNQER LCAFKDPYQQ DLGIGESRIS

51 HENGTILCSK GSTCYGLWEK SKGDINLVKQ GCWSHIGDPQ ECHYEECVVT

101 TTPPSIQNGT YRFCCCSTDL CNVNFTENFP PPDTTPLSPP HSFNRDETGG

151 GTHTCPPCPA PELLGGPSVF LFPPKPKDTL MISRTPEVTC VVVDVSHEDP

201 EVKFNWYVDG VEVHNAKTKP REEQYNSTYR VVSVLTVLHQ DWLNGKEYKC

251 KVSNKALPAP IEKTISKAKG QPREPQVYTL PPSRKEMTKN QVSLTCLVKG

301 FYPSDIAVEW ESNGQPENNY KTTPPVLKSD GSFFLYSKLT VDKSRWQQGN

351 VFSCSVMHEA LHNHYTQKSL SLSPGK
```

The leader sequence and linker sequence are underlined. To promote formation of the BMPRII-Fc:ALK1-Fc heterodimer rather than either of the possible homodimeric complexes, two amino acid substitutions (replacing acidic amino acids with lysine) can be introduced into the Fc domain of the BMPRII-Fc fusion protein as indicated by double underline above. The amino acid sequence of SEQ ID NO: 121 may optionally be provided with the lysine removed from the C-terminus.

This BMPRII-Fc fusion protein is encoded by the following nucleic acid sequence (SEQ ID NO: 122):

```
                                                         (SEQ ID NO: 122)
  1 ATGGATGCAA TGAAGAGAGG GCTCTGCTGT GTGCTGCTGC TGTGTGGAGC

51 AGTCTTCGTT TCGCCCGGCG CCTCGCAGAA TCAAGAACGC CTATGTGCGT

101 TTAAAGATCC GTATCAGCAA GACCTTGGGA TAGGTGAGAG TAGAATCTCT

151 CATGAAAATG GGACAATATT ATGCTCGAAA GGTAGCACCT GCTATGGCCT

201 TTGGGAGAAA TCAAAAGGGG ACATAAATCT TGTAAAACAA GGATGTTGGT

251 CTCACATTGG AGATCCCCAA GAGTGTCACT ATGAAGAATG TGTAGTAACT

301 ACCACTCCTC CCTCAATTCA GAATGGAACA TACCGTTTCT GCTGTTGTAG

351 CACAGATTTA TGTAATGTCA ACTTTACTGA GAATTTTCCA CCTCCTGACA

401 CAACACCACT CAGTCCACCT CATTCATTTA ACCGAGATGA GACCGGTGGT

451 GGAACTCACA CATGCCCACC GTGCCCAGCA CCTGAACTCC TGGGGGGACC

501 GTCAGTCTTC CTCTTCCCCC CAAAACCCAA GGACACCCTC ATGATCTCCC

551 GGACCCCTGA GGTCACATGC GTGGTGGTGG ACGTGAGCCA CGAAGACCCT

601 GAGGTCAAGT TCAACTGGTA CGTGGACGGC GTGGAGGTGC ATAATGCCAA

651 GACAAAGCCG CGGGAGGAGC AGTACAACAG CACGTACCGT GTGGTCAGCG

701 TCCTCACCGT CCTGCACCAG GACTGGCTGA ATGGCAAGGA GTACAAGTGC

751 AAGGTCTCCA ACAAAGCCCT CCCAGCCCCC ATCGAGAAAA CCATCTCCAA

801 AGCCAAAGGG CAGCCCCGAG AACCACAGGT GTACACCCTG CCCCCATCCC

851 GGAAGGAGAT GACCAAGAAC CAGGTCAGCC TGACCTGCCT GGTCAAAGGC

901 TTCTATCCCA GCGACATCGC CGTGGAGTGG GAGAGCAATG GGCAGCCGGA

951 GAACAACTAC AAGACCACGC CTCCCGTGCT GAAGTCCGAC GGCTCCTTCT
```

-continued

```
1001 TCCTCTATAG CAAGCTCACC GTGGACAAGA GCAGGTGGCA GCAGGGGAAC

1051 GTCTTCTCAT GCTCCGTGAT GCATGAGGCT CTGCACAACC ACTACACGCA

1101 GAAGAGCCTC TCCCTGTCTC CGGGTAAA
```

The mature BMPRII-Fc fusion polypeptide (SEQ ID NO: 123) is as follows and may optionally be provided with the lysine removed from the C-terminus.

```
                                          (SEQ ID NO: 123)
  1 SQNQERLCAF KDPYQQDLGI GESRISHENG TILCSKGSTC YGLWEKSKGD

51 INLVKQGCWS HIGDPQECHY EECVVTTTPP SIQNGTYRFC CCSTDLCNVN

101 FTENFPPPDT TPLSPPHSFN RDETGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPSR KEMTKNQVSL TCLVKGFYPS DIAVEWESNG QPENNYKTTP

301 PVLKSDGSFF LYSKLTVDKS RWQQGNVFSC SVMHEALHNH YTQKSLSLSP

351 GK
```

The complementary form of ALK1-Fc fusion polypeptide (SEQ ID NO: 124) is as follows:

```
                                          (SEQ ID NO: 124)
  1 MDAMKRGLCC VLLLCGAVFV SPGADPVKPS RGPLVTCTCE SPHCKGPTCR

51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPSR EEMTKNQVSL TCLVKGFYPS DIAVEWESNG QPENNYDTTP

301 PVLDSDGSFF LYSDLTVDKS RWQQGNVFSC SVMHEALHNH YTQKSLSLSP

351 G
```

The leader sequence and linker sequence are underlined. To guide heterodimer formation with the BMPRII-Fc fusion polypeptide of SEQ ID NOs: 121 and 123 above, two amino acid substitutions (replacing lysines with aspartic acids) can be introduced into the Fc domain of the ALK1-Fc fusion polypeptide as indicated by double underline above. The amino acid sequence of SEQ ID NO: 124 may optionally be provided with a lysine added at the C-terminus.

This ALK1-Fc fusion protein is encoded by the following nucleic acid (SEQ ID NO: 125):

```
                                          (SEQ ID NO: 125)
  1 ATGGATGCAA TGAAGAGAGG GCTCTGCTGT GTGCTGCTGC TGTGTGGAGC

51 AGTCTTCGTT TCGCCCGGCG CCGACCCTGT GAAGCCGTCT CGGGGCCCGC

101 TGGTGACCTG CACGTGTGAG AGCCCACATT GCAAGGGGCC TACCTGCCGG

151 GGGGCCTGGT GCACAGTAGT GCTGGTGCGG GAGGAGGGA GGCACCCCCA

201 GGAACATCGG GGCTGCGGGA ACTTGCACAG GGAGCTCTGC AGGGGCCGCC

251 CCACCGAGTT CGTCAACCAC TACTGCTGCG ACAGCCACCT CTGCAACCAC

301 AACGTGTCCC TGGTGCTGGA GGCCACCCAA CCTCCTTCGG AGCAGCCGGG

351 AACAGATGGC CAGCTGGCCA CCGGTGGTGG AACTCACACA TGCCCACCGT

401 GCCCAGCACC TGAACTCCTG GGGGGACCGT CAGTCTTCCT CTTCCCCCCA

451 AAACCCAAGG ACACCCTCAT GATCTCCCGG ACCCCTGAGG TCACATGCGT
```

-continued

```
 501 GGTGGTGGAC GTGAGCCACG AAGACCCTGA GGTCAAGTTC AACTGGTACG

551 TGGACGGCGT GGAGGTGCAT AATGCCAAGA CAAAGCCGCG GGAGGAGCAG

601 TACAACAGCA CGTACCGTGT GGTCAGCGTC CTCACCGTCC TGCACCAGGA

651 CTGGCTGAAT GGCAAGGAGT ACAAGTGCAA GGTCTCCAAC AAAGCCCTCC

701 CAGCCCCCAT CGAGAAAACC ATCTCCAAAG CCAAAGGGCA GCCCCGAGAA

751 CCACAGGTGT ACACCCTGCC CCCATCCCGG GAGGAGATGA CCAAGAACCA

801 GGTCAGCCTG ACCTGCCTGG TCAAAGGCTT CTATCCCAGC GACATCGCCG

851 TGGAGTGGGA GAGCAATGGG CAGCCGGAGA ACAACTACGA CACCACGCCT

901 CCCGTGCTGG ACTCCGACGG CTCCTTCTTC CTCTATAGCG ACCTCACCGT

951 GGACAAGAGC AGGTGGCAGC AGGGGAACGT CTTCTCATGC TCCGTGATGC

1001 ATGAGGCTCT GCACAACCAC TACACGCAGA AGAGCCTCTC CCTGTCTCCG

1051 GGT
```

The mature ALK1-Fc fusion protein sequence (SEQ ID NO: 126) is as follows and may optionally be provided with a lysine added at the C-terminus.

```
                                                        (SEQ ID NO: 126)
  1 DPVKPSRGPL VTCTCESPHC KGPTCRGAWC TVVLVREEGR HPQEHRGCGN

51 LHRELCRGRP TEFVNHYCCD SHLCNHNVSL VLEATQPPSE QPGTDGQLAT

101 GGGTHTCPPC PAPELLGGPS VFLFPPKPKD TLMISRTPEV TCVVVDVSHE

151 DPEVKFNWYV DGVEVHNAKT KPREEQYNST YRVVSVLTVL HQDWLNGKEY

201 KCKVSNKALP APIEKTISKA KGQPREPQVY TLPPSREEMT KNQVSLTCLV

251 KGFYPSDIAV EWESNGQPEN NYDTTPPVLD SDGSFFLYSD LTVDKSRWQQ

301 GNVFSCSVMH EALHNHYTQK SLSLSPG
```

The BMPRII-Fc and ALK1-Fc proteins of SEQ ID NO: 123 and SEQ ID NO: 126, respectively, may be co-expressed and purified from a CHO cell line, to give rise to a heteromeric complex comprising BMPRII-Fc:ALK1-Fc.

In a second approach to promote the formation of heteromultimer complexes using asymmetric Fc fusion proteins, the Fc domains are altered to introduce complementary hydrophobic interactions and an additional intermolecular disulfide bond.

The BMPRII-Fc polypeptide sequence (SEQ ID NO: 411) is shown below:

```
                                                        (SEQ ID NO: 411)
  1 MDAMKRGLCC VLLLCGAVFV SPGASQNQER LCAFKDPYQQ DLGIGESRIS

51 HENGTILCSK GSTCYGLWEK SKGDINLVKQ GCWSHIGDPQ ECHYEECVVT

101 TTPPSIQNGT YRFCCCSTDL CNVNFTENFP PPDTTPLSPP HSFNRDETGG

151 GTHTCPPCPA PELLGGPSVF LFPPKPKDTL MISRTPEVTC VVVDVSHEDP

201 EVKFNWYVDG VEVHNAKTKP REEQYNSTYR VVSVLTVLHQ DWLNGKEYKC

251 KVSNKALPAP IEKTISKAKG QPREPQVYTL PPCREEMTKN QVSLWCLVKG

301 FYPSDIAVEW ESNGQPENNY KTTPPVLDSD GSFFLYSKLT VDKSRWQQGN

351 VFSCSVMHEA LHNHYTQKSL SLSPGK
```

The leader sequence and linker sequence are underlined. To promote formation of the BMPRII-Fc:ALKT-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 411 may optionally be provided with the lysine removed from the C-terminus.

The mature BMPRII-Fc fusion polypeptide (SEQ ID NO: 412) is as follows and may optionally be provided with the lysine (K) removed from the C-terminus.

```
                                                       (SEQ ID NO: 412)
  1 SQNQERLCAF KDPYQQDLGI GESRISHENG TILCSKGSTC YGLWEKSKGD

51 INLVKQGCWS HIGDPQECHY EECVVTTTPP SIQNGTYRFC CCSTDLCNVN

101 FTENFPPPDT TPLSPPHSFN RDETGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPCR EEMTKNQVSL WCLVKGFYPS DIAVEWESNG QPENNYKTTP

301 PVLDSDGSFF LYSKLTVDKS RWQQGNVFSC SVMHEALHNH YTQKSLSLSP

351 GK
```

The complementary form of ALK1-Fc fusion polypeptide (SEQ ID NO: 413) is as follows:

```
                                                       (SEQ ID NO: 413)
  1 MDAMKRGLCC VLLLCGAVFV SPGADPVKPS RGPLVTCTCE SPHCKGPTCR

51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVCTLPPSR EEMTKNQVSL SCAVKGFYPS DIAVEWESNG QPENNYKTTP

301 PVLDSDGSFF LVSKLTVDKS RWQQGNVFSC SVMHEALHNH YTQKSLSLSP

351 GK
```

The leader sequence and linker sequence are underlined. To guide heterodimer formation with the BMPRII-Fc fusion polypeptide of SEQ ID NOs: 411 and 412 above, four amino acid substitutions can be introduced into the Fc domain of the ALK1 fusion polypeptide as indicated by double underline above. The amino acid sequence of SEQ ID NO: 413 may optionally be provided with the lysine removed from the C-terminus.

The mature ALK1-Fc fusion protein sequence (SEQ ID NO: 414) is as follows and may optionally be provided with the lysine removed from the C-terminus.

```
                                                       (SEQ ID NO: 414)
  1 DPVKPSRGPL VTCTCESPHC KGPTCRGAWC TVVLVREEGR HPQEHRGCGN

51 LHRELCRGRP TEFVNHYCCD SHLCNHNVSL VLEATQPPSE QPGTDGQLAT

101 GGGTHTCPPC PAPELLGGPS VFLFPPKPKD TLMISRTPEV TCVVVDVSHE

151 DPEVKFNWYV DGVEVHNAKT KPREEQYNST YRVVSVLTVL HQDWLNGKEY

201 KCKVSNKALP APIEKTISKA KGQPREPQVC    TLPPSREEMT KNQVSLSCAV

251 KGFYPSDIAV EWESNGQPEN NYKTTPPVLD SDGSFFLVSK LTVDKSRWQQ

301 GNVFSCSVMH EALHNHYTQK SLSLSPGK
```

The BMPRII-Fc and ALK1-Fc proteins of SEQ ID NO: 412 and SEQ ID NO: 414, respectively, may be co-expressed and purified from a CHO cell line, to give rise to a heteromeric complex comprising BMPRII-Fc:ALK1-Fc.

Purification of various BMPRII-Fc:ALK1-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 17. Ligand Binding Profile of BMPRII-Fc:ALK1-Fc Heterodimer Compared to BMPRII-Fc Homodimer and ALK1-Fc Homodimer A Biacore®-based binding assay was used to compare ligand binding selectivity of the BMPRII-Fc:ALK1-Fc heterodimeric complex described above with that of BMPRII-Fc and ALK1-Fc homodimeric complexes. The BMPRII-Fc:ALK1-Fc heterodimer, BMPRII-Fc homodimer, and ALK1-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profile of BMPRII-Fc:ALK1-Fc heterodimer compared to BMPRII-Fc homodimer and ALK1-Fc homodimer

| | BMPRII-Fc homodimer | | | ALK1-Fc homodimer | | | BMPRII-Fc:ALK1-Fc heterodimer | | |
|---|---|---|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| BMP9  | $1.2 \times 10^7$ | $2.6 \times 10^{-2}$ | 2100 | $7.8 \times 10^6$ | $\mathbf{1.3 \times 10^{-4}}$ | 16 | $1.2 \times 10^6$ | $\mathbf{4.1 \times 10^{-4}}$ | 360 |
| BMP10 | $2.6 \times 10^7$ | $2.5 \times 10^{-3}$ | 100  | $4.1 \times 10^6$ | $\mathbf{1.6 \times 10^{-4}}$ | 38 | $1.5 \times 10^7$ | $\mathbf{3.5 \times 10^{-4}}$ | 23 |
| BMP15 | $9.9 \times 10^6$ | $2.8 \times 10^{-3}$ | 290  | No binding | | | $1.2 \times 10^7$ | $4.2 \times 10^{-2}$ | 3500 |

Figure 11:
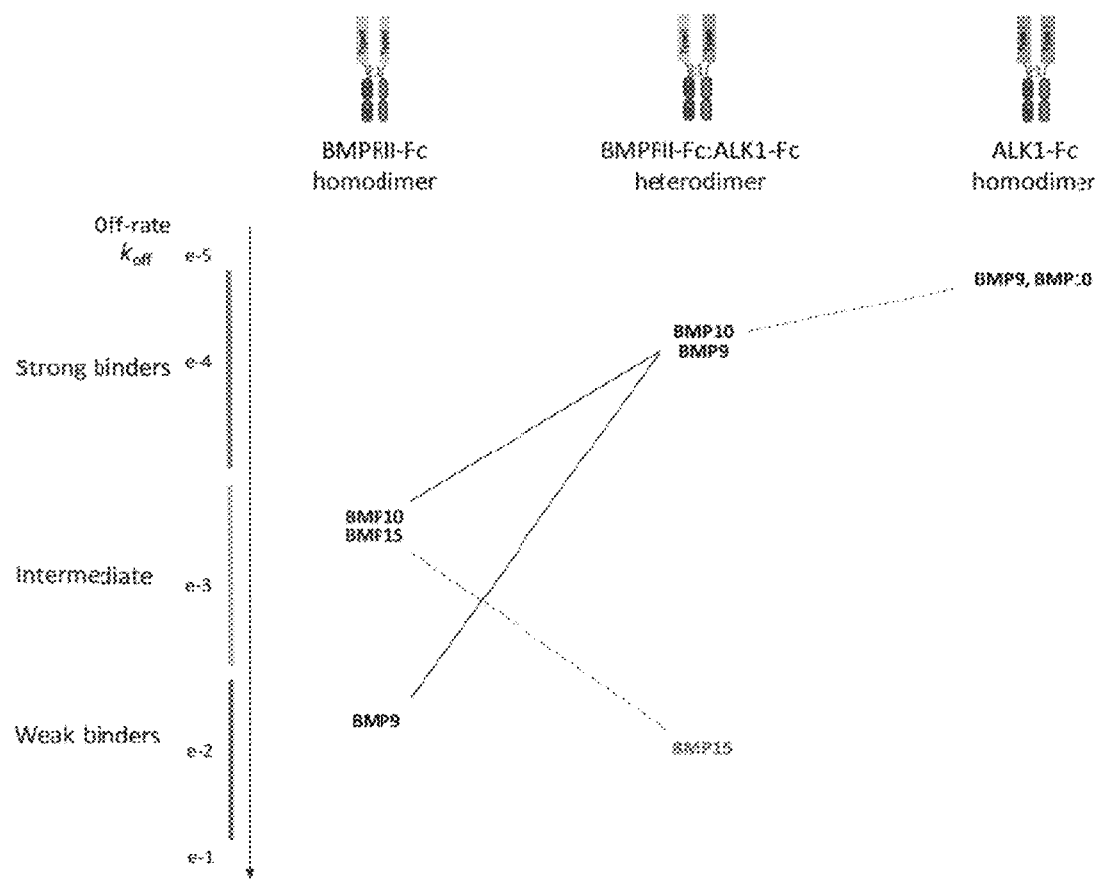
FIG. 11 shows ligand binding data for a BMPRII-Fc:ALK1-Fc heterodimeric protein complex as compared to ActRIIB-Fc homodimer and ALKT-Fc homodimer. Format is the same as in FIG. 6. As shown, the BMPRII-Fc:ALKT-Fc heterodimer largely retains the strong binding to BMP9 and BMP10 characteristic of ALK1-Fc homodimer; however, the heterodimer displays modest selectivity for BMP10 over BMP9 not present with the homodimer. Also unlike ALKT-Fc homodimer, the BMPRII-Fc:ALK1-Fc heterodimer binds to BMP15, albeit with an off-rate approximately ten times faster than that of BMPRII-Fc homodimer.

These comparative binding data demonstrate that the BMPRII-Fc:ALKT-Fc heterodimer has a binding profile/selectivity which differs from that of BMPRII-Fc homodimer but is similar to that of ALK1-Fc homodimer. For example, the BMPRII-Fc:ALK1-Fc heterodimer largely retains the strong binding to BMP9 and BMP10 characteristic of ALK1-Fc homodimer; however, the heterodimer displays modest selectivity for BMP10 over BMP9 not present with the homodimer. Also unlike ALKT-Fc homodimer, the BMPRII-Fc:ALK1-Fc heterodimer binds to BMP15, albeit with an affinity approximately an order of magnitude weaker than that of BMPRII-Fc homodimer. See FIG. 11. Accordingly, a BMPRII-Fc:ALK1-Fc heterodimer will be unexpectedly useful in certain therapeutic applications where selective antagonism of BMP9 and particularly BMP10 is advantageous, e.g., for inhibition of angiogenesis, or in applications where antagonism of BMP15 is also advantageous.

Example 18. Generation of a BMPRII-Fc:ALK2-Fc Heterodimer

Applicants constructed a soluble BMPRII-Fc:ALK2-Fc heteromeric complex comprising the extracellular domains of human BMPRII and human ALK2, which are each separately fused to an Fc domain with a linker positioned between the extracellular domain and the Fc domain. The individual constructs are referred to as BMPRII-Fc fusion polypeptide and ALK2-Fc fusion polypeptide, respectively, and the sequences for each are provided herein.

Formation of heteromeric BMPRII-Fc:ALK2-Fc may be guided by approaches similar to those described in Example 1. In a first approach, one Fc domain is altered to introduce cationic amino acids at the interaction face, while the other Fc domain is altered to introduce anionic amino acids at the interaction face. The polypeptide sequence of the BMPRII-Fc fusion polypeptide and a nucleic acid sequence encoding it are provided above in Example 16 as SEQ ID NOs: 121-123. To promote formation of the BMPRII-Fc:ALK2-Fc heterodimer rather than either of the possible homodimeric complexes, two amino acid substitutions (replacing acidic amino acids with lysine) can be introduced into the Fc domain of the BMPRII-Fc fusion protein as indicated in Example 16. The amino acid sequences of SEQ ID NOs: 121 and 123 may optionally be provided with the lysine removed from the C-terminus.

The polypeptide sequence of the complementary ALK2-Fc fusion polypeptide and a nucleic acid sequence encoding it are provided in Example 9 as SEQ ID NOs: 136-138. To guide heterodimer formation with the BMPRII-Fc fusion polypeptide of SEQ ID NOs: 121 and 123, two amino acid substitutions (replacing lysines with aspartic acids) can be introduced into the Fc domain of the ALK2-Fc fusion polypeptide as indicated in Example 9. The amino acid sequences of SEQ ID NOs: 136 and 138 may optionally be provided with a lysine added at the C-terminus.

The BMPRII-Fc and ALK2-Fc fusion polypeptides of SEQ ID NO: 123 and SEQ ID NO: 138, respectively, may be co-expressed and purified from a CHO cell line, to give rise to a heteromeric complex comprising BMPRII-Fc:ALK2-Fc.

In a second approach to promote the formation of heteromultimer complexes using asymmetric Fc fusion proteins, the Fc domains are altered to introduce complementary hydrophobic interactions and an additional intermolecular disulfide bond. BMPRII-Fc fusion polypeptide sequences (SEQ ID NOs: 411-412) are discussed in Example 16. To promote formation of the BMPRII-Fc:ALK2-Fc heterodimer rather than either of the possible homodimeric complexes, two amino acid substitutions (replacing a serine with a cysteine and a threonine with a trytophan) can be introduced into the Fc domain of the BMPRII-Fc polypeptide as indicated in Example 16. The amino acid sequences of SEQ ID NOs: 411 and 412 may optionally be provided with the lysine removed from the C-terminus.

Polypeptide sequences of the complementary ALK2-Fc fusion polypeptide (SEQ ID NOs: 421-422) are discussed in Example 9. To guide heterodimer formation with the BMPRII-Fc fusion polypeptide of SEQ ID NOs: 411-412, four amino acid substitutions can be introduced into the Fc domain of the ALK2 fusion polypeptide as indicated in Example 9. The amino acid sequences of SEQ ID NOs: 421-422 may optionally be provided with the lysine removed from the C-terminus.

The BMPRII-Fc and ALK2-Fc fusion polypeptides of SEQ ID NO: 412 and SEQ ID NO: 422, respectively, may be co-expressed and purified from a CHO cell line, to give rise to a heteromeric complex comprising BMPRII-Fc: ALK2-Fc.

Purification of various BMPRII-Fc:ALK2-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 19. Ligand Binding Profile of BMPRII-Fc:ALK2-Fc Heterodimer Compared to BMPRII-Fc Homodimer and ALK2-Fc Homodimer A Biacore™-based binding assay was used to compare ligand binding selectivity of the BMPRII-Fc:ALK2-Fc heterodimeric complex described above with that of BMPRII-Fc and ALK2-Fc homodimeric complexes. The BMPRII-Fc:ALK2-Fc heterodimer, BMPRII-Fc homodimer, and ALK2-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

cationic amino acids at the interaction face, while the other Fc domain is altered to introduce anionic amino acids at the interaction face. The polypeptide sequence of the BMPRII-Fc fusion polypeptide and a nucleic acid sequence encoding it are provided above in Example 16 as SEQ ID NOs: 121-123. To promote formation of the BMPRII-Fc:ALK3-Fc heterodimer rather than either of the possible homodimeric complexes, two amino acid substitutions (replacing acidic amino acids with lysine) can be introduced into the Fc domain of the BMPRII-Fc fusion protein as indicated in Example 16. The amino acid sequences of SEQ ID NOs: 121 and 123 may optionally be provided with the lysine removed from the C-terminus.

The polypeptide sequence of the complementary ALK3-Fc fusion polypeptide and a nucleic acid sequence encoding it are provided in Example 4 as SEQ ID NOs: 115-117. To guide heterodimer formation with the BMPRII-Fc fusion polypeptide of SEQ ID NOs: 121 and 123, two amino acid substitutions (replacing lysines with aspartic acids) can be introduced into the Fc domain of the ALK3-Fc fusion polypeptide as indicated in Example 4. The amino acid sequences of SEQ ID NOs: 115 and 117 may optionally be provided with a lysine added at the C-terminus.

The BMPRII-Fc and ALK3-Fc fusion polypeptides of SEQ ID NO: 123 and SEQ ID NO: 117, respectively, may be co-expressed and purified from a CHO cell line, to give rise to a heteromeric complex comprising BMPRII-Fc: ALK3-Fc.

In a second approach to promote the formation of heteromultimer complexes using asymmetric Fc fusion proteins, the Fc domains are altered to introduce complementary hydrophobic interactions and an additional intermolecular disulfide bond. BMPRII-Fc fusion polypeptide sequences (SEQ ID NOs: 411-412) are discussed in Example 16. To promote formation of the BMPRII-Fc:

Ligand binding profile of BMPRII-Fc:ALK2-Fc heterodimer compared to BMPRII-Fc homodimer and ALK2-Fc homodimer

| Ligand | BMPRII-Fc homodimer | | | ALK2-Fc homodimer | | | BMPRII-Fc:ALK2-Fc heterodimer | | |
| --- | --- | --- | --- | --- | --- | --- | --- | --- | --- |
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin B | $1.9 \times 10^6$ | $4.9 \times 10^{-3}$ | 2600 | No binding | | | $5.9 \times 10^5$ | $3.1 \times 10^{-3}$ | 5200 |
| BMP5 | $1.9 \times 10^6$ | $1.9 \times 10^{-2}$ | 9900 | No binding | | | $1.8 \times 10^6$ | $5.0 \times 10^{-3}$ | 2800 |
| BMP7 | Transient* | | >93000 | No binding | | | $1.5 \times 10^7$ | $1.2 \times 10^{-2}$ | 760 |
| BMP9 | $4.5 \times 10^7$ | $7.3 \times 10^{-2}$ | 1600 | No binding | | | $1.0 \times 10^7$ | $5.1 \times 10^{-3}$ | 500 |
| BMP10 | $3.8 \times 10^7$ | $5.0 \times 10^{-3}$ | 130 | No binding | | | $1.1 \times 10^8$ | $3.4 \times 10^{-2}$ | 300 |
| BMP15 | $5.8 \times 10^6$ | $4.2 \times 10^{-3}$ | 720 | No binding | | | $9.6 \times 10^6$ | $1.1 \times 10^{-2}$ | 1100 |

*Indeterminate due to transient nature of interaction

Example 20. Generation of a BMPRII-Fc:ALK3-Fc Heterodimer

Applicants constructed a soluble BMPRII-Fc:ALK3-Fc heteromeric complex comprising the extracellular domains of human BMPRII and human ALK3, which are each separately fused to an Fc domain with a linker positioned between the extracellular domain and the Fc domain. The individual constructs are referred to as BMPRII-Fc fusion polypeptide and ALK3-Fc fusion polypeptide, respectively, and the sequences for each are provided herein.

Formation of heteromeric BMPRII-Fc:ALK3-Fc may be guided by approaches similar to those described in Example 1. In a first approach, one Fc domain is altered to introduce ALK3-Fc heterodimer rather than either of the possible homodimeric complexes, two amino acid substitutions (replacing a serine with a cysteine and a threonine with a trytophan) can be introduced into the Fc domain of the BMPRII-Fc polypeptide as indicated in Example 16. The amino acid sequences of SEQ ID NOs: 411 and 412 may optionally be provided with the lysine removed from the C-terminus.

Polypeptide sequences of the complementary ALK3-Fc fusion polypeptide (SEQ ID NOs: 407-408) are discussed in Example 4. To guide heterodimer formation with the BMPRII-Fc fusion polypeptide of SEQ ID NOs: 411-412, four amino acid substitutions can be introduced into the Fc domain of the ALK3 fusion polypeptide as indicated in Example 4. The amino acid sequences of SEQ ID NOs: 407 and 408 may optionally be provided with the lysine removed from the C-terminus.

The BMPRII-Fc and ALK3-Fc fusion polypeptides of SEQ ID NO: 412 and SEQ ID NO: 408, respectively, may be co-expressed and purified from a CHO cell line, to give rise to a heteromeric complex comprising BMPRII-Fc:ALK3-Fc.

Purification of various BMPRII-Fc:ALK3-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Figure 12:
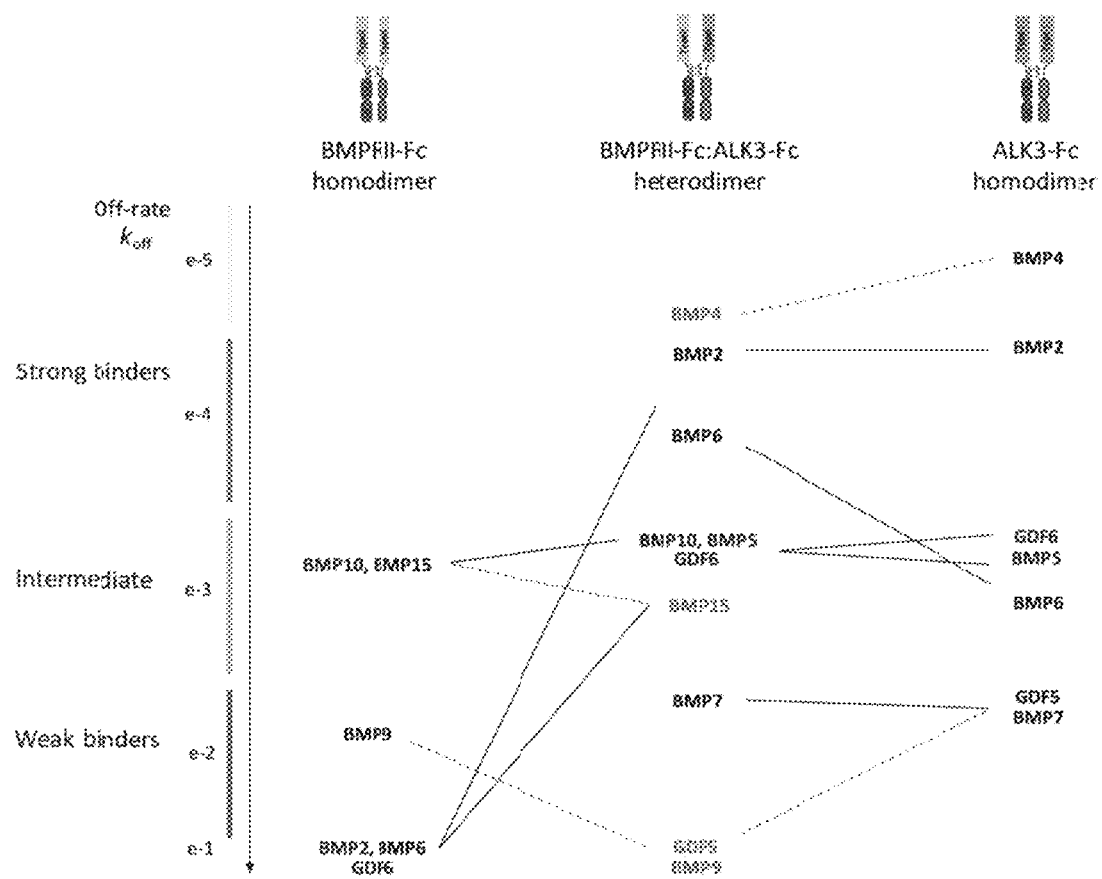
FIG. 12 shows ligand binding data for a BMPRII-Fc:ALK3-Fc heterodimeric protein complex as compared to BMPRII-Fc homodimer and ALK3-Fc homodimer. Format is the same as in FIG. 6. As shown, the BMPRII-Fc:ALK3-Fc heterodimer binds much more strongly to BMP6 than does ALK3-Fc homodimer, reflecting an off-rate nearly ten times slower. With its largely unchanged binding to BMP2 and BMP4, the BMPRII-Fc:ALK3 heterodimer can therefore be considered a joint inhibitor of BMP2, BMP4, and BMP6. This binding profile contrasts with that of ALK3-Fc homodimer, whose exceptionally strongly binding to BMP4 and BMP2 identifies it as highly selective for this ligand pair compared to four ligands with intermediate-level binding, including BMP6.

Example 21. Ligand Binding Profile of BMPRII-Fc:ALK3-Fc Heterodimer Compared to BMPRII-Fc Homodimer and ALK3-Fc Homodimer A Biacore™-based binding assay was used to compare ligand binding selectivity of the BMPRII-Fc:ALK3-Fc heterodimeric complex described above with that of BMPRII-Fc and ALK3-Fc homodimeric complexes. The BMPRII-Fc:ALK3-Fc heterodimer, BMPRII-Fc homodimer, and ALK3-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

binding, including BMP6. See FIG. 12. Accordingly, a BMPRII-Fc:ALK3-Fc heterodimer will be unexpectedly useful in certain therapeutic applications where joint antagonism of BMP2, BMP4, and BMP6 is advantageous.

Example 22. Generation of a BMPRII-Fc:ALK4-Fc Heterodimer

Applicants constructed a soluble BMPRII-Fc:ALK4-Fc heteromeric complex comprising the extracellular domains of human BMPRII and human ALK4, which are each separately fused to an Fc domain with a linker positioned between the extracellular domain and the Fc domain. The individual constructs are referred to as BMPRII-Fc fusion polypeptide and ALK4-Fc fusion polypeptide, respectively, and the sequences for each are provided herein.

Formation of heteromeric BMPRII-Fc:ALK4-Fc may be guided by approaches similar to those described in Example 1. In a first approach, one Fc domain is altered to introduce cationic amino acids at the interaction face, while the other Fc domain is altered to introduce anionic amino acids at the interaction face. The polypeptide sequence of the BMPRII-Fc fusion polypeptide and a nucleic acid sequence encoding it are provided above in Example 16 as SEQ ID NOs: 121-123. To promote formation of the BMPRII-Fc:ALK4-Fc heterodimer rather than either of the possible homodimeric complexes, two amino acid substitutions (replacing acidic amino acids with lysine) can be introduced into the Fc domain of the BMPRII-Fc fusion protein as indicated in Example 16. The amino acid sequences of SEQ ID NOs: 121 and 123 may optionally be provided with the lysine removed from the C-terminus.

| | Ligand binding profile of BMPRII-Fc:ALK3-Fc heterodimer compared to BMPRII-Fc homodimer and ALK3-Fc homodimer | | | | | | | | |
|---|---|---|---|---|---|---|---|---|---|
| | BMPRII-Fc homodimer | | | ALK3-Fc homodimer | | | BMPRII-Fc:ALK3-Fc heterodimer | | |
| Ligand | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin B | $2.0 \times 10^7$ | $7.5 \times 10^{-2}$ | 3800 | No binding | | | Minimal binding | | |
| BMP2 | Transient* | | $>2 \times 10^6$ | $6.2 \times 10^5$ | $\mathbf{1.4 \times 10^{-4}}$ | 230 | $2.9 \times 10^6$ | $\mathbf{1.5 \times 10^{-4}}$ | 51 |
| BMP4 | — | | | $2.6 \times 10^5$ | $\mathbf{5.5 \times 10^{-5}}$ | 210 | $9.1 \times 10^5$ | $\mathbf{9.1 \times 10^{-5}}$ | 100 |
| BMP5 | — | | | $2.9 \times 10^4$ | $2.3 \times 10^{-3}$ | 70000 | $4.3 \times 10^5$ | $1.4 \times 10^{-3}$ | 3200 |
| BMP6 | Transient* | | >8900 | $1.4 \times 10^5$ | $4.9 \times 10^{-3}$ | 35000 | $3.6 \times 10^5$ | $\mathbf{5.9 \times 10^{-4}}$ | 1600 |
| BMP7 | Transient* | | >38000 | $1.2 \times 10^6$ | $1.8 \times 10^{-2}$ | 15000 | $1.2 \times 10^7$ | $1.2 \times 10^{-2}$ | 1000 |
| BMP9 | $1.2 \times 10^7$ | $2.6 \times 10^{-2}$ | 2100 | No binding | | | No binding | | |
| BMP10 | $2.6 \times 10^7$ | $2.5 \times 10^{-3}$ | 100 | — | | | $6.8 \times 10^5$ | $1.6 \times 10^{-3}$ | 2400 |
| BMP15 | $9.9 \times 10^6$ | $2.8 \times 10^{-3}$ | 290 | — | | | $9.1 \times 10^5$ | $5.5 \times 10^{-3}$ | 6000 |
| GDF5 | No binding | | | $4.3 \times 10^5$ | $1.1 \times 10^{-2}$ | 22000 | Minimal binding | | |
| GDF6 | Transient* | | >88000 | $3.4 \times 10^4$ | $1.3 \times 10^{-3}$ | 40000 | $1.4 \times 10^6$ | $1.9 \times 10^{-3}$ | 1400 |

*Indeterminate due to transient nature of interaction
— Not tested

These comparative binding data demonstrate that the BMPRII-Fc:ALK3-Fc heterodimer has ligand binding selectivity which is clearly unlike that of BMPRII-Fc homodimer but also differs from that of ALK3-Fc homodimer. BMPRII-Fc:ALK3-Fc heterodimer binds much more strongly to BMP6 than does ALK3-Fc homodimer, reflecting an off-rate nearly ten-fold slower. With its largely unchanged binding to BMP2 and BMP4, the BMPRII-Fc:ALK3 heterodimer can therefore be considered a joint inhibitor of BMP2, BMP4, and BMP6. This binding profile contrasts with that of ALK3-Fc homodimer, whose exceptionally strongly binding to BMP4 and BMP2 identifies it as highly selective for this ligand pair compared to four ligands with intermediate-level The polypeptide sequence of the complementary ALK4-Fc fusion polypeptide and a nucleic acid sequence encoding it are provided in Example 1 as SEQ ID NOs: 104-106. To guide heterodimer formation with the BMPRII-Fc fusion polypeptide of SEQ ID NOs: 121 and 123, two amino acid substitutions (replacing lysines with aspartic acids) can be introduced into the Fc domain of the ALK4-Fc fusion polypeptide as indicated in Example 1. The amino acid sequences of SEQ ID NOs: 104 and 106 may optionally be provided with a lysine added at the C-terminus.

The BMPRII-Fc and ALK4-Fc fusion polypeptides of SEQ ID NO: 123 and SEQ ID NO: 106, respectively, may be co-expressed and purified from a CHO cell line, to give rise to a heteromeric complex comprising BMPRII-Fc:ALK4-Fc.

In a second approach to promote the formation of heteromultimer complexes using asymmetric Fc fusion proteins, the Fc domains are altered to introduce complementary hydrophobic interactions and an additional intermolecular disulfide bond. BMPRII-Fc fusion polypeptide sequences (SEQ ID NOs: 411 and 412) are discussed in erodimeric complex described above with that of BMPRII-Fc and ALK4-Fc homodimeric complexes. The BMPRII-Fc:ALK4-Fc heterodimer, BMPRII-Fc homodimer, and ALK4-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

| | Ligand binding profile of BMPRII-Fc:ALK4-Fc heterodimer compared to BMPRII-Fc homodimer and ALK4-Fc homodimer | | | | | | | | |
|---|---|---|---|---|---|---|---|---|---|
| | BMPRII-Fc homodimer | | | ALK4-Fc homodimer | | | BMPRII-Fc:ALK4-Fc heterodimer | | |
| Ligand | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | Transient* | | >43000 | $5.8 \times 10^5$ | $1.2 \times 10^{-2}$ | 20000 | $2.0 \times 10^6$ | $2.2 \times 10^{-3}$ | 1100 |
| Activin B | $2.0 \times 10^7$ | $7.5 \times 10^{-2}$ | 3800 | No binding | | | $1.6 \times 10^6$ | $2.6 \times 10^{-3}$ | 1700 |
| Activin AB | — | — | — | $4.4 \times 10^6$ | $6.4 \times 10^{-3}$ | 1500 | $3.6 \times 10^6$ | $\mathbf{5.0 \times 10^{-4}}$ | 140 |
| BMP9 | $1.2 \times 10^7$ | $2.6 \times 10^{-2}$ | 2100 | No binding | | | Transient* | | >140000 |
| BMP10 | $2.6 \times 10^7$ | $2.5 \times 10^{-3}$ | 100 | No binding | | | $8.0 \times 10^5$ | $1.8 \times 10^{-3}$ | 2200 |
| BMP15 | $9.9 \times 10^6$ | $2.8 \times 10^{-3}$ | 290 | No binding | | | $2.8 \times 10^7$ | $4.8 \times 10^{-2}$ | 1700 |

*Indeterminate due to transient nature of interaction
— Not tested

Example 16. To promote formation of the BMPRII-Fc:ALK4-Fc heterodimer rather than either of the possible homodimeric complexes, two amino acid substitutions (replacing a serine with a cysteine and a threonine with a trytophan) can be introduced into the Fc domain of the BMPRII-Fc polypeptide as indicated in Example 16. The amino acid sequences of SEQ ID NOs: 411 and 412 may optionally be provided with the lysine removed from the C-terminus.

Polypeptide sequences of the complementary ALK4-Fc fusion polypeptide (SEQ ID NOs: 403 and 404) are discussed in Example 1. To guide heterodimer formation with the BMPRII-Fc fusion polypeptide of SEQ ID NOs: 411 and 412, four amino acid substitutions can be introduced into the Fc domain of the ALK4 fusion polypeptide as indicated in Example 1. The amino acid sequences of SEQ ID NOs: 403 and 404 may optionally be provided with the lysine removed from the C-terminus.

The BMPRII-Fc and ALK4-Fc fusion polypeptides of SEQ ID NO: 412 and SEQ ID NO: 404, respectively, may be co-expressed and purified from a CHO cell line, to give rise to a heteromeric complex comprising BMPRII-Fc:ALK4-Fc.

Purification of various BMPRII-Fc:ALK4-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Figure 13:
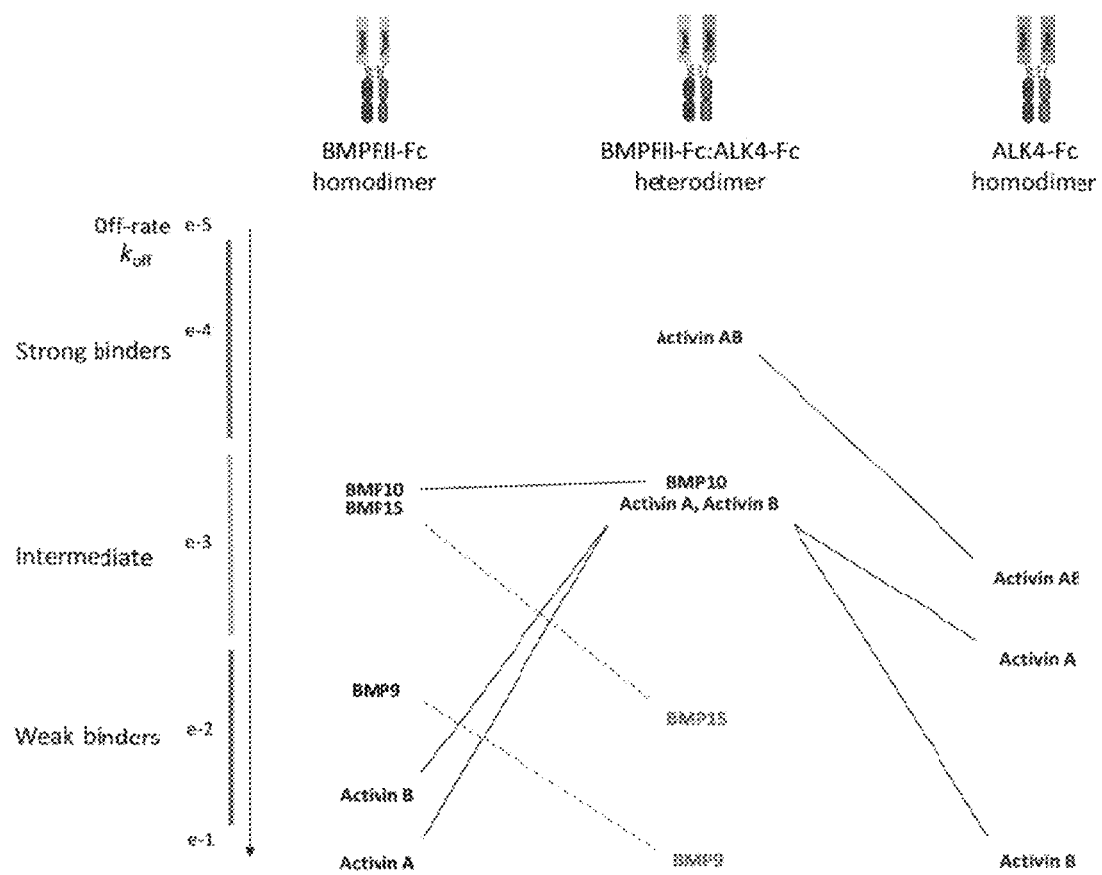
FIG. 13 shows ligand binding data for a BMPRII-Fc:ALK4-Fc heterodimeric protein complex as compared to BMPRII-Fc homodimer and ALK4-Fc homodimer. Format is the same as in FIG. 6. BMPRII-Fc:ALK4-Fc heterodimer differs from both homodimers by binding several activin ligands with high or intermediate strength and differs from BMPRII-Fc homodimer by binding BMP15 only weakly. Most notably, BMPRII-Fc:ALK4-Fc heterodimer binds strongly and with high selectivity to the heterodimeric ligand activin AB.

Example 23. Ligand Binding Profile of BMPRII-Fc:ALK4-Fc Heterodimer Compared to BMPRII-Fc Homodimer and ALK4-Fc Homodimer A Biacore™-based binding assay was used to compare ligand binding selectivity of the BMPRII-Fc:ALK4-Fc het- These comparative binding data demonstrate that the BMPRII-Fc:ALK4-Fc heterodimer has ligand binding selectivity which is unlike that of either BMPRII-Fc homodimer or ALK4-Fc homodimer. BMPRII-Fc:ALK4-Fc heterodimer differs from both homodimers by binding several activin ligands with high or intermediate strength and differs from BMPRII-Fc homodimer by binding BMP15 only weakly. Most notably, BMPRII-Fc:ALK4-Fc heterodimer binds strongly and preferentially to the heterodimeric ligand activin AB. See FIG. 13. Accordingly, a BMPRII-Fc:ALK4-Fc heterodimer will be unexpectedly useful in certain therapeutic applications where antagonism of activin A, activin B, and particularly activin AB are advantageous and where antagonism of BMP15 (which is heavily implicated in ovulation) is to be avoided.

Example 24. Generation of a TGFβRII-Fc:ALK1-Fc Heterodimer

Applicants constructed a soluble TGFβRII-Fc:ALK1-Fc heteromeric complex comprising the extracellular domains of the short (canonical) isoform of human TGFβRII and human ALK1, which are each separately fused to an Fc domain with a linker positioned between the extracellular domain and the Fc domain. The individual constructs are referred to as TGFβRII$_{SHORT}$-Fc fusion polypeptide and ALKT-Fc fusion polypeptide, respectively, and the sequences for each are provided herein.

Formation of heteromeric TGFβRII$_{SHORT}$-Fc:ALK1-Fc may be guided by approaches similar to those described in Example 1. In a first approach, one Fc domain is altered to introduce cationic amino acids at the interaction face, while the other Fc domain is altered to introduce anionic amino acids at the interaction face.

The TGFβRII$_{SHORT}$-Fc polypeptide sequence (SEQ ID NO: 127) is shown below:

(SEQ ID NO: 127)

```
  1 MDAMKRGLCC VLLLCGAVFV SPGATIPPHV QKSVNNDMIV TDNNGAVKFP
 51 QLCKFCDVRF STCDNQKSCM SNCSITSICE KPQEVCVAVW RKNDENITLE
101 TVCHDPKLPY HDFILEDAAS PKCIMKEKKK PGETFFMCSC SSDECNDNII
151 FSEEYNTSNP DTGGGTHTCP PCPAPELLGG PSVFLFPPKP KDTLMISRTP
201 EVTCVVVDVS HEDPEVKFNW YVDGVEVHNA KTKPREEQYN STYRVVSVLT
251 VLHQDWLNGK EYKCKVSNKA LPAPIEKTIS KAKGQPREPQ VYTLPPSRKE
301 MTKNQVSLTC LVKGFYPSDI AVEWESNGQP ENNYKTTPPV LKSDGSFFLY
351 SKLTVDKSRW QQGNVFSCSV MHEALHNHYT QKSLSLSPGK
```

The leader sequence and linker sequence are underlined. To promote formation of the TGFβRII$_{SHORT}$-Fc:ALK1-Fc heterodimer rather than either of the possible homodimeric complexes, two amino acid substitutions (replacing acidic amino acids with lysine) can be introduced into the Fc domain of the TGFβRII$_{SHORT}$-Fc fusion protein as indicated by double underline above. The amino acid sequence of SEQ ID NO: 127 may optionally be provided with the lysine removed from the C-terminus.

This TGFβRII$_{SHORT}$-Fc fusion protein is encoded by the following nucleic acid sequence (SEQ ID NO: 128):

(SEQ ID NO: 128)

```
   1 ATGGATGCAA TGAAGAGAGG GCTCTGCTGT GTGCTGCTGC TGTGTGGAGC
  51 AGTCTTCGTT TCGCCCGGCG CCACGATCCC ACCGCACGTT CAGAAGTCGG
 101 TTAATAACGA CATGATAGTC ACTGACAACA ACGGTGCAGT CAAGTTTCCA
 151 CAACTGTGTA AATTTTGTGA TGTGAGATTT TCCACCTGTG ACAACCAGAA
 201 ATCCTGCATG AGCAACTGCA GCATCACCTC CATCTGTGAG AAGCCACAGG
 251 AAGTCTGTGT GGCTGTATGG AGAAAGAATG ACGAGAACAT AACACTAGAG
 301 ACAGTTTGCC ATGACCCCAA GCTCCCCTAC CATGACTTTA TTCTGGAAGA
 351 TGCTGCTTCT CCAAAGTGCA TTATGAAGGA AAAAAAAAAG CCTGGTGAGA
 401 CTTTCTTCAT GTGTTCCTGT AGCTCTGATG AGTGCAATGA CAACATCATC
 451 TTCTCAGAAG AATATAACAC CAGCAATCCT GACACCGGTG GTGGAACTCA
 501 CACATGCCCA CCGTGCCCAG CACCTGAACT CCTGGGGGGA CCGTCAGTCT
 551 TCCTCTTCCC CCCAAAACCC AAGGACACCC TCATGATCTC CCGGACCCCT
 601 GAGGTCACAT GCGTGGTGGT GGACGTGAGC CACGAAGACC CTGAGGTCAA
 651 GTTCAACTGG TACGTGGACG GCGTGGAGGT GCATAATGCC AAGACAAAGC
 701 CGCGGGAGGA GCAGTACAAC AGCACGTACC GTGTGGTCAG CGTCCTCACC
 751 GTCCTGCACC AGGACTGGCT GAATGGCAAG GAGTACAAGT GCAAGGTCTC
 801 CAACAAAGCC CTCCCAGCCC CCATCGAGAA AACCATCTCC AAAGCCAAAG
 851 GGCAGCCCCG AGAACCACAG GTGTACACCC TGCCCCCATC CCGGAAGGAG
 901 ATGACCAAGA ACCAGGTCAG CCTGACCTGC CTGGTCAAAG GCTTCTATCC
 951 CAGCGACATC GCCGTGGAGT GGGAGAGCAA TGGGCAGCCG GAGAACAACT
1001 ACAAGACCAC GCCTCCCGTG CTGAAGTCCG ACGGCTCCTT CTTCCTCTAT
1051 AGCAAGCTCA CCGTGGACAA GAGCAGGTGG CAGCAGGGGA ACGTCTTCTC
1101 ATGCTCCGTG ATGCATGAGG CTCTGCACAA CCACTACACG CAGAAGAGCC
1151 TCTCCCTGTC TCCGGGTAAA
```

The mature TGFβRII$_{SHORT}$-Fc fusion polypeptide (SEQ ID NO: 129) is as follows and may optionally be provided with the lysine removed from the C-terminus.

(SEQ ID NO: 129)
```
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE YNTSNPDTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVYTL PPSRKEMTKN QVSLTCLVKG FYPSDIAVEW

301 ESNGQPENNY KTTPPVLKSD GSFFLYSKLT VDKSRWQQGN VFSCSVMHEA

351 LHNHYTQKSL SLSPGK
```

The polypeptide sequence of the complementary ALK1-Fc fusion polypeptide and a nucleic acid sequence encoding it are provided in Example 16 as SEQ ID NOs: 124-126. To guide heterodimer formation with the TGFβRII$_{SHORT}$-Fc fusion polypeptide of SEQ ID NOs: 127 and 129, two amino acid substitutions (replacing lysines with aspartic acids) can be introduced into the Fc domain of the ALK1-Fc fusion polypeptide as indicated in Example 16. The amino acid sequences of SEQ ID NOs: 124 and 126 may optionally be provided with a lysine added at the C-terminus.

The TGFβRII$_{SHORT}$-Fc and ALK1-Fc proteins of SEQ ID NO: 129 and SEQ ID NO: 126, respectively, may be co-expressed and purified from a CHO cell line, to give rise to a heteromeric complex comprising TGFβRII$_{SHORT}$-Fc:ALK1-Fc.

A variant TGFβRII-Fc:ALK1-Fc heteromeric complex may be generated in which the ALK1-Fc polypeptide described above (SEQ ID NO: 126) is paired with an Fc fusion protein comprising the extracellular domain of the long (A) isoform of TGFβRII (TGFβRII$_{LONG}$) in place of the extracellular domain of the short isoform.

The TGFβRII$_{LONG}$-Fc polypeptide sequence (SEQ ID NO: 130) is shown below:

(SEQ ID NO: 130)
```
  1 MDAMKRGLCC VLLLCGAVFV SPGATIPPHV QKSDVEMEAQ KDEITCPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG THTCPPCPAP

201 ELLGGPSVFL FPPKPKDTLM ISRTPEVTCV VVDVSHEDPE VKFNWYVDGV

251 EVHNAKTKPR EEQYNSTYRV VSVLTVLHQD WLNGKEYKCK VSNKALPAPI

301 EKTISKAKGQ PREPQVYTLP PSRKEMTKNQ VSLTCLVKGF YPSDIAVEWE

351 SNGQPENNYK TTPPVLKSDG SFFLYSKLTV DKSRWQQGNV FSCSVMHEAL

401 HNHYTQKSLS LSPGK
```

The leader sequence and linker sequence are underlined. To promote formation of the TGFβRII$_{LONG}$-Fc:ALK1-Fc heterodimer rather than either of the possible homodimeric complexes, two amino acid substitutions (replacing acidic amino acids with lysine) can be introduced into the Fc domain of the TGFβRII$_{LONG}$-Fc fusion protein as indicated by double underline above. The amino acid sequence of SEQ ID NO: 130 may optionally be provided with the lysine removed from the C-terminus.

This TGFβRII$_{LONG}$-Fc fusion protein is encoded by the following nucleic acid sequence (SEQ ID NO: 131):

(SEQ ID NO: 131)
```
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT
```

-continued
```
151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGTGGA ACTCACACAT GCCCACCGTG CCCAGCACCT

601 GAACTCCTGG GGGACCGTC AGTCTTCCTC TTCCCCCCAA AACCCAAGGA

651 CACCCTCATG ATCTCCCGGA CCCCTGAGGT CACATGCGTG GTGGTGGACG

701 TGAGCCACGA AGACCCTGAG GTCAAGTTCA ACTGGTACGT GGACGGCGTG

751 GAGGTGCATA ATGCCAAGAC AAAGCCGCGG GAGGAGCAGT ACAACAGCAC

801 GTACCGTGTG GTCAGCGTCC TCACCGTCCT GCACCAGGAC TGGCTGAATG

851 GCAAGGAGTA CAAGTGCAAG GTCTCCAACA AAGCCCTCCC AGCCCCCATC

901 GAGAAAACCA TCTCCAAAGC CAAAGGGCAG CCCCGAGAAC CACAGGTGTA

951 CACCCTGCCC CCATCCCGGA AGGAGATGAC CAAGAACCAG GTCAGCCTGA

1001 CCTGCCTGGT CAAAGGCTTC TATCCCAGCG ACATCGCCGT GGAGTGGGAG

1051 AGCAATGGGC AGCCGGAGAA CAACTACAAG ACCACGCCTC CCGTGCTGAA

1101 GTCCGACGGC TCCTTCTTCC TCTATAGCAA GCTCACCGTG GACAAGAGCA

1151 GGTGGCAGCA GGGGAACGTC TTCTCATGCT CCGTGATGCA TGAGGCTCTG

1201 CACAACCACT ACACGCAGAA GAGCCTCTCC CTGTCTCCGG GTAAA
```

The mature TGFβRII$_{LONG}$-Fc fusion polypeptide (SEQ ID NO: 132) is as follows and may optionally be provided with the lysine removed from the C-terminus.

(SEQ ID NO: 132)
```
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PDTGGGTHTC PPCPAPELLG GPSVFLFPPK PKDTLMISRT

201 PEVTCVVVDV SHEDPEVKFN WYVDGVEVHN AKTKPREEQY NSTYRVVSVL

251 TVLHQDWLNG KEYKCKVSNK ALPAPIEKTI SKAKGQPREP QVYTLPPSRK

301 EMTKNQVSLT CLVKGFYPSD IAVEWESNGQ PENNYKTTPP VLKSDGSFFL

351 YSKLTVDKSR WQQGNVFSCS VMHEALHNHY TQKSLSLSPG K
```

In a second approach to promote the formation of heteromultimer complexes using asymmetric Fc fusion proteins, the Fc domains are altered to introduce complementary hydrophobic interactions and an additional intermolecular disulfide bond.

The TGFβRII$_{SHORT}$-Fc polypeptide sequence (SEQ ID NO: 415) is shown below:

```
                                                     (SEQ ID NO: 415)
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYNTSNP DTGGGTHTCP PCPAPELLGG PSVFLFPPKP KDTLMISRTP

201 EVTCVVVDVS HEDPEVKFNW YVDGVEVHNA KTKPREEQYN STYRVVSVLT

251 VLHQDWLNGK EYKCKVSNKA LPAPIEKTIS KAKGQPREPQ VYTLPPCREE

301 MTKNQVSLWC LVKGFYPSDI AVEWESNGQP ENNYKTTPPV LDSDGSFFLY

351 SKLTVDKSRW QQGNVFSCSV MHEALHNHYT QKSLSLSPGK
```

The leader sequence and linker sequence are underlined. To promote formation of the TGFβRII$_{SHORT}$-Fc:ALK1-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 415 may optionally be provided with the lysine removed from the C-terminus.

The mature TGFβRII$_{SHORT}$-Fc fusion polypeptide (SEQ ID NO: 416) is as follows and may optionally be provided with the lysine removed from the C-terminus.

```
                                                     (SEQ ID NO: 416)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE YNTSNPDTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVYTL PPCREEMTKN QVSLWCLVKG FYPSDIAVEW

301 ESNGQPENNY KTTPPVLDSD GSFFLYSKLT VDKSRWQQGN VFSCSVMHEA

351 LHNHYTQKSL SLSPGK
```

Polypeptide sequences of the complementary ALK1-Fc fusion polypeptide (SEQ ID NOs: 413 and 414) are discussed in Example 16. To guide heterodimer formation with the TGFβRII$_{SHORT}$-Fc fusion polypeptide of SEQ ID NOs: 415 and 416, four amino acid substitutions can be introduced into the Fc domain of the ALK1 fusion polypeptide as indicated in Example 16. The amino acid sequences of SEQ ID NOs: 413 and 414 may optionally be provided with the lysine removed from the C-terminus.

The TGFβRII$_{SHORT}$-Fc and ALK1-Fc proteins of SEQ ID NO: 416 and SEQ ID NO: 414, respectively, may be co-expressed and purified from a CHO cell line, to give rise to a heteromeric complex comprising TGFβRII-Fc:ALK1-Fc.

A variant TGFβRII-Fc:ALK1-Fc heteromeric complex may be generated in which the ALK1-Fc polypeptide described above (SEQ ID NO: 414) is paired with an Fc fusion protein comprising the extracellular domain of the long (A) isoform of TGFβRII (TGFβRII$_{LONG}$) in place of the extracellular domain of the short isoform.

The TGFβRII$_{LONG}$-Fc polypeptide sequence (SEQ ID NO: 417) is shown below:

(SEQ ID NO: 417)

```
  1 MDAMKRGLCC VLLLCGAVFV SPGATIPPHV QKSDVEMEAQ KDEITCPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG THTCPPCPAP

201 ELLGGPSVFL FPPKPKDTLM ISRTPEVTCV VVDVSHEDPE VKFNWYVDGV

251 EVHNAKTKPR EEQYNSTYRV VSVLTVLHQD WLNGKEYKCK VSNKALPAPI

301 EKTISKAKGQ PREPQVYTLP PCREEMTKNQ VSLWCLVKGF YPSDIAVEWE

351 SNGQPENNYK TTPPVLDSDG SFFLYSKLTV DKSRWQQGNV FSCSVMHEAL

401 HNHYTQKSLS LSPGK
```

The leader sequence and linker sequence are underlined. To promote formation of the TGFβRII$_{LONG}$-Fc:ALK1-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 417 may optionally be provided with the lysine removed from the C-terminus.

The mature TGFβRII$_{LONG}$-Fc fusion polypeptide (SEQ ID NO: 418) is as follows and may optionally be provided with the lysine removed from the C-terminus.

(SEQ ID NO: 418)

```
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PDTGGGTHTC PPCPAPELLG GPSVFLFPPK PKDTLMISRT

201 PEVTCVVVDV SHEDPEVKFN WYVDGVEVHN AKTKPREEQY NSTYRVVSVL

251 TVLHQDWLNG KEYKCKVSNK ALPAPIEKTI SKAKGQPREP QVYTLPPCRE

301 EMTKNQVSLW CLVKGFYPSD IAVEWESNGQ PENNYKTTPP VLDSDGSFFL

351 YSKLTVDKSR WQQGNVFSCS VMHEALHNHY TQKSLSLSPG K
```

The TGFβRII$_{LONG}$-Fc and ALK1-Fc proteins of SEQ ID NO: 418 and SEQ ID NO: 414, respectively, may be co-expressed and purified from a CHO cell line, to give rise to a heteromeric complex comprising TGFβRII$_{LONG}$-Fc:ALK1-Fc.

Purification of various TGFβRII-Fc:ALK1-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 25. Ligand Binding Profile of TGFβRII-Fc:ALK1-Fc Heterodimer Compared to TGFβRII-Fc Homodimer and ALK1-Fc Homodimer A Biacore™-based binding assay was used to compare ligand binding selectivity of the TGFβRII$_{SHORT}$-Fc:ALK1-Fc heterodimeric complex described above with that of TGFβRII$_{SHORT}$-Fc and ALK1-Fc homodimeric complexes. The TGFβRII$_{SHORT}$-Fc:ALK1-Fc heterodimer, TGFβRII$_{SHORT}$-Fc homodimer, and ALK1-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profile of TGFBRII$_{SHORT}$-Fc:ALK1-Fc heterodimer compared to TGFBRII$_{SHORT}$-Fc homodimer and ALK1-Fc homodimer

| | TGFBRII$_{SHORT}$-Fc homodimer | | | ALK1-Fc homodimer | | | TGFBRII$_{SHORT}$-Fc:ALK1-Fc heterodimer | | |
|---|---|---|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| BMP9 | No binding | | | $7.9 \times 10^6$ | $\mathbf{1.3 \times 10^{-4}}$ | 16 | $2.1 \times 10^7$ | $2.2 \times 10^{-3}$ | 110 |
| BMP10 | No binding | | | $1.7 \times 10^7$ | $\mathbf{1.1 \times 10^{-4}}$ | 6 | $1.2 \times 10^7$ | $\mathbf{9.6 \times 10^{-4}}$ | 78 |
| TGFβ1 | $4.2 \times 10^7$ | $1.1 \times 10^{-3}$ | 25 | No binding | | | Transient* | | >5300 |
| TGFβ2 | Transient* | | >44000 | No binding | | | No binding | | |
| TGFβ3 | $5.9 \times 10^7$ | $5.9 \times 10^{-3}$ | 99 | No binding | | | Transient* | | >4700 |

*Indeterminate due to transient nature of interaction

Example 26. Generation of a TGFβRII$_{SHORT}$-Fc:ALK5-Fc Heterodimer

Applicants constructed a soluble TGFβRII$_{SHORT}$-Fc:ALK5-Fc heteromeric complex comprising the extracellular domains of the human TGFβRII short (canonical) isoform and human ALK5, which are each separately fused to an Fc domain with a linker positioned between the extracellular domain and the Fc domain. The individual constructs are referred to as TGFβRII$_{SHORT}$-Fc fusion polypeptide and ALK5-Fc fusion polypeptide, respectively, and the sequences for each are provided herein.

Formation of heteromeric TGFβRII$_{SHORT}$-Fc:ALK5-Fc may be guided by approaches similar to those described in Example 1. In a first approach, one Fc domain is altered to introduce cationic amino acids at the interaction face, while the other Fc domain is altered to introduce anionic amino acids at the interaction face. The polypeptide sequence of the TGFβRII$_{SHORT}$-Fc fusion polypeptide and a nucleic acid sequence encoding it are provided above in Example 24 as SEQ ID NOs: 127-129. To promote formation of the TGFβRII$_{SHORT}$-Fc:ALK5-Fc heterodimer rather than either of the possible homodimeric complexes, two amino acid substitutions (replacing acidic amino acids with lysine) can be introduced into the Fc domain of the TGFβRII$_{SHORT}$-Fc fusion protein as indicated in Example 24. The amino acid sequences of SEQ ID NOs: 127 and 129 may optionally be provided with the lysine removed from the C-terminus.

The polypeptide sequence of the complementary ALK5-Fc fusion polypeptide and a nucleic acid sequence encoding it are provided in Example 11 as SEQ ID NOs: 139-141. To guide heterodimer formation with the TGFβRII$_{SHORT}$-Fc fusion polypeptide of SEQ ID NOs: 127 and 129, two amino acid substitutions (replacing lysines with aspartic acids) can be introduced into the Fc domain of the ALK5-Fc fusion polypeptide as indicated in Example 11. The amino acid sequences of SEQ ID NOs: 139 and 141 may optionally be provided with a lysine added at the C-terminus.

The TGFβRII$_{SHORT}$-Fc and ALK5-Fc fusion polypeptides of SEQ ID NO: 129 and SEQ ID NO: 141, respectively, may be co-expressed and purified from a CHO cell line, to give rise to a heteromeric complex comprising TGFβRII$_{SHORT}$-Fc:ALK5-Fc.

In a second approach to promote the formation of heteromultimer complexes using asymmetric Fc fusion proteins, the Fc domains are altered to introduce complementary hydrophobic interactions and an additional intermolecular disulfide bond. TGFβRII$_{SHORT}$-Fc fusion polypeptide sequences (SEQ ID NOs: 415-416) are discussed in Example 24. To promote formation of the TGFβRII$_{SHORT}$-Fc:ALK5-Fc heterodimer rather than either of the possible homodimeric complexes, two amino acid substitutions (replacing a serine with a cysteine and a threonine with a trytophan) can be introduced into the Fc domain of the TGFβRII$_{SHORT}$-Fc polypeptide as indicated in Example 24. The amino acid sequences of SEQ ID NOs: 415-416 may optionally be provided with the lysine removed from the C-terminus.

Polypeptide sequences of the complementary ALK5-Fc fusion polypeptide (SEQ ID NOs: 423-424) are discussed in Example 11. To guide heterodimer formation with the TGFβRII$_{SHORT}$-Fc fusion polypeptide of SEQ ID NOs: 415-416, four amino acid substitutions can be introduced into the Fc domain of the ALK5 fusion polypeptide as indicated in Example 11. The amino acid sequences of SEQ ID NOs: 423-424 may optionally be provided with the lysine removed from the C-terminus.

The TGFβRII$_{SHORT}$-Fc and ALK5-Fc fusion polypeptides of SEQ ID NO: 416 and SEQ ID NO: 424, respectively, may be co-expressed and purified from a CHO cell line, to give rise to a heteromeric complex comprising TGFβRII$_{SHORT}$-Fc:ALK5-Fc.

Purification of various TGFβRII$_{SHORT}$-Fc:ALK5-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 27. Generation of a TGFβRII$_{LONG}$-Fc:ALK5-Fc Heterodimer

Applicants constructed a soluble TGFβRII$_{LONG}$-Fc:ALK5-Fc heteromeric complex comprising the extracellular domain of the long (A) isoform of human TGFβRII and the extracellular domain of human ALK5, which are each separately fused to an Fc domain with a linker positioned between the extracellular domain and the Fc domain. The individual constructs are referred to as TGFβRII$_{LONG}$-Fc fusion polypeptide and ALK5-Fc fusion polypeptide, respectively, and the sequences for each are provided herein.

Formation of heteromeric TGFβRII$_{LONG}$-Fc:ALK5-Fc may be guided by approaches similar to those described in Example 1. In a first approach, one Fc domain is altered to introduce cationic amino acids at the interaction face, while the other Fc domain is altered to introduce anionic amino acids at the interaction face. The polypeptide sequence of the TGFβRII$_{LONG}$-Fc fusion polypeptide and a nucleic acid sequence encoding it are provided above in Example 24 as SEQ ID NOs: 130-132. To promote formation of the TGFβRII$_{LONG}$-Fc:ALK5-Fc heterodimer rather than either of the possible homodimeric complexes, two amino acid substitutions (replacing acidic amino acids with lysine) can be introduced into the Fc domain of the TGFβRII$_{LONG}$-Fc fusion protein as indicated in Example 24. The amino acid sequences of SEQ ID NOs: 130 and 132 may optionally be provided with the lysine removed from the C-terminus.

The polypeptide sequence of the complementary ALK5-Fc fusion polypeptide and a nucleic acid sequence encoding it are provided in Example 11 as SEQ ID NOs: 139-141. To guide heterodimer formation with the TGFβRII$_{LONG}$-Fc fusion polypeptide of SEQ ID NOs: 130 and 132, two amino acid substitutions (replacing lysines with aspartic acids) can be introduced into the Fc domain of the ALK5-Fc fusion polypeptide as indicated in Example 11. The amino acid sequences of SEQ ID NOs: 139 and 142 may optionally be provided with a lysine added at the C-terminus.

The TGFβRII$_{LONG}$-Fc and ALK5-Fc fusion polypeptides of SEQ ID NO: 132 and SEQ ID NO: 141, respectively, may be co-expressed and purified from a CHO cell line, to give rise to a heteromeric complex comprising TGFβRII$_{LONG}$-Fc:ALK5-Fc.

In a second approach to promote the formation of heteromultimer complexes using asymmetric Fc fusion proteins, the Fc domains are altered to introduce complementary hydrophobic interactions and an additional intermolecular disulfide bond. TGFβRII$_{LONG}$-Fc fusion polypeptide sequences (SEQ ID NOs: 417-418) are discussed in Example 24. To promote formation of the TGFβRII$_{LONG}$-Fc:ALK5-Fc heterodimer rather than either of the possible homodimeric complexes, two amino acid substitutions (replacing a serine with a cysteine and a threonine with a trytophan) can be introduced into the Fc domain of the TGFβRII$_{LONG}$-Fc polypeptide as indicated in Example 24. The amino acid sequences of SEQ ID NOs: 417-418 may optionally be provided with the lysine removed from the C-terminus.

Polypeptide sequences of the complementary ALK5-Fc fusion polypeptide (SEQ ID NOs: 423-424) are discussed in Example 11. To guide heterodimer formation with the TGFβRII$_{LONG}$-Fc fusion polypeptide of SEQ ID NOs: 417-418, four amino acid substitutions can be introduced into the Fc domain of the ALK5 fusion polypeptide as indicated in Example 11. The amino acid sequences of SEQ ID NOs: 423-424 may optionally be provided with the lysine removed from the C-terminus.

The TGFβRII$_{LONG}$-Fc and ALK5-Fc fusion polypeptides of SEQ ID NO: 418 and SEQ ID NO: 424, respectively, may be co-expressed and purified from a CHO cell line, to give rise to a heteromeric complex comprising TGFβRII$_{LONG}$-Fc:ALK5-Fc.

Purification of various TGFβRII$_{LONG}$-Fc:ALK5-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 28. Activity Profiles of TGFβRII-Fc:ALK5-Fc Heterodimers Compared to TGFβRII-Fc Homodimer and ALK5-Fc Homodimer A Biacore™-based binding assay was used to compare ligand binding selectivity of the TGFβRII$_{SHORT}$-Fc:ALK5-Fc and TGFβRII$_{LONG}$-Fc:ALK5-Fc heterodimeric complexes described in Examples 26-27 with that of TGFβRII$_{SHORT}$-Fc and ALK5-Fc homodimeric complexes. The heteromeric or homomeric protein complexes were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profiles of TGFβRII-Fc:ALK5-Fc heterodimers compared to TGFβRII-Fc homodimer and ALK5-Fc homodimer

| | ALK5-Fc Homodimer | | | TGFβRII$_{SHORT}$-Fc Homodimer | | | TGFβRII$_{SHORT}$:ALK5-Fc Heterodimer* | | | TGFβRII$_{LONG}$-Fc:ALK5-Fc Heterodimer* | | |
|---|---|---|---|---|---|---|---|---|---|---|---|---|
| Ligand | $k_a$ | $k_d$ | $K_D$ | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| TGFβ1 | No binding | | | $5.6 \times 10^7$ | $1.1 \times 10^{-3}$ | 20 | $1.4 \times 10^8$ | $1.7 \times 10^{-3}$ | 12 | $6.6 \times 10^7$ | $9.2 \times 10^{-4}$ | 14 |
| TGFβ2 | No binding | | | $2.1 \times 10^5$ | $2.2 \times 10^{-3}$ | 11000 | $6.6 \times 10^6$ | $2.9 \times 10^{-6}$ | 0.4 | $4.2 \times 10^6$ | $2.8 \times 10^{-7}$ | 0.07 |
| TGFβ3 | No binding | | | $1.9 \times 10^7$ | $1.4 \times 10^{-3}$ | 71 | $2.7 \times 10^7$ | $1.0 \times 10^{-3}$ | 38 | $2.7 \times 10^7$ | $1.0 \times 10^{-3}$ | 38 |

Figure 14:
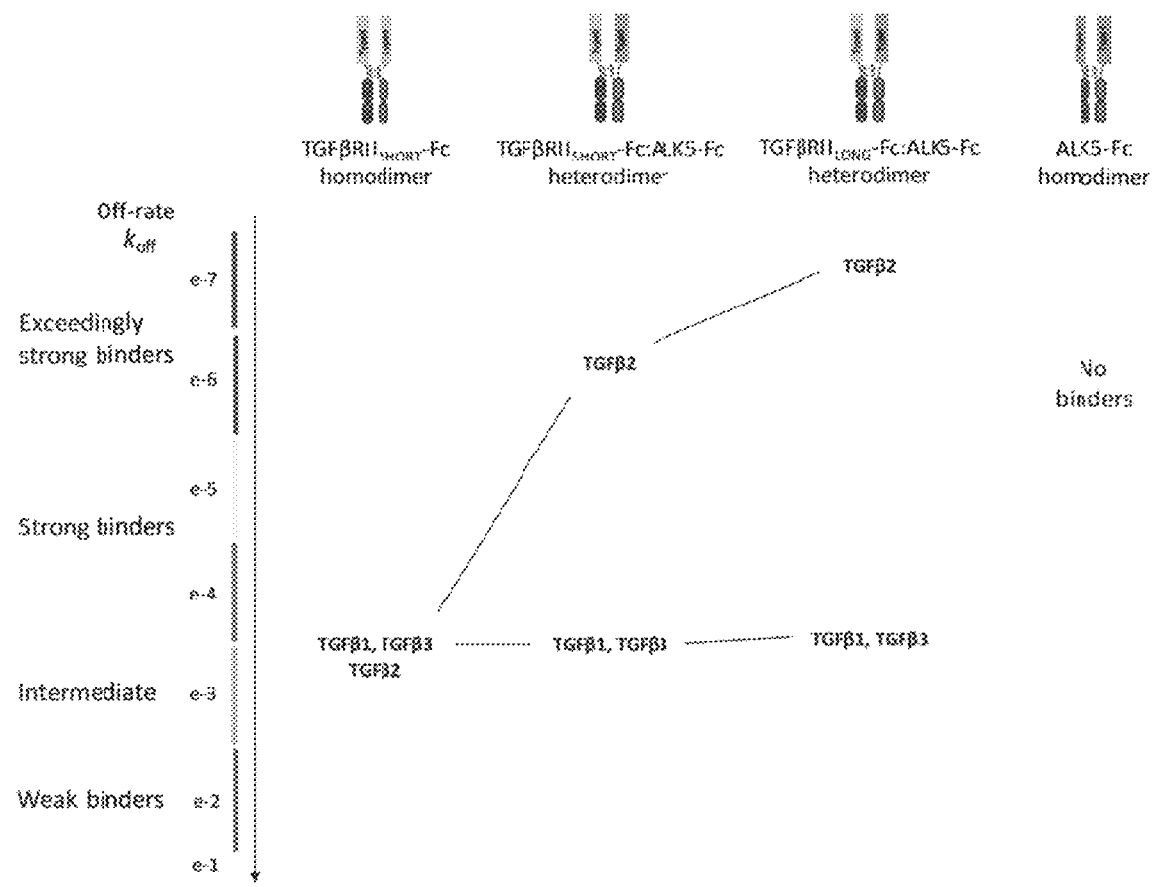
FIG. 14 shows ligand binding data for two different TGFβRII-Fc:ALK5-Fc heterodimeric protein complexes as compared to TGFβRII-Fc homodimer and ALK5-Fc homodimer. Format is the same as in FIG. 6. As shown, TGFβRII-Fc:ALK5-Fc heterodimers differ markedly from TGFβRII-Fc homodimer in their high selectivity for TGFβ2 while still retaining considerable affinity for TGFβ1 and TGFβ3. The heterodimer incorporating the long isoform of TGFβRII bound TGFβ2 more strongly and selectively than did its short-isoform counterpart. No ligands tested bind to ALK5-Fc homodimer.
Figure 15A:
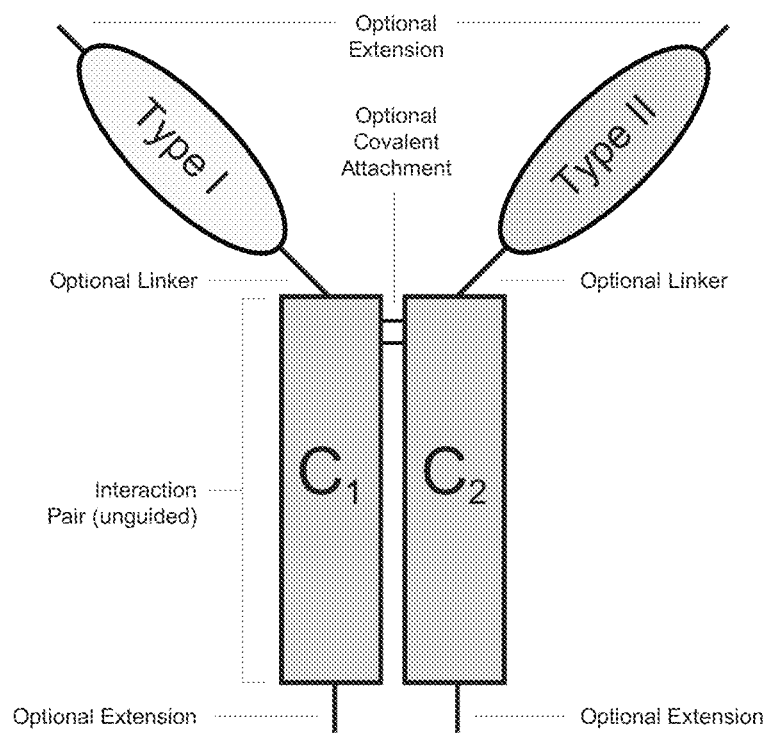
FIGS. 15A-15D show schematic examples of heteromeric protein complexes comprising a type I receptor polypeptide (indicated as "I") (e.g. a polypeptide that is at least 80%, 85%, 90%, 95%, 97%, 98%, 99% or 100% identical to an extracellular domain of an ALK1, ALK2, ALK3, ALK4, ALK5, ALK6 or ALK7 protein from humans or other species such as those described herein, e.g., SEQ ID Nos: 14, 15, 124, 126, 413, 414, 18, 19, 136, 138, 421, 422, 22, 23, 115, 117, 407, 408, 26, 27, 83, 84, 104, 106, 403, 404, 30, 31, 87, 88, 139, 141, 423, 424, 34, 35, 91, 92, 142, 144, 425, 426, 38, 39, 301, 302, 305, 306, 309, 310, 313, 112, 114, 405, and 406) and a type II receptor polypeptide (indicated as "II") (e.g. a polypeptide that is at least 80%, 85%, 90%, 95%, 97%, 98%, 99% or 100% identical to an extracellular domain of an ActRIIA, ActRIIB, MISRII, BMPRII, or TGFBRII protein from humans or other species such as those described herein, e.g., 9, 10, 11, 118, 120, 409, 410, 1, 2, 3, 4, 5, 6, 100, 102, 401, 402, 46, 47, 71, 72, 121, 123, 411, 412, 50, 51, 75, 76, 79, 80, 42, 43, 67, 68, 127, 129, 130, 132, 415, 416, 417, and 418). In the illustrated embodiments, the a type I receptor polypeptide is part of a fusion polypeptide that comprises a first member of an interaction pair ("$C_1$"), and a type II receptor polypeptide is part of a fusion polypeptide that comprises a second member of an interaction pair ("$C_2$"). Suitable interaction pairs included, for example, heavy chain and/or light chain immunoglobulin interaction pairs, truncations, and variants thereof such as those described herein [e.g., Spiess et al (2015) Molecular Immunology 67(2A): 95-106]. In each fusion polypeptide, a linker may be positioned between the a type I receptor polypeptide or a type II receptor polypeptide and the corresponding member of the interaction pair. The first and second members of the interaction pair may be unguided, meaning that the members of the pair may associate with each other or self-associate without substantial preference, and they may have the same or different amino acid sequences. See FIG. 15A. Alternatively, the interaction pair may be a guided (asymmetric) pair, meaning that the members of the pair associate preferentially with each other rather than self-associate. See FIG. 15B. Complexes of higher order can be envisioned. See FIGS. 15C and 15D.
Figure 15B:
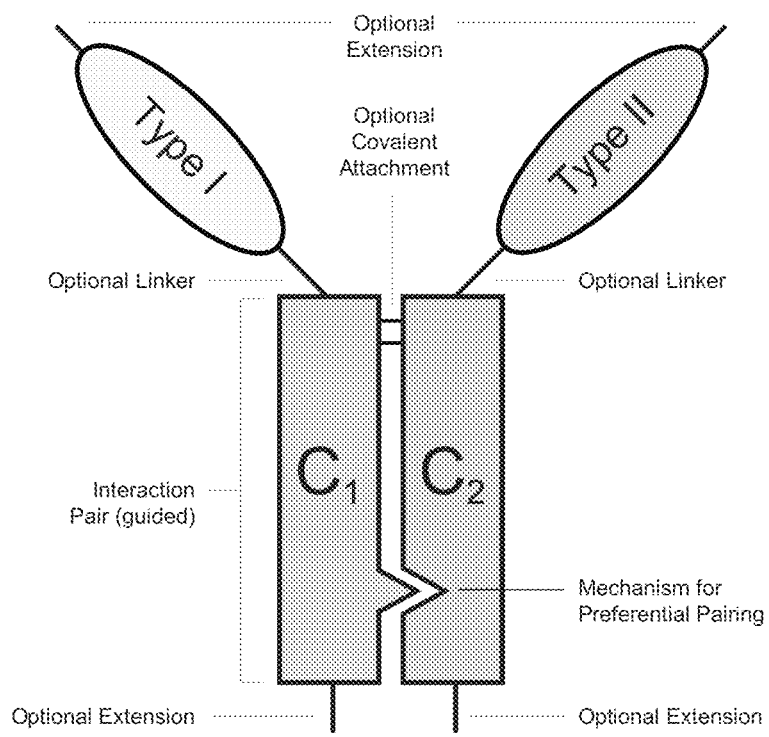
Figure 15C:
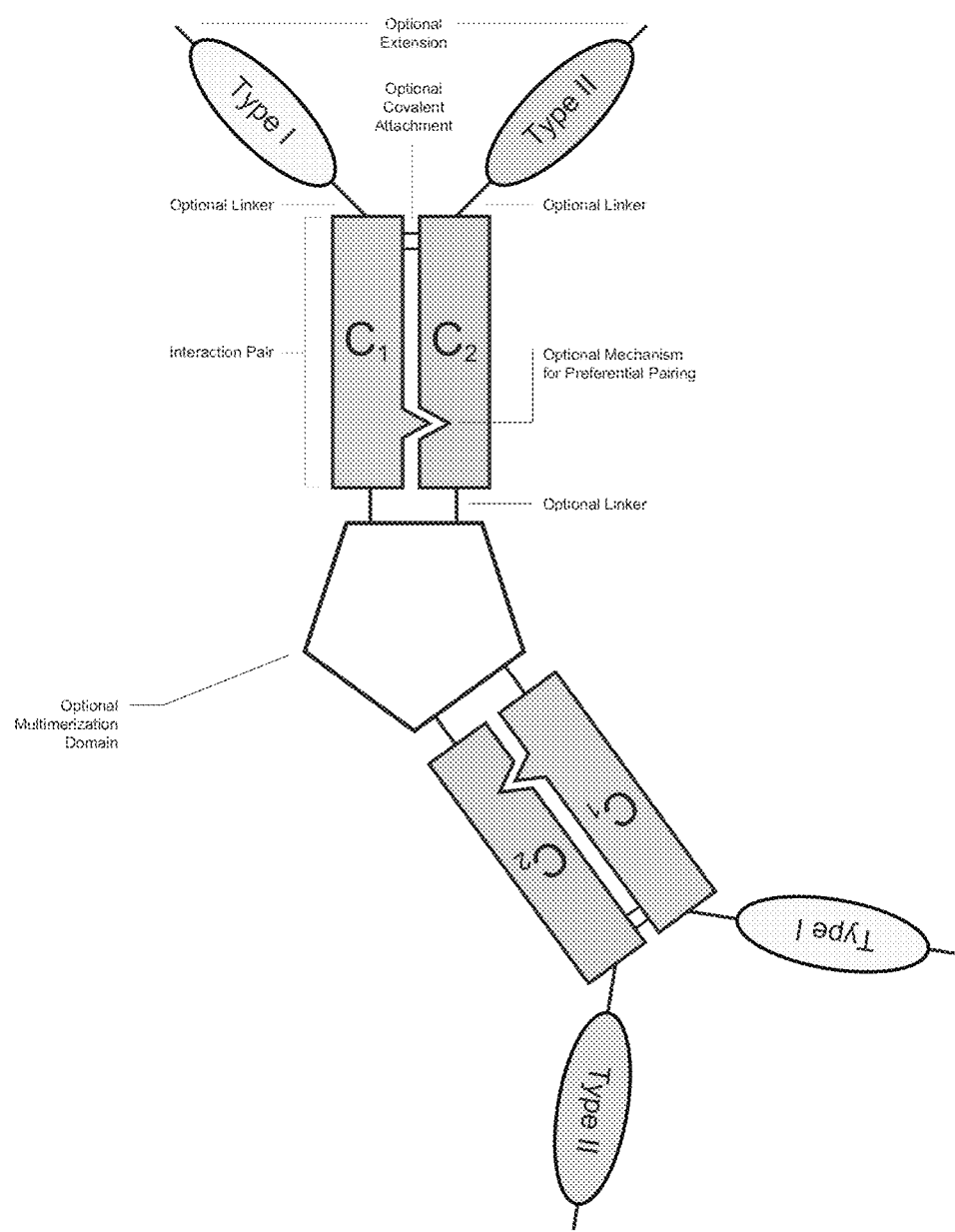
Figure 15D:
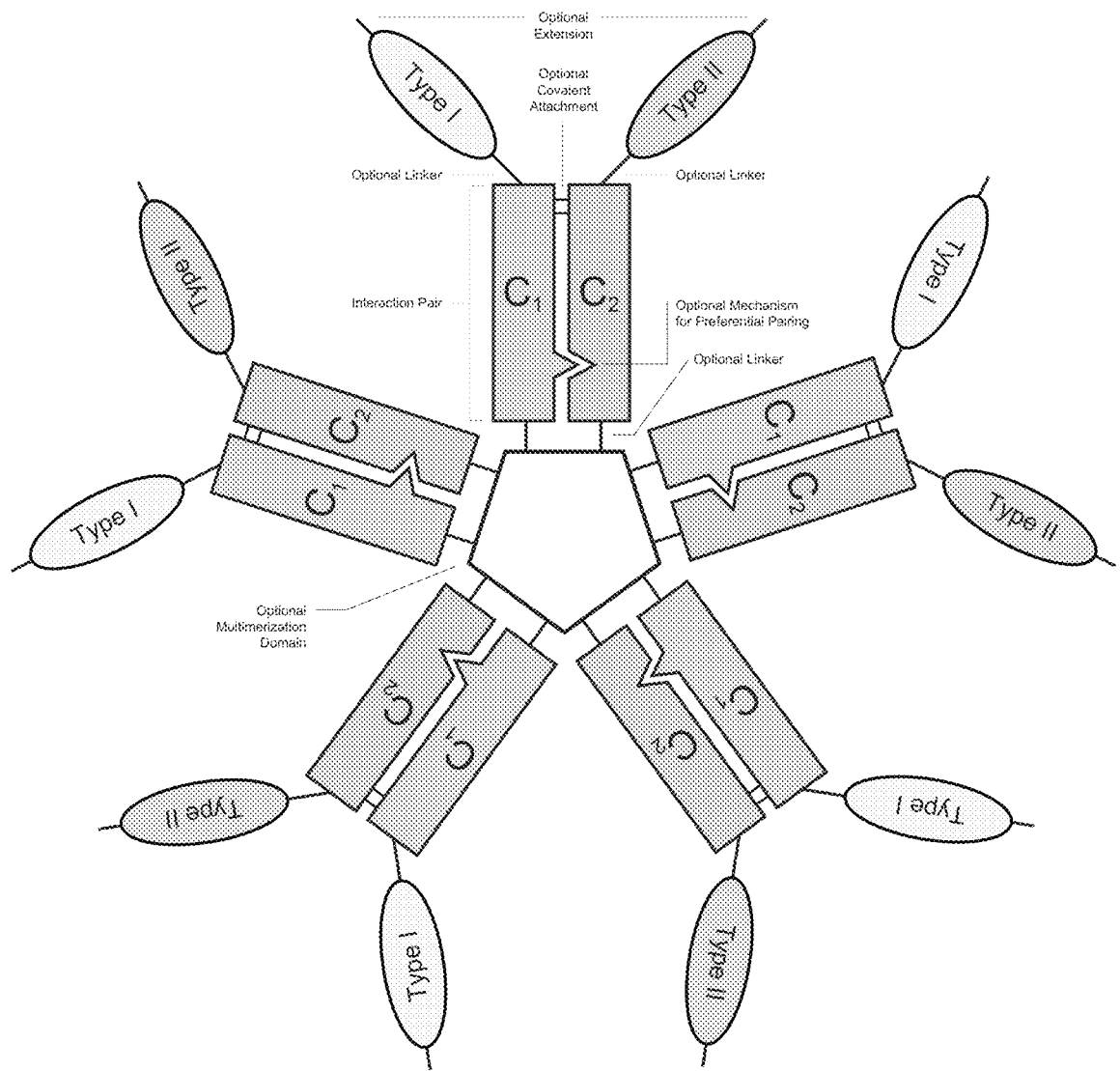

*Low signal which suggests that a substantial fraction of the protein is inactive These comparative binding data indicate that the ligand binding profiles of TGFβRII-Fc:ALK5-Fc heterodimers are markedly different from that of TGFβRII-Fc homodimer and from ALK5-Fc homodimer, which did not bind any ligands. Based on the equilibrium dissociation constant ($K_D$), TGFβRII-Fc homodimer bound TGFβ1 and TGFβ3 with much higher affinity than TGFβ1, even though off-rates for the three TGFβ ligands were similar. In contrast, TGFβRII-Fc:ALK5-Fc heterodimers displayed high selectivity for TGFβ2 over TGFβ1/TGFβ3. In particular, TGFβRII$_{LONG}$-Fc:ALK5-Fc heterodimer bound TGFβ2 with an affinity approximately five orders of magnitude higher and an off-rate approximately four orders of magnitude slower than did TGFβRII-Fc homodimer. TGFβRII$_{LONG}$-Fc:ALK5-Fc heterodimer also bound TGFβ2 more strongly than did heterodimer containing the short isoform. See FIG. 14. Neither of the TGFβRII-Fc:ALK5-Fc heterodimers was able to bind BMP9 or BMP10 (data not shown), which distinguishes these TGFβRII-Fc:ALK5-Fc heterodimers from TGFβRII-Fc:ALK1-Fc heterodimer (see Example 25). Sensograms for the two TGFβRII-Fc:ALK5-Fc heterodimers exhibited low signal amplitude which suggests that a substantial fraction of each protein was inactive.

To better interpret these data obtained by surface plasmon resonance, a reporter gene assay in A549 cells was used to determine the ability of TGFβRII fusion proteins to inhibit activity of TGFβ1, TGFβ2, and TGFβ3. This assay is based on a human lung carcinoma cell line transfected with reporter plasmids pGL3(CAGA)12-firefly luciferase (Dennler et al, 1998, EMBO 17: 3091-3100) and pRLCMV-Renilla luciferase, the latter to control for transfection efficiency. The CAGA motif is present in the promoters of TGFβ-responsive genes (for example, PAI-1), so this vector is of general use for factors signaling through SMAD2 and SMAD3.

On the first day of the assay, A549 cells (ATCC®: CCL-185™) were distributed in 48-well plates at $6.5 \times 10^4$ cells per well and incubated overnight. All incubations were at 37° C. and 5% $CO_2$ in a tissue culture incubator unless otherwise indicated. On the second day, a solution containing 10 μg pGL3(CAGA)12-firefly luciferase, 100 ng pRLCMV-Renilla luciferase, 30 μL X-tremeGENE 9 (Roche Applied Science), and 970 μL OptiMEM (Invitrogen) was preincubated for 30 min at room temperature, then added to 24 mL Eagle's minimum essential medium (EMEM, ATCC®) supplemented with 0.1% BSA. Medium was removed from the plated cells and this transfection mixture was applied to the cells (500 μl/well) for an overnight incubation. On the third day, medium was removed, and cells were incubated overnight with a mixture of ligands and inhibitors prepared as described below.

Serial dilutions of test articles were made in a 48-well plate in a 200 μL volume of assay buffer (EMEM+0.1% BSA). An equal volume of assay buffer containing the test ligand was added to obtain a final ligand concentration equal to the $EC_{50}$ determined previously. Human TGFβ1, TGFβ2, and TGFβ3 were obtained from PeproTech. Test solutions were incubated for 30 minutes, then 250 μL of the mixture was added to the transfected cells. Each concentration of test article was determined in duplicate. After incubation with test solutions overnight, cells were rinsed with phosphate-buffered saline, then lysed with passive lysis buffer (Promega E1941) and stored overnight at −70° C. On the fourth and final day, plates were warmed to room temperature with gentle shaking. Cell lysates were transferred to a chemiluminescence plate (96-well) and analyzed in a luminometer with reagents from a Dual-Luciferase Reporter Assay system (Promega E1980) to determine normalized luciferase activity.

This assay was used to compare the ability of TGFβRII fusion protein variants to inhibit cell signaling by TGFβRII ligands. Results are shown in the table below.

Inhibitory Activity of TGFβRII Fusion Proteins in A549 Cells

| Construct | $IC_{50}$ (pM) | | |
|---|---|---|---|
| | TGFβ1 (640 pg/mL) | TGFβ2 (480 pg/mL) | TGFβ3 (270 pg/mL) |
| TGFβRII$_{SHORT}$-Fc homodimer | 90 | — | 9 |
| TGFβRII$_{SHORT}$-Fc: ALK5-Fc heterodimer* | <350* | ~200* | <90* |
| TGFβRII$_{LONG}$-Fc: ALK5-Fc heterodimer | 204 | 154 | 35 |

— No inhibition (tested at concentrations up to 10 nM)
*Value imprecise due to range of concentrations tested Results with TGFβRII-Fc homodimer were consistent with previous reports concerning wild-type TGFβRII$_{SHORT}$-Fc and TGFβRII$_{LONG}$-Fc homodimers (del Re et al., J Biol Chem 279:22765, 2004). In this experiment, TGFβRII$_{SHORT}$-Fc homodimer potently inhibited TGFβ1 and TGFβ3 but was unable to inhibit TGFβ2 at homodimer concentrations up to 10 nM. This finding is consistent with the low affinity of TGFβ2 binding to TGFβRII-Fc homodimer but oddly inconsistent with its slow off-rate (see binding results above). In contrast, TGFβRII-Fc:ALK5-Fc heterodimers potently inhibited all three TGFβ ligands in a cellular environment. Accordingly, a TGFβRII-Fc:ALK5-Fc heterodimer will be unexpectedly useful in certain therapeutic applications where preferential antagonism of TGFβ2—or combined antagonism of TGFβ1, TGFβ2, and TGFβ3—are advantageous.

(SEQ ID NO: 7)

```
  1 ATGACGGCGC CTGGGTGGC CCTCGCCCTC CTCTGGGGAT CGCTGTGCGC

51 CGGCTCTGGG CGTGGGGAGG CTGAGACACG GGAGTGCATC TACTACAACG

101 CCAACTGGGA GCTGGAGCGC ACCAACCAGA GCGGCCTGGA GCGCTGCGAA

151 GGCGAGCAGG ACAAGCGGCT GCACTGCTAC GCCTCCTGGC GCAACAGCTC

201 TGGCACCATC GAGCTCGTGA AGAAGGGCTG CTGGCTAGAT GACTTCAACT

251 GCTACGATAG GCAGGAGTGT GTGGCCACTG AGGAGAACCC CCAGGTGTAC

301 TTCTGCTGCT GTGAAGGCAA CTTCTGCAAC GAACGCTTCA CTCATTTGCC

351 AGAGGCTGGG GGCCCGGAAG TCACGTACGA GCCACCCCCG ACAGCCCCCA

401 CCCTGCTCAC GGTGCTGGCC TACTCACTGC TGCCCATCGG GGGCCTTTCC

451 CTCATCGTCC TGCTGGCCTT TTGGATGTAC CGGCATCGCA AGCCCCCCTA

501 CGGTCATGTG GACATCCATG AGGACCCTGG GCCTCCACCA CCATCCCCTC

551 TGGTGGGCCT GAAGCCACTG CAGCTGCTGG AGATCAAGGC TCGGGGCGC

601 TTTGGCTGTG TCTGGAAGGC CCAGCTCATG AATGACTTTG TAGCTGTCAA

651 GATCTTCCCA CTCCAGGACA AGCAGTCGTG GCAGAGTGAA CGGGAGATCT

701 TCAGCACACC TGGCATGAAG CACGAGAACC TGCTACAGTT CATTGCTGCC
```

-continued

```
 751 GAGAAGCGAG GCTCCAACCT CGAAGTAGAG CTGTGGCTCA TCACGGCCTT

801 CCATGACAAG GGCTCCCTCA CGGATTACCT CAAGGGGAAC ATCATCACAT

851 GGAACGAACT GTGTCATGTA GCAGAGACGA TGTCACGAGG CCTCTCATAC

901 CTGCATGAGG ATGTGCCCTG GTGCCGTGGC GAGGGCCACA AGCCGTCTAT

951 TGCCCACAGG GACTTTAAAA GTAAGAATGT ATTGCTGAAG AGCGACCTCA

1001 CAGCCGTGCT GGCTGACTTT GGCTTGGCTG TTCGATTTGA GCCAGGGAAA

1051 CCTCCAGGGG ACACCCACGG ACAGGTAGGC ACGAGACGGT ACATGGCTCC

1101 TGAGGTGCTC GAGGGAGCCA TCAACTTCCA GAGAGATGCC TTCCTGCGCA

1151 TTGACATGTA TGCCATGGGG TTGGTGCTGT GGGAGCTTGT GTCTCGCTGC

1201 AAGGCTGCAG ACGGACCCGT GGATGAGTAC ATGCTGCCCT TTGAGGAAGA

1251 GATTGGCCAG CACCCTTCGT TGGAGGAGCT GCAGGAGGTG GTGGTGCACA

1301 AGAAGATGAG GCCCACCATT AAAGATCACT GGTTGAAACA CCCGGGCCTG

1351 GCCCAGCTTT GTGTGACCAT CGAGGAGTGC TGGGACCATG ATGCAGAGGC

1401 TCGCTTGTCC GCGGGCTGTG TGGAGGAGCG GGTGTCCCTG ATTCGGAGGT

1451 CGGTCAACGG CACTACCTCG GACTGTCTCG TTTCCCTGGT GACCTCTGTC

1501 ACCAATGTGG ACCTGCCCCC TAAAGAGTCA AGCATC
```

(SEQ ID NO: 8)

```
  1 GGGCGTGGGG AGGCTGAGAC ACGGGAGTGC ATCTACTACA ACGCCAACTG

51 GGAGCTGGAG CGCACCAACC AGAGCGGCCT GGAGCGCTGC GAAGGCGAGC

101 AGGACAAGCG GCTGCACTGC TACGCCTCCT GGCGCAACAG CTCTGGCACC

151 ATCGAGCTCG TGAAGAAGGG CTGCTGGCTA GATGACTTCA ACTGCTACGA

201 TAGGCAGGAG TGTGTGGCCA CTGAGGAGAA CCCCCAGGTG TACTTCTGCT

251 GCTGTGAAGG CAACTTCTGC AACGAACGCT TCACTCATTT GCCAGAGGCT

301 GGGGGCCCGG AAGTCACGTA CGAGCCACCC CCGACAGCCC CCACC
```

(SEQ ID NO: 12)

```
  1 ATGGGAGCTG CTGCAAAGTT GGCGTTTGCC GTCTTTCTTA TCTCCTGTTC

51 TTCAGGTGCT ATACTTGGTA GATCAGAAAC TCAGGAGTGT CTTTTCTTTA

101 ATGCTAATTG GGAAAAAGAC AGAACCAATC AAACTGGTGT TGAACCGTGT

151 TATGGTGACA AGATAAACG GCGGCATTGT TTTGCTACCT GGAAGAATAT

201 TTCTGGTTCC ATTGAAATAG TGAAACAAGG TTGTTGGCTG ATGATATCA

251 ACTGCTATGA CAGGACTGAT TGTGTAGAAA AAAAGACAG CCCTGAAGTA

301 TATTTTTGTT GCTGTGAGGG CAATATGTGT AATGAAAAGT TTTCTTATTT

351 TCCGGAGATG GAAGTCACAC AGCCCACTTC AAATCCAGTT ACACCTAAGC

401 CACCCTATTA CAACATCCTG CTCTATTCCT TGGTGCCACT TATGTTAATT

451 GCGGGGATTG TCATTTGTGC ATTTTGGGTG TACAGGCATC ACAAGATGGC

501 CTACCCTCCT GTACTTGTTC CAACTCAAGA CCCAGGACCA CCCCCACCTT

551 CTCCATTACT AGGTTTGAAA CCACTGCAGT TATTAGAAGT GAAAGCAAGG

601 GGAAGATTTG GTTGTGTCTG GAAAGCCCAG TTGCTTAACG AATATATGTGGC

651 TGTCAAAATA TTTCCAATAC AGGACAAACA GTCATGGCAA AATGAATACG

701 AAGTCTACAG TTTGCCTGGA ATGAAGCATG AGAACATATT ACAGTTCATT

751 GGTGCAGAAA AACGAGGCAC CAGTGTTGAT GTGGATCTTT GGCTGATCAC

801 AGCATTTCAT GAAAAGGGTT CACTATCAGA CTTTCTTAAG GCTAATGTGG
```

```
 851 TCTCTTGGAA TGAACTGTGT CATATTGCAG AAACCATGGC TAGAGGATTG

901 GCATATTTAC ATGAGGATAT ACCTGGCCTA AAAGATGGCC ACAAACCTGC

951 CATATCTCAC AGGGACATCA AAAGTAAAAA TGTGCTGTTG AAAAACAACC

1001 TGACAGCTTG CATTGCTGAC TTTGGGTTGG CCTTAAAATT TGAGGCTGGC

1051 AAGTCTGCAG GCGATACCCA TGGACAGGTT GGTACCCGGA GGTACATGGC

1101 TCCAGAGGTA TTAGAGGGTG CTATAAACTT CCAAAGGGAT GCATTTTTGA

1151 GGATAGATAT GTATGCCATG GGATTAGTCC TATGGGAACT GGCTTCTCGC

1201 TGTACTGCTG CAGATGGACC TGTAGATGAA TACATGTTGC CATTTGAGGA

1251 GGAAATTGGC CAGCATCCAT CTCTTGAAGA CATGCAGGAA GTTGTTGTGC

1301 ATAAAAAAAA GAGGCCTGTT TTAAGAGATT ATTGGCAGAA ACATGCTGGA

1351 ATGGCAATGC TCTGTGAAAC CATTGAAGAA TGTTGGGATC ACGACGCAGA

1401 AGCCAGGTTA TCAGCTGGAT GTGTAGGTGA AAGAATTACC CAGATGCAGA

1451 GACTAACAAA TATTATTACC ACAGAGGACA TTGTAACAGT GGTCACAATG

1501 GTGACAAATG TTGACTTTCC TCCCAAAGAA TCTAGTCTA
```

(SEQ ID NO: 13)
```
  1 ATACTTGGTA GATCAGAAAC TCAGGAGTGT CTTTTCTTTA ATGCTAATTG

51 GGAAAAAGAC AGAACCAATC AAACTGGTGT TGAACCGTGT TATGGTGACA

101 AAGATAAACG GCGGCATTGT TTTGCTACCT GGAAGAATAT TTCTGGTTCC

151 ATTGAAATAG TGAAACAAGG TTGTTGGCTG GATGATATCA ACTGCTATGA

201 CAGGACTGAT TGTGTAGAAA AAAAAGACAG CCCTGAAGTA TATTTTTGTT

251 GCTGTGAGGG CAATATGTGT AATGAAAAGT TTTCTTATTT TCCGGAGATG

301 GAAGTCACAC AGCCCACTTC AAATCCAGTT ACACCTAAGC CACCC
```

(SEQ ID NO: 44)

<u>ATGGGTCGGGGCTGCTCAGGGGCCTGTGGCCGCTGCACATCGTCCTGT</u>

<u>GGACGCGTATCGCCAGC</u>ACGATCCCACCGCACGTTCAGAAGTCGGTTAA

TAACGACATGATAGTCACTGACAACAACGGTGCAGTCAAGTTTCCACAA

CTGTGTAAATTTTGTGATGTGAGATTTTCCACCTGTGACAACCAGAAAT

CCTGCATGAGCAACTGCAGCATCACCTCCATCTGTGAGAAGCCACAGGA

AGTCTGTGTGGCTGTATGGAGAAAGAATGACGAGAACATAACACTAGAG

ACAGTTTGCCATGACCCCAAGCTCCCCTACCATGACTTTATTCTGGAAG

ATGCTGCTTCTCCAAAGTGCATTATGAAGGAAAAAAAAAAGCCTGGTGA

GACTTTCTTCATGTGTTCCTGTAGCTCTGATGAGTGCAATGACAACATC

ATCTTCTCAGAAGAATATAACACCAGCAATCCTGACTTGTTGCTAGTCA

TATTTCAAGTGACAGGCATCAGCCTCCTGCCACCACTGGGAGTTGCCAT

ATCTGTCATCATCATCTTCTACTGCTACCGCGTTAACCGGCAGCAGAAG

CTGAGTTCAACCTGGGAAACCGGCAAGACGCGGAAGCTCATGGAGTTCA

GCGAGCACTGTGCCATCATCCTGGAAGATGACCGCTCTGACATCAGCTC

CACGTGTGCCAACAACATCAACCACAACACAGAGCTGCTGCCCATTGAG

CTGGACACCCTGGTGGGGAAAGGTCGCTTTGCTGAGGTCTATAAGGCCA

AGCTGAAGCAGAACACTTCAGAGCAGTTTGAGACAGTGGCAGTCAAGAT

CTTTCCCTATGAGGAGTATGCCTCTTGGAAGACAGAGAAGGACATCTTC

-continued

TCAGACATCAATCTGAAGCATGAGAACATACTCCAGTTCCTGACGGCTG

AGGAGCGGAAGACGGAGTTGGGGAAACAATACTGGCTGATCACCGCCTT

CCACGCCAAGGGCAACCTACAGGAGTACCTGACGCGGCATGTCATCAGC

TGGGAGGACCTGCGCAAGCTGGGCAGCTCCCTCGCCCGGGGGATTGCTC

ACCTCCACAGTGATCACACTCCATGTGGGAGGCCCAAGATGCCCATCGT

GCACAGGGACCTCAAGAGCTCCAATATCCTCGTGAAGAACGACCTAACC

TGCTGCCTGTGTGACTTTGGGCTTTCCCTGCGTCTGGACCCTACTCTGT

CTGTGGATGACCTGGCTAACAGTGGGCAGGTGGGAACTGCAAGATACAT

GGCTCCAGAAGTCCTAGAATCCAGGATGAATTTGGAGAATGTTGAGTCC

TTCAAGCAGACCGATGTCTACTCCATGGCTCTGGTGCTCTGGGAAATGA

CATCTCGCTGTAATGCAGTGGGAGAAGTAAAAGATTATGAGCCTCCATT

TGGTTCCAAGGTGCGGGAGCACCCCTGTGTCGAAAGCATGAAGGACAAC

GTGTTGAGAGATCGAGGGCGACCAGAAATTCCCAGCTTCTGGCTCAACC

ACCAGGGCATCCAGATGGTGTGTGAGACGTTGACTGAGTGCTGGGACCA

CGACCCAGAGGCCCGTCTCACAGCCCAGTGTGTGGCAGAACGCTTCAGT

GAGCTGGAGCATCTGGACAGGCTCTCGGGGAGGAGCTGCTCGGAGGAGA

AGATTCCTGAAGACGGCTCCCTAAACACTACCAAA (SEQ ID NO: 45)

ACGATCCCACCGCACGTTCAGAAGTCGGTTAATAACGACATGATAGTCA

CTGACAACAACGGTGCAGTCAAGTTTCCACAACTGTGTAAATTTTGTGA

TGTGAGATTTTCCACCTGTGACAACCAGAAATCCTGCATGAGCAACTGC

AGCATCACCTCCATCTGTGAGAAGCCACAGGAAGTCTGTGTGGCTGTAT

GGAGAAAGAATGACGAGAACATAACACTAGAGACAGTTTGCCATGACCCC

AAGCTCCCCTACCATGACTTTATTCTGGAAGATGCTGCTTCTCCAAAGTG

CATTATGAAGGAAAAAAAAAAGCCTGGTGAGACTTTCTTCATGTGTTCC

TGTAGCTCTGATGAGTGCAATGACAACATCATCTTCTCAGAAGAATATA

ACACCAGCAATCCTGACTTGTTGCTAGTCATATTTCAA (SEQ ID NO: 69)

<u>ATGGGTCGGGGCTGCTCAGGGGCCTGTGGCCGCTGCACATCGTCCTGT</u>

<u>GGACGCGTATCGCCAGC</u>ACGATCCCACCGCACGTTCAGAAGTCGGATGT

GGAAATGGAGGCCCAGAAAGATGAAATCATCTGCCCCAGCTGTAATAGG

ACTGCCCATCCACTGAGACATATTAATAACGACATGATAGTCACTGACA

ACAACGGTGCAGTCAAGTTTCCACAACTGTGTAAATTTTGTGATGTGAG

ATTTTCCACCTGTGACAACCAGAAATCCTGCATGAGCAACTGCAGCATC

ACCTCCATCTGTGAGAAGCCACAGGAAGTCTGTGTGGCTGTATGGAGAA

AGAATGACGAGAACATAACACTAGAGACAGTTTGCCATGACCCCAAGCT

CCCCTACCATGACTTTATTCTGGAAGATGCTGCTTCTCCAAAGTGCATT

ATGAAGGAAAAAAAAAAGCCTGGTGAGACTTTCTTCATGTGTTCCTGTA

GCTCTGATGAGTGCAATGACAACATCATCTTCTCAGAAGAATATAACAC

CAGCAATCCTGACTTGTTGCTAGTCATATTTCAAGTGACAGGCATCAGC

CTCCTGCCACCACTGGGAGTTGCCATATCTGTCATCATCATCTTCTACT

GCTACCGCGTTAACCGGCAGCAGAAGCTGAGTTCAACCTGGGAAACCGG

-continued

```
CAAGACGCGGAAGCTCATGGAGTTCAGCGAGCACTGTGCCATCATCCTG

GAAGATGACCGCTCTGACATCAGCTCCACGTGTGCCAACAACATCAACC

ACAACACAGAGCTGCTGCCCATTGAGCTGGACACCCTGGTGGGGAAAGG

TCGCTTTGCTGAGGTCTATAAGGCCAAGCTGAAGCAGAACACTTCAGAG

CAGTTTGAGACAGTGGCAGTCAAGATCTTTCCCTATGAGGAGTATGCCT

CTTGGAAGACAGAGAAGGACATCTTCTCAGACATCAATCTGAAGCATGA

GAACATACTCCAGTTCCTGACGGCTGAGGAGCGGAAGACGGAGTTGGGG

AAACAATACTGGCTGATCACCGCCTTCCACGCCAAGGGCAACCTACAGG

AGTACCTGACGCGGCATGTCATCAGCTGGGAGGACCTGCGCAAGCTGGG

CAGCTCCCTCGCCCGGGGATTGCTCACCTCCACAGTGATCACACTCCA

TGTGGGAGGCCCAAGATGCCCATCGTGCACAGGGACCTCAAGAGCTCCA

ATATCCTCGTGAAGAACGACCTAACCTGCTGCCTGTGTGACTTTGGGCT

TTCCCTGCGTCTGGACCCTACTCTGTCTGTGGATGACCTGGCTAACAGT

GGGCAGGTGGGAACTGCAAGATACATGGCTCCAGAAGTCCTAGAATCCA

GGATGAATTTGGAGAATGTTGAGTCCTTCAAGCAGACCGATGTCTACTC

CATGGCTCTGGTGCTCTGGGAAATGACATCTCGCTGTAATGCAGTGGGA

GAAGTAAAAGATTATGAGCCTCCATTTGGTTCCAAGGTGCGGGAGCACC

CCTGTGTCGAAAGCATGAAGGACAACGTGTTGAGAGATCGAGGGCGACC

AGAAATTCCCAGCTTCTGGCTCAACCACCAGGGCATCCAGATGGTGTGT

GAGACGTTGACTGAGTGCTGGGACCACGACCCAGAGGCCCGTCTCACAG

CCCAGTGTGTGGCAGAACGCTTCAGTGAGCTGGAGCATCTGGACAGGCT

CTCGGGGAGGAGCTGCTCGGAGGAGAAGATTCCTGAAGACGGCTCCCTA

AACACTACCAAA
```

(SEQ ID NO: 70)
```
ACGATCCCACCGCACGTTCAGAAGTCGGATGTGGAAATGGAGGCCCAGA

AAGATGAAATCATCTGCCCCAGCTGTAATAGGACTGCCCATCCACTGAG

ACATATTAATAACGACATGATAGTCACTGACAACAACGGTGCAGTCAAG

TTTCCACAACTGTGTAAATTTTGTGATGTGAGATTTTCCACCTGTGACA

ACCAGAAATCCTGCATGAGCAACTGCAGCATCACCTCCATCTGTGAGAA

GCCACAGGAAGTCTGTGTGGCTGTATGGAGAAAGAATGACGAGAACATA

ACACTAGAGACAGTTTGCCATGACCCCAAGCTCCCCTACCATGACTTTA

TTCTGGAAGATGCTGCTTCTCCAAAGTGCATTATGAAGGAAAAAAAAAA

GCCTGGTGAGACTTTCTTCATGTGTTCCTGTAGCTCTGATGAGTGCAAT

GACAACATCATCTTCTCAGAAGAATATAACACCAGCAATCCTGACTTGT

TGCTAGTCATATTTCAA.
```

(SEQ ID NO: 48)
```
ATGACTTCCTCGCTGCAGCGGCCCTGGCGGGTGCCCTGGCTACCATGGA

CCATCCTGCTGGTCAGCACTGCGGCTGCTTCGCAGAATCAAGAACGGCT

ATGTGCGTTTAAAGATCCGTATCAGCAAGACCTTGGGATAGGTGAGAGT

AGAATCTCTCATGAAAATGGGACAATATTATGCTCGAAAGGTAGCACCT

GCTATGGCCTTTGGGAGAAATCAAAAGGGGACATAAATCTTGTAAAACA
```

-continued

```
AGGATGTTGGTCTCACATTGGAGATCCCCAAGAGTGTCACTATGAAGAA

TGTGTAGTAACTACCACTCCTCCCTCAATTCAGAATGGAACATACCGTT

TCTGCTGTTGTAGCACAGATTTATGTAATGTCAACTTTACTGAGAATTT

TCCACCTCCTGACACAACACCACTCAGTCCACCTCATTCATTTAACCGA

GATGAGACAATAATCATTGCTTTGGCATCAGTCTCTGTATTAGCTGTTT

TGATAGTTGCCTTATGCTTTGGATACAGAATGTTGACAGGAGACCGTAA

ACAAGGTCTTCACAGTATGAACATGATGGAGGCAGCAGCATCCGAACCC

TCTCTTGATCTAGATAATCTGAAACTGTTGGACTGATTGGCCGAGGTCG

ATATGGAGCAGTATATAAAGGCTCCTTGGATGAGCGTCCAGTTGCTGTA

AAAGTGTTTTCCTTTGCAAACCGTCAGAATTTTATCAACGAAAAGAACA

TTTACAGAGTGCCTTTGATGGAACATGACAACATTGCCCGCTTTATAGT

TGGAGATGAGAGAGTCACTGCAGATGGACGCATGGAATATTTGCTTGTG

ATGGAGTACTATCCCAATGGATCTTTATGCAAGTATTTAAGTCTCCACA

CAAGTGACTGGGTAAGCTCTTGCCGTCTTGCTCATTCTGTTACTAGAGG

ACTGGCTTATCTTCACACAGAATTACCACGAGGAGATCATTATAAACCT

GCAATTTCCCATCGAGATTTAAACAGCAGAAATGTCCTAGTGAAAAATG

ATGGAACCTGTGTTATTAGTGACTTTGGACTGTCCATGAGGCTGACTGG

AAATAGACTGGTGCGCCCAGGGGAGGAAGATAATGCAGCCATAAGCGAG

GTTGGCACTATCAGATATATGGCACCAGAAGTGCTAGAAGGAGCTGTGA

ACTTGAGGGACTGTGAATCAGCTTTGAAACAAGTAGACATGTATGCTCT

TGGACTAATCTATTGGGAGATATTTATGAGATGTACAGACCTCTTCCCA

GGGGAATCCGTACCAGAGTACCAGATGGCTTTTCAGACAGAGGTTGGAA

ACCATCCCACTTTTGAGGATATGCAGGTTCTCGTGTCTAGGGAAAAACA

GAGACCCAAGTTCCCAGAAGCCTGGAAAGAAAATAGCCTGGCAGTGAGG

TCACTCAAGGAGACAATCGAAGACTGTTGGGACCAGGATGCAGAGGCTC

GGCTTACTGCACAGTGTGCTGAGGAAAGGATGGCTGAACTTATGATGAT

TTGGGAAAGAAACAAATCTGTGAGCCCAACAGTCAATCCAATGTCTACT

GCTATGCAGAATGAACGCAACCTGTCACATAATAGGCGTGTGCCAAAAA

TTGGTCCTTATCCAGATTATTCTTCCTCCTCATACATTGAAGACTCTAT

CCATCATACTGACAGCATCGTGAAGAATATTTCCTCTGAGCATTCTATG

TCCAGCACACCTTTGACTATAGGGAAAAAAACCGAAATTCAATTAACT

ATGAACGACAGCAAGCACAAGCTCGAATCCCCAGCCCTGAAACAAGTGT

CACCAGCCTCTCCACCAACACAACAACCACAAACACCACAGGACTCACG

CCAAGTACTGGCATGACTACTATATCTGAGATGCCATACCCAGATGAAA

CAAATCTGCATACCACAAATGTTGCACAGTCAATTGGGCCAACCCCTGT

CTGCTTACAGCTGACAGAAGAAGACTTGGAAACCAACAAGCTAGACCCA

AAAGAAGTTGATAAGAACCTCAAGGAAAGCTCTGATGAGAATCTCATGG

AGCACTCTCTTAAACAGTTCAGTGGCCCAGACCCACTGAGCAGTACTAG

TTCTAGCTTGCTTTACCCACTCATAAAACTTGCAGTAGAAGCAACTGGA

CAGCAGGACTTCACACAGACTGCAAATGGCCAAGCATGTTTGATTCCTG

ATGTTCTGCCTACTCAGATCTATCCTCTCCCCAAGCAGCAGAACCTTCC
```

```
CAAGAGACCTACTAGTTTGCCTTTGAACACCAAAAATTCAACAAAAGAG

CCCCGGCTAAAATTTGGCAGCAAGCACAAATCAAACTTGAAACAAGTCG

AAACTGGAGTTGCCAAGATGAATACAATCAATGCAGCAGAACCTCATGT

GGTGACAGTCACCATGAATGGTGTGGCAGGTAGAAACCACAGTGTTAAC

TCCCATGCTGCCACAACCCAATATGCCAATGGGACAGTACTATCTGGCC

AAACAACCAACATAGTGACACATAGGGCCCAAGAAATGTTGCAGAATCA

GTTTATTGGTGAGGACACCCGGCTGAATATTAATTCCAGTCCTGATGAG

CATGAGCCTTTACTGAGACGAGAGCAACAAGCTGGCCATGATGAAGGTG

TTCTGGATCGTCTTGTGGACAGGAGGGAACGGCCACTAGAAGGTGGCCG

AACTAATTCCAATAACAACAACAGCAATCCATGTTCAGAACAAGATGTT

CTTGCACAGGGTGTTCCAAGCACAGCAGCAGATCCTGGGCCATCAAAGC

CCAGAAGAGCACAGAGGCCTAATTCTCTGGATCTTTCAGCCACAAATGT

CCTGGATGGCAGCAGTATACAGATAGGTGAGTCAACACAAGATGGCAAA

TCAGGATCAGGTGAAAAGATCAAGAAACGTGTGAAAACTCCCTATTCTC

TTAAGCGGTGGCGCCCCTCCACCTGGGTCATCTCCACTGAATCGCTGGA

CTGTGAAGTCAACAATAATGGCAGTAACAGGGCAGTTCATTCCAAATCC

AGCACTGCTGTTTACCTTGCAGAAGGAGGCACTGCTACAACCATGGTGT

CTAAAGATATAGGAATGAACTGTCTG
```

```
                                                    (SEQ ID NO: 49)
TCGCAGAATCAAGAACGGCTATGTGCGTTTAAAGATCCGTATCAGCAAG

ACCTTGGGATAGGTGAGAGTAGAATCTCTCATGAAAATGGGACAATATT

ATGCTCGAAAGGTAGCACCTGCTATGGCCTTTGGGAGAAATCAAAAGGG

GACATAAATCTTGTAAAACAAGGATGTTGGTCTCACATTGGAGATCCCC

AAGAGTGTCACTATGAAGAATGTGTAGTAACTACCACTCCTCCCTCAAT

TCAGAATGGAACATACCGTTTCTGCTGTTGTAGCACAGATTTATGTAAT

GTCAACTTTACTGAGAATTTTCCACCTCCTGACACAACACCACTCAGTC

CACCTCATTCATTTAACCGAGATGAGACA
```

```
                                                    (SEQ ID NO: 73)
ATGACTTCCTCGCTGCAGCGGCCCTGGCGGGTGCCCTGGCTACCATGGA

CCATCCTGCTGGTCAGCACTGCGGCTGCTTCGCAGAATCAAGAACGGCT

ATGTGCGTTTAAAGATCCGTATCAGCAAGACCTTGGGATAGGTGAGAGT

AGAATCTCTCATGAAAATGGGACAATATTATGCTCGAAAGGTAGCACCT

GCTATGGCCTTTGGGAGAAATCAAAAGGGGACATAAATCTTGTAAAACA

AGGATGTTGGTCTCACATTGGAGATCCCCAAGAGTGTCACTATGAAGAA

TGTGTAGTAACTACCACTCCTCCCTCAATTCAGAATGGAACATACCGTT

TCTGCTGTTGTAGCACAGATTTATGTAATGTCAACTTTACTGAGAATTT

TCCACCTCCTGACACAACACCACTCAGTCCACCTCATTCATTTAACCGA

GATGAGACAATAATCATTGCTTTGGCATCAGTCTCTGTATTAGCTGTTT

TGATAGTTGCCTTATGCTTTGGATACAGAATGTTGACAGGAGACCGTAA

ACAAGGTCTTCACAGTATGAACATGATGGAGGCAGCAGCATCCGAACCC

TCTCTTGATCTAGATAATCTGAAACTGTTGGAGCTGATTGGCCGAGGTC
```

-continued

```
GATATGGAGCAGTATATAAAGGCTCCTTGGATGAGCGTCCAGTTGCTGT

AAAAGTGTTTTCCTTTGCAAACCGTCAGAATTTTATCAACGAAAAGAAC

ATTTACAGAGTGCCTTTGATGGAACATGACAACATTGCCCGCTTTATAG

TTGGAGATGAGAGAGTCACTGCAGATGGACGCATGGAATATTTGCTTGT

GATGGAGTACTATCCCAATGGATCTTTATGCAAGTATTTAAGTCTCCAC

ACAAGTGACTGGGTAAGCTCTTGCCGTCTTGCTCATTCTGTTACTAGAG

GACTGGCTTATCTTCACACAGAATTACCACGAGGAGATCATTATAAACC

TGCAATTTCCCATCGAGATTTAAACAGCAGAAATGTCCTAGTGAAAAAT

GATGGAACCTGTGTTATTAGTGACTTTGGACTGTCCATGAGGCTGACTG

GAAATAGACTGGTGCGCCCAGGGGAGGAAGATAATGCAGCCATAAGCGA

GGTTGGCACTATCAGATATATGGCACCAGAAGTGCTAGAAGGAGCTGTG

AACTTGAGGGACTGTGAATCAGCTTTGAAACAAGTAGACATGTATGCTC

TTGGACTAATCTATTGGGAGATATTTATGAGATGTACAGACCTCTTCCC

AGGGGAATCCGTACCAGAGTACCAGATGGCTTTTCAGACAGAGGTTGGA

AACCATCCCACTTTTGAGGATATGCAGGTTCTCGTGTCTAGGGAAAAAC

AGAGACCCAAGTTCCCAGAAGCCTGGAAAGAAAATAGCCTGGCAGTGAG

GTCACTCAAGGAGACAATCGAAGACTGTTGGGACCAGGATGCAGAGGCT

CGGCTTACTGCACAGTGTGCTGAGGAAAGGATGGCTGAACTTATGATGA

TTTGGGAAAGAAACAAATCTGTGAGCCCAACAGTCAATCCAATGTCTAC

TGCTATGCAGAATGAACGTAGG
```

(SEQ ID NO: 74)

```
TCGCAGAATCAAGAACGGCTATGTGCGTTTAAAGATCCGTATCAGCAAG

ACCTTGGGATAGGTGAGAGTAGAATCTCTCATGAAAATGGGACAATATT

ATGCTCGAAAGGTAGCACCTGCTATGGCCTTTGGGAGAAATCAAAAGGG

GACATAAATCTTGTAAAACAAGGATGTTGGTCTCACATTGGAGATCCCC

AAGAGTGTCACTATGAAGAATGTGTAGTAACTACCACTCCTCCCTCAAT

TCAGAATGGAACATACCGTTTCTGCTGTTGTAGCACAGATTTATGTAAT

GTCAACTTTACTGAGAATTTTCCACCTCCTGACACAACACCACTCAGTC

CACCTCATTCATTTAACCGAGATGAGACA
```

(SEQ ID NO: 52)

```
ATGCTAGGGTCTTTGGGGCTTTGGGCATTACTTCCCACAGCTGTGGAAG

CACCCCCAAACAGGCGAACCTGTGTGTTCTTTGAGGCCCCTGGAGTGCG

GGGAAGCACAAAGACACTGGGAGAGCTGCTAGATACAGGCACAGAGCTC

CCCAGAGCTATCCGCTGCCTCTACAGCCGCTGCTGCTTTGGGATCTGGA

ACCTGACCCAAGACCGGGCACAGGTGGAAATGCAAGGATGCCGAGACAG

TGATGAGCCAGGCTGTGAGTCCCTCCACTGTGACCCAAGTCCCCGAGCC

CACCCCAGCCCTGGCTCCACTCTCTTCACCTGCTCCTGTGGCACTGACT

TCTGCAATGCCAATTACAGCCATCTGCCTCCTCCAGGGAGCCCTGGGAC

TCCTGGCTCCCAGGGTCCCCAGGCTGCCCCAGGTGAGTCCATCTGGATG

GCACTGGTGCTGCTGGGGCTGTTCCTCCTCCTCCTGCTGCTGCTGGGCA

GCATCATCTTGGCCCTGCTACAGCGAAAGAACTACAGAGTGCGAGGTGA

GCCAGTGCCAGAGCCAAGGCCAGACTCAGGCAGGGACTGGAGTGTGGAG
```

```
CTGCAGGAGCTGCCTGAGCTGTGTTTCTCCCAGGTAATCCGGGAAGGAG

GTCATGCAGTGGTTTGGGCCGGGCAGCTGCAAGGAAAACTGGTTGCCAT

CAAGGCCTTCCCACCGAGGTCTGTGGCTCAGTTCCAAGCTGAGAGAGCA

TTGTACGAACTTCCAGGCCTACAGCACGACCACATTGTCCGATTTATCA

CTGCCAGCCGGGGGGTCCTGGCCGCCTGCTCTCTGGGCCCCTGCTGGT

ACTGGAACTGCATCCCAAGGGCTCCCTGTGCCACTACTTGACCCAGTAC

ACCAGTGACTGGGGAAGTTCCCTGCGGATGGCACTGTCCCTGGCCCAGG

GCCTGGCATTTCTCCATGAGGAGCGCTGGCAGAATGGCCAATATAAACC

AGGTATTGCCCACCGAGATCTGAGCAGCCAGAATGTGCTCATTCGGGAA

GATGGATCGTGTGCCATTGGAGACCTGGGCCTTGCCTTGGTGCTCCCTG

GCCTCACTCAGCCCCCTGCCTGGACCCCTACTCAACCACAAGGCCCAGC

TGCCATCATGGAAGCTGGCACCCAGAGGTACATGGCACCAGAGCTCTTG

GACAAGACTCTGGACCTACAGGATTGGGGCATGGCCCTCCGACGAGCTG

ATATTTACTCTTTGGCTCTGCTCCTGTGGGAGATACTGAGCCGCTGCCC

AGATTTGAGGCCTGACAGCAGTCCACCACCCTTCCAACTGGCCTATGAG

GCAGAACTGGGCAATACCCCTACCTCTGATGAGCTATGGGCCTTGGCAG

TGCAGGAGAGGAGGCGTCCCTACATCCCATCCACCTGGCGCTGCTTTGC

CACAGACCCTGATGGGCTGAGGGAGCTCCTAGAAGACTGTTGGGATGCA

GACCCAGAAGCACGGCTGACAGCTGAGTGTGTACAGCAGCGCCTGGCTG

CCTTGGCCCATCCTCAAGAGAGCCACCCCTTTCCAGAGAGCTGTCCACG

TGGCTGCCCACCTCTCTGCCCAGAAGACTGTACTTCAATTCCTGCCCCT

ACCATCCTCCCCTGTAGGCCTCAGCGGAGTGCCTGCCACTTCAGCGTTC

AGCAAGGCCCTTGTTCCAGGAATCCTCAGCCTGCCTGTACCCTTTCTCC

TGTG
```

```
                                                  (SEQ ID NO: 53)
CCCCCAAACAGGCGAACCTGTGTGTTCTTTGAGGCCCCTGGAGTGCGGG

GAAGCACAAAGACACTGGGAGAGCTGCTAGATACAGGCACAGAGCTCCC

CAGAGCTATCCGCTGCCTCTACAGCCGCTGCTGCTTTGGGATCTGGAAC

CTGACCCAAGACCGGGCACAGGTGGAAATGCAAGGATGCCGAGACAGTG

ATGAGCCAGGCTGTGAGTCCCTCCACTGTGACCCAAGTCCCCGAGCCCA

CCCCAGCCCTGGCTCCACTCTCTTCACCTGCTCCTGTGGCACTGACTTC

TGCAATGCCAATTACAGCCATCTGCCTCCTCCAGGGAGCCCTGGGACTC

CTGGCTCCAGGGTCCCCAGGCTGCCCCAGGTGAGTCCATCTGGATGGC

ACTG
```

```
                                                  (SEQ ID NO: 77)
ATGCTAGGGTCTTTGGGGCTTTGGGCATTACTTCCCACAGCTGTGGAAG

CACCCCCAAACAGGCGAACCTGTGTGTTCTTTGAGGCCCCTGGAGTGCG

GGGAAGCACAAAGACACTGGGAGAGCTGCTAGATACAGGCACAGAGCTC

CCCAGAGCTATCCGCTGCCTCTACAGCCGCTGCTGCTTTGGGATCTGGA

ACCTGACCCAAGACCGGGCACAGGTGGAAATGCAAGGATGCCGAGACAG

TGATGAGCCAGGCTGTGAGTCCCTCCACTGTGACCCAAGTCCCCGAGCC
```

-continued
```
CACCCCAGCCCTGGCTCCACTCTCTTCACCTGCTCCTGTGGCACTGACT

TCTGCAATGCCAATTACAGCCATCTGCCTCCTCCAGGGAGCCCTGGGAC

TCCTGGCTCCCAGGGTCCCCAGGCTGCCCCAGGTGAGTCCATCTGGATG

GCACTGGTGCTGCTGGGGCTGTTCCTCCTCCTCCTGCTGCTGCTGGGCA

GCATCATCTTGGCCCTGCTACAGCGAAAGAACTACAGAGTGCGAGGTGA

GCCAGTGCCAGAGCCAAGGCCAGACTCAGGCAGGGACTGGAGTGTGGAG

CTGCAGGAGCTGCCTGAGCTGTGTTTCTCCCAGGTAATCCGGGAAGGAG

GTCATGCAGTGGTTTGGGCCGGGCAGCTGCAAGGAAAACTGGTTGCCAT

CAAGGCCTTCCCACCGAGGTCTGTGGCTCAGTTCCAAGCTGAGAGAGCA

TTGTACGAACTTCCAGGCCTACAGCACGACCACATTGTCCGATTTATCA

CTGCCAGCCGGGGGGTCCTGGCCGCCTGCTCTCTGGGCCCCTGCTGGT

ACTGGAACTGCATCCCAAGGGCTCCCTGTGCCACTACTTGACCCAGTAC

ACCAGTGACTGGGGAAGTTCCCTGCGGATGGCACTGTCCCTGGCCCAGG

GCCTGGCATTTCTCCATGAGGAGCGCTGGCAGAATGGCCAATATAAACC

AGGTATTGCCCACCGAGATCTGAGCAGCCAGAATGTGCTCATTCGGGAA

GATGGATCGTGTGCCATTGGAGACCTGGGCCTTGCCTTGGTGCTCCCTG

GCCTCACTCAGCCCCCTGCCTGGACCCCTACTCAACCACAAGGCCCAGC

TGCCATCATGGAAGCTGGCACCCAGAGGTACATGGCACCAGAGCTCTTG

GACAAGACTCTGGACCTACAGGATTGGGGCATGGCCCTCCGACGAGCTG

ATATTTACTCTTTGGCTCTGCTCCTGTGGGAGATACTGAGCCGCTGCCC

AGATTTGAGGCCTGCAGTCCACCACCCTTCCAACTGGCCTATGAGGCAG

AACTGGGCAATACCCCTACCTCTGATGAGCTATGGGCCTTGGCAGTGCA

GGAGAGGAGGCGTCCCTACATCCCATCCACCTGGCGCTGCTTTGCCACA

GACCCTGATGGGC

CCCCCAAACAGGCGAACCTGTGTGTTCTTTGAGGCCCCTGGAGTGCGGG

GAAGCACAAAGACACTGGGAGAGCTGCTAGATACAGGCACAGAGCTCCC

CAGAGCTATCCGCTGCCTCTACAGCCGCTGCTGCTTTGGGATCTGGAAC

CTGACCCAAGACCGGGCACAGGTGGAAATGCAAGGATGCCGAGACAGTG

ATGAGCCAGGCTGTGAGTCCCTCCACTGTGACCCAAGTCCCCGAGCCCA

CCCCAGCCCTGGCTCCACTCTCTTCACCTGCTCCTGTGGCACTGACTTC

TGCAATGCCAATTACAGCCATCTGCCTCCTCCAGGGAGCCCTGGGACTC

CTGGCTCCCAGGGTCCCCAGGCTGCCCCAGGTGAGTCCATCTGGATGGC

ACTG

ATGCTAGGGTCTTTGGGGCTTTGGGCATTACTTCCCACAGCTGTGGAAG

CACCCCCAAACAGGCGAACCTGTGTGTTCTTTGAGGCCCCTGGAGTGCG

GGGAAGCACAAAGACACTGGGAGAGCTGCTAGATACAGGCACAGAGCTC

CCCAGAGCTATCCGCTGCCTCTACAGCCGCTGCTGCTTTGGGATCTGGA

ACCTGACCCAAGACCGGGCACAGGTGGAAATGCAAGGATGCCGAGACAG

TGATGAGCCAGGCTGTGAGTCCCTCCACTGTGACCCAAGTCCCCGAGCC

CACCCCAGCCCTGGCTCCACTCTCTTCACCTGCTCCTGTGGCACTGACT
```

(SEQ ID NO: 78)

(SEQ ID NO: 81)

-continued

```
TCTGCAATGCCAATTACAGCCATCTGCCTCCTCCAGGGAGCCCTGGGAC
TCCTGGCTCCCAGGGTCCCCAGGCTGCCCCAGGTGAGTCCATCTGGATG
GCACTGGTGCTGCTGGGGCTGTTCCTCCTCCTCCTGCTGCTGCTGGGCA
GCATCATCTTGGCCCTGCTACAGCGAAAGAACTACAGAGTGCGAGGTGA
GCCAGTGCCAGAGCCAAGGCCAGACTCAGGCAGGGACTGGAGTGTGGAG
CTGCAGGAGCTGCCTGAGCTGTGTTTCTCCCAGGTAATCCGGGAAGGAG
GTCATGCAGTGGTTTGGGCCGGGCAGCTGCAAGGAAAACTGGTTGCCAT
CAAGGCCTTCCCACCGAGGTCTGTGGCTCAGTTCCAAGCTGAGAGAGCA
TTGTACGAACTTCCAGGCCTACAGCACGACCACATTGTCCGATTTATCA
CTGCCAGCCGGGGGGTCCTGGCCGCCTGCTCTCTGGGCCCTGCTGGT
ACTGGAACTGCATCCCAAGGGCTCCCTGTGCCACTACTTGACCCAGTAC
ACCAGTGACTGGGGAAGTTCCCTGCGGATGGCACTGTCCCTGGCCCAGG
GCCTGGCATTTCTCCATGAGGAGCGCTGGCAGAATGGCCAATATAAACC
AGGTATTGCCCACCGAGATCTGAGCAGCCAGAATGTGCTCATTCGGGAA
GATGGATCGTGTGCCATTGGAGACCTGGGCCTTGCCTTGGTGCTCCCTG
GCCTCACTCAGCCCCCTGCCTGGACCCCTACTCAACCACAAGGCCCAGC
TGCCATCATGGAAGACCCTGATGGGCTGAGGGAGCTCCTAGAAGACTGT
TGGGATGCAGACCCAGAAGCACGGCTGACAGCTGAGTGTGTACAGCAGC
GCCTGGCTGCCTTGGCCCATCCTCAAGAGAGCCACCCCTTTCCAGAGAG
CTGTCCACGTGGCTGCCCACCTCTCTGCCCAGAAGACTGTACTTCAATT
CCTGCCCCTACCATCCTCCCCTGTAGGCCTCAGCGGAGTGCCTGCCACT
TCAGCGTTCAGCAAGGCCCTTGTTCCAGGAATCCTCAGCCTGCCTGTAC
CCTTTCTCCTGTG
```

(SEQ ID NO: 82)

```
CCCCCAAACAGGCGAACCTGTGTGTTCTTTGAGGCCCCTGGAGTGCGGG
GAAGCACAAAGACACTGGGAGAGCTGCTAGATACAGGCACAGAGCTCCC
CAGAGCTATCCGCTGCCTCTACAGCCGCTGCTGCTTTGGGATCTGGAAC
CTGACCCAAGACCGGGCACAGGTGGAAATGCAAGGATGCCGAGACAGTG
ATGAGCCAGGCTGTGAGTCCCTCCACTGTGACCCAAGTCCCCGAGCCCA
CCCCAGCCCTGGCTCCACTCTCTTCACCTGCTCCTGTGGCACTGACTTC
TGCAATGCCAATTACAGCCATCTGCCTCCTCCAGGGAGCCCTGGGACTC
CTGGCTCCCAGGGTCCCCAGGCTGCCCCAGGTGAGTCCATCTGGATGGC
ACTG
```

(SEQ ID NO: 7)

```
  1 ATGACGGCGC CCTGGGTGGC CCTCGCCCTC CTCTGGGGAT CGCTGTGCGC
 51 CGGCTCTGGG CGTGGGGAGG CTGAGACACG GGAGTGCATC TACTACAACG
101 CCAACTGGGA GCTGGAGCGC ACCAACCAGA GCGGCCTGGA GCGCTGCGAA
151 GGCGAGCAGG ACAAGCGGCT GCACTGCTAC GCCTCCTGGC GCAACAGCTC
201 TGGCACCATC GAGCTCGTGA AGAAGGGCTG CTGGCTAGAT GACTTCAACT
251 GCTACGATAG GCAGGAGTGT GTGGCCACTG AGGAGAACCC CCAGGTGTAC
301 TTCTGCTGCT GTGAAGGCAA CTTCTGCAAC GAACGCTTCA CTCATTTGCC
```

-continued

```
 351 AGAGGCTGGG GGCCCGGAAG TCACGTACGA GCCACCCCCG ACAGCCCCCA

401 CCCTGCTCAC GGTGCTGGCC TACTCACTGC TGCCCATCGG GGGCCTTTCC

451 CTCATCGTCC TGCTGGCCTT TTGGATGTAC CGGCATCGCA AGCCCCCCTA

501 CGGTCATGTG GACATCCATG AGGACCCTGG GCCTCCACCA CCATCCCCTC

551 TGGTGGGCCT GAAGCCACTG CAGCTGCTGG AGATCAAGGC TCGGGGCGC

601 TTTGGCTGTG TCTGGAAGGC CCAGCTCATG AATGACTTTG TAGCTGTCAA

651 GATCTTCCCA CTCCAGGACA AGCAGTCGTG GCAGAGTGAA CGGGAGATCT

701 TCAGCACACC TGGCATGAAG CACGAGAACC TGCTACAGTT CATTGCTGCC

751 GAGAAGCGAG GCTCCAACCT CGAAGTAGAG CTGTGGCTCA TCACGGCCTT

801 CCATGACAAG GGCTCCCTCA CGGATTACCT CAAGGGGAAC ATCATCACAT

851 GGAACGAACT GTGTCATGTA GCAGAGACGA TGTCACGAGG CCTCTCATAC

901 CTGCATGAGG ATGTGCCCTG GTGCCGTGGC GAGGGCCACA AGCCGTCTAT

951 TGCCCACAGG GACTTTAAAA GTAAGAATGT ATTGCTGAAG AGCGACCTCA

1001 CAGCCGTGCT GGCTGACTTT GGCTTGGCTG TTCGATTTGA GCCAGGGAAA

1051 CCTCCAGGGG ACACCCACGG ACAGGTAGGC ACGAGACGGT ACATGGCTCC

1101 TGAGGTGCTC GAGGGAGCCA TCAACTTCCA GAGAGATGCC TTCCTGCGCA

1151 TTGACATGTA TGCCATGGGG TTGGTGCTGT GGGAGCTTGT GTCTCGCTGC

1201 AAGGCTGCAG ACGGACCCGT GGATGAGTAC ATGCTGCCCT TTGAGGAAGA

1251 GATTGGCCAG CACCCTTCGT TGGAGGAGCT GCAGGAGGTG GTGGTGCACA

1301 AGAAGATGAG GCCCACCATT AAAGATCACT GGTTGAAACA CCCGGGCCTG

1351 GCCCAGCTTT GTGTGACCAT CGAGGAGTGC TGGGACCATG ATGCAGAGGC

1401 TCGCTTGTCC GCGGGCTGTG TGGAGGAGCG GGTGTCCCTG ATTCGGAGGT

1451 CGGTCAACGG CACTACCTCG GACTGTCTCG TTTCCCTGGT GACCTCTGTC

1501 ACCAATGTGG ACCTGCCCCC TAAAGAGTCA AGCATC
```

(SEQ ID NO: 8)

```
  1 GGGCGTGGGG AGGCTGAGAC ACGGGAGTGC ATCTACTACA ACGCCAACTG

51 GGAGCTGGAG CGCACCAACC AGAGCGGCCT GGAGCGCTGC GAAGGCGAGC

101 AGGACAAGCG GCTGCACTGC TACGCCTCCT GGCGCAACAG CTCTGGCACC

151 ATCGAGCTCG TGAAGAAGGG CTGCTGGCTA GATGACTTCA ACTGCTACGA

201 TAGGCAGGAG TGTGTGGCCA CTGAGGAGAA CCCCCAGGTG TACTTCTGCT

251 GCTGTGAAGG CAACTTCTGC AACGAACGCT TCACTCATTT GCCAGAGGCT

301 GGGGGCCCGG AAGTCACGTA CGAGCCACCC CCGACAGCCC CCACC
```

(SEQ ID NO: 12)

```
  1 ATGGGAGCTG CTGCAAAGTT GGCGTTTGCC GTCTTTCTTA TCTCCTGTTC

51 TTCAGGTGCT ATACTTGGTA GATCAGAAAC TCAGGAGTGT CTTTTCTTTA

101 ATGCTAATTG GGAAAAAGAC AGAACCAATC AAACTGGTGT TGAACCGTGT

151 TATGGTGACA AAGATAAACG GCGGCATTGT TTTGCTACCT GGAAGAATAT

201 TTCTGGTTCC ATTGAAATAG TGAAACAAGG TTGTTGGCTG GATGATATCA

251 ACTGCTATGA CAGGACTGAT TGTGTAGAAA AAAAAGACAG CCCTGAAGTA

301 TATTTTTGTT GCTGTGAGGG CAATATGTGT AATGAAAAGT TTTCTTATTT

351 TCCGGAGATG GAAGTCACAC AGCCCACTTC AAATCCAGTT ACACCTAAGC

401 CACCCTATTA CAACATCCTG CTCTATTCCT TGGTGCCACT TATGTTAATT
```

-continued

```
 451 GCGGGGATTG TCATTTGTGC ATTTTGGGTG TACAGGCATC ACAAGATGGC
 501 CTACCCTCCT GTACTTGTTC CAACTCAAGA CCCAGGACCA CCCCCACCTT
 551 CTCCATTACT AGGTTTGAAA CCACTGCAGT TATTAGAAGT GAAAGCAAGG
 601 GGAAGATTTG GTTGTGTCTG GAAAGCCCAG TTGCTTAACG AATATGTGGC
 651 TGTCAAAATA TTTCCAATAC AGGACAAACA GTCATGGCAA ATGAATACG
 701 AAGTCTACAG TTTGCCTGGA ATGAAGCATG AGAACATATT ACAGTTCATT
 751 GGTGCAGAAA ACGAGGCAC CAGTGTTGAT GTGGATCTTT GGCTGATCAC
 801 AGCATTTCAT GAAAAGGGTT CACTATCAGA CTTTCTTAAG GCTAATGTGG
 851 TCTCTTGGAA TGAACTGTGT CATATTGCAG AAACCATGGC TAGAGGATTG
 901 GCATATTTAC ATGAGGATAT ACCTGGCCTA AAAGATGGCC ACAAACCTGC
 951 CATATCTCAC AGGGACATCA AAGTAAAAA TGTGCTGTTG AAAACAACC
1001 TGACAGCTTG CATTGCTGAC TTTGGGTTGG CCTTAAAATT TGAGGCTGGC
1051 AAGTCTGCAG GCGATACCCA TGGACAGGTT GGTACCCGGA GGTACATGGC
1101 TCCAGAGGTA TTAGAGGGTG CTATAAACTT CCAAAGGGAT GCATTTTTGA
1151 GGATAGATAT GTATGCCATG GGATTAGTCC TATGGGAACT GGCTTCTCGC
1201 TGTACTGCTG CAGATGGACC TGTAGATGAA TACATGTTGC CATTTGAGGA
1251 GGAAATTGGC CAGCATCCAT CTCTTGAAGA CATGCAGGAA GTTGTTGTGC
1301 ATAAAAAAA GAGGCCTGTT TTAAGAGATT ATTGGCAGAA ACATGCTGGA
1351 ATGGCAATGC TCTGTGAAAC CATTGAAGAA TGTTGGGATC ACGACGCAGA
1401 AGCCAGGTTA TCAGCTGGAT GTGTAGGTGA AAGAATTACC CAGATGCAGA
1451 GACTAACAAA TATTATTACC ACAGAGGACA TTGTAACAGT GGTCACAATG
1501 GTGACAAATG TTGACTTTCC TCCCAAGAA TCTAGTCTA
```

(SEQ ID NO: 13)

```
  1 ATACTTGGTA GATCAGAAAC TCAGGAGTGT CTTTTCTTTA ATGCTAATTG
 51 GGAAAAAGAC AGAACCAATC AAACTGGTGT TGAACCGTGT TATGGTGACA
101 AAGATAAACG GCGGCATTGT TTTGCTACCT GGAAGAATAT TTCTGGTTCC
151 ATTGAAATAG TGAAACAAGG TTGTTGGCTG GATGATATCA ACTGCTATGA
201 CAGGACTGAT TGTGTAGAAA AAAAGACAG CCCTGAAGTA TATTTTTGTT
251 GCTGTGAGGG CAATATGTGT AATGAAAAGT TTTCTTATTT TCCGGAGATG
301 GAAGTCACAC AGCCCACTTC AAATCCAGTT ACACCTAAGC CACCC
```

(SEQ ID NO: 44)

<u>ATGGGTCGGGGCTGCTCAGGGGCCTGTGGCCGCTGCACATCGTCCTGT</u>
<u>GGACGCGTATCGCCAGC</u>ACGATCCCACCGCACGTTCAGAAGTCGGTTAA
TAACGACATGATAGTCACTGACAACAACGGTGCAGTCAAGTTTCCACAA
CTGTGTAAATTTTGTGATGTGAGATTTTCCACCTGTGACAACCAGAAAT
CCTGCATGAGCAACTGCAGCATCACCTCCATCTGTGAGAAGCCACAGGA
AGTCTGTGTGGCTGTATGGAGAAAGAATGACGAGAACATAACACTAGAG
ACAGTTTGCCATGACCCCAAGCTCCCCTACCATGACTTTATTCTGGAAG
ATGCTGCTTCTCCAAAGTGCATTATGAAGGAAAAAAAAAAGCCTGGTGA
GACTTTCTTCATGTGTTCCTGTAGCTCTGATGAGTGCAATGACAACATC
ATCTTCTCAGAAGAATATAACACCAGCAATCCTGACTTGTTGCTAGTCA

-continued

```
TATTTCAAGTGACAGGCATCAGCCTCCTGCCACCACTGGGAGTTGCCAT
ATCTGTCATCATCATCTTCTACTGCTACCGCGTTAACCGGCAGCAGAAG
CTGAGTTCAACCTGGGAAACCGGCAAGACGCGGAAGCTCATGGAGTTCA
GCGAGCACTGTGCCATCATCCTGGAAGATGACCGCTCTGACATCAGCTC
CACGTGTGCCAACAACATCAACCACAACACAGAGCTGCTGCCCATTGAG
CTGGACACCCTGGTGGGGAAAGGTCGCTTTGCTGAGGTCTATAAGGCCA
AGCTGAAGCAGAACACTTCAGAGCAGTTTGAGACAGTGGCAGTCAAGAT
CTTTCCCTATGAGGAGTATGCCTCTTGGAAGACAGAGAAGGACATCTTC
TCAGACATCAATCTGAAGCATGAGAACATACTCCAGTTCCTGACGGCTG
AGGAGCGGAAGACGGAGTTGGGGAAACAATACTGGCTGATCACCGCCTT
CCACGCCAAGGGCAACCTACAGGAGTACCTGACGCGGCATGTCATCAGC
TGGGAGGACCTGCGCAAGCTGGGCAGCTCCCTCGCCCGGGGGATTGCTC
ACCTCCACAGTGATCACACTCCATGTGGGAGGCCCAAGATGCCCATCGT
GCACAGGGACCTCAAGAGCTCCAATATCCTCGTGAAGAACGACCTAACC
TGCTGCCTGTGTGACTTTGGGCTTTCCCTGCGTCTGGACCCTACTCTGT
CTGTGGATGACCTGGCTAACAGTGGGCAGGTGGGAACTGCAAGATACAT
GGCTCCAGAAGTCCTAGAATCCAGGATGAATTTGGAGAATGTTGAGTCC
TTCAAGCAGACCGATGTCTACTCCATGGCTCTGGTGCTCTGGGAAATGA
CATCTCGCTGTAATGCAGTGGGAGAAGTAAAAGATTATGAGCCTCCATT
TGGTTCCAAGGTGCGGGAGCACCCCTGTGTCGAAAGCATGAAGGACAAC
GTGTTGAGAGATCGAGGGCGACCAGAAATTCCCAGCTTCTGGCTCAACC
ACCAGGGCATCCAGATGGTGTGTGAGACGTTGACTGAGTGCTGGGACCA
CGACCCAGAGGCCCGTCTCACAGCCCAGTGTGTGGCAGAACGCTTCAGT
GAGCTGGAGCATCTGGACAGGCTCTCGGGGAGGAGCTGCTCGGAGGAGA
AGATTCCTGAAGACGGCTCCCTAAACACTACCAAA
```
(SEQ ID NO: 45)

```
ACGATCCCACCGCACGTTCAGAAGTCGGTTAATAACGACATGATAGTCA
CTGACAACAACGGTGCAGTCAAGTTTCCACAACTGTGTAAATTTTGTGA
TGTGAGATTTTCCACCTGTGACAACCAGAAATCCTGCATGAGCAACTGC
AGCATCACCTCCATCTGTGAGAAGCCACAGGAAGTCTGTGTGGCTGTAT
GGAGAAAGAATGACGAGAACATAACACTAGAGACAGTTTGCCATGACCC
CAAGCTCCCCTACCATGACTTTATTCTGGAAGATGCTGCTTCTCCAAAG
TGCATTATGAAGGAAAAAAAAAAGCCTGGTGAGACTTTCTTCATGTGTT
CCTGTAGCTCTGATGAGTGCAATGACAACATCATCTTCTCAGAAGAATA
TAACACCAGCAATCCTGACTTGTTGCTAGTCATATTTCAA
```
(SEQ ID NO: 69)

<u>ATGGGTCGGGGCTGCTCAGGGGCCTGTGGCCGCTGCACATCGTCCTGT</u>
<u>GGACGCGTATCGCCAGC</u>ACGATCCCACCGCACGTTCAGAAGTCGGATGT
GGAAATGGAGGCCCAGAAAGATGAAATCATCTGCCCCAGCTGTAATAGG
ACTGCCCATCCACTGAGACATATTAATAACGACATGATAGTCACTGACA
ACAACGGTGCAGTCAAGTTTCCACAACTGTGTAAATTTTGTGATGTGAG
ATTTTCCACCTGTGACAACCAGAAATCCTGCATGAGCAACTGCAGCATC

-continued

ACCTCCATCTGTGAGAAGCCACAGGAAGTCTGTGTGGCTGTATGGAGAA
AGAATGACGAGAACATAACACTAGAGACAGTTTGCCATGACCCCAAGCT
CCCCTACCATGACTTTATTCTGGAAGATGCTGCTTCTCCAAAGTGCATT
ATGAAGGAAAAAAAAAAGCCTGGTGAGACTTTCTTCATGTGTTCCTGTA
GCTCTGATGAGTGCAATGACAACATCATCTTCTCAGAAGAATATAACAC
CAGCAATCCTGACTTGTTGCTAGTCATATTTCAAGTGACAGGCATCAGC
CTCCTGCCACCACTGGGAGTTGCCATATCTGTCATCATCATCTTCTACT
GCTACCGCGTTAACCGGCAGCAGAAGCTGAGTTCAACCTGGGAAACCGG
CAAGACGCGGAAGCTCATGGAGTTCAGCGAGCACTGTGCCATCATCCTG
GAAGATGACCGCTCTGACATCAGCTCCACGTGTGCCAACAACATCAACC
ACAACACAGAGCTGCTGCCCATTGAGCTGGACACCCTGGTGGGGAAAGG
TCGCTTTGCTGAGGTCTATAAGGCCAAGCTGAAGCAGAACACTTCAGAG
CAGTTTGAGACAGTGGCAGTCAAGATCTTTCCCTATGAGGAGTATGCCT
CTTGGAAGACAGAGAAGGACATCTTCTCAGACATCAATCTGAAGCATGA
GAACATACTCCAGTTCCTGACGGCTGAGGAGCGGAAGACGGAGTTGGGG
AAACAATACTGGCTGATCACCGCCTTCCACGCCAAGGGCAACCTACAGG
AGTACCTGACGCGGCATGTCATCAGCTGGGAGGACCTGCGCAAGCTGGG
CAGCTCCCTCGCCCGGGGATTGCTCACCTCCACAGTGATCACACTCCA
TGTGGGAGGCCCAAGATGCCCATCGTGCACAGGGACCTCAAGAGCTCCA
ATATCCTCGTGAAGAACGACCTAACCTGCTGCCTGTGTGACTTTGGGCT
TTCCCTGCGTCTGGACCCTACTCTGTCTGTGGATGACCTGGCTAACAGT
GGGCAGGTGGGAACTGCAAGATACATGGCTCCAGAAGTCCTAGAATCCA
GGATGAATTTGGAGAATGTTGAGTCCTTCAAGCAGACCGATGTCTACTC
CATGGCTCTGGTGCTCTGGGAAATGACATCTCGCTGTAATGCAGTGGGA
GAAGTAAAAGATTATGAGCCTCCATTTGGTTCCAAGGTGCGGGAGCACC
CCTGTGTCGAAAGCATGAAGGACAACGTGTTGAGAGATCGAGGGCGACC
AGAAATTCCCAGCTTCTGGCTCAACCACCAGGGCATCCAGATGGTGTGT
GAGACGTTGACTGAGTGCTGGGACCACGACCCAGAGGCCCGTCTCACAG
CCCAGTGTGTGGCAGAACGCTTCAGTGAGCTGGAGCATCTGGACAGGCT
CTCGGGGAGGAGCTGCTCGGAGGAGAAGATTCCTGAAGACGGCTCCCTA
AACACTACCAAA

ACGATCCCACCGCACGTTCAGAAGTCGGATGTGGAAATGGAGGCCCAGA                              (SEQ ID NO: 70)
AAGATGAAATCATCTGCCCCAGCTGTAATAGGACTGCCCATCCACTGAG
ACATATTAATAACGACATGATAGTCACTGACAACAACGGTGCAGTCAAG
TTTCCACAACTGTGTAAATTTTGTGATGTGAGATTTTCCACCTGTGACA
ACCAGAAATCCTGCATGAGCAACTGCAGCATCACCTCCATCTGTGAGAA
GCCACAGGAAGTCTGTGTGGCTGTATGGAGAAAGAATGACGAGAACATA
ACACTAGAGACAGTTTGCCATGACCCCAAGCTCCCCTACCATGACTTTA
TTCTGGAAGATGCTGCTTCTCCAAAGTGCATTATGAAGGAAAAAAAAAA
GCCTGGTGAGACTTTCTTCATGTGTTCCTGTAGCTCTGATGAGTGCAAT

-continued

GACAACATCATCTTCTCAGAAGAATATAACACCAGCAATCCTGACTTGT

TGCTAGTCATATTTCAA.

(SEQ ID NO: 48)

<u>ATGACTTCCTCGCTGCAGCGGCCCTGGCGGGTGCCCTGGCTACCATGGA</u>

<u>CCATCCTGCTGGTCAGCACTGCGGCTGCTT</u>CGCAGAATCAAGAACGGCT

ATGTGCGTTTAAAGATCCGTATCAGCAAGACCTTGGGATAGGTGAGAGT

AGAATCTCTCATGAAAATGGGACAATATTATGCTCGAAAGGTAGCACCT

GCTATGGCCTTTGGGAGAAATCAAAAGGGGACATAAATCTTGTAAAACA

AGGATGTTGGTCTCACATTGGAGATCCCCAAGAGTGTCACTATGAAGAA

TGTGTAGTAACTACCACTCCTCCCTCAATTCAGAATGGAACATACCGTT

TCTGCTGTTGTAGCACAGATTTATGTAATGTCAACTTTACTGAGAATTT

TCCACCTCCTGACACAACACCACTCAGTCCACCTCATTCATTTAACCGA

GATGAGACAATAATCATTGCTTTGGCATCAGTCTCTGTATTAGCTGTTT

TGATAGTTGCCTTATGCTTTGGATACAGAATGTTGACAGGAGACCGTAA

ACAAGGTCTTCACAGTATGAACATGATGGAGGCAGCAGCATCCGAACCC

TCTCTTGATCTAGATAATCTGAAACTGTTGGAGCTGATTGGCCGAGGTC

GATATGGAGCAGTATATAAAGGCTCCTTGGATGAGCGTCCAGTTGCTGT

AAAAGTGTTTTCCTTTGCAAACCGTCAGAATTTTATCAACGAAAAGAAC

ATTTACAGAGTGCCTTTGATGGAACATGACAACATTGCCCGCTTTATAG

TTGGAGATGAGAGAGTCACTGCAGATGGACGCATGGAATATTTGCTTGT

GATGGAGTACTATCCCAATGGATCTTTATGCAAGTATTTAAGTCTCCAC

ACAAGTGACTGGGTAAGCTCTTGCCGTCTTGCTCATTCTGTTACTAGAG

GACTGGCTTATCTTCACACAGAATTACCACGAGGAGATCATTATAAACC

TGCAATTTCCCATCGAGATTTAAACAGCAGAAATGTCCTAGTGAAAAAT

GATGGAACCTGTGTTATTAGTGACTTTGGACTGTCCATGAGGCTGACTG

GAAATAGACTGGTGCGCCCAGGGGAGGAAGATAATGCAGCCATAAGCGA

GGTTGGCACTATCAGATATATGGCACCAGAAGTGCTAGAAGGAGCTGTG

AACTTGAGGGACTGTGAATCAGCTTTGAAACAAGTAGACATGTATGCTC

TTGGACTAATCTATTGGGAGATATTTATGAGATGTACAGACCTCTTCCC

AGGGGAATCCGTACCAGAGTACCAGATGGCTTTTCAGACAGAGGTTGGA

AACCATCCCACTTTTGAGGATATGCAGGTTCTCGTGTCTAGGGAAAAAC

AGAGACCCAAGTTCCCAGAAGCCTGGAAAGAAAATAGCCTGGCAGTGAG

GTCACTCAAGGAGACAATCGAAGACTGTTGGGACCAGGATGCAGAGGCT

CGGCTTACTGCACAGTGTGCTGAGGAAAGGATGGCTGAACTTATGATGA

TTTGGGAAAGAAACAAATCTGTGAGCCCAACAGTCAATCCAATGTCTAC

TGCTATGCAGAATGAACGCAACCTGTCACATAATAGGCGTGTGCCAAAA

ATTGGTCCTTATCCAGATTATTCTTCCTCCTCATACATTGAAGACTCTA

TCCATCATACTGACAGCATCGTGAAGAATATTTCCTCTGAGCATTCTAT

GTCCAGCACACCTTTGACTATAGGGGAAAAAAACCGAAATTCAATTAAC

TATGAACGACAGCAAGCACAAGCTCGAATCCCCAGCCCTGAAACAAGTG

TCACCAGCCTCTCCACCAACACAACAACCACAAACACCACAGGACTCAC

```
GCCAAGTACTGGCATGACTACTATATCTGAGATGCCATACCCAGATGAA

ACAAATCTGCATACCACAAATGTTGCACAGTCAATTGGGCCAACCCCTG

TCTGCTTACAGCTGACAGAAGAAGACTTGGAAACCAACAAGCTAGACCC

AAAAGAAGTTGATAAGAACCTCAAGGAAAGCTCTGATGAGAATCTCATG

GAGCACTCTCTTAAACAGTTCAGTGGCCCAGACCCACTGAGCAGTACTA

GTTCTAGCTTGCTTTACCCACTCATAAAACTTGCAGTAGAAGCAACTGG

ACAGCAGGACTTCACACAGACTGCAAATGGCCAAGCATGTTTGATTCCT

GATGTTCTGCCTACTCAGATCTATCCTCTCCCCAAGCAGCAGAACCTTC

CCAAGAGACCTACTAGTTTGCCTTTGAACACCAAAAATTCAACAAAAGA

GCCCCGGCTAAAATTTGGCAGCAAGCACAAATCAAACTTGAAACAAGTC

GAAACTGGAGTTGCCAAGATGAATACAATCAATGCAGCAGAACCTCATG

TGGTGACAGTCACCATGAATGGTGTGGCAGGTAGAAACCACAGTGTTAA

CTCCCATGCTGCCACAACCCAATATGCCAATGGGACAGTACTATCTGGC

CAAACAACCAACATAGTGACACATAGGGCCCAAGAAATGTTGCAGAATC

AGTTTATTGGTGAGGACACCCGGCTGAATATTAATTCCAGTCCTGATGA

GCATGAGCCTTTACTGAGACGAGAGCAACAAGCTGGCCATGATGAAGGT

GTTCTGGATCGTCTTGTGGACAGGAGGGAACGGCCACTAGAAGGTGGCC

GAACTAATTCCAATAACAACAACAGCAATCCATGTTCAGAACAAGATGT

TCTTGCACAGGGTGTTCCAAGCACAGCAGCAGATCCTGGGCCATCAAAG

CCCAGAAGAGCACAGAGGCCTAATTCTCTGGATCTTTCAGCCACAAATG

TCCTGGATGGCAGCAGTATACAGATAGGTGAGTCAACACAAGATGGCAA

ATCAGGATCAGGTGAAAAGATCAAGAAACGTGTGAAAACTCCCTATTCT

CTTAAGCGGTGGCGCCCCTCCACCTGGGTCATCTCCACTGAATCGCTGG

ACTGTGAAGTCAACAATAATGGCAGTAACAGGGCAGTTCATTCCAAATC

CAGCACTGCTGTTTACCTTGCAGAAGGAGGCACTGCTACAACCATGGTG

TCTAAAGATATAGGAATGAACTGTCTG
                                                  (SEQ ID NO: 49)
TCGCAGAATCAAGAACGGCTATGTGCGTTTAAAGATCCGTATCAGCAAG

ACCTTGGGATAGGTGAGAGTAGAATCTCTCATGAAAATGGGACAATATT

ATGCTCGAAAGGTAGCACCTGCTATGGCCTTTGGGAGAAATCAAAAGGG

GACATAAATCTTGTAAAACAAGGATGTTGGTCTCACATTGGAGATCCCC

AAGAGTGTCACTATGAAGAATGTGTAGTAACTACCACTCCTCCCTCAAT

TCAGAATGGAACATACCGTTTCTGCTGTTGTAGCACAGATTTATGTAAT

GTCAACTTTACTGAGAATTTTCCACCTCCTGACACAACACCACTCAGTC

CACCTCATTCATTTAACCGAGATGAGACA
                                                  (SEQ ID NO: 73)
ATGACTTCCTCGCTGCAGCGGCCCTGGCGGGTGCCCTGGCTACCATGGA

CCATCCTGCTGGTCAGCACTGCGGCTGCTTCGCAGAATCAAGAACGGCT

ATGTGCGTTTAAAGATCCGTATCAGCAAGACCTTGGGATAGGTGAGAGT

AGAATCTCTCATGAAAATGGGACAATATTATGCTCGAAAGGTAGCACCT

GCTATGGCCTTTGGGAGAAATCAAAAGGGGACATAAATCTTGTAAAACA
```

```
                                                              -continued
AGGATGTTGGTCTCACATTGGAGATCCCCAAGAGTGTCACTATGAAGAA

TGTGTAGTAACTACCACTCCTCCCTCAATTCAGAATGGAACATACCGTT

TCTGCTGTTGTAGCACAGATTTATGTAATGTCAACTTTACTGAGAATTT

TCCACCTCCTGACACAACACCACTCAGTCCACCTCATTCATTTAACCGA

GATGAGACAATAATCATTGCTTTGGCATCAGTCTCTGTATTAGCTGTTT

TGATAGTTGCCTTATGCTTTGGATACAGAATGTTGACAGGAGACCGTAA

ACAAGGTCTTCACAGTATGAACATGATGGAGGCAGCAGCATCCGAACCC

TCTCTTGATCTAGATAATCTGAAACTGTTGGAGCTGATTGGCCGAGGTC

GATATGGAGCAGTATATAAAGGCTCCTTGGATGAGCGTCCAGTTGCTGT

AAAAGTGTTTTCCTTTGCAAACCGTCAGAATTTTATCAACGAAAAGAAC

ATTTACAGAGTGCCTTTGATGGAACATGACAACATTGCCCGCTTTATAG

TTGGAGATGAGAGAGTCACTGCAGATGGACGCATGGAATATTTGCTTGT

GATGGAGTACTATCCCAATGGATCTTTATGCAAGTATTTAAGTCTCCAC

ACAAGTGACTGGGTAAGCTCTTGCCGTCTTGCTCATTCTGTTACTAGAG

GACTGGCTTATCTTCACACAGAATTACCACGAGGAGATCATTATAAACC

TGCAATTTCCCATCGAGATTTAAACAGCAGAAATGTCCTAGTGAAAAAT

GATGGAACCTGTGTTATTAGTGACTTTGGACTGTCCATGAGGCTGACTG

GAAATAGACTGGTGCGCCCAGGGGAGGAAGATAATGCAGCCATAAGCGA

GGTTGGCACTATCAGATATATGGCACCAGAAGTGCTAGAAGGAGCTGTG

AACTTGAGGGACTGTGAATCAGCTTTGAAACAAGTAGACATGTATGCTC

TTGGACTAATCTATTGGGAGATATTTATGAGATGTACAGACCTCTTCCC

AGGGGAATCCGTACCAGAGTACCAGATGGCTTTTCAGACAGAGGTTGGA

AACCATCCCACTTTTGAGGATATGCAGGTTCTCGTGTCTAGGGAAAAAC

AGAGACCCAAGTTCCCAGAAGCCTGGAAAGAAAATAGCCTGGCAGTGAG

GTCACTCAAGGAGACAATCGAAGACTGTTGGGACCAGGATGCAGAGGCT

CGGCTTACTGCACAGTGTGCTGAGGAAAGGATGGCTGAACTTATGATGA

TTTGGGAAAGAAACAAATCTGTGAGCCCAACAGTCAATCCAATGTCTAC

TGCTATGCAGAATGAACGTAGG (SEQ ID NO: 74)
TCGCAGAATCAAGAACGGCTATGTGCGTTTAAAGATCCGTATCAGCAAG

ACCTTGGGATAGGTGAGAGTAGAATCTCTCATGAAAATGGGACAATATT

ATGCTCGAAAGGTAGCACCTGCTATGGCCTTTGGGAGAAATCAAAAGGG

GACATAAATCTTGTAAAACAAGGATGTTGGTCTCACATTGGAGATCCCC

AAGAGTGTCACTATGAAGAATGTGTAGTAACTACCACTCCTCCCTCAAT

TCAGAATGGAACATACCGTTTCTGCTGTTGTAGCACAGATTTATGTAAT

GTCAACTTTACTGAGAATTTTCCACCTCCTGACACAACACCACTCAGTC

CACCTCATTCATTTAACCGAGATGAGACA (SEQ ID NO: 52)
ATGCTAGGGTCTTTGGGGCTTTGGGCATTACTTCCCACAGCTGTGGAAG

CACCCCCAAACAGGCGAACCTGTGTGTTCTTTGAGGCCCCTGGAGTGCG

GGGAAGCACAAAGACACTGGGAGAGCTGCTAGATACAGGCACAGAGCTC

CCCAGAGCTATCCGCTGCCTCTACAGCCGCTGCTGCTTTGGGATCTGGA
```

ACCTGACCCAAGACCGGGCACAGGTGGAAATGCAAGGATGCCGAGACAG

TGATGAGCCAGGCTGTGAGTCCCTCCACTGTGACCCAAGTCCCCGAGCC

CACCCCAGCCCTGGCTCCACTCTCTTCACCTGCTCCTGTGGCACTGACT

TCTGCAATGCCAATTACAGCCATCTGCCTCCTCCAGGGAGCCCTGGGAC

TCCTGGCTCCCAGGGTCCCCAGGCTGCCCCAGGTGAGTCCATCTGGATG

GCACTGGTGCTGCTGGGGCTGTTCCTCCTCCTCCTGCTGCTGCTGGGCA

GCATCATCTTGGCCCTGCTACAGCGAAAGAACTACAGAGTGCGAGGTGA

GCCAGTGCCAGAGCCAAGGCCAGACTCAGGCAGGGACTGGAGTGTGGAG

CTGCAGGAGCTGCCTGAGCTGTGTTTCTCCCAGGTAATCCGGGAAGGAG

GTCATGCAGTGGTTTGGGCCGGGCAGCTGCAAGGAAAACTGGTTGCCAT

CAAGGCCTTCCCACCGAGGTCTGTGGCTCAGTTCCAAGCTGAGAGAGCA

TTGTACGAACTTCCAGGCCTACAGCACGACCACATTGTCCGATTTATCA

CTGCCAGCCGGGGGGTCCTGGCCGCCTGCTCTCTGGGCCCCTGCTGGT

ACTGGAACTGCATCCCAAGGGCTCCCTGTGCCACTACTTGACCCAGTAC

ACCAGTGACTGGGGAAGTTCCCTGCGGATGGCACTGTCCCTGGCCCAGG

GCCTGGCATTTCTCCATGAGGAGCGCTGGCAGAATGGCCAATATAAACC

AGGTATTGCCCACCGAGATCTGAGCAGCCAGAATGTGCTCATTCGGGAA

GATGGATCGTGTGCCATTGGAGACCTGGGCCTTGCCTTGGTGCTCCCTG

GCCTCACTCAGCCCCTGCCTGGACCCCTACTCAACCACAAGGCCCAGC

TGCCATCATGGAAGCTGGCACCCAGAGGTACATGGCACCAGAGCTCTTG

GACAAGACTCTGGACCTACAGGATTGGGGCATGGCCCTCCGACGAGCTG

ATATTTACTCTTTGGCTCTGCTCCTGTGGGAGATACTGAGCCGCTGCCC

AGATTTGAGGCCTGACAGCAGTCCACCACCCTTCCAACTGGCCTATGAG

GCAGAACTGGGCAATACCCCTACCTCTGATGAGCTATGGGCCTTGGCAG

TGCAGGAGAGGAGGCGTCCCTACATCCCATCCACCTGGCGCTGCTTTGC

CACAGACCCTGATGGGCTGAGGGAGCTCCTAGAAGACTGTTGGGATGCA

GACCCAGAAGCACGGCTGACAGCTGAGTGTGTACAGCAGCGCCTGGCTG

CCTTGGCCCATCCTCAAGAGAGCCACCCCTTTCCAGAGAGCTGTCCACG

TGGCTGCCCACCTCTCTGCCCAGAAGACTGTACTTCAATTCCTGCCCCT

ACCATCCTCCCCTGTAGGCCTCAGCGGAGTGCCTGCCACTTCAGCGTTC

AGCAAGGCCCTTGTTCCAGGAATCCTCAGCCTGCCTGTACCCTTTCTCC

TGTG (SEQ ID NO: 53)

CCCCCAAACAGGCGAACCTGTGTGTTCTTTGAGGCCCCTGGAGTGCGGG

GAAGCACAAAGACACTGGGAGAGCTGCTAGATACAGGCACAGAGCTCCC

CAGAGCTATCCGCTGCCTCTACAGCCGCTGCTGCTTTGGGATCTGGAAC

CTGACCCAAGACCGGGCACAGGTGGAAATGCAAGGATGCCGAGACAGTG

ATGAGCCAGGCTGTGAGTCCCTCCACTGTGACCCAAGTCCCCGAGCCCA

CCCCAGCCCTGGCTCCACTCTCTTCACCTGCTCCTGTGGCACTGACTTC

TGCAATGCCAATTACAGCCATCTGCCTCCTCCAGGGAGCCCTGGGACTC

-continued

CTGGCTCCCAGGGTCCCCAGGCTGCCCCAGGTGAGTCCATCTGGATGGC

ACTG (SEQ ID NO: 77)

<u>ATGCTAGGGTCTTTGGGGCTTTGGGCATTACTTCCCACAGCTGTGGAAG</u>

<u>C</u>ACCCCCAAACAGGCGAACCTGTGTGTTCTTTGAGGCCCCTGGAGTGCG

GGGAAGCACAAAGACACTGGGAGAGCTGCTAGATACAGGCACAGAGCTC

CCCAGAGCTATCCGCTGCCTCTACAGCCGCTGCTGCTTTGGGATCTGGA

ACCTGACCCAAGACCGGGCACAGGTGGAAATGCAAGGATGCCGAGACAG

TGATGAGCCAGGCTGTGAGTCCCTCCACTGTGACCCAAGTCCCCGAGCC

CACCCCAGCCCTGGCTCCACTCTCTTCACCTGCTCCTGTGGCACTGACT

TCTGCAATGCCAATTACAGCCATCTGCCTCCTCCAGGGAGCCCTGGGAC

TCCTGGCTCCCAGGGTCCCCAGGCTGCCCCAGGTGAGTCCATCTGGATG

GCACTGGTGCTGCTGGGGCTGTTCCTCCTCCTCCTGCTGCTGCTGGGCA

GCATCATCTTGGCCCTGCTACAGCGAAAGAACTACAGAGTGCGAGGTGA

GCCAGTGCCAGAGCCAAGGCCAGACTCAGGCAGGGACTGGAGTGTGGAG

CTGCAGGAGCTGCCTGAGCTGTGTTTCTCCCAGGTAATCCGGGAAGGAG

GTCATGCAGTGGTTTGGGCCGGGCAGCTGCAAGGAAAACTGGTTGCCAT

CAAGGCCTTCCCACCGAGGTCTGTGGCTCAGTTCCAAGCTGAGAGAGCA

TTGTACGAACTTCCAGGCCTACAGCACGACCACATTGTCCGATTTATCA

CTGCCAGCCGGGGGGGTCCTGGCCGCCTGCTCTCTGGGCCCCTGCTGGT

ACTGGAACTGCATCCCAAGGGCTCCCTGTGCCACTACTTGACCCAGTAC

ACCAGTGACTGGGGAAGTTCCCTGCGGATGGCACTGTCCCTGGCCCAGG

GCCTGGCATTTCTCCATGAGGAGCGCTGGCAGAATGGCCAATATAAACC

AGGTATTGCCCACCGAGATCTGAGCAGCCAGAATGTGCTCATTCGGGAA

GATGGATCGTGTGCCATTGGAGACCTGGGCCTTGCCTTGGTGCTCCCTG

GCCTCACTCAGCCCCCTGCCTGGACCCCTACTCAACCACAAGGCCCAGC

TGCCATCATGGAAGCTGGCACCCAGAGGTACATGGCACCAGAGCTCTTG

GACAAGACTCTGGACCTACAGGATTGGGGCATGGCCCTCCGACGAGCTG

ATATTTACTCTTTGGCTCTGCTCCTGTGGGAGATACTGAGCCGCTGCCC

AGATTTGAGGCCTGCAGTCCACCACCCTTCCAACTGGCCTATGAGGCAG

AACTGGGCAATACCCCTACCTCTGATGAGCTATGGGCCTTGGCAGTGCA

GGAGAGGAGGCGTCCCTACATCCCATCCACCTGGCGCTGCTTTGCCACA

GACCCTGATGGGC (SEQ ID NO: 78)

CCCCCAAACAGGCGAACCTGTGTGTTCTTTGAGGCCCCTGGAGTGCGGG

GAAGCACAAAGACACTGGGAGAGCTGCTAGATACAGGCACAGAGCTCCC

CAGAGCTATCCGCTGCCTCTACAGCCGCTGCTGCTTTGGGATCTGGAAC

CTGACCCAAGACCGGGCACAGGTGGAAATGCAAGGATGCCGAGACAGTG

ATGAGCCAGGCTGTGAGTCCCTCCACTGTGACCCAAGTCCCCGAGCCCA

CCCCAGCCCTGGCTCCACTCTCTTCACCTGCTCCTGTGGCACTGACTTC

TGCAATGCCAATTACAGCCATCTGCCTCCTCCAGGGAGCCCTGGGACTC

CTG

GCTCCCAGGGTCCCCAGGCTGCCCCAGGTGAGTCCATCTGGATGCACT
G (SEQ ID NO: 81)

ATGCTAGGGTCTTTGGGGCTTTGGGCATTACTTCCCACAGCTGTGGAAG
CACCCCCAAACAGGCGAACCTGTGTGTTCTTTGAGGCCCCTGGAGTGCG
GGGAAGCACAAAGACACTGGGAGAGCTGCTAGATACAGGCACAGAGCTC
CCCAGAGCTATCCGCTGCCTCTACAGCCGCTGCTGCTTTGGGATCTGGA
ACCTGACCCAAGACCGGGCACAGGTGGAAATGCAAGGATGCCGAGACAG
TGATGAGCCAGGCTGTGAGTCCCTCCACTGTGACCCAAGTCCCCGAGCC
CACCCCAGCCCTGGCTCCACTCTCTTCACCTGCTCCTGTGGCACTGACT
TCTGCAATGCCAATTACAGCCATCTGCCTCCTCCAGGGAGCCCTGGGAC
TCCTGGCTCCCAGGGTCCCCAGGCTGCCCCAGGTGAGTCCATCTGGATG
GCACTGGTGCTGCTGGGGCTGTTCCTCCTCCTCCTGCTGCTGCTGGGCA
GCATCATCTTGGCCCTGCTACAGCGAAAGAACTACAGAGTGCGAGGTGA
GCCAGTGCCAGAGCCAAGGCCAGACTCAGGCAGGGACTGGAGTGTGGAG
CTGCAGGAGCTGCCTGAGCTGTGTTTCTCCCAGGTAATCCGGGAAGGAG
GTCATGCAGTGGTTTGGGCCGGGCAGCTGCAAGGAAAACTGGTTGCCAT
CAAGGCCTTCCCACCGAGGTCTGTGGCTCAGTTCCAAGCTGAGAGAGCA
TTGTACGAACTTCCAGGCCTACAGCACGACCACATTGTCCGATTTATCA
CTGCCAGCCGGGGGGGTCCTGGCCGCCTGCTCTCTGGGCCCCTGCTGGT
ACTGGAACTGCATCCCAAGGGCTCCCTGTGCCACTACTTGACCCAGTAC
ACCAGTGACTGGGGAAGTTCCCTGCGGATGGCACTGTCCCTGGCCCAGG
GCCTGGCATTTCTCCATGAGGAGCGCTGGCAGAATGGCCAATATAAACC
AGGTATTGCCCACCGAGATCTGAGCAGCCAGAATGTGCTCATTCGGGAA
GATGGATCGTGTGCCATTGGAGACCTGGGCCTTGCCTTGGTGCTCCCTG
GCCTCACTCAGCCCCCTGCCTGGACCCCTACTCAACCACAAGGCCCAGC
TGCCATCATGGAAGACCCTGATGGGCTGAGGGAGCTCCTAGAAGACTGT
TGGGATGCAGACCCAGAAGCACGGCTGACAGCTGAGTGTGTACAGCAGC
GCCTGGCTGCCTTGGCCCATCCTCAAGAGAGCCACCCCTTTCCAGAGAG
CTGTCCACGTGGCTGCCCACCTCTCTGCCCAGAAGACTGTACTTCAATT
CCTGCCCCTACCATCCTCCCCTGTAGGCCTCAGCGGAGTGCCTGCCACT
TCAGCGTTCAGCAAGGCCCTTGTTCCAGGAATCCTCAGCCTGCCTGTAC
CCTTTCTCCTGTG (SEQ ID NO: 82)

CCCCCAAACAGGCGAACCTGTGTGTTCTTTGAGGCCCCTGGAGTGCGGG
GAAGCACAAAGACACTGGGAGAGCTGCTAGATACAGGCACAGAGCTCCC
CAGAGCTATCCGCTGCCTCTACAGCCGCTGCTGCTTTGGGATCTGGAAC
CTGACCCAAGACCGGGCACAGGTGGAAATGCAAGGATGCCGAGACAGTG
ATGAGCCAGGCTGTGAGTCCCTCCACTGTGACCCAAGTCCCCGAGCCCA
CCCCAGCCCTGGCTCCACTCTCTTCACCTGCTCCTGTGGCACTGACTTC
TGCAATGCCAATTACAGCCATCTGCCTCCTCCAGGGAGCCCTGGGACTC

CTGGCTCCCAGGGTCCCCAGGCTGCCCCAGGTGAGTCCATCTGGATGGC

ACTG (SEQ ID NO: 16)

<u>SATGACCTTGGGCTCCCCAGGAAAGGCCTTCTGATGCTGCTGATGGCC</u>

<u>TTGGTGACCCAGGGA</u>GACCCTGTGAAGCCGTCTCGGGGCCCGCTGGTGA

CCTGCACGTGTGAGAGCCCACATTGCAAGGGGCCTACCTGCCGGGGGGC

CTGGTGCACAGTAGTGCTGGTGCGGGAGGAGGGGAGGCACCCCCAGGAA

CATCGGGGCTGCGGGAACTTGCACAGGGAGCTCTGCAGGGGGCGCCCCA

CCGAGTTCGTCAACCACTACTGCTGCGACAGCCACCTCTGCAACCACAA

CGTGTCCCTGGTGCTGGAGGCCACCCAACCTCCTTCGGAGCAGCCGGGA

ACAGATGGCCAGCTGGCCCTGATCCTGGGCCCCGTGCTGGCCTTGCTGG

CCCTGGTGGCCCTGGGTGTCCTGGGCCTGTGGCATGTCCGACGGAGGCA

GGAGAAGCAGCGTGGCCTGCACAGCGAGCTGGGAGAGTCCAGTCTCATC

CTGAAAGCATCTGAGCAGGGCGACAGCATGTTGGGGGACCTCCTGGACA

GTGACTGCACCACAGGGAGTGGCTCAGGGCTCCCCTTCCTGGTGCAGAG

GACAGTGGCACGGCAGGTTGCCTTGGTGGAGTGTGTGGGAAAAGGCCGC

TATGGCGAAGTGTGGCGGGGCTTGTGGCACGGTGAGAGTGTGGCCGTCA

AGATCTTCTCCTCGAGGGATGAACAGTCCTGGTTCCGGGAGACTGAGAT

CTATAACACAGTGTTGCTCAGACACGACAACATCCTAGGCTTCATCGCC

TCAGACATGACCTCCCGCAACTCGAGCACGCAGCTGTGGCTCATCACGC

ACTACCACGAGCACGGCTCCCTCTACGACTTTCTGCAGAGACAGACGCT

GGAGCCCCATCTGGCTCTGAGGCTAGCTGTGTCCGCGGCATGCGGCCTG

GCGCACCTGCACGTGGAGATCTTCGGTACACAGGGCAAACCAGCCATTG

CCCACCGCGACTTCAAGAGCCGCAATGTGCTGGTCAAGAGCAACCTGCA

GTGTTGCATCGCCGACCTGGGCCTGGCTGTGATGCACTCACAGGGCAGC

GATTACCTGGACATCGGCAACAACCCGAGAGTGGGCACCAAGCGGTACA

TGGCACCCGAGGTGCTGGACGAGCAGATCCGCACGGACTGCTTTGAGTC

CTACAAGTGGACTGACATCTGGGCCTTTGGCCTGGTGCTGTGGGAGATT

GCCCGCCGGACCATCGTGAATGGCATCGTGGAGGACTATAGACCACCCT

TCTATGATGTGGTGCCCAATGACCCCAGCTTTGAGGACATGAAGAAGGT

GGTGTGTGTGGATCAGCAGACCCCCACCATCCCTAACCGGCTGGCTGCA

GACCCGGTCCTCTCAGGCCTAGCTCAGATGATGCGGGAGTGCTGGTACC

CAAACCCCTCTGCCCGACTCACCGCGCTGCGGATCAAGAAGACACTACA

AAAAATTAGCAACAGTCCAGAGAAGCCTAAAGTGATTCAA (SEQ ID NO: 17)

GACCCTGTGAAGCCGTCTCGGGGCCCGCTGGTGACCTGCACGTGTGAGA

GCCCACATTGCAAGGGGCCTACCTGCCGGGGGGCCTGGTGCACAGTAGT

GCTGGTGCGGGAGGAGGGGAGGCACCCCCAGGAACATCGGGGCTGCGGG

AACTTGCACAGGGAGCTCTGCAGGGGGCGCCCCACCGAGTTCGTCAACC

ACTACTGCTGCGACAGCCACCTCTGCAACCACAACGTGTCCCTGGTGCT

GGAGGCCACCCAACCTCCTTCGGAGCAGCCGGGAACAGATGGCCAG

-continued (SEQ ID NO: 20)

<u>ATGGTAGATGGAGTGATGATTCTTCCTGTGCTTATCATGATTGCTCTCC</u>

<u>CCTCCCCTAGT</u>ATGGAAGATGAGAAGCCCAAGGTCAACCCCAAACTCTA

CATGTGTGTGTGTGAAGGTCTCTCCTGCGGTAATGAGGACCACTGTGAA

GGCCAGCAGTGCTTTTCCTCACTGAGCATCAACGATGGCTTCCACGTCT

ACCAGAAAGGCTGCTTCCAGGTTTATGAGCAGGGAAAGATGACCTGTAA

GACCCCGCCGTCCCCTGGCCAAGCCGTGGAGTGCTGCCAAGGGGACTGG

TGTAACAGGAACATCACGGCCCAGCTGCCCACTAAAGGAAAATCCTTCC

CTGGAACACAGAATTTCCACTTGGAGGTTGGCCTCATTATTCTCTCTGT

AGTGTTCGCAGTATGTCTTTTAGCCTGCCTGCTGGGAGTTGCTCTCCGA

AAATTTAAAAGGCGCAACCAAGAACGCCTCAATCCCCGAGACGTGGAGT

ATGGCACTATCGAAGGGCTCATCACCACCAATGTTGGAGACAGCACTTT

AGCAGATTTATTGGATCATTCGTGTACATCAGGAAGTGGCTCTGGTCTT

CCTTTTCTGGTACAAAGAACAGTGGCTCGCCAGATTACACTGTTGGAGT

GTGTCGGGAAAGGCAGGTATGGTGAGGTGTGGAGGGGCAGCTGGCAAGG

GGAGAATGTTGCCGTGAAGATCTTCTCCTCCCGTGATGAGAAGTCATGG

TTCAGGGAAACGGAATTGTACAACACTGTGATGCTGAGGCATGAAAATA

TCTTAGGTTTCATTGCTTCAGACATGACATCAAGACACTCCAGTACCCA

GCTGTGGTTAATTACACATTATCATGAAATGGGATCGTTGTACGACTAT

CTTCAGCTTACTACTCTGGATACAGTTAGCTGCCTTCGAATAGTGCTGT

CCATAGCTAGTGGTCTTGCACATTTGCACATAGAGATATTTGGGACCCA

AGGGAAACCAGCCATTGCCCATCGAGATTTAAAGAGCAAAAATATTCTG

GTTAAGAAGAATGGACAGTGTTGCATAGCAGATTTGGGCCTGGCAGTCA

TGCATTCCCAGAGCACCAATCAGCTTGATGTGGGGAACAATCCCCGTGT

GGGCACCAAGCGCTACATGGCCCCCGAAGTTCTAGATGAAACCATCCAG

GTGGATTGTTTCGATTCTTATAAAAGGGTCGATATTTGGGCCTTTGGAC

TTGTTTTGTGGGAAGTGGCCAGGCGGATGGTGAGCAATGGTATAGTGGA

GGATTACAAGCCACCGTTCTACGATGTGGTTCCCAATGACCCAAGTTTT

GAAGATATGAGGAAGGTAGTCTGTGTGGATCAACAAAGGCCAAACATAC

CCAACAGATGGTTCTCAGACCCGACATTAACCTCTCTGGCCAAGCTAAT

GAAAGAATGCTGGTATCAAAATCCATCCGCAAGACTCACAGCACTGCGT

ATCAAAAAGACTTTGACCAAAATTGATAATTCCCTCGACAAATTGAAAA

CTGACTGT (SEQ ID NO: 21)

ATGGAAGATGAGAAGCCCAAGGTCAACCCCAAACTCTACATGTGTGTGT

GTGAAGGTCTCTCCTGCGGTAATGAGGACCACTGTGAAGGCCAGCAGTG

CTTTTCCTCACTGAGCATCAACGATGGCTTCCACGTCTACCAGAAAGGC

TGCTTCCAGGTTTATGAGCAGGGAAAGATGACCTGTAAGACCCCGCCGT

CCCCTGGCCAAGCCGTGGAGTGCTGCCAAGGGGACTGGTGTAACAGGAA

CATCACGGCCCAGCTGCCCACTAAAGGAAAATCCTTCCCTGGAACACAG

AATTTCCACTTGGAG

-continued (SEQ ID NO: 24)
```
   1 ATGCCTCAGC TATACATTTA CATCAGATTA TTGGGAGCCT ATTTGTTCAT CATTTCTCGT
  61 GTTCAAGGAC AGAATCTGGA TAGTATGCTT CATGGCACTG GGATGAAATC AGACTCCGAC
 121 CAGAAAAAGT CAGAAAATGG AGTAACCTTA GCACCAGAGG ATACCTTGCC TTTTTTAAAG
 181 TGCTATTGCT CAGGGCACTG TCCAGATGAT GCTATTAATA ACACATGCAT AACTAATGGA
 241 CATTGCTTTG CCATCATAGA AGAAGATGAC CAGGGAGAAA CCACATTAGC TTCAGGGTGT
 301 ATGAAATATG AAGGATCTGA TTTTCAGTGC AAAGATTCTC CAAAAGCCCA GCTACGCCGG
 361 ACAATAGAAT GTTGTCGGAC CAATTTATGT AACCAGTATT TGCAACCCAC ACTGCCCCCT
 421 GTTGTCATAG GTCCGTTTTT TGATGGCAGC ATTCGATGGC TGGTTTTGCT CATTTCTATG
 481 GCTGTCTGCA TAATTGCTAT GATCATCTTC TCCAGCTGCT TTTGTTACAA ACATTATTGC
 541 AAGAGCATCT CAAGCAGACG TCGTTACAAT CGTGATTTGG AACAGGATGA AGCATTTATT
 601 CCAGTTGGAG AATCACTAAA AGACCTTATT GACCAGTCAC AAAGTTCTGG TAGTGGGTCT
 661 GGACTACCTT TATTGGTTCA GCGAACTATT GCCAACAGA TTCAGATGGT CCGGCAAGTT
 721 GGTAAAGGCC GATATGGAGA AGTATGGATG GGCAATGGC GTGGCGAAAA AGTGGCGGTG
 781 AAAGTATTCT TTACCACTGA AGAAGCCAGC TGGTTTCGAG AAACAGAAAT CTACCAAACT
 841 GTGCTAATGC GCCATGAAAA CATACTTGGT TTCATAGCGG CAGACATTAA AGGTACAGGT
 901 TCCTGGACTC AGCTCTATTT GATTACTGAT TACCATGAAA ATGGATCTCT CTATGACTTC
 961 CTGAAATGTG CTACACTGGA CACCAGAGCC CTGCTTAAAT TGGCTTATTC AGCTGCCTGT
1021 GGTCTGTGCC ACCTGCACAC AGAAATTTAT GGCACCCAAG AAAGCCCGC AATTGCTCAT
1081 CGAGACCTAA AGAGCAAAAA CATCCTCATC AAGAAAAATG GGAGTTGCTG CATTGCTGAC
1141 CTGGGCCTTG CTGTTAAATT CAACAGTGAC ACAAATGAAG TTGATGTGCC CTTGAATACC
1201 AGGGTGGGCA CCAAACGCTA CATGGCTCCC GAAGTGCTGG ACGAAAGCCT GAACAAAAC
1261 CACTTCCAGC CCTACATCAT GGCTGACATC TACAGCTTCG GCCTAATCAT TTGGGAGATG
1321 GCTCGTCGTT GTATCACAGG AGGGATCGTG GAAGAATACC AATTGCCATA TTACAACATG
1381 GTACCGAGTG ATCCGTCATA CGAAGATATG CGTGAGGTTG TGTGTGTCAA CGTTTGCGG
1441 CCAATTGTGT CTAATCGGTG AACAGTGAT GAATGTCTAC GAGCAGTTTT GAAGCTAATG
1501 TCAGAATGCT GGGCCCACAA TCCAGCCTCC AGACTCACAG CATTGAGAAT TAAGAAGACG
1561 CTTGCCAAGA TGGTTGAATC CAAGATGTA AAAATC
```
(SEQ ID NO: 25)
```
   1 CAGAATCTGG ATAGTATGCT TCATGGCACT GGGATGAAAT CAGACTCCGA CCAGAAAAAG
  61 TCAGAAAATG GAGTAACCTT AGCACCAGAG GATACCTTGC CTTTTTTAAA GTGCTATTGC
 121 TCAGGGCACT GTCCAGATGA TGCTATTAAT AACACATGCA TAACTAATGG ACATTGCTTT
 181 GCCATCATAG AAGAAGATGA CCAGGGAGAA ACCACATTAG CTTCAGGGTG TATGAAATAT
 241 GAAGGATCTG ATTTTCAGTG CAAAGATTCT CCAAAAGCCC AGCTACGCCG GACAATAGAA
 301 TGTTGTCGGA CCAATTTATG TAACCAGTAT TTGCAACCCA CACTGCCCCC TGTTGTCATA
 361 GGTCCGTTTT TTGATGGCAG CATTCGA
```
(SEQ ID NO: 28)
```
ATGGCGGAGTCGGCCGGAGCCTCCTCCTTCTTCCCCCTTGTTGTCCTCC
TGCTCGCCGGCAGCGGCGGGTCCGGGCCCCGGGGGGTCCAGGCTCTGCT
GTGTGCGTGCACCAGCTGCCTCCAGGCCAACTACACGTGTGAGACAGAT
GGGGCCTGCATGGTTTCCATTTTCAATCTGGATGGGATGGAGCACCATG
TGCGCACCTGCATCCCCAAAGTGGAGCTGGTCCCTGCCGGGAAGCCCTT
```

```
                CTACTGCCTGAGCTCGGAGGACCTGCGCAACACCCACTGCTGCTACACT

GACTACTGCAACAGGATCGACTTGAGGGTGCCCAGTGGTCACCTCAAGG

AGCCTGAGCACCCGTCCATGTGGGGCCCGGTGGAGCTGGTAGGCATCAT

CGCCGGCCCGGTGTTCCTCCTGTTCCTCATCATCATCATTGTTTTCCTT

GTCATTAACTATCATCAGCGTGTCTATCACAACCGCCAGAGACTGGACA

TGGAAGATCCCTCATGTGAGATGTGTCTCTCCAAAGACAAGACGCTCCA

GGATCTTGTCTACGATCTCTCCACCTCAGGGTCTGGCTCAGGGTTACCC

CTCTTTGTCCAGCGCACAGTGGCCCGAACCATCGTTTTACAAGAGATTA

TTGGCAAGGGTCGGTTTGGGGAAGTATGGCGGGGCCGCTGGAGGGGTGG

TGATGTGGCTGTGAAAATATTCTCTTCTCGTGAAGAACGGTCTTGGTTC

AGGGAAGCAGAGATATACCAGACGGTCATGCTGCGCCATGAAAACATCC

TTGGATTTATTGCTGCTGACAATAAAGATAATGGCACCTGGACACAGCT

GTGGCTTGTTTCTGACTATCATGAGCACGGGTCCCTGTTTGATTATCTG

AACCGGTACACAGTGACAATTGAGGGGATGATTAAGCTGGCCTTGTCTG

CTGCTAGTGGGCTGGCACACCTGCACATGGAGATCGTGGGCACCCAAGG

GAAGCCTGGAATTGCTCATCGAGACTTAAAGTCAAAGAACATTCTGGTG

AAGAAAAATGGCATGTGTGCCATAGCAGACCTGGGCCTGGCTGTCCGTC

ATGATGCAGTCACTGACACCATTGACATTGCCCCGAATCAGAGGGTGGG

GACCAAACGATACATGGCCCCTGAAGTACTTGATGAAACCATTAATATG

AAACACTTTGACTCCTTTAAATGTGCTGATATTTATGCCCTCGGGCTTG

TATATTGGGAGATTGCTCGAAGATGCAATTCTGGAGGAGTCCATGAAGA

ATATCAGCTGCCATATTACGACTTAGTGCCCTCTGACCCTTCCATTGAG

GAAATGCGAAAGGTTGTATGTGATCAGAAGCTGCGTCCCAACATCCCCA

ACTGGTGGCAGAGTTATGAGGCACTGCGGGTGATGGGGAAGATGATGCG

AGAGTGTTGGTATGCCAACGGCGCAGCCCGCCTGACGGCCCTGCGCATC

AAGAAGACCCTCTCCCAGCTCAGCGTGCAGGAAGACGTGAAGATC
                                                                     (SEQ ID NO: 29)

TCCGGGCCCCGGGGGGTCCAGGCTCTGCTGTGTGCGTGCACCAGCTGCC

TCCAGGCCAACTACACGTGTGAGACAGATGGGGCCTGCATGGTTTCCAT

TTTCAATCTGGATGGGATGGAGCACCATGTGCGCACCTGCATCCCCAAA

GTGGAGCTGGTCCCTGCCGGGAAGCCCTTCTACTGCCTGAGCTCGGAGG

ACCTGCGCAACACCCACTGCTGCTACACTGACTACTGCAACAGGATCGA

CTTGAGGGTGCCCAGTGGTCACCTCAAGGAGCCTGAGCACCCGTCCATG

TGGGGCCCGGTGGAG
                                                                     (SEQ ID NO: 85)

ATGGCGGAGTCGGCCGGAGCCTCCTCCTTCTTCCCCCTTGTTGTCCTCC
                ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                TGCTCGCCGGCAGCGGCGGGTCCGGGCCCCGGGGGGTCCAGGCTCTGCT
                ‾‾‾‾‾‾‾‾‾‾‾‾‾‾‾‾‾‾‾‾

GTGTGCGTGCACCAGCTGCCTCCAGGCCAACTACACGTGTGAGACAGAT

GGGGCCTGCATGGTTTCCATTTTCAATCTGGATGGGATGGAGCACCATG

TGCGCACCTGCATCCCCAAAGTGGAGCTGGTCCCTGCCGGGAAGCCCTT

CTACTGCCTGAGCTCGGAGGACCTGCGCAACACCCACTGCTGCTACACT
```

-continued

GACTACTGCAACAGGATCGACTTGAGGGTGCCCAGTGGTCACCTCAAGG

AGCCTGAGCACCCGTCCATGTGGGGCCCGGTGGAGCTGGTAGGCATCAT

CGCCGGCCCGGTGTTCCTCCTGTTCCTCATCATCATCATTGTTTCCTTG

TCATTAACTATCATCAGCGTGTCTATCACAACCGCCAGAGACTGGACAT

GGAAGATCCCTCATGTGAGATGTGTCTCTCCAAAGACAAGACGCTCCAG

GATCTTGTCTACGATCTCTCCACCTCAGGGTCTGGCTCAGGGTTACCCC

TCTTTGTCCAGCGCACAGTGGCCCGAACCATCGTTTTACAAGAGATTAT

TGGCAAGGGTCGGTTTGGGGAAGTATGGCGGGGCCGCTGGAGGGGTGGT

GATGTGGCTGTGAAAATATTCTCTTCTCGTGAAGAACGGTCTTGGTTCA

GGGAAGCAGAGATATACCAGACGGTCATGCTGCGCCATGAAAACATCCT

TGGATTTATTGCTGCTGACAATAAAGCAGACTGCTCATTCCTCACATTG

CCATGGGAAGTTGTAATGGTCTCTGCTGCCCCCAAGCTGAGGAGCCTTA

GACTCCAATACAAGGGAGGAAGGGGAAGAGCAAGATTTTTATTCCCACT

GAATAATGGCACCTGGACACAGCTGTGGCTTGTTTCTGACTATCATGAG

CACGGGTCCCTGTTTGATTATCTGAACCGGTACACAGTGACAATTGAGG

GGATGATTAAGCTGGCCTTGTCTGCTGCTAGTGGGCTGGCACACCTGCA

CATGGAGATCGTGGGCACCCAAGGGAAGCCTGGAATTGCTCATCGAGAC

TTAAAGTCAAAGAACATTCTGGTGAAGAAAAATGGCATGTGTGCCATAG

CAGACCTGGGCCTGGCTGTCCGTCATGATGCAGTCACTGACACCATTGA

CATTGCCCCGAATCAGAGGGTGGGGACCAAACGATACATGGCCCCTGAA

GTACTTGATGAAACCATTAATATGAAACACTTTGACTCCTTTAAATGTG

CTGATATTTATGCCCTCGGGCTTGTATATTGGGAGATTGCTCGAAGATG

CAATTCTGGAGGAGTCCATGAAGAATATCAGCTGCCATATTACGACTTA

GTGCCCTCTGACCCTTCCATTGAGGAAATGCGAAAGGTTGTATGTGATC

AGAAGCTGCGTCCCAACATCCCCAACTGGTGGCAGAGTTATGAGGCACT

GCGGGTGATGGGAAGATGATGCGAGAGTGTTGGTATGCCAACGGCGCA

GCCCGCCTGACGGCCCTGCGCATCAAGAAGACCCTCTCCCAGCTCAGCG

TGCAGGAAGACGTGAAGATC (SEQ ID NO: 86)

TCCGGGCCCCGGGGGGTCCAGGCTCTGCTGTGTGCGTGCACCAGCTGCC

TCCAGGCCAACTACACGTGTGAGACAGATGGGGCCTGCATGGTTTCCAT

TTTCAATCTGGATGGGATGGAGCACCATGTGCGCACCTGCATCCCCAAA

GTGGAGCTGGTCCCTGCCGGGAAGCCCTTCTACTGCCTGAGCTCGGAGG

ACCTGCGCAACACCCACTGCTGCTACACTGACTACTGCAACAGGATCGA

CTTGAGGGTGCCCAGTGGTCACCTCAAGGAGCCTGAGCACCCGTCCATG

TGGGGCCCGGTGGAG (SEQ ID NO: 32)

ATGGAGGCGGCGGTCGCTGCTCCGCGTCCCCGGCTGCTCCTCCTCGTGC

TGGCGGCGGCGGCGGCGGCGGCGGCGCTGCTCCCGGGGCGACGGC

GTTACAGTGTTTCTGCCACCTCTGTACAAAAGACAATTTTACTTGTGTG

ACAGATGGGCTCTGCTTTGTCTCTGTCACAGAGACCACAGACAAAGTTA

TACACAACAGCATGTGTATAGCTGAAATTGACTTAATTCCTCGAGATAG

-continued

GCCGTTTGTATGTGCACCCTCTTCAAAAACTGGGTCTGTGACTACAACA

TATTGCTGCAATCAGGACCATTGCAATAAAATAGAACTTCCAACTACTG

TAAAGTCATCACCTGGCCTTGGTCCTGTGGAACTGGCAGCTGTCATTGC

TGGACCAGTGTGCTTCGTCTGCATCTCACTCATGTTGATGGTCTATATC

TGCCACAACCGCACTGTCATTCACCATCGAGTGCCAAATGAAGAGGACC

CTTCATTAGATCGCCCTTTTATTTCAGAGGGTACTACGTTGAAAGACTT

AATTTATGATATGACAACGTCAGGTTCTGGCTCAGGTTTACCATTGCTT

GTTCAGAGAACAATTGCGAGAACTATTGTGTTACAAGAAAGCATTGGCA

AAGGTCGATTTGGAGAAGTTTGGAGAGGAAAGTGGCGGGGAGAAGAAGT

TGCTGTTAAGATATTCTCCTCTAGAGAAGAACGTTCGTGGTTCCGTGAG

GCAGAGATTTATCAAACTGTAATGTTACGTCATGAAAACATCCTGGGAT

TTATAGCAGCAGACAATAAAGACAATGGTACTTGGACTCAGCTCTGGTT

GGTGTCAGATTATCATGAGCATGGATCCCTTTTTGATTACTTAAACAGA

TACACAGTTACTGTGGAAGGAATGATAAAACTTGCTCTGTCCACGGCGA

GCGGTCTTGCCCATCTTCACATGGAGATTGTTGGTACCCAAGGAAAGCC

AGCCATTGCTCATAGAGATTTGAAATCAAAGAATATCTTGGTAAAGAAG

AATGGAACTTGCTGTATTGCAGACTTAGGACTGGCAGTAAGACATGATT

CAGCCACAGATACCATTGATATTGCTCCAAACCACAGAGTGGGAACAAA

AAGGTACATGGCCCCTGAAGTTCTCGATGATTCCATAAATATGAAACAT

TTTGAATCCTTCAAACGTGCTGACATCTATGCAATGGGCTTAGTATTCT

GGGAAATTGCTCGACGATGTTCCATTGGTGGAATTCATGAAGATTACCA

ACTGCCTTATTATGATCTTGTACCTTCTGACCCATCAGTTGAAGAAATG

AGAAAAGTTGTTTGTGAACAGAAGTTAAGGCCAAATATCCCAAACAGAT

GGCAGAGCTGTGAAGCCTTGAGAGTAATGGCTAAAATTATGAGAGAATG

TTGGTATGCCAATGGAGCAGCTAGGCTTACAGCATTGCGGATTAAGAAA

ACATTATCGCAACTCAGTCAACAGGAAGGCATCAAAATG (SEQ ID NO: 33)

GCGGCGCTGCTCCCGGGGGCGACGGCGTTACAGTGTTTCTGCCACCTCT

GTACAAAAGACAATTTTACTTGTGTGACAGATGGGCTCTGCTTTGTCTC

TGTCACAGAGACCACAGACAAAGTTATACACAACAGCATGTGTATAGCT

GAAATTGACTTAATTCCTCGAGATAGGCCGTTTGTATGTGCACCCTCTT

CAAAAACTGGGTCTGTGACTACAACATATTGCTGCAATCAGGACCATTG

CAATAAAATAGAACTTCCAACTACTGTAAAGTCATCACCTGGCCTTGGT

CCTGTGGAACTG (SEQ ID NO: 89)

<u>ATGGAGGCGGCGGTCGCTGCTCCGCGTCCCCGGCTGCTCCTCCTCGTGC</u>
<u>TGGCGGCGGCGGCGGCGGCG</u>GCGGCGCTGCTCCCGGGGGCGACGGC

GTTACAGTGTTTCTGCCACCTCTGTACAAAAGACAATTTTACTTGTGTG

ACAGATGGGCTCTGCTTTGTCTCTGTCACAGAGACCACAGACAAAGTTA

TACACAACAGCATGTGTATAGCTGAAATTGACTTAATTCCTCGAGATAG

GCCGTTTGTATGTGCACCCTCTTCAAAAACTGGGTCTGTGACTACAACA

```
TATTGCTGCAATCAGGACCATTGCAATAAAATAGAACTTCCAACTACTG

GCCCTTTTTCAGTAAAGTCATCACCTGGCCTTGGTCCTGTGGAACTGGC

AGCTGTCATTGCTGGACCAGTGTGCTTCGTCTGCATCTCACTCATGTTG

ATGGTCTATATCTGCCACAACCGCACTGTCATTCACCATCGAGTGCCAA

ATGAAGAGGACCCTTCATTAGATCGCCCTTTTATTTCAGAGGGTACTAC

GTTGAAAGACTTAATTTATGATATGACAACGTCAGGTTCTGGCTCAGGT

TTACCATTGCTTGTTCAGAGAACAATTGCGAGAACTATTGTGTTACAAG

AAAGCATTGGCAAAGGTCGATTTGGAGAAGTTTGGAGAGGAAAGTGGCG

GGGAGAAGAAGTTGCTGTTAAGATATTCTCCTCTAGAGAAGAACGTTCG

TGGTTCCGTGAGGCAGAGATTTATCAAACTGTAATGTTACGTCATGAAA

ACATCCTGGGATTTATAGCAGCAGACAATAAAGACAATGGTACTTGGAC

TCAGCTCTGGTTGGTGTCAGATTATCATGAGCATGGATCCCTTTTTGAT

TACTTAAACAGATACACAGTTACTGTGGAAGGAATGATAAAACTTGCTC

TGTCCACGGCGAGCGGTCTTGCCCATCTTCACATGGAGATTGTTGGTAC

CCAAGGAAAGCCAGCCATTGCTCATAGAGATTTGAAATCAAAGAATATC

TTGGTAAAGAAGAATGGAACTTGCTGTATTGCAGACTTAGGACTGGCAG

TAAGACATGATTCAGCCACAGATACCATTGATATTGCTCCAAACCACAG

AGTGGGAACAAAAAGGTACATGGCCCCTGAAGTTCTCGATGATTCCATA

AATATGAAACATTTTGAATCCTTCAAACGTGCTGACATCTATGCAATGG

GCTTAGTATTCTGGGAAATTGCTCGACGATGTTCCATTGGTGGAATTCA

TGAAGATTACCAACTGCCTTATTATGATCTTGTACCTTCTGACCCATCA

GTTGAAGAAATGAGAAAAGTTGTTTGTGAACAGAAGTTAAGGCCAAATA

TCCCAAACAGATGGCAGAGCTGTGAAGCCTTGAGAGTAATGGCTAAAAT

TATGAGAGAATGTTGGTATGCCAATGGAGCAGCTAGGCTTACAGCATTG

CGGATTAAGAAAACATTATCGCAACTCAGTCAACAGGAAGGCATCAAAA

TG (SEQ ID NO: 90)
GCGGCGCTGCTCCCGGGGGCGACGGCGTTACAGTGTTTCTGCCACCTCT

GTACAAAAGACAATTTTACTTGTGTGACAGATGGGCTCTGCTTTGTCTC

TGTCACAGAGACCACAGACAAAGTTATACACAACAGCATGTGTATAGCT

GAAATTGACTTAATTCCTCGAGATAGGCCGTTTGTATGTGCACCCTCTT

CAAAAACTGGGTCTGTGACTACAACATATTGCTGCAATCAGGACCATTG

CAATAAAATAGAACTTCCAACTACTGGCCCTTTTTCAGTAAAGTCATCA

CCTGGCCTTGGTCCTGTGGAACTG (SEQ ID NO: 36)
ATGCTTTTGCGAAGTGCAGGAAAATTAAATGTGGGCACCAAGAAAGAGG

ATGGTGAGAGTACAGCCCCCACCCCCCGTCCAAAGGTCTTGCGTTGTAA

ATGCCACCACCATTGTCCAGAAGACTCAGTCAACAATATTTGCAGCACA

GACGGATATTGTTTCACGATGATAGAAGAGGATGACTCTGGGTTGCCTG

TGGTCACTTCTGGTTGCCTAGGACTAGAAGGCTCAGATTTTCAGTGTCG

GGACACTCCCATTCCTCATCAAAGAAGATCAATTGAATGCTGCACAGAA

AGGAACGAATGTAATAAAGACCTACACCCTACACTGCCTCCATTGAAAA
```

-continued

ACAGAGATTTTGTTGATGGACCTATACACCACAGGGCTTTACTTATATC
TGTGACTGTCTGTAGTTTGCTCTTGGTCCTTATCATATTATTTTGTTAC
TTCCGGTATAAAAGACAAGAAACCAGACCTCGATACAGCATTGGGTTAG
AACAGGATGAAACTTACATTCCTCCTGGAGAATCCCTGAGAGACTTAAT
TGAGCAGTCTCAGAGCTCAGGAAGTGGATCAGGCCTCCCTCTGCTGGTC
CAAAGGACTATAGCTAAGCAGATTCAGATGGTGAAACAGATTGGAAAAG
GTCGCTATGGGAAGTTTGGATGGAAAGTGGCGTGGCGAAAAGGTAGC
TGTGAAAGTGTTCTTCACCACAGAGGAAGCCAGCTGGTTCAGAGAGACA
GAAATATATCAGACAGTGTTGATGAGGCATGAAAACATTTTGGGTTTCA
TTGCTGCAGATATCAAAGGGACAGGGTCCTGGACCCAGTTGTACCTAAT
CACAGACTATCATGAAAATGGTTCCCTTTATGATTATCTGAAGTCCACC
ACCCTAGACGCTAAATCAATGCTGAAGTTAGCCTACTCTTCTGTCAGTG
GCTTATGTCATTTACACACAGAAATCTTTAGTACTCAAGGCAAACCAGC
AATTGCCCATCGAGATCTGAAAAGTAAAAACATTCTGGTGAAGAAAAAT
GGAACTTGCTGTATTGCTGACCTGGGCCTGGCTGTTAAATTTATTAGTG
ATACAAATGAAGTTGACATACCACCTAACACTCGAGTTGGCACCAAACG
CTATATGCCTCCAGAAGTGTTGGACGAGAGCTTGAACAGAAATCACTTC
CAGTCTTACATCATGGCTGACATGTATAGTTTTGGCCTCATCCTTTGGG
AGGTTGCTAGGAGATGTGTATCAGGAGGTATAGTGGAAGAATACCAGCT
TCCTTATCATGACCTAGTGCCCAGTGACCCCTCTTATGAGGACATGAGG
GAGATTGTGTGCATCAAGAAGTTACGCCCCTCATTCCCAAACCGGTGGA
GCAGTGATGAGTGTCTAAGGCAGATGGGAAAACTCATGACAGAATGCTG
GGCTCACAATCCTGCATCAAGGCTGACAGCCCTGCGGGTTAAGAAAACA
CTTGCCAAAATGTCAGAGTCCCAGGACATTAAACTC (SEQ ID NO: 37)

AAGAAAGAGGATGGTGAGAGTACAGCCCCCACCCCCCGTCCAAAGGTCT
TGCGTTGTAAATGCCACCACCATTGTCCAGAAGACTCAGTCAACAATAT
TTGCAGCACAGACGGATATTGTTTCACGATGATAGAAGAGGATGACTCT
GGGTTGCCTGTGGTCACTTCTGGTTGCCTAGGACTAGAAGGCTCAGATT
TTCAGTGTCGGGACACTCCCATTCCTCATCAAAGAAGATCAATTGAATG
CTGCACAGAAAGGAACGAATGTAATAAAGACCTACACCCTACACTGCCT
CCATTGAAAAACAGAGATTTTGTTGATGGACCTATACACCACAGG (SEQ ID NO: 93)

<u>ATGGGTTGGCTGGAAGAACTAAACTGGCAGCTTCACATTTTCTTGCTCA</u>
<u>TTCTTCTCTCTATGCACACAAGGGCA</u>AACTTCCTTGATAACATGCTTTT
GCGAAGTGCAGGAAAATTAAATGTGGGCACCAAGAAAGAGGATGGTGAG
AGTACAGCCCCCACCCCCCGTCCAAAGGTCTTGCGTTGTAAATGCCACC
ACCATTGTCCAGAAGACTCAGTCAACAATATTTGCAGCACAGACGGATA
TTGTTTCACGATGATAGAAGAGGATGACTCTGGGTTGCCTGTGGTCACT
TCTGGTTGCCTAGGACTAGAAGGCTCAGATTTTCAGTGTCGGGACACTC
CCATTCCTCATCAAAGAAGATCAATTGAATGCTGCACAGAAAGGAACGA

-continued

ATGTAATAAAGACCTACACCCTACACTGCCTCCATTGAAAAACAGAGAT
TTTGTTGATGGACCTATACACCACAGGGCTTTACTTATATCTGTGACTG
TCTGTAGTTTGCTCTTGGTCCTTATCATATTATTTTGTTACTTCCGGTA
TAAAAGACAAGAAACCAGACCTCGATACAGCATTGGGTTAGAACAGGAT
GAAACTTACATTCCTCCTGGAGAATCCCTGAGAGACTTAATTGAGCAGT
CTCAGAGCTCAGGAAGTGGATCAGGCCTCCCTCTGCTGGTCCAAAGGAC
TATAGCTAAGCAGATTCAGATGGTGAAACAGATTGGAAAAGGTCGCTAT
GGGGAAGTTTGGATGGGAAAGTGGCGTGGCGAAAAGGTAGCTGTGAAAG
TGTTCTTCACCACAGAGGAAGCCAGCTGGTTCAGAGAGACAGAAATATA
TCAGACAGTGTTGATGAGGCATGAAAACATTTTGGGTTTCATTGCTGCA
GATATCAAAGGGACAGGGTCCTGGACCCAGTTGTACCTAATCACAGACT
ATCATGAAAATGGTTCCCTTTATGATTATCTGAAGTCCACCACCCTAGA
CGCTAAATCAATGCTGAAGTTAGCCTACTCTTCTGTCAGTGGCTTATGT
CATTTACACACAGAAATCTTTAGTACTCAAGGCAAACCAGCAATTGCCC
ATCGAGATCTGAAAAGTAAAAACATTCTGGTGAAGAAAAATGGAACTTG
CTGTATTGCTGACCTGGGCCTGGCTGTTAAATTTATTAGTGATACAAAT
GAAGTTGACATACCACCTAACACTCGAGTTGGCACCAAACGCTATATGC
CTCCAGAAGTGTTGGACGAGAGCTTGAACAGAAATCACTTCCAGTCTTA
CATCATGGCTGACATGTATAGTTTTGGCCTCATCCTTTGGGAGGTTGCT
AGGAGATGTGTATCAGGAGGTATAGTGGAAGAATACCAGCTTCCTTATC
ATGACCTAGTGCCCAGTGACCCCTCTTATGAGGACATGAGGGAGATTGT
GTGCATCAAGAAGTTACGCCCCTCATTCCCAAACCGGTGGAGCAGTGAT
GAGTGTCTAAGGCAGATGGGAAAACTCATGACAGAATGCTGGGCTCACA
ATCCTGCATCAAGGCTGACAGCCCTGCGGGTTAAGAAAACACTTGCCAA
AATGTCAGAGTCCCAGGACATTAAACTC (SEQ ID NO: 94)
AACTTCCTTGATAACATGCTTTTGCGAAGTGCAGGAAAATTAAATGTGG
GCACCAAGAAAGAGGATGGTGAGAGTACAGCCCCCACCCCCCGTCCAAA
GGTCTTGCGTTGTAAATGCCACCACCATTGTCCAGAAGACTCAGTCAAC
AATATTTGCAGCACAGACGGATATTGTTTCACGATGATAGAAGAGGATG
ACTCTGGGTTGCCTGTGGTCACTTCTGGTTGCCTAGGACTAGAAGGCTC
AGATTTTCAGTGTCGGGACACTCCCATTCCTCATCAAAGAAGATCAATT
GAATGCTGCACAGAAAGGAACGAATGTAATAAAGACCTACACCCTACAC
TGCCTCCATTGAAAAACAGAGATTTTGTTGATGGACCTATACACCACAG
G (SEQ ID NO: 40)
<u>ATGACCCGGGCGCTCTGCTCAGCGCTCCGCCAGGCTCTCCTGCTGCTCG</u>
<u>CAGCGGCCGCC</u>GAGCTCTCGCCAGGACTGAAGTGTGTATGTCTTTTGTG
TGATTCTTCAAACTTTACCTGCCAAACAGAAGGAGCATGTTGGGCATCA
GTCATGCTAACCAATGGAAAAGAGCAGGTGATCAAATCCTGTGTCTCCC
TTCCAGAACTGAATGCTCAAGTCTTCTGTCATAGTTCCAACAATGTTAC
CAAAACCGAATGCTGCTTCACAGATTTTTGCAACAACATAACACTGCAC

-continued

CTTCCAACAGCATCACCAAATGCCCCAAAACTTGGACCCATGGAGCTGG

CCATCATTATTACTGTGCCTGTTTGCCTCCTGTCCATAGCTGCGATGCT

GACAGTATGGGCATGCCAGGGTCGACAGTGCTCCTACAGGAAGAAAAG

AGACCAAATGTGGAGGAACCACTCTCTGAGTGCAATCTGGTAAATGCTG

GAAAAACTCTGAAAGATCTGATTTATGATGTGACCGCCTCTGGATCTGG

CTCTGGTCTACCTCTGTTGGTTCAAAGGACAATTGCAAGGACGATTGTG

CTTCAGGAAATAGTAGGAAAAGGTAGATTTGGTGAGGTGTGGCATGGAA

GATGGTGTGGGAAGATGTGGCTGTGAAAATATTCTCCTCCAGAGATGA

AAGATCTTGGTTTCGTGAGGCAGAAATTTACCAGACGGTCATGCTGCGA

CATGAAAACATCCTTGGTTTCATTGCTGCTGACAACAAAGATAATGGAA

CTTGGACTCAACTTTGGCTGGTATCTGAATATCATGAACAGGGCTCCTT

ATATGACTATTTGAATAGAAATATAGTGACCGTGGCTGGAATGATCAAG

CTGGCGCTCTCAATTGCTAGTGGTCTGGCACACCTTCATATGGAGATTG

TTGGTACACAAGGTAAACCTGCTATTGCTCATCGAGACATAAAATCAAA

GAATATCTTAGTGAAAAGTGTGAAACTTGTGCCATAGCGGACTTAGGG

TTGGCTGTGAAGCATGATTCAATACTGAACACTATCGACATACCTCAGA

ATCCTAAAGTGGGAACCAAGAGGTATATGGCTCCTGAAATGCTTGATGA

TACAATGAATGTGAATATCTTTGAGTCCTTCAAACGAGCTGACATCTAT

TCTGTTGGTCTGGTTTACTGGGAAATAGCCCGGAGGTGTTCAGTCGGAG

GAATTGTTGAGGAGTACCAATTGCCTTATTATGACATGGTGCCTTCAGA

TCCCTCGATAGAGGAAATGAGAAAGGTTGTTTGTGACCAGAAGTTTCGA

CCAAGTATCCCAAACCAGTGGCAAAGTTGTGAAGCACTCCGAGTCATGG

GGAGAATAATGCGTGAGTGTTGGTATGCCAACGGAGCGGCCCGCCTAAC

TGCTCTTCGTATTAAGAAGACTATATCTCAACTTTGTGTCAAAGAAGAC

TGCAAAGCC (SEQ ID NO: 41)
GAGCTCTCGCCAGGACTGAAGTGTGTATGTCTTTTGTGTGATTCTTCAA

ACTTTACCTGCCAAACAGAAGGAGCATGTTGGGCATCAGTCATGCTAAC

CAATGGAAAAGAGCAGGTGATCAAATCCTGTGTCTCCCTTCCAGAACTG

AATGCTCAAGTCTTCTGTCATAGTTCCAACAATGTTACCAAAACCGAAT

GCTGCTTCACAGATTTTTGCAACAACATAACACTGCACCTTCCAACAGC

ATCACCAAATGCCCCAAAACTTGGACCCATGGAG (SEQ ID NO: 303)
ATGCTAACCAATGGAAAAGAGCAGGTGATCAAATCCTGTGTCTCCCTTC

CAGAACTGAATGCTCAAGTCTTCTGTCATAGTTCCAACAATGTTACCAA

AACCGAATGCTGCTTCACAGATTTTTGCAACAACATAACACTGCACCTT

CCAACAGCATCACCAAATGCCCCAAAACTTGGACCCATGGAGCTGGCCA

TCATTATTACTGTGCCTGTTTGCCTCCTGTCCATAGCTGCGATGCTGAC

AGTATGGGCATGCCAGGGTCGACAGTGCTCCTACAGGAAGAAAAGAGA

CCAAATGTGGAGGAACCACTCTCTGAGTGCAATCTGGTAAATGCTGGAA

AAACTCTGAAAGATCTGATTTATGATGTGACCGCCTCTGGATCTGGCTC

```
TGGTCTACCTCTGTTGGTTCAAAGGACAATTGCAAGGACGATTGTGCTT

CAGGAAATAGTAGGAAAAGGTAGATTTGGTGAGGTGTGGCATGGAAGAT

GGTGTGGGGAAGATGTGGCTGTGAAAATATTCTCCTCCAGAGATGAAAG

ATCTTGGTTTCGTGAGGCAGAAATTTACCAGACGGTCATGCTGCGACAT

GAAAACATCCTTGGTTTCATTGCTGCTGACAACAAAGATAATGGAACTT

GGACTCAACTTTGGCTGGTATCTGAATATCATGAACAGGGCTCCTTATA

TGACTATTTGAATAGAAATATAGTGACCGTGGCTGGAATGATCAAGCTG

GCGCTCTCAATTGCTAGTGGTCTGGCACACCTTCATATGGAGATTGTTG

GTACACAAGGTAAACCTGCTATTGCTCATCGAGACATAAAATCAAAGAA

TATCTTAGTGAAAAAGTGTGAAACTTGTGCCATAGCGGACTTAGGGTTG

GCTGTGAAGCATGATTCAATACTGAACACTATCGACATACCTCAGAATC

CTAAAGTGGGAACCAAGAGGTATATGGCTCCTGAAATGCTTGATGATAC

AATGAATGTGAATATCTTTGAGTCCTTCAAACGAGCTGACATCTATTCT

GTTGGTCTGGTTTACTGGGAAATAGCCCGGAGGTGTTCAGTCGGAGGAA

TTGTTGAGGAGTACCAATTGCCTTATTATGACATGGTGCCTTCAGATCC

CTCGATAGAGGAAATGAGAAAGGTTGTTTGTGACCAGAAGTTTCGACCA

AGTATCCCAAACCAGTGGCAAAGTTGTGAAGCACTCCGAGTCATGGGGA

GAATAATGCGTGAGTGTTGGTATGCCAACGGAGCGGCCCGCCTAACTGC

TCTTCGTATTAAGAAGACTATATCTCAACTTTGTGTCAAAGAAGACTGC

AAAGCC (SEQ ID NO: 304)
ATGCTAACCAATGGAAAAGAGCAGGTGATCAAATCCTGTGTCTCCCTTC

CAGAACTGAATGCTCAAGTCTTCTGTCATAGTTCCAACAATGTTACCAA

AACCGAATGCTGCTTCACAGATTTTTGCAACAACATAACACTGCACCTT

CCAACAGCATCACCAAATGCCCCAAAACTTGGACCCATGGAG (SEQ ID NO: 307)
ATGACCCGGGCGCTCTGCTCAGCGCTCCGCCAGGCTCTCCTGCTGCTCGCAGCGGCCGCCGAGCTCTC

GCCAGGACTGAAGTGTGTATGTCTTTTGTGTGATTCTTCAAACTTTACCTGCCAAACAGAAGGAGCAT

GTTGGGCATCAGTCATGCTAACCAATGGAAAAGAGCAGGTGATCAAATCCTGTGTCTCCCTTCCAGAA

CTGAATGCTCAAGTCTTCTGTCATAGTTCCAACAATGTTACCAAAACCGAATGCTGCTTCACAGATTT

TTGCAACAACATAACACTGCACCTTCCAACAGGTCTACCTCTGTTGGTTCAAAGGACAATTGCAAGGA

CGATTGTGCTTCAGGAAATAGTAGGAAAAGGTAGATTTGGTGAGGTGTGGCATGGAAGATGGTGTGGG

GAAGATGTGGCTGTGAAAATATTCTCCTCCAGAGATGAAAGATCTTGGTTTCGTGAGGCAGAAATTTA

CCAGACGGTCATGCTGCGACATGAAAACATCCTTGGTTTCATTGCTGCTGACAACAAAGATAATGGAA

CTTGGACTCAACTTTGGCTGGTATCTGAATATCATGAACAGGGCTCCTTATATGACTATTTGAATAGA

AATATAGTGACCGTGGCTGGAATGATCAAGCTGGCGCTCTCAATTGCTAGTGGTCTGGCACACCTTCA

TATGGAGATTGTTGGTACACAAGGTAAACCTGCTATTGCTCATCGAGACATAAAATCAAAGAATATCT

TAGTGAAAAAGTGTGAAACTTGTGCCATAGCGGACTTAGGGTTGGCTGTGAAGCATGATTCAATACTG

AACACTATCGACATACCTCAGAATCCTAAAGTGGGAACCAAGAGGTATATGGCTCCTGAAATGCTTGA

TGATACAATGAATGTGAATATCTTTGAGTCCTTCAAACGAGCTGACATCTATTCTGTTGGTCTGGTTT

ACTGGGAAATAGCCCGGAGGTGTTCAGTCGGAGGAATTGTTGAGGAGTACCAATTGCCTTATTATGAC

ATGGTGCCTTCAGATCCCTCGATAGAGGAAATGAGAAAGGTTGTTTGTGACCAGAAGTTTCGACCAAG
```

-continued

TATCCCAAACCAGTGGCAAAGTTGTGAAGCACTCCGAGTCATGGGGAGAATAATGCGTGAGTGTTGGT

ATGCCAACGGAGCGGCCCGCCTAACTGCTCTTCGTATTAAGAAGACTATATCTCAACTTTGTGTCAAA

GAAGACTGCAAAGCC (SEQ ID NO: 308)

GAGCTCTCGCCAGGACTGAAGTGTGTATGTCTTTTGTGTGATTCTTCAA

ACTTTACCTGCCAAACAGAAGGAGCATGTTGGGCATCAGTCATGCTAAC

CAATGGAAAAGAGCAGGTGATCAAATCCTGTGTCTCCCTTCCAGAACTG

AATGCTCAAGTCTTCTGTCATAGTTCCAACAATGTTACCAAAACCGAAT

GCTGCTTCACAGATTTTTGCAACAACATAACACTGCACCTTCCAACAGG

TCTACCTCTGTTGGTTCAAAGGACAATTGCAAGGACGATTGTGCTTCAG

GAAATAGTAGGAAAAGGTAGATTTGGTGAGGTGTGGCATGGAAGATGGT

GTGGGGAAGATGTGGCTGTGAAAATATTCTCCTCCAGAGATGAAAGATC

TTGGTTTCGTGAGGCAGAAATTTACCAGACGGTCATGCTGCGACATGAA

AACATCCTTGGTTTCATTGCTGCTGACAACAAAGATAATGGAACTTGGA

CTCAACTTTGGCTGGTATCTGAATATCATGAACAGGGCTCCTTATATGA

CTATTTGAATAGAAATATAGTGACCGTGGCTGGAATGATCAAGCTGGCG

CTCTCAATTGCTAGTGGTCTGGCACACCTTCATATGGAGATTGTTGGTA

CACAAGGTAAACCTGCTATTGCTCATCGAGACATAAAATCAAAGAATAT

CTTAGTGAAAAAGTGTGAAACTTGTGCCATAGCGGACTTAGGGTTGGCT

GTGAAGCATGATTCAATACTGAACACTATCGACATACCTCAGAATCCTA

AAGTGGGAACCAAGAGGTATATGGCTCCTGAAATGCTTGATGATACAAT

GAATGTGAATATCTTTGAGTCCTTCAAACGAGCTGACATCTATTCTGTT

GGTCTGGTTTACTGGGAAATAGCCCGGAGGTGTTCAGTCGGAGGAATTG

TTGAGGAGTACCAATTGCCTTATTATGACATGGTGCCTTCAGATCCCTC

GATAGAGGAAATGAGAAAGGTTGTTTGTGACCAGAAGTTTCGACCAAGT

ATCCCAAACCAGTGGCAAAGTTGTGAAGCACTCCGAGTCATGGGGAGAA

TAATGCGTGAGTGTTGGTATGCCAACGGAGCGGCCCGCCTAACTGCTCT

TCGTATTAAGAAGACTATATCTCAACTTTGTGTCAAAGAAGACTGCAAA

GCC (SEQ ID NO: 311)

<u>ATGACCCGGCGCTCTGCTCAGCGCTCCGCCAGGCTCTCCTGCTGCTCG</u>

<u>CAGCGGCCGCC</u>GAGCTCTCGCCAGGACTGAAGTGTGTATGTCTTTTGTG

TGATTCTTCAAACTTTACCTGCCAAACAGAAGGAGCATGTTGGGCATCA

GTCATGCTAACCAATGGAAAAGAGCAGGTGATCAAATCCTGTGTCTCCC

TTCCAGAACTGAATGCTCAAGTCTTCTGTCATAGTTCCAACAATGTTAC

CAAAACCGAATGCTGCTTCACAGATTTTTGCAACAACATAACACTGCAC

CTTCCAACAGATAATGGAACTTGGACTCAACTTTGGCTGGTATCTGAAT

ATCATGAACAGGGCTCCTTATATGACTATTTGAATAGAAATATAGTGAC

CGTGGCTGGAATGATCAAGCTGGCGCTCTCAATTGCTAGTGGTCTGGCA

CACCTTCATATGGAGATTGTTGGTACACAAGGTAAACCTGCTATTGCTC

ATCGAGACATAAAATCAAAGAATATCTTAGTGAAAAAGTGTGAAACTTG

-continued

```
TGCCATAGCGGACTTAGGGTTGGCTGTGAAGCATGATTCAATACTGAAC

ACTATCGACATACCTCAGAATCCTAAAGTGGGAACCAAGAGGTATATGG

CTCCTGAAATGCTTGATGATACAATGAATGTGAATATCTTTGAGTCCTT

CAAACGAGCTGACATCTATTCTGTTGGTCTGGTTTACTGGGAAATAGCC

CGGAGGTGTTCAGTCGGAGGAATTGTTGAGGAGTACCAATTGCCTTATT

ATGACATGGTGCCTTCAGATCCCTCGATAGAGGAAATGAGAAAGGTTGT

TTGTGACCAGAAGTTTCGACCAAGTATCCCAAACCAGTGGCAAAGTTGT

GAAGCACTCCGAGTCATGGGGAGAATAATGCGTGAGTGTTGGTATGCCA

ACGGAGCGGCCCGCCTAACTGCTCTTCGTATTAAGAAGACTATATCTCA

ACTTTGTGTCAAAGAAGACTGCAAAGCCTAA
```

(SEQ ID NO: 312)

```
GAGCTCTCGCCAGGACTGAAGTGTGTATGTCTTTTGTGTGATTCTTCAA

ACTTTACCTGCCAAACAGAAGGAGCATGTTGGGCATCAGTCATGCTAAC

CAATGGAAAGAGCAGGTGATCAAATCCTGTGTCTCCCTTCCAGAACTG

AATGCTCAAGTCTTCTGTCATAGTTCCAACAATGTTACCAAAACCGAAT

GCTGCTTCACAGATTTTTGCAACAACATAACACTGCACCTTCCAACAGA

TAATGGAACTTGGACTCAACTTTGGCTGGTATCTGAATATCATGAACAG

GGCTCCTTATATGACTATTTGAATAGAAATATAGTGACCGTGGCTGGAA

TGATCAAGCTGGCGCTCTCAATTGCTAGTGGTCTGGCACACCTTCATAT

GGAGATTGTTGGTACACAAGGTAAACCTGCTATTGCTCATCGAGACATA

AAATCAAAGAATATCTTAGTGAAAAAGTGTGAAACTTGTGCCATAGCGG

ACTTAGGGTTGGCTGTGAAGCATGATTCAATACTGAACACTATCGACAT

ACCTCAGAATCCTAAAGTGGGAACCAAGAGGTATATGGCTCCTGAAATG

CTTGATGATACAATGAATGTGAATATCTTTGAGTCCTTCAAACGAGCTG

ACATCTATTCTGTTGGTCTGGTTTACTGGGAAATAGCCCGGAGGTGTTC

AGTCGGAGGAATTGTTGAGGAGTACCAATTGCCTTATTATGACATGGTG

CCTTCAGATCCCTCGATAGAGGAAATGAGAAAGGTTGTTTGTGACCAGA

AGTTTCGACCAAGTATCCCAAACCAGTGGCAAAGTTGTGAAGCACTCCG

AGTCATGGGGAGAATAATGCGTGAGTGTTGGTATGCCAACGGAGCGGCC

CGCCTAACTGCTCTTCGTATTAAGAAGACTATATCTCAACTTTGTGTCA

AGAAGACTGCAAAGCCTAA
```

SEQUENCE LISTING

```
Sequence total quantity: 3502
SEQ ID NO: 1        moltype = AA  length = 512
FEATURE             Location/Qualifiers
source              1..512
                    mol_type = protein
                    organism = Homo sapiens
SEQUENCE: 1
MTAPWVALAL LWGSLCAGSG RGEAETRECI YYNANWELER TNQSGLERCE GEQDKRLHCY   60
ASWRNSSGTI ELVKKGCWLD DFNCYDRQEC VATEENPQVY FCCCEGNFCN ERFTHLPEAG  120
GPEVTYEPPP TAPTLLTVLA YSLLPIGGLS LIVLLAFWMY RHRKPPYGHV DIHEDPGPPP  180
PSPLVGLKPL QLLEIKARGR FGCVWKAQLM NDFVAVKIFP LQDKQSWQSE REIFSTPGMK  240
HENLLQFIAA EKRGSNLEVE LWLITAFHDK GSLTDYLKGN IITWNELCHV AETMSRGLSY  300
LHEDVPWCRG EGHKPSIAHR DFKSKNVLLK SDLTAVLADF GLAVRFEPGK PPGDTHGQVG  360
TRRYMAPEVL EGAINFQRDA FLRIDMYAMG LVLWELVSRC KAADGPVDEY MLPFEEEIGQ  420
```

```
HPSLEELQEV VVHKKMRPTI KDHWLKHPGL AQLCVTIEEC WDHDAEARLS AGCVEERVSL    480
IRRSVNGTTS DCLVSLVTSV TNVDLPPKES SI                                 512

SEQ ID NO: 2            moltype = AA  length = 115
FEATURE                 Location/Qualifiers
source                  1..115
                        mol_type = protein
                        organism = Homo sapiens
SEQUENCE: 2
GRGEAETREC IYYNANWELE RTNQSGLERC EGEQDKRLHC YASWRNSSGT IELVKKGCWL    60
DDFNCYDRQE CVATEENPQV YFCCCEGNFC NERFTHLPEA GGPEVTYEPP PTAPT         115

SEQ ID NO: 3            moltype = AA  length = 100
FEATURE                 Location/Qualifiers
source                  1..100
                        mol_type = protein
                        organism = Homo sapiens
SEQUENCE: 3
GRGEAETREC IYYNANWELE RTNQSGLERC EGEQDKRLHC YASWRNSSGT IELVKKGCWL    60
DDFNCYDRQE CVATEENPQV YFCCCEGNFC NERFTHLPEA                         100

SEQ ID NO: 4            moltype = AA  length = 512
FEATURE                 Location/Qualifiers
source                  1..512
                        mol_type = protein
                        organism = Homo sapiens
SEQUENCE: 4
MTAPWVALAL LWGSLCAGSG RGEAETRECI YYNANWELER TNQSGLERCE GEQDKRLHCY    60
ASWANSSGTI ELVKKGCWLD DFNCYDRQEC VATEENPQVY FCCCEGNFCN ERFTHLPEAG    120
GPEVTYEPPP TAPTLLTVLA YSLLPIGGLS LIVLLAFWMY RHRKPPYGHV DIHEDPGPPP    180
PSPLVGLKPL QLLEIKARGR FGCVWKAQLM NDFVAVKIFP LQDKQSWQSE REIFSTPGMK    240
HENLLQFIAA EKRGSNLEVE LWLITAFHDK GSLTDYLKGN IITWNELCHV AETMSRGLSY    300
LHEDVPWCRG EGHKPSIAHR DFKSKNVLLK SDLTAVLADF GLAVRFEPGK PPGDTHGQVG    360
TRRYMAPEVL EGAINFQRDA FLRIDMYAMG LVLWELVSRC KAADGPVDEY MLPFEEEIGQ    420
HPSLEELQEV VVHKKMRPTI KDHWLKHPGL AQLCVTIEEC WDHDAEARLS AGCVEERVSL    480
IRRSVNGTTS DCLVSLVTSV TNVDLPPKES SI                                 512

SEQ ID NO: 5            moltype = AA  length = 115
FEATURE                 Location/Qualifiers
source                  1..115
                        mol_type = protein
                        organism = Homo sapiens
SEQUENCE: 5
GRGEAETREC IYYNANWELE RTNQSGLERC EGEQDKRLHC YASWANSSGT IELVKKGCWL    60
DDFNCYDRQE CVATEENPQV YFCCCEGNFC NERFTHLPEA GGPEVTYEPP PTAPT         115

SEQ ID NO: 6            moltype = AA  length = 100
FEATURE                 Location/Qualifiers
source                  1..100
                        mol_type = protein
                        organism = Homo sapiens
SEQUENCE: 6
GRGEAETREC IYYNANWELE RTNQSGLERC EGEQDKRLHC YASWANSSGT IELVKKGCWL    60
DDFNCYDRQE CVATEENPQV YFCCCEGNFC NERFTHLPEA                         100

SEQ ID NO: 7            moltype = DNA  length = 1536
FEATURE                 Location/Qualifiers
source                  1..1536
                        mol_type = other DNA
                        organism = Homo sapiens
SEQUENCE: 7
atgacggcgc cctgggtggc cctcgccctc ctctggggat cgctgtgcgc cggctctggg    60
cgtggggagg ctgagacacg ggagtgcatc tactacaacg ccaactggga gctggagcgc    120
accaaccaga gcggcctgga gcgctgcgaa ggcgagcagg acaagcggct gcactgctac    180
gcctcctggc gcaacagctc tggcaccatc gagctcgtga agaagggctg ctggctagat    240
gacttcaact gctacgatag gcaggagtgt gtggccactg aggagaaccc ccaggtgtac    300
ttctgctgct gtgaaggcaa cttctgcaac gaacgcttca ctcatttgcc agaggctggg    360
ggcccggaag tcacgtacga gccaccccg acagccccca cctgctcac ggtgctggcc     420
tactcactgc tgcccatcgg ggggcttttcc ctcatcgtcc tgctggccct ttggatgtac    480
cggcatcgca agcccccta cggtcatgtg acatccatg aggaccctgg gcctccacca     540
ccatcccctc tggtggggcct gaagccactg cagctgctgg agatcaaggc tcggggcgc    600
tttggctgtg tctggaaggc ccagctcatg aatgactttg tagctgtcaa gatcttccca    660
ctccaggaca agcagtcgtg gcagagtgaa cgggagatct tcagcacacc tggcatgaag    720
cacgagaacc tgctacagtt cattgctgcc gagaagcgag gctcaacct gagtagag      780
ctgtggctca tcacggcctt ccatgacaag ggctccctca ggattacct aaggggaac     840
atcatcacat ggaacgaact gtgtcatgta cagagacga tgtcacgagg cctctctac     900
ctgcatgagg atgtgccctg gtgccgtggc gagggccaca gccgtctat tgcccacagg    960
gactttaaaa gtaagaatgt attgctgaag agcgacctca cagccgtgct ggctgacttt    1020
ggcttggctc ttcgatttga gccagggaaa cctccagggg acacccacgg acaggtaggc    1080
```

```
acgagacggt acatggctcc tgaggtgctc gagggagcca tcaacttcca gagagatgcc    1140
ttcctgcgca ttgacatgta tgccatgggg ttggtgctgt gggagcttgt gtctcgctgc    1200
aaggctgcag acggacccgt ggatgagtac atgctgccct tgaggaaga gattggccag     1260
caccttcgt tggaggagct gcaggaggtg gtggtgcaca agaagatgag gcccaccatt     1320
aaagatcact ggttgaaaca cccgggcctg gcccagcttt gtgtgaccat cgaggagtgc    1380
tgggaccatg atgcagaggc tcgcttgtcc gcgggctgtg tggaggagcg ggtgtccctg    1440
attcggaggt cggtcaacgg cactacctcg gactgtctcg tttccctggt gacctctgtc    1500
accaatgtgg acctgccccc taaagagtca agcatc                              1536

SEQ ID NO: 8              moltype = DNA   length = 345
FEATURE                   Location/Qualifiers
source                    1..345
                          mol_type = other DNA
                          organism = Homo sapiens
SEQUENCE: 8
gggcgtgggg aggctgagac acgggagtgc atctactaca acgccaactg ggagctggag    60
cgcaccaacc agagcggcct ggagcgctgc gaaggcgagc aggacaagcg gctgcactgc    120
tacgcctcct ggcgcaacag ctctggcacc atcgagctcg tgaaacaggg ctgctggcta    180
gatgacttca actgctacga taggcaggag tgtgtggcca ctgaggagaa cccccaggtg    240
tacttctgct gctgtgaagg caacttctgc aacgaacgct tcactcattt gccagaggct    300
gggggccccgg aagtcacgta cgagccaccc ccgacagccc ccacc                   345

SEQ ID NO: 9              moltype = AA   length = 513
FEATURE                   Location/Qualifiers
source                    1..513
                          mol_type = protein
                          organism = Homo sapiens
SEQUENCE: 9
MGAAAKLAFA VFLISCSSGA ILGRSETQEC LFFNANWEKD RTNQTGVEPC YGDKDKRRHC     60
FATWKNISGS IEIVKQGCWL DDINCYDRTD CVEKKDSPEV YFCCCEGNMC NEKFSYFPEM    120
EVTQPTSNPV TPKPPYYNIL LYSLVPLMLI AGIVICAFWV YRHHKMAYPP VLVPTQDPGP    180
PPPSPLLGLK PLQLLEVKAR GRFGCVWKAQ LLNEYVAVKI FPIQDKQSWQ NEYEVYSLPG    240
MKHENILQFI GAEKRGTSVD VDLWLITAFH EKGSLSDFLK ANVVSWNELC HIAETMARGL    300
AYLHEDIPGL KDGHKPAISH RDIKSKNVLL KNNLTACIAD FGLALKFEAG KSAGDTHGQV    360
GTRRYMAPEV LEGAINFQRD AFLRIDMYAM GLVLWELASR CTAADGPVDE YMLPFEEEIG    420
QHPSLEDMQE VVVHKKKRPV LRDYWQKHAG MAMLCETIEE CWDHDAEARL SAGCVGERIT    480
QMQRLTNIIT TEDIVTVVTM VTNVDFPPKE SSL                                 513

SEQ ID NO: 10             moltype = AA   length = 115
FEATURE                   Location/Qualifiers
source                    1..115
                          mol_type = protein
                          organism = Homo sapiens
SEQUENCE: 10
ILGRSETQEC LFFNANWEKD RTNQTGVEPC YGDKDKRRHC FATWKNISGS IEIVKQGCWL     60
DDINCYDRTD CVEKKDSPEV YFCCCEGNMC NEKFSYFPEM EVTQPTSNPV TPKPP         115

SEQ ID NO: 11             moltype = AA   length = 100
FEATURE                   Location/Qualifiers
source                    1..100
                          mol_type = protein
                          organism = Homo sapiens
SEQUENCE: 11
ILGRSETQEC LFFNANWEKD RTNQTGVEPC YGDKDKRRHC FATWKNISGS IEIVKQGCWL     60
DDINCYDRTD CVEKKDSPEV YFCCCEGNMC NEKFSYFPEM                          100

SEQ ID NO: 12             moltype = DNA   length = 1539
FEATURE                   Location/Qualifiers
source                    1..1539
                          mol_type = other DNA
                          organism = Homo sapiens
SEQUENCE: 12
atgggagctg ctgcaaagtt ggcgtttgcc gtctttctta tctcctgttc ttcaggtgct     60
atacttggta gatcagaaac tcaggagtgt cttttcttta atgctaattg ggaaaaagac    120
agaaccaatc aaactggtgt tgaaccgtgt tatggtgaca agataaaacg gcggcattgt    180
tttgctacct ggaagaatat ttctggttcc attgaaatag tgaaacaagg ttgttggctg    240
gatgatatca actgctatga caggactgat tgtgtagaaa aaaagacag ccctgaagta     300
tattttgtt gctgtgaggg caatatgtgt aatgaaaagt tttcttattt tccggagatg     360
gaagtcacac agcccacttc aaatccagtt acacctaagc caccctatta caacatcctg    420
ctctattcct tggtgccact tatgttaatt gcggggattg tcatttgtgc attttgggtg    480
tacaggcatc acaagatggc ctaccctcct gtacttgttc caactcaaga cccaggacca    540
cccccaccttt ctccattact aggtttgaaa ccactgcagt tattagaagt gaaagcaggg    600
ggaagatttg gttgtgtctg gaaagccag ttgcttaacg aatatgtggc tgtcaaaata     660
tttccaatac aggacaaaca gtcatggcaa aatgaatacg aagtctacag tttgcctgga    720
atgaagcatg agaacatatt acagttcatt ggtgcagaaa aacgaggcac cagtgttgat    780
gtggatcttt ggctgatcac agcatttcat gaaaagggtt cactatcaga ctttcttaag    840
gctaatgtgg tctcttggaa tgaactgtgt catattgcag aaaccatggc tagaggattg    900
gcatatttac atgaggatat acctggccta aagatggcc acaaacctgc catatctcac    960
agggacatca aaagtaaaaa tgtgctgttg aaaaacaacc tgacagcttg cattgctgac    1020
```

```
tttgggttgg ccttaaaatt tgaggctggc aagtctgcag gcgatacccca tggacaggtt    1080
ggtacccgga ggtacatggc tccagaggta ttagagggtg ctataaactt ccaaagggat    1140
gcattttttga ggatagatat gtatgccatg ggattagtcc tatgggaact ggcttctcgc    1200
tgtactgctg cagatggacc tgtagatgaa tacatgttgc catttgagga ggaaattggc    1260
cagcatccat ctcttgaaga catgcaggaa gttgttgtgc ataaaaaaaa gaggcctgtt    1320
ttaagagatt attggcagaa acatgctgga atggcaatgc tctgtgaaac cattgaagaa    1380
tgttgggatc acgacgcaga agccaggtta tcagctggat gtgtaggtga aagaattacc    1440
cagatgcaga gactaacaaa tattattacc acagaggaca ttgtaacagt ggtcacaatg    1500
gtgacaaatg ttgactttcc tcccaaagaa tctagtcta                            1539

SEQ ID NO: 13           moltype = DNA   length = 345
FEATURE                 Location/Qualifiers
source                  1..345
                        mol_type = other DNA
                        organism = Homo sapiens
SEQUENCE: 13
atacttggta gatcagaaac tcaggagtgt cttttcttta atgctaattg ggaaaaagac    60
agaaccaatc aaactggtgt tgaaccgtgt tatggtgaca aagataaagg gcggcattgt   120
tttgctacct ggaagaatat ttctggttcc attgaaatag tgaaacaagg ttgttggctg   180
gatgatatca actgctatga caggactgat tgtgtagaaa aaaagacag ccctgaagta    240
tattttgtt gctgtgaggg caatatgtgt aatgaaaagt tttcttattt tccggagatg    300
gaagtcacac agcccacttc aaatccagtt acacctaagc caccc                    345

SEQ ID NO: 14           moltype = AA   length = 503
FEATURE                 Location/Qualifiers
source                  1..503
                        mol_type = protein
                        organism = Homo sapiens
SEQUENCE: 14
MTLGSPRKGL LMLLMALVTQ GDPVKPSRGP LVTCTCESPH CKGPTCRGAW CTVVLVREEG     60
RHPQEHRGCG NLHRELCRGR PTEFVNHYCC DSHLCNHNVS LVLEATQPPS EQPGTDGQLA    120
LILGPVLALL ALVALGVLGL WHVRRRQEKQ RGLHSELGES SLILKASEQG DSMLGDLLDS    180
DCTTGSGSGL PFLVQRTVAR QVALVECVGK GRYGEVWRGL WHGESVAVKI FSSRDEQSWF    240
RETEIYNTVL LRHDNILGFI ASDMTSRNSS TQLWLITHYH EHGSLYDFLQ RQTLEPHLAL    300
RLAVSAACGL AHLHVEIFGT QGKPAIAHRD FKSRNVLVKS NLQCCIADLG LAVMHSQGSD    360
YLDIGNNPRV GTKRYMAPEV LDEQIRTDCF ESYKWTDIWA FGLVLWEIAR RTIVNGIVED    420
YRPPFYDVVP NDPSFEDMKK VVCVDQQTPT IPNRLAADPV LSGLAQMMRE CWYPNPSARL    480
TALRIKKTLQ KISNSPEKPK VIQ                                             503

SEQ ID NO: 15           moltype = AA   length = 97
FEATURE                 Location/Qualifiers
source                  1..97
                        mol_type = protein
                        organism = Homo sapiens
SEQUENCE: 15
DPVKPSRGPL VTCTCESPHC KGPTCRGAWC TVVLVREEGR HPQEHRGCGN LHRELCRGRP     60
TEFVNHYCCD SHLCNHNVSL VLEATQPPSE QPGTDGQ                               97

SEQ ID NO: 16           moltype = DNA   length = 1509
FEATURE                 Location/Qualifiers
source                  1..1509
                        mol_type = other DNA
                        organism = Homo sapiens
SEQUENCE: 16
atgaccttgg gctcccccag gaaaggcctt ctgatgctgc tgatggcctt ggtgacccag     60
ggagaccctg tgaagccgtc tcggggcccg ctggtgacct gcacgtgtga gagcccacat    120
tgcaaggggc ctacctgccg ggggctggtg cacagtag tgctggtgcg ggaggagggg     180
aggcaccccc aggaacatcg gggctgcggg aacttgcaca gggagctctg caggggggcg    240
cccaccgagt tcgtcaacca ctactgtgc gacagccac tctgcaacca caacgtgtcc     300
ctggtgctgg aggccaccca acctccttcg gagcagccgg aacagatgg ccagctggcc     360
ctgatcctgg gccccgtgct ggccttgctg gccctggtgg ccctgggtgt cctgggcctg    420
tggcatgtcc gacggaggca ggagaagcag cgtggcctgc acagcgagct gggagagtcc    480
agtctcatcc tgaaagcatc tgagcagggc gacagcatgt tggggaccct cctggacagt    540
gactgcacca caggagtgg ctcagggctc ccttcctgg tgcagaggac agtggcacgg     600
caggttgcct tggtggagtg tgtgggaaaa ggccgctatg gcgaagtgtg gcggggcttg    660
tggcacggtg agagtgtggc cgtcaagatc ttctcctcga gggatgaaca gtcctggttc    720
cgggagactg agatctataa cacagtgttg ctcagacacg acaacatcct aggcttcatc    780
gcctcagaca tgaccttcccg caactcgagc acgcagctgt ggctcatcac gcactaccac    840
gagcacggct ccctctacga ctttctgcag agacagacg tggaccccca tctggctctg    900
aggctagctg tgtccgcggc atgcggcctg cgcacccgc acgtggagat cttcggtaca    960
cagggcaaac cagccattgc ccaccgcgac ttcaagagcc gcaatgtgct ggtcaagagc   1020
aacctgcagt gttgcatcgc cgacctgggc ctggctgtga tgcactcaca gggcagcgat   1080
tacctggaca tcggcaacaa cccgagagtg ggcaccaagc ggtacatggc acccgaggtg   1140
ctggacgaga tcaggacaac ggactgcttt gagtcctaca agtggacgga catctgggcc   1200
tttggcctgg tgctgtggga gattgcccgc cggaccatcg tgaatggcat cgtcgaggac   1260
tatagaccac ccttctatga tgtggtgccc aatgaccca gctttgagga catgaagaag   1320
gtggtgtgtg tggatcagca gaccccaca tccctaacc ggctggctgc agacccggtc    1380
ctctcaggcc tagctcagat gatgcgggag tgctggtacc caaacccctc tgcccgactc   1440
accgcgctgc ggatcaagaa gacactacaa aaaattagca cagtccaga gaagcctaaa    1500
```

```
                                       -continued
gtgattcaa                                                            1509

SEQ ID NO: 17           moltype = DNA  length = 291
FEATURE                 Location/Qualifiers
source                  1..291
                        mol_type = other DNA
                        organism = Homo sapiens
SEQUENCE: 17
gaccctgtga agccgtctcg gggcccgctg gtgacctgca cgtgtgagag cccacattgc    60
aaggggccta cctgccgggg ggctggtgc acagtagtgc tggtgcggga ggaggggagg    120
cacccccagg aacatcgggg ctgcgggaac ttgcacaggg agctctgcag ggggcgcccc   180
accgagttcg tcaaccacta ctgctgcgac agccaccctct gcaaccacaa cgtgtccctg   240
gtgctggagg ccacccaacc tccttcggag cagccgggaa cagatggcca g            291

SEQ ID NO: 18           moltype = AA   length = 509
FEATURE                 Location/Qualifiers
source                  1..509
                        mol_type = protein
                        organism = Homo sapiens
SEQUENCE: 18
MVDGVMILPV LIMIALPSPS MEDEKPKVNP KLYMCVCEGL SCGNEDHCEG QQCFSSLSIN    60
DGFHVYQKGC FQVYEQGKMT CKTPPSPGQA VECCQGDWCN RNITAQLPTK GKSFPGTQNF   120
HLEVGLIILS VVFAVCLLAC LLGVALRKFK RRNQERLNPR DVEYGTIEGL ITTNVGDSTL   180
ADLLDHSCTS GSGSGLPFLV QRTVARQITL LECVGKGRYG EVWRGSWQGE NVAVKIFSSR   240
DEKSWFRETE LYNTVMLRHE NILGFIASDM TSRHSSTQLW LITHYHEMGS LYDYLQLTTL   300
DTVSCLRIVL SIASGLAHLH IEIFGTQGKP AIAHRDLKSK NILVKKNGQC CIADLGLAVM   360
HSQSTNQLDV GNNPRVGTKR YMAPEVLDET IQVDCFDSYK RVDIWAFGLV LWEVARRMVS   420
NGIVEDYKPP FYDVVPNDPS FEDMRKVVCV DQQRPNIPNR WFSDPTLTSL AKLMKECWYQ   480
NPSARLTALR IKKTLTKIDN SLDKLKTDC                                     509

SEQ ID NO: 19           moltype = AA   length = 103
FEATURE                 Location/Qualifiers
source                  1..103
                        mol_type = protein
                        organism = Homo sapiens
SEQUENCE: 19
MEDEKPKVNP KLYMCVCEGL SCGNEDHCEG QQCFSSLSIN DGFHVYQKGC FQVYEQGKMT    60
CKTPPSPGQA VECCQGDWCN RNITAQLPTK GKSFPGTQNF HLE                     103

SEQ ID NO: 20           moltype = DNA  length = 1527
FEATURE                 Location/Qualifiers
source                  1..1527
                        mol_type = other DNA
                        organism = Homo sapiens
SEQUENCE: 20
atggtagatg gagtgatgat tcttcctgtg cttatcatga ttgctctccc ctcccctagt    60
atggaagatg agaagcccaa ggtcaacccc aaactctaca tgtgtgtgtg tgaaggtctc   120
tcctgcggta atgaggacca ctgtgaaggc cagcagtgct tttcctcact gagcatcaac   180
gatggcttcc acgtctacca gaaaggctgc ttccaggttt atgagcaggg aaagatgacc   240
tgtaagaccc cgccgtcccc tggccaagcc gtggagtgct gccaagggga ctggtgtaac   300
aggaacatca cggcccagct gcccactaaa ggaaaatctt tccctggaac acagaatttc   360
cacttggagg ttggcctcat tattctctct gtagtgttcg cagtatgtct tttagcctgc   420
ctgctgggag ttgctctccg aaaatttaaa aggcgcaacc aagaacgcct caatccccga   480
gacgtggagt atggcactat cgaagggctc atcaccacca atgttggaga cagcacttta   540
gcagatttat tggatcattc gtgtacatca ggaagtggct ctggtcttcc ttttctggta   600
caaagaacag tggctcgcca gattacactg ttggagtgtg tcgggaaagg caggtatggt   660
gaggtgtgga gggcagctg gcaaggggag aatgttgccg tgaagatctt ctcctcccgt   720
gatgagaagt catggttcag ggaaacggaa ttgtacaaca ctgtgatgct gaggcatgaa   780
aatatcttag gtttcattgc ttcagacatg acatccagtac ccagctgtgg                840
ttaattacac attatcatga aatgggatcg ttgtacgact atcttcagct tactactctg   900
gatacagtta gctgccttcg aatagtgctc tccatagcta gtggtcttgc acatttgcac   960
atagagatat ttgggaccca agggaaacca gccattgccc atcgagattt aaagagcaaa  1020
aatattctgt ttaagaagaa tggacagtgt tgcatagcag atttgggcct ggcagtcatg  1080
cattcccaga gcaccaatca gcttgatgtg gggaacaatc ccagagtggg caccaagcgc  1140
tacatggccc ccgaagttct agatgaaacc atccaggtgg attgtttcga ttcttataaa  1200
agggtcgata tttgggcctt tggacttgtt ttgtgggaag tggccaggcg gatggtgagc  1260
aatggtatag tggaggatta caagccaccg ttctacgatg tggttcccaa tgacccaagt  1320
tttgaagata tgaggaaggt agtctgtgtg gatcaacaaa ggccaaacat acccaacaga  1380
tggttctcag acccgacatt aacctctctg gccaagctaa tgaaagaatg ctggtatcaa  1440
aatccatccg caagactcac agcactgcgt atcaaaaaga ctttgaccaa aattgataat  1500
tccctcgaca aattgaaaac tgactgt                                      1527

SEQ ID NO: 21           moltype = DNA  length = 309
FEATURE                 Location/Qualifiers
source                  1..309
                        mol_type = other DNA
                        organism = Homo sapiens
SEQUENCE: 21
atggaagatg agaagcccaa ggtcaacccc aaactctaca tgtgtgtgtg tgaaggtctc    60
```

```
tcctgcggta atgaggacca ctgtgaaggc cagcagtgct tttcctcact gagcatcaac    120
gatggcttcc acgtctacca gaaaggctgc ttccaggttt atgagcaggg aaagatgacc    180
tgtaagaccc cgccgtcccc tggccaagcc gtggagtgct gccaagggga ctggtgtaac    240
aggaacatca cggcccagct gcccactaaa ggaaaatcct tccctggaac acagaatttc    300
cacttggag                                                            309

SEQ ID NO: 22           moltype = AA  length = 532
FEATURE                 Location/Qualifiers
source                  1..532
                        mol_type = protein
                        organism = Homo sapiens
SEQUENCE: 22
MPQLYIYIRL LGAYLFIISR VQGQNLDSML HGTGMKSDSD QKKSENGVTL APEDTLPFLK     60
CYCSGHCPDD AINNTCITNG HCFAIIEEDD QGETTLASGC MKYEGSDFQC KDSPKAQLRR    120
TIECCRTNLC NQYLQPTLPP VVIGPFFDGS IRWLVLLISM AVCIIAMIIF SSCFCYKHYC    180
KSISSRRRYN RDLEQDEAFI PVGESLKDLI DQSQSSGSGS GLPLLVQRTI AKQIQMVRQV    240
GKGRYGEVWM GKWRGEKVAV KVFFTTEEAS WFRETEIYQT VLMRHENILG FIAADIKGTG    300
SWTQLYLITD YHENGSLYDF LKCATLDTRA LLKLAYSAAC GLCHLHTEIY GTQGKPAIAH    360
RDLKSKNILI KKNGSCCIAD LGLAVKFNSD TNEVDVPLNT RVGTKRYMAP EVLDESLNKN    420
HFQPYIMADI YSFGLIIWEM ARRCITGGIV EEYQLPYYNM VPSDPSYEDM REVVCVKRLR    480
PIVSNRWNSD ECLRAVLKLM SECWAHNPAS RLTALRIKKT LAKMVESQDV KI            532

SEQ ID NO: 23           moltype = AA  length = 129
FEATURE                 Location/Qualifiers
source                  1..129
                        mol_type = protein
                        organism = Homo sapiens
SEQUENCE: 23
QNLDSMLHGT GMKSDSDQKK SENGVTLAPE DTLPFLKCYC SGHCPDDAIN NTCITNGHCF     60
AIIEEDDQGE TTLASGCMKY EGSDFQCKDS PKAQLRRTIE CCRTNLCNQY LQPTLPPVVI    120
GPFFDGSIR                                                            129

SEQ ID NO: 24           moltype = DNA  length = 1596
FEATURE                 Location/Qualifiers
source                  1..1596
                        mol_type = other DNA
                        organism = Homo sapiens
SEQUENCE: 24
atgcctcagc tatacattta catcagatta ttgggagcct atttgttcat catttctcgt     60
gttcaaggac agaatctgga tagtatgctt catggcactg ggatgaaatc agactccgac    120
cagaaaaagt cagaaaatgg agtaaccttg gcaccagagg ataccttgcc ttttttaaag    180
tgctattgct cagggcactg tccagatgat gctattaata cacatgcat aactaatgga    240
cattgctttg ccatcataga agaagatgac cagggagaaa ccacattgc ttcagggtgt    300
atgaaatatg aaggatctga ttttcagtgc aaagattctc caaaagccca gctacgccgg    360
acaatagaat gttgtcggac caatttatgt aaccagtatt tgcaacccac actgcccct    420
gttgtcatag gtccgttttt tgatggcagc attcgatggc tggttttgct catttctatg    480
gctgtctgca taattgctat gatcatcttc tccagctgct tttgttacaa acattattgc    540
aagagcatct caagcagacg tcgttacaat cgtgatttgg aacaggatga agcatttatt    600
ccagttggag aatcactaaa agaccttatt gaccagtcac aaagttctgg tagtgggtct    660
ggactacctt tattggttca gcgaactatt gccaaacaga ttcagatggt ccggcaagtt    720
ggtaaaggcc gatatggaga gtatggatg gcaaatggc gtggcgaaaa agtggcggtt    780
aaagtattct ttaccactga agaagccagc tggtttcgag aaacagaaat ctaccaaact    840
gtgctaatgc gccatgaaaa catacttggt ttcatagcgg cagacattaa aggtacaggt    900
tcctggactc agctctattt gattactgat taccatgaaa atggatctct ctatgacttc    960
ctgaaatgtg ctacactgga caccagagcc ctgcttaata tggcttattc agctgcctgt   1020
ggtctgtgcc acctgcacac agaaatttat ggcacccaag gaaagccgc aattgctcat   1080
cgagacctaa agagcaaaaa catcctcatc aagaaaatg ggagttgctg cattgctgac   1140
ctgggccttg ctgttaaatt caacagtgac acaaatgaag ttgatgtgcc cttgaatacc   1200
agggtgggca ccaaacgcta catggctccc gaagtgctgg acgaaagcct gaacaaaaac   1260
cacttccagc cctacatcat ggctgacatc tacagcttcg gcctaatcat ttgggagatg   1320
gctcgtcgtt gtatcacagg agggatcgtg gaagaatacc aattgccata ttacaacatg   1380
gtaccgagtg atccgtcata cgaagatatg cgtgaggttg tgtgtgtcaa acgtttgcgg   1440
ccaattgtgt ctaatcggtg gaacagtgat gaatgtctac gagcagtttt gaagctaatg   1500
tcagaatgct gggcccacaa tccagcctcc agactcacag cattgagaat taagaagacg   1560
cttgccaaga tggttgaatc ccaagatgta aaaatc                              1596

SEQ ID NO: 25           moltype = DNA  length = 387
FEATURE                 Location/Qualifiers
source                  1..387
                        mol_type = other DNA
                        organism = Homo sapiens
SEQUENCE: 25
cagaatctgg atagtatgct tcatggcact gggatgaaat cagactccga ccagaaaaag     60
tcagaaaatg gagtaacctt gcaccagag gataccttgc cttttttaaa gtgctattgc    120
tcagggcact gtccagatga tgctattaat aacacatgca taactaatgg acattgcttt    180
gccatcatag aagaagatga ccagggagaa accacattag cttcagggtg tatgaaatat    240
gaaggatctg attttcagtg caaagattct ccaaaagccc agctacgccg gacaatagaa    300
tgttgtcgga ccaattatg taaccagtat ttgcaaccca cactgccccc tgttgtcata    360
ggtccgtttt tgatggcag cattcga                                         387
```

```
SEQ ID NO: 26              moltype = AA  length = 505
FEATURE                    Location/Qualifiers
source                     1..505
                           mol_type = protein
                           organism = Homo sapiens
SEQUENCE: 26
MAESAGASSF FPLVVLLLAG SGGSGPRGVQ ALLCACTSCL QANYTCETDG ACMVSIFNLD      60
GMEHHVRTCI PKVELVPAGK PFYCLSSEDL RNTHCCYTDY CNRIDLRVPS GHLKEPEHPS     120
MWGPVELVGI IAGPVFLLFL IIIIVFLVIN YHQRVYHNRQ RLDMEDPSCE MCLSKDKTLQ     180
DLVYDLSTSG SGSGLPLFVQ RTVARTIVLQ EIIGKGRFGE VWRGRWRGGD VAVKIFSSRE     240
ERSWFREAEI YQTVMLRHEN ILGFIAADNK DNGTWTQLWL VSDYHEHGSL FDYLNRYTVT     300
IEGMIKLALS AASGLAHLHM EIVGTQGKPG IAHRDLKSKN ILVKKNGMCA IADLGLAVRH     360
DAVTDTIDIA PNQRVGTKRY MAPEVLDETI NMKHFDSFKC ADIYALGLVY WEIARRCNSG     420
GVHEEYQLPY YDLVPSDPSI EEMRKVVCDQ KLRPNIPNWW QSYEALRVMG KMMRECWYAN     480
GAARLTALRI KKTLSQLSVQ EDVKI                                          505

SEQ ID NO: 27              moltype = AA  length = 103
FEATURE                    Location/Qualifiers
source                     1..103
                           mol_type = protein
                           organism = Homo sapiens
SEQUENCE: 27
SGPRGVQALL CACTSCLQAN YTCETDGACM VSIFNLDGME HHVRTCIPKV ELVPAGKPFY      60
CLSSEDLRNT HCCYTDYCNR IDLRVPSGHL KEPEHPSMWG PVE                      103

SEQ ID NO: 28              moltype = DNA  length = 1515
FEATURE                    Location/Qualifiers
source                     1..1515
                           mol_type = other DNA
                           organism = Homo sapiens
SEQUENCE: 28
atggcggagt cggccggagc ctcctccttc ttccccttg ttgtcctcct gctcgccggc       60
agcggcgggt ccgggcccccg gggggtccag gctctgctgt gtgcgtgcac cagctgcctc    120
caggccaact acacgtgtga gacagatggg gcctgcatgg tttccatttt caatctggat    180
gggatggagc accatgtgcg cacctgcatc cccaaagtgg agctggtccc tgccgggaag    240
cccttctact gcctgagctc ggaggacctg cgcaacaccc actgctgcta cactgactac    300
tgcaacagga tcgacttgag ggtgcccagt ggtcacctca aggagcctga gcacccgtcc    360
atgtggggcc cggtggagct ggtaggcatc atcgccggcc cggtgttcct cctgttcctc    420
atcatcatca ttgttttcct tgtcattaac tatcatcagc gtgtctatca caaccgccaa    480
agactggaca tggaagatcc ctcatgtgag atgtgtctct ccaaagacaa gacgctccag    540
gatcttgtct acgatctctc cacctcaggg tctggctcag ggttacccct cttttgtccag   600
cgcacagtgg cccgaaccat cgttttacaa gagattattg gcaagggtcg gtttggggaa    660
gtatggcggg gccgctggag gggtggtgat gtggctgtga aaatattctc ttctcgtgaa    720
gaacggtctt ggttcaggga agcagagata taccagacgg tcatgctgcg ccatgaaaac    780
atccttggat ttattgctgc tgacaataaa gataatggca cctggacaca gctgtggctt    840
gtttctgact atcatgagca cgggtccctg ttttgattat cgaaccggta cagtgaca     900
attgagggga tgattaagct ggccttgtct gctgctagtg ggctggcaca cctgcacatg    960
gagatcgtgg gcacccaagg gaagcctgga attgctcatc gagacttaaa gtcaaagaac   1020
attctggtga agaaaaatgg catgtgtgcc atagcagacc tgggcctggc tgtccgtcat   1080
gatgcagtca ctgacaccat tgacattgcc ccgaatcaga gggtgggac caaacgatac   1140
atggcccctg aagtacttga tgaaaccatt aatatgaaac actttgactc ctttaaatgt   1200
gctgatattt atgccctcgg gcttgtatat tgggagattg ctcgaagatg caattctgga   1260
ggagtccatg aagaatatca gctgccatat tacgacttag tgccctctga cccttccatt   1320
gaggaaatgc gaaaggttgt atgtgatcag aagctgcgtc ccaacatccc caactggtgg   1380
cagagttatg aggcactgcg ggtgatgggg aagatgatgc gagagtgttg gtatgccaac   1440
ggcgcagccc gcctgacggc cctgcgcatc aagaagaccc tctcccagct cagcgtgcag   1500
gaagacgtga agatc                                                   1515

SEQ ID NO: 29              moltype = DNA  length = 309
FEATURE                    Location/Qualifiers
source                     1..309
                           mol_type = other DNA
                           organism = Homo sapiens
SEQUENCE: 29
tccgggcccc gggggtcca ggctctgctg tgtgcgtgca ccagctgcct ccaggccaac       60
tacacgtgtg agacagatgg ggcctgcatg gtttccattt tcaatctgga tgggatggag    120
caccatgtgc gcacctgcat ccccaaagtg gagctggtcc ctgccgggaa gcccttctac    180
tgcctgagct cggaggacct gcgcaacacc cactgctgct acactgacta ctgcaacagg    240
atcgacttga gggtgcccag tggtcacctc aaggagcctg agcacccgtc catgtgggc    300
ccggtggag                                                          309

SEQ ID NO: 30              moltype = AA  length = 503
FEATURE                    Location/Qualifiers
source                     1..503
                           mol_type = protein
                           organism = Homo sapiens
SEQUENCE: 30
MEAAVAAPRP RLLLLVLAAA AAAAAALLPG ATALQCFCHL CTKDNFTCVT DGLCFVSVTE      60
```

```
TTDKVIHNSM CIAEIDLIPR DRPFVCAPSS KTGSVTTTYC CNQDHCNKIE LPTTVKSSPG    120
LGPVELAAVI AGPVCFVCIS LMLMVYICHN RTVIHHRVPN EEDPSLDRPF ISEGTTLKDL    180
IYDMTTSGSG SGLPLLVQRT IARTIVLQES IGKGRFGEVW RGKWRGEEVA VKIFSSREER    240
SWFREAEIYQ TVMLRHENIL GFIAADNKDN GTWTQLWLVS DYHEHGSLFD YLNRYTVTVE    300
GMIKLALSTA SGLAHLHMEI VGTQGKPAIA HRDLKSKNIL VKKNGTCCIA DLGLAVRHDS    360
ATDTIDIAPN HRVGTKRYMA PEVLDDSINM KHFESFKRAD IYAMGLVFWE IARRCSIGGI    420
HEDYQLPYYD LVPSDPSVEE MRKVVCEQKL RPNIPNRWQS CEALRVMAKI MRECWYANGA    480
ARLTALRIKK TLSQLSQQEG IKM                                           503

SEQ ID NO: 31             moltype = AA  length = 102
FEATURE                   Location/Qualifiers
source                    1..102
                          mol_type = protein
                          organism = Homo sapiens
SEQUENCE: 31
AALLPGATAL QCFCHLCTKD NFTCVTDGLC FVSVTETTDK VIHNSMCIAE IDLIPRDRPF     60
VCAPSSKTGS VTTTYCCNQD HCNKIELPTT VKSSPGLGPV EL                      102

SEQ ID NO: 32             moltype = DNA  length = 1509
FEATURE                   Location/Qualifiers
source                    1..1509
                          mol_type = other DNA
                          organism = Homo sapiens
SEQUENCE: 32
atggaggcgg cggtcgctgc tccgcgtccc cggctgctcc tcctcgtgct ggcggcggcg     60
gcggcggcgg cggcggcgct gctcccgggg gcgacggcgt tacagtgttt ctgccacctc    120
tgtacaaaag acaattttac ttgtgtgaca gatgggctct gctttgtctc tgtcacagag    180
accacagaca agttatacaa caacagcatg tgtatagctg aaattgactt aattcctcga    240
gataggccgt ttgtatgtgc accctcttca aaaactgggt ctgtgactac aacatattgc    300
tgcaatcagg accattgcaa taaaatagaa cttccaacta ctgtaaagtc atcacctggc    360
cttggtcctg tggaactggc agctgtcatt gctggaccag tgtgcttcgt ctgcatctca    420
ctcatgttga tggtctatat ctgccacaac cgcactgtca ttcaccatcg agtgccaaat    480
gaagaggacc cttcattaga tcgcccttt atttcagagg gtactacgtt gaaagactta    540
atttatgata tgcaacgtc aggttctggc tcaggttcat cattgcttgt tcagagaaca    600
attgcgagaa ctattgtgtt acaagaaagc attggcaaag gtcgattgg agaagtttga    660
agaggaaagt ggcggggaga agaagttgct gttaagatat tctcctcag agaagaacgt    720
tcgtggttcc gtgaggcaga gatttatcaa actgtaatgt tacgtcatga aacatcctg    780
ggatttatag cagcagacaa taaagacaat ggtacttgga ctcagtctg gttggtgtca    840
gattatcatg agcatggatc ccttttgat tacttaaaca gatacacagt tactgtggaa    900
ggaatgataa aacttgctct gtccacggcg agcggtcttg cccatcttca catggagatt    960
gttggtaccc aaggaaagcc agccattgct catagagatt tgaaatcaaa gaatatcttg    1020
gtaaagaaga atggaacttg ctgtattgca gacttaggac tggcagtaag acatgattca    1080
gccacagata ccattgatat tgctccaaac cacagagtgg aacaaaaag gtacatgcc    1140
cctgaagttc tcgatgattc cataaatatg aaacattttg aatccttcaa acgtgctgac    1200
atctatgcaa tgggcttagt attctgggaa attgctcgac gatgttccat ggtggaatt    1260
catgaagatt accaactgcc ttattatgat cttgtacctt ctgacccatc agttgaagaa    1320
atgagaaaag ttgtttgtga acagaagtta aggccaaata tcccaaacag atggcagagc    1380
tgtgaagcct tgagagtaat ggctaaaatt atgagagaat gttggtatgc caatggagca    1440
gctaggctta cagcattgcg gattaagaaa acattatcgc aactcagtca acaggaaggc    1500
atcaaaatg                                                          1509

SEQ ID NO: 33             moltype = DNA  length = 306
FEATURE                   Location/Qualifiers
source                    1..306
                          mol_type = other DNA
                          organism = Homo sapiens
SEQUENCE: 33
gcggcgctgc tcccggggc gacggcgtta cagtgtttct gccacctctg tacaaaagac     60
aattttactt gtgtgacaga tgggctctgc tttgtctctg tcacagagac cacagacaaa    120
gttatacaca acagcatgtg tatagctgaa attgacttaa ttcctcgaga taggccgttt    180
gtatgtgcac cctcttcaaa aactgggtct gtgactacaa catattgctg caatcaggac    240
cattgcaata aaatagaact tccaactact gtaaagtcat cacctggcct tggtcctgtg    300
gaactg                                                              306

SEQ ID NO: 34             moltype = AA  length = 502
FEATURE                   Location/Qualifiers
source                    1..502
                          mol_type = protein
                          organism = Homo sapiens
SEQUENCE: 34
MLLRSAGKLN VGTKKEDGES TAPTPRPKVL RCKCHHHCPE DSVNNICSTD GYCFTMIEED     60
DSGLPVVTSG CLGLEGSDFQ CRDTPIPHQR RSIECCTERN ECNKDLHPTL PPLKNRDFVD    120
GPIHHRALLI SVTVCSLLLV LIILFCYFRY KRQETRPRYS IGLEQDETYI PPGESLRDLI    180
EQSQSSGSGS GLPLLVQRTI AKQIQMVKQI GKGRYGEVWM GKWRGEKVAV KVFFTTEEAS    240
WFRETEIYQT VLMRHENILG FIAADIKGTG SWTQLYLITD YHENGSLYDY LKSTTLDAKS    300
MLKLAYSSVS GLCHLHTEIF STQGKPAIAH RDLKSKNILV KKNGTCCIAD LGLAVKFISD    360
TNEVDIPPNT RVGTKRYMPP EVLDESLNRN HFQSYIMADM YSFGLILWEV ARRCVSGGIV    420
EEYQLPYHDL VPSDPSYEDM REIVCIKKLR PSFPNRWSSD ECLRQMGKLM TECWAHNPAS    480
RLTALRVKKT LAKMSESQDI KL                                            502
```

```
SEQ ID NO: 35            moltype = AA  length = 113
FEATURE                  Location/Qualifiers
source                   1..113
                         mol_type = protein
                         organism = Homo sapiens
SEQUENCE: 35
KKEDGESTAP TPRPKVLRCK CHHHCPEDSV NNICSTDGYC FTMIEEDDSG LPVVTSGCLG    60
LEGSDFQCRD TPIPHQRRSI ECCTERNECN KDLHPTLPPL KNRDFVDGPI HHR          113

SEQ ID NO: 36            moltype = DNA  length = 1506
FEATURE                  Location/Qualifiers
source                   1..1506
                         mol_type = other DNA
                         organism = Homo sapiens
SEQUENCE: 36
atgcttttgc gaagtgcagg aaaattaaat gtgggcacca agaaagagga tggtgagagt    60
acagccccca cccccgtcc aaaggtcttg cgttgtaaat gccaccacca ttgtccagaa    120
gactcagtca acaatatttg cagcacagac ggatattgtt tcacgatgat agaaggagt    180
gactctgggt tgcctgtggt cacttctggt tgcctaggac tagaaggctc agattttcag    240
tgtcgggaca ctcccattcc tcatcaaaga agatcaattg aatgctgcac agaaaggaac    300
gaatgtaata aagacctaca ccctacactg cctccattga aaaacagaga ttttgttgat    360
ggacctatac accacaggcc tttacttata tctgtgactg tctgtagttt gctcttggtc    420
cttatcatat tattttgtta cttccggtat aaaagacaag aaaccagacc tcgatacagc    480
attgggttag aacaggatga aacttacatt cctcctggag aatccctgag agacttaatt    540
gagcagtctc agagctcagg aagtggatca ggcctccctc tgctggtcca aaggactata    600
gctaagcaga ttcagatggt gaaacagatt ggaaaaggtc gctatgggca agtttggatg    660
ggaaagtggc gtggcgaaaa ggtagctgtg aaagtgttct tcaccacaga ggaagccagc    720
tggttcagag agacagaaat atatcagaca gtgttgatga ggcatgaaaa cattttgggt    780
ttcattgctg cagatatcaa agggacaggg tcctggacca agttgtacct aatcacagac    840
tatcatgaaa atggttccct ttatgattat ctgaagtcca ccaccctaga cgctaaatca    900
atgctgaagt tagcctactc ttctgtcagt ggcttatgtc atttacacac agaaatcttt    960
agtactcaag gcaaaccagc aattgcccat cgagatctga aaagtaaaaa cattctggtt   1020
aagaaaaatg gaacttgctg tattgctgac ctgggcctgg ctgttaaatt tattagtgat   1080
acaaatgaag ttgacatacc acctaacact cgagttggca ccaaacgcta tgcctcca    1140
gaagtgttgg acgagagctt gaacagaaat cacttccagt cttacatcat ggctgacatg   1200
tatagttttg gcctcatcct tgggaggtt gctaggagat gtgtatcagg aggtatagtg   1260
gaagaatacc agcttcctta tcatgaccta gtgcccagtg accccttaa tgaggacatg   1320
agggagattg tgtgcatcaa gaagttacgc ccctcattcc caaaccggtg gagcagtgat   1380
gagtgtctaa ggcagatggg aaaactcatg acagaatgc gggctcacaa tcctgcatca   1440
aggctgacag ccctgcgggt taagaaaaca cttgccaaaa tgtcagagtc ccaggacatt   1500
aaactc                                                              1506

SEQ ID NO: 37            moltype = DNA  length = 339
FEATURE                  Location/Qualifiers
source                   1..339
                         mol_type = other DNA
                         organism = Homo sapiens
SEQUENCE: 37
aagaaagagg atggtgagag tacagccccc accccccgtc caaaggtctt gcgttgtaaa    60
tgccaccacc attgtccaga agactcagtc aacaatattt gcagcacaga cggatatttt   120
ttcacgatga tagaagagga tgactctggg ttgcctgtgg tcacttctgg ttgcctagga   180
ctagaaggct cagattttca gtgtcgggac actcccattc ctcatcaaag aagatcaatt   240
gaatgctgca gaaaggaa cgaatgtaat aaagacctac accctacact gcctccattg   300
aaaaacagag attttgttga tggacctata caccacagg                         339

SEQ ID NO: 38            moltype = AA  length = 493
FEATURE                  Location/Qualifiers
source                   1..493
                         mol_type = protein
                         organism = Homo sapiens
SEQUENCE: 38
MTRALCSALR QALLLLAAAA ELSPGLKCVC LLCDSSNFTC QTEGACWASV MLTNGKEQVI    60
KSCVSLPELN AQVFCHSSNN VTKTECCFTD FCNNITLHLP TASPNAPKLG PMELAIIITV   120
PVCLLSIAAM LTVWACQGRQ CSYRKKKRPN VEEPLSECNL VNAGKTLKDL IYDVTASGSG   180
SGLPLLVQRT IARTIVLQEI VGKGRFGEVW HGRWCGEDVA VKIFSSRDER SWFREAEIYQ   240
TVMLRHENIL GFIAADNKDN GTWTQLWLVS EYHEQGSLYD YLNRNIVTVA GMIKLALSIA   300
SGLAHLHMEI VGTQGKPAIA HRDIKSKNIL VKKCETCAIA DLGLAVKHDS ILNTIDIPQN   360
PKVGTKRYMA PEMLDDTMNV NIFESFKRAD IYSVGLVYWE IARRCSVGGI VEEYQLPYYD   420
MVPSDPSIEE MRKVVCDQKF RPSIPNQWQS CEALRVMGRI MRECWYANGA ARLTALRIKK   480
TISQLCVKED CKA                                                      493

SEQ ID NO: 39            moltype = AA  length = 93
FEATURE                  Location/Qualifiers
source                   1..93
                         mol_type = protein
                         organism = Homo sapiens
SEQUENCE: 39
ELSPGLKCVC LLCDSSNFTC QTEGACWASV MLTNGKEQVI KSCVSLPELN AQVFCHSSNN    60
```

VTKTECCFTD FCNNITLHLP TASPNAPKLG PME                                        93

SEQ ID NO: 40           moltype = DNA   length = 1479
FEATURE                 Location/Qualifiers
source                  1..1479
                        mol_type = other DNA
                        organism = Homo sapiens
SEQUENCE: 40
atgacccggg cgctctgctc agcgctccgc caggctctcc tgctgctcgc agcggccgcc    60
gagctctcgc caggactgaa gtgtgtatgt cttttgtgtg attcttcaaa ctttacctgc   120
caaacagaag gagcatgttg ggcatcagtc atgctaacca atggaaaaga gcaggtgatc   180
aaatcctgtg tctcccttcc agaactgaat gctcaagtct tctgtcatag ttccaacaat   240
gttaccaaaa ccgaatgctg cttcacagat ttttgcaaca acataacact gcaccttcca   300
acagcatcac caaatgcccc aaaacttgga cccatggagc tggccatcat tattactgta   360
cctgtttgcc tcctgtccat agctgcgatg ctgacagtat gggcatgcca gggtcgacag   420
tgctcctaca ggaagaaaaa gagaccaaat gtggaggaac cactctctga gtgcaatctg   480
gtaaatgctg gaaaaactct gaaagatctg atttatgatg tgaccgcctc tggatctggc   540
tctggtctac ctctgttggt tcaaaggaca attgcaagga cgattgtgct tcaggaaata   600
gtaggaaaag gtagatttgg tgaggtgtgg catggaagat ggtgtgggga agatgtggct   660
gtgaaaatat tctcctccag agatgaaaga tcttggtttc gtgaggcaga aatttaccag   720
acggtcatgc tgcgacatga aaacatcctt ggtttcattg ctgctgacaa caagataat   780
ggaacttgga ctcaactttg gctggtatct gaatatcatg aacagggctc cttatatgca   840
tatttgaata gaaatatagt gaccgtggct ggaatgatca agctggcgct ctcaattgct   900
agtggtctgg cacaccttca tatggagatt gttggtacac aagtaaacc tgctattgct   960
catcgagaca taaaatcaaa gaatatctta gtgaaaagt gtgaaacttg tgccatagcg  1020
gacttagggt tggctgtgaa gcatgattca atactgaaca ctatcgacat acctcagaat  1080
cctaaagtgg gaaccaagag gtatatggct cctgaaatgc ttgatgatac aatgaatgtg  1140
aatatctttg agtccttcaa acgagctgac atctattctg ttggtctggt ttactgggaa  1200
atagcccgga ggtgttcagt cggaggaatt gttgaggagt accaattgcc ttattatgac  1260
atggtgcctt cagatccctc gatagaggaa atgagaaggg ttgtttgtga ccagaagttt  1320
cgaccaagta tcccaaacca gtggcaaagt tgtgaagcac tccgagtcat ggggagaata  1380
atgcgtgagt gttggtatgc caacggagcg gcccgcctaa ctgctcttcg tattaagaag  1440
actatatctc aactttgtgt caagaagac tgcaaagcc                          1479

SEQ ID NO: 41           moltype = DNA   length = 279
FEATURE                 Location/Qualifiers
source                  1..279
                        mol_type = other DNA
                        organism = Homo sapiens
SEQUENCE: 41
gagctctcgc caggactgaa gtgtgtatgt cttttgtgtg attcttcaaa ctttacctgc    60
caaacagaag gagcatgttg ggcatcagtc atgctaacca atggaaaaga gcaggtgatc   120
aaatcctgtg tctcccttcc agaactgaat gctcaagtct tctgtcatag ttccaacaat   180
gttaccaaaa ccgaatgctg cttcacagat ttttgcaaca acataacact gcaccttcca   240
acagcatcac caaatgcccc aaaacttgga cccatggag                          279

SEQ ID NO: 42           moltype = AA   length = 567
FEATURE                 Location/Qualifiers
source                  1..567
                        mol_type = protein
                        organism = Homo sapiens
SEQUENCE: 42
MGRGLLRGLW PLHIVLWTRI ASTIPPHVQK SVNNDMIVTD NNGAVKFPQL CKFCDVRFST    60
CDNQKSCMSN CSITSICEKP QEVCVAVWRK NDENITLETV CHDPKLPYHD FILEDAASPK   120
CIMKEKKKPG ETFFMCSCSS DECNDNIIFS EEYNTSNPDL LLVIFQVTGI SLLPPLGVAI   180
SVIIIFYCYR VNRQQKLSST WETGKTRKLM EFSEHCAIIL EDDRSDISST CANNINHNTE   240
LLPIELDTLV GKGRFAEVYK AKLKQNTSEQ FETVAVKIFP YEEYASWKTE KDIFSDINLK   300
HENILQFLTA EERKTELGKQ YWLITAFHAK GNLQEYLTRH VISWEDLRKL GSSLARGIAH   360
LHSDHTPCGR PKMPIVHRDL KSSNILVKND LTCCLCDFGL SLRLDPTLSV DDLANSGQVG   420
TARYMAPEVL ESRMNLENVE SFKQTDVYSM ALVLWEMTSR CNAVGEVKDY EPPFGSKVRE   480
HPCVESMKDN VLRDRGRPEI PSFWLNHQGI QMVCETLTEC WDHDPEARLT AQCVAERFSE   540
LEHLDRLSGR SCSEEKIPED GSLNTTK                                       567

SEQ ID NO: 43           moltype = AA   length = 144
FEATURE                 Location/Qualifiers
source                  1..144
                        mol_type = protein
                        organism = Homo sapiens
SEQUENCE: 43
TIPPHVQKSV NNDMIVTDNN GAVKFPQLCK FCDVRFSTCD NQKSCMSNCS ITSICEKPQE    60
VCVAVWRKND ENITLETVCH DPKLPYHDFI LEDAASPKCI MKEKKKPGET FFMCSCSSDE   120
CNDNIIFSEE YNTSNPDLLL VIFQ                                          144

SEQ ID NO: 44           moltype = DNA   length = 1701
FEATURE                 Location/Qualifiers
source                  1..1701
                        mol_type = other DNA
                        organism = Homo sapiens
SEQUENCE: 44

```
atgggtcggg ggctgctcag gggcctgtgg ccgctgcaca tcgtcctgtg gacgcgtatc    60
gccagcacga tcccaccgca cgttcagaag tcgttaata  cgacatgat  agtcactgac   120
aacaacggtg cagtcaagtt tccacaactg tgtaaatttt gtgatgtgag attttccacc   180
tgtgacaacc agaaatcctg catgagcaac tgcagcatca cctccatctg tgagaagcca   240
caggaagtct gtgtggctgt atggagaaag aatgacgaga acataacact agagacagtt   300
tgccatgacc ccaagctccc ctaccatgac tttattctgg aagatgctgc ttctccaaag   360
tgcattatga aggaaaaaaa aaagcctggt gagactttct tcatgtgttc ctgtagctct   420
gatgagtgca atgacaacat catcttctca gaagaatata acaccagcaa tcctgacttg   480
ttgctagtca tatttcaagt gacaggcatc agcctcctgc caccactggg agttgccata   540
tctgtcatca tcatcttcta ctgctaccgc gttaacctgc agcagaagct gagttcaacc   600
tgggaaaccg gcaagacgcg gaagctcatg gagttcagcg agcactgtgc catcatcctg   660
gaagatgacc gctctgacat cagctccacg tgtgccaaca acatcaacca caacacagag   720
ctgctgccca ttgagctgga caccctggtg gggaaaggtc gctttgctga ggtctataag   780
gccaagctga agcagaacac ttcagacgag tttgagacag tggcagtcaa gatcttttcc   840
tatgaggagt atgcctcttg aagacagag  aaggacatct tctcagacat caatctgaag   900
catgagaaca tactccagtt cctgacggct gaggagcgga gacggagtt  ggggaaacaa   960
tactggctga tcaccgcctt ccacgccaag ggcaacctac aggagtacct gacgcggcat  1020
gtcatcagct gggaggacct gcgcaagctg ggcagctccc tcgcccgggg gattgctcac  1080
ctccacagtg atcacactcc atgtgggagg cccaagatgc ccatcgtgca cagggacctc  1140
aagagctcca atatcctcgt gaagaacgac ctaacctgct gcctgtgtga ctttgggctt  1200
tccctgcgtc tggaccctac tctgtctgtg atgacctgg  ctaacagtgg gcaggtggga  1260
actgcaagat acatgctcc  agaagtcctaa gaatccagga tgaatttgga gaatgttgag  1320
tccttcaagc agaccgatgt ctactccatg gctctggtgc tctgggaaat gacatctcgc  1380
tgtaatgcag tgggagaagt aaaagattat gagcctccat ttggttccaa ggtgcgggag  1440
cacccctgtg tcgaaagcat gaaggacaac gtgttgagag atcgagggcg accagaaatt  1500
cccagcttct ggctcaacca ccagggcatc cagatggtgt ggagacgtt  gactgagtgc  1560
tgggaccacg acccagaggc ccgtctcaca gcccagtgtg tggcagaacg cttcagtgag  1620
ctggagcatc tggacaggct ctcggggagg agctgctcgg aggagaagat tcctgaagac  1680
ggctccctaa acactaccaa a                                             1701

SEQ ID NO: 45             moltype = DNA  length = 432
FEATURE                   Location/Qualifiers
source                    1..432
                          mol_type = other DNA
                          organism = Homo sapiens
SEQUENCE: 45
acgatcccac cgcacgttca gaagtcggtt aataacgaca tgatagtcac tgacaacaac    60
ggtgcagtca agtttccaca actgtgtaaa ttttgtgatg tgagattttc cacctgtgac   120
aaccagaaat cctgcatgag caactgcagc atcacctcc  tctgtgagaa gccacaggaa   180
gtctgtgtgg ctgtatggag aaagaatgac gagaacataa cactagagac agtttgccat   240
gaccccaagc tcccctacca tgactttatt ctggaagatg ctgcttctcc aaagtgcatt   300
atgaaggaaa aaaaaaagcc tggtgagact ttcttcatgt gttcctgtag ctctgatgag   360
tgcaatgaca acatcatctt ctcagaagaa tataacacca gcaatcctga cttgttgcta   420
gtcatatttc aa                                                       432

SEQ ID NO: 46             moltype = AA  length = 1038
FEATURE                   Location/Qualifiers
source                    1..1038
                          mol_type = protein
                          organism = Homo sapiens
SEQUENCE: 46
MTSSLQRPWR VPWLPWTILL VSTAAASQNQ ERLCAFKDPY QQDLGIGESR ISHENGTILC    60
SKGSTCYGLW EKSKGDINLV KQGCWSHIGD PQECHYEECV VTTTPPSIQN GTYRFCCCST   120
DLCNVNFTEN FPPPDTTPLS PPHSFNRDET IIIALASVSV LAVLIVALCF GYRMLTGDRK   180
QGLHSMNMME AAASEPSLDL DNLKLLELIG RGRYGAVYKG SLDERPVAVK VFSFANRQNF   240
INEKNIYRVP LMEHDNIARF IVGDERVTAD GRMEYLLVME YYPNGSLCKY LSLHTSDWVS   300
SCRLAHSVTR GLAYLHTELP RGDHYKPAIS HRDLNSRNVL VKNDGTCVIS DFGLSMRLTG   360
NRLVRPGEED NAAISEVGTI RYMAPEVLEG AVNLRDCESA LKQVDMYALG LIYWEIFMRC   420
TDLFPGESVP EYQMAFQTEV GNHPTFEDMQ VLVSREKQRP KPPEAWKENS LAVRSLKETI   480
EDCWDQDAEA RLTAQCAEER MAELMMIWER NKSVSPTVNP MSTAMQNERN LSHNRRVPKI   540
GPYPDYSSSS YIEDSIHHTD SIVKNISSEH SMSSTPLTIG EKNRNSINYE RQQAQARIPS   600
PETSVTSLST NTTTTNTTGL TPSTGMTTIS EMPYPDETNL HTTNVAQSIG PTPVCLQLTE   660
EDLETNKLDP KEVDKNLKES SDENLMEHSL KQFSGPDPLS STSSSLLYPL IKLAVEATGQ   720
QDFTQTANGQ ACLIPDVLPT QIYPLPKQQN LPKRPTSLPL NTKNSTKEPR LKFGSKHKSN   780
LKQVETGVAK MNTINAAEPH VVTVTMNGVA GRNHSVNSHA ATTQYANGTV LSGQTTNIVT   840
HRAQEMLQNQ FIGEDTRLNI NSSPDEHEPL LRREQQAGHD EGVLDRLVDR RERPLEGGRT   900
NSNNNNSNPC SEQDVLAQGV PSTAADPGPS KPRRAQRPNS LDLSATNVLD GSSIQIGEST   960
QDGKSGSGEK IKKRVKTPYS LKRWRPSTWV ISTESLDCEV NNNGSNRAVH SKSSTAVYLA  1020
EGGTATTMVS KDIGMNCL                                                1038

SEQ ID NO: 47             moltype = AA  length = 124
FEATURE                   Location/Qualifiers
source                    1..124
                          mol_type = protein
                          organism = Homo sapiens
SEQUENCE: 47
SQNQERLCAF KDPYQQDLGI GESRISHENG TILCSKGSTC YGLWEKSKGD INLVKQGCWS    60
HIGDPQECHY EECVVTTTPP SIQNGTYRFC CCSTDLCNVN FTENFPPPDT TPLSPPHSFN   120
RDET                                                                124
```

| SEQ ID NO: 48 | moltype = DNA length = 3114 |
| --- | --- |
| FEATURE | Location/Qualifiers |
| source | 1..3114 |
| | mol_type = other DNA |
| | organism = Homo sapiens |

SEQUENCE: 48

```
atgacttcct cgctgcagcg gccctggcgg gtgccctggc taccatggac catcctgctg    60
gtcagcactg cggctgcttc gcagaatcaa gaacggctat gtgcgtttaa agatccgtat   120
cagcaagacc ttgggatagg tgagagtaga atctctcatg aaaatgggac aatattatgc   180
tcgaaaggta gcacctgcta tggcctttgg gagaaatcaa aagggacat aaatcttgta    240
aaacaaggat gttggtctca cattggagat ccccaagagt gtcactatga agaatgtgta   300
gtaactacca ctcctccctc aattcagaat ggaacatacc gtttctgctg ttgtagcaca   360
gatttatgta atgtcaactt tactgagaat tttccacctc ctgacacaac accactcagt   420
ccacctcatt catttaaccg agatgagaca ataatcattg ctttggcatc agtctctgta   480
ttagctgttt tgatagttgc cttatgcttt ggatacagaa tgttgacagg agaccgtaaa   540
caaggtcttc acagtatgaa catgatggag gcagcagcat ccgaaccctc tcttgatcta   600
gataatctga aactgttgga gctgattggc cgaggtcgat atggagcagt atataaaggc   660
tccttggatg agcgtccagt tgctgtaaaa gtgttttcct ttgcaaaccg tcagaatttt   720
atcaacgaaa agaacattta cagagtgcct tgatggaac atgacaacat tgcccgcttt   780
atagttggag atgagagagt cactgcagat ggacgcatgg aatatttgct tgtgatggag   840
tactatccca atggatcttt atgcaagtat ttaagtctcc acacaagtga ctgggtaagc   900
tcttgccgtc ttgctcattc tgttactaga ggactggctt atcttcacac agaattacca   960
cgaggagatc attataaacc tgcaatttcc catcgagatt taaacagcag aaatgtccta  1020
gtgaaaaatg atggaacctg tgttattagt gactttggac tgtccatgag gctgactgga  1080
aatagactgg tgcgcccagg ggaggaagat aatgcagcca taagcgaggt tggcactatc  1140
agatatatgg caccagaagt gctagaagga gctgtgaact tgagggactg tgaatcagct  1200
ttgaaacaag tagacatgta tgctcttgga ctaatctatt gggagatatt tatgagatgt  1260
acagacctct tcccagggga atccgtacca gagtaccaga tggcttttca gacagaggtt  1320
ggaaaccatc ccacttttga ggatatgcag gttctcgtgt ctagggaaaa acagagaccc  1380
aagttcccag aagcctggaa agaaaatagc ctggcagtga ggtcactcaa ggagacaatc  1440
gaagactgtt gggaccagga tgcagaggct cggcttactg cacagtgtgc tgaggaaagg  1500
atggctgaac ttatgatgat ttgggaaaga aacaaatctg tgagcccaac agtcaatcca  1560
atgtctactg ctatgcagaa tgaacgcaac ctgtcacata ataggcgtgt gccaaaaatt  1620
ggtcctatc cagattattc ttcctcctca tacattgaag actctatcca tcatactgac  1680
agcatcgtga agaatatttc ctctgagcat tctatgtcca gcacacctt gactataggg  1740
gaaaaaaacc gaaattcaat taactatgaa cgacagcaag cacaagctcg aatccccagc  1800
cctgaaacaa gtgtcaccag cctctccacc aacacaacaa ccacaaaac cacaggactc  1860
acgccaagta ctggcatgac tactatatct gagatgccat acccagatga acaaatctg  1920
cataccacaa atgttgcaca gtcaattggg ccaaccctg tctgcttaca gctgacagaa  1980
gaagacttgg aaccaacaa gctagacca aagaagttg ataagaacct caaggaaagc   2040
tctgatgaga atctcatgga gcactctctt aaacagttca gtggcccaga cccactgagc  2100
agtactagtt ctagcttgct ttacccactc ataaaactg cagtagaagc aactggacag  2160
caggacttca cacagactgc aaatggccaa gcatgtttga ttcctgatgt tctgcctact  2220
cagatctatc ctctccccaa gcagcagaac cttcccaaga gacctactag tttgcctttg  2280
aacaccaaaa attcaacaaa agagcccgg ctaaatttg gcagcaagca caatcaaac  2340
ttgaaacaag tcgaaactgg agttgccaag atgaataacaa tcaatgccgc agaaaccat  2400
gtggtgacag tcaccatgaa tggtgtggca ggtagaaaacc acagtgttaa ctcccatgct  2460
gccacaaccc aatatgccaa tgggacagta ctatctggcc aaaacaaccaa catagtgaca  2520
catagggccc aagaaatgtt gcagaatcag tttattggtg aggacaccg gctgaatatt  2580
aattccagtc ctgatgagca tgagccttta ctgagacgaa agcaacaagc tggccatgat  2640
gaaggtgttc tggatcgtct tgtggacagg agggaacggc cactagaagg tggccgaact  2700
aattccaata acaacaacag caatccatgt tcagaacaag atgttcttgc acagggtgtt  2760
ccaagcacag cagcagatcc tgggccatca agcccagaa agcacagag cctaattct   2820
ctggatcttt cagccacaaa tgtcctggat ggcagcagta tacagatagg tgagtcaaca  2880
caagatggca aatcaggatc aggtgaaaag atcaagaaac gtgtgaaaac tccctattct  2940
cttaagcggt ggcgcccctc cacctgggtc atctccactg aatcgctgga ctgtgaagtc  3000
aacaataatg gcagtaacag ggcagttcat tccaaatcca gcactgctgt ttaccttgca  3060
gaaggaggca ctgctacaac catggtgtct aaagatatag gaatgaactg tctg        3114
```

| SEQ ID NO: 49 | moltype = DNA length = 372 |
| --- | --- |
| FEATURE | Location/Qualifiers |
| source | 1..372 |
| | mol_type = other DNA |
| | organism = Homo sapiens |

SEQUENCE: 49

```
tcgcagaatc aagaacggct atgtgcgttt aaagatccgt atcagcaaga ccttgggata    60
ggtgagagta gaatctctca tgaaaatggg acaatattat gctcgaaagg tagcacctgc   120
tatggccttt gggagaaatc aaaagggac ataaatcttg taaaacaagg atgttggtct    180
cacattggag atccccaaga gtgtcactat gaagaatgtg tagtaactac cactcctccc   240
tcaattcaga tggaacata ccgtttctgc tgttgtagca cagatttatg taatgtcaac    300
tttactgaga ttttccacc tcctgacaca caccactca gtccacctca ttcatttaac    360
cgagatgaga ca                                                       372
```

| SEQ ID NO: 50 | moltype = AA length = 573 |
| --- | --- |
| FEATURE | Location/Qualifiers |
| source | 1..573 |
| | mol_type = protein |
| | organism = Homo sapiens |

```
SEQUENCE: 50
MLGSLGLWAL LPTAVEAPPN RRTCVFFEAP GVRGSTKTLG ELLDTGTELP RAIRCLYSRC    60
CFGIWNLTQD RAQVEMQGCR DSDEPGCESL HCDPSPRAHP SPGSTLFTCS CGTDFCNANY   120
SHLPPPGSPG TPGSQGPQAA PGESIWMALV LLGLFLLLLL LLGSIILALL QRKNYRVRGE   180
PVPEPRPDSG RDWSVELQEL PELCFSQVIR EGGHAVVWAG QLQGKLVAIK AFPPRSVAQF   240
QAERALYELP GLQHDHIVRF ITASRGGPGR LLSGPLLVLE LHPKGSLCHY LTQYTSDWGS   300
SLRMALSLAQ GLAFLHEERW QNGQYKPGIA HRDLSSQNVL IREDGSCAIG DLGLALVLPG   360
LTQPPAWTPT QPQGPAAIME AGTQRYMAPE LLDKTLDLQD WGMALRRADI YSLALLLWEI   420
LSRCPDLRPD SSPPPFQLAY EAELGNTPTS DELWALAVQE RRRPYIPSTW RCFATDPDGL   480
RELLEDCWDA DPEARLTAEC VQQRLAALAH PQESHPFPES CPRGCPPLCP EDCTSIPAPT   540
ILPCRPQRSA CHFSVQQGPC SRNPQPACTL SPV                                573

SEQ ID NO: 51           moltype = AA  length = 132
FEATURE                 Location/Qualifiers
source                  1..132
                        mol_type = protein
                        organism = Homo sapiens
SEQUENCE: 51
PPNRRTCVFF EAPGVRGSTK TLGELLDTGT ELPRAIRCLY SRCCFGIWNL TQDRAQVEMQ    60
GCRDSDEPGC ESLHCDPSPR AHPSPGSTLF TCSCGTDFCN ANYSHLPPPG SPGTPGSQGP   120
QAAPGESIWM AL                                                       132

SEQ ID NO: 52           moltype = DNA  length = 1719
FEATURE                 Location/Qualifiers
source                  1..1719
                        mol_type = other DNA
                        organism = Homo sapiens
SEQUENCE: 52
atgctagggt ctttggggct ttgggcatta cttcccacag ctgtggaagc accccccaaac    60
aggcgaacct gtgtgttctt tgaggcccct ggagtgcggg aagcacaaa gacactggga   120
gagctgctag atacaggcac agagctcccc agagctatcc gctgcctcta cagccgctgc   180
tgctttggga tctggaacct gacccaagac cgggcacagg tggaaatgca aggatgccga   240
gacagtgatg agccaggctg tgagtccctc cactgtgacc caagtcccg agcccacccc   300
agccctggct ccactctctt cacctgctcc tgtggcactg acttctgcaa tgccaattac   360
agccatctgc ctcctccagg gagccctggg actcctggct cccagggtcc ccaggctgcc   420
ccaggtgagt ccatctggat ggcactggtg ctgctgggc tgttcctcct cctcctgctg   480
ctgctgggca gcatcatctt ggccctgcta cagcgaaaga actacagagt gcgaggtgag   540
ccagtgccag agccaaggcc agactcaggc agggactgga gtgtggagct gcaggagctg   600
cctgagctgt gtttctccca ggtaatccgg gaaggaggtc atgcagtggt ttgggccggga  660
cagctgcaag gaaaactggt tgccatcaag gccttccac cgaggtctgt ggctcagttc    720
caagctgaga gagcattgta cgaacttcca ggcctacagc acgaccacat tgtccgattt   780
atcactgcca gccggggggg tcctggccgc ctgctctctg gcccctgct ggtactgaa    840
ctgcatccca agggctccct gtgccactac ttgacccagt acaccagtga ctggggaagt   900
tccctgcgga tggcactgtc cctggcccag ggctggcat ttctccatga ggagcgctgg   960
cagaatggcc aatataaacc aggtattgcc cacagagtc tgagcagca gaatgtgctc   1020
attcgggaag atggatcgtg tgccattgga cctgggcc ttgccttggt gctccctgc    1080
ctcactcagc cccctgcctg gacccctact caaccacaag gccagctgc catcatggaa   1140
gctggcaccc agaggtacat ggcaccagag ctcttggaca agactctgga cctacaggat   1200
tggggcatgg ccctccgacg agctgatatt tactcttttgg ctctgctcct gtgggagata  1260
ctgagccgct gcccagattt gaggcctgac agcagtccac caccccttcca actggccttat 1320
gaggcagaac tgggcaatac ccctacctct gatgagctat gggccttgg agtgcaggag  1380
aggaggcgtc cctacatccc atccacctgg cgctgctttg ccacagaccc tgatgggctg  1440
agggagctcc tagaagactg ttgggatgca gacccagaag cacggctgac agctgagtgt  1500
gtacagcagc gcctggctgc cttggccccat cctcaagaga gccacccctt ccagagagc  1560
tgtccacgtg gctgccaccc tctctgccca gaagactgta cttcaattcc tgcccctacc  1620
atcctcccct gtaggcctca gcggagtgcc tgccacttca gcgttcagca aggcccttgt  1680
tccaggaatc ctcagcctgc ctgtaccctt tctcctgtg                          1719

SEQ ID NO: 53           moltype = DNA  length = 396
FEATURE                 Location/Qualifiers
source                  1..396
                        mol_type = other DNA
                        organism = Homo sapiens
SEQUENCE: 53
cccccaaaca ggcgaacctg tgtgttcttt gaggcccctg gagtgcgggg aagcacaaag    60
acactgggag agctgctaga tacaggcaca gagctcccca gagctatccg ctgcctctac   120
agccgctgct gctttgggat ctggaacctg acccaagacc gggcacaggt ggaaatgcaa   180
ggatgccgag acagtgatga gccaggctgt gagtccctcc actgtgaccc aagtcccga   240
gcccaccca gccctggctc cactctcttc acctgctcct gtggcactga cttctgcaat   300
gccaattaca gccatctgcc tcctccaggg agccctggga ctcctggctc ccagggtccc   360
caggctgccc caggtgagtc catctggatg gcactg                              396

SEQ ID NO: 54           moltype =     length =
SEQUENCE: 54
000

SEQ ID NO: 55           moltype =     length =
SEQUENCE: 55
000
```

| | | |
|---|---|---|
| SEQ ID NO: 56<br>SEQUENCE: 56<br>000 | moltype = | length = |
| SEQ ID NO: 57<br>SEQUENCE: 57<br>000 | moltype = | length = |
| SEQ ID NO: 58<br>SEQUENCE: 58<br>000 | moltype = | length = |

SEQ ID NO: 59          moltype = AA   length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 59
GGGG                                                                    4

SEQ ID NO: 60          moltype = AA   length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 60
TGGGG                                                                   5

SEQ ID NO: 61          moltype = AA   length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 61
SGGGG                                                                   5

SEQ ID NO: 62          moltype = AA   length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 62
TGGG                                                                    4

SEQ ID NO: 63          moltype = AA   length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 63
SGGG                                                                    4

SEQ ID NO: 64          moltype =     length =
SEQUENCE: 64
000

SEQ ID NO: 65          moltype =     length =
SEQUENCE: 65
000

SEQ ID NO: 66          moltype =     length =
SEQUENCE: 66
000

SEQ ID NO: 67          moltype = AA   length = 592
FEATURE                Location/Qualifiers
source                 1..592
                       mol_type = protein

```
                        organism = Homo sapiens
SEQUENCE: 67
MGRGLLRGLW  PLHIVLWTRI  ASTIPPHVQK  SDVEMEAQKD  EIICPSCNRT  AHPLRHINND   60
MIVTDNNGAV  KFPQLCKFCD  VRFSTCDNQK  SCMSNCSITS  ICEKPQEVCV  AVWRKNDENI  120
TLETVCHDPK  LPYHDFILED  AASPKCIMKE  KKKPGETFFM  CSCSSDECND  NIIFSEEYNT  180
SNPDLLLVIF  QVTGISLLPP  LGVAISVIII  FYCYRVNRQQ  KLSSTWETGK  TRKLMEFSEH  240
CAIILEDDRS  DISSTCANNI  NHNTELLPIE  LDTLVGKGRF  AEVYKAKLKQ  NTSEQFETVA  300
VKIFPYEEYA  SWKTEKDIFS  DINLKHENIL  QFLTAEERKT  ELGKQYWLIT  AFHAKGNLQE  360
YLTRHVISWE  DLRKLGSSLA  RGIAHLHSDH  TPCGRPKMPI  VHRDLKSSNI  LVKNDLTCCL  420
CDFGLSLRLD  PTLSVDDLAN  SGQVGTARYM  APEVLESRMN  LENVESFKQT  DVYSMALVLW  480
EMTSRCNAVG  EVKDYEPPFG  SKVREHPCVE  SMKDNVLRDR  GRPEIPSFWL  NHQGIQMVCE  540
TLTECWDHDP  EARLTAQCVA  ERFSELEHLD  RLSGRSCSEE  KIPEDGSLNT  TK          592

SEQ ID NO: 68           moltype = AA  length = 169
FEATURE                 Location/Qualifiers
source                  1..169
                        mol_type = protein
                        organism = Homo sapiens
SEQUENCE: 68
TIPPHVQKSD  VEMEAQKDEI  ICPSCNRTAH  PLRHINNDMI  VTDNNGAVKF  PQLCKFCDVR   60
FSTCDNQKSC  MSNCSITSIC  EKPQEVCVAV  WRKNDENITL  ETVCHDPKLP  YHDFILEDAA  120
SPKCIMKEKK  KPGETFFMCS  CSSDECNDNI  IFSEEYNTSN  PDLLLVIFQ               169

SEQ ID NO: 69           moltype = DNA  length = 1776
FEATURE                 Location/Qualifiers
source                  1..1776
                        mol_type = other DNA
                        organism = Homo sapiens
SEQUENCE: 69
atgggtcggg  ggctgctcag  gggcctgtgg  ccgctgcaca  tcgtcctgtg  gacgcgtatc    60
gccagcacga  tcccaccgca  cgttcagaag  tcggatgtgg  aaatggaggc  cagaaaagat   120
gaaatcatct  gccccagctg  taataggact  gcccatccac  tgagacatat  taataacgac   180
atgatagtca  ctgacaacaa  cggtgcagtc  aagtttccac  aactgtgtaa  attttgtgat   240
gtgagatttt  ccacctgtga  caaccagaaa  tcctgcatga  gcaactgcag  catcacctct   300
atctgtgaga  agccacagga  agtctgtgtg  gctgtatgga  gaaagaatga  cgagaacata   360
acactagaga  cagtttgcca  tgaccccaag  ctcccctacc  atgactttat  tctggaagat   420
gctgcttctc  caaagtgcat  tatgaaggaa  aaaaaaaagc  ctggtgagac  tttcttcatg   480
tgttcctgta  gctctgatga  gtgcaatgac  aacatcatct  tctcagaaga  atataacacc   540
agcaatcctg  acttgttgct  agtcatattt  caagtgacag  gcatcagcct  cctgccacca   600
ctggagttg   ccatatctgt  catcatcatc  ttctactgct  accgcgttaa  ccggcagcag   660
aagctgagtt  caacctggga  aaccggcaag  acgcggaagc  tcatggagtt  cagcgagcac   720
tgtgccatca  tcctggaaga  tgaccgctct  gacatcagct  ccacgtgtgc  caacaacatc   780
aaccacaaca  cagagctgct  gcccattgaa  ctggacacto  tggtggggaa  aggtcgcttc   840
gctgaggtct  ataaggccaa  gctgaagcag  aacacttcag  agcagtttga  gacagtggca   900
gtcaagatct  ttccctatga  ggagtatgcc  tcttggaaga  cagagaagga  catcttctca   960
gacatcaatc  tgaagcatga  gaacatactc  cagttcctga  cggctgagga  gcggaagacg  1020
gagttgggga  aacaatactg  gctgatcacc  gccttccacg  ccaagggcaa  cctacaggag  1080
tacctgacgc  ggcatgtcat  cagctgggag  gacctgcgca  agctgggcag  ctccctcgcc  1140
cgggggattg  ctcacctcca  cagtgatcac  actccatgtg  gaggcccaa   gatgccatc   1200
gtgcacaggg  acctcaagag  ctccaatatc  ctcgtgaaga  acgacctaac  ctgctgcctg  1260
tgtgactttg  ggctttccct  gcgtctggac  cctactctgt  ctgtggatga  cctggctaac  1320
agtgggcagg  tgggaactgc  aagatacatg  gctccagaag  tcctagaatc  caggatgaat  1380
ttggagaatg  ttgagtcctt  caagcagacc  gatgtctact  ccatggctct  ggtgctctgg  1440
gaaatgacat  ctcgctgtaa  tgcagtggga  gaagtaaaag  attatgagcc  tccatttggt  1500
tccaaggtgc  gggagcaccc  ctgtgtcgaa  agcatgaagg  acaacgtgtt  gagagatcga  1560
gggcgaccag  aaattcccag  cttctggctc  aaccaccagg  gcatccagat  ggtgtgtgag  1620
acgttgactg  agtgctggga  ccacgaccca  gaggcccgtc  tcacagccca  gtgtgtggca  1680
gaacgcttca  gtgagctgga  gcatctggac  aggctctcgg  ggaggagctg  ctcggaggag  1740
aagattcctg  aagacggctc  cctaaacact  accaaa                              1776

SEQ ID NO: 70           moltype = DNA  length = 507
FEATURE                 Location/Qualifiers
source                  1..507
                        mol_type = other DNA
                        organism = Homo sapiens
SEQUENCE: 70
acgatcccac  cgcacgttca  gaagtcggat  gtggaaatgg  aggcccagaa  agatgaaatc    60
atctgcccca  gctgtaatag  gactgcccat  ccactgagac  atattaataa  cgacatgata   120
gtcactgaca  acaacggtgc  agtcaagttt  ccacaactgt  gtaaattttg  tgatgtgaga   180
ttttccacct  gtgacaacca  gaaatcctgc  atgagcaact  gcagcatcac  ctccatctgt   240
gagaagccac  aggaagtctg  tgtggctgta  tggagaaaga  atgacgagaa  cataacacta   300
gagacagttt  gccatgaccc  caagctcccc  taccatgact  ttattctgga  agatgctgct   360
tctccaaagt  gcattatgaa  ggaaaaaaaa  aagcctggtg  agacttttct  catgtgttcc   420
tgtagctctg  atgagtgcaa  tgacaacatc  atcttctcag  aagaatataa  caccagcaat   480
cctgacttgt  tgctagtcat  atttcaa                                          507

SEQ ID NO: 71           moltype = AA  length = 530
FEATURE                 Location/Qualifiers
source                  1..530
```

```
                        mol_type = protein
                        organism = Homo sapiens
SEQUENCE: 71
MTSSLQRPWR  VPWLPWTILL  VSTAAASQNQ  ERLCAFKDPY  QQDLGIGESR  ISHENGTILC    60
SKGSTCYGLW  EKSKGDINLV  KQGCWSHIGD  PQECHYEECV  VTTTPPSIQN  GTYRFCCCST   120
DLCNVNFTEN  FPPPDTTPLS  PPHSFNRDET  IIIALASVSV  LAVLIVALCF  GYRMLTGDRK   180
QGLHSMNMME  AAASEPSLDL  DNLKLLELIG  RGRYGAVYKG  SLDERPVAVK  VFSFANRQNF   240
INEKNIYRVP  LMEHDNIARF  IVGDERVTAD  GRMEYLLVME  YYPNGSLCKY  LSLHTSDWVS   300
SCRLAHSVTR  GLAYLHTELP  RGDHYKPAIS  HRDLNSRNVL  VKNDGTCVIS  DFGLSMRLTG   360
NRLVRPGEED  NAAISEVGTI  RYMAPEVLEG  AVNLRDCESA  LKQVDMYALG  LIYWEIFMRC   420
TDLFPGESVP  EYQMAFQTEV  GNHPTFEDMQ  VLVSREKQRP  KFPEAWKENS  LAVRSLKETI   480
EDCWDQDAEA  RLTAQCAEER  MAELMMIWER  NKSVSPTVNP  MSTAMQNERR              530

SEQ ID NO: 72           moltype = AA   length = 124
FEATURE                 Location/Qualifiers
source                  1..124
                        mol_type = protein
                        organism = Homo sapiens
SEQUENCE: 72
SQNQERLCAF  KDPYQQDLGI  GESRISHENG  TILCSKGSTC  YGLWEKSKGD  INLVKQGCWS    60
HIGDPQECHY  EECVVTTTPP  SIQNGTYRFC  CCSTDLCNVN  FTENFPPPDT  TPLSPPHSFN   120
RDET                                                                    124

SEQ ID NO: 73           moltype = DNA  length = 1590
FEATURE                 Location/Qualifiers
source                  1..1590
                        mol_type = other DNA
                        organism = Homo sapiens
SEQUENCE: 73
atgacttcct cgctgcagcg gccctggcgg gtgccctggc taccatggac catcctgctg          60
gtcagcactg cggctgcttc gcagaatcaa gaacggctat gtgcgtttaa agatccgtat        120
cagcaagacc ttgggatagg tgagagtaga atctctcatg aaaatgggac aatattatgc        180
tcgaaaggta gcacctgcta tggcctttgg gagaaatcaa aaggggacat aaatcttgta        240
aaacaaggat gttggtctca cattggagat ccccaagagt gtcactatga agaatgtgta        300
gtaactacca ctcctcccte aattcagaat ggaacatacc gtttctgctg ttgtagcaca        360
gatttatgta atgtcaactt tactgagaat tttccacctc ctgacacaac accactcagt        420
ccacctcatt catttaaccg agatgagaca ataatcattg ctttggcatc agtctctgta        480
ttagctgttt tgatagttgc cttatgcttt ggatacagaa tgttgacagg agaccgtaaa        540
caaggtcttc acagtatgaa catgatggag gcagcagcat ccgaaccctc tcttgatcta        600
gataatctga aactgttgga gctgattggc cgaggtcgat atggagcagt atataaaggc        660
tccttggatg agcgtccagt tgctgtaaaa gtgttttcct ttgcaaaccg tcagaatttt        720
atcaacgaaa agaacattta cagagtgcct ttgatggaac atgacaacat tgcccgcttt        780
atagttggag atgagagagt cactgcagat ggactgatgg aatatttgct tgtgatggag        840
tactatccca atggatcttt atgcaagtat ttaagtctcc acacaagtga ctgggtaagc        900
tcttgccgtc ttgctcattc tgttactaga ggactggctt atcttcacac agaattacca        960
cgaggagatc attataaacc tgcaatttcc catcgagatt taaacagcag aaatgtccta       1020
gtgaaaaatg atggaacctg tgttattagt gactttggac tgtccatgag gctgactgga       1080
aatagactgg tgcgcccagg ggaggaagat aatgcagcca taagcgaggt tggcactatc       1140
agatatatgg caccagaagt gctagaagga ctgtgaact tgagggactg tgaatcagct       1200
ttgaaacaag tagacatgta tgctcttgga ctaatctatt gggagatatt tatgagatgt       1260
acagacctct tcccagggga atccgtacca gagtaccaga tggcttttca gacagaggtt       1320
ggaaaccatc ccacttttga ggatatgcag gttctcgtgt ctagggaaaa acagagaccc       1380
aagttcccag aagcctggaa agaaaatagc ctggcagtga ggtcactcaa ggagacaatc       1440
gaagactgtt gggaccagga tgcagaggct cggcttactg cacagtgtgc tgaggaaagg       1500
atggctgaac ttatgatgat ttgggaaaga acaaatctg tgagcccaac agtcaatcca       1560
atgtctactg ctatgcagaa tgaacgtagg                                       1590

SEQ ID NO: 74           moltype = DNA  length = 372
FEATURE                 Location/Qualifiers
source                  1..372
                        mol_type = other DNA
                        organism = Homo sapiens
SEQUENCE: 74
tcgcagaatc aagaacggct atgtgcgttt aaagatccgt atcagcaaga ccttgggata          60
ggtgagagta gaatctctca tgaaaatggg acaatattat gctcgaaagg tagcacctgc        120
tatggccttt gggagaaatc aaaaggggac ataaatcttg taaaacaagg atgttggtct        180
cacattggag atccccaaga gtgtcactat gaagaatgtg tagtaactac cactcctccc        240
tcaattcaga atgaacata ccgtttctgc tgttgtagca cagatttatg taatgtcaac        300
tttactgaga atttttccacc tcctgacaca acaccactca gtccacctca ttcatttaac        360
cgagatgaga ca                                                           372

SEQ ID NO: 75           moltype = AA   length = 478
FEATURE                 Location/Qualifiers
source                  1..478
                        mol_type = protein
                        organism = Homo sapiens
SEQUENCE: 75
MLGSLGLWAL  LPTAVEAPPN  RRTCVFFEAP  GVRGSTKTLG  ELLDTGTELP  RAIRCLYSRC    60
CFGIWNLTQD  RAQVEMQGCR  DSDEPGCESL  HCDPSPRAHP  SPGSTLFTCS  CGTDFCNANY   120
```

```
SHLPPPGSPG TPGSQGPQAA PGESIWMALV LLGLFLLLLL LLGSIILALL QRKNYRVRGE   180
PVPEPRPDSG RDWSVELQEL PELCFSQVIR EGGHAVVWAG QLQGKLVAIK AFPPRSVAQF   240
QAERALYELP GLQHDHIVRF ITASRGGPGR LLSGPLLVLE LHPKGSLCHY LTQYTSDWGS   300
SLRMALSLAQ GLAFLHEERW QNGQYKPGIA HRDLSSQNVL IREDGSCAIG DLGLALVLPG   360
LTQPPAWTPT QPQGPAAIME AGTQRYMAPE LLDKTLDLQD WGMALRRADI YSLALLLWEI   420
LSRCPDLRPA VHHPSNWPMR QNWAIPLPLM SYGPWQCRRG GVPTSHPPGA ALPQTLMG    478

SEQ ID NO: 76         moltype = AA  length = 132
FEATURE               Location/Qualifiers
source                1..132
                      mol_type = protein
                      organism = Homo sapiens
SEQUENCE: 76
PPNRRTCVFF EAPGVRGSTK TLGELLDTGT ELPRAIRCLY SRCCFGIWNL TQDRAQVEMQ    60
GCRDSDEPGC ESLHCDPSPR AHPSPGSTLF TCSCGTDFCN ANYSHLPPPG SPGTPGSQGP   120
QAAPGESIWM AL                                                      132

SEQ ID NO: 77         moltype = DNA  length = 1434
FEATURE               Location/Qualifiers
source                1..1434
                      mol_type = other DNA
                      organism = Homo sapiens
SEQUENCE: 77
atgctagggt ctttggggct ttgggcatta cttcccacag ctgtggaagc accccccaaac   60
aggcgaacct gtgtgttctt tgaggcccct ggagtgcggg aagcacaaa gacactggga   120
gagctgctag atacaggcac agagctcccc gagctatccg ctgcctcta cagccgctgc   180
tgctttggga tctggaacct gacccaagac cgggcacagg tggaaatgca aggatgccga   240
gacagtgatg agccaggctg tgagtccctc cactgtgacc caagtccccg agcccacccc   300
agccctggct ccactctctt cacctgctcc tgtggcactg acttctgcaa tgccaattac   360
agccatctgc ctcctccagg gagccctggg actcctggct ccagggtccc caggctgcc   420
ccaggtgagt ccatctggat ggcactggtg ctgctgggc tgttcctcct cctcctgctg   480
ctgctgggca gcatcatctt ggccctgcta cagcgaaaga actacagagt gcgaggtgag   540
ccagtgccag agcaaggcc agactcaggc agggactgga gtgtggagct gcaggagctg   600
cctgagctgt gtttctccca ggtaatccgg gaaggaggtc atgcagtggt ttgggccggg   660
cagctgcaag gaaaactggt tgccatcaag gccttcccac cgaggtctgt ggctcagttc   720
caagctgaga gagcattgta cgaacttcca ggcctacagc acgaccacat tgtccgattt   780
atcactgcca gccgggggg tcctggccgc ctgctctctg gcccctgct ggtactggaa   840
ctgcatccca agggctccct gtgccactac ttgacccagt acaccagtga ctggggaagt   900
tccctgcggga tggcactgtc cctggccag ggctggcat ttctccatga ggagcgctgg   960
cagaatggcc aatataaacc aggtattgcc caccgagatc tgagcagcca aatgtgctc   1020
attcgggaag atggatcgtg tgccattga gacctgggcc ttgcctttggt gctccctggc  1080
ctcactcagc ccctgcctg gaccctact caaccacaag gccagctgc catcatgaa   1140
gctggcaccc agaggtacat ggcaccagag ctcttggaca catctga cctacaggat   1200
tggggcatgg ccctccgacg agctgatat tactcttgg ctctgctcct gtgggagata   1260
ctgagccgct gcccagatt gaggcctgca gtccaccacc cttccaactg gcctatgagg   1320
cagaactggg caatacccct acctctgatg agctatgggc cttggcagtg caggagagga   1380
ggcgtcccta catcccatcc acctggcgct gctttgccac agaccctgat gggc          1434

SEQ ID NO: 78         moltype = DNA  length = 396
FEATURE               Location/Qualifiers
source                1..396
                      mol_type = other DNA
                      organism = Homo sapiens
SEQUENCE: 78
cccccaaaca ggcgaacctg tgtgttcttt gaggcccctg gagtgcgggg aagcacaaag    60
acactgggag agctgctaga tacaggcaca gagctcccca gagctatccg ctgcctctac   120
agccgctgct gctttgggat ctggaacctg acccaagacc gggcacaggt ggaaatgcaa   180
ggatgccgag acagtgatga gccaggctgt gagtccctcc actgtgaccc aagtccccga   240
gcccacccca gccctggctc cactctcttc acctgctcct gtggcactga cttctgcaat   300
gccaattaca gccatctgcc tcctccaggg agccctggga ctcctggctc ccagggtccc   360
caggctgccc caggtgagtc catctggatg gcactg                             396

SEQ ID NO: 79         moltype = AA  length = 478
FEATURE               Location/Qualifiers
source                1..478
                      mol_type = protein
                      organism = Homo sapiens
SEQUENCE: 79
MLGSLGLWAL LPTAVEAPPN RRTCVFFEAP GVRGSTKTLG ELLDTGTELP RAIRCLYSRC    60
CFGIWNLTQD RAQVEMQGCR DSDEPGCESL HCDPSPRAHP SPGSTLFTCS CGTDFCNANY   120
SHLPPPGSPG TPGSQGPQAA PGESIWMALV LLGLFLLLLL LLGSIILALL QRKNYRVRGE   180
PVPEPRPDSG RDWSVELQEL PELCFSQVIR EGGHAVVWAG QLQGKLVAIK AFPPRSVAQF   240
QAERALYELP GLQHDHIVRF ITASRGGPGR LLSGPLLVLE LHPKGSLCHY LTQYTSDWGS   300
SLRMALSLAQ GLAFLHEERW QNGQYKPGIA HRDLSSQNVL IREDGSCAIG DLGLALVLPG   360
LTQPPAWTPT QPQGPAAIME DPDGLRELLE DCWDADPEAR LTAECVQQRL AALAHPQESH   420
PFPESCPRGC PPLCPEDCTS IPAPTILPCR PQRSACHFSV QQGPCSRNPQ PACTLSPV     478

SEQ ID NO: 80         moltype = AA  length = 132
FEATURE               Location/Qualifiers
```

```
source                      1..132
                            mol_type = protein
                            organism = Homo sapiens
SEQUENCE: 80
PPNRRTCVFF EAPGVRGSTK TLGELLDTGT ELPRAIRCLY SRCCFGIWNL TQDRAQVEMQ    60
GCRDSDEPGC ESLHCDPSPR AHPSPGSTLF TCSCGTDFCN ANYSHLPPPG SPGTPGSQGP   120
QAAPGESIWM AL                                                      132

SEQ ID NO: 81               moltype = DNA  length = 1434
FEATURE                     Location/Qualifiers
source                      1..1434
                            mol_type = other DNA
                            organism = Homo sapiens
SEQUENCE: 81
atgctagggt ctttggggct tgggcatta cttcccacag ctgtggaagc accccaaac      60
aggcgaacct gtgtgttctt tgaggcccct ggagtgcggg gaagcacaaa gacactggga   120
gagctgctag atacaggcac agagctcccc agagctatcc gctgcctcta cagccgctgc   180
tgctttggga tctggaacct gacccaagac cgggcacagg tggaaatgca aggatgccga   240
gacagtgatg agccaggctg tgagtccctc cactgtgacc caagtccccg agcccacccc   300
agccctggct ccactctctt cacctgctcc tgtggcactg acttctgcaa tgccaattac   360
agccatctgc ctcctccagg gagccctggg actcctggct cccagggtcc ccaggctgcc   420
ccaggtgagt ccatctggat ggcactggtg ctgctgggtg tgttcctcct cctcctgctg   480
ctgctgggca gcatcatctt ggccctgcta cagcgaaaga actacagagt gcgaggtgag   540
ccagtgccag agccaaggcc agactcaggc agggactgga gtgtggagct gcaggagctg   600
cctgagctgt gtttctccca ggtaatccgg aaggaggtc atgcagtggt ttgggccggg   660
cagctgcaag gaaaactggt tgccatcaag gccttcccac cgaagtctgt ggctcagttc   720
caagctgaga gagcattgta cgaacttcca ggcctacagc acgaccacat tgtccgattt   780
atcactgcca gccgggggg tcctggccgc ctgctctctg ggcccctgct ggtactggaa   840
ctgcatccca agggctccct gtgccactac ttgacccagt acaccagtga ctggggaagt   900
tccctgcacta tggcactgtc cctggccag ggcctggcta ttctccatga ggagcgctgg   960
cagaatggcc aatataaacc aggtattgcc caccgagatc tgagcagcca aatgtgctc   1020
attcgggaag atggatcgtg tgccattgga gacctgggcc ttgccttggt gctccctggc  1080
ctcactcagc ccctgcctg gacccctact caaccacaag gcccagctgc catcatgaa   1140
gaccctgatg ggctgaggga gctcctagaa gactgttggg atgcagaccc agaagcacgg  1200
ctgacagctg agtgtgtaca gcagcgcctg gctgccttga cccatcctca agagagccac  1260
cccctttccag agagctgtcc acgtggctgc ccacctctct gcccagaaga ctgtacttca  1320
attcctgccc ctaccatcct cccctgtagg cctcagcgga gtgcctgcca cttcagcgtt  1380
cagcaaggcc cttgttccag gaatcctcag cctgcctgta ccctttctcc tgtg          1434

SEQ ID NO: 82               moltype = DNA  length = 396
FEATURE                     Location/Qualifiers
source                      1..396
                            mol_type = other DNA
                            organism = Homo sapiens
SEQUENCE: 82
ccccaaaca ggcgaacctg tgtgttcttt gaggcccctg gagtgcgggg aagcacaaag      60
acactgggag agctgctaga tacaggcaca gagctcccc gagctatccg ctgcctctac    120
agccgctgct gctttgggat ctggaacctg acccaagacc gggcacaggt ggaaatgcaa   180
ggatgccgag acagtgatga gccaggctgt gagtccctcc actgtgaccc aagtccccga   240
gcccacccca gccctggctc cactctcttc acctgctcct gtggcactga cttctgcaat   300
gccaattaca gccatctgcc tcctccaggg agccctggga ctcctggctc ccagggtccc   360
caggctgccc aggtgagtc catctggatg gcactg                                396

SEQ ID NO: 83               moltype = AA  length = 546
FEATURE                     Location/Qualifiers
source                      1..546
                            mol_type = protein
                            organism = Homo sapiens
SEQUENCE: 83
MAESAGASSF FPLVVLLLAG SGGSGPRGVQ ALLCACTSCL QANYTCETDG ACMVSIFNLD    60
GMEHHVRTCI PKVELVPAGK PFYCLSSEDL RNTHCCYTDY CNRIDLRVPS GHLKEPEHPS   120
MWGPVELVGI IAGPVFLLFL IIIIVFLVIN YHQRVYHNRQ RLDMEDPSCE MCLSKDKTLQ   180
DLVYDLSTSG SGSGLPLFVQ RTVARTIVLQ EIIGKGRFGE VWRGRWRGGD VAVKIFSSRE   240
ERSWFREAEI YQTVMLRHEN ILGFIAADNK ADCSFLTLPW EVVMSAAPK LRSLRLQYKG    300
GRGRARFLFP LNNGTWTQLW LVSDYHEHGS LFDYLNRYTV TIEGMIKLAL SAASGLAHLH   360
MEIVGTQGKP GIAHRDLKSK NILVKKNGMC AIADLGLAVR HDAVTDTIDI APNQRVGTKR   420
YMAPEVLDET INMKHFDSFK CADIYALGLV YWEIARRCNS GGVHEEYQLP YYDLVPSDPS   480
IEEMRKVVCD QKLRPNIPNW WQSYEALRVM GKMMRECWYA NGAARLTALR IKKTLSQLSV   540
QEDVKI                                                             546

SEQ ID NO: 84               moltype = AA  length = 103
FEATURE                     Location/Qualifiers
source                      1..103
                            mol_type = protein
                            organism = Homo sapiens
SEQUENCE: 84
SGPRGVQALL CACTSCLQAN YTCETDGACM VSIFNLDGME HHVRTCIPKV ELVPAGKPFY    60
CLSSEDLRNT HCCYTDYCNR IDLRVPSGHL KEPEHPSMWG PVE                     103
```

| SEQ ID NO: 85 | moltype = DNA length = 1638 |
|---|---|
| FEATURE | Location/Qualifiers |
| source | 1..1638 |
| | mol_type = other DNA |
| | organism = Homo sapiens |

SEQUENCE: 85

```
atggcggagt cggccggagc ctcctccttc ttcccccttg ttgtcctcct gctcgccggc    60
agcggcgggt ccgggccccg gggggtccag gctctgctgt gtgcgtgcac cagctgcctc   120
caggccaact acacgtgtga gacagatggg gcctgcatgg tttccatttt caatctggat   180
gggatggagc accatgtgcg cacctgcatc cccaaagtgg agctggtccc tgccgggaag   240
cccttctact gcctgagctc ggaggacctg cgcaacaccc actgctgcta cactgactac   300
tgcaacagga tcgacttgag ggtgcccagt ggtcacctca aggagcctga gcacccgtcc   360
atgtggggcc cggtggagct ggtaggcatc atcgccggcc cggtgttcct cctgttcctc   420
atcatcatca ttgttttcct tgtcattaac tatcatcagc gtgtctatca caaccgccag   480
agactggaca tggaagatcc ctcatgtgag atgtgtctct ccaaagacaa gacgctccag   540
gatcttgtct acgatctctc cacctcaggg tctggctcag ggttacccct ctttgtccag   600
cgcacagtgg cccgaaccat cgttttacaa gagattattg caagggtcg gtttgggaa    660
gtatggcggg gccgctgag gggtggtgat gtggctgtga aaatattctc ttctcgtgaa   720
gaacggtctt ggttcaggga agcagagata taccagacgg tcatgctgcg ccatgaaaac   780
atccttggat ttattgctgc tgacaataaa gcagactgct cattcctcac attgccatgg   840
gaagtttgaa tggtctctgc tgcccccaag ctgaggagcc ttagactcca atacaaggga   900
ggaaggggaa gagcaagatt tttattccca ctgaataatg gcacctggac acagctgtgg   960
cttgtttctg actatcatga gcacgggtcc ctgtttgatt atctgaaccg gtacacagtg  1020
acaattgagg ggatgattaa gctggccttg tctgctgcta gtgggctggc acacctgcac  1080
atggagatcg tgggcaccca agggaagcct ggaattgctc atcgagactt aaagtcaaag  1140
aacattctgg tgaagaaaaa tggcatgtgt gccatagcag acctggtcct ggctgtccgt  1200
catgatgcag tcactgacac cattgacatt gccccgaatc agagggtggg gaccaaacga  1260
tacatggccc tgaagtactg tgatgaaacc attaatatga aacactttga ctcctttaaa  1320
tgtgctgata tttatgccct cgggcttgta tattgggaga ttgctcgaag atgcaattct  1380
ggaggagtcc atgaagaata tcagctgcca tattacgact tagtgccctc tgaccctcc   1440
attgaggaaa tgcgaaaggt tgtatgtgat cagaagctgc gtcccaacat ccccaactgg  1500
tggcagagtt atgaggcact gcgggtgatg gggaagatga tgcgagagtg ttggtatgcc  1560
aacggcgcag cccgcctgac ggccctgcgc atcaagaaga ccctctccca gctcagcgtg  1620
caggaagacg tgaagatc                                                 1638
```

| SEQ ID NO: 86 | moltype = DNA length = 309 |
|---|---|
| FEATURE | Location/Qualifiers |
| source | 1..309 |
| | mol_type = other DNA |
| | organism = Homo sapiens |

SEQUENCE: 86

```
tccgggcccc gggggtccca ggctctgctg tgtgcgtgca ccagctgcct ccaggccaac    60
tacacgtgtg agacagatgg ggcctgcatg gtttccattt tcaatctgga tgggatggag   120
caccatgtgc gcacctgcat ccccaaagtg gagctggtcc ctgccgggaa gcccttctac   180
tgcctgagct cggaggacct gcgcaacacc cactgctgct acactgacta ctgcaacagg   240
atcgacttga gggtgcccag tggtcacctc aaggagcctg agcacccgtc catgtgggc   300
ccggtggag                                                            309
```

| SEQ ID NO: 87 | moltype = AA length = 507 |
|---|---|
| FEATURE | Location/Qualifiers |
| source | 1..507 |
| | mol_type = protein |
| | organism = Homo sapiens |

SEQUENCE: 87

```
MEAAVAAPRP RLLLLVLAAA AAAAAALLPG ATALQCFCHL CTKDNFTCVT DGLCFVSVTE    60
TTDKVIHNSM CIAEIDLIPR DRPFVCAPSS KTGSVTTTYC CNQDHCNKIE LPTTGPFSVK   120
SSPGLGPVEL AAVIAGPVCF VCISLMLMVY ICHNRTVIHH RVPNEEDPSL DRPFISEGTT   180
LKDLIYDMTT SGSGSGLPLL VQRTIARTIV LQESIGKGRF GEVWRGKWRG EEVAVKIFSS   240
REERSWFREA EIYQTVMLRH ENILGFIAAD NKDNGTWTQL WLVSDYHEHG SLFDYLNRYT   300
VTVEGMIKLA LSTASGLAHL HMEIVGTQGK PAIAHRDLKS KNILVKKNGT CCIADLGLAV   360
RHDSATDTID IAPNHRVGTK RYMAPEVLDD SINMKHFESF KRADIYAMGL VFWEIARRCS   420
IGGIHEDYQL PYYDLVPSDP SVEEMRKVVC EQKLRPNIPN RWQSCEALRV MAKIMRECWY   480
ANGAARLTAL RIKKTLSQLS QQEGIKM                                       507
```

| SEQ ID NO: 88 | moltype = AA length = 106 |
|---|---|
| FEATURE | Location/Qualifiers |
| source | 1..106 |
| | mol_type = protein |
| | organism = Homo sapiens |

SEQUENCE: 88

```
AALLPGATAL QCFCHLCTKD NFTCVTDGLC FVSVTETTDK VIHNSMCIAE IDLIPRDRPF    60
VCAPSSKTGS VTTTYCCNQD HCNKIELPTT GPFSVKSSPG LGPVEL                  106
```

| SEQ ID NO: 89 | moltype = DNA length = 1521 |
|---|---|
| FEATURE | Location/Qualifiers |
| source | 1..1521 |
| | mol_type = other DNA |
| | organism = Homo sapiens |

SEQUENCE: 89

```
atggaggcgg cggtcgctgc tccgcgtccc cggctgctcc tcctcgtgct ggcggcggcg    60
gcggcggcgg cggcggcgct gctcccgggg gcgacggcgt tacagtgttt ctgccacctc   120
tgtacaaaag acaattttac ttgtgtgaca gatgggctct gctttgtctc tgtcacagag   180
accacagaca aagttataca caacagcatg tgtatagctg aaattgactt aattcctcga   240
gataggccgt ttgtatgtgc accctcttca aaaactgggt ctgtgactac aacatattgc   300
tgcaatcagg accattgcaa taaaatagaa cttccaacta ctggccctt ttcagtaaag   360
tcatcacctg gccttggtcc tgtggaactg gcagctgtca ttgctggacc agtgtgcttc   420
gtctgcatct cactcatgtt gatggtctat atctgccaca accgcactgt cattcaccat   480
cgatgtgccaa atgaagagga cccttcatta gatcgccctt ttatttcaga gggtactacg   540
ttgaaagact taatttatga tatgacaacg tcaggttctg gctcaggtat accattgctt   600
gttcagagaa caattgcgag aactattgtg ttacaagaaa gcattggcaa aggtcgattt   660
ggagaagttt ggagaggaaa gtggcgggga aagaagttg ctgttaagat attctcctct   720
agagaagaac gttcgtggtt ccgtgaggca gagatttatc aaactgtaat gttacgtcat   780
gaaaacatcc tgggatttat agcagcagac aataaagaca atggtacttg gactcagctc   840
tggttggtgt cagattatca tgagcatgga tccctttttg attacttaaa cagatacaca   900
gttactgtgg aaggaatgat aaaacttgct ctgtccacgg cgagcggtct tgcccatctt   960
cacatggaga ttgttggtac ccaaggaaag ccagccattg ctcatagaga tttgaaatca  1020
aagaatatct tggtaaagaa gaatggaact tgctgtatag cagacttagg actggcagta  1080
agacatgatt cagccacaga taccattgat attgctccaa accacagagt gggaacaaaa  1140
aggtacatgc cccctgaagt tctcgatgat ccataaaata tgaaacattt tgaatccttc  1200
aaacgtgctg acatctatgc aatgggctta gtattctggg aaattgctcg acgatgttcc  1260
attggtggaa ttcatgaaga ttaccaactg ccttattatg atcttgtacc ttctgaccca  1320
tcagttgaag aaatgagaaa agttgtttgt gaacagaagt taaggccaaa tatcccaaac  1380
agatggcaga gctgtgaagc cttgagagta atggctaaaa ttatgagaga atgttggtat  1440
gccaatggag cagctaggct tacagcattg cggattaaga aaacattatc gcaactcagt  1500
caacaggaag gcatcaaaat g                                             1521

SEQ ID NO: 90          moltype = DNA  length = 318
FEATURE                Location/Qualifiers
source                 1..318
                       mol_type = other DNA
                       organism = Homo sapiens
SEQUENCE: 90
gcggcgctgc tcccggggc gacggcgtta cagtgtttct gccacctctg tacaaaagac    60
aattttactt gtgtgacaga tgggctctgc tttgtctctg tcacagagac cacagacaaa   120
gttatacaca acagcatgtg tatagctgaa attgacttaa ttcctcgaga taggccgttt   180
gtatgtgcac cctcttcaaa aactgggtct gtgactacaa catattgctg caatcaggac   240
cattgcaata aaatagaact tccaactact ggccctttt cagtaaagtc atcacctggc    300
cttggtcctg tggaactg                                                 318

SEQ ID NO: 91          moltype = AA  length = 532
FEATURE                Location/Qualifiers
source                 1..532
                       mol_type = protein
                       organism = Homo sapiens
SEQUENCE: 91
MGWLEELNWQ LHIFLLILLS MHTRANFLDN MLLRSAGKLN VGTKKEDGES TAPTPRPKVL    60
RCKCHHHCPE DSVNNICSTD GYCFTMIEED DSGLPVVTSG CLGLEGSDFQ CRDTPIPHQR   120
RSIECCTERN ECNKDLHPTL PPLKNRDFVD GPIHHRALLI SVTVCSLLLV LIILFCYFRY   180
KRQETRPRYS IGLEQDETYI PPGESLRDLI EQSQSSGSGS GLPLLVQRTI AKQIQMVKQI   240
GKGRYGEVWM GKWRGEKVAV KVFFTTEEAS WFRETEIYQT VLMRHENILG FIAADIKGTG   300
SWTQLYLITD YHENGSLYDY LKSTTLDAKS MLKLAYSSVS GLCHLHTEIF STQGKPAIAH   360
RDLKSKNILV KKNGTCCIAD LGLAVKFISD TNEVDIPPNT RVGTKRYMPP EVLDESLNRN   420
HFQSYIMADM YSFGLILWEV ARRCVSGGIV EEYQLPYHDL VPSDPSYEDM REIVCIKKLR   480
PSFPNRWSSD ECLRQMGKLM TECWAHNPAS RLTALRVKKT LAKMSESQDI KL           532

SEQ ID NO: 92          moltype = AA  length = 131
FEATURE                Location/Qualifiers
source                 1..131
                       mol_type = protein
                       organism = Homo sapiens
SEQUENCE: 92
NFLDNMLLRS AGKLNVGTKK EDGESTAPTP RPKVLRCKCH HHCPEDSVNN ICSTDGYCFT    60
MIEEDDSGLP VVTSGCLGLE GSDFQCRDTP IPHQRRSIEC CTERNECNKD LHPTLPPLKN   120
RDFVDGPIHH R                                                        131

SEQ ID NO: 93          moltype = DNA  length = 1596
FEATURE                Location/Qualifiers
source                 1..1596
                       mol_type = other DNA
                       organism = Homo sapiens
SEQUENCE: 93
atgggttggc tggaagaact aaactggcag cttcacattt tcttgctcat tcttctctct    60
atgcacacaa gggcaaactt ccttgataac atgcttttgc gaagtgcagg aaaattaaat   120
gtgggcacca gaaaagagga tggtgagagt acagccccca ccccccgtcc aaaggtcttg   180
cgttgtaaat gccaccacca ttgtccagaa gactcagtca acaatatttg cagcacagac   240
ggatattgtt tcacgatgat agaagaggat gactctgggt tgcctgtggt cacttctggt   300
tgcctaggac tagaaggctc agattttcag tgtcgggaca ctcccattcc tcatcaaaga   360
agatcaattg aatgctgcac agaaaggaac gaatgtaata agacctaca ccctacactg    420
```

```
cctccattga aaaacagaga ttttgttgat ggacctatac accacagggc tttacttata    480
tctgtgactg tctgtagttt gctcttggtc cttatcatat tatttgtta cttccggtat    540
aaaagacaag aaaccagacc tcgatacagc attgggttag aacaggatga aacttacatt    600
cctcctggaa aatccctgag agacttaatt gagcagtctc agagctcagg aagtggatca    660
ggcctccctc tgctggtcca aaggactata gctaagcaga ttcagatggt gaaacagatt    720
ggaaaaggtc gctatgggga agtttggatg ggaaagtggc gtggcgaaaa ggtagctgtg    780
aaagtgttct tcaccacaga ggaagccagc tggttcagag agacagaaat atatcagaca    840
gtgttgatga ggcatgaaaa cattttgggt tcattgctg cagatatcaa agggacaggg    900
tcctggaccc agttgtacct aatcacagac tatcatgaaa atggttccct ttatgattat    960
ctgaagtcca ccaccctaga cgctaaatca atgctgaagt tagcctactc ttctgtcagt   1020
ggcttatgtc atttacacac agaaatcttt agtactcaag caaaccagc aattgcccat   1080
cgagatctga aaagtaaaaa cattctggtg aagaaaaatg gaacttgctg tattgctgac   1140
ctgggcctgg ctgttaaatt tattagtgat acaaatgaat tgacatacc acctaacact   1200
cgagttggca ccaaacgcta tgcctccaa gaagtgttgg acgagagctt gaacagaaat   1260
cacttccagt cttacatcat ggctgacatg tatagtttttg gcctcatcct ttgggaggtt   1320
gctaggagat gtgtatcagg aggtatagtg gaagaatacc agcttcctta tcatgaccta   1380
gtgcccagtg acccctctta tgaggacatg agggagattg tgtgcatcaa gaagttacgc   1440
ccctcattcc caaaccggtg gagcagtgat gagtgtccaa ggcagatggg aaaactcatg   1500
acagaatgct gggctcacaa tcctgcatca aggctgacag ccctgcgggt taagaaaaca   1560
cttgccaaaa tgtcagagtc ccaggacatt aaactc                             1596

SEQ ID NO: 94           moltype = DNA  length = 393
FEATURE                 Location/Qualifiers
source                  1..393
                        mol_type = other DNA
                        organism = Homo sapiens
SEQUENCE: 94
aacttccttg ataacatgct tttgcgaagt gcaggaaaat taaatgtggg caccaagaaa     60
gaggatggtg agagtacagc ccccaccccc cgtccaaagg tcttgcgttg taaatgccac    120
caccattgtc cagaagactc agtcaacaat atttgcagca cagacggata ttgttttcacg   180
atgatagaag aggatgactc tgggttgcct gtggtcactt ctggttgcct aggactagaa    240
ggctcagatt tcagtgtcg ggacactccc attcctcatc aaagaagatc aattgaatgc     300
tgcacagaaa ggaacgaatg taataaagac ctacacccta cactgcctcc attgaaaaac    360
agagattttg ttgatggacc tatacaccac agg                                 393

SEQ ID NO: 95           moltype = AA  length = 36
FEATURE                 Location/Qualifiers
source                  1..36
                        mol_type = protein
                        organism = Homo sapiens
SEQUENCE: 95
GRCKIRHIGS NNRLQRSTCQ NTGWESAHVM KTPGFR                                36

SEQ ID NO: 96           moltype =    length =
SEQUENCE: 96
000

SEQ ID NO: 97           moltype =    length =
SEQUENCE: 97
000

SEQ ID NO: 98           moltype = AA  length = 22
FEATURE                 Location/Qualifiers
REGION                  1..22
                        note = Description of Unknown: Tissue plasminogen activator
                        (TPA) sequence
source                  1..22
                        mol_type = protein
                        organism = unidentified
SEQUENCE: 98
MDAMKRGLCC VLLLCGAVFV SP                                               22

SEQ ID NO: 99           moltype =    length =
SEQUENCE: 99
000

SEQ ID NO: 100          moltype = AA  length = 368
FEATURE                 Location/Qualifiers
REGION                  1..368
                        note = Description of Artificial Sequence: Synthetic
                        polypeptide
source                  1..368
                        mol_type = protein
                        organism = synthetic construct
SEQUENCE: 100
MDAMKRGLCC VLLLCGAVFV SPGASGRGEA ETRECIYYNA NWELERTNQS GLERCEGEQD      60
KRLHCYASWR NSSGTIELVK KGCWLDDFNC YDRQECVATE ENPQVYFCCC EGNFCNERFT    120
HLPEAGGPEV TYEPPPTAPT GGGTHTCPPC PAPELLGGPS VFLFPPKPKD TLMISRTPEV    180
TCVVVDVSHE DPEVKFNWYV DGVEVHNAKT KPREEQYNST YRVVSVLTVL HQDWLNGKEY    240
```

```
KCKVSNKALP APIEKTISKA KGQPREPQVY TLPPSRKEMT KNQVSLTCLV KGFYPSDIAV    300
EWESNGQPEN NYKTTPPVLK SDGSFFLYSK LTVDKSRWQQ GNVFSCSVMH EALHNHYTQK    360
SLSLSPGK                                                            368

SEQ ID NO: 101              moltype = DNA  length = 1104
FEATURE                     Location/Qualifiers
misc_feature                1..1104
                            note = Description of Artificial Sequence: Synthetic
                             polynucleotide
source                      1..1104
                            mol_type = other DNA
                            organism = synthetic construct
SEQUENCE: 101
atggatgcaa tgaagagagg gctctgctgt gtgctgctgc tgtgtggagc agtcttcgtt    60
tcgcccggcg cctctgggcg tggggaggct gagacacggg agtgcatcta ctacaacgcc    120
aactgggagc tggagcgcac caaccagagc ggcctgagc gctgcgaagg cgagcaggac    180
aagcggctgc actgctacgc ctcctggcgc aacagctctg gcaccatcga gctcgtgaag    240
aagggctgct ggctagatga cttcaactgc tacgataggc aggagtgtgt ggccactgag    300
gagaaccccc aggtgtactt ctgctgctgt gaaggcaact tctgcaacga gcgcttcact    360
catttgccag aggctggggg cccggaagtc acgtacgagc cccccgac agcccccacc    420
ggtggtggaa ctcacacatg cccaccgtgc ccagcacctg aactcctggg gggaccgtca    480
gtcttcctct tccccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gcccccatcg agaaaaccat ctccaaagcc    780
aaagggcagc cccgagaacc acaggtgtac accctgcccc catcccggaa ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctgaag    960
tccgacggct ccttcttcct ctatagcaag ctcaccgtgg acaagagcag gtggcagcag    1020
gggaacgtct tctcatgctc cgtgatgcat gaggctctgc acaaccacta cacgcagaag    1080
agcctctccc tgtctccggg taaa                                          1104

SEQ ID NO: 102              moltype = AA  length = 343
FEATURE                     Location/Qualifiers
REGION                      1..343
                            note = Description of Artificial Sequence: Synthetic
                             polypeptide
source                      1..343
                            mol_type = protein
                            organism = synthetic construct
SEQUENCE: 102
GRGEAETREC IYYNANWELE RTNQSGLERC EGEQDKRLHC YASWRNSSGT IELVKKGCWL    60
DDFNCYDRQE CVATEENPQV YFCCCEGNFC NERFTHLPEA GGPEVTYEPP PTAPTGGGTH    120
TCPPCPAPEL LGGPSVFLFP PKPKDTLMIS RTPEVTCVVV DVSHEDPEVK FNWYVDGVEV    180
HNAKTKPREE QYNSTYRVVS VLTVLHQDWL NGKEYKCKVS NKALPAPIEK TISKAKGQPR    240
EPQVYTLPPS RKEMTKNQVS LTCLVKGFYP SDIAVEWESN GQPENNYKTT PPVLKSDGSF    300
FLYSKLTVDK SRWQQGNVFS CSVMHEALHN HYTQKSLSLS PGK                     343

SEQ ID NO: 103              moltype =   length =
SEQUENCE: 103
000

SEQ ID NO: 104              moltype = AA  length = 355
FEATURE                     Location/Qualifiers
REGION                      1..355
                            note = Description of Artificial Sequence: Synthetic
                             polypeptide
source                      1..355
                            mol_type = protein
                            organism = synthetic construct
SEQUENCE: 104
MDAMKRGLCC VLLLCGAVFV SPGASGPRGV QALLCACTSC LQANYTCETD GACMVSIFNL    60
DGMEHHVRTC IPKVELVPAG KPFYCLSSED LRNTHCCYTD YCNRIDLRVP SGHLKEPEHP    120
SMWGPVETGG GTHTCPPCPA PELLGGPSVF LFPPKPKDTL MISRTPEVTC VVVDVSHEDP    180
EVKFNWYVDG VEVHNAKTKP REEQYNSTYR VVSVLTVLHQ DWLNGKEYKC KVSNKALPAP    240
IEKTISKAKG QPREPQVYTL PPSREEMTKN QVSLTCLVKG FYPSDIAVEW ESNGQPENNY    300
DTTPPVLDSD GSFFLYSDLT VDKSRWQQGN VFSCSVMHEA LHNHYTQKSL SLSPG        355

SEQ ID NO: 105              moltype = DNA  length = 1065
FEATURE                     Location/Qualifiers
misc_feature                1..1065
                            note = Description of Artificial Sequence: Synthetic
                             polynucleotide
source                      1..1065
                            mol_type = other DNA
                            organism = synthetic construct
SEQUENCE: 105
atggatgcaa tgaagagagg gctctgctgt gtgctgctgc tgtgtggagc agtcttcgtt    60
```

```
tcgcccggcg cctccgggcc ccggggggtc caggctctgc tgtgtgcgtg caccagctgc   120
ctccaggcca actacacgtg tgagacagat ggggcctgca tggtttccat tttcaatctg   180
gatgggatgg agcaccatgt gcgcacctgc atccccaaag tggagctggt ccctgccggg   240
aagcccttct actgcctgag ctcggaggac ctgcgcaaca cccactgctg ctacactgac   300
tactgcaaca ggatcgactt gagggtgccc agtggtcacc tcaaggagcc tgagcacccg   360
tccatgtggg gcccggtgga gaccggtggt ggaactcaca catgcccacc gtgcccagca   420
cctgaactcc tggggggacc gtcagtcttc ctcttccccc caaaacccaa ggacaccctc   480
atgatctccc ggacccctga ggtcacatgc gtggtggtgg acgtgagcca cgaagaccct   540
gaggtcaagt tcaactggta cgtggacggc gtggaggtgc ataatgccaa gacaaagccg   600
cgggaggagc agtacaacag cacgtaccgt gtggtcagcg tcctcaccgt cctgcaccag   660
gactggctga atggcaagga gtacaagtgc aaggtctcca acaaagccct cccagccccc   720
atcgagaaaa ccatctccaa agccaaaggg cagccccgag aaccacaggt gtacaccctg   780
cccccatccc gggaggagat gaccaagaac caggtcagcc tgacctgcct ggtcaaaggc   840
ttctatccca gcgacatcgc cgtggagtgg gagagcaatg ggcagccgga gaacaactac   900
gacaccacgc ctcccgtgct ggactccgac ggctccttct tcctctatag cgacctcacc   960
gtggacaaga gcaggtggca gcaggggaac gtcttctcat gctccgtgat gcatgaggct  1020
ctgcacaacc actacacgca gaagagcctc tccctgtctc cgggt              1065

SEQ ID NO: 106          moltype = AA  length = 331
FEATURE                 Location/Qualifiers
REGION                  1..331
                        note = Description of Artificial Sequence: Synthetic
                         polypeptide
source                  1..331
                        mol_type = protein
                        organism = synthetic construct
SEQUENCE: 106
SGPRGVQALL CACTSCLQAN YTCETDGACM VSIFNLDGME HHVRTCIPKV ELVPAGKPFY    60
CLSSEDLRNT HCCYTDYCNR IDLRVPSGHL KEPEHPSMWG PVETGGTHT CPPCPAPELL    120
GGPSVFLFPP KPKDTLMISR TPEVTCVVVD VSHEDPEVKF NWYVDGVEVH NAKTKPREEQ   180
YNSTYRVVSV LTVLHQDWLN GKEYKCKVSN KALPAPIEKT ISKAKGQPRE PQVYTLPPSR   240
EEMTKNQVSL TCLVKGFYPS DIAVEWESNG QPENNYDTTP PVLDSDGSFF LYSDLTVDKS   300
RWQQGNVFSC SVMHEALHNH YTQKSLSLSP G                                  331

SEQ ID NO: 107          moltype =     length =
SEQUENCE: 107
000

SEQ ID NO: 108          moltype =     length =
SEQUENCE: 108
000

SEQ ID NO: 109          moltype =     length =
SEQUENCE: 109
000

SEQ ID NO: 110          moltype =     length =
SEQUENCE: 110
000

SEQ ID NO: 111          moltype =     length =
SEQUENCE: 111
000

SEQ ID NO: 112          moltype = AA  length = 341
FEATURE                 Location/Qualifiers
REGION                  1..341
                        note = Description of Artificial Sequence: Synthetic
                         polypeptide
source                  1..341
                        mol_type = protein
                        organism = synthetic construct
SEQUENCE: 112
MDAMKRGLCC VLLLCGAVFV SPGAGLKCVC LLCDSSNFTC QTEGACWASV MLTNGKEQVI    60
KSCVSLPELN AQVFCHSSNN VTKTECCFTD FCNNITLHLP TASPNAPKLG PMETGGGTHT   120
CPPCPAPELL GGPSVFLFPP KPKDTLMISR TPEVTCVVVD VSHEDPEVKF NWYVDGVEVH   180
NAKTKPREEQ YNSTYRVVSV LTVLHQDWLN GKEYKCKVSN KALPAPIEKT ISKAKGQPRE   240
PQVYTLPPSR EEMTKNQVSL TCLVKGFYPS DIAVEWESNG QPENNYDTTP PVLDSDGSFF   300
LYSDLTVDKS RWQQGNVFSC SVMHEALHNH YTQKSLSLSP G                       341

SEQ ID NO: 113          moltype = DNA  length = 1023
FEATURE                 Location/Qualifiers
misc_feature            1..1023
                        note = Description of Artificial Sequence: Synthetic
                         polynucleotide
source                  1..1023
                        mol_type = other DNA
                        organism = synthetic construct
SEQUENCE: 113
```

```
atggatgcaa tgaagagagg gctctgctgt gtgctgctgc tgtgtggagc agtcttcgtt    60
tcgcccggcg ccggactgaa gtgtgtatgt cttttgtgtg attcttcaaa ctttacctgc   120
caaacagaag gagcatgttg ggcatcagtc atgctaacca atggaaaaga gcaggtgatc   180
aaatcctgtg tctcccttcc agaactgaat gctcaagtct tctgtcatag ttccaacaat   240
gttaccaaaa ccgaatgctg cttcacagat ttttgcaaca acataacact gcaccttcca   300
acagcatcac caaatgcccc aaaacttgga cccatggaga ccggtggtgg aactcacaca   360
tgcccaccgt gcccagcacc tgaactcctg ggggaccgt cagtcttcct cttcccccca   420
aaacccaagg acaccctcat gatctcccgg acccctgagg tcacatgcgt ggtggtggac   480
gtgagccacg aagaccctga ggtcaagttc aactggtacg tggacggcgt ggaggtgcat   540
aatgccaaga caaagccgcg ggaggagcag tacaacagca cgtaccgtgt ggtcagcgtc   600
ctcaccgtcc tgcaccagga ctggctgaat ggcaaggagt acaagtgcaa ggtctccaac   660
aaagccctcc cagcccccat cgagaaaacc atctccaaag ccaagggcag ccccgagaa   720
ccacaggtgt acaccctgcc cccatcccgg gaggagatga ccaagaacca ggtcagcctg   780
acctgcctgg tcaaaggctt ctatcccagc gacatcgccg tggagtggga gagcaatggg   840
cagccggaga acaactacga caccacgcct cccgtgctgg actccgacgg ctccttcttc   900
ctctatagcg acctcaccgt ggacaagagc aggtggcagc aggggaacgt cttctcatgc   960
tccgtgatgc atgaggctct gcacaaccac tacacgcaga gagcctctc cctgtctccg  1020
ggt                                                                1023

SEQ ID NO: 114           moltype = AA  length = 317
FEATURE                  Location/Qualifiers
REGION                   1..317
                         note = Description of Artificial Sequence: Synthetic
                          polypeptide
source                   1..317
                         mol_type = protein
                         organism = synthetic construct
SEQUENCE: 114
GLKCVCLLCD SSNFTCQTEG ACWASVMLTN GKEQVIKSCV SLPELNAQVF CHSSNNVTKT    60
ECCFTDFCNN ITLHLPTASP NAPKLGPMET GGGTHTCPPC PAPELLGGPS VFLFPPKPKD   120
TLMISRTPEV TCVVVDVSHE DPEVKFNWYV DGVEVHNAKT KPREEQYNST YRVVSVLTVL   180
HQDWLNGKEY KCKVSNKALP APIEKTISKA KGQPREPQVY TLPPSREEMT KNQVSLTCLV   240
KGFYPSDIAV EWESNGQPEN NYDTTPPVLD SDGSFFLYSD LTVDKSRWQQ GNVFSCSVMH   300
EALHNHYTQK SLSLSPG                                                 317

SEQ ID NO: 115           moltype = AA  length = 381
FEATURE                  Location/Qualifiers
REGION                   1..381
                         note = Description of Artificial Sequence: Synthetic
                          polypeptide
source                   1..381
                         mol_type = protein
                         organism = synthetic construct
SEQUENCE: 115
MDAMKRGLCC VLLLCGAVFV SPGAQNLDSM LHGTGMKSDS DQKKSENGVT LAPEDTLPFL    60
KCYCSGHCPD DAINNTCITN GHCFAIIEED DQGETTLASG CMKYEGSDFQ CKDSPKAQLR   120
RTIECCRTNL CNQYLQPTLP PVVIGPFFDG SIRTGGGTHT CPPCPAPELL GGPSVFLFPP   180
KPKDTLMISR TPEVTCVVVD VSHEDPEVKF NWYVDGVEVH NAKTKPREEQ YNSTYRVVSV   240
LTVLHQDWLN GKEYKCKVSN KALPAPIEKT ISKAKGQPRE PQVYTLPPSR EEMTKNQVSL   300
TCLVKGFYPS DIAVEWESNG QPENNYDTTP PVLDSDGSFF LYSDLTVDKS RWQQGNVFSC   360
SVMHEALHNH YTQKSLSLSP G                                            381

SEQ ID NO: 116           moltype = DNA  length = 1143
FEATURE                  Location/Qualifiers
misc_feature             1..1143
                         note = Description of Artificial Sequence: Synthetic
                          polynucleotide
source                   1..1143
                         mol_type = other DNA
                         organism = synthetic construct
SEQUENCE: 116
atggatgcaa tgaagagagg gctctgctgt gtgctgctgc tgtgtggagc agtcttcgtt    60
tcgcccggcg ccccagaatct ggatagtatg cttcatggca ctgggatgaa atcagactcc   120
gaccagaaaa agtcagaaaa tggagtaacc ttagcaccag aggatacctt gccttttta   180
aagtgctatt gctcagggca ctgtccagat gatgctatta ataacacatg cataactaat   240
ggacattgct ttgccatcat agaagaagat gaccagggag aaaccacatt agcttcaggg   300
tgtatgaaat atgaaggatc tgattttcag tgcaaagatt ctccaaaagc ccagctacgc   360
cggacaatag aatgttgtcg gaccaattta tgtaaccagt atttgcaacc cacactgcca   420
cctgttgtca taggtccgtt ttttgatggc agcattcgaa ccggtggtgg aactcacaca   480
tgcccaccgt gcccagcacc tgaactcctg ggggaccgt cagtcttcct cttcccccca   540
aaacccaagg acaccctcat gatctcccgg acccctgagg tcacatgcgt ggtggtggac   600
gtgagccacg aagaccctga ggtcaagttc aactggtacg tggacggcgt ggaggtgcat   660
aatgccaaga caaagccgcg ggaggagcag tacaacagca cgtaccgtgt ggtcagcgtc   720
ctcaccgtcc tgcaccagga ctggctgaat ggcaaggagt acaagtgcaa ggtctccaac   780
aaagccctcc cagcccccat cgagaaaacc atctccaaag ccaagggcag ccccgagaa   840
ccacaggtgt acaccctgcc cccatcccgg gaggagatga ccaagaacca ggtcagcctg   900
acctgcctgg tcaaaggctt ctatcccagc gacatcgccg tggagtggga gagcaatggg   960
cagccggaga acaactacga caccacgcct cccgtgctgg actccgacgg ctccttcttc  1020
ctctatagcg acctcaccgt ggacaagagc aggtggcagc aggggaacgt cttctcatgc  1080
```

```
tccgtgatgc atgaggctct gcacaaccac tacacgcaga agagcctctc cctgtctccg  1140
ggt                                                                1143

SEQ ID NO: 117          moltype = AA  length = 359
FEATURE                 Location/Qualifiers
REGION                  1..359
                        note = Description of Artificial Sequence: Synthetic
                         polypeptide
source                  1..359
                        mol_type = protein
                        organism = synthetic construct
SEQUENCE: 117
GAQNLDSMLH GTGMKSDSDQ KKSENGVTLA PEDTLPFLKC YCSGHCPDDA INNTCITNGH   60
CFAIIEEDDQ GETTLASGCM KYEGSDFQCK DSPKAQLRRT IECCRTNLCN QYLPQTLPPV  120
VIGPFFDGSI RTGGGTHTCP PCPAPELLGG PSVFLFPPKP KDTLMISRTP EVTCVVVDVS  180
HEDPEVKFNW YVDGVEVHNA KTKPREEQYN STYRVVSVLT VLHQDWLNGK EYKCKVSNKA  240
LPAPIEKTIS KAKGQPREPQ VYTLPPSREE MTKNQVSLTC LVKGFYPSDI AVEWESNGQP  300
ENNYDTTPPV LDSDGSFFLY SDLTVDKSRW QQGNVFSCSV MHEALHNHYT QKSLSLSPG   359

SEQ ID NO: 118          moltype = AA  length = 369
FEATURE                 Location/Qualifiers
REGION                  1..369
                        note = Description of Artificial Sequence: Synthetic
                         polypeptide
source                  1..369
                        mol_type = protein
                        organism = synthetic construct
SEQUENCE: 118
MDAMKRGLCC VLLLCGAVFV SPGAAILGRS ETQECLFFNA NWEKDRTNQT GVEPCYGDKD   60
KRRHCFATWK NISGSIEIVK QGCWLDDINC YDRTDCVEKK DSPEVYFCCC EGNMCNEKFS  120
YFPEMEVTQP TSNPVTPKPP TGGGTHTCPP CPAPELLGGP SVFLFPPKPK DTLMISRTPE  180
VTCVVVDVSH EDPEVKFNWY VDGVEVHNAK TKPREEQYNS TYRVVSVLTV LHQDWLNGKE  240
YKCKVSNKAL PAPIEKTISK AKGQPREPQV YTLPPSRKEM TKNQVSLTCL VKGFYPSDIA  300
VEWESNGQPE NNYKTTPPVL KSDGSFFLYS KLTVDKSRWQ QGNVFSCSVM HEALHNHYTQ  360
KSLSLSPGK                                                          369

SEQ ID NO: 119          moltype = DNA  length = 1107
FEATURE                 Location/Qualifiers
misc_feature            1..1107
                        note = Description of Artificial Sequence: Synthetic
                         polynucleotide
source                  1..1107
                        mol_type = other DNA
                        organism = synthetic construct
SEQUENCE: 119
atggatgcaa tgaagagagg gctctgctgt gtgctgctgc tgtgtggagc agtcttcgtt   60
tcgccggcgg ccgctatact tggtagatca gaaactcagg agtgtctttt ctttaatgct  120
aattgggaaa aagacagaac caatcaaact ggtgttgaac cgtgttatgg tgacaaagat  180
aaacggcggc attgtttgc tacctggaag aatatttctg gttccattga atagtgaaa    240
caaggttgtt ggctggatga tatcaactgc tatgacagga ctgattgtgt agaaaaaaaa  300
gacagccctg aagtatattt ctgttgctgt gagggcaata tgtgtaatga aaagttttct  360
tattttccgg agatggaagt cacacagccc acttcaaatc cagttacacc taagccaccc  420
accggtggtg gaactcacac atgcccaccg tgcccagcac ctgaactcct gggggaccg   480
tcagtcttcc tcttcccccc aaaacccaag gacaccctca tgatctcccg gacccctgag  540
gtcacatgcg tggtggtgga cgtgagccac gaagaccctg aggtcaagtt caactggtac  600
gtggacggcg tggaggtgca taatgccaag acaaagccgc gggaggagca gtacaacagc  660
acgtaccgtg tggtcagcgt cctcaccgtc ctgcaccagg actggctgaa tggcaaggag  720
tacaagtgca aggtctccaa caaagccctc ccagccccca tcgagaaaac catctccaaa  780
gccaaagggc agccccgaga accacaggtg tacaccctgc ccccatcccg gaaggagatg  840
accaagaacc aggtcagcct gacctgcctg gtcaaaggct tctatcccag cgacatcgcc  900
gtggagtggg agagcaatgg gcagccggag aacaactaca agaccacgcc tcccgtgctg  960
aagtccgacg gctccttctt cctctatagc aagctcaccg tggacaagag caggtggcag 1020
caggggaacg tcttctcatg ctccgtgatg catgaggctc tgcacaacca ctacacgcag 1080
aagagcctct ccctgtctcc gggtaaa                                     1107

SEQ ID NO: 120          moltype = AA  length = 344
FEATURE                 Location/Qualifiers
REGION                  1..344
                        note = Description of Artificial Sequence: Synthetic
                         polypeptide
source                  1..344
                        mol_type = protein
                        organism = synthetic construct
SEQUENCE: 120
ILGRSETQEC LFFNANWEKD RTNQTGVEPC YGDKDKRRHC FATWKNISGS IEIVKQGCWL   60
DDINCYDRTD CVEKKDSPEV YFCCCEGNMC NEKFSYFPEM EVTQPTSNPV TPKPPTGGGT  120
HTCPPCPAPE LLGGPSVFLF PPKPKDTLMI SRTPEVTCVV VDVSHEDPEV KFNWYVDGVE  180
VHNAKTKPRE EQYNSTYRVV SVLTVLHQDW LNGKEYKCKV SNKALPAPIE KTISKAKGQP  240
REPQVYTLPP SRKEMTKNQV SLTCLVKGFY PSDIAVEWES NGQPENNYKT TPPVLKSDGS  300
```

```
FFLYSKLTVD KSRWQQGNVF SCSVMHEALH NHYTQKSLSL SPGK           344

SEQ ID NO: 121             moltype = AA   length = 376
FEATURE                    Location/Qualifiers
REGION                     1..376
                           note = Description of Artificial Sequence: Synthetic
                             polypeptide
source                     1..376
                           mol_type = protein
                           organism = synthetic construct
SEQUENCE: 121
MDAMKRGLCC VLLLCGAVFV SPGASQNQER LCAFKDPYQQ DLGIGESRIS HENGTILCSK  60
GSTCYGLWEK SKGDINLVKQ GCWSHIGDPQ ECHYEECVVT TTPPSIQNGT YRFCCCSTDL 120
CNVNFTENFP PPDTTPLSPP HSFNRDETGG GTHTCPPCPA PELLGGPSVF LFPPKPKDTL 180
MISRTPEVTC VVVDVSHEDP EVKFNWYVDG VEVHNAKTKP REEQYNSTYR VVSVLTVLHQ 240
DWLNGKEYKC KVSNKALPAP IEKTISKAKG QPREPQVYTL PPSRKEMTKN QVSLTCLVKG 300
FYPSDIAVEW ESNGQPENNY KTTPPVLKSD GSFFLYSKLT VDKSRWQQGN VFSCSVMHEA 360
LHNHYTQKSL SLSPGK                                                376

SEQ ID NO: 122             moltype = DNA   length = 1128
FEATURE                    Location/Qualifiers
misc_feature               1..1128
                           note = Description of Artificial Sequence: Synthetic
                             polynucleotide
source                     1..1128
                           mol_type = other DNA
                           organism = synthetic construct
SEQUENCE: 122
atggatgcaa tgaagagagg gctctgctgt gtgctgctgc tgtgtggagc agtcttcgtt   60
tcgcccggcg cctcgcagaa tcaagaacgc ctatgtgcgt ttaaagatcc gtatcagcaa  120
gaccttggga taggtgagag tagaatctct catgaaaatg gacaatatt atgctcaaa    180
ggtagcacct gctatggcct ttgggagaaa tcaaaagggg acataaatct tgtaaaacaa  240
ggatgttggt ctcacattgg agatcccaa gagtgtcact atgaagaatg tgtagtaact   300
accactcctc cctcaattca gaatggaaca taccgtttct gctgttgtag cacagattta  360
tgtaatgtca actttactga gaattttcca cctcctgaca caacacccact cagtccacct  420
cattcattta accgagatga gaccggtggt ggaactcaca catgcccacc gtgcccagca  480
cctgaactcc tggggggacc gtcagtcttc ctcttccccc caaaacccaa ggacacctc   540
atgatctccc ggacccctga ggtcacatgc gtggtggtgg acgtgagcca cgaagaccct  600
gaggtcaagt tcaactggta cgtggacggc gtggaggtgc ataatgccaa gacaaagccg  660
cgggaggagc agtacaacag cacgtaccgt gtggtcagcg tcctcaccgt cctgcaccag  720
gactggctga atggcaagga gtacaagtgc aaggtctcca acaaagccct cccagccccc  780
atcgagaaaa ccatctccaa agccaaaggg cagccccgag aaccacaggt gtacaccctg  840
cccccatccc ggaaggagat gaccaagaac caggtcagcc tgacctgcct ggtcaaaggc  900
ttctatccca gcgacatcgc cgtggagtgg gagagcaatg ggcagccgga gaacaactac  960
aagaccacgc ctcccgtgct ggaagtcgac ggctccttct tcctctatag caagctcacc 1020
gtggacaaga gcaggtggca gcaggggaac gtcttctcat gctccgtgat gcatgaggct 1080
ctgcacaacc actacacgca gaagagcctc tccctgtctc cgggtaaa             1128

SEQ ID NO: 123             moltype = AA   length = 352
FEATURE                    Location/Qualifiers
REGION                     1..352
                           note = Description of Artificial Sequence: Synthetic
                             polypeptide
source                     1..352
                           mol_type = protein
                           organism = synthetic construct
SEQUENCE: 123
SQNQERLCAF KDPYQQDLGI GESRISHENG TILCSKGSTC YGLWEKSKGD INLVKQGCWS  60
HIGDPQECHY EECVVTTTPP SIQNGTYRFC CCSTDLCNVN FTENFPPPDT TPLSPPHSFN 120
RDETGGGTHT CPPCPAPELL GGPSVFLFPP KPKDTLMISR TPEVTCVVVD VSHEDPEVKF 180
NWYVDGVEVH NAKTKPREEQ YNSTYRVVSV LTVLHQDWLN GKEYKCKVSN KALPAPIEKT 240
ISKAKGQPRE PQVYTLPPSR KEMTKNQVSL TCLVKGFYPS DIAVEWESNG QPENNYKTTP 300
PVLKSDGSFF LYSKLTVDKS RWQQGNVFSC SVMHEALHNH YTQKSLSLSP GK         352

SEQ ID NO: 124             moltype = AA   length = 351
FEATURE                    Location/Qualifiers
REGION                     1..351
                           note = Description of Artificial Sequence: Synthetic
                             polypeptide
source                     1..351
                           mol_type = protein
                           organism = synthetic construct
SEQUENCE: 124
MDAMKRGLCC VLLLCGAVFV SPGADPVKPS RGPLVTCTCE SPHCKGPTCR GAWCTVVLVR  60
EEGRHPQEHR GCGNLHRELC RGRPTEFVNH YCCDSHLCNH NVSLVLEATQ PPSEQPGTDG 120
QLATGGGTHT CPPCPAPELL GGPSVFLFPP KPKDTLMISR TPEVTCVVVD VSHEDPEVKF 180
NWYVDGVEVH NAKTKPREEQ YNSTYRVVSV LTVLHQDWLN GKEYKCKVSN KALPAPIEKT 240
ISKAKGQPRE PQVYTLPPSR EEMTKNQVSL TCLVKGFYPS DIAVEWESNG QPENNYDTTP 300
PVLDSDGSFF LYSDLTVDKS RWQQGNVFSC SVMHEALHNH YTQKSLSLSP G          351
```

```
SEQ ID NO: 125         moltype = DNA  length = 1053
FEATURE                Location/Qualifiers
misc_feature           1..1053
                       note = Description of Artificial Sequence: Synthetic
                        polynucleotide
source                 1..1053
                       mol_type = other DNA
                       organism = synthetic construct
SEQUENCE: 125
atggatgcaa tgaagagagg gctctgctgt gtgctgctgc tgtgtggagc agtcttcgtt   60
tcgcccggcg ccgaccctgt gaagccgtct cggggcccgc tggtgacctg cacgtgtgag  120
agcccacatt gcaaggggcc tacctgccgg ggggcctggt gcacagtagt gctggtgcgg  180
gaggagggga ggcaccccca ggaacatcgg ggctgcggga acttgcacag ggagctctgc  240
aggggccgcc ccaccgagtt cgtcaaccac tactgctgcg acagccacct ctgcaaccac  300
aacgtgtccc tggtgctgga ggccacccaa cctccttcgg agcagccggg aacagatggc  360
cagctggcca ccggtggtgg aactcacaca tgcccaccgt gcccagcacc tgaactcctg  420
ggggaccgt cagtcttcct cttccccca aaacccaagg acacccctca tgatctcccgg  480
accctgagg tcacatgcgt ggtggtggac gtgagccacg aagaccctga ggtcaagttc  540
aactggtacg tggacggcgt ggaggtgcat aatgccaaga caaagccgcg ggaggagcag  600
tacaacagca cgtaccgtgt ggtcagcgtc ctcaccgtcc tgcaccagga ctggctgaat  660
ggcaaggagt acaagtgcaa ggtctccaac aaagccctcc cagccccat cgagaaaacc  720
atctccaaag ccaaagggca gccccgagaa ccacaggtgt acaccctgcc cccatcccgg  780
gaggagatga ccaagaacca ggtcagcctg acctgcctgg tcaaaggctt ctatcccagc  840
gacatcgccg tggagtggga gagcaatggg cagccggaga acaactacga caccacgcct  900
cccgtgctgg actccgacgg ctccttcttc tctatagcg acctcaccgt ggacaagagc  960
aggtggcagc aggggaacgt cttctcatgc tccgtgatgc atgaggctct gcacaaccac 1020
tacacgcaga gagcctctc cctgtctccg ggt                              1053

SEQ ID NO: 126         moltype = AA  length = 327
FEATURE                Location/Qualifiers
REGION                 1..327
                       note = Description of Artificial Sequence: Synthetic
                        polypeptide
source                 1..327
                       mol_type = protein
                       organism = synthetic construct
SEQUENCE: 126
DPVKPSRGPL VTCTCESPHC KGPTCRGAWC TVVLVREEGR HPQEHRGCGN LHRELCRGRP   60
TEFVNHYCCD SHLCNHNVSL VLEATQPPSE QPGTDGQLAT GGGTHTCPPC PAPELLGGPS  120
VFLFPPKPKD TLMISRTPEV TCVVVDVSHE DPEVKFNWYV DGVEVHNAKT KPREEQYNST  180
YRVVSVLTVL HQDWLNGKEY KCKVSNKALP APIEKTISKA KGQPREPQVY TLPPSREEMT  240
KNQVSLTCLV KGFYPSDIAV EWESNGQPEN NYDTTPPVLD SDGSFFLYSD LTVDKSRWQQ  300
GNVFSCSVMH EALHNHYTQK SLSLSPG                                     327

SEQ ID NO: 127         moltype = AA  length = 390
FEATURE                Location/Qualifiers
REGION                 1..390
                       note = Description of Artificial Sequence: Synthetic
                        polypeptide
source                 1..390
                       mol_type = protein
                       organism = synthetic construct
SEQUENCE: 127
MDAMKRGLCC VLLLCGAVFV SPGATIPPHV QKSVNNDMIV TDNNGAVKFP QLCKFCDVRF   60
STCDNQKSCM SNCSITSICE KPQEVCVAVW RKNDENITLE TVCHDPKLPY HDFILEDAAS  120
PKCIMKEKKK PGETFFMCSC SSDECNDNII FSEEYNTSNP DTGGGTHTCP PCPAPELLGG  180
PSVFLFPPKP KDTLMISRTP EVTCVVVDVS HEDPEVKFNW YVDGVEVHNA KTKPREEQYN  240
STYRVVSVLT VLHQDWLNGK EYKCKVSNKA LPAPIEKTIS KAKGQPREPQ VYTLPPSRKE  300
MTKNQVSLTC LVKGFYPSDI AVEWESNGQP ENNYKTTPPV LKSDGSFFLY SKLTVDKSRW  360
QQGNVFSCSV MHEALHNHYT QKSLSLSPGK                                  390

SEQ ID NO: 128         moltype = DNA  length = 1170
FEATURE                Location/Qualifiers
misc_feature           1..1170
                       note = Description of Artificial Sequence: Synthetic
                        polynucleotide
source                 1..1170
                       mol_type = other DNA
                       organism = synthetic construct
SEQUENCE: 128
atggatgcaa tgaagagagg gctctgctgt gtgctgctgc tgtgtggagc agtcttcgtt   60
tcgcccggcg ccacgatccc accgcacgtt cagaagtcgg ttaataacga catgatagtc  120
actgacaaca acggtgcagt caagtttcca caactgtgta aattttgtga tgtgagattt  180
tccacctgtg acaaccagaa atcctgcatg agcaactgca gcatcacctc catctgtgag  240
aagccacagg aagtctgtgt ggctgtatgg agaaagaatg acgagaacat aacactagag  300
acagtttgcc atgaccccaa gctcccctac atgacttta ttctggaaga tgctgcttct  360
ccaaagtgca ttatgaagga aaaaaaaaag cctggtgaga cttcttcat gtgttcctgt  420
agctctgatg agtgcaatga caacatcatc ttctcagaag aatataacac cagcaatcct  480
```

-continued

```
gacaccggtg gtggaactca cacatgccca ccgtgcccag cacctgaact cctgggggga  540
ccgtcagtct tcctcttccc cccaaaaccc aaggacaccc tcatgatctc ccggacccct  600
gaggtcacat gcgtggtggt ggacgtgagc cacgaagacc ctgaggtcaa gttcaactgg  660
tacgtggacg gcgtggaggt gcataatgcc aagacaaagc cgcgggagga gcagtacaac  720
agcacgtacc gtgtggtcag cgtcctcacc gtcctgcacc aggactggct gaatggcaag  780
gagtacaagt gcaaggtctc caacaaagcc ctcccagccc ccatcgagaa aaccatctcc  840
aaagccaaag gcagccccg agaaccacag gtgtacaccc tgcccccatc ccggaaggag  900
atgaccaaga accaggtcag cctgacctgc ctggtcaaag gcttctatcc cagcgacatc  960
gccgtggagt gggagagcaa tgggcagccg gagaacaact acaagaccac gcctcccgtg 1020
ctgaagtccg acggctcctt cttcctctat agcaagctca ccgtggacaa gagcaggtgg 1080
cagcagggga acgtcttctc atgctccgtg atgcatgagg ctctgcacaa ccactacacg 1140
cagaagagcc tctccctgtc tccgggtaaa                                  1170

SEQ ID NO: 129           moltype = AA   length = 366
FEATURE                  Location/Qualifiers
REGION                   1..366
                         note = Description of Artificial Sequence: Synthetic
                          polypeptide
source                   1..366
                         mol_type = protein
                         organism = synthetic construct
SEQUENCE: 129
TIPPHVQKSV NNDMIVTDNN GAVKFPQLCK FCDVRFSTCD NQKSCMSNCS ITSICEKPQE   60
VCVAVWRKND ENITLETVCH DPKLPYHDFI LEDAASPKCI MKEKKKPGET FFMCSCSSDE  120
CNDNIIFSEE YNTSNPDTGG GTHTCPPCPA PELLGGPSVF LFPPKPKDTL MISRTPEVTC  180
VVVDVSHEDP EVKFNWYVDG VEVHNAKTKP REEQYNSTYR VVSVLTVLHQ DWLNGKEYKC  240
KVSNKALPAP IEKTISKAKG QPREPQVYTL PPSRKEMTKN QVSLTCLVKG FYPSDIAVEW  300
ESNGQPENNY KTTPPVLKSD GSFFLYSKLT VDKSRWQQGN VFSCSVMHEA LHNHYTQKSL  360
SLSPGK                                                             366

SEQ ID NO: 130           moltype = AA   length = 415
FEATURE                  Location/Qualifiers
REGION                   1..415
                         note = Description of Artificial Sequence: Synthetic
                          polypeptide
source                   1..415
                         mol_type = protein
                         organism = synthetic construct
SEQUENCE: 130
MDAMKRGLCC VLLLCGAVFV SPGATIPPHV QKSDVEMEAQ KDEIICPSCN RTAHPLRHIN   60
NDMIVTDNNG AVKFPQLCKF CDVRFSTCDN QKSCMSNCSI TSICEKPQEV CVAVWRKNDE  120
NITLETVCHD PKLPYHDFIL EDAASPKCIM KEKKKPGETF FMCSCSSDEC NDNIIFSEEY  180
NTSNPDTGGG THTCPPCPAP ELLGGPSVFL FPPKPKDTLM ISRTPEVTCV VVDVSHEDPE  240
VKFNWYVDGV EVHNAKTKPR EEQYNSTYRV VSVLTVLHQD WLNGKEYKCK VSNKALPAPI  300
EKTISKAKGQ PREPQVYTLP PSRKEMTKNQ VSLTCLVKGF YPSDIAVEWE SNGQPENNYK  360
TTPPVLKSDG SFFLYSKLTV DKSRWQQGNV FSCSVMHEAL HNHYTQKSLS LSPGK       415

SEQ ID NO: 131           moltype = DNA   length = 1245
FEATURE                  Location/Qualifiers
misc_feature             1..1245
                         note = Description of Artificial Sequence: Synthetic
                          polynucleotide
source                   1..1245
                         mol_type = other DNA
                         organism = synthetic construct
SEQUENCE: 131
atggatgcaa tgaagagagg gctctgctgt gtgctgctgc tgtgtggagc agtcttcgtt   60
tcgcccggcg ccacgatccc accgcacgtt cagaagtcgg atgtggaaat ggaggcccag  120
aaagatgaaa tcatctgccc cagctgtaat aggactgcac atccactgag acatattaat  180
aacgacatga tagtcactga caacaacggt gcagtcaagt tccacaact gtgtaaattt  240
tgtgatgtga gattttccac ctgtgacaac cagaaatcct gcatgagcaa ctgcagcatc  300
acctccatct gtgagaagcc acaggaagtc tgtgtggctg tatggagaaa gaatgacgag  360
aacataacac tagagacagt ttgccatgac cccaagctcc cctaccatga ctttattctg  420
gaagatgctg cttctccaaa gtgcattatg aaggaaaaaa aaaagcctgg tgagactttc  480
ttcatgtgtt cctgtagctc tgatgagtgc aatgacaaca tcatcttctc agaagaatat  540
aacaccagca tcctgacac cggtggtgga actcacacat gcccaccgtg cccagcacct  600
gaactcctgg ggaccgtc agtcttcctc ttccccccaa acccaagga caccctcatg  660
atctcccgga cccctgaggt cacatgcgtg gtggacg tgagccacga agaccctgag  720
gtcaagttca actggtacgt ggacggcgtg gaggtgcata atgccaagac aaagccgcgg  780
gaggagcagt acaacagcac gtaccgtgtg gtcagcgtcc tcaccgtcct gcaccaggac  840
tggctgaatg gcaaggagta caagtgcaag gtctccaaca agccctccc agcccccatc  900
gagaaaacca tctccaaagc caagggcag ccccgagaac acaggtgta caccctgccc  960
ccatcccgga aggagatgac caagaaccag gtcagcctga cctgcctggt caaaggcttc 1020
tatcccagcg acatcgccgt ggagtgggag agcaatgggc agccggagaa caactacaag 1080
accacgcctc ccgtgctgaa gtccgacggc tccttcttcc tctatagcaa gctcaccgtg 1140
gacaagagca ggtggcagca ggggaacgtc ttctcatgct ccgtgatgca tgaggctctg 1200
cacaaccact acacgcagaa gagcctctcc ctgtctccgg gtaaa                 1245

SEQ ID NO: 132           moltype = AA   length = 391
```

```
FEATURE                 Location/Qualifiers
REGION                  1..391
                        note = Description of Artificial Sequence: Synthetic
                        polypeptide
source                  1..391
                        mol_type = protein
                        organism = synthetic construct
SEQUENCE: 132
TIPPHVQKSD VEMEAQKDEI ICPSCNRTAH PLRHINNDMI VTDNNGAVKF PQLCKFCDVR    60
FSTCDNQKSC MSNCSITSIC EKPQEVCVAV WRKNDENITL ETVCHDPKLP YHDFILEDAA   120
SPKCIMKEKK KPGETFFMCS CSSDECNDNI IFSEEYNTSN PDTGGGTHTC PPCPAPELLG   180
GPSVFLFPPK PKDTLMISRT PEVTCVVVDV SHEDPEVKFN WYVDGVEVHN AKTKPREEQY   240
NSTYRVVSVL TVLHQDWLNG KEYKCKVSNK ALPAPIEKTI SKAKGQPREP QVYTLPPSRK   300
EMTKNQVSLT CLVKGFYPSD IAVEWESNGQ PENNYKTTPP VLKSDGSFFL YSKLTVDKSR   360
WQQGNVFSCS VMHEALHNHY TQKSLSLSPG K                                  391

SEQ ID NO: 133          moltype =    length =
SEQUENCE: 133
000

SEQ ID NO: 134          moltype =    length =
SEQUENCE: 134
000

SEQ ID NO: 135          moltype =    length =
SEQUENCE: 135
000

SEQ ID NO: 136          moltype = AA   length = 355
FEATURE                 Location/Qualifiers
REGION                  1..355
                        note = Description of Artificial Sequence: Synthetic
                        polypeptide
source                  1..355
                        mol_type = protein
                        organism = synthetic construct
SEQUENCE: 136
MDAMKRGLCC VLLLCGAVFV SPGAMEDEKP KVNPKLYMCV CEGLSCGNED HCEGQQCFSS    60
LSINDGFHVY QKGCFQVYEQ GKMTCKTPPS PGQAVECCQG DWCNRNITAQ LPTKGKSFPG   120
TQNFHLETGG GTHTCPPCPA PELLGGPSVF LFPPKPKDTL MISRTPEVTC VVVDVSHEDP   180
EVKFNWYVDG VEVHNAKTKP REEQYNSTYR VVSVLTVLHQ DWLNGKEYKC KVSNKALPAP   240
IEKTISKAKG QPREPQVYTL PPSREEMTKN QVSLTCLVKG FYPSDIAVEW ESNGQPENNY   300
DTTPPVLDSD GSFFLYSDLT VDKSRWQQGN VFSCSVMHEA LHNHYTQKSL SLSPG        355

SEQ ID NO: 137          moltype = DNA  length = 1065
FEATURE                 Location/Qualifiers
misc_feature            1..1065
                        note = Description of Artificial Sequence: Synthetic
                        polynucleotide
source                  1..1065
                        mol_type = other DNA
                        organism = synthetic construct
SEQUENCE: 137
atggatgcaa tgaagagagg gctctgctgt gtgctgctgc tgtgtggagc agtcttcgtt    60
tcgcccggcg ccatggaaga tgagaagccc aaggtcaacc ccaaactcta catgtgtgtg   120
tgtgaaggtc tctcctgcgg taatgaggac cactgtgaag ccagcagtg cttttcctca   180
ctgagcatca acgatggctt ccacgtctac cagaaaggct gcttccaggt ttatgagcag   240
ggaaagatga cctgtaagac cccgccgtcc cctggccaag ctgtggagtg ctgccaaggg   300
gactggtgta acaggaacat cacggcccag ctgcccacta aaggaaaatc cttccctgga   360
acacagaatt tccacttgga gaccggtggt ggaactcaca catgcccacc gtgcccagca   420
cctgaactcc tggggggacc gtcagtcttc ctcttccccc caaaacccaa ggacaccctc   480
atgatctccc ggacccctga ggtcacatgc gtggtggtgg acgtgagcca cgaagaccct   540
gaggtcaagt tcaactggta cgtggacggc gtggaggtgc ataatgccaa gacaaagccg   600
cgggaggagc agtacaacag cacgtaccgt gtggtcagcg tcctcaccgt cctgcaccag   660
gactggctga atggcaagga gtacaagtgc aaggtctcca acaaagccct cccagccccc   720
atcgagaaaa ccatctccaa agccaaaggg cagccccgag aaccacaggt gtacaccctg   780
cccccatccc gggaggagat gaccaagaac caggtcagcc tgacctgcct ggtcaaaggc   840
ttctatccca gcgacatcgc cgtggagtgg gagagcaatg ggcagccgga gaacaactac   900
gacaccacgc ctcccgtgct ggactccgac ggctccttct tcctctatag cgacctcacc   960
gtggacaaga gcaggtggca gcagggga gtcttctcat gctccgtgat gcatgaggct  1020
ctgcacaacc actacacgca gaagagcctc tccctgtctc cgggt                 1065

SEQ ID NO: 138          moltype = AA   length = 331
FEATURE                 Location/Qualifiers
REGION                  1..331
                        note = Description of Artificial Sequence: Synthetic
                        polypeptide
source                  1..331
                        mol_type = protein
```

-continued

```
                         organism = synthetic construct
SEQUENCE: 138
MEDEKPKVNP KLYMCVCEGL SCGNEDHCEG QQCFSSLSIN DGFHVYQKGC FQVYEQGKMT     60
CKTPPSPGQA VECCQGDWCN RNITAQLPTK GKSFPGTQNF HLETGGGTHT CPPCPAPELL    120
GGPSVFLFPP KPKDTLMISR TPEVTCVVVD VSHEDPEVKF NWYVDGVEVH NAKTKPREEQ    180
YNSTYRVVSV LTVLHQDWLN GKEYKCKVSN KALPAPIEKT ISKAKGQPRE PQVYTLPPSR    240
EEMTKNQVSL TCLVKGFYPS DIAVEWESNG QPENNYDTTP PVLDSDGSFF LYSDLTVDKS    300
RWQQGNVFSC SVMHEALHNH YTQKSLSLSP G                                  331

SEQ ID NO: 139          moltype = AA   length = 352
FEATURE                 Location/Qualifiers
REGION                  1..352
                        note = Description of Artificial Sequence: Synthetic
                         polypeptide
source                  1..352
                        mol_type = protein
                        organism = synthetic construct
SEQUENCE: 139
MDAMKRGLCC VLLLCGAVFV SPGAALLPGA TALQCFCHLC TKDNFTCVTD GLCFVSVTET     60
TDKVIHNSMC IAEIDLIPRD RPFVCAPSSK TGSVTTTYCC NQDHCNKIEL PTTVKSSPGL    120
GPVETGGGTH TCPPCPAPEL LGGPSVFLFP PKPKDTLMIS RTPEVTCVVV DVSHEDPEVK    180
FNWYVDGVEV HNAKTKPREE QYNSTYRVVS VLTVLHQDWL NGKEYKCKVS NKALPAPIEK    240
TISKAKGQPR EPQVYTLPPS REEMTKNQVS LTCLVKGFYP SDIAVEWESN GQPENNYDTT    300
PPVLDSDGSF FLYSDLTVDK SRWQQGNVFS CSVMHEALHN HYTQKSLSLS PG            352

SEQ ID NO: 140          moltype = DNA   length = 1056
FEATURE                 Location/Qualifiers
misc_feature            1..1056
                        note = Description of Artificial Sequence: Synthetic
                         polynucleotide
source                  1..1056
                        mol_type = other DNA
                        organism = synthetic construct
SEQUENCE: 140
atggatgcaa tgaagagagg gctctgctgt gtgctgctgc tgtgtggagc agtcttcgtt     60
tcgcccggcg ccgcgctgct cccgggggcg acggcgttac agtgtttctg ccacctctgt    120
acaaaagaca attttacttg tgtgacagat gggctctgct ttgtctctgt cacagagacc    180
acagacaaag ttatacacaa cagcatgtgt atagctgaaa ttgacttaat tcctcgagat    240
aggccgtttg tatgtgcacc ctcttcaaaa actgggtctg tgactacaac atattgctgc    300
aatcaggacc attgcaataa aatagaactt ccaactacta taaagtcatc acctggcctt    360
ggtcctgtgg aaaccggtgg tggaactcac acatgcccac cgtgcccagc acctgaactc    420
ctgggggac cgtcagtctt cctcttcccc ccaaaaccca aggacaccct catgatctcc    480
cggacccctg aggtcacatg cgtggtggtg gacgtgagcc acgaagaccc tgaggtcaag    540
ttcaactggt acgtggacgg cgtggaggtg cataatgcca agacaaagcc gcgggaggag    600
cagtacaaca gcacgtaccg tgtggtcagc gtcctcaccg tcctgcacca ggactggctg    660
aatggcaagg agtacaagtg caaggtctcc aacaaagccc tcccagcccc catcgagaaa    720
accatctcca aagccaaagg gcagccccga gaaccacagg tgtacaccct gcccccatcc    780
cgggaggaga tgaccaagaa ccaggtcagc ctgacctgcc tggtcaaagg cttctatccc    840
agcgacatcg ccgtggagtg ggagagcaat gggcagccgg agaacaacta cgacaccacg    900
cctcccgtgc tggactccga cggctccttc ttcctctata gcgacctcac cgtggacaag    960
agcaggtggc agcaggggaa cgtcttctca tgctccgtga tgcatgaggc tctgcacaac   1020
cactacacgc agaagagcct ctccctgtct ccgggt                             1056

SEQ ID NO: 141          moltype = AA   length = 328
FEATURE                 Location/Qualifiers
REGION                  1..328
                        note = Description of Artificial Sequence: Synthetic
                         polypeptide
source                  1..328
                        mol_type = protein
                        organism = synthetic construct
SEQUENCE: 141
ALLPGATALQ CFCHLCTKDN FTCVTDGLCF VSVTETTDKV IHNSMCIAEI DLIPRDRPFV     60
CAPSSKTGSV TTTYCCNQDH CNKIELPTTV KSSPGLGPVE TGGGTHTCPP CPAPELLGGP    120
SVFLFPPKPK DTLMISRTPE VTCVVVDVSH EDPEVKFNWY VDGVEVHNAK TKPREEQYNS    180
TYRVVSVLTV LHQDWLNGKE YKCKVSNKAL PAPIEKTISK AKGQPREPQV YTLPPSREEM    240
TKNQVSLTCL VKGFYPSDIA VEWESNGQPE NNYDTTPPVL DSDGSFFLYS DLTVDKSRWQ    300
QGNVFSCSVM HEALHNHYTQ KSLSLSPG                                      328

SEQ ID NO: 142          moltype = AA   length = 365
FEATURE                 Location/Qualifiers
REGION                  1..365
                        note = Description of Artificial Sequence: Synthetic
                         polypeptide
source                  1..365
                        mol_type = protein
                        organism = synthetic construct
SEQUENCE: 142
MDAMKRGLCC VLLLCGAVFV SPGAKKEDGE STAPTPRPKV LRCKCHHHCP EDSVNNICST     60
```

```
DGYCFTMIEE DDSGLPVVTS GCLGLEGSDF QCRDTPIPHQ RRSIECCTER NECNKDLHPT    120
LPPLKNRDFV DGPIHHRTGG GTHTCPPCPA PELLGGPSVF LFPPKPKDTL MISRTPEVTC    180
VVVDVSHEDP EVKFNWYVDG VEVHNAKTKP REEQYNSTYR VVSVLTVLHQ DWLNGKEYKC    240
KVSNKALPAP IEKTISKAKG QPREPQVYTL PPSREEMTKN QVSLTCLVKG FYPSDIAVEW    300
ESNGQPENNY DTTPPVLDSD GSFFLYSDLT VDKSRWQQGN VFSCSVMHEA LHNHYTQKSL    360
SLSPG                                                               365

SEQ ID NO: 143          moltype = DNA   length = 1095
FEATURE                 Location/Qualifiers
misc_feature            1..1095
                        note = Description of Artificial Sequence: Synthetic
                         polynucleotide
source                  1..1095
                        mol_type = other DNA
                        organism = synthetic construct
SEQUENCE: 143
atggatgcaa tgaagagagg gctctgctgt gtgctgctgc tgtgtggagc agtcttcgtt    60
tcgcccggcg ccaagaaaga ggatggtgag agtacagccc ccaccccccg tccaaaggtc   120
ttgcgtttgta aatgccacca ccattgtcca gaagactcag tcaacaatat ttgcagcaca   180
gacggatatt gtttcacgat gatagaagag gatgactctg ggttgcctgt ggtcacttct   240
ggttgcctag gactagaagg ctcagatttt cagtgtcggg acactcccat tcctcatcaa   300
agaagatcaa ttgaatgctg cacagaaagg aacgaatgta ataaagacct acaccctaca   360
ctgcctccat tgaaaaacag agattttgtt gatggaccta taccacacag gaccggtggt   420
ggaactcaca catgcccacc gtgcccagca cctgaactcc tggggggacc gtcagtcttc   480
ctcttccccc caaaacccaa ggacaccctc atgatctccc ggacccctga ggtcacatgc   540
gtggtggtgg acgtgagcca cgaagaccct gaggtcaagt tcaactggta cgtggacggc   600
gtggaggtgc ataatgccaa gacaaagccg cgggaggagc agtacaacag cacgtaccgt   660
gtggtcagcg tcctcaccgt cctgcaccag gactggctga atggcaagga gtacaagtgc   720
aaggtctcca acaaagccct cccagccccc atcgagaaaa ccatctccaa agccaaaggg   780
cagccccgag aaccacaggt gtacaccctg cccccatccc gggaggagat gaccaagaac   840
caggtcagcc tgacctgcct ggtcaaaggc ttctatccca gcgacatcgc cgtggagtgg   900
gagagcaatg ggcagccgga gaacaactac gacaccacgc tcccgtgctg gactccgac    960
ggctccttct tcctctatag cgacctcacc gtggacaaga gcaggtggca gcaggggaac   1020
gtcttctcat gctccgtgat gcatgaggct ctgcacaacc actacacgca gaagagcctc   1080
tccctgtctc cgggt                                                   1095

SEQ ID NO: 144          moltype = AA    length = 341
FEATURE                 Location/Qualifiers
REGION                  1..341
                        note = Description of Artificial Sequence: Synthetic
                         polypeptide
source                  1..341
                        mol_type = protein
                        organism = synthetic construct
SEQUENCE: 144
KKEDGESTAP TPRPKVLRCK CHHHCPEDSV NNICSTDGYC FTMIEEDDSG LPVVTSGCLG    60
LEGSDFQCRD TPIPHQRRSI ECCTERNECN KDLHPTLPPL KNRDFVDGPI HHRTGGGTHT   120
CPPCPAPELL GGPSVFLFPP KPKDTLMISR TPEVTCVVVD VSHEDPEVKF NWYVDGVEVH   180
NAKTKPREEQ YNSTYRVVSV LTVLHQDWLN GKEYKCKVSN KALPAPIEKT ISKAKGQPRE   240
PQVYTLPPSR EEMTKNQVSL TCLVKGFYPS DIAVEWESNG QPENNYDTTP PVLDSDGSFF   300
LYSDLTVDKS RWQQGNVFSC SVMHEALHNH YTQKSLSLSP G                      341

SEQ ID NO: 145          moltype =       length =
SEQUENCE: 145
000

SEQ ID NO: 146          moltype =       length =
SEQUENCE: 146
000

SEQ ID NO: 147          moltype =       length =
SEQUENCE: 147
000

SEQ ID NO: 148          moltype =       length =
SEQUENCE: 148
000

SEQ ID NO: 149          moltype =       length =
SEQUENCE: 149
000

SEQ ID NO: 150          moltype =       length =
SEQUENCE: 150
000

SEQ ID NO: 151          moltype =       length =
SEQUENCE: 151
000
```

| | | |
|---|---|---|
| SEQ ID NO: 152<br>SEQUENCE: 152<br>000 | moltype = | length = |
| SEQ ID NO: 153<br>SEQUENCE: 153<br>000 | moltype = | length = |
| SEQ ID NO: 154<br>SEQUENCE: 154<br>000 | moltype = | length = |
| SEQ ID NO: 155<br>SEQUENCE: 155<br>000 | moltype = | length = |
| SEQ ID NO: 156<br>SEQUENCE: 156<br>000 | moltype = | length = |
| SEQ ID NO: 157<br>SEQUENCE: 157<br>000 | moltype = | length = |
| SEQ ID NO: 158<br>SEQUENCE: 158<br>000 | moltype = | length = |
| SEQ ID NO: 159<br>SEQUENCE: 159<br>000 | moltype = | length = |
| SEQ ID NO: 160<br>SEQUENCE: 160<br>000 | moltype = | length = |
| SEQ ID NO: 161<br>SEQUENCE: 161<br>000 | moltype = | length = |
| SEQ ID NO: 162<br>SEQUENCE: 162<br>000 | moltype = | length = |
| SEQ ID NO: 163<br>SEQUENCE: 163<br>000 | moltype = | length = |
| SEQ ID NO: 164<br>SEQUENCE: 164<br>000 | moltype = | length = |
| SEQ ID NO: 165<br>SEQUENCE: 165<br>000 | moltype = | length = |
| SEQ ID NO: 166<br>SEQUENCE: 166<br>000 | moltype = | length = |
| SEQ ID NO: 167<br>SEQUENCE: 167<br>000 | moltype = | length = |
| SEQ ID NO: 168<br>SEQUENCE: 168<br>000 | moltype = | length = |
| SEQ ID NO: 169<br>SEQUENCE: 169<br>000 | moltype = | length = |
| SEQ ID NO: 170<br>SEQUENCE: 170<br>000 | moltype = | length = |
| SEQ ID NO: 171<br>SEQUENCE: 171 | moltype = | length = |

-continued

000

SEQ ID NO: 172            moltype =     length =
SEQUENCE: 172
000

SEQ ID NO: 173            moltype =     length =
SEQUENCE: 173
000

SEQ ID NO: 174            moltype =     length =
SEQUENCE: 174
000

SEQ ID NO: 175            moltype =     length =
SEQUENCE: 175
000

SEQ ID NO: 176            moltype =     length =
SEQUENCE: 176
000

SEQ ID NO: 177            moltype =     length =
SEQUENCE: 177
000

SEQ ID NO: 178            moltype =     length =
SEQUENCE: 178
000

SEQ ID NO: 179            moltype =     length =
SEQUENCE: 179
000

SEQ ID NO: 180            moltype =     length =
SEQUENCE: 180
000

SEQ ID NO: 181            moltype =     length =
SEQUENCE: 181
000

SEQ ID NO: 182            moltype =     length =
SEQUENCE: 182
000

SEQ ID NO: 183            moltype =     length =
SEQUENCE: 183
000

SEQ ID NO: 184            moltype =     length =
SEQUENCE: 184
000

SEQ ID NO: 185            moltype =     length =
SEQUENCE: 185
000

SEQ ID NO: 186            moltype =     length =
SEQUENCE: 186
000

SEQ ID NO: 187            moltype =     length =
SEQUENCE: 187
000

SEQ ID NO: 188            moltype =     length =
SEQUENCE: 188
000

SEQ ID NO: 189            moltype =     length =
SEQUENCE: 189
000

SEQ ID NO: 190            moltype =     length =
SEQUENCE: 190
000

SEQ ID NO: 191            moltype =     length =

```
SEQUENCE: 191
000

SEQ ID NO: 192          moltype =    length =
SEQUENCE: 192
000

SEQ ID NO: 193          moltype =    length =
SEQUENCE: 193
000

SEQ ID NO: 194          moltype =    length =
SEQUENCE: 194
000

SEQ ID NO: 195          moltype =    length =
SEQUENCE: 195
000

SEQ ID NO: 196          moltype =    length =
SEQUENCE: 196
000

SEQ ID NO: 197          moltype =    length =
SEQUENCE: 197
000

SEQ ID NO: 198          moltype =    length =
SEQUENCE: 198
000

SEQ ID NO: 199          moltype =    length =
SEQUENCE: 199
000

SEQ ID NO: 200          moltype = AA  length = 225
FEATURE                 Location/Qualifiers
REGION                  1..225
                        note = Description of Artificial Sequence: Synthetic
                         polypeptide
source                  1..225
                        mol_type = protein
                        organism = synthetic construct
SEQUENCE: 200
THTCPPCPAP ELLGGPSVFL FPPKPKDTLM ISRTPEVTCV VVDVSHEDPE VKFNWYVDGV    60
EVHNAKTKPR EEQYNSTYRV VSVLTVLHQD WLNGKEYKCK VSNKALPAPI EKTISKAKGQ   120
PREPQVYTLP PSRKEMTKNQ VSLTCLVKGF YPSDIAVEWE SNGQPENNYK TTPPVLKSDG   180
SFFLYSKLTV DKSRWQQGNV FSCSVMHEAL HNHYTQKSLS LSPGK                   225

SEQ ID NO: 201          moltype = AA  length = 225
FEATURE                 Location/Qualifiers
REGION                  1..225
                        note = Description of Artificial Sequence: Synthetic
                         polypeptide
source                  1..225
                        mol_type = protein
                        organism = synthetic construct
SEQUENCE: 201
THTCPPCPAP ELLGGPSVFL FPPKPKDTLM ISRTPEVTCV VVDVSHEDPE VKFNWYVDGV    60
EVHNAKTKPR EEQYNSTYRV VSVLTVLHQD WLNGKEYKCK VSNKALPAPI EKTISKAKGQ   120
PREPQVYTLP PSREEMTKNQ VSLTCLVKGF YPSDIAVEWE SNGQPENNYD TTPPVLDSDG   180
SFFLYSDLTV DKSRWQQGNV FSCSVMHEAL HNHYTQKSLS LSPGK                   225

SEQ ID NO: 202          moltype = AA  length = 225
FEATURE                 Location/Qualifiers
REGION                  1..225
                        note = Description of Artificial Sequence: Synthetic
                         polypeptide
source                  1..225
                        mol_type = protein
                        organism = synthetic construct
SEQUENCE: 202
THTCPPCPAP ELLGGPSVFL FPPKPKDTLM ISRTPEVTCV VVDVSHEDPE VKFNWYVDGV    60
EVHNAKTKPR EEQYNSTYRV VSVLTVLHQD WLNGKEYKCK VSNKALPAPI EKTISKAKGQ   120
PREPQVYTLP PSREEMTKNQ VSLYCLVKGF YPSDIAVEWE SNGQPENNYK TTPPVLDSDG   180
SFFLYSKLTV DKSRWQQGNV FSCSVMHEAL HNHYTQKSLS LSPGK                   225

SEQ ID NO: 203          moltype = AA  length = 225
FEATURE                 Location/Qualifiers
```

```
REGION                  1..225
                        note = Description of Artificial Sequence: Synthetic
                         polypeptide
source                  1..225
                        mol_type = protein
                        organism = synthetic construct
SEQUENCE: 203
THTCPPCPAP ELLGGPSVFL FPPKPKDTLM ISRTPEVTCV VVDVSHEDPE VKFNWYVDGV   60
EVHNAKTKPR EEQYNSTYRV VSVLTVLHQD WLNGKEYKCK VSNKALPAPI EKTISKAKGQ  120
PREPQVYTLP PSREEMTKNQ VSLTCLVKGF YPSDIAVEWE SNGQPENNYK TTPPVLDSDG  180
SFFLTSKLTV DKSRWQQGNV FSCSVMHEAL HNHYTQKSLS LSPGK                  225

SEQ ID NO: 204          moltype = AA  length = 225
FEATURE                 Location/Qualifiers
REGION                  1..225
                        note = Description of Artificial Sequence: Synthetic
                         polypeptide
source                  1..225
                        mol_type = protein
                        organism = synthetic construct
SEQUENCE: 204
THTCPPCPAP ELLGGPSVFL FPPKPKDTLM ISRTPEVTCV VVDVSHEDPE VKFNWYVDGV   60
EVHNAKTKPR EEQYNSTYRV VSVLTVLHQD WLNGKEYKCK VSNKALPAPI EKTISKAKGQ  120
PREPQVYTLP PCREEMTKNQ VSLWCLVKGF YPSDIAVEWE SNGQPENNYK TTPPVLDSDG  180
SFFLYSKLTV DKSRWQQGNV FSCSVMHEAL HNHYTQKSLS LSPGK                  225

SEQ ID NO: 205          moltype = AA  length = 225
FEATURE                 Location/Qualifiers
REGION                  1..225
                        note = Description of Artificial Sequence: Synthetic
                         polypeptide
source                  1..225
                        mol_type = protein
                        organism = synthetic construct
SEQUENCE: 205
THTCPPCPAP ELLGGPSVFL FPPKPKDTLM ISRTPEVTCV VVDVSHEDPE VKFNWYVDGV   60
EVHNAKTKPR EEQYNSTYRV VSVLTVLHQD WLNGKEYKCK VSNKALPAPI EKTISKAKGQ  120
PREPQVCTLP PSREEMTKNQ VSLSCAVKGF YPSDIAVEWE SNGQPENNYK TTPPVLDSDG  180
SFFLVSKLTV DKSRWQQGNV FSCSVMHEAL HNHYTQKSLS LSPGK                  225

SEQ ID NO: 206          moltype = AA  length = 228
FEATURE                 Location/Qualifiers
REGION                  1..228
                        note = Description of Artificial Sequence: Synthetic
                         polypeptide
source                  1..228
                        mol_type = protein
                        organism = synthetic construct
SEQUENCE: 206
THTCPPCPAP ELLGGPSVFL FPPKPKDTLM ISRTPEVTCV VVDVSHEDPE VKFNWYVDGV   60
EVHNAKTKPR EEQYNSTYRV VSVLTVLHQD WLNGKEYKCK VSNKALPAPI EKTISKAKGQ  120
PFRPEVHLLP PSREEMTKNQ VSLTCLARGF YPKDIAVEWE SNGQPENNYK TTPSRQEPSQ  180
GTTTFAVTSK LTVDKSRWQQ GNVFSCSVMH EALHNHYTQK TISLSPGK               228

SEQ ID NO: 207          moltype = AA  length = 228
FEATURE                 Location/Qualifiers
REGION                  1..228
                        note = Description of Artificial Sequence: Synthetic
                         polypeptide
source                  1..228
                        mol_type = protein
                        organism = synthetic construct
SEQUENCE: 207
THTCPPCPAP ELLGGPSVFL FPPKPKDTLM ISRTPEVTCV VVDVSHEDPE VKFNWYVDGV   60
EVHNAKTKPR EEQYNSTYRV VSVLTVLHQD WLNGKEYKCK VSNKALPAPI EKTISKAKGQ  120
PREPQVYTLP PPSEELALNE LVTLTCLVKG FYPSDIAVEW ESNGQELPRE KYLTWAPVLD  180
SDGSFFLYSI LRVAAEDWKK GDTFSCSVMH EALHNHYTQK SLDRSPGK               228

SEQ ID NO: 208          moltype =    length =
SEQUENCE: 208
000

SEQ ID NO: 209          moltype =    length =
SEQUENCE: 209
000

SEQ ID NO: 210          moltype =    length =
SEQUENCE: 210
000
```

SEQ ID NO: 211           moltype =    length =
SEQUENCE: 211
000

SEQ ID NO: 212           moltype =    length =
SEQUENCE: 212
000

SEQ ID NO: 213           moltype = AA   length = 261
FEATURE                  Location/Qualifiers
REGION                   1..261
                         note = Description of Artificial Sequence: Synthetic
                          polypeptide
source                   1..261
                         mol_type = protein
                         organism = synthetic construct
SEQUENCE: 213
THTCPPCPAP ELLGGPSVFL FPPKPKDTLM ISRTPEVTCV VVDVSHEDPE VKFNWYVDGV    60
EVHNAKTKPR EEQYNSTYRV VSVLTVLHQD WLNGKEYKCK VSNKALPAPI EKTISKAKGQ   120
PREPQVYTLP PSREEMTKNQ VSLTCLVKGF YPSDIAVEWE SNGQPENNYK TTPPVLDSDG   180
SFFLYSKLTV DKSRWQQGNV FSCSVMHEAL HNHYTQKSLS LSPGKGGSAQ LEKELQALEK   240
ENAQLEWELQ ALEKELAQGA T                                             261

SEQ ID NO: 214           moltype = AA   length = 261
FEATURE                  Location/Qualifiers
REGION                   1..261
                         note = Description of Artificial Sequence: Synthetic
                          polypeptide
source                   1..261
                         mol_type = protein
                         organism = synthetic construct
SEQUENCE: 214
THTCPPCPAP ELLGGPSVFL FPPKPKDTLM ISRTPEVTCV VVDVSHEDPE VKFNWYVDGV    60
EVHNAKTKPR EEQYNSTYRV VSVLTVLHQD WLNGKEYKCK VSNKALPAPI EKTISKAKGQ   120
PREPQVYTLP PSREEMTKNQ VSLTCLVKGF YPSDIAVEWE SNGQPENNYK TTPPVLDSDG   180
SFFLYSKLTV DKSRWQQGNV FSCSVMHEAL HNHYTQKSLS LSPGKGGSAQ LKKKLQALKK   240
KNAQLKWKLQ ALKKKLAQGA T                                             261

SEQ ID NO: 215           moltype =    length =
SEQUENCE: 215
000

SEQ ID NO: 216           moltype =    length =
SEQUENCE: 216
000

SEQ ID NO: 217           moltype =    length =
SEQUENCE: 217
000

SEQ ID NO: 218           moltype =    length =
SEQUENCE: 218
000

SEQ ID NO: 219           moltype =    length =
SEQUENCE: 219
000

SEQ ID NO: 220           moltype =    length =
SEQUENCE: 220
000

SEQ ID NO: 221           moltype =    length =
SEQUENCE: 221
000

SEQ ID NO: 222           moltype =    length =
SEQUENCE: 222
000

SEQ ID NO: 223           moltype =    length =
SEQUENCE: 223
000

SEQ ID NO: 224           moltype =    length =
SEQUENCE: 224
000

| | | |
|---|---|---|
| SEQ ID NO: 225<br>SEQUENCE: 225<br>000 | moltype = | length = |
| SEQ ID NO: 226<br>SEQUENCE: 226<br>000 | moltype = | length = |
| SEQ ID NO: 227<br>SEQUENCE: 227<br>000 | moltype = | length = |
| SEQ ID NO: 228<br>SEQUENCE: 228<br>000 | moltype = | length = |
| SEQ ID NO: 229<br>SEQUENCE: 229<br>000 | moltype = | length = |
| SEQ ID NO: 230<br>SEQUENCE: 230<br>000 | moltype = | length = |
| SEQ ID NO: 231<br>SEQUENCE: 231<br>000 | moltype = | length = |
| SEQ ID NO: 232<br>SEQUENCE: 232<br>000 | moltype = | length = |
| SEQ ID NO: 233<br>SEQUENCE: 233<br>000 | moltype = | length = |
| SEQ ID NO: 234<br>SEQUENCE: 234<br>000 | moltype = | length = |
| SEQ ID NO: 235<br>SEQUENCE: 235<br>000 | moltype = | length = |
| SEQ ID NO: 236<br>SEQUENCE: 236<br>000 | moltype = | length = |
| SEQ ID NO: 237<br>SEQUENCE: 237<br>000 | moltype = | length = |
| SEQ ID NO: 238<br>SEQUENCE: 238<br>000 | moltype = | length = |
| SEQ ID NO: 239<br>SEQUENCE: 239<br>000 | moltype = | length = |
| SEQ ID NO: 240<br>SEQUENCE: 240<br>000 | moltype = | length = |
| SEQ ID NO: 241<br>SEQUENCE: 241<br>000 | moltype = | length = |
| SEQ ID NO: 242<br>SEQUENCE: 242<br>000 | moltype = | length = |
| SEQ ID NO: 243<br>SEQUENCE: 243<br>000 | moltype = | length = |
| SEQ ID NO: 244<br>SEQUENCE: 244<br>000 | moltype = | length = |

| | | |
|---|---|---|
| SEQ ID NO: 245 SEQUENCE: 245 000 | moltype = | length = |
| SEQ ID NO: 246 SEQUENCE: 246 000 | moltype = | length = |
| SEQ ID NO: 247 SEQUENCE: 247 000 | moltype = | length = |
| SEQ ID NO: 248 SEQUENCE: 248 000 | moltype = | length = |
| SEQ ID NO: 249 SEQUENCE: 249 000 | moltype = | length = |
| SEQ ID NO: 250 SEQUENCE: 250 000 | moltype = | length = |
| SEQ ID NO: 251 SEQUENCE: 251 000 | moltype = | length = |
| SEQ ID NO: 252 SEQUENCE: 252 000 | moltype = | length = |
| SEQ ID NO: 253 SEQUENCE: 253 000 | moltype = | length = |
| SEQ ID NO: 254 SEQUENCE: 254 000 | moltype = | length = |
| SEQ ID NO: 255 SEQUENCE: 255 000 | moltype = | length = |
| SEQ ID NO: 256 SEQUENCE: 256 000 | moltype = | length = |
| SEQ ID NO: 257 SEQUENCE: 257 000 | moltype = | length = |
| SEQ ID NO: 258 SEQUENCE: 258 000 | moltype = | length = |
| SEQ ID NO: 259 SEQUENCE: 259 000 | moltype = | length = |
| SEQ ID NO: 260 SEQUENCE: 260 000 | moltype = | length = |
| SEQ ID NO: 261 SEQUENCE: 261 000 | moltype = | length = |
| SEQ ID NO: 262 SEQUENCE: 262 000 | moltype = | length = |
| SEQ ID NO: 263 SEQUENCE: 263 000 | moltype = | length = |
| SEQ ID NO: 264 SEQUENCE: 264 | moltype = | length = |

```
000

SEQ ID NO: 265         moltype =    length =
SEQUENCE: 265
000

SEQ ID NO: 266         moltype =    length =
SEQUENCE: 266
000

SEQ ID NO: 267         moltype =    length =
SEQUENCE: 267
000

SEQ ID NO: 268         moltype =    length =
SEQUENCE: 268
000

SEQ ID NO: 269         moltype =    length =
SEQUENCE: 269
000

SEQ ID NO: 270         moltype =    length =
SEQUENCE: 270
000

SEQ ID NO: 271         moltype =    length =
SEQUENCE: 271
000

SEQ ID NO: 272         moltype =    length =
SEQUENCE: 272
000

SEQ ID NO: 273         moltype =    length =
SEQUENCE: 273
000

SEQ ID NO: 274         moltype =    length =
SEQUENCE: 274
000

SEQ ID NO: 275         moltype =    length =
SEQUENCE: 275
000

SEQ ID NO: 276         moltype =    length =
SEQUENCE: 276
000

SEQ ID NO: 277         moltype =    length =
SEQUENCE: 277
000

SEQ ID NO: 278         moltype =    length =
SEQUENCE: 278
000

SEQ ID NO: 279         moltype =    length =
SEQUENCE: 279
000

SEQ ID NO: 280         moltype =    length =
SEQUENCE: 280
000

SEQ ID NO: 281         moltype =    length =
SEQUENCE: 281
000

SEQ ID NO: 282         moltype =    length =
SEQUENCE: 282
000

SEQ ID NO: 283         moltype =    length =
SEQUENCE: 283
000

SEQ ID NO: 284         moltype =    length =
```

```
SEQUENCE: 284
000

SEQ ID NO: 285          moltype =    length =
SEQUENCE: 285
000

SEQ ID NO: 286          moltype =    length =
SEQUENCE: 286
000

SEQ ID NO: 287          moltype =    length =
SEQUENCE: 287
000

SEQ ID NO: 288          moltype =    length =
SEQUENCE: 288
000

SEQ ID NO: 289          moltype =    length =
SEQUENCE: 289
000

SEQ ID NO: 290          moltype =    length =
SEQUENCE: 290
000

SEQ ID NO: 291          moltype =    length =
SEQUENCE: 291
000

SEQ ID NO: 292          moltype =    length =
SEQUENCE: 292
000

SEQ ID NO: 293          moltype =    length =
SEQUENCE: 293
000

SEQ ID NO: 294          moltype =    length =
SEQUENCE: 294
000

SEQ ID NO: 295          moltype =    length =
SEQUENCE: 295
000

SEQ ID NO: 296          moltype =    length =
SEQUENCE: 296
000

SEQ ID NO: 297          moltype =    length =
SEQUENCE: 297
000

SEQ ID NO: 298          moltype =    length =
SEQUENCE: 298
000

SEQ ID NO: 299          moltype =    length =
SEQUENCE: 299
000

SEQ ID NO: 300          moltype =    length =
SEQUENCE: 300
000

SEQ ID NO: 301          moltype = AA   length = 443
FEATURE                 Location/Qualifiers
source                  1..443
                        mol_type = protein
                        organism = Homo sapiens
SEQUENCE: 301
MLTNGKEQVI KSCVSLPELN AQVFCHSSNN VTKTECCFTD FCNNITLHLP TASPNAPKLG   60
PMELAIIITV PVCLLSIAAM LTVWACQGRQ CSYRKKKRPN VEEPLSECNL VNAGKTLKDL  120
IYDVTASGSG SGLPLLVQRT IARTIVLQEI VGKGRFGEVW HGRWCGEDVA VKIFSSRDER  180
SWFREAEIYQ TVMLRHENIL GFIAADNKDN GTWTQLWLVS EYHEQGSLYD YLNRNIVTVA  240
GMIKLALSIA SGLAHLHMEI VGTQGKPAIA HRDIKSKNIL VKKCETCAIA DLGLAVKHDS  300
ILNTIDIPQN PKVGTKRYMA PEMLDDTMNV NIFESFKRAD IYSVGLVYWE IARRCSVGGI  360
```

```
VEEYQLPYYD MVPSDPSIEE MRKVVCDQKF RPSIPNQWQS CEALRVMGRI MRECWYANGA    420
ARLTALRIKK TISQLCVKED CKA                                           443

SEQ ID NO: 302           moltype = AA  length = 63
FEATURE                  Location/Qualifiers
source                   1..63
                         mol_type = protein
                         organism = Homo sapiens
SEQUENCE: 302
MLTNGKEQVI KSCVSLPELN AQVFCHSSNN VTKTECCFTD FCNNITLHLP TASPNAPKLG    60
PME                                                                 63

SEQ ID NO: 303           moltype = DNA  length = 1329
FEATURE                  Location/Qualifiers
source                   1..1329
                         mol_type = other DNA
                         organism = Homo sapiens
SEQUENCE: 303
atgctaacca atggaaaaga gcaggtgatc aaatcctgtg tctcccttcc agaactgaat    60
gctcaagtct tctgtcatag ttccaacaat gttaccaaaa ccgaatgctg cttcacagat    120
ttttgcaaca acataaacact gcaccttcca acagcatcac caaatgcccc aaaacttgga    180
cccatggagc tggccatcat tattactgtg cctgtttgcc tcctgtccat agctgcgatg    240
ctgacagtat gggcatgcca gggtcgacga tgctcctaca ggaagaaaaa gagaccaaat    300
gtggaggaac cactctctga gtgcaatctg gtaaatgctg gaaaaactct gaaagatctg    360
atttatgatg tgaccgcctc tggatctggc tctggtctac ctctgttggt tcaaggaca     420
attgcaagga cgattgtgct tcaggaaata gtaggaaaag gtagatttgg tgaggtgtgg    480
catggaagat ggtgtgggga agatgtggct gtgaaaatat tcctccag agatgaaaga     540
tcttggtttc gtgaggcaga aatttaccag acggtcatgc tgcgacatga aaacatcctt    600
ggtttcattg ctgctgacaa caagataat ggaacttgga ctcaactttg gctggtatct    660
gaatatcatg aacagggctc cttatatgac tatttgaata gaaatatagt gaccgtggct    720
ggaatgatca gctggcgct tcaattgct agtggtctgg cacaccttca tatggagatt    780
gttggtacac aaggtaaacc tgctattgct catcgagaca taaatcaaa gaatatctta    840
gtgaaaaagt gtgaaacttg tgccatagcg acttagggt tggctgtgaa gcatgattca    900
atactgaaca ctatcgacat accctcagaat cctaaagttgg aacaaggag gtatatggct    960
cctgaaatgc ttgatgatac aatgaatgtg aatatcttg agtccttcaa acgagctgac    1020
atctattctg ttggtctggt ttactgggaa atagcccgga ggtgttcagt cggaggaatt    1080
gttgaggagt accaattgcc ttattatgac atggtgcctt cagatccctc gatagaggaa    1140
atgagaaagg ttgtttgtga ccagaagttt cgaccagta tcccaaacca gtggcaaagt    1200
tgtgaagcac tccgagtcat ggggagaata atgcgtgagt gttggtatgc caacggagcg    1260
gcccgcctaa ctgctcttcg tattaagaag actatatctc aactttgtgt caagaagac    1320
tgcaaagcc                                                          1329

SEQ ID NO: 304           moltype = DNA  length = 189
FEATURE                  Location/Qualifiers
source                   1..189
                         mol_type = other DNA
                         organism = Homo sapiens
SEQUENCE: 304
atgctaacca atggaaaaga gcaggtgatc aaatcctgtg tctcccttcc agaactgaat    60
gctcaagtct tctgtcatag ttccaacaat gttaccaaaa ccgaatgctg cttcacagat    120
ttttgcaaca acataaacact gcaccttcca acagcatcac caaatgcccc aaaacttgga    180
cccatggag                                                           189

SEQ ID NO: 305           moltype = AA  length = 413
FEATURE                  Location/Qualifiers
source                   1..413
                         mol_type = protein
                         organism = Homo sapiens
SEQUENCE: 305
MTRALCSALR QALLLLAAAA ELSPGLKCVC LLCDSSNFTC QTEGACWASV MLTNGKEQVI    60
KSCVSLPELN AQVFCHSSNN VTKTECCFTD FCNNITLHLP TGLPLLVQRT IARTIVLQEI    120
VGKGRFGEVW HGRWCGEDVA VKIFSSRDER SWFREAEIYQ TVMLRHENIL GFIAADNKDN    180
GTWTQLWLVS EYHEQGSLYD YLNRNIVTVA GMIKLALSIA SGLAHLHMEI VGTQGKPAIA    240
HRDIKSKNIL VKKCETCAIA DLGLAVKHDS ILNTIDIPQN PKVGTKRYMA PEMLDDTMNV    300
NIFESFKRAD IYSVGLVYWE IARRCSVGGI VEEYQLPYYD MVPSDPSIEE MRKVVCDQKF    360
RPSIPNQWQS CEALRVMGRI MRECWYANGA ARLTALRIKK TISQLCVKED CKA          413

SEQ ID NO: 306           moltype = AA  length = 393
FEATURE                  Location/Qualifiers
source                   1..393
                         mol_type = protein
                         organism = Homo sapiens
SEQUENCE: 306
ELSPGLKCVC LLCDSSNFTC QTEGACWASV MLTNGKEQVI KSCVSLPELN AQVFCHSSNN    60
VTKTECCFTD FCNNITLHLP TGLPLLVQRT IARTIVLQEI VGKGRFGEVW HGRWCGEDVA    120
VKIFSSRDER SWFREAEIYQ TVMLRHENIL GFIAADNKDN GTWTQLWLVS EYHEQGSLYD    180
YLNRNIVTVA GMIKLALSIA SGLAHLHMEI VGTQGKPAIA HRDIKSKNIL VKKCETCAIA    240
DLGLAVKHDS ILNTIDIPQN PKVGTKRYMA PEMLDDTMNV NIFESFKRAD IYSVGLVYWE    300
IARRCSVGGI VEEYQLPYYD MVPSDPSIEE MRKVVCDQKF RPSIPNQWQS CEALRVMGRI    360
```

MRECWYANGA ARLTALRIKK TISQLCVKED CKA                                             393

SEQ ID NO: 307         moltype = DNA   length = 1239
FEATURE                Location/Qualifiers
source                 1..1239
                       mol_type = other DNA
                       organism = Homo sapiens
SEQUENCE: 307
atgacccggg cgctctgctc agcgctccgc caggctctcc tgctgctcgc agcggccgcc     60
gagctctcgc caggactgaa gtgtgtatgt cttttgtgtg attcttcaaa ctttacctgc    120
caaacagaag gagcatgttg ggcatcagtc atgctaacca atggaaaaga gcaggtgatc    180
aaatcctgtg tctcccttcc agaactgaat gctcaagtct tctgtcatag ttccaacaat    240
gttaccaaaa ccgaatgctg cttcacagat ttttgcaaca cataacact gcaccttcca     300
acaggtctac ctctgttggt tcaaaggaca attgcaagga cgattgtgct tcaggaaata    360
gtaggaaaag gtagatttgg tgaggtgtgg catggaagat ggtgtgggga agatgtggct    420
gtgaaaatat tctcctccag agatgaaaga tcttggtttc gtgaggcaga aatttaccag    480
acggtcatgc tgcgacatga aaacatcctt ggtttcattg ctgctgacaa caaagataat    540
ggaacttgga ctcaactttg gctggtatct gaatatcatg aacagggctc cttatatgac    600
tatttgaata gaaatatagt gaccgtggct ggaatgatca agctggcgct ctcaattgct    660
agtggtctgg cacaccttca tatggagatt gttggtacac aaggtaaacc tgctattgct    720
catcgagaca taaaatcaaa gaatatctta gtgaaaaagt gtgaaacttg tgccatagcg    780
gacttagggt tggctgtgaa gcatgattca atactgaaca ctatcgacat acctcagaat    840
cctaaagtgg gaaccaagag gtatatggct cctgaaatgc ttgatgatac aatgaatgtg    900
aatatctttg agtccttcaa acgagctgac atctattctg ttggtctggt ttactgggaa    960
atagcccgga ggtgttcagt cggaggaatt gttgaggagt accaattgcc ttattatgac   1020
atggtgcctt cagatccctc gatagaggaa atgagaaagg ttgttgtttga ccagaagttt   1080
cgaccaagta tcccaaacca gtggcaaagt tgtgaagcac tccgagtcat ggggagaata   1140
atgcgtgagt gttggtatgc caacggagcg gcccgcctaa ctgctcttcg tattaagaag   1200
actatatctc aactttgtgt caagaagac tgcaaagcc                           1239

SEQ ID NO: 308         moltype = DNA   length = 1179
FEATURE                Location/Qualifiers
source                 1..1179
                       mol_type = other DNA
                       organism = Homo sapiens
SEQUENCE: 308
gagctctcgc caggactgaa gtgtgtatgt cttttgtgtg attcttcaaa ctttacctgc     60
caaacagaag gagcatgttg ggcatcagtc atgctaacca atggaaaaga gcaggtgatc    120
aaatcctgtg tctcccttcc agaactgaat gctcaagtct tctgtcatag ttccaacaat    180
gttaccaaaa ccgaatgctg cttcacagat ttttgcaaca cataacact gcaccttcca     240
acaggtctac ctctgttggt tcaaaggaca attgcaagga cgattgtgct tcaggaaata    300
gtaggaaaag gtagatttgg tgaggtgtgg catggaagat ggtgtgggga agatgtggct    360
gtgaaaatat tctcctccag agatgaaaga tcttggtttc gtgaggcaga aatttaccag    420
acggtcatgc tgcgacatga aaacatcctt ggtttcattg ctgctgacaa caaagataat    480
ggaacttgga ctcaactttg gctggtatct gaatatcatg aacagggctc cttatatgac    540
tatttgaata gaaatatagt gaccgtggct ggaatgatca agctggcgct ctcaattgct    600
agtggtctgg cacaccttca tatggagatt gttggtacac aaggtaaacc tgctattgct    660
catcgagaca taaaatcaaa gaatatctta gtgaaaaagt gtgaaacttg tgccatagcg    720
gacttagggt tggctgtgaa gcatgattca atactgaaca ctatcgacat acctcagaat    780
cctaaagtgg gaaccaagag gtatatggct cctgaaatgc ttgatgatac aatgaatgtg    840
aatatctttg agtccttcaa acgagctgac atctattctg ttggtctggt ttactgggaa    900
atagcccgga ggtgttcagt cggaggaatt gttgaggagt accaattgcc ttattatgac    960
atggtgcctt cagatccctc gatagaggaa atgagaaagg ttgttgtttga ccagaagttt   1020
cgaccaagta tcccaaacca gtggcaaagt tgtgaagcac tccgagtcat ggggagaata   1080
atgcgtgagt gttggtatgc caacggagcg gcccgcctaa ctgctcttcg tattaagaag   1140
actatatctc aactttgtgt caagaagac tgcaaagcc                           1179

SEQ ID NO: 309         moltype = AA   length = 336
FEATURE                Location/Qualifiers
source                 1..336
                       mol_type = protein
                       organism = Homo sapiens
SEQUENCE: 309
MTRALCSALR QALLLLAAAA ELSPGLKCVC LLCDSSNFTC QTEGACWASV MLTNGKEQVI     60
KSCVSLPELN AQVFCHSSNN VTKTECCFTD FCNNITLHLP TDNGTWTQLW LVSEYHEQGS    120
LYDYLNRNIV TVAGMIKLAL SIASGLAHLH MEIVGTQGKP AIAHRDIKSK NILVKKCETC    180
AIADLGLAVK HDSILNTIDI PQNPKVGTKR YMAPEMLDDT MNVNIFESFK RADIYSVGLV    240
YWEIARRCSV GGIVEEYQLP YYDMVPSDPS IEEMRKVVCD QKFRPSIPNQ WQSCEALRVM    300
GRIMRECWYA NGAARLTALR IKKTISQLCV KEDCKA                              336

SEQ ID NO: 310         moltype = AA   length = 316
FEATURE                Location/Qualifiers
source                 1..316
                       mol_type = protein
                       organism = Homo sapiens
SEQUENCE: 310
ELSPGLKCVC LLCDSSNFTC QTEGACWASV MLTNGKEQVI KSCVSLPELN AQVFCHSSNN     60
VTKTECCFTD FCNNITLHLP TDNGTWTQLW LVSEYHEQGS LYDYLNRNIV TVAGMIKLAL    120
SIASGLAHLH MEIVGTQGKP AIAHRDIKSK NILVKKCETC AIADLGLAVK HDSILNTIDI    180

```
PQNPKVGTKR YMAPEMLDDT MNVNIFESFK RADIYSVGLV YWEIARRCSV GGIVEEYQLP   240
YYDMVPSDPS IEEMRKVVCD QKFRPSIPNQ WQSCEALRVM GRIMRECWYA NGAARLTALR   300
IKKTISQLCV KEDCKA                                                  316

SEQ ID NO: 311          moltype = DNA  length = 1011
FEATURE                 Location/Qualifiers
source                  1..1011
                        mol_type = other DNA
                        organism = Homo sapiens
SEQUENCE: 311
atgacccggg cgctctgctc agcgctccgc caggctctcc tgctgctcgc agcggccgcc    60
gagctctcgc caggactgaa gtgtgtatgt cttttgtgtg attcttcaaa ctttacctgc   120
caaacagaag gagcatgttg ggcatcagtc atgctaacca atggaaaaga gcaggtgatc   180
aaatcctgtg tctcccttcc agaactgaat gctcaagtct tctgtcatag ttccaacaat   240
gttaccaaaa ccgaatgctg cttcacagat ttttgcaaca acataacact gcaccttcca   300
acagataatg gaacttggac tcaactttgg ctggtatctg aatatcatga acagggctcc   360
ttatatgact atttgaatag aaatatagtg accgtggctg gaatgatcaa gctggcgctc   420
tcaattgcta gtggtctggc acaccttcat atggagattg ttggtacaca aggtaaacct   480
gctattgctc atcgagacat aaaatcaaag aatatcttag tgaaaagtg tgaaacttgt   540
gccatagcgg acttagggtt ggctgtgaag catgattcaa tactgaacac tatcgacata   600
cctcagaatc ctaaagtggg aaccaagagg tatatggctc tgaaatgct tgatgataca   660
atgaatgtga atatctttga gtccttcaaa cgagctgaca tctattctgt tggtctggtt   720
tactgggaaa tagcccggag tgttcagtc ggaggaattg ttgaggagta ccaattgcct   780
tattatgaca tggtgccttc agatccctcg atagaggaaa tgagaaaggt tgtttgtgac   840
cagaagtttc gaccaagtat cccaaaccag tggcaaagtt gtgaagcact ccgagtcatg   900
gggagaataa tgcgtgagtg ttggtatgcc aacggagcgg cccgcctaac tgctcttcgt   960
attaagaaga ctatatctca actttgtgtc aagaagact gcaaagccta a            1011

SEQ ID NO: 312          moltype = DNA  length = 951
FEATURE                 Location/Qualifiers
source                  1..951
                        mol_type = other DNA
                        organism = Homo sapiens
SEQUENCE: 312
gagctctcgc caggactgaa gtgtgtatgt cttttgtgtg attcttcaaa ctttacctgc    60
caaacagaag gagcatgttg ggcatcagtc atgctaacca atggaaaaga gcaggtgatc   120
aaatcctgtg tctcccttcc agaactgaat gctcaagtct tctgtcatag ttccaacaat   180
gttaccaaaa ccgaatgctg cttcacagat ttttgcaaca acataacact gcaccttcca   240
acagataatg gaacttggac tcaactttgg ctggtatctg aatatcatga acagggctcc   300
ttatatgact atttgaatag aaatatagtg accgtggctg gaatgatcaa gctggcgctc   360
tcaattgcta gtggtctggc acaccttcat atggagattg ttggtacaca aggtaaacct   420
gctattgctc atcgagacat aaaatcaaag aatatcttag tgaaaagtg tgaaacttgt   480
gccatagcgg acttagggtt ggctgtgaag catgattcaa tactgaacac tatcgacata   540
cctcagaatc ctaaagtggg aaccaagagg tatatggctc tgaaatgct tgatgataca   600
atgaatgtga atatctttga gtccttcaaa cgagctgaca tctattctgt tggtctggtt   660
tactgggaaa tagcccggag tgttcagtc ggaggaattg ttgaggagta ccaattgcct   720
tattatgaca tggtgccttc agatccctcg atagaggaaa tgagaaaggt tgtttgtgac   780
cagaagtttc gaccaagtat cccaaaccag tggcaaagtt gtgaagcact ccgagtcatg   840
gggagaataa tgcgtgagtg ttggtatgcc aacggagcgg cccgcctaac tgctcttcgt   900
attaagaaga ctatatctca actttgtgtc aagaagact gcaaagccta a             951

SEQ ID NO: 313          moltype = AA  length = 88
FEATURE                 Location/Qualifiers
source                  1..88
                        mol_type = protein
                        organism = Homo sapiens
SEQUENCE: 313
LKCVCLLCDS SNFTCQTEGA CWASVMLTNG KEQVIKSCVS LPELNAQVFC HSSNNVTKTE    60
CCFTDFCNNI TLHLPTASPN APKLGPME                                      88

SEQ ID NO: 314          moltype =    length =
SEQUENCE: 314
000

SEQ ID NO: 315          moltype =    length =
SEQUENCE: 315
000

SEQ ID NO: 316          moltype =    length =
SEQUENCE: 316
000

SEQ ID NO: 317          moltype =    length =
SEQUENCE: 317
000

SEQ ID NO: 318          moltype =    length =
SEQUENCE: 318
000
```

SEQ ID NO: 319    moltype =    length =
SEQUENCE: 319
000

SEQ ID NO: 320    moltype =    length =
SEQUENCE: 320
000

SEQ ID NO: 321    moltype =    length =
SEQUENCE: 321
000

SEQ ID NO: 322    moltype =    length =
SEQUENCE: 322
000

SEQ ID NO: 323    moltype =    length =
SEQUENCE: 323
000

SEQ ID NO: 324    moltype =    length =
SEQUENCE: 324
000

SEQ ID NO: 325    moltype =    length =
SEQUENCE: 325
000

SEQ ID NO: 326    moltype =    length =
SEQUENCE: 326
000

SEQ ID NO: 327    moltype =    length =
SEQUENCE: 327
000

SEQ ID NO: 328    moltype =    length =
SEQUENCE: 328
000

SEQ ID NO: 329    moltype =    length =
SEQUENCE: 329
000

SEQ ID NO: 330    moltype =    length =
SEQUENCE: 330
000

SEQ ID NO: 331    moltype =    length =
SEQUENCE: 331
000

SEQ ID NO: 332    moltype =    length =
SEQUENCE: 332
000

SEQ ID NO: 333    moltype =    length =
SEQUENCE: 333
000

SEQ ID NO: 334    moltype =    length =
SEQUENCE: 334
000

SEQ ID NO: 335    moltype =    length =
SEQUENCE: 335
000

SEQ ID NO: 336    moltype =    length =
SEQUENCE: 336
000

SEQ ID NO: 337    moltype =    length =
SEQUENCE: 337
000

SEQ ID NO: 338    moltype =    length =
SEQUENCE: 338

000

SEQ ID NO: 339      moltype =      length =
SEQUENCE: 339
000

SEQ ID NO: 340      moltype =      length =
SEQUENCE: 340
000

SEQ ID NO: 341      moltype =      length =
SEQUENCE: 341
000

SEQ ID NO: 342      moltype =      length =
SEQUENCE: 342
000

SEQ ID NO: 343      moltype =      length =
SEQUENCE: 343
000

SEQ ID NO: 344      moltype =      length =
SEQUENCE: 344
000

SEQ ID NO: 345      moltype =      length =
SEQUENCE: 345
000

SEQ ID NO: 346      moltype =      length =
SEQUENCE: 346
000

SEQ ID NO: 347      moltype =      length =
SEQUENCE: 347
000

SEQ ID NO: 348      moltype =      length =
SEQUENCE: 348
000

SEQ ID NO: 349      moltype =      length =
SEQUENCE: 349
000

SEQ ID NO: 350      moltype =      length =
SEQUENCE: 350
000

SEQ ID NO: 351      moltype =      length =
SEQUENCE: 351
000

SEQ ID NO: 352      moltype =      length =
SEQUENCE: 352
000

SEQ ID NO: 353      moltype =      length =
SEQUENCE: 353
000

SEQ ID NO: 354      moltype =      length =
SEQUENCE: 354
000

SEQ ID NO: 355      moltype =      length =
SEQUENCE: 355
000

SEQ ID NO: 356      moltype =      length =
SEQUENCE: 356
000

SEQ ID NO: 357      moltype =      length =
SEQUENCE: 357
000

SEQ ID NO: 358      moltype =      length =

| | | |
|---|---|---|
| SEQUENCE: 358 000 | | |
| SEQ ID NO: 359 SEQUENCE: 359 000 | moltype = | length = |
| SEQ ID NO: 360 SEQUENCE: 360 000 | moltype = | length = |
| SEQ ID NO: 361 SEQUENCE: 361 000 | moltype = | length = |
| SEQ ID NO: 362 SEQUENCE: 362 000 | moltype = | length = |
| SEQ ID NO: 363 SEQUENCE: 363 000 | moltype = | length = |
| SEQ ID NO: 364 SEQUENCE: 364 000 | moltype = | length = |
| SEQ ID NO: 365 SEQUENCE: 365 000 | moltype = | length = |
| SEQ ID NO: 366 SEQUENCE: 366 000 | moltype = | length = |
| SEQ ID NO: 367 SEQUENCE: 367 000 | moltype = | length = |
| SEQ ID NO: 368 SEQUENCE: 368 000 | moltype = | length = |
| SEQ ID NO: 369 SEQUENCE: 369 000 | moltype = | length = |
| SEQ ID NO: 370 SEQUENCE: 370 000 | moltype = | length = |
| SEQ ID NO: 371 SEQUENCE: 371 000 | moltype = | length = |
| SEQ ID NO: 372 SEQUENCE: 372 000 | moltype = | length = |
| SEQ ID NO: 373 SEQUENCE: 373 000 | moltype = | length = |
| SEQ ID NO: 374 SEQUENCE: 374 000 | moltype = | length = |
| SEQ ID NO: 375 SEQUENCE: 375 000 | moltype = | length = |
| SEQ ID NO: 376 SEQUENCE: 376 000 | moltype = | length = |
| SEQ ID NO: 377 SEQUENCE: 377 000 | moltype = | length = |

| | | |
|---|---|---|
| SEQ ID NO: 378<br>SEQUENCE: 378<br>000 | moltype = | length = |
| SEQ ID NO: 379<br>SEQUENCE: 379<br>000 | moltype = | length = |
| SEQ ID NO: 380<br>SEQUENCE: 380<br>000 | moltype = | length = |
| SEQ ID NO: 381<br>SEQUENCE: 381<br>000 | moltype = | length = |
| SEQ ID NO: 382<br>SEQUENCE: 382<br>000 | moltype = | length = |
| SEQ ID NO: 383<br>SEQUENCE: 383<br>000 | moltype = | length = |
| SEQ ID NO: 384<br>SEQUENCE: 384<br>000 | moltype = | length = |
| SEQ ID NO: 385<br>SEQUENCE: 385<br>000 | moltype = | length = |
| SEQ ID NO: 386<br>SEQUENCE: 386<br>000 | moltype = | length = |
| SEQ ID NO: 387<br>SEQUENCE: 387<br>000 | moltype = | length = |
| SEQ ID NO: 388<br>SEQUENCE: 388<br>000 | moltype = | length = |
| SEQ ID NO: 389<br>SEQUENCE: 389<br>000 | moltype = | length = |
| SEQ ID NO: 390<br>SEQUENCE: 390<br>000 | moltype = | length = |
| SEQ ID NO: 391<br>SEQUENCE: 391<br>000 | moltype = | length = |
| SEQ ID NO: 392<br>SEQUENCE: 392<br>000 | moltype = | length = |
| SEQ ID NO: 393<br>SEQUENCE: 393<br>000 | moltype = | length = |
| SEQ ID NO: 394<br>SEQUENCE: 394<br>000 | moltype = | length = |
| SEQ ID NO: 395<br>SEQUENCE: 395<br>000 | moltype = | length = |
| SEQ ID NO: 396<br>SEQUENCE: 396<br>000 | moltype = | length = |
| SEQ ID NO: 397<br>SEQUENCE: 397<br>000 | moltype = | length = |

```
SEQ ID NO: 398              moltype =    length =
SEQUENCE: 398
000

SEQ ID NO: 399              moltype =    length =
SEQUENCE: 399
000

SEQ ID NO: 400              moltype =    length =
SEQUENCE: 400
000

SEQ ID NO: 401              moltype = AA   length = 368
FEATURE                     Location/Qualifiers
REGION                      1..368
                            note = Description of Artificial Sequence: Synthetic
                             polypeptide
source                      1..368
                            mol_type = protein
                            organism = synthetic construct
SEQUENCE: 401
MDAMKRGLCC VLLLCGAVFV SPGASGRGEA ETRECIYYNA NWELERTNQS GLERCEGEQD   60
KRLHCYASWR NSSGTIELVK KGCWLDDFNC YDRQECVATE ENPVYFCCC  EGNFCNERFT  120
HLPEAGGPEV TYEPPPTAPT GGGTHTCPPC PAPELLGGPS VFLFPPKPKD TLMISRTPEV  180
TCVVVDVSHE DPEVKFNWYV DGVEVHNAKT KPREEQYNST YRVVSVLTVL HQDWLNGKEY  240
KCKVSNKALP APIEKTISKA KGQPREPQVY TLPPCREEMT KNQVSLWCLV KGFYPSDIAV  300
EWESNGQPEN NYKTTPPVLD SDGSFFLYSK LTVDKSRWQQ GNVFSCSVMH EALHNHYTQK  360
SLSLSPGK                                                           368

SEQ ID NO: 402              moltype = AA   length = 343
FEATURE                     Location/Qualifiers
REGION                      1..343
                            note = Description of Artificial Sequence: Synthetic
                             polypeptide
source                      1..343
                            mol_type = protein
                            organism = synthetic construct
SEQUENCE: 402
GRGEAETREC IYYNANWELE RTNQSGLERC EGEQDKRLHC YASWRNSSGT IELVKKGCWL   60
DDFNCYDRQE CVATEENPQV YFCCCEGNFC NERFTHLPEA GGPEVTYEPP PTAPTGGGTH  120
TCPPCPAPEL LGGPSVFLFP PKPKDTLMIS RTPEVTCVVV DVSHEDPEVK FNWYVDGVEV  180
HNAKTKPREE QYNSTYRVVS VLTVLHQDWL NGKEYKCKVS NKALPAPIEK TISKAKGQPR  240
EPQVYTLPPC REEMTKNQVS LWCLVKGFYP SDIAVEWESN GQPENNYKTT PPVLDSDGSF  300
FLYSKLTVDK SRWQQGNVFS CSVMHEALHN HYTQKSLSLS PGK                    343

SEQ ID NO: 403              moltype = AA   length = 356
FEATURE                     Location/Qualifiers
REGION                      1..356
                            note = Description of Artificial Sequence: Synthetic
                             polypeptide
source                      1..356
                            mol_type = protein
                            organism = synthetic construct
SEQUENCE: 403
MDAMKRGLCC VLLLCGAVFV SPGASGPRGV QALLCACTSC LQANYTCETD GACMVSIFNL   60
DGMEHHVRTC IPKVELVPAG KPFYCLSSED LRNTHCCYTD YCNRIDLRVP SGHLKEPEHP  120
SMWGPVETGG GTHTCPPCPA PELLGGPSVF LFPPKPKDTL MISRTPEVTC VVVDVSHEDP  180
EVKFNWYVDG VEVHNAKTKP REEQYNSTYR VVSVLTVLHQ DWLNGKEYKC KVSNKALPAP  240
IEKTISKAKG QPREPQVCTL PPSREEMTKN QVSLSCAVKG FYPSDIAVEW ESNGQPENNY  300
KTTPPVLDSD GSFFLVSKLT VDKSRWQQGN VFSCSVMHEA LHNHYTQKSL SLSPGK      356

SEQ ID NO: 404              moltype = AA   length = 332
FEATURE                     Location/Qualifiers
REGION                      1..332
                            note = Description of Artificial Sequence: Synthetic
                             polypeptide
source                      1..332
                            mol_type = protein
                            organism = synthetic construct
SEQUENCE: 404
SGPRGVQALL CACTSCLQAN YTCETDGACM VSIFNLDGME HHVRTCIPKV ELVPAGKPFY   60
CLSSEDLRNT HCCYTDYCNR IDLRVPSGHL KEPEHPSMWG PVETGGGTHT CPPCPAPELL  120
GGPSVFLFPP KPKDTLMISR TPEVTCVVVD VSHEDPEVKF NWYVDGVEVH NAKTKPREEQ  180
YNSTYRVVSV LTVLHQDWLN GKEYKCKVSN KALPAPIEKT ISKAKGQPRE PQVCTLPPSR  240
EEMTKNQVSL SCAVKGFYPS DIAVEWESNG QPENNYKTTP PVLDSDGSFF LVSKLTVDKS  300
RWQQGNVFSC SVMHEALHNH YTQKSLSLSP GK                                332

SEQ ID NO: 405              moltype = AA   length = 342
```

```
FEATURE                  Location/Qualifiers
REGION                   1..342
                         note = Description of Artificial Sequence: Synthetic
                            polypeptide
source                   1..342
                         mol_type = protein
                         organism = synthetic construct
SEQUENCE: 405
MDAMKRGLCC VLLLCGAVFV SPGAGLKCVC LLCDSSNFTC QTEGACWASV MLTNGKEQVI    60
KSCVSLPELN AQVFCHSSNN VTKTECCFTD FCNNITLHLP TASPNAPKLG PMETGGGTHT   120
CPPCPAPELL GGPSVFLFPP KPKDTLMISR TPEVTCVVVD VSHEDPEVKF NWYVDGVEVH   180
NAKTKPREEQ YNSTYRVVSV LTVLHQDWLN GKEYKCKVSN KALPAPIEKT ISKAKGQPRE   240
PQVCTLPPSR EEMTKNQVSL SCAVKGFYPS DIAVEWESNG QPENNYKTTP PVLDSDGSFF   300
LVSKLTVDKS RWQQGNVFSC SVMHEALHNH YTQKSLSLSP GK                     342

SEQ ID NO: 406           moltype = AA  length = 318
FEATURE                  Location/Qualifiers
REGION                   1..318
                         note = Description of Artificial Sequence: Synthetic
                            polypeptide
source                   1..318
                         mol_type = protein
                         organism = synthetic construct
SEQUENCE: 406
GLKCVCLLCD SSNFTCQTEG ACWASVMLTN GKEQVIKSCV SLPELNAQVF CHSSNNVTKT    60
ECCFTDFCNN ITLHLPTASP NAPKLGPMET GGGTHTCPPC PAPELLGGPS VFLFPPKPKD   120
TLMISRTPEV TCVVVDVSHE DPEVKFNWYV DGVEVHNAKT KPREEQYNST YRVVSVLTVL   180
HQDWLNGKEY KCKVSNKALP APIEKTISKA KGQPREPQVC TLPPSREEMT KNQVSLSCAV   240
KGFYPSDIAV EWESNGQPEN NYKTTPPVLD SDGSFFLVSK LTVDKSRWQQ GNVFSCSVMH   300
EALHNHYTQK SLSLSPGK                                                 318

SEQ ID NO: 407           moltype = AA  length = 382
FEATURE                  Location/Qualifiers
REGION                   1..382
                         note = Description of Artificial Sequence: Synthetic
                            polypeptide
source                   1..382
                         mol_type = protein
                         organism = synthetic construct
SEQUENCE: 407
MDAMKRGLCC VLLLCGAVFV SPGAQNLDSM LHGTGMKSDS DQKKSENGVT LAPEDTLPFL    60
KCYCSGHCPD DAINNTCITN GHCFAIIEED DQGETTLASG CMKYEGSDFQ CKDSPKAQLR   120
RTIECCRTNL CNQYLQPTLP PVVIGPFFDG SIRTGGGTHT CPPCPAPELL GGPSVFLFPP   180
KPKDTLMISR TPEVTCVVVD VSHEDPEVKF NWYVDGVEVH NAKTKPREEQ YNSTYRVVSV   240
LTVLHQDWLN GKEYKCKVSN KALPAPIEKT ISKAKGQPRE PQVCTLPPSR EEMTKNQVSL   300
SCAVKGFYPS DIAVEWESNG QPENNYKTTP PVLDSDGSFF LVSKLTVDKS RWQQGNVFSC   360
SVMHEALHNH YTQKSLSLSP GK                                            382

SEQ ID NO: 408           moltype = AA  length = 360
FEATURE                  Location/Qualifiers
REGION                   1..360
                         note = Description of Artificial Sequence: Synthetic
                            polypeptide
source                   1..360
                         mol_type = protein
                         organism = synthetic construct
SEQUENCE: 408
GAQNLDSMLH GTGMKSDSDQ KKSENGVTLA PEDTLPFLKC YCSGHCPDDA INNTCITNGH    60
CFAIIEEDDQ GETTLASGCM KYEGSDFQCK DSPKAQLRRT IECCRTNLCN QYLQPTLPPV   120
VIGPFFDGSI RTGGGTHTCP PCPAPELLGG PSVFLFPPKP KDTLMISRTP EVTCVVVDVS   180
HEDPEVKFNW YVDGVEVHNA KTKPREEQYN STYRVVSVLT VLHQDWLNGK EYKCKVSNKA   240
LPAPIEKTIS KAKGQPREPQ VCTLPPSREE MTKNQVSLSC AVKGFYPSDI AVEWESNGQP   300
ENNYKTTPPV LDSDGSFFLV SKLTVDKSRW QQGNVFSCSV MHEALHNHYT QKSLSLSPGK   360

SEQ ID NO: 409           moltype = AA  length = 369
FEATURE                  Location/Qualifiers
REGION                   1..369
                         note = Description of Artificial Sequence: Synthetic
                            polypeptide
source                   1..369
                         mol_type = protein
                         organism = synthetic construct
SEQUENCE: 409
MDAMKRGLCC VLLLCGAVFV SPGAAILGRS ETQECLFFNA NWEKDRTNQT GVEPCYGDKD    60
KRRHCFATWK NISGSIEIVK QGCWLDDINC YDRTDCVEKK DSPEVYFCCC EGNMCNEKFS   120
YFPPEMEVTQ PTSNPVTPKP PTGGGTHTCP CPAPELLGGP SVFLFPPKPK DTLMISRTPE   180
VTCVVVDVSH EDPEVKFNWY VDGVEVHNAK TKPREEQYNS TYRVVSVLTV LHQDWLNGKE   240
YKCKVSNKAL PAPIEKTISK AKGQPREPQV YTLPPCREEM TKNQVSLWCL VKGFYPSDIA   300
VEWESNGQPE NNYKTTPPVL DSDGSFFLYS KLTVDKSRWQ QGNVFSCSVM HEALHNHYTQ   360
```

KSLSLSPGK                                                                        369

SEQ ID NO: 410              moltype = AA  length = 344
FEATURE                     Location/Qualifiers
REGION                      1..344
                            note = Description of Artificial Sequence: Synthetic
                             polypeptide
source                      1..344
                            mol_type = protein
                            organism = synthetic construct
SEQUENCE: 410
ILGRSETQEC LFFNANWEKD RTNQTGVEPC YGDKDKRRHC FATWKNISGS IEIVKQGCWL  60
DDINCYDRTD CVEKKDSPEV YFCCCEGNMC NEKFSYFPEM EVTQPTSNPV TPKPPTGGGT 120
HTCPPCPAPE LLGGPSVFLF PPKPKDTLMI SRTPEVTCVV VDVSHEDPEV KFNWYVDGVE 180
VHNAKTKPRE EQYNSTYRVV SVLTVLHQDW LNGKEYKCKV SNKALPAPIE KTISKAKGQP 240
REPQVYTLPP CREEMTKNQV SLWCLVKGFY PSDIAVEWES NGQPENNYKT TPPVLDSDGS 300
FFLYSKLTVD KSRWQQGNVF SCSVMHEALH NHYTQKSLSL SPGK                 344

SEQ ID NO: 411              moltype = AA  length = 376
FEATURE                     Location/Qualifiers
REGION                      1..376
                            note = Description of Artificial Sequence: Synthetic
                             polypeptide
source                      1..376
                            mol_type = protein
                            organism = synthetic construct
SEQUENCE: 411
MDAMKRGLCC VLLLCGAVFV SPGASQNQER LCAFKDPYQQ DLGIGESRIS HENGTILCSK  60
GSTCYGLWEK SKGDINLVKQ GCWSHIGDPQ ECHYEECVVT TTPPSIQNGT YRFCCCSTDL 120
CNVNFTENFP PPDTTPLSPP HSFNRDETGG GTHTCPPCPA PELLGGPSVF LFPPKPKDTL 180
MISRTPEVTC VVVDVSHEDP EVKFNWYVDG VEVHNAKTKP REEQYNSTYR VVSVLTVLHQ 240
DWLNGKEYKC KVSNKALPAP IEKTISKAKG QPREPQVYTL PPCREEMTKN QVSLWCLVKG 300
FYPSDIAVEW ESNGQPENNY KTTPPVLDSD GSFFLYSKLT VDKSRWQQGN VFSCSVMHEA 360
LHNHYTQKSL SLSPGK                                                376

SEQ ID NO: 412              moltype = AA  length = 352
FEATURE                     Location/Qualifiers
REGION                      1..352
                            note = Description of Artificial Sequence: Synthetic
                             polypeptide
source                      1..352
                            mol_type = protein
                            organism = synthetic construct
SEQUENCE: 412
SQNQERLCAF KDPYQQDLGI GESRISHENG TILCSKGSTC YGLWEKSKGD INLVKQGCWS  60
HIGDPQECHY EECVVTTTPP SIQNGTYRFC CCSTDLCNVN FTENFPPPDT TPLSPPHSFN 120
RDETGGTHT CPPCPAPELL GGPSVFLFPP KPKDTLMISR TPEVTCVVVD VSHEDPEVKF 180
NWYVDGVEVH NAKTKPREEQ YNSTYRVVSL TVLHQDWLN GKEYKCKVSN KALPAPIEKT 240
ISKAKGQPRE PQVYTLPPCR EEMTKNQVSL WCLVKGFYPS DIAVEWESNG QPENNYKTTP 300
PVLDSDGSFF LYSKLTVDKS RWQQGNVFSC SVMHEALHNH YTQKSLSLSP GK        352

SEQ ID NO: 413              moltype = AA  length = 352
FEATURE                     Location/Qualifiers
REGION                      1..352
                            note = Description of Artificial Sequence: Synthetic
                             polypeptide
source                      1..352
                            mol_type = protein
                            organism = synthetic construct
SEQUENCE: 413
MDAMKRGLCC VLLLCGAVFV SPGADPVKPS RGPLVTCTCE SPHCKGPTCR GAWCTVVLVR  60
EEGRHPQEHR GCGNLHRELC RGRPTEFVNH YCCDSHLCNH NVSLVLEATQ PPSEQPGTDG 120
QLATGGGTHT CPPCPAPELL GGPSVFLFPP KPKDTLMISR TPEVTCVVVD VSHEDPEVKF 180
NWYVDGVEVH NAKTKPREEQ YNSTYRVVSL TVLHQDWLN GKEYKCKVSN KALPAPIEKT 240
ISKAKGQPRE PQVCTLPPSR EEMTKNQVSL SCAVKGFYPS DIAVEWESNG QPENNYKTTP 300
PVLDSDGSFF LVSKLTVDKS RWQQGNVFSC SVMHEALHNH YTQKSLSLSP GK        352

SEQ ID NO: 414              moltype = AA  length = 328
FEATURE                     Location/Qualifiers
REGION                      1..328
                            note = Description of Artificial Sequence: Synthetic
                             polypeptide
source                      1..328
                            mol_type = protein
                            organism = synthetic construct
SEQUENCE: 414
DPVKPSRGPL VTCTCESPHC KGPTCRGAWC TVVLVREEGR HPQEHRGCGN LHRELCRGRP  60
TEFVNHYCCD SHLCNHNVSL VLEATQPPSE QPGTDGQLAT GGGTHTCPPC PAPELLGGPS 120
VFLFPPKPKD TLMISRTPEV TCVVVDVSHE DPEVKFNWYV DGVEVHNAKT KPREEQYNST 180

```
YRVVSVLTVL HQDWLNGKEY KCKVSNKALP APIEKTISKA KGQPREPQVC TLPPSREEMT    240
KNQVSLSCAV KGFYPSDIAV EWESNGQPEN NYKTTPPVLD SDGSFFLVSK LTVDKSRWQQ    300
GNVFSCSVMH EALHNHYTQK SLSLSPGK                                      328

SEQ ID NO: 415          moltype = AA   length = 390
FEATURE                 Location/Qualifiers
REGION                  1..390
                        note = Description of Artificial Sequence: Synthetic
                         polypeptide
source                  1..390
                        mol_type = protein
                        organism = synthetic construct
SEQUENCE: 415
MDAMKRGLCC VLLLCGAVFV SPGATIPPHV QKSVNNDMIV TDNNGAVKFP QLCKFCDVRF     60
STCDNQKSCM SNCSITSICE KPQEVCVAVW RKNDENITLE TVCHDPKLPY HDFILEDAAS    120
PKCIMKEKKK PGETFFMCSC SSDECNDNII FSEEYNTSNP DTGGGTHTCP PCPAPELLGG    180
PSVFLFPPKP KDTLMISRTP EVTCVVVDVS HEDPEVKFNW YVDGVEVHNA KTKPREEQYN    240
STYRVVSVLT VLHQDWLNGK EYKCKVSNKA LPAPIEKTIS KAKGQPREPQ VYTLPPCREE    300
MTKNQVSLWC LVKGFYPSDI AVEWESNGQP ENNYKTTPPV LDSDGSFFLY SKLTVDKSRW    360
QQGNVFSCSV MHEALHNHYT QKSLSLSPGK                                    390

SEQ ID NO: 416          moltype = AA   length = 366
FEATURE                 Location/Qualifiers
REGION                  1..366
                        note = Description of Artificial Sequence: Synthetic
                         polypeptide
source                  1..366
                        mol_type = protein
                        organism = synthetic construct
SEQUENCE: 416
TIPPHVQKSV NNDMIVTDNN GAVKFPQLCK FCDVRFSTCD NQKSCMSNCS ITSICEKPQE     60
VCVAVWRKND ENITLETVCH DPKLPYHDFI LEDAASPKCI MKEKKKPGET FFMCSCSSDE    120
CNDNIIFSEE YNTSNPDTGG GTHTCPPCPA PELLGGPSVF LFPPKPKDTL MISRTPEVTC    180
VVVDVSHEDP EVKFNWYVDG VEVHNAKTKP REEQYNSTYR VVSVLTVLHQ DWLNGKEYKC    240
KVSNKALPAP IEKTISKAKG QPREPQVYTL PPCREEMTKN QVSLWCLVKG FYPSDIAVEW    300
ESNGQPENNY KTTPPVLDSD GSFFLYSKLT VDKSRWQQGN VFSCSVMHEA LHNHYTQKSL    360
SLSPGK                                                              366

SEQ ID NO: 417          moltype = AA   length = 415
FEATURE                 Location/Qualifiers
REGION                  1..415
                        note = Description of Artificial Sequence: Synthetic
                         polypeptide
source                  1..415
                        mol_type = protein
                        organism = synthetic construct
SEQUENCE: 417
MDAMKRGLCC VLLLCGAVFV SPGATIPPHV QKSDVEMEAQ KDEIICPSCN RTAHPLRHIN     60
NDMIVTDNNG AVKFPQLCKF CDVRFSTCDN QKSCMSNCSI TSICEKPQEV CVAVWRKNDE    120
NITLETVCHD PKLPYHDFIL EDAASPKCIM KEKKKPGETF FMCSCSSDEC NDNIIFSEEY    180
NTSNPDTGGG THTCPPCPAP ELLGGPSVFL FPPKPKDTLM ISRTPEVTCV VVDVSHEDPE    240
VKFNWYVDGV EVHNAKTKPR EEQYNSTYRV VSVLTVLHQD WLNGKEYKCK VSNKALPAPI    300
EKTISKAKGQ PREPQVYTLP PCREEMTKNQ VSLWCLVKGF YPSDIAVEWE SNGQPENNYK    360
TTPPVLDSDG SFFLYSKLTV DKSRWQQGNV FSCSVMHEAL HNHYTQKSLS LSPGK         415

SEQ ID NO: 418          moltype = AA   length = 391
FEATURE                 Location/Qualifiers
REGION                  1..391
                        note = Description of Artificial Sequence: Synthetic
                         polypeptide
source                  1..391
                        mol_type = protein
                        organism = synthetic construct
SEQUENCE: 418
TIPPHVQKSD VEMEAQKDEI ICPSCNRTAH PLRHINNDMI VTDNNGAVKF PQLCKFCDVR     60
FSTCDNQKSC MSNCSITSIC EKPQEVCVAV WRKNDENITL ETVCHDPKLP YHDFILEDAA    120
SPKCIMKEKK KPGETFFMCS CSSDECNDNI IFSEEYNTSN PDTGGGTHTC PPCPAPELLG    180
GPSVFLFPPK PKDTLMISRT PEVTCVVVDV SHEDPEVKFN WYVDGVEVHN AKTKPREEQY    240
NSTYRVVSVL TVLHQDWLNG KEYKCKVSNK ALPAPIEKTI SKAKGQPREP QVYTLPPCRE    300
EMTKNQVSLW CLVKGFYPSD IAVEWESNGQ PENNYKTTPP VLDSDGSFFL YSKLTVDKSR    360
WQQGNVFSCS VMHEALHNHY TQKSLSLSPG K                                  391

SEQ ID NO: 419          moltype =      length =
SEQUENCE: 419
000

SEQ ID NO: 420          moltype =      length =
SEQUENCE: 420
000
```

```
SEQ ID NO: 421          moltype = AA   length = 356
FEATURE                 Location/Qualifiers
REGION                  1..356
                        note = Description of Artificial Sequence: Synthetic
                         polypeptide
source                  1..356
                        mol_type = protein
                        organism = synthetic construct
SEQUENCE: 421
MDAMKRGLCC VLLLCGAVFV SPGAMEDEKP KVNPKLYMCV CEGLSCGNED HCEGQQCFSS   60
LSINDGFHVY QKGCFQVYEQ GKMTCKTPPS PGQAVECCQG DWCNRNITAQ LPTKGKSFPG  120
TQNFHLETGG GTHTCPPCPA PELLGGPSVF LFPPKPKDTL MISRTPEVTC VVVDVSHEDP  180
EVKFNWYVDG VEVHNAKTKP REEQYNSTYR VVSVLTVLHQ DWLNGKEYKC KVSNKALPAP  240
IEKTISKAKG QPREPQVCTL PPSREEMTKN QVSLSCAVKG FYPSDIAVEW ESNGQPENNY  300
KTTPPVLDSD GSFFLVSKLT VDKSRWQQGN VFSCSVMHEA LHNHYTQKSL SLSPGK      356

SEQ ID NO: 422          moltype = AA   length = 332
FEATURE                 Location/Qualifiers
REGION                  1..332
                        note = Description of Artificial Sequence: Synthetic
                         polypeptide
source                  1..332
                        mol_type = protein
                        organism = synthetic construct
SEQUENCE: 422
MEDEKPKVNP KLYMCVCEGL SCGNEDHCEG QQCFSSLSIN DGFHVYQKGC FQVYEQGKMT   60
CKTPPSPGQA VECCQGDWCN RNITAQLPTK GKSFPGTQNF HLETGGGTHT CPPCPAPELL  120
GGPSVFLFPP KPKDTLMISR TPEVTCVVVD VSHEDPEVKF NWYVDGVEVH NAKTKPREEQ  180
YNSTYRVVSV LTVLHQDWLN GKEYKCKVSN KALPAPIEKT ISKAKGQPRE PQVCTLPPSR  240
EEMTKNQVSL SCAVKGFYPS DIAVEWESNG QPENNYKTTP PVLDSDGSFF LVSKLTVDKS  300
RWQQGNVFSC SVMHEALHNH YTQKSLSLSP GK                                332

SEQ ID NO: 423          moltype = AA   length = 353
FEATURE                 Location/Qualifiers
REGION                  1..353
                        note = Description of Artificial Sequence: Synthetic
                         polypeptide
source                  1..353
                        mol_type = protein
                        organism = synthetic construct
SEQUENCE: 423
MDAMKRGLCC VLLLCGAVFV SPGAALLPGA TALQCFCHLC TKDNFTCVTD GLCFVSVTET   60
TDKVIHNSMC IAEIDLIPRD RPFVCAPSSK TGSVTTTYCC NQDHCNKIEL PTTVKSSPGL  120
GPVETGGGTH TCPPCPAPEL LGGPSVFLFP PKPKDTLMIS RTPEVTCVVV DVSHEDPEVK  180
FNWYVDGVEV HNAKTKPREE QYNSTYRVVS VLTVLHQDWL NGKEYKCKVS NKALPAPIEK  240
TISKAKGQPR EPQVCTLPPS REEMTKNQVS LSCAVKGFYP SDIAVEWESN GQPENNYKTT  300
PPVLDSDGSF FLVSKLTVDK SRWQQGNVFS CSVMHEALHN HYTQKSLSLS PGK         353

SEQ ID NO: 424          moltype = AA   length = 329
FEATURE                 Location/Qualifiers
REGION                  1..329
                        note = Description of Artificial Sequence: Synthetic
                         polypeptide
source                  1..329
                        mol_type = protein
                        organism = synthetic construct
SEQUENCE: 424
ALLPGATALQ CFCHLCTKDN FTCVTDGLCF VSVTETTDKV IHNSMCIAEI DLIPRDRPFV   60
CAPSSKTGSV TTTYCCNQDH CNKIELPTTV KSSPGLGPVE TGGGTHTCPP CPAPELLGGP  120
SVFLFPPKPK DTLMISRTPE VTCVVVDVSH EDPEVKFNWY VDGVEVHNAK TKPREEQYNS  180
TYRVVSVLTV LHQDWLNGKE YKCKVSNKAL PAPIEKTISK AKGQPREPQV CTLPPSREEM  240
TKNQVSLSCA VKGFYPSDIA VEWESNGQPE NNYKTTPPVL DSDGSFFLVS KLTVDKSRWQ  300
QGNVFSCSVM HEALHNHYTQ KSLSLSPGK                                    329

SEQ ID NO: 425          moltype = AA   length = 366
FEATURE                 Location/Qualifiers
REGION                  1..366
                        note = Description of Artificial Sequence: Synthetic
                         polypeptide
source                  1..366
                        mol_type = protein
                        organism = synthetic construct
SEQUENCE: 425
MDAMKRGLCC VLLLCGAVFV SPGAKKEDGE STAPTPRPKV LRCKCHHHCP EDSVNNICST   60
DGYCFTMIEE DDSGLPVVTS GCLGLEGSDF QCRDTPIPHQ RRSIECCTER NECNKDLHPT  120
LPPLKNRDFV DGPIHHRTGG GTHTCPPCPA PELLGGPSVF LFPPKPKDTL MISRTPEVTC  180
VVVDVSHEDP EVKFNWYVDG VEVHNAKTKP REEQYNSTYR VVSVLTVLHQ DWLNGKEYKC  240
KVSNKALPAP IEKTISKAKG QPREPQVCTL PPSREEMTKN QVSLSCAVKG FYPSDIAVEW  300
```

```
ESNGQPENNY KTTPPVLDSD GSFFLVSKLT VDKSRWQQGN VFSCSVMHEA LHNHYTQKSL    360
SLSPGK                                                                366

SEQ ID NO: 426          moltype = AA  length = 342
FEATURE                 Location/Qualifiers
REGION                  1..342
                        note = Description of Artificial Sequence: Synthetic
                         polypeptide
source                  1..342
                        mol_type = protein
                        organism = synthetic construct
SEQUENCE: 426
KKEDGESTAP TPRPKVLRCK CHHHCPEDSV NNICSTDGYC FTMIEEDDSG LPVVTSGCLG     60
LEGSDFQCRD TPIPHQRRSI ECCTERNECN KDLHPTLPPL KNRDFVDGPI HHRTGGGTHT    120
CPPCPAPELL GGPSVFLFPP KPKDTLMISR TPEVTCVVVD VSHEDPEVKF NWYVDGVEVH    180
NAKTKPREEQ YNSTYRVVSV LTVLHQDWLN GKEYKCKVSN KALPAPIEKT ISKAKGQPRE    240
PQVCTLPPSR EEMTKNQVSL SCAVKGFYPS DIAVEWESNG QPENNYKTTP PVLDSDGSFF    300
LVSKLTVDKS RWQQGNVFSC SVMHEALHNH YTQKSLSLSP GK                       342

SEQ ID NO: 427          moltype =   length =
SEQUENCE: 427
000

SEQ ID NO: 428          moltype =   length =
SEQUENCE: 428
000

SEQ ID NO: 429          moltype =   length =
SEQUENCE: 429
000

SEQ ID NO: 430          moltype =   length =
SEQUENCE: 430
000

SEQ ID NO: 431          moltype =   length =
SEQUENCE: 431
000

SEQ ID NO: 432          moltype =   length =
SEQUENCE: 432
000

SEQ ID NO: 433          moltype =   length =
SEQUENCE: 433
000

SEQ ID NO: 434          moltype =   length =
SEQUENCE: 434
000

SEQ ID NO: 435          moltype =   length =
SEQUENCE: 435
000

SEQ ID NO: 436          moltype =   length =
SEQUENCE: 436
000

SEQ ID NO: 437          moltype =   length =
SEQUENCE: 437
000

SEQ ID NO: 438          moltype =   length =
SEQUENCE: 438
000

SEQ ID NO: 439          moltype =   length =
SEQUENCE: 439
000

SEQ ID NO: 440          moltype =   length =
SEQUENCE: 440
000

SEQ ID NO: 441          moltype =   length =
SEQUENCE: 441
000
```

| | | |
|---|---|---|
| SEQ ID NO: 442<br>SEQUENCE: 442<br>000 | moltype = | length = |
| SEQ ID NO: 443<br>SEQUENCE: 443<br>000 | moltype = | length = |
| SEQ ID NO: 444<br>SEQUENCE: 444<br>000 | moltype = | length = |
| SEQ ID NO: 445<br>SEQUENCE: 445<br>000 | moltype = | length = |
| SEQ ID NO: 446<br>SEQUENCE: 446<br>000 | moltype = | length = |
| SEQ ID NO: 447<br>SEQUENCE: 447<br>000 | moltype = | length = |
| SEQ ID NO: 448<br>SEQUENCE: 448<br>000 | moltype = | length = |
| SEQ ID NO: 449<br>SEQUENCE: 449<br>000 | moltype = | length = |
| SEQ ID NO: 450<br>SEQUENCE: 450<br>000 | moltype = | length = |
| SEQ ID NO: 451<br>SEQUENCE: 451<br>000 | moltype = | length = |
| SEQ ID NO: 452<br>SEQUENCE: 452<br>000 | moltype = | length = |
| SEQ ID NO: 453<br>SEQUENCE: 453<br>000 | moltype = | length = |
| SEQ ID NO: 454<br>SEQUENCE: 454<br>000 | moltype = | length = |
| SEQ ID NO: 455<br>SEQUENCE: 455<br>000 | moltype = | length = |
| SEQ ID NO: 456<br>SEQUENCE: 456<br>000 | moltype = | length = |
| SEQ ID NO: 457<br>SEQUENCE: 457<br>000 | moltype = | length = |
| SEQ ID NO: 458<br>SEQUENCE: 458<br>000 | moltype = | length = |
| SEQ ID NO: 459<br>SEQUENCE: 459<br>000 | moltype = | length = |
| SEQ ID NO: 460<br>SEQUENCE: 460<br>000 | moltype = | length = |
| SEQ ID NO: 461<br>SEQUENCE: 461<br>000 | moltype = | length = |

| | | |
|---|---|---|
| SEQ ID NO: 462<br>SEQUENCE: 462<br>000 | moltype = | length = |
| SEQ ID NO: 463<br>SEQUENCE: 463<br>000 | moltype = | length = |
| SEQ ID NO: 464<br>SEQUENCE: 464<br>000 | moltype = | length = |
| SEQ ID NO: 465<br>SEQUENCE: 465<br>000 | moltype = | length = |
| SEQ ID NO: 466<br>SEQUENCE: 466<br>000 | moltype = | length = |
| SEQ ID NO: 467<br>SEQUENCE: 467<br>000 | moltype = | length = |
| SEQ ID NO: 468<br>SEQUENCE: 468<br>000 | moltype = | length = |
| SEQ ID NO: 469<br>SEQUENCE: 469<br>000 | moltype = | length = |
| SEQ ID NO: 470<br>SEQUENCE: 470<br>000 | moltype = | length = |
| SEQ ID NO: 471<br>SEQUENCE: 471<br>000 | moltype = | length = |
| SEQ ID NO: 472<br>SEQUENCE: 472<br>000 | moltype = | length = |
| SEQ ID NO: 473<br>SEQUENCE: 473<br>000 | moltype = | length = |
| SEQ ID NO: 474<br>SEQUENCE: 474<br>000 | moltype = | length = |
| SEQ ID NO: 475<br>SEQUENCE: 475<br>000 | moltype = | length = |
| SEQ ID NO: 476<br>SEQUENCE: 476<br>000 | moltype = | length = |
| SEQ ID NO: 477<br>SEQUENCE: 477<br>000 | moltype = | length = |
| SEQ ID NO: 478<br>SEQUENCE: 478<br>000 | moltype = | length = |
| SEQ ID NO: 479<br>SEQUENCE: 479<br>000 | moltype = | length = |
| SEQ ID NO: 480<br>SEQUENCE: 480<br>000 | moltype = | length = |
| SEQ ID NO: 481<br>SEQUENCE: 481 | moltype = | length = |

```
000

SEQ ID NO: 482           moltype =    length =
SEQUENCE: 482
000

SEQ ID NO: 483           moltype =    length =
SEQUENCE: 483
000

SEQ ID NO: 484           moltype =    length =
SEQUENCE: 484
000

SEQ ID NO: 485           moltype =    length =
SEQUENCE: 485
000

SEQ ID NO: 486           moltype =    length =
SEQUENCE: 486
000

SEQ ID NO: 487           moltype =    length =
SEQUENCE: 487
000

SEQ ID NO: 488           moltype =    length =
SEQUENCE: 488
000

SEQ ID NO: 489           moltype =    length =
SEQUENCE: 489
000

SEQ ID NO: 490           moltype =    length =
SEQUENCE: 490
000

SEQ ID NO: 491           moltype =    length =
SEQUENCE: 491
000

SEQ ID NO: 492           moltype =    length =
SEQUENCE: 492
000

SEQ ID NO: 493           moltype =    length =
SEQUENCE: 493
000

SEQ ID NO: 494           moltype =    length =
SEQUENCE: 494
000

SEQ ID NO: 495           moltype =    length =
SEQUENCE: 495
000

SEQ ID NO: 496           moltype =    length =
SEQUENCE: 496
000

SEQ ID NO: 497           moltype =    length =
SEQUENCE: 497
000

SEQ ID NO: 498           moltype =    length =
SEQUENCE: 498
000

SEQ ID NO: 499           moltype =    length =
SEQUENCE: 499
000

SEQ ID NO: 500           moltype = AA   length = 116
FEATURE                  Location/Qualifiers
source                   1..116
                         mol_type = protein
                         organism = Homo sapiens
```

```
SEQUENCE: 500
ILGRSETQEC LFFNANWEKD RTNQTGVEPC YGDKDKRRHC FATWKNISGS IEIVKQGCWL    60
DDINCYDRTD CVEKKDSPEV YFCCCEGNMC NEKFSYFPEM EVTQPTSNPV TPKPPT       116

SEQ ID NO: 501          moltype = AA  length = 150
FEATURE                 Location/Qualifiers
source                  1..150
                        mol_type = protein
                        organism = Rattus sp.
SEQUENCE: 501
MTAPWAALAL LWGSLCAGSG RGEAETRECI YYNANWELER TNQSGLERCE GEQDKRLHCY    60
ASWPNSSGTI ELVKKGCWLD DFNCYDRQEC VATEENPQVY FCCCEGNFCN ERFTHLPEPG   120
GPEVTYEPPP TAPTLLTVLA YSLLPIGGLS                                    150

SEQ ID NO: 502          moltype = AA  length = 150
FEATURE                 Location/Qualifiers
source                  1..150
                        mol_type = protein
                        organism = Sus scrofa
SEQUENCE: 502
MTAPWAALAL LWGSLCVGSG RGEAETRECI YYNANWELER TNQSGLERCE GEQDKRLHCY    60
ASWRNSSGTI ELVKKGCWLD DFNCYDRQEC VATEENPQVY FCCCEGNFCN ERFTHLPEAG   120
GPEVTYEPPP TAPTLLTVLA YSLLPIGGLS                                    150

SEQ ID NO: 503          moltype = AA  length = 150
FEATURE                 Location/Qualifiers
source                  1..150
                        mol_type = protein
                        organism = Mus musculus
SEQUENCE: 503
MTAPWAALAL LWGSLCAGSG RGEAETRECI YYNANWELER TNQSGLERCE GEQDKRLHCY    60
ASWRNSSGTI ELVKKGCWLD DFNCYDRQEC VATEENPQVY FCCCEGNFCN ERFTHLPEPG   120
GPEVTYEPPP TAPTLLTVLA YSLLPIGGLS                                    150

SEQ ID NO: 504          moltype = AA  length = 150
FEATURE                 Location/Qualifiers
source                  1..150
                        mol_type = protein
                        organism = Homo sapiens
SEQUENCE: 504
MTAPWVALAL LWGSLCAGSG RGEAETRECI YYNANWELER TNQSGLERCE GEQDKRLHCY    60
ASWRNSSGTI ELVKKGCWLD DFNCYDRQEC VATEENPQVY FCCCEGNFCN ERFTHLPEAG   120
GPEVTYEPPP TAPTLLTVLA YSLLPIGGLS                                    150

SEQ ID NO: 505          moltype = AA  length = 150
FEATURE                 Location/Qualifiers
source                  1..150
                        mol_type = protein
                        organism = Bos taurus
SEQUENCE: 505
MTAPWAALAL LWGSLCAGSG RGEAETRECI YYNANWELER TNQSGLERCE GERDKRLHCY    60
ASWRNSSGTI ELVKKGCWLD DFNCYDRQEC VATEENPQVY FCCCEGNFCN ERFTHLPEAG   120
GPEVTYEPPP TAPTLLTVLA YSLLPVGGLS                                    150

SEQ ID NO: 506          moltype = AA  length = 150
FEATURE                 Location/Qualifiers
source                  1..150
                        mol_type = protein
                        organism = Xenopus sp.
SEQUENCE: 506
MGASVALTFL LLLATFRAGS GHDEVETREC IYYNANWELE KTNQSGVERL VEGKKDKRLH    60
CYASWRNNSG FIELVKKGCW LDDFNCYDRQ ECIAKEENPQ VFFCCCEGNY CNKKFTHLPE   120
VETFDPKPQP SASVLNILIY SLLPIVGLSM                                    150

SEQ ID NO: 507          moltype = AA  length = 150
FEATURE                 Location/Qualifiers
source                  1..150
                        mol_type = protein
                        organism = Homo sapiens
SEQUENCE: 507
MGAAAKLAFA VFLISCSSGA ILGRSETQEC LFFNANWEKD RTNQTGVEPC YGDKDKRRHC    60
FATWKNISGS IEIVKQGCWL DDINCYDRTD CVEKKDSPEV YFCCCEGNMC NEKFSYFPEM   120
EVTQPTSNPV TPKPPYYNIL LYSLVPLMLI                                    150

SEQ ID NO: 508          moltype = AA  length = 154
FEATURE                 Location/Qualifiers
REGION                  1..154
                        note = Description of Artificial Sequence: Synthetic
                        polypeptide
```

```
MOD_RES              8
                     note = Thr, Ala or not present
MOD_RES              121
                     note = Pro, Ala, Val or Met
source               1..154
                     mol_type = protein
                     organism = synthetic construct
SEQUENCE: 508
MTAPWAAXLA LLWGSLCAGS GRGEAETREC IYYNANWELE RTNQSGLERL CEGEQDKRLH  60
CYASWRNSSG TIELVKKGCW LDDFNCYDRQ ECVATEENPQ VYFCCCEGNF CNERFTHLPE 120
XGGPEVTYEP KPPTAPTLLT VLAYSLLPIG GLSM                             154

SEQ ID NO: 509           moltype =    length =
SEQUENCE: 509
000

SEQ ID NO: 510           moltype =    length =
SEQUENCE: 510
000

SEQ ID NO: 511           moltype =    length =
SEQUENCE: 511
000

SEQ ID NO: 512           moltype =    length =
SEQUENCE: 512
000

SEQ ID NO: 513           moltype =    length =
SEQUENCE: 513
000

SEQ ID NO: 514           moltype =    length =
SEQUENCE: 514
000

SEQ ID NO: 515           moltype =    length =
SEQUENCE: 515
000

SEQ ID NO: 516           moltype =    length =
SEQUENCE: 516
000

SEQ ID NO: 517           moltype =    length =
SEQUENCE: 517
000

SEQ ID NO: 518           moltype =    length =
SEQUENCE: 518
000

SEQ ID NO: 519           moltype =    length =
SEQUENCE: 519
000

SEQ ID NO: 520           moltype =    length =
SEQUENCE: 520
000

SEQ ID NO: 521           moltype =    length =
SEQUENCE: 521
000

SEQ ID NO: 522           moltype =    length =
SEQUENCE: 522
000

SEQ ID NO: 523           moltype =    length =
SEQUENCE: 523
000

SEQ ID NO: 524           moltype =    length =
SEQUENCE: 524
000

SEQ ID NO: 525           moltype =    length =
SEQUENCE: 525
000
```

| | | |
|---|---|---|
| SEQ ID NO: 526<br>SEQUENCE: 526<br>000 | moltype = | length = |
| SEQ ID NO: 527<br>SEQUENCE: 527<br>000 | moltype = | length = |
| SEQ ID NO: 528<br>SEQUENCE: 528<br>000 | moltype = | length = |
| SEQ ID NO: 529<br>SEQUENCE: 529<br>000 | moltype = | length = |
| SEQ ID NO: 530<br>SEQUENCE: 530<br>000 | moltype = | length = |
| SEQ ID NO: 531<br>SEQUENCE: 531<br>000 | moltype = | length = |
| SEQ ID NO: 532<br>SEQUENCE: 532<br>000 | moltype = | length = |
| SEQ ID NO: 533<br>SEQUENCE: 533<br>000 | moltype = | length = |
| SEQ ID NO: 534<br>SEQUENCE: 534<br>000 | moltype = | length = |
| SEQ ID NO: 535<br>SEQUENCE: 535<br>000 | moltype = | length = |
| SEQ ID NO: 536<br>SEQUENCE: 536<br>000 | moltype = | length = |
| SEQ ID NO: 537<br>SEQUENCE: 537<br>000 | moltype = | length = |
| SEQ ID NO: 538<br>SEQUENCE: 538<br>000 | moltype = | length = |
| SEQ ID NO: 539<br>SEQUENCE: 539<br>000 | moltype = | length = |
| SEQ ID NO: 540<br>SEQUENCE: 540<br>000 | moltype = | length = |
| SEQ ID NO: 541<br>SEQUENCE: 541<br>000 | moltype = | length = |
| SEQ ID NO: 542<br>SEQUENCE: 542<br>000 | moltype = | length = |
| SEQ ID NO: 543<br>SEQUENCE: 543<br>000 | moltype = | length = |
| SEQ ID NO: 544<br>SEQUENCE: 544<br>000 | moltype = | length = |
| SEQ ID NO: 545<br>SEQUENCE: 545 | moltype = | length = |

000

SEQ ID NO: 546        moltype =    length =
SEQUENCE: 546
000

SEQ ID NO: 547        moltype =    length =
SEQUENCE: 547
000

SEQ ID NO: 548        moltype =    length =
SEQUENCE: 548
000

SEQ ID NO: 549        moltype =    length =
SEQUENCE: 549
000

SEQ ID NO: 550        moltype =    length =
SEQUENCE: 550
000

SEQ ID NO: 551        moltype =    length =
SEQUENCE: 551
000

SEQ ID NO: 552        moltype =    length =
SEQUENCE: 552
000

SEQ ID NO: 553        moltype =    length =
SEQUENCE: 553
000

SEQ ID NO: 554        moltype =    length =
SEQUENCE: 554
000

SEQ ID NO: 555        moltype =    length =
SEQUENCE: 555
000

SEQ ID NO: 556        moltype =    length =
SEQUENCE: 556
000

SEQ ID NO: 557        moltype =    length =
SEQUENCE: 557
000

SEQ ID NO: 558        moltype =    length =
SEQUENCE: 558
000

SEQ ID NO: 559        moltype =    length =
SEQUENCE: 559
000

SEQ ID NO: 560        moltype =    length =
SEQUENCE: 560
000

SEQ ID NO: 561        moltype =    length =
SEQUENCE: 561
000

SEQ ID NO: 562        moltype =    length =
SEQUENCE: 562
000

SEQ ID NO: 563        moltype =    length =
SEQUENCE: 563
000

SEQ ID NO: 564        moltype =    length =
SEQUENCE: 564
000

SEQ ID NO: 565        moltype =    length =

| | | |
|---|---|---|
| SEQUENCE: 565 000 | | |
| SEQ ID NO: 566 SEQUENCE: 566 000 | moltype = | length = |
| SEQ ID NO: 567 SEQUENCE: 567 000 | moltype = | length = |
| SEQ ID NO: 568 SEQUENCE: 568 000 | moltype = | length = |
| SEQ ID NO: 569 SEQUENCE: 569 000 | moltype = | length = |
| SEQ ID NO: 570 SEQUENCE: 570 000 | moltype = | length = |
| SEQ ID NO: 571 SEQUENCE: 571 000 | moltype = | length = |
| SEQ ID NO: 572 SEQUENCE: 572 000 | moltype = | length = |
| SEQ ID NO: 573 SEQUENCE: 573 000 | moltype = | length = |
| SEQ ID NO: 574 SEQUENCE: 574 000 | moltype = | length = |
| SEQ ID NO: 575 SEQUENCE: 575 000 | moltype = | length = |
| SEQ ID NO: 576 SEQUENCE: 576 000 | moltype = | length = |
| SEQ ID NO: 577 SEQUENCE: 577 000 | moltype = | length = |
| SEQ ID NO: 578 SEQUENCE: 578 000 | moltype = | length = |
| SEQ ID NO: 579 SEQUENCE: 579 000 | moltype = | length = |
| SEQ ID NO: 580 SEQUENCE: 580 000 | moltype = | length = |
| SEQ ID NO: 581 SEQUENCE: 581 000 | moltype = | length = |
| SEQ ID NO: 582 SEQUENCE: 582 000 | moltype = | length = |
| SEQ ID NO: 583 SEQUENCE: 583 000 | moltype = | length = |
| SEQ ID NO: 584 SEQUENCE: 584 000 | moltype = | length = |

SEQ ID NO: 585	moltype =	length =
SEQUENCE: 585
000

SEQ ID NO: 586	moltype =	length =
SEQUENCE: 586
000

SEQ ID NO: 587	moltype =	length =
SEQUENCE: 587
000

SEQ ID NO: 588	moltype =	length =
SEQUENCE: 588
000

SEQ ID NO: 589	moltype =	length =
SEQUENCE: 589
000

SEQ ID NO: 590	moltype =	length =
SEQUENCE: 590
000

SEQ ID NO: 591	moltype =	length =
SEQUENCE: 591
000

SEQ ID NO: 592	moltype =	length =
SEQUENCE: 592
000

SEQ ID NO: 593	moltype =	length =
SEQUENCE: 593
000

SEQ ID NO: 594	moltype =	length =
SEQUENCE: 594
000

SEQ ID NO: 595	moltype =	length =
SEQUENCE: 595
000

SEQ ID NO: 596	moltype =	length =
SEQUENCE: 596
000

SEQ ID NO: 597	moltype =	length =
SEQUENCE: 597
000

SEQ ID NO: 598	moltype =	length =
SEQUENCE: 598
000

SEQ ID NO: 599	moltype =	length =
SEQUENCE: 599
000

SEQ ID NO: 600	moltype =	length =
SEQUENCE: 600
000

SEQ ID NO: 601	moltype =	length =
SEQUENCE: 601
000

SEQ ID NO: 602	moltype =	length =
SEQUENCE: 602
000

SEQ ID NO: 603	moltype =	length =
SEQUENCE: 603
000

SEQ ID NO: 604	moltype =	length =
SEQUENCE: 604
000

| | | |
|---|---|---|
| SEQ ID NO: 605<br>SEQUENCE: 605<br>000 | moltype = | length = |
| SEQ ID NO: 606<br>SEQUENCE: 606<br>000 | moltype = | length = |
| SEQ ID NO: 607<br>SEQUENCE: 607<br>000 | moltype = | length = |
| SEQ ID NO: 608<br>SEQUENCE: 608<br>000 | moltype = | length = |
| SEQ ID NO: 609<br>SEQUENCE: 609<br>000 | moltype = | length = |
| SEQ ID NO: 610<br>SEQUENCE: 610<br>000 | moltype = | length = |
| SEQ ID NO: 611<br>SEQUENCE: 611<br>000 | moltype = | length = |
| SEQ ID NO: 612<br>SEQUENCE: 612<br>000 | moltype = | length = |
| SEQ ID NO: 613<br>SEQUENCE: 613<br>000 | moltype = | length = |
| SEQ ID NO: 614<br>SEQUENCE: 614<br>000 | moltype = | length = |
| SEQ ID NO: 615<br>SEQUENCE: 615<br>000 | moltype = | length = |
| SEQ ID NO: 616<br>SEQUENCE: 616<br>000 | moltype = | length = |
| SEQ ID NO: 617<br>SEQUENCE: 617<br>000 | moltype = | length = |
| SEQ ID NO: 618<br>SEQUENCE: 618<br>000 | moltype = | length = |
| SEQ ID NO: 619<br>SEQUENCE: 619<br>000 | moltype = | length = |
| SEQ ID NO: 620<br>SEQUENCE: 620<br>000 | moltype = | length = |
| SEQ ID NO: 621<br>SEQUENCE: 621<br>000 | moltype = | length = |
| SEQ ID NO: 622<br>SEQUENCE: 622<br>000 | moltype = | length = |
| SEQ ID NO: 623<br>SEQUENCE: 623<br>000 | moltype = | length = |
| SEQ ID NO: 624<br>SEQUENCE: 624 | moltype = | length = |

```
000

SEQ ID NO: 625           moltype =      length =
SEQUENCE: 625
000

SEQ ID NO: 626           moltype =      length =
SEQUENCE: 626
000

SEQ ID NO: 627           moltype =      length =
SEQUENCE: 627
000

SEQ ID NO: 628           moltype =      length =
SEQUENCE: 628
000

SEQ ID NO: 629           moltype =      length =
SEQUENCE: 629
000

SEQ ID NO: 630           moltype =      length =
SEQUENCE: 630
000

SEQ ID NO: 631           moltype =      length =
SEQUENCE: 631
000

SEQ ID NO: 632           moltype =      length =
SEQUENCE: 632
000

SEQ ID NO: 633           moltype =      length =
SEQUENCE: 633
000

SEQ ID NO: 634           moltype =      length =
SEQUENCE: 634
000

SEQ ID NO: 635           moltype =      length =
SEQUENCE: 635
000

SEQ ID NO: 636           moltype =      length =
SEQUENCE: 636
000

SEQ ID NO: 637           moltype =      length =
SEQUENCE: 637
000

SEQ ID NO: 638           moltype =      length =
SEQUENCE: 638
000

SEQ ID NO: 639           moltype =      length =
SEQUENCE: 639
000

SEQ ID NO: 640           moltype =      length =
SEQUENCE: 640
000

SEQ ID NO: 641           moltype =      length =
SEQUENCE: 641
000

SEQ ID NO: 642           moltype =      length =
SEQUENCE: 642
000

SEQ ID NO: 643           moltype =      length =
SEQUENCE: 643
000

SEQ ID NO: 644           moltype =      length =
```

```
SEQUENCE: 644
000

SEQ ID NO: 645            moltype =     length =
SEQUENCE: 645
000

SEQ ID NO: 646            moltype =     length =
SEQUENCE: 646
000

SEQ ID NO: 647            moltype =     length =
SEQUENCE: 647
000

SEQ ID NO: 648            moltype =     length =
SEQUENCE: 648
000

SEQ ID NO: 649            moltype =     length =
SEQUENCE: 649
000

SEQ ID NO: 650            moltype =     length =
SEQUENCE: 650
000

SEQ ID NO: 651            moltype =     length =
SEQUENCE: 651
000

SEQ ID NO: 652            moltype =     length =
SEQUENCE: 652
000

SEQ ID NO: 653            moltype =     length =
SEQUENCE: 653
000

SEQ ID NO: 654            moltype =     length =
SEQUENCE: 654
000

SEQ ID NO: 655            moltype =     length =
SEQUENCE: 655
000

SEQ ID NO: 656            moltype =     length =
SEQUENCE: 656
000

SEQ ID NO: 657            moltype =     length =
SEQUENCE: 657
000

SEQ ID NO: 658            moltype =     length =
SEQUENCE: 658
000

SEQ ID NO: 659            moltype =     length =
SEQUENCE: 659
000

SEQ ID NO: 660            moltype = AA   length = 225
FEATURE                   Location/Qualifiers
REGION                    1..225
                          note = Description of Artificial Sequence: Synthetic
                           polypeptide
source                    1..225
                          mol_type = protein
                          organism = synthetic construct
SEQUENCE: 660
THTCPPCPAP ELLGGPSVFL FPPKPKDTLM ISRTPEVTCV VVDVSHEDPE VKFNWYVDGV    60
EVHNAKTKPR EEQYNSTYRV VSVLTVLHQD WLNGKEYKCK VSNKALPAPI EKTISKAKGQ   120
PREPQVYTLP PCREEMTENQ VSLWCLVKGF YPSDIAVEWE SNGQPENNYK TTPPVLDSDG   180
SFFLYSKLTV DKSRWQQGNV FSCSVMHEAL HNHYTQDSLS LSPGK                  225

SEQ ID NO: 661            moltype =     length =
SEQUENCE: 661
```

```
SEQ ID NO: 662          moltype =    length =
SEQUENCE: 662
000

SEQ ID NO: 663          moltype =    length =
SEQUENCE: 663
000

SEQ ID NO: 664          moltype =    length =
SEQUENCE: 664
000

SEQ ID NO: 665          moltype =    length =
SEQUENCE: 665
000

SEQ ID NO: 666          moltype =    length =
SEQUENCE: 666
000

SEQ ID NO: 667          moltype =    length =
SEQUENCE: 667
000

SEQ ID NO: 668          moltype =    length =
SEQUENCE: 668
000

SEQ ID NO: 669          moltype =    length =
SEQUENCE: 669
000

SEQ ID NO: 670          moltype = AA  length = 225
FEATURE                 Location/Qualifiers
REGION                  1..225
                        note = Description of Artificial Sequence: Synthetic
                         polypeptide
source                  1..225
                        mol_type = protein
                        organism = synthetic construct
SEQUENCE: 670
THTCPPCPAP ELLGGPSVFL FPPKPKDTLM ISRTPEVTCV VVDVSHEDPE VKFNWYVDGV   60
EVHNAKTKPR EEQYNSTYRV VSVLTVLHQD WLNGKEYKCK VSNKALPAPI EKTISKAKGQ  120
PREPQVCTLP PSREEMTKNQ VSLSCAVKGF YPSDIAVEWE SRGQPENNYK TTPPVLDSRG  180
SFFLVSKLTV DKSRWQQGNV FSCSVMHEAL HNHYTQKSLS LSPGK                 225

SEQ ID NO: 671          moltype =    length =
SEQUENCE: 671
000

SEQ ID NO: 672          moltype =    length =
SEQUENCE: 672
000

SEQ ID NO: 673          moltype =    length =
SEQUENCE: 673
000

SEQ ID NO: 674          moltype =    length =
SEQUENCE: 674
000

SEQ ID NO: 675          moltype =    length =
SEQUENCE: 675
000

SEQ ID NO: 676          moltype =    length =
SEQUENCE: 676
000

SEQ ID NO: 677          moltype =    length =
SEQUENCE: 677
000

SEQ ID NO: 678          moltype =    length =
SEQUENCE: 678
000
```

```
SEQ ID NO: 679          moltype =   length =
SEQUENCE: 679
000

SEQ ID NO: 680          moltype = AA  length = 225
FEATURE                 Location/Qualifiers
REGION                  1..225
                        note = Description of Artificial Sequence: Synthetic
                         polypeptide
source                  1..225
                        mol_type = protein
                        organism = synthetic construct
SEQUENCE: 680
THTCPPCPAP ELLGGPSVFL FPPKPKDTLM ISRTPEVTCV VVDVSHEDPE VKFNWYVDGV    60
EVHNAKTKPR EEQYNSTYRV VSVLTVLHQD WLNGKEYKCK VSNKALPAPI EKTISKAKGQ   120
PREPQVYTLP PCREEMTKNQ VSLWCLVKGF YPSDIAVEWE SNGQPENNYK TTPPVLDSDG   180
SFFLYSKLTV DKSRWQQGNV FSCSVMHEAL HNRYTQKSLS LSPGK                  225

SEQ ID NO: 681          moltype =   length =
SEQUENCE: 681
000

SEQ ID NO: 682          moltype =   length =
SEQUENCE: 682
000

SEQ ID NO: 683          moltype =   length =
SEQUENCE: 683
000

SEQ ID NO: 684          moltype =   length =
SEQUENCE: 684
000

SEQ ID NO: 685          moltype =   length =
SEQUENCE: 685
000

SEQ ID NO: 686          moltype =   length =
SEQUENCE: 686
000

SEQ ID NO: 687          moltype =   length =
SEQUENCE: 687
000

SEQ ID NO: 688          moltype =   length =
SEQUENCE: 688
000

SEQ ID NO: 689          moltype =   length =
SEQUENCE: 689
000

SEQ ID NO: 690          moltype =   length =
SEQUENCE: 690
000

SEQ ID NO: 691          moltype =   length =
SEQUENCE: 691
000

SEQ ID NO: 692          moltype =   length =
SEQUENCE: 692
000

SEQ ID NO: 693          moltype =   length =
SEQUENCE: 693
000

SEQ ID NO: 694          moltype =   length =
SEQUENCE: 694
000

SEQ ID NO: 695          moltype =   length =
SEQUENCE: 695
000
```

| SEQ ID NO: 696 | moltype = length = |
|---|---|
| SEQUENCE: 696 | |
| 000 | |

| SEQ ID NO: 697 | moltype = length = |
|---|---|
| SEQUENCE: 697 | |
| 000 | |

| SEQ ID NO: 698 | moltype = length = |
|---|---|
| SEQUENCE: 698 | |
| 000 | |

| SEQ ID NO: 699 | moltype = length = |
|---|---|
| SEQUENCE: 699 | |
| 000 | |

| SEQ ID NO: 700 | moltype = AA   length = 367 |
|---|---|
| FEATURE | Location/Qualifiers |
| REGION | 1..367 |
| | note = Description of Artificial Sequence: Synthetic polypeptide |
| source | 1..367 |
| | mol_type = protein |
| | organism = synthetic construct |

SEQUENCE: 700
```
MDAMKRGLCC VLLLCGAVFV SPGASGRGEA ETRECIYYNA NWELERTNQS GLERCEGEQD   60
KRLHCYASWR NSSGTIELVK KGCWLDDFNC YDRQECVATE ENPQVYFCCC EGNFCNERFT  120
HLPEAGGPEV TYEPPPTAPT GGGTHTCPPC PAPELLGGPS VFLFPPKPKD TLMISRTPEV  180
TCVVVDVSHE DPEVKFNWYV DGVEVHNAKT KPREEQYNST YRVVSVLTVL HQDWLNGKEY  240
KCKVSNKALP APIEKTISKA KGQPREPQVY TLPPCREEMT ENQVSLWCLV KGFYPSDIAV  300
EWESNGQPEN NYKTTPPVLD SDGSFFLYSK LTVDKSRWQQ GNVFSCSVMH EALHNHYTQD  360
SLSLSPG                                                           367
```

| SEQ ID NO: 701 | moltype = length = |
|---|---|
| SEQUENCE: 701 | |
| 000 | |

| SEQ ID NO: 702 | moltype = length = |
|---|---|
| SEQUENCE: 702 | |
| 000 | |

| SEQ ID NO: 703 | moltype = length = |
|---|---|
| SEQUENCE: 703 | |
| 000 | |

| SEQ ID NO: 704 | moltype = length = |
|---|---|
| SEQUENCE: 704 | |
| 000 | |

| SEQ ID NO: 705 | moltype = length = |
|---|---|
| SEQUENCE: 705 | |
| 000 | |

| SEQ ID NO: 706 | moltype = length = |
|---|---|
| SEQUENCE: 706 | |
| 000 | |

| SEQ ID NO: 707 | moltype = length = |
|---|---|
| SEQUENCE: 707 | |
| 000 | |

| SEQ ID NO: 708 | moltype = length = |
|---|---|
| SEQUENCE: 708 | |
| 000 | |

| SEQ ID NO: 709 | moltype = length = |
|---|---|
| SEQUENCE: 709 | |
| 000 | |

| SEQ ID NO: 710 | moltype = DNA   length = 1101 |
|---|---|
| FEATURE | Location/Qualifiers |
| misc_feature | 1..1101 |
| | note = Description of Artificial Sequence: Synthetic polynucleotide |
| source | 1..1101 |
| | mol_type = other DNA |
| | organism = synthetic construct |

SEQUENCE: 710
```
atggatgcaa tgaagagagg gctctgctgt gtgctgctgc tgtgtggagc agtcttcgtt   60
```

```
tcgcccggcg cctctgggcg tggggaggct gagacacggg agtgcatcta ctacaacgcc    120
aactgggagc tggagcgcac caaccagagc ggcctggagc gctgcgaagg cgagcaggac    180
aagcggctgc actgctacgc ctcctggcgc aacagctctg gcaccatcga gctcgtgaag    240
aagggctgct ggctagatga cttcaactgc tacgataggc aggagtgtgt ggccactgag    300
gagaacccca aggtgtactt ctgctgctgt gaaggcaact tctgcaacga gcgcttcact    360
catttgccag aggctggggg cccggaagtc acgtacgacg caccccccgac agcccccacc    420
ggtggtggaa ctcacacatg cccaccgtgc ccagcacctg aactcctggg gggaccgtca    480
gtcttcctct tccccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gcccccatcg agaaaaccat ctccaaagcc    780
aaagggcagc cccgagaacc acaggtgtac accctgcccc catgccggga ggagatgacc    840
aagaaccagg tcagcctgtg tgtcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcaggac   1080
agcctctccc tgtctccggg t                                             1101

SEQ ID NO: 711          moltype =      length =
SEQUENCE: 711
000

SEQ ID NO: 712          moltype =      length =
SEQUENCE: 712
000

SEQ ID NO: 713          moltype =      length =
SEQUENCE: 713
000

SEQ ID NO: 714          moltype =      length =
SEQUENCE: 714
000

SEQ ID NO: 715          moltype =      length =
SEQUENCE: 715
000

SEQ ID NO: 716          moltype =      length =
SEQUENCE: 716
000

SEQ ID NO: 717          moltype =      length =
SEQUENCE: 717
000

SEQ ID NO: 718          moltype =      length =
SEQUENCE: 718
000

SEQ ID NO: 719          moltype =      length =
SEQUENCE: 719
000

SEQ ID NO: 720          moltype = AA   length = 342
FEATURE                 Location/Qualifiers
REGION                  1..342
                        note = Description of Artificial Sequence: Synthetic
                         polypeptide
source                  1..342
                        mol_type = protein
                        organism = synthetic construct
SEQUENCE: 720
GRGEAETREC IYYNANWELE RTNQSGLERC EGEQDKRLHC YASWRNSSGT IELVKKGCWL     60
DDFNCYDRQE CVATEENPQV YFCCCEGNFC NERFTHLPEA GGPEVTYEPP PTAPTGGGTH    120
TCPPCPAPEL LGGPSVFLFP PKPKDTLMIS RTPEVTCVVV DVSHEDPEVK FNWYVDGVEV    180
HNAKTKPREE QYNSTYRVVS VLTVLHQDWL NGKEYKCKVS NKALPAPIEK TISKAKGQPR    240
EPQVYTLPPC REEMTENQVS LWCLVKGFYP SDIAVEWESN GQPENNYKTT PPVLDSDGSF    300
FLYSKLTVDK SRWQQGNVFS CSVMHEALHN HYTQDSLSLS PG                       342

SEQ ID NO: 721          moltype =      length =
SEQUENCE: 721
000

SEQ ID NO: 722          moltype =      length =
SEQUENCE: 722
000
```

| | | |
|---|---|---|
| SEQ ID NO: 723 | moltype = | length = |
| SEQUENCE: 723 000 | | |
| SEQ ID NO: 724 | moltype = | length = |
| SEQUENCE: 724 000 | | |
| SEQ ID NO: 725 | moltype = | length = |
| SEQUENCE: 725 000 | | |
| SEQ ID NO: 726 | moltype = | length = |
| SEQUENCE: 726 000 | | |
| SEQ ID NO: 727 | moltype = | length = |
| SEQUENCE: 727 000 | | |
| SEQ ID NO: 728 | moltype = | length = |
| SEQUENCE: 728 000 | | |
| SEQ ID NO: 729 | moltype = | length = |
| SEQUENCE: 729 000 | | |

```
SEQ ID NO: 730          moltype = DNA   length = 1026
FEATURE                 Location/Qualifiers
misc_feature            1..1026
                        note = Description of Artificial Sequence: Synthetic
                        polynucleotide
source                  1..1026
                        mol_type = other DNA
                        organism = synthetic construct
SEQUENCE: 730
gggcgtgggg aggctgagac acgggagtgc atctactaca acgccaactg ggagctggag   60
cgcaccaacc agagcggcct ggagcgctgc gaaggcgagc aggacaagcg gctgcactgc  120
tacgcctcct ggcgcaacag ctctggcacc atcgagctcg tgaagaaggg ctgctggcta  180
gatgacttca actgctacga taggcaggag tgtgtggcca ctgaggagaa cccccaggtg  240
tacttctgct gctgtgaagg caacttctgc aacgagcgct tcactcattt gccagaggct  300
gggggcccgg aagtcacgta cgagccaccc ccgacagccc ccaccggtgg tggaactcac  360
acatgcccac cgtgcccagc acctgaactc ctggggggac cgtcagtctt cctcttcccc  420
ccaaaaccca aggacaccct catgatctcc cggaccctg aggtcacatg cgtggtggtg  480
gacgtgagcc acgaagaccc tgaggtcaag ttcaactggt acgtgacgg cgtggaggtg  540
cataatgcca agacaaagcc gcgggaggag cagtacaaca gcacgtaccg tgtggtcagc  600
gtcctcaccg tcctgcacca ggactggctg aatggcaagg agtacaagtg caaggtctcc  660
aacaaagccc tcccagcccc catcgagaaa accatctcca aagccaaagg gcagccccga  720
gaaccacagg tgtacaccct gcccccatgc cgggaggaga tgaccgagaa ccaggtcagc  780
ctgtgtgcc tggtcaaagg cttctatccc agcgacatcg ccgtggagtg ggagagcaat  840
gggcagccgg agaacaacta caagaccacg cctcccgtgc tggactccga cggctccttc  900
ttcctctata gcaagctcac cgtggacaag agcaggtggc agcaggggaa cgtcttctca  960
tgctccgtga tgcatgaggc tctgcacaac cactacacgc aggacagcct ctccctgtct 1020
ccgggt                                                           1026
```

| | | |
|---|---|---|
| SEQ ID NO: 731 | moltype = | length = |
| SEQUENCE: 731 000 | | |
| SEQ ID NO: 732 | moltype = | length = |
| SEQUENCE: 732 000 | | |
| SEQ ID NO: 733 | moltype = | length = |
| SEQUENCE: 733 000 | | |
| SEQ ID NO: 734 | moltype = | length = |
| SEQUENCE: 734 000 | | |
| SEQ ID NO: 735 | moltype = | length = |
| SEQUENCE: 735 000 | | |
| SEQ ID NO: 736 | moltype = | length = |
| SEQUENCE: 736 000 | | |

SEQ ID NO: 737          moltype =    length =
SEQUENCE: 737
000

SEQ ID NO: 738          moltype =    length =
SEQUENCE: 738
000

SEQ ID NO: 739          moltype =    length =
SEQUENCE: 739
000

SEQ ID NO: 740          moltype = AA   length = 356
FEATURE                 Location/Qualifiers
REGION                  1..356
                        note = Description of Artificial Sequence: Synthetic
                         polypeptide
source                  1..356
                        mol_type = protein
                        organism = synthetic construct
SEQUENCE: 740
MDAMKRGLCC VLLLCGAVFV SPGASGPRGV QALLCACTSC LQANYTCETD GACMVSIFNL    60
DGMEHHVRTC IPKVELVPAG KPFYCLSSED LRNTHCCYTD YCNRIDLRVP SGHLKEPEHP   120
SMWGPVETGG GTHTCPPCPA PELLGGPSVF LFPPKPKDTL MISRTPEVTC VVVDVSHEDP   180
EVKFNWYVDG VEVHNAKTKP REEQYNSTYR VVSVLTVLHQ DWLNGKEYKC KVSNKALPAP   240
IEKTISKAKG QPREPQVCTL PPSREEMTKN QVSLSCAVKG FYPSDIAVEW ESRGQPENNY   300
KTTPPVLDSR GSFFLVSKLT VDKSRWQQGN VFSCSVMHEA LHNHYTQKSL SLSPGK       356

SEQ ID NO: 741          moltype =    length =
SEQUENCE: 741
000

SEQ ID NO: 742          moltype =    length =
SEQUENCE: 742
000

SEQ ID NO: 743          moltype =    length =
SEQUENCE: 743
000

SEQ ID NO: 744          moltype =    length =
SEQUENCE: 744
000

SEQ ID NO: 745          moltype =    length =
SEQUENCE: 745
000

SEQ ID NO: 746          moltype =    length =
SEQUENCE: 746
000

SEQ ID NO: 747          moltype =    length =
SEQUENCE: 747
000

SEQ ID NO: 748          moltype =    length =
SEQUENCE: 748
000

SEQ ID NO: 749          moltype =    length =
SEQUENCE: 749
000

SEQ ID NO: 750          moltype = DNA   length = 1068
FEATURE                 Location/Qualifiers
misc_feature            1..1068
                        note = Description of Artificial Sequence: Synthetic
                         polynucleotide
source                  1..1068
                        mol_type = other DNA
                        organism = synthetic construct
SEQUENCE: 750
atggatgcaa tgaagagagg gctctgctgt gtgctgctgc tgtgtggagc agtcttcgtt    60
tcgcccggcg cctccgggcc ccggggggtc caggctctgc tgtgtgcgtg caccagctgc   120
ctccaggcca actacacgtg tgagacagat ggggcctgca tggttccat tttcaatctg   180
gatgggatgg agcaccatgt gcgcacctgc atccccaaag tggagctggt ccctgccggg   240
aagcccttct actgcctgag ctcggaggac ctgcgcaaca cccactgctg ctacactgac   300

```
tactgcaaca ggatcgactt gagggtgccc agtggtcacc tcaaggagcc tgagcacccg    360
tccatgtggg gccggtggga gaccggtggt ggaactcaca catgcccacc gtgcccagca    420
cctgaactcc tggggggacc gtcagtcttc ctcttccccc caaaacccaa ggacaccctc    480
atgatctccc ggacccctga ggtcacatgc gtggtggtgg acgtgagcca cgaagaccct    540
gaggtcaagt tcaactggta cgtggacggc gtggaggtgc ataatgccaa gacaaagccg    600
cgggaggagc agtacaacag cacgtaccgt gtggtcagcg tcctcaccgt cctgcaccag    660
gactggctga atggcaagga gtacaagtgc aaggtctcca acaaagccct cccagccccc    720
atcgagaaaa ccatctccaa agccaaaggg cagccccgag aaccacaggt gtgcaccctg    780
cccccatccc gggaggagat gaccaagaac caggtcagcc tgtcctgcgc cgtcaaaggc    840
ttctatccca gcgacatcgc cgtggagtgg gagagcaggc ggcagccgga gaacaactac    900
aagaccacgc ctcccgtgct ggactccgac ggctccttct tcctcgtgag caagctcacc    960
gtggacaaga gcaggtggca gcaggggaac gtcttctcat gctccgtgat gcatgaggct   1020
ctgcacaacc actacacgca gaagagcctc tccctgtctc cgggtaaa              1068
```

| SEQ ID NO: 751 | moltype = | length = |
|---|---|---|
| SEQUENCE: 751 | | |
| 000 | | |

| SEQ ID NO: 752 | moltype = | length = |
|---|---|---|
| SEQUENCE: 752 | | |
| 000 | | |

| SEQ ID NO: 753 | moltype = | length = |
|---|---|---|
| SEQUENCE: 753 | | |
| 000 | | |

| SEQ ID NO: 754 | moltype = | length = |
|---|---|---|
| SEQUENCE: 754 | | |
| 000 | | |

| SEQ ID NO: 755 | moltype = | length = |
|---|---|---|
| SEQUENCE: 755 | | |
| 000 | | |

| SEQ ID NO: 756 | moltype = | length = |
|---|---|---|
| SEQUENCE: 756 | | |
| 000 | | |

| SEQ ID NO: 757 | moltype = | length = |
|---|---|---|
| SEQUENCE: 757 | | |
| 000 | | |

| SEQ ID NO: 758 | moltype = | length = |
|---|---|---|
| SEQUENCE: 758 | | |
| 000 | | |

| SEQ ID NO: 759 | moltype = | length = |
|---|---|---|
| SEQUENCE: 759 | | |
| 000 | | |

| SEQ ID NO: 760 | moltype = AA | length = 332 |
|---|---|---|
| FEATURE | Location/Qualifiers | |
| REGION | 1..332 | |
| | note = Description of Artificial Sequence: Synthetic polypeptide | |
| source | 1..332 | |
| | mol_type = protein | |
| | organism = synthetic construct | |

```
SEQUENCE: 760
SGPRGVQALL CACTSCLQAN YTCETDGACM VSIFNLDGME HHVRTCIPKV ELVPAGKPFY     60
CLSSEDLRNT HCCYTDYCNR IDLRVPSGHL KEPEHPSMWG PVETGGGTHT CPPCPAPELL    120
GGPSVFLFPP KPKDTLMISR TPEVTCVVVD VSHEDPEVKF NWYVDGVEVH NAKTKPREEQ    180
YNSTYRVVSV LTVLHQDWLN GKEYKCKVSN KALPAPIEKT ISKAKGQPRE PQVCTLPPSR    240
EEMTKNQVSL SCAVKGFYPS DIAVEWESRG QPENNYKTTP PVLDSRGSFF LVSKLTVDKS    300
RWQQGNVFSC SVMHEALHNH YTQKSLSLSP GK                                  332
```

| SEQ ID NO: 761 | moltype = | length = |
|---|---|---|
| SEQUENCE: 761 | | |
| 000 | | |

| SEQ ID NO: 762 | moltype = | length = |
|---|---|---|
| SEQUENCE: 762 | | |
| 000 | | |

| SEQ ID NO: 763 | moltype = | length = |
|---|---|---|
| SEQUENCE: 763 | | |
| 000 | | |

| SEQ ID NO: 764 | moltype = | length = |

```
SEQUENCE: 764
000

SEQ ID NO: 765          moltype =    length =
SEQUENCE: 765
000

SEQ ID NO: 766          moltype =    length =
SEQUENCE: 766
000

SEQ ID NO: 767          moltype =    length =
SEQUENCE: 767
000

SEQ ID NO: 768          moltype =    length =
SEQUENCE: 768
000

SEQ ID NO: 769          moltype =    length =
SEQUENCE: 769
000

SEQ ID NO: 770          moltype = DNA   length = 996
FEATURE                 Location/Qualifiers
misc_feature            1..996
                        note = Description of Artificial Sequence: Synthetic
                         polynucleotide
source                  1..996
                        mol_type = other DNA
                        organism = synthetic construct
SEQUENCE: 770
tccgggcccc ggggggtcca ggctctgctg tgtgcgtgca ccagctgcct ccaggccaac    60
tacacgtgtg agacagatgg ggcctgcatg gtttccattt tcaatctgga tgggatggag   120
caccatgtgc gcacctgcat ccccaaagtg gagctggtcc ctgccgggaa gcccttctac   180
tgcctgagct cggaggacct cgcaacaccc cactgctgct acactgacta ctgcaacagg   240
atcgacttga gggtgcccag tggtcacctc aaggagcctg agcacccgtc catgtggggc   300
ccggtggaga ccggtggtgg aactcacaca tgcccaccgt gcccagcacc tgaactcctg   360
gggggaccgt cagtcttcct cttccccca aaacccaagg acacccctca tgatctcccgg   420
acccctgagg tcacatgcgt ggtggtggac gtgagccacg aagaccctga ggtcaagttc   480
aactggtacg tggacggcgt ggaggtgcat aatgccaaga caaagccgcg ggaggagcag   540
tacaacagca cgtaccgtgt ggtcagcgtc ctcaccgtcc tgcaccagga ctggctgaat   600
ggcaaggagt acaagtgcaa ggtctccaac aaagccctcc cagccccat cgagaaaacc    660
atctccaaag ccaaagggca gccccgagaa ccacaggtgt gcaccctgcc cccatcccgg   720
gaggagatga ccaagaacca ggtcagcctg tcctgcgccg tcaaaggctt ctatcccagc   780
gacatcgccg tggagtggga gagccgcggg cagccggaga caactacaa gaccacgcct    840
cccgtgctgg actcccgcgg ctccttcttc ctctgtgagca agctcaccgt ggacaagagc   900
aggtggcagc aggggaacgt cttctcatgc tccgtgatgc atgaggctct gcacaaccac   960
tacacgcaga agagcctctc cctgtctccg ggtaaa                              996

SEQ ID NO: 771          moltype =    length =
SEQUENCE: 771
000

SEQ ID NO: 772          moltype =    length =
SEQUENCE: 772
000

SEQ ID NO: 773          moltype =    length =
SEQUENCE: 773
000

SEQ ID NO: 774          moltype =    length =
SEQUENCE: 774
000

SEQ ID NO: 775          moltype =    length =
SEQUENCE: 775
000

SEQ ID NO: 776          moltype =    length =
SEQUENCE: 776
000

SEQ ID NO: 777          moltype =    length =
SEQUENCE: 777
000

SEQ ID NO: 778          moltype =    length =
```

```
SEQUENCE: 778
000

SEQ ID NO: 779          moltype =    length =
SEQUENCE: 779
000

SEQ ID NO: 780          moltype = AA   length = 368
FEATURE                 Location/Qualifiers
REGION                  1..368
                        note = Description of Artificial Sequence: Synthetic
                         polypeptide
source                  1..368
                        mol_type = protein
                        organism = synthetic construct
SEQUENCE: 780
MDAMKRGLCC VLLLCGAVFV SPGASGRGEA ETRECIYYNA NWELERTNQS GLERCEGEQD   60
KRLHCYASWR NSSGTIELVK KGCWLDDFNC YDRQECVATE ENPQVYFCCC EGNFCNERFT  120
HLPEAGGPEV TYEPPPTAPT GGGTHTCPPC PAPELLGGPS VFLFPPKPKD TLMISRTPEV  180
TCVVVDVSHE DPEVKFNWYV DGVEVHNAKT KPREEQYNST YRVVSVLTVL HQDWLNGKEY  240
KCKVSNKALP APIEKTISKA KGQPREPQVY TLPPCREEMT KNQVSLWCLV KGFYPSDIAV  300
EWESNGQPEN NYKTTPPVLD SDGSFFLYSK LTVDKSRWQQ GNVFSCSVMH EALHNRYTQK  360
SLSLSPGK                                                          368

SEQ ID NO: 781          moltype =    length =
SEQUENCE: 781
000

SEQ ID NO: 782          moltype =    length =
SEQUENCE: 782
000

SEQ ID NO: 783          moltype =    length =
SEQUENCE: 783
000

SEQ ID NO: 784          moltype =    length =
SEQUENCE: 784
000

SEQ ID NO: 785          moltype =    length =
SEQUENCE: 785
000

SEQ ID NO: 786          moltype =    length =
SEQUENCE: 786
000

SEQ ID NO: 787          moltype =    length =
SEQUENCE: 787
000

SEQ ID NO: 788          moltype =    length =
SEQUENCE: 788
000

SEQ ID NO: 789          moltype =    length =
SEQUENCE: 789
000

SEQ ID NO: 790          moltype = DNA  length = 1104
FEATURE                 Location/Qualifiers
misc_feature            1..1104
                        note = Description of Artificial Sequence: Synthetic
                         polynucleotide
source                  1..1104
                        mol_type = other DNA
                        organism = synthetic construct
SEQUENCE: 790
atggatgcaa tgaagagagg gctctgctgt gtgctgctgc tgtgtggagc agtcttcgtt   60
tcgcccggcg cctctgggcg tggggaggct gagacgggg agtgcatcta ctacaacgcc  120
aactgggagc tggagcgcac caaccagagc ggcctggagc gctgcgaagg cgagcaggac  180
aagcggctgc actgctacgc ctcctggcgc aacagctctg gcaccatcga gctcgtgaag  240
aagggctgct ggctagatga cttcaactgc tacgataggc aggagtgtgt ggccactgag  300
gagaaccccc aggtgtactt ctgctgtgt gaaggcaact tctgcaacga gcgcttcact  360
catttgccag aggctggggg cccggaagtc acgtacgagc caccccccac agcccccacc  420
ggtggtggaa ctcacacatg cccaccgtgc ccagcacctg aactcctggg gggaccgtca  480
gtcttcctct tccccccaaa acccaaggac accctcatga tctcccggac ccctgaggtc  540
acatgcgtgg tggtggacgt gagccacgaa gaccctgagg tcaagttcaa ctggtacgtg  600
```

```
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gcccccatcg agaaaaccat ctccaaagcc    780
aaagggcagc cccgagaacc acaggtgtac accctgcccc catgccggga ggagatgacc    840
aagaaccagg tcagcctgtg tgtgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccgcta cacgcagaag   1080
agcctctccc tgtctccggg taaa                                          1104
```

| | | |
|---|---|---|
| SEQ ID NO: 791<br>SEQUENCE: 791<br>000 | moltype = | length = |
| SEQ ID NO: 792<br>SEQUENCE: 792<br>000 | moltype = | length = |
| SEQ ID NO: 793<br>SEQUENCE: 793<br>000 | moltype = | length = |
| SEQ ID NO: 794<br>SEQUENCE: 794<br>000 | moltype = | length = |
| SEQ ID NO: 795<br>SEQUENCE: 795<br>000 | moltype = | length = |
| SEQ ID NO: 796<br>SEQUENCE: 796<br>000 | moltype = | length = |
| SEQ ID NO: 797<br>SEQUENCE: 797<br>000 | moltype = | length = |
| SEQ ID NO: 798<br>SEQUENCE: 798<br>000 | moltype = | length = |
| SEQ ID NO: 799<br>SEQUENCE: 799<br>000 | moltype = | length = |

```
SEQ ID NO: 800            moltype = AA   length = 343
FEATURE                   Location/Qualifiers
REGION                    1..343
                          note = Description of Artificial Sequence: Synthetic
                           polypeptide
source                    1..343
                          mol_type = protein
                          organism = synthetic construct
SEQUENCE: 800
GRGEAETREC IYYNANWELE RTNQSGLERC EGEQDKRLHC YASWRNSSGT IELVKKGCWL     60
DDFNCYDRQE CVATEENPQV YFCCCEGNFC NERFTHLPEA GGPEVTYEPP PTAPTGGGTH    120
TCPPCPAPEL LGGPSVFLFP PKPKDTLMIS RTPEVTCVVV DVSHEDPEVK FNWYVDGVEV    180
HNAKTKPREE QYNSTYRVVS VLTVLHQDWL NGKEYKCKVS NKALPAPIEK TISKAKGQPR    240
EPQVYTLPPC REEMTKNQVS LWCLVKGFYP SDIAVEWESN GQPENNYKTT PPVLDSDGSF    300
FLYSKLTVDK SRWQQGNVFS CSVMHEALHN RYTQKSLSLS PGK                      343
```

| | | |
|---|---|---|
| SEQ ID NO: 801<br>SEQUENCE: 801<br>000 | moltype = | length = |
| SEQ ID NO: 802<br>SEQUENCE: 802<br>000 | moltype = | length = |
| SEQ ID NO: 803<br>SEQUENCE: 803<br>000 | moltype = | length = |
| SEQ ID NO: 804<br>SEQUENCE: 804<br>000 | moltype = | length = |
| SEQ ID NO: 805 | moltype = | length = |

```
SEQUENCE: 805
000

SEQ ID NO: 806          moltype =    length =
SEQUENCE: 806
000

SEQ ID NO: 807          moltype =    length =
SEQUENCE: 807
000

SEQ ID NO: 808          moltype =    length =
SEQUENCE: 808
000

SEQ ID NO: 809          moltype =    length =
SEQUENCE: 809
000

SEQ ID NO: 810          moltype = DNA   length = 1029
FEATURE                 Location/Qualifiers
misc_feature            1..1029
                        note = Description of Artificial Sequence: Synthetic
                         polynucleotide
source                  1..1029
                        mol_type = other DNA
                        organism = synthetic construct
SEQUENCE: 810
gggcgtgggg aggctgagac acgggagtgc atctactaca acgccaactg ggagctggag    60
cgcaccaacc agagcggcct ggagcgctgc gaaggcgagc aggacaagcg gctgcactgc   120
tacgcctcct ggcgcaacag ctctggcacc atcgagctcg tgaagaaggg ctgctggcta   180
gatgacttca actgctacga taggcaggag tgtgtggcca ctgaggagaa cccccaggtg   240
tacttctgct gctgtgaagg caacttctgc aacgagcgct tcactcattt gccagaggct   300
gggggccccg aagtcacgta cgagccaccc cgacagccc ccaccggtgg tggaactcac   360
acatgcccac cgtgcccagc acctgaactc ctgggggac cgtcagtctt cctcttcccc   420
ccaaaaccca aggacaccct catgatctcc cggacccctg aggtcacatg cgtggtggtg   480
gacgtgagcc acgaagaccc tgaggtcaag ttcaactggt acgtggacgg cgtggaggtg   540
cataatgcca agacaaagcc gcgggaggag cagtacaaca gcacgtaccg tgtggtcagc   600
gtcctcaccg tcctgcacca ggactggctg aatggcaagg agtacaagtg caaggtctcc   660
aacaaagccc tcccagcccc catcgagaaa accatctcca aagccaaagg gcagccccga   720
gaaccacagg tgtacaccct gcccccatgc cgggaggaga tgaccaagaa ccaggtcagc   780
ctgtggtgcc tggtcaaagg cttctatccc agcgacatcg ccgtggagtg ggagagcaat   840
gggcagccgg agaacaacta caagaccacg cctcccgtgc tggactccga cggctccttc   900
ttcctctata gcaagctcac cgtggacaag agcaggtggc agcagggaa cgtcttctca   960
tgctccgtga tgcatgaggc tctgcacaac cgctacacgc agaagagcct ctccctgtct  1020
ccgggtaaa                                                          1029

SEQ ID NO: 811          moltype =    length =
SEQUENCE: 811
000

SEQ ID NO: 812          moltype =    length =
SEQUENCE: 812
000

SEQ ID NO: 813          moltype =    length =
SEQUENCE: 813
000

SEQ ID NO: 814          moltype =    length =
SEQUENCE: 814
000

SEQ ID NO: 815          moltype =    length =
SEQUENCE: 815
000

SEQ ID NO: 816          moltype =    length =
SEQUENCE: 816
000

SEQ ID NO: 817          moltype =    length =
SEQUENCE: 817
000

SEQ ID NO: 818          moltype =    length =
SEQUENCE: 818
000
```

| SEQ ID NO: 819 | moltype = length = |
| --- | --- |
| SEQUENCE: 819 | |
| 000 | |

SEQ ID NO: 820   moltype = DNA   length = 1068
FEATURE          Location/Qualifiers
misc_feature     1..1068
                 note = Description of Artificial Sequence: Synthetic
                 polynucleotide
source           1..1068
                 mol_type = other DNA
                 organism = synthetic construct
SEQUENCE: 820
```
atggatgcaa tgaagagagg gctctgctgt gtgctgctgc tgtgtggagc agtcttcgtt   60
tcgcccggcg cctccgggcc ccggggggtc caggctctgc tgtgtgcgtg caccagctgc  120
ctccaggcca actacacgtg tgagacagat ggggcctgca tggtttccat tttcaatctg  180
gatgggatgg agcaccatgt gcgcacctgc atccccaaag tggagctggt ccctgccggg  240
aagcccttct actgcctgag ctcggaggac ctgcgcaaca cccactgctg ctacactgac  300
tactgcaaca ggatcgactt gagggtgccc agtggtcacc tcaaggagcc tgagcacccg  360
tccatgtggg gccggtggga gaccggtggt ggaactcaca catgcccacc gtgcccagca  420
cctgaactcc tggggggacc gtcagtcttc ctcttcccc caaaacccaa ggacaccctc  480
atgatctccc ggacccctga ggtcacatgc gtggtggtgg acgtgagcca cgaagaccct  540
gaggtcaagt tcaactggta cgtggacggc gtggaggtgc ataatgccaa gacaaagccg  600
cgggaggagc agtacaacag cacgtaccgt gtggtcagcg tcctcaccgt cctgcaccag  660
gactggctga atggcaagga gtacaagtgc aaggtctcca acaaagccct cccagccccc  720
atcgagaaaa ccatctccaa agccaaaggg cagccccgag aaccacaggt gtgcacctg  780
cccccatccc gggaggagat gaccaagaac caggtcagcc tgtcctgcgc cgtcaaaggc  840
ttctatccca gcgacatcgc cgtggagtgg gagagcaatg ggcagccgga gaacaactac  900
aagaccacgc ctcccgtgct ggactccgac ggctccttct tcctcgtgag caagctcacc  960
gtggacaaga gcaggtggca gcaggggaac gtcttctcat gctccgtgat gcatgaggct 1020
ctgcacaacc actacacgca gaagagcctc tccctgtctc cgggtaaa             1068
```

| SEQ ID NO: 821 | moltype = length = |
| --- | --- |
| SEQUENCE: 821 | |
| 000 | |

| SEQ ID NO: 822 | moltype = length = |
| --- | --- |
| SEQUENCE: 822 | |
| 000 | |

| SEQ ID NO: 823 | moltype = length = |
| --- | --- |
| SEQUENCE: 823 | |
| 000 | |

| SEQ ID NO: 824 | moltype = length = |
| --- | --- |
| SEQUENCE: 824 | |
| 000 | |

| SEQ ID NO: 825 | moltype = length = |
| --- | --- |
| SEQUENCE: 825 | |
| 000 | |

| SEQ ID NO: 826 | moltype = length = |
| --- | --- |
| SEQUENCE: 826 | |
| 000 | |

| SEQ ID NO: 827 | moltype = length = |
| --- | --- |
| SEQUENCE: 827 | |
| 000 | |

| SEQ ID NO: 828 | moltype = length = |
| --- | --- |
| SEQUENCE: 828 | |
| 000 | |

| SEQ ID NO: 829 | moltype = length = |
| --- | --- |
| SEQUENCE: 829 | |
| 000 | |

SEQ ID NO: 830   moltype = DNA   length = 996
FEATURE          Location/Qualifiers
misc_feature     1..996
                 note = Description of Artificial Sequence: Synthetic
                 polynucleotide
source           1..996
                 mol_type = other DNA
                 organism = synthetic construct
SEQUENCE: 830
```
tccgggcccc gggggtcca ggctctgctg tgtgcgtgca ccagctgcct ccaggccaac   60
tacacgtgtg agacagatgg ggcctgcatg gtttccattt tcaatctgga tgggatggag  120
```

```
caccatgtgc gcacctgcat ccccaaagtg gagctggtcc ctgccgggaa gcccttctac    180
tgcctgagct cggaggacct gcgcaacacc cactgctgct acactgacta ctgcaacagg    240
atcgacttga gggtgcccag tggtcacctc aaggagcctg agcacccgtc catgtggggc    300
ccggtggaga ccgtggtgg aactcacaca tgcccaccgt gcccagcacc tgaactcctg     360
ggggaccgt cagtcttcct cttcccccca aaacccaagg acaccctcat gatctcccgg     420
acccctgagg tcacatgcgt ggtggtggac gtgagccacg aagaccctga ggtcaagttc    480
aactggtacg tggacggcgt ggaggtgcat aatgccaaga caaagccgcg ggaggagcag    540
tacaacagca cgtaccgtgt ggtcagcgtc ctcaccgtcc tgcaccagga ctggctgaat    600
ggcaaggagt acaagtgcaa ggtctccaac aaagccctcc cagcccccat cgagaaaacc    660
atctccaaag ccaaagggca gccccgagaa ccacaggtgt gcaccctgcc cccatcccgg    720
gaggagatga ccaagaacca ggtcagcctg tcctgcgccg tcaaaggctt ctatcccagc    780
gacatcgccg tggagtggga gagcaatggg cagccggaga caactacaa gaccacgcct    840
cccgtgctgg actccgacgg ctccttcttc ctcgtgagca agctcaccgt ggacaagagc    900
aggtggcagc aggggaacgt cttctcatgc tccgtgatgc atgaggctct gcacaaccac    960
tacacgcaga agagcctctc cctgtctccg ggtaaa                              996

SEQ ID NO: 831           moltype =    length =
SEQUENCE: 831
000

SEQ ID NO: 832           moltype =    length =
SEQUENCE: 832
000

SEQ ID NO: 833           moltype =    length =
SEQUENCE: 833
000

SEQ ID NO: 834           moltype =    length =
SEQUENCE: 834
000

SEQ ID NO: 835           moltype =    length =
SEQUENCE: 835
000

SEQ ID NO: 836           moltype =    length =
SEQUENCE: 836
000

SEQ ID NO: 837           moltype =    length =
SEQUENCE: 837
000

SEQ ID NO: 838           moltype =    length =
SEQUENCE: 838
000

SEQ ID NO: 839           moltype =    length =
SEQUENCE: 839
000

SEQ ID NO: 840           moltype =    length =
SEQUENCE: 840
000

SEQ ID NO: 841           moltype =    length =
SEQUENCE: 841
000

SEQ ID NO: 842           moltype =    length =
SEQUENCE: 842
000

SEQ ID NO: 843           moltype =    length =
SEQUENCE: 843
000

SEQ ID NO: 844           moltype =    length =
SEQUENCE: 844
000

SEQ ID NO: 845           moltype =    length =
SEQUENCE: 845
000

SEQ ID NO: 846           moltype =    length =
SEQUENCE: 846
000
```

SEQ ID NO: 847    moltype =    length =
SEQUENCE: 847
000

SEQ ID NO: 848    moltype =    length =
SEQUENCE: 848
000

SEQ ID NO: 849    moltype =    length =
SEQUENCE: 849
000

SEQ ID NO: 850    moltype =    length =
SEQUENCE: 850
000

SEQ ID NO: 851    moltype =    length =
SEQUENCE: 851
000

SEQ ID NO: 852    moltype =    length =
SEQUENCE: 852
000

SEQ ID NO: 853    moltype =    length =
SEQUENCE: 853
000

SEQ ID NO: 854    moltype =    length =
SEQUENCE: 854
000

SEQ ID NO: 855    moltype =    length =
SEQUENCE: 855
000

SEQ ID NO: 856    moltype =    length =
SEQUENCE: 856
000

SEQ ID NO: 857    moltype =    length =
SEQUENCE: 857
000

SEQ ID NO: 858    moltype =    length =
SEQUENCE: 858
000

SEQ ID NO: 859    moltype =    length =
SEQUENCE: 859
000

SEQ ID NO: 860    moltype =    length =
SEQUENCE: 860
000

SEQ ID NO: 861    moltype =    length =
SEQUENCE: 861
000

SEQ ID NO: 862    moltype =    length =
SEQUENCE: 862
000

SEQ ID NO: 863    moltype =    length =
SEQUENCE: 863
000

SEQ ID NO: 864    moltype =    length =
SEQUENCE: 864
000

SEQ ID NO: 865    moltype =    length =
SEQUENCE: 865
000

SEQ ID NO: 866    moltype =    length =
SEQUENCE: 866

000

SEQ ID NO: 867           moltype =     length =
SEQUENCE: 867
000

SEQ ID NO: 868           moltype =     length =
SEQUENCE: 868
000

SEQ ID NO: 869           moltype =     length =
SEQUENCE: 869
000

SEQ ID NO: 870           moltype =     length =
SEQUENCE: 870
000

SEQ ID NO: 871           moltype =     length =
SEQUENCE: 871
000

SEQ ID NO: 872           moltype =     length =
SEQUENCE: 872
000

SEQ ID NO: 873           moltype =     length =
SEQUENCE: 873
000

SEQ ID NO: 874           moltype =     length =
SEQUENCE: 874
000

SEQ ID NO: 875           moltype =     length =
SEQUENCE: 875
000

SEQ ID NO: 876           moltype =     length =
SEQUENCE: 876
000

SEQ ID NO: 877           moltype =     length =
SEQUENCE: 877
000

SEQ ID NO: 878           moltype =     length =
SEQUENCE: 878
000

SEQ ID NO: 879           moltype =     length =
SEQUENCE: 879
000

SEQ ID NO: 880           moltype =     length =
SEQUENCE: 880
000

SEQ ID NO: 881           moltype =     length =
SEQUENCE: 881
000

SEQ ID NO: 882           moltype =     length =
SEQUENCE: 882
000

SEQ ID NO: 883           moltype =     length =
SEQUENCE: 883
000

SEQ ID NO: 884           moltype =     length =
SEQUENCE: 884
000

SEQ ID NO: 885           moltype =     length =
SEQUENCE: 885
000

SEQ ID NO: 886           moltype =     length =

| | | |
|---|---|---|
| SEQUENCE: 886 000 | | |
| SEQ ID NO: 887 SEQUENCE: 887 000 | moltype = | length = |
| SEQ ID NO: 888 SEQUENCE: 888 000 | moltype = | length = |
| SEQ ID NO: 889 SEQUENCE: 889 000 | moltype = | length = |
| SEQ ID NO: 890 SEQUENCE: 890 000 | moltype = | length = |
| SEQ ID NO: 891 SEQUENCE: 891 000 | moltype = | length = |
| SEQ ID NO: 892 SEQUENCE: 892 000 | moltype = | length = |
| SEQ ID NO: 893 SEQUENCE: 893 000 | moltype = | length = |
| SEQ ID NO: 894 SEQUENCE: 894 000 | moltype = | length = |
| SEQ ID NO: 895 SEQUENCE: 895 000 | moltype = | length = |
| SEQ ID NO: 896 SEQUENCE: 896 000 | moltype = | length = |
| SEQ ID NO: 897 SEQUENCE: 897 000 | moltype = | length = |
| SEQ ID NO: 898 SEQUENCE: 898 000 | moltype = | length = |
| SEQ ID NO: 899 SEQUENCE: 899 000 | moltype = | length = |
| SEQ ID NO: 900 SEQUENCE: 900 000 | moltype = | length = |
| SEQ ID NO: 901 SEQUENCE: 901 000 | moltype = | length = |
| SEQ ID NO: 902 SEQUENCE: 902 000 | moltype = | length = |
| SEQ ID NO: 903 SEQUENCE: 903 000 | moltype = | length = |
| SEQ ID NO: 904 SEQUENCE: 904 000 | moltype = | length = |
| SEQ ID NO: 905 SEQUENCE: 905 000 | moltype = | length = |

| | | |
|---|---|---|
| SEQ ID NO: 906 SEQUENCE: 906 | moltype = | length = 000 |
| SEQ ID NO: 907 SEQUENCE: 907 | moltype = | length = 000 |
| SEQ ID NO: 908 SEQUENCE: 908 | moltype = | length = 000 |
| SEQ ID NO: 909 SEQUENCE: 909 | moltype = | length = 000 |
| SEQ ID NO: 910 SEQUENCE: 910 | moltype = | length = 000 |
| SEQ ID NO: 911 SEQUENCE: 911 | moltype = | length = 000 |
| SEQ ID NO: 912 SEQUENCE: 912 | moltype = | length = 000 |
| SEQ ID NO: 913 SEQUENCE: 913 | moltype = | length = 000 |
| SEQ ID NO: 914 SEQUENCE: 914 | moltype = | length = 000 |
| SEQ ID NO: 915 SEQUENCE: 915 | moltype = | length = 000 |
| SEQ ID NO: 916 SEQUENCE: 916 | moltype = | length = 000 |
| SEQ ID NO: 917 SEQUENCE: 917 | moltype = | length = 000 |
| SEQ ID NO: 918 SEQUENCE: 918 | moltype = | length = 000 |
| SEQ ID NO: 919 SEQUENCE: 919 | moltype = | length = 000 |
| SEQ ID NO: 920 SEQUENCE: 920 | moltype = | length = 000 |
| SEQ ID NO: 921 SEQUENCE: 921 | moltype = | length = 000 |
| SEQ ID NO: 922 SEQUENCE: 922 | moltype = | length = 000 |
| SEQ ID NO: 923 SEQUENCE: 923 | moltype = | length = 000 |
| SEQ ID NO: 924 SEQUENCE: 924 | moltype = | length = 000 |
| SEQ ID NO: 925 SEQUENCE: 925 | moltype = | length = 000 |

| | | |
|---|---|---|
| SEQ ID NO: 926<br>SEQUENCE: 926<br>000 | moltype = | length = |
| SEQ ID NO: 927<br>SEQUENCE: 927<br>000 | moltype = | length = |
| SEQ ID NO: 928<br>SEQUENCE: 928<br>000 | moltype = | length = |
| SEQ ID NO: 929<br>SEQUENCE: 929<br>000 | moltype = | length = |
| SEQ ID NO: 930<br>SEQUENCE: 930<br>000 | moltype = | length = |
| SEQ ID NO: 931<br>SEQUENCE: 931<br>000 | moltype = | length = |
| SEQ ID NO: 932<br>SEQUENCE: 932<br>000 | moltype = | length = |
| SEQ ID NO: 933<br>SEQUENCE: 933<br>000 | moltype = | length = |
| SEQ ID NO: 934<br>SEQUENCE: 934<br>000 | moltype = | length = |
| SEQ ID NO: 935<br>SEQUENCE: 935<br>000 | moltype = | length = |
| SEQ ID NO: 936<br>SEQUENCE: 936<br>000 | moltype = | length = |
| SEQ ID NO: 937<br>SEQUENCE: 937<br>000 | moltype = | length = |
| SEQ ID NO: 938<br>SEQUENCE: 938<br>000 | moltype = | length = |
| SEQ ID NO: 939<br>SEQUENCE: 939<br>000 | moltype = | length = |
| SEQ ID NO: 940<br>SEQUENCE: 940<br>000 | moltype = | length = |
| SEQ ID NO: 941<br>SEQUENCE: 941<br>000 | moltype = | length = |
| SEQ ID NO: 942<br>SEQUENCE: 942<br>000 | moltype = | length = |
| SEQ ID NO: 943<br>SEQUENCE: 943<br>000 | moltype = | length = |
| SEQ ID NO: 944<br>SEQUENCE: 944<br>000 | moltype = | length = |
| SEQ ID NO: 945<br>SEQUENCE: 945 | moltype = | length = |

000

SEQ ID NO: 946          moltype =    length =
SEQUENCE: 946
000

SEQ ID NO: 947          moltype =    length =
SEQUENCE: 947
000

SEQ ID NO: 948          moltype =    length =
SEQUENCE: 948
000

SEQ ID NO: 949          moltype =    length =
SEQUENCE: 949
000

SEQ ID NO: 950          moltype =    length =
SEQUENCE: 950
000

SEQ ID NO: 951          moltype =    length =
SEQUENCE: 951
000

SEQ ID NO: 952          moltype =    length =
SEQUENCE: 952
000

SEQ ID NO: 953          moltype =    length =
SEQUENCE: 953
000

SEQ ID NO: 954          moltype =    length =
SEQUENCE: 954
000

SEQ ID NO: 955          moltype =    length =
SEQUENCE: 955
000

SEQ ID NO: 956          moltype =    length =
SEQUENCE: 956
000

SEQ ID NO: 957          moltype =    length =
SEQUENCE: 957
000

SEQ ID NO: 958          moltype =    length =
SEQUENCE: 958
000

SEQ ID NO: 959          moltype =    length =
SEQUENCE: 959
000

SEQ ID NO: 960          moltype =    length =
SEQUENCE: 960
000

SEQ ID NO: 961          moltype =    length =
SEQUENCE: 961
000

SEQ ID NO: 962          moltype =    length =
SEQUENCE: 962
000

SEQ ID NO: 963          moltype =    length =
SEQUENCE: 963
000

SEQ ID NO: 964          moltype =    length =
SEQUENCE: 964
000

SEQ ID NO: 965          moltype =    length =

| | | |
|---|---|---|
| SEQUENCE: 965 000 | | |
| SEQ ID NO: 966 SEQUENCE: 966 000 | moltype = | length = |
| SEQ ID NO: 967 SEQUENCE: 967 000 | moltype = | length = |
| SEQ ID NO: 968 SEQUENCE: 968 000 | moltype = | length = |
| SEQ ID NO: 969 SEQUENCE: 969 000 | moltype = | length = |
| SEQ ID NO: 970 SEQUENCE: 970 000 | moltype = | length = |
| SEQ ID NO: 971 SEQUENCE: 971 000 | moltype = | length = |
| SEQ ID NO: 972 SEQUENCE: 972 000 | moltype = | length = |
| SEQ ID NO: 973 SEQUENCE: 973 000 | moltype = | length = |
| SEQ ID NO: 974 SEQUENCE: 974 000 | moltype = | length = |
| SEQ ID NO: 975 SEQUENCE: 975 000 | moltype = | length = |
| SEQ ID NO: 976 SEQUENCE: 976 000 | moltype = | length = |
| SEQ ID NO: 977 SEQUENCE: 977 000 | moltype = | length = |
| SEQ ID NO: 978 SEQUENCE: 978 000 | moltype = | length = |
| SEQ ID NO: 979 SEQUENCE: 979 000 | moltype = | length = |
| SEQ ID NO: 980 SEQUENCE: 980 000 | moltype = | length = |
| SEQ ID NO: 981 SEQUENCE: 981 000 | moltype = | length = |
| SEQ ID NO: 982 SEQUENCE: 982 000 | moltype = | length = |
| SEQ ID NO: 983 SEQUENCE: 983 000 | moltype = | length = |
| SEQ ID NO: 984 SEQUENCE: 984 000 | moltype = | length = |

| | | |
|---|---|---|
| SEQ ID NO: 985<br>SEQUENCE: 985<br>000 | moltype = | length = |
| SEQ ID NO: 986<br>SEQUENCE: 986<br>000 | moltype = | length = |
| SEQ ID NO: 987<br>SEQUENCE: 987<br>000 | moltype = | length = |
| SEQ ID NO: 988<br>SEQUENCE: 988<br>000 | moltype = | length = |
| SEQ ID NO: 989<br>SEQUENCE: 989<br>000 | moltype = | length = |
| SEQ ID NO: 990<br>SEQUENCE: 990<br>000 | moltype = | length = |
| SEQ ID NO: 991<br>SEQUENCE: 991<br>000 | moltype = | length = |
| SEQ ID NO: 992<br>SEQUENCE: 992<br>000 | moltype = | length = |
| SEQ ID NO: 993<br>SEQUENCE: 993<br>000 | moltype = | length = |
| SEQ ID NO: 994<br>SEQUENCE: 994<br>000 | moltype = | length = |
| SEQ ID NO: 995<br>SEQUENCE: 995<br>000 | moltype = | length = |
| SEQ ID NO: 996<br>SEQUENCE: 996<br>000 | moltype = | length = |
| SEQ ID NO: 997<br>SEQUENCE: 997<br>000 | moltype = | length = |
| SEQ ID NO: 998<br>SEQUENCE: 998<br>000 | moltype = | length = |
| SEQ ID NO: 999<br>SEQUENCE: 999<br>000 | moltype = | length = |
| SEQ ID NO: 1000<br>SEQUENCE: 1000<br>000 | moltype = | length = |
| SEQ ID NO: 1001<br>SEQUENCE: 1001<br>000 | moltype = | length = |
| SEQ ID NO: 1002<br>SEQUENCE: 1002<br>000 | moltype = | length = |
| SEQ ID NO: 1003<br>SEQUENCE: 1003<br>000 | moltype = | length = |
| SEQ ID NO: 1004<br>SEQUENCE: 1004<br>000 | moltype = | length = |

| | | |
|---|---|---|
| SEQ ID NO: 1005 SEQUENCE: 1005 000 | moltype = | length = |
| SEQ ID NO: 1006 SEQUENCE: 1006 000 | moltype = | length = |
| SEQ ID NO: 1007 SEQUENCE: 1007 000 | moltype = | length = |
| SEQ ID NO: 1008 SEQUENCE: 1008 000 | moltype = | length = |
| SEQ ID NO: 1009 SEQUENCE: 1009 000 | moltype = | length = |
| SEQ ID NO: 1010 SEQUENCE: 1010 000 | moltype = | length = |
| SEQ ID NO: 1011 SEQUENCE: 1011 000 | moltype = | length = |
| SEQ ID NO: 1012 SEQUENCE: 1012 000 | moltype = | length = |
| SEQ ID NO: 1013 SEQUENCE: 1013 000 | moltype = | length = |
| SEQ ID NO: 1014 SEQUENCE: 1014 000 | moltype = | length = |
| SEQ ID NO: 1015 SEQUENCE: 1015 000 | moltype = | length = |
| SEQ ID NO: 1016 SEQUENCE: 1016 000 | moltype = | length = |
| SEQ ID NO: 1017 SEQUENCE: 1017 000 | moltype = | length = |
| SEQ ID NO: 1018 SEQUENCE: 1018 000 | moltype = | length = |
| SEQ ID NO: 1019 SEQUENCE: 1019 000 | moltype = | length = |
| SEQ ID NO: 1020 SEQUENCE: 1020 000 | moltype = | length = |
| SEQ ID NO: 1021 SEQUENCE: 1021 000 | moltype = | length = |
| SEQ ID NO: 1022 SEQUENCE: 1022 000 | moltype = | length = |
| SEQ ID NO: 1023 SEQUENCE: 1023 000 | moltype = | length = |
| SEQ ID NO: 1024 SEQUENCE: 1024 | moltype = | length = |

000

SEQ ID NO: 1025          moltype =      length =
SEQUENCE: 1025
000

SEQ ID NO: 1026          moltype =      length =
SEQUENCE: 1026
000

SEQ ID NO: 1027          moltype =      length =
SEQUENCE: 1027
000

SEQ ID NO: 1028          moltype =      length =
SEQUENCE: 1028
000

SEQ ID NO: 1029          moltype =      length =
SEQUENCE: 1029
000

SEQ ID NO: 1030          moltype =      length =
SEQUENCE: 1030
000

SEQ ID NO: 1031          moltype =      length =
SEQUENCE: 1031
000

SEQ ID NO: 1032          moltype =      length =
SEQUENCE: 1032
000

SEQ ID NO: 1033          moltype =      length =
SEQUENCE: 1033
000

SEQ ID NO: 1034          moltype =      length =
SEQUENCE: 1034
000

SEQ ID NO: 1035          moltype =      length =
SEQUENCE: 1035
000

SEQ ID NO: 1036          moltype =      length =
SEQUENCE: 1036
000

SEQ ID NO: 1037          moltype =      length =
SEQUENCE: 1037
000

SEQ ID NO: 1038          moltype =      length =
SEQUENCE: 1038
000

SEQ ID NO: 1039          moltype =      length =
SEQUENCE: 1039
000

SEQ ID NO: 1040          moltype =      length =
SEQUENCE: 1040
000

SEQ ID NO: 1041          moltype =      length =
SEQUENCE: 1041
000

SEQ ID NO: 1042          moltype =      length =
SEQUENCE: 1042
000

SEQ ID NO: 1043          moltype =      length =
SEQUENCE: 1043
000

SEQ ID NO: 1044          moltype =      length =

```
SEQUENCE: 1044
000

SEQ ID NO: 1045          moltype =    length =
SEQUENCE: 1045
000

SEQ ID NO: 1046          moltype =    length =
SEQUENCE: 1046
000

SEQ ID NO: 1047          moltype =    length =
SEQUENCE: 1047
000

SEQ ID NO: 1048          moltype =    length =
SEQUENCE: 1048
000

SEQ ID NO: 1049          moltype =    length =
SEQUENCE: 1049
000

SEQ ID NO: 1050          moltype =    length =
SEQUENCE: 1050
000

SEQ ID NO: 1051          moltype =    length =
SEQUENCE: 1051
000

SEQ ID NO: 1052          moltype =    length =
SEQUENCE: 1052
000

SEQ ID NO: 1053          moltype =    length =
SEQUENCE: 1053
000

SEQ ID NO: 1054          moltype =    length =
SEQUENCE: 1054
000

SEQ ID NO: 1055          moltype =    length =
SEQUENCE: 1055
000

SEQ ID NO: 1056          moltype =    length =
SEQUENCE: 1056
000

SEQ ID NO: 1057          moltype =    length =
SEQUENCE: 1057
000

SEQ ID NO: 1058          moltype =    length =
SEQUENCE: 1058
000

SEQ ID NO: 1059          moltype =    length =
SEQUENCE: 1059
000

SEQ ID NO: 1060          moltype =    length =
SEQUENCE: 1060
000

SEQ ID NO: 1061          moltype =    length =
SEQUENCE: 1061
000

SEQ ID NO: 1062          moltype =    length =
SEQUENCE: 1062
000

SEQ ID NO: 1063          moltype =    length =
SEQUENCE: 1063
000
```

| | | |
|---|---|---|
| SEQ ID NO: 1064
SEQUENCE: 1064
000 | moltype = | length = |
| SEQ ID NO: 1065
SEQUENCE: 1065
000 | moltype = | length = |
| SEQ ID NO: 1066
SEQUENCE: 1066
000 | moltype = | length = |
| SEQ ID NO: 1067
SEQUENCE: 1067
000 | moltype = | length = |
| SEQ ID NO: 1068
SEQUENCE: 1068
000 | moltype = | length = |
| SEQ ID NO: 1069
SEQUENCE: 1069
000 | moltype = | length = |
| SEQ ID NO: 1070
SEQUENCE: 1070
000 | moltype = | length = |
| SEQ ID NO: 1071
SEQUENCE: 1071
000 | moltype = | length = |
| SEQ ID NO: 1072
SEQUENCE: 1072
000 | moltype = | length = |
| SEQ ID NO: 1073
SEQUENCE: 1073
000 | moltype = | length = |
| SEQ ID NO: 1074
SEQUENCE: 1074
000 | moltype = | length = |
| SEQ ID NO: 1075
SEQUENCE: 1075
000 | moltype = | length = |
| SEQ ID NO: 1076
SEQUENCE: 1076
000 | moltype = | length = |
| SEQ ID NO: 1077
SEQUENCE: 1077
000 | moltype = | length = |
| SEQ ID NO: 1078
SEQUENCE: 1078
000 | moltype = | length = |
| SEQ ID NO: 1079
SEQUENCE: 1079
000 | moltype = | length = |
| SEQ ID NO: 1080
SEQUENCE: 1080
000 | moltype = | length = |
| SEQ ID NO: 1081
SEQUENCE: 1081
000 | moltype = | length = |
| SEQ ID NO: 1082
SEQUENCE: 1082
000 | moltype = | length = |
| SEQ ID NO: 1083
SEQUENCE: 1083
000 | moltype = | length = |

| | | |
|---|---|---|
| SEQ ID NO: 1084 SEQUENCE: 1084 000 | moltype = | length = |
| SEQ ID NO: 1085 SEQUENCE: 1085 000 | moltype = | length = |
| SEQ ID NO: 1086 SEQUENCE: 1086 000 | moltype = | length = |
| SEQ ID NO: 1087 SEQUENCE: 1087 000 | moltype = | length = |
| SEQ ID NO: 1088 SEQUENCE: 1088 000 | moltype = | length = |
| SEQ ID NO: 1089 SEQUENCE: 1089 000 | moltype = | length = |
| SEQ ID NO: 1090 SEQUENCE: 1090 000 | moltype = | length = |
| SEQ ID NO: 1091 SEQUENCE: 1091 000 | moltype = | length = |
| SEQ ID NO: 1092 SEQUENCE: 1092 000 | moltype = | length = |
| SEQ ID NO: 1093 SEQUENCE: 1093 000 | moltype = | length = |
| SEQ ID NO: 1094 SEQUENCE: 1094 000 | moltype = | length = |
| SEQ ID NO: 1095 SEQUENCE: 1095 000 | moltype = | length = |
| SEQ ID NO: 1096 SEQUENCE: 1096 000 | moltype = | length = |
| SEQ ID NO: 1097 SEQUENCE: 1097 000 | moltype = | length = |
| SEQ ID NO: 1098 SEQUENCE: 1098 000 | moltype = | length = |
| SEQ ID NO: 1099 SEQUENCE: 1099 000 | moltype = | length = |
| SEQ ID NO: 1100 SEQUENCE: 1100 000 | moltype = | length = |
| SEQ ID NO: 1101 SEQUENCE: 1101 000 | moltype = | length = |
| SEQ ID NO: 1102 SEQUENCE: 1102 000 | moltype = | length = |
| SEQ ID NO: 1103 SEQUENCE: 1103 | moltype = | length = |

000

SEQ ID NO: 1104    moltype =    length =
SEQUENCE: 1104
000

SEQ ID NO: 1105    moltype =    length =
SEQUENCE: 1105
000

SEQ ID NO: 1106    moltype =    length =
SEQUENCE: 1106
000

SEQ ID NO: 1107    moltype =    length =
SEQUENCE: 1107
000

SEQ ID NO: 1108    moltype =    length =
SEQUENCE: 1108
000

SEQ ID NO: 1109    moltype =    length =
SEQUENCE: 1109
000

SEQ ID NO: 1110    moltype =    length =
SEQUENCE: 1110
000

SEQ ID NO: 1111    moltype =    length =
SEQUENCE: 1111
000

SEQ ID NO: 1112    moltype =    length =
SEQUENCE: 1112
000

SEQ ID NO: 1113    moltype =    length =
SEQUENCE: 1113
000

SEQ ID NO: 1114    moltype =    length =
SEQUENCE: 1114
000

SEQ ID NO: 1115    moltype =    length =
SEQUENCE: 1115
000

SEQ ID NO: 1116    moltype =    length =
SEQUENCE: 1116
000

SEQ ID NO: 1117    moltype =    length =
SEQUENCE: 1117
000

SEQ ID NO: 1118    moltype =    length =
SEQUENCE: 1118
000

SEQ ID NO: 1119    moltype =    length =
SEQUENCE: 1119
000

SEQ ID NO: 1120    moltype =    length =
SEQUENCE: 1120
000

SEQ ID NO: 1121    moltype =    length =
SEQUENCE: 1121
000

SEQ ID NO: 1122    moltype =    length =
SEQUENCE: 1122
000

SEQ ID NO: 1123    moltype =    length =

| | | |
|---|---|---|
| SEQUENCE: 1123 000 | | |
| SEQ ID NO: 1124 SEQUENCE: 1124 000 | moltype = | length = |
| SEQ ID NO: 1125 SEQUENCE: 1125 000 | moltype = | length = |
| SEQ ID NO: 1126 SEQUENCE: 1126 000 | moltype = | length = |
| SEQ ID NO: 1127 SEQUENCE: 1127 000 | moltype = | length = |
| SEQ ID NO: 1128 SEQUENCE: 1128 000 | moltype = | length = |
| SEQ ID NO: 1129 SEQUENCE: 1129 000 | moltype = | length = |
| SEQ ID NO: 1130 SEQUENCE: 1130 000 | moltype = | length = |
| SEQ ID NO: 1131 SEQUENCE: 1131 000 | moltype = | length = |
| SEQ ID NO: 1132 SEQUENCE: 1132 000 | moltype = | length = |
| SEQ ID NO: 1133 SEQUENCE: 1133 000 | moltype = | length = |
| SEQ ID NO: 1134 SEQUENCE: 1134 000 | moltype = | length = |
| SEQ ID NO: 1135 SEQUENCE: 1135 000 | moltype = | length = |
| SEQ ID NO: 1136 SEQUENCE: 1136 000 | moltype = | length = |
| SEQ ID NO: 1137 SEQUENCE: 1137 000 | moltype = | length = |
| SEQ ID NO: 1138 SEQUENCE: 1138 000 | moltype = | length = |
| SEQ ID NO: 1139 SEQUENCE: 1139 000 | moltype = | length = |
| SEQ ID NO: 1140 SEQUENCE: 1140 000 | moltype = | length = |
| SEQ ID NO: 1141 SEQUENCE: 1141 000 | moltype = | length = |
| SEQ ID NO: 1142 SEQUENCE: 1142 000 | moltype = | length = |

| | | |
|---|---|---|
| SEQ ID NO: 1143<br>SEQUENCE: 1143<br>000 | moltype = | length = |
| SEQ ID NO: 1144<br>SEQUENCE: 1144<br>000 | moltype = | length = |
| SEQ ID NO: 1145<br>SEQUENCE: 1145<br>000 | moltype = | length = |
| SEQ ID NO: 1146<br>SEQUENCE: 1146<br>000 | moltype = | length = |
| SEQ ID NO: 1147<br>SEQUENCE: 1147<br>000 | moltype = | length = |
| SEQ ID NO: 1148<br>SEQUENCE: 1148<br>000 | moltype = | length = |
| SEQ ID NO: 1149<br>SEQUENCE: 1149<br>000 | moltype = | length = |
| SEQ ID NO: 1150<br>SEQUENCE: 1150<br>000 | moltype = | length = |
| SEQ ID NO: 1151<br>SEQUENCE: 1151<br>000 | moltype = | length = |
| SEQ ID NO: 1152<br>SEQUENCE: 1152<br>000 | moltype = | length = |
| SEQ ID NO: 1153<br>SEQUENCE: 1153<br>000 | moltype = | length = |
| SEQ ID NO: 1154<br>SEQUENCE: 1154<br>000 | moltype = | length = |
| SEQ ID NO: 1155<br>SEQUENCE: 1155<br>000 | moltype = | length = |
| SEQ ID NO: 1156<br>SEQUENCE: 1156<br>000 | moltype = | length = |
| SEQ ID NO: 1157<br>SEQUENCE: 1157<br>000 | moltype = | length = |
| SEQ ID NO: 1158<br>SEQUENCE: 1158<br>000 | moltype = | length = |
| SEQ ID NO: 1159<br>SEQUENCE: 1159<br>000 | moltype = | length = |
| SEQ ID NO: 1160<br>SEQUENCE: 1160<br>000 | moltype = | length = |
| SEQ ID NO: 1161<br>SEQUENCE: 1161<br>000 | moltype = | length = |
| SEQ ID NO: 1162<br>SEQUENCE: 1162<br>000 | moltype = | length = |

| | | |
|---|---|---|
| SEQ ID NO: 1163<br>SEQUENCE: 1163<br>000 | moltype = | length = |
| SEQ ID NO: 1164<br>SEQUENCE: 1164<br>000 | moltype = | length = |
| SEQ ID NO: 1165<br>SEQUENCE: 1165<br>000 | moltype = | length = |
| SEQ ID NO: 1166<br>SEQUENCE: 1166<br>000 | moltype = | length = |
| SEQ ID NO: 1167<br>SEQUENCE: 1167<br>000 | moltype = | length = |
| SEQ ID NO: 1168<br>SEQUENCE: 1168<br>000 | moltype = | length = |
| SEQ ID NO: 1169<br>SEQUENCE: 1169<br>000 | moltype = | length = |
| SEQ ID NO: 1170<br>SEQUENCE: 1170<br>000 | moltype = | length = |
| SEQ ID NO: 1171<br>SEQUENCE: 1171<br>000 | moltype = | length = |
| SEQ ID NO: 1172<br>SEQUENCE: 1172<br>000 | moltype = | length = |
| SEQ ID NO: 1173<br>SEQUENCE: 1173<br>000 | moltype = | length = |
| SEQ ID NO: 1174<br>SEQUENCE: 1174<br>000 | moltype = | length = |
| SEQ ID NO: 1175<br>SEQUENCE: 1175<br>000 | moltype = | length = |
| SEQ ID NO: 1176<br>SEQUENCE: 1176<br>000 | moltype = | length = |
| SEQ ID NO: 1177<br>SEQUENCE: 1177<br>000 | moltype = | length = |
| SEQ ID NO: 1178<br>SEQUENCE: 1178<br>000 | moltype = | length = |
| SEQ ID NO: 1179<br>SEQUENCE: 1179<br>000 | moltype = | length = |
| SEQ ID NO: 1180<br>SEQUENCE: 1180<br>000 | moltype = | length = |
| SEQ ID NO: 1181<br>SEQUENCE: 1181<br>000 | moltype = | length = |
| SEQ ID NO: 1182<br>SEQUENCE: 1182 | moltype = | length = |

000

SEQ ID NO: 1183            moltype =       length =
SEQUENCE: 1183
000

SEQ ID NO: 1184            moltype =       length =
SEQUENCE: 1184
000

SEQ ID NO: 1185            moltype =       length =
SEQUENCE: 1185
000

SEQ ID NO: 1186            moltype =       length =
SEQUENCE: 1186
000

SEQ ID NO: 1187            moltype =       length =
SEQUENCE: 1187
000

SEQ ID NO: 1188            moltype =       length =
SEQUENCE: 1188
000

SEQ ID NO: 1189            moltype =       length =
SEQUENCE: 1189
000

SEQ ID NO: 1190            moltype =       length =
SEQUENCE: 1190
000

SEQ ID NO: 1191            moltype =       length =
SEQUENCE: 1191
000

SEQ ID NO: 1192            moltype =       length =
SEQUENCE: 1192
000

SEQ ID NO: 1193            moltype =       length =
SEQUENCE: 1193
000

SEQ ID NO: 1194            moltype =       length =
SEQUENCE: 1194
000

SEQ ID NO: 1195            moltype =       length =
SEQUENCE: 1195
000

SEQ ID NO: 1196            moltype =       length =
SEQUENCE: 1196
000

SEQ ID NO: 1197            moltype =       length =
SEQUENCE: 1197
000

SEQ ID NO: 1198            moltype =       length =
SEQUENCE: 1198
000

SEQ ID NO: 1199            moltype =       length =
SEQUENCE: 1199
000

SEQ ID NO: 1200            moltype =       length =
SEQUENCE: 1200
000

SEQ ID NO: 1201            moltype =       length =
SEQUENCE: 1201
000

SEQ ID NO: 1202            moltype =       length =

```
SEQUENCE: 1202
000

SEQ ID NO: 1203          moltype =    length =
SEQUENCE: 1203
000

SEQ ID NO: 1204          moltype =    length =
SEQUENCE: 1204
000

SEQ ID NO: 1205          moltype =    length =
SEQUENCE: 1205
000

SEQ ID NO: 1206          moltype =    length =
SEQUENCE: 1206
000

SEQ ID NO: 1207          moltype =    length =
SEQUENCE: 1207
000

SEQ ID NO: 1208          moltype =    length =
SEQUENCE: 1208
000

SEQ ID NO: 1209          moltype =    length =
SEQUENCE: 1209
000

SEQ ID NO: 1210          moltype =    length =
SEQUENCE: 1210
000

SEQ ID NO: 1211          moltype =    length =
SEQUENCE: 1211
000

SEQ ID NO: 1212          moltype =    length =
SEQUENCE: 1212
000

SEQ ID NO: 1213          moltype =    length =
SEQUENCE: 1213
000

SEQ ID NO: 1214          moltype =    length =
SEQUENCE: 1214
000

SEQ ID NO: 1215          moltype =    length =
SEQUENCE: 1215
000

SEQ ID NO: 1216          moltype =    length =
SEQUENCE: 1216
000

SEQ ID NO: 1217          moltype =    length =
SEQUENCE: 1217
000

SEQ ID NO: 1218          moltype =    length =
SEQUENCE: 1218
000

SEQ ID NO: 1219          moltype =    length =
SEQUENCE: 1219
000

SEQ ID NO: 1220          moltype =    length =
SEQUENCE: 1220
000

SEQ ID NO: 1221          moltype =    length =
SEQUENCE: 1221
000
```

| | | |
|---|---|---|
| SEQ ID NO: 1222<br>SEQUENCE: 1222 | moltype = | length = 000 |
| SEQ ID NO: 1223<br>SEQUENCE: 1223 | moltype = | length = 000 |
| SEQ ID NO: 1224<br>SEQUENCE: 1224 | moltype = | length = 000 |
| SEQ ID NO: 1225<br>SEQUENCE: 1225 | moltype = | length = 000 |
| SEQ ID NO: 1226<br>SEQUENCE: 1226 | moltype = | length = 000 |
| SEQ ID NO: 1227<br>SEQUENCE: 1227 | moltype = | length = 000 |
| SEQ ID NO: 1228<br>SEQUENCE: 1228 | moltype = | length = 000 |
| SEQ ID NO: 1229<br>SEQUENCE: 1229 | moltype = | length = 000 |
| SEQ ID NO: 1230<br>SEQUENCE: 1230 | moltype = | length = 000 |
| SEQ ID NO: 1231<br>SEQUENCE: 1231 | moltype = | length = 000 |
| SEQ ID NO: 1232<br>SEQUENCE: 1232 | moltype = | length = 000 |
| SEQ ID NO: 1233<br>SEQUENCE: 1233 | moltype = | length = 000 |
| SEQ ID NO: 1234<br>SEQUENCE: 1234 | moltype = | length = 000 |
| SEQ ID NO: 1235<br>SEQUENCE: 1235 | moltype = | length = 000 |
| SEQ ID NO: 1236<br>SEQUENCE: 1236 | moltype = | length = 000 |
| SEQ ID NO: 1237<br>SEQUENCE: 1237 | moltype = | length = 000 |
| SEQ ID NO: 1238<br>SEQUENCE: 1238 | moltype = | length = 000 |
| SEQ ID NO: 1239<br>SEQUENCE: 1239 | moltype = | length = 000 |
| SEQ ID NO: 1240<br>SEQUENCE: 1240 | moltype = | length = 000 |
| SEQ ID NO: 1241<br>SEQUENCE: 1241 | moltype = | length = 000 |

SEQ ID NO: 1242         moltype =     length =
SEQUENCE: 1242
000

SEQ ID NO: 1243         moltype =     length =
SEQUENCE: 1243
000

SEQ ID NO: 1244         moltype =     length =
SEQUENCE: 1244
000

SEQ ID NO: 1245         moltype =     length =
SEQUENCE: 1245
000

SEQ ID NO: 1246         moltype =     length =
SEQUENCE: 1246
000

SEQ ID NO: 1247         moltype =     length =
SEQUENCE: 1247
000

SEQ ID NO: 1248         moltype =     length =
SEQUENCE: 1248
000

SEQ ID NO: 1249         moltype =     length =
SEQUENCE: 1249
000

SEQ ID NO: 1250         moltype =     length =
SEQUENCE: 1250
000

SEQ ID NO: 1251         moltype =     length =
SEQUENCE: 1251
000

SEQ ID NO: 1252         moltype =     length =
SEQUENCE: 1252
000

SEQ ID NO: 1253         moltype =     length =
SEQUENCE: 1253
000

SEQ ID NO: 1254         moltype =     length =
SEQUENCE: 1254
000

SEQ ID NO: 1255         moltype =     length =
SEQUENCE: 1255
000

SEQ ID NO: 1256         moltype =     length =
SEQUENCE: 1256
000

SEQ ID NO: 1257         moltype =     length =
SEQUENCE: 1257
000

SEQ ID NO: 1258         moltype =     length =
SEQUENCE: 1258
000

SEQ ID NO: 1259         moltype =     length =
SEQUENCE: 1259
000

SEQ ID NO: 1260         moltype =     length =
SEQUENCE: 1260
000

SEQ ID NO: 1261         moltype =     length =
SEQUENCE: 1261

-continued

000

SEQ ID NO: 1262          moltype =      length =
SEQUENCE: 1262
000

SEQ ID NO: 1263          moltype =      length =
SEQUENCE: 1263
000

SEQ ID NO: 1264          moltype =      length =
SEQUENCE: 1264
000

SEQ ID NO: 1265          moltype =      length =
SEQUENCE: 1265
000

SEQ ID NO: 1266          moltype =      length =
SEQUENCE: 1266
000

SEQ ID NO: 1267          moltype =      length =
SEQUENCE: 1267
000

SEQ ID NO: 1268          moltype =      length =
SEQUENCE: 1268
000

SEQ ID NO: 1269          moltype =      length =
SEQUENCE: 1269
000

SEQ ID NO: 1270          moltype =      length =
SEQUENCE: 1270
000

SEQ ID NO: 1271          moltype =      length =
SEQUENCE: 1271
000

SEQ ID NO: 1272          moltype =      length =
SEQUENCE: 1272
000

SEQ ID NO: 1273          moltype =      length =
SEQUENCE: 1273
000

SEQ ID NO: 1274          moltype =      length =
SEQUENCE: 1274
000

SEQ ID NO: 1275          moltype =      length =
SEQUENCE: 1275
000

SEQ ID NO: 1276          moltype =      length =
SEQUENCE: 1276
000

SEQ ID NO: 1277          moltype =      length =
SEQUENCE: 1277
000

SEQ ID NO: 1278          moltype =      length =
SEQUENCE: 1278
000

SEQ ID NO: 1279          moltype =      length =
SEQUENCE: 1279
000

SEQ ID NO: 1280          moltype =      length =
SEQUENCE: 1280
000

SEQ ID NO: 1281          moltype =      length =

| | | |
|---|---|---|
| SEQUENCE: 1281 000 | | |
| SEQ ID NO: 1282 SEQUENCE: 1282 000 | moltype = | length = |
| SEQ ID NO: 1283 SEQUENCE: 1283 000 | moltype = | length = |
| SEQ ID NO: 1284 SEQUENCE: 1284 000 | moltype = | length = |
| SEQ ID NO: 1285 SEQUENCE: 1285 000 | moltype = | length = |
| SEQ ID NO: 1286 SEQUENCE: 1286 000 | moltype = | length = |
| SEQ ID NO: 1287 SEQUENCE: 1287 000 | moltype = | length = |
| SEQ ID NO: 1288 SEQUENCE: 1288 000 | moltype = | length = |
| SEQ ID NO: 1289 SEQUENCE: 1289 000 | moltype = | length = |
| SEQ ID NO: 1290 SEQUENCE: 1290 000 | moltype = | length = |
| SEQ ID NO: 1291 SEQUENCE: 1291 000 | moltype = | length = |
| SEQ ID NO: 1292 SEQUENCE: 1292 000 | moltype = | length = |
| SEQ ID NO: 1293 SEQUENCE: 1293 000 | moltype = | length = |
| SEQ ID NO: 1294 SEQUENCE: 1294 000 | moltype = | length = |
| SEQ ID NO: 1295 SEQUENCE: 1295 000 | moltype = | length = |
| SEQ ID NO: 1296 SEQUENCE: 1296 000 | moltype = | length = |
| SEQ ID NO: 1297 SEQUENCE: 1297 000 | moltype = | length = |
| SEQ ID NO: 1298 SEQUENCE: 1298 000 | moltype = | length = |
| SEQ ID NO: 1299 SEQUENCE: 1299 000 | moltype = | length = |
| SEQ ID NO: 1300 SEQUENCE: 1300 000 | moltype = | length = |

| | | |
|---|---|---|
| SEQ ID NO: 1301 SEQUENCE: 1301 | moltype = | length = 000 |
| SEQ ID NO: 1302 SEQUENCE: 1302 | moltype = | length = 000 |
| SEQ ID NO: 1303 SEQUENCE: 1303 | moltype = | length = 000 |
| SEQ ID NO: 1304 SEQUENCE: 1304 | moltype = | length = 000 |
| SEQ ID NO: 1305 SEQUENCE: 1305 | moltype = | length = 000 |
| SEQ ID NO: 1306 SEQUENCE: 1306 | moltype = | length = 000 |
| SEQ ID NO: 1307 SEQUENCE: 1307 | moltype = | length = 000 |
| SEQ ID NO: 1308 SEQUENCE: 1308 | moltype = | length = 000 |
| SEQ ID NO: 1309 SEQUENCE: 1309 | moltype = | length = 000 |
| SEQ ID NO: 1310 SEQUENCE: 1310 | moltype = | length = 000 |
| SEQ ID NO: 1311 SEQUENCE: 1311 | moltype = | length = 000 |
| SEQ ID NO: 1312 SEQUENCE: 1312 | moltype = | length = 000 |
| SEQ ID NO: 1313 SEQUENCE: 1313 | moltype = | length = 000 |
| SEQ ID NO: 1314 SEQUENCE: 1314 | moltype = | length = 000 |
| SEQ ID NO: 1315 SEQUENCE: 1315 | moltype = | length = 000 |
| SEQ ID NO: 1316 SEQUENCE: 1316 | moltype = | length = 000 |
| SEQ ID NO: 1317 SEQUENCE: 1317 | moltype = | length = 000 |
| SEQ ID NO: 1318 SEQUENCE: 1318 | moltype = | length = 000 |
| SEQ ID NO: 1319 SEQUENCE: 1319 | moltype = | length = 000 |
| SEQ ID NO: 1320 SEQUENCE: 1320 | moltype = | length = 000 |

| | | |
|---|---|---|
| SEQ ID NO: 1321 SEQUENCE: 1321 000 | moltype = | length = |
| SEQ ID NO: 1322 SEQUENCE: 1322 000 | moltype = | length = |
| SEQ ID NO: 1323 SEQUENCE: 1323 000 | moltype = | length = |
| SEQ ID NO: 1324 SEQUENCE: 1324 000 | moltype = | length = |
| SEQ ID NO: 1325 SEQUENCE: 1325 000 | moltype = | length = |
| SEQ ID NO: 1326 SEQUENCE: 1326 000 | moltype = | length = |
| SEQ ID NO: 1327 SEQUENCE: 1327 000 | moltype = | length = |
| SEQ ID NO: 1328 SEQUENCE: 1328 000 | moltype = | length = |
| SEQ ID NO: 1329 SEQUENCE: 1329 000 | moltype = | length = |
| SEQ ID NO: 1330 SEQUENCE: 1330 000 | moltype = | length = |
| SEQ ID NO: 1331 SEQUENCE: 1331 000 | moltype = | length = |
| SEQ ID NO: 1332 SEQUENCE: 1332 000 | moltype = | length = |
| SEQ ID NO: 1333 SEQUENCE: 1333 000 | moltype = | length = |
| SEQ ID NO: 1334 SEQUENCE: 1334 000 | moltype = | length = |
| SEQ ID NO: 1335 SEQUENCE: 1335 000 | moltype = | length = |
| SEQ ID NO: 1336 SEQUENCE: 1336 000 | moltype = | length = |
| SEQ ID NO: 1337 SEQUENCE: 1337 000 | moltype = | length = |
| SEQ ID NO: 1338 SEQUENCE: 1338 000 | moltype = | length = |
| SEQ ID NO: 1339 SEQUENCE: 1339 000 | moltype = | length = |
| SEQ ID NO: 1340 SEQUENCE: 1340 | moltype = | length = |

000

SEQ ID NO: 1341       moltype =     length =
SEQUENCE: 1341
000

SEQ ID NO: 1342       moltype =     length =
SEQUENCE: 1342
000

SEQ ID NO: 1343       moltype =     length =
SEQUENCE: 1343
000

SEQ ID NO: 1344       moltype =     length =
SEQUENCE: 1344
000

SEQ ID NO: 1345       moltype =     length =
SEQUENCE: 1345
000

SEQ ID NO: 1346       moltype =     length =
SEQUENCE: 1346
000

SEQ ID NO: 1347       moltype =     length =
SEQUENCE: 1347
000

SEQ ID NO: 1348       moltype =     length =
SEQUENCE: 1348
000

SEQ ID NO: 1349       moltype =     length =
SEQUENCE: 1349
000

SEQ ID NO: 1350       moltype =     length =
SEQUENCE: 1350
000

SEQ ID NO: 1351       moltype =     length =
SEQUENCE: 1351
000

SEQ ID NO: 1352       moltype =     length =
SEQUENCE: 1352
000

SEQ ID NO: 1353       moltype =     length =
SEQUENCE: 1353
000

SEQ ID NO: 1354       moltype =     length =
SEQUENCE: 1354
000

SEQ ID NO: 1355       moltype =     length =
SEQUENCE: 1355
000

SEQ ID NO: 1356       moltype =     length =
SEQUENCE: 1356
000

SEQ ID NO: 1357       moltype =     length =
SEQUENCE: 1357
000

SEQ ID NO: 1358       moltype =     length =
SEQUENCE: 1358
000

SEQ ID NO: 1359       moltype =     length =
SEQUENCE: 1359
000

SEQ ID NO: 1360       moltype =     length =

| | | |
|---|---|---|
| SEQUENCE: 1360 000 | | |
| SEQ ID NO: 1361 SEQUENCE: 1361 000 | moltype = | length = |
| SEQ ID NO: 1362 SEQUENCE: 1362 000 | moltype = | length = |
| SEQ ID NO: 1363 SEQUENCE: 1363 000 | moltype = | length = |
| SEQ ID NO: 1364 SEQUENCE: 1364 000 | moltype = | length = |
| SEQ ID NO: 1365 SEQUENCE: 1365 000 | moltype = | length = |
| SEQ ID NO: 1366 SEQUENCE: 1366 000 | moltype = | length = |
| SEQ ID NO: 1367 SEQUENCE: 1367 000 | moltype = | length = |
| SEQ ID NO: 1368 SEQUENCE: 1368 000 | moltype = | length = |
| SEQ ID NO: 1369 SEQUENCE: 1369 000 | moltype = | length = |
| SEQ ID NO: 1370 SEQUENCE: 1370 000 | moltype = | length = |
| SEQ ID NO: 1371 SEQUENCE: 1371 000 | moltype = | length = |
| SEQ ID NO: 1372 SEQUENCE: 1372 000 | moltype = | length = |
| SEQ ID NO: 1373 SEQUENCE: 1373 000 | moltype = | length = |
| SEQ ID NO: 1374 SEQUENCE: 1374 000 | moltype = | length = |
| SEQ ID NO: 1375 SEQUENCE: 1375 000 | moltype = | length = |
| SEQ ID NO: 1376 SEQUENCE: 1376 000 | moltype = | length = |
| SEQ ID NO: 1377 SEQUENCE: 1377 000 | moltype = | length = |
| SEQ ID NO: 1378 SEQUENCE: 1378 000 | moltype = | length = |
| SEQ ID NO: 1379 SEQUENCE: 1379 000 | moltype = | length = |

| | | |
|---|---|---|
| SEQ ID NO: 1380 SEQUENCE: 1380 | moltype = | length = 000 |
| SEQ ID NO: 1381 SEQUENCE: 1381 | moltype = | length = 000 |
| SEQ ID NO: 1382 SEQUENCE: 1382 | moltype = | length = 000 |
| SEQ ID NO: 1383 SEQUENCE: 1383 | moltype = | length = 000 |
| SEQ ID NO: 1384 SEQUENCE: 1384 | moltype = | length = 000 |
| SEQ ID NO: 1385 SEQUENCE: 1385 | moltype = | length = 000 |
| SEQ ID NO: 1386 SEQUENCE: 1386 | moltype = | length = 000 |
| SEQ ID NO: 1387 SEQUENCE: 1387 | moltype = | length = 000 |
| SEQ ID NO: 1388 SEQUENCE: 1388 | moltype = | length = 000 |
| SEQ ID NO: 1389 SEQUENCE: 1389 | moltype = | length = 000 |
| SEQ ID NO: 1390 SEQUENCE: 1390 | moltype = | length = 000 |
| SEQ ID NO: 1391 SEQUENCE: 1391 | moltype = | length = 000 |
| SEQ ID NO: 1392 SEQUENCE: 1392 | moltype = | length = 000 |
| SEQ ID NO: 1393 SEQUENCE: 1393 | moltype = | length = 000 |
| SEQ ID NO: 1394 SEQUENCE: 1394 | moltype = | length = 000 |
| SEQ ID NO: 1395 SEQUENCE: 1395 | moltype = | length = 000 |
| SEQ ID NO: 1396 SEQUENCE: 1396 | moltype = | length = 000 |
| SEQ ID NO: 1397 SEQUENCE: 1397 | moltype = | length = 000 |
| SEQ ID NO: 1398 SEQUENCE: 1398 | moltype = | length = 000 |
| SEQ ID NO: 1399 SEQUENCE: 1399 | moltype = | length = 000 |

| | | |
|---|---|---|
| SEQ ID NO: 1400 SEQUENCE: 1400 | moltype = | length = 000 |
| SEQ ID NO: 1401 SEQUENCE: 1401 | moltype = | length = 000 |
| SEQ ID NO: 1402 SEQUENCE: 1402 | moltype = | length = 000 |
| SEQ ID NO: 1403 SEQUENCE: 1403 | moltype = | length = 000 |
| SEQ ID NO: 1404 SEQUENCE: 1404 | moltype = | length = 000 |
| SEQ ID NO: 1405 SEQUENCE: 1405 | moltype = | length = 000 |
| SEQ ID NO: 1406 SEQUENCE: 1406 | moltype = | length = 000 |
| SEQ ID NO: 1407 SEQUENCE: 1407 | moltype = | length = 000 |
| SEQ ID NO: 1408 SEQUENCE: 1408 | moltype = | length = 000 |
| SEQ ID NO: 1409 SEQUENCE: 1409 | moltype = | length = 000 |
| SEQ ID NO: 1410 SEQUENCE: 1410 | moltype = | length = 000 |
| SEQ ID NO: 1411 SEQUENCE: 1411 | moltype = | length = 000 |
| SEQ ID NO: 1412 SEQUENCE: 1412 | moltype = | length = 000 |
| SEQ ID NO: 1413 SEQUENCE: 1413 | moltype = | length = 000 |
| SEQ ID NO: 1414 SEQUENCE: 1414 | moltype = | length = 000 |
| SEQ ID NO: 1415 SEQUENCE: 1415 | moltype = | length = 000 |
| SEQ ID NO: 1416 SEQUENCE: 1416 | moltype = | length = 000 |
| SEQ ID NO: 1417 SEQUENCE: 1417 | moltype = | length = 000 |
| SEQ ID NO: 1418 SEQUENCE: 1418 | moltype = | length = 000 |
| SEQ ID NO: 1419 SEQUENCE: 1419 | moltype = | length = |

000

SEQ ID NO: 1420    moltype =     length =
SEQUENCE: 1420
000

SEQ ID NO: 1421    moltype =     length =
SEQUENCE: 1421
000

SEQ ID NO: 1422    moltype =     length =
SEQUENCE: 1422
000

SEQ ID NO: 1423    moltype =     length =
SEQUENCE: 1423
000

SEQ ID NO: 1424    moltype =     length =
SEQUENCE: 1424
000

SEQ ID NO: 1425    moltype =     length =
SEQUENCE: 1425
000

SEQ ID NO: 1426    moltype =     length =
SEQUENCE: 1426
000

SEQ ID NO: 1427    moltype =     length =
SEQUENCE: 1427
000

SEQ ID NO: 1428    moltype =     length =
SEQUENCE: 1428
000

SEQ ID NO: 1429    moltype =     length =
SEQUENCE: 1429
000

SEQ ID NO: 1430    moltype =     length =
SEQUENCE: 1430
000

SEQ ID NO: 1431    moltype =     length =
SEQUENCE: 1431
000

SEQ ID NO: 1432    moltype =     length =
SEQUENCE: 1432
000

SEQ ID NO: 1433    moltype =     length =
SEQUENCE: 1433
000

SEQ ID NO: 1434    moltype =     length =
SEQUENCE: 1434
000

SEQ ID NO: 1435    moltype =     length =
SEQUENCE: 1435
000

SEQ ID NO: 1436    moltype =     length =
SEQUENCE: 1436
000

SEQ ID NO: 1437    moltype =     length =
SEQUENCE: 1437
000

SEQ ID NO: 1438    moltype =     length =
SEQUENCE: 1438
000

SEQ ID NO: 1439    moltype =     length =

```
SEQUENCE: 1439
000

SEQ ID NO: 1440         moltype =    length =
SEQUENCE: 1440
000

SEQ ID NO: 1441         moltype =    length =
SEQUENCE: 1441
000

SEQ ID NO: 1442         moltype =    length =
SEQUENCE: 1442
000

SEQ ID NO: 1443         moltype =    length =
SEQUENCE: 1443
000

SEQ ID NO: 1444         moltype =    length =
SEQUENCE: 1444
000

SEQ ID NO: 1445         moltype =    length =
SEQUENCE: 1445
000

SEQ ID NO: 1446         moltype =    length =
SEQUENCE: 1446
000

SEQ ID NO: 1447         moltype =    length =
SEQUENCE: 1447
000

SEQ ID NO: 1448         moltype =    length =
SEQUENCE: 1448
000

SEQ ID NO: 1449         moltype =    length =
SEQUENCE: 1449
000

SEQ ID NO: 1450         moltype =    length =
SEQUENCE: 1450
000

SEQ ID NO: 1451         moltype =    length =
SEQUENCE: 1451
000

SEQ ID NO: 1452         moltype =    length =
SEQUENCE: 1452
000

SEQ ID NO: 1453         moltype =    length =
SEQUENCE: 1453
000

SEQ ID NO: 1454         moltype =    length =
SEQUENCE: 1454
000

SEQ ID NO: 1455         moltype =    length =
SEQUENCE: 1455
000

SEQ ID NO: 1456         moltype =    length =
SEQUENCE: 1456
000

SEQ ID NO: 1457         moltype =    length =
SEQUENCE: 1457
000

SEQ ID NO: 1458         moltype =    length =
SEQUENCE: 1458
000
```

| | | |
|---|---|---|
| SEQ ID NO: 1459
SEQUENCE: 1459
000 | moltype = | length = |
| SEQ ID NO: 1460
SEQUENCE: 1460
000 | moltype = | length = |
| SEQ ID NO: 1461
SEQUENCE: 1461
000 | moltype = | length = |
| SEQ ID NO: 1462
SEQUENCE: 1462
000 | moltype = | length = |
| SEQ ID NO: 1463
SEQUENCE: 1463
000 | moltype = | length = |
| SEQ ID NO: 1464
SEQUENCE: 1464
000 | moltype = | length = |
| SEQ ID NO: 1465
SEQUENCE: 1465
000 | moltype = | length = |
| SEQ ID NO: 1466
SEQUENCE: 1466
000 | moltype = | length = |
| SEQ ID NO: 1467
SEQUENCE: 1467
000 | moltype = | length = |
| SEQ ID NO: 1468
SEQUENCE: 1468
000 | moltype = | length = |
| SEQ ID NO: 1469
SEQUENCE: 1469
000 | moltype = | length = |
| SEQ ID NO: 1470
SEQUENCE: 1470
000 | moltype = | length = |
| SEQ ID NO: 1471
SEQUENCE: 1471
000 | moltype = | length = |
| SEQ ID NO: 1472
SEQUENCE: 1472
000 | moltype = | length = |
| SEQ ID NO: 1473
SEQUENCE: 1473
000 | moltype = | length = |
| SEQ ID NO: 1474
SEQUENCE: 1474
000 | moltype = | length = |
| SEQ ID NO: 1475
SEQUENCE: 1475
000 | moltype = | length = |
| SEQ ID NO: 1476
SEQUENCE: 1476
000 | moltype = | length = |
| SEQ ID NO: 1477
SEQUENCE: 1477
000 | moltype = | length = |
| SEQ ID NO: 1478
SEQUENCE: 1478
000 | moltype = | length = |

| | | |
|---|---|---|
| SEQ ID NO: 1479<br>SEQUENCE: 1479<br>000 | moltype = | length = |
| SEQ ID NO: 1480<br>SEQUENCE: 1480<br>000 | moltype = | length = |
| SEQ ID NO: 1481<br>SEQUENCE: 1481<br>000 | moltype = | length = |
| SEQ ID NO: 1482<br>SEQUENCE: 1482<br>000 | moltype = | length = |
| SEQ ID NO: 1483<br>SEQUENCE: 1483<br>000 | moltype = | length = |
| SEQ ID NO: 1484<br>SEQUENCE: 1484<br>000 | moltype = | length = |
| SEQ ID NO: 1485<br>SEQUENCE: 1485<br>000 | moltype = | length = |
| SEQ ID NO: 1486<br>SEQUENCE: 1486<br>000 | moltype = | length = |
| SEQ ID NO: 1487<br>SEQUENCE: 1487<br>000 | moltype = | length = |
| SEQ ID NO: 1488<br>SEQUENCE: 1488<br>000 | moltype = | length = |
| SEQ ID NO: 1489<br>SEQUENCE: 1489<br>000 | moltype = | length = |
| SEQ ID NO: 1490<br>SEQUENCE: 1490<br>000 | moltype = | length = |
| SEQ ID NO: 1491<br>SEQUENCE: 1491<br>000 | moltype = | length = |
| SEQ ID NO: 1492<br>SEQUENCE: 1492<br>000 | moltype = | length = |
| SEQ ID NO: 1493<br>SEQUENCE: 1493<br>000 | moltype = | length = |
| SEQ ID NO: 1494<br>SEQUENCE: 1494<br>000 | moltype = | length = |
| SEQ ID NO: 1495<br>SEQUENCE: 1495<br>000 | moltype = | length = |
| SEQ ID NO: 1496<br>SEQUENCE: 1496<br>000 | moltype = | length = |
| SEQ ID NO: 1497<br>SEQUENCE: 1497<br>000 | moltype = | length = |
| SEQ ID NO: 1498<br>SEQUENCE: 1498 | moltype = | length = |

000

SEQ ID NO: 1499        moltype =      length =
SEQUENCE: 1499
000

SEQ ID NO: 1500        moltype =      length =
SEQUENCE: 1500
000

SEQ ID NO: 1501        moltype =      length =
SEQUENCE: 1501
000

SEQ ID NO: 1502        moltype =      length =
SEQUENCE: 1502
000

SEQ ID NO: 1503        moltype =      length =
SEQUENCE: 1503
000

SEQ ID NO: 1504        moltype =      length =
SEQUENCE: 1504
000

SEQ ID NO: 1505        moltype =      length =
SEQUENCE: 1505
000

SEQ ID NO: 1506        moltype =      length =
SEQUENCE: 1506
000

SEQ ID NO: 1507        moltype =      length =
SEQUENCE: 1507
000

SEQ ID NO: 1508        moltype =      length =
SEQUENCE: 1508
000

SEQ ID NO: 1509        moltype =      length =
SEQUENCE: 1509
000

SEQ ID NO: 1510        moltype =      length =
SEQUENCE: 1510
000

SEQ ID NO: 1511        moltype =      length =
SEQUENCE: 1511
000

SEQ ID NO: 1512        moltype =      length =
SEQUENCE: 1512
000

SEQ ID NO: 1513        moltype =      length =
SEQUENCE: 1513
000

SEQ ID NO: 1514        moltype =      length =
SEQUENCE: 1514
000

SEQ ID NO: 1515        moltype =      length =
SEQUENCE: 1515
000

SEQ ID NO: 1516        moltype =      length =
SEQUENCE: 1516
000

SEQ ID NO: 1517        moltype =      length =
SEQUENCE: 1517
000

SEQ ID NO: 1518        moltype =      length =

| | | |
|---|---|---|
| SEQUENCE: 1518 000 | | |
| SEQ ID NO: 1519 SEQUENCE: 1519 000 | moltype = | length = |
| SEQ ID NO: 1520 SEQUENCE: 1520 000 | moltype = | length = |
| SEQ ID NO: 1521 SEQUENCE: 1521 000 | moltype = | length = |
| SEQ ID NO: 1522 SEQUENCE: 1522 000 | moltype = | length = |
| SEQ ID NO: 1523 SEQUENCE: 1523 000 | moltype = | length = |
| SEQ ID NO: 1524 SEQUENCE: 1524 000 | moltype = | length = |
| SEQ ID NO: 1525 SEQUENCE: 1525 000 | moltype = | length = |
| SEQ ID NO: 1526 SEQUENCE: 1526 000 | moltype = | length = |
| SEQ ID NO: 1527 SEQUENCE: 1527 000 | moltype = | length = |
| SEQ ID NO: 1528 SEQUENCE: 1528 000 | moltype = | length = |
| SEQ ID NO: 1529 SEQUENCE: 1529 000 | moltype = | length = |
| SEQ ID NO: 1530 SEQUENCE: 1530 000 | moltype = | length = |
| SEQ ID NO: 1531 SEQUENCE: 1531 000 | moltype = | length = |
| SEQ ID NO: 1532 SEQUENCE: 1532 000 | moltype = | length = |
| SEQ ID NO: 1533 SEQUENCE: 1533 000 | moltype = | length = |
| SEQ ID NO: 1534 SEQUENCE: 1534 000 | moltype = | length = |
| SEQ ID NO: 1535 SEQUENCE: 1535 000 | moltype = | length = |
| SEQ ID NO: 1536 SEQUENCE: 1536 000 | moltype = | length = |
| SEQ ID NO: 1537 SEQUENCE: 1537 000 | moltype = | length = |

| | | |
|---|---|---|
| SEQ ID NO: 1538<br>SEQUENCE: 1538<br>000 | moltype = | length = |
| SEQ ID NO: 1539<br>SEQUENCE: 1539<br>000 | moltype = | length = |
| SEQ ID NO: 1540<br>SEQUENCE: 1540<br>000 | moltype = | length = |
| SEQ ID NO: 1541<br>SEQUENCE: 1541<br>000 | moltype = | length = |
| SEQ ID NO: 1542<br>SEQUENCE: 1542<br>000 | moltype = | length = |
| SEQ ID NO: 1543<br>SEQUENCE: 1543<br>000 | moltype = | length = |
| SEQ ID NO: 1544<br>SEQUENCE: 1544<br>000 | moltype = | length = |
| SEQ ID NO: 1545<br>SEQUENCE: 1545<br>000 | moltype = | length = |
| SEQ ID NO: 1546<br>SEQUENCE: 1546<br>000 | moltype = | length = |
| SEQ ID NO: 1547<br>SEQUENCE: 1547<br>000 | moltype = | length = |
| SEQ ID NO: 1548<br>SEQUENCE: 1548<br>000 | moltype = | length = |
| SEQ ID NO: 1549<br>SEQUENCE: 1549<br>000 | moltype = | length = |
| SEQ ID NO: 1550<br>SEQUENCE: 1550<br>000 | moltype = | length = |
| SEQ ID NO: 1551<br>SEQUENCE: 1551<br>000 | moltype = | length = |
| SEQ ID NO: 1552<br>SEQUENCE: 1552<br>000 | moltype = | length = |
| SEQ ID NO: 1553<br>SEQUENCE: 1553<br>000 | moltype = | length = |
| SEQ ID NO: 1554<br>SEQUENCE: 1554<br>000 | moltype = | length = |
| SEQ ID NO: 1555<br>SEQUENCE: 1555<br>000 | moltype = | length = |
| SEQ ID NO: 1556<br>SEQUENCE: 1556<br>000 | moltype = | length = |
| SEQ ID NO: 1557<br>SEQUENCE: 1557<br>000 | moltype = | length = |

| | | |
|---|---|---|
| SEQ ID NO: 1558<br>SEQUENCE: 1558<br>000 | moltype = | length = |
| SEQ ID NO: 1559<br>SEQUENCE: 1559<br>000 | moltype = | length = |
| SEQ ID NO: 1560<br>SEQUENCE: 1560<br>000 | moltype = | length = |
| SEQ ID NO: 1561<br>SEQUENCE: 1561<br>000 | moltype = | length = |
| SEQ ID NO: 1562<br>SEQUENCE: 1562<br>000 | moltype = | length = |
| SEQ ID NO: 1563<br>SEQUENCE: 1563<br>000 | moltype = | length = |
| SEQ ID NO: 1564<br>SEQUENCE: 1564<br>000 | moltype = | length = |
| SEQ ID NO: 1565<br>SEQUENCE: 1565<br>000 | moltype = | length = |
| SEQ ID NO: 1566<br>SEQUENCE: 1566<br>000 | moltype = | length = |
| SEQ ID NO: 1567<br>SEQUENCE: 1567<br>000 | moltype = | length = |
| SEQ ID NO: 1568<br>SEQUENCE: 1568<br>000 | moltype = | length = |
| SEQ ID NO: 1569<br>SEQUENCE: 1569<br>000 | moltype = | length = |
| SEQ ID NO: 1570<br>SEQUENCE: 1570<br>000 | moltype = | length = |
| SEQ ID NO: 1571<br>SEQUENCE: 1571<br>000 | moltype = | length = |
| SEQ ID NO: 1572<br>SEQUENCE: 1572<br>000 | moltype = | length = |
| SEQ ID NO: 1573<br>SEQUENCE: 1573<br>000 | moltype = | length = |
| SEQ ID NO: 1574<br>SEQUENCE: 1574<br>000 | moltype = | length = |
| SEQ ID NO: 1575<br>SEQUENCE: 1575<br>000 | moltype = | length = |
| SEQ ID NO: 1576<br>SEQUENCE: 1576<br>000 | moltype = | length = |
| SEQ ID NO: 1577<br>SEQUENCE: 1577 | moltype = | length = |

000

SEQ ID NO: 1578         moltype =     length =
SEQUENCE: 1578
000

SEQ ID NO: 1579         moltype =     length =
SEQUENCE: 1579
000

SEQ ID NO: 1580         moltype =     length =
SEQUENCE: 1580
000

SEQ ID NO: 1581         moltype =     length =
SEQUENCE: 1581
000

SEQ ID NO: 1582         moltype =     length =
SEQUENCE: 1582
000

SEQ ID NO: 1583         moltype =     length =
SEQUENCE: 1583
000

SEQ ID NO: 1584         moltype =     length =
SEQUENCE: 1584
000

SEQ ID NO: 1585         moltype =     length =
SEQUENCE: 1585
000

SEQ ID NO: 1586         moltype =     length =
SEQUENCE: 1586
000

SEQ ID NO: 1587         moltype =     length =
SEQUENCE: 1587
000

SEQ ID NO: 1588         moltype =     length =
SEQUENCE: 1588
000

SEQ ID NO: 1589         moltype =     length =
SEQUENCE: 1589
000

SEQ ID NO: 1590         moltype =     length =
SEQUENCE: 1590
000

SEQ ID NO: 1591         moltype =     length =
SEQUENCE: 1591
000

SEQ ID NO: 1592         moltype =     length =
SEQUENCE: 1592
000

SEQ ID NO: 1593         moltype =     length =
SEQUENCE: 1593
000

SEQ ID NO: 1594         moltype =     length =
SEQUENCE: 1594
000

SEQ ID NO: 1595         moltype =     length =
SEQUENCE: 1595
000

SEQ ID NO: 1596         moltype =     length =
SEQUENCE: 1596
000

SEQ ID NO: 1597         moltype =     length =

| | | |
|---|---|---|
| SEQUENCE: 1597 000 | | |
| SEQ ID NO: 1598 SEQUENCE: 1598 000 | moltype = | length = |
| SEQ ID NO: 1599 SEQUENCE: 1599 000 | moltype = | length = |
| SEQ ID NO: 1600 SEQUENCE: 1600 000 | moltype = | length = |
| SEQ ID NO: 1601 SEQUENCE: 1601 000 | moltype = | length = |
| SEQ ID NO: 1602 SEQUENCE: 1602 000 | moltype = | length = |
| SEQ ID NO: 1603 SEQUENCE: 1603 000 | moltype = | length = |
| SEQ ID NO: 1604 SEQUENCE: 1604 000 | moltype = | length = |
| SEQ ID NO: 1605 SEQUENCE: 1605 000 | moltype = | length = |
| SEQ ID NO: 1606 SEQUENCE: 1606 000 | moltype = | length = |
| SEQ ID NO: 1607 SEQUENCE: 1607 000 | moltype = | length = |
| SEQ ID NO: 1608 SEQUENCE: 1608 000 | moltype = | length = |
| SEQ ID NO: 1609 SEQUENCE: 1609 000 | moltype = | length = |
| SEQ ID NO: 1610 SEQUENCE: 1610 000 | moltype = | length = |
| SEQ ID NO: 1611 SEQUENCE: 1611 000 | moltype = | length = |
| SEQ ID NO: 1612 SEQUENCE: 1612 000 | moltype = | length = |
| SEQ ID NO: 1613 SEQUENCE: 1613 000 | moltype = | length = |
| SEQ ID NO: 1614 SEQUENCE: 1614 000 | moltype = | length = |
| SEQ ID NO: 1615 SEQUENCE: 1615 000 | moltype = | length = |
| SEQ ID NO: 1616 SEQUENCE: 1616 000 | moltype = | length = |

-continued

SEQ ID NO: 1617        moltype =    length =
SEQUENCE: 1617
000

SEQ ID NO: 1618        moltype =    length =
SEQUENCE: 1618
000

SEQ ID NO: 1619        moltype =    length =
SEQUENCE: 1619
000

SEQ ID NO: 1620        moltype =    length =
SEQUENCE: 1620
000

SEQ ID NO: 1621        moltype =    length =
SEQUENCE: 1621
000

SEQ ID NO: 1622        moltype =    length =
SEQUENCE: 1622
000

SEQ ID NO: 1623        moltype =    length =
SEQUENCE: 1623
000

SEQ ID NO: 1624        moltype =    length =
SEQUENCE: 1624
000

SEQ ID NO: 1625        moltype =    length =
SEQUENCE: 1625
000

SEQ ID NO: 1626        moltype =    length =
SEQUENCE: 1626
000

SEQ ID NO: 1627        moltype =    length =
SEQUENCE: 1627
000

SEQ ID NO: 1628        moltype =    length =
SEQUENCE: 1628
000

SEQ ID NO: 1629        moltype =    length =
SEQUENCE: 1629
000

SEQ ID NO: 1630        moltype =    length =
SEQUENCE: 1630
000

SEQ ID NO: 1631        moltype =    length =
SEQUENCE: 1631
000

SEQ ID NO: 1632        moltype =    length =
SEQUENCE: 1632
000

SEQ ID NO: 1633        moltype =    length =
SEQUENCE: 1633
000

SEQ ID NO: 1634        moltype =    length =
SEQUENCE: 1634
000

SEQ ID NO: 1635        moltype =    length =
SEQUENCE: 1635
000

SEQ ID NO: 1636        moltype =    length =
SEQUENCE: 1636
000

| | | |
|---|---|---|
| SEQ ID NO: 1637<br>SEQUENCE: 1637<br>000 | moltype = | length = |
| SEQ ID NO: 1638<br>SEQUENCE: 1638<br>000 | moltype = | length = |
| SEQ ID NO: 1639<br>SEQUENCE: 1639<br>000 | moltype = | length = |
| SEQ ID NO: 1640<br>SEQUENCE: 1640<br>000 | moltype = | length = |
| SEQ ID NO: 1641<br>SEQUENCE: 1641<br>000 | moltype = | length = |
| SEQ ID NO: 1642<br>SEQUENCE: 1642<br>000 | moltype = | length = |
| SEQ ID NO: 1643<br>SEQUENCE: 1643<br>000 | moltype = | length = |
| SEQ ID NO: 1644<br>SEQUENCE: 1644<br>000 | moltype = | length = |
| SEQ ID NO: 1645<br>SEQUENCE: 1645<br>000 | moltype = | length = |
| SEQ ID NO: 1646<br>SEQUENCE: 1646<br>000 | moltype = | length = |
| SEQ ID NO: 1647<br>SEQUENCE: 1647<br>000 | moltype = | length = |
| SEQ ID NO: 1648<br>SEQUENCE: 1648<br>000 | moltype = | length = |
| SEQ ID NO: 1649<br>SEQUENCE: 1649<br>000 | moltype = | length = |
| SEQ ID NO: 1650<br>SEQUENCE: 1650<br>000 | moltype = | length = |
| SEQ ID NO: 1651<br>SEQUENCE: 1651<br>000 | moltype = | length = |
| SEQ ID NO: 1652<br>SEQUENCE: 1652<br>000 | moltype = | length = |
| SEQ ID NO: 1653<br>SEQUENCE: 1653<br>000 | moltype = | length = |
| SEQ ID NO: 1654<br>SEQUENCE: 1654<br>000 | moltype = | length = |
| SEQ ID NO: 1655<br>SEQUENCE: 1655<br>000 | moltype = | length = |
| SEQ ID NO: 1656<br>SEQUENCE: 1656 | moltype = | length = |

-continued

000

SEQ ID NO: 1657       moltype =    length =
SEQUENCE: 1657
000

SEQ ID NO: 1658       moltype =    length =
SEQUENCE: 1658
000

SEQ ID NO: 1659       moltype =    length =
SEQUENCE: 1659
000

SEQ ID NO: 1660       moltype =    length =
SEQUENCE: 1660
000

SEQ ID NO: 1661       moltype =    length =
SEQUENCE: 1661
000

SEQ ID NO: 1662       moltype =    length =
SEQUENCE: 1662
000

SEQ ID NO: 1663       moltype =    length =
SEQUENCE: 1663
000

SEQ ID NO: 1664       moltype =    length =
SEQUENCE: 1664
000

SEQ ID NO: 1665       moltype =    length =
SEQUENCE: 1665
000

SEQ ID NO: 1666       moltype =    length =
SEQUENCE: 1666
000

SEQ ID NO: 1667       moltype =    length =
SEQUENCE: 1667
000

SEQ ID NO: 1668       moltype =    length =
SEQUENCE: 1668
000

SEQ ID NO: 1669       moltype =    length =
SEQUENCE: 1669
000

SEQ ID NO: 1670       moltype =    length =
SEQUENCE: 1670
000

SEQ ID NO: 1671       moltype =    length =
SEQUENCE: 1671
000

SEQ ID NO: 1672       moltype =    length =
SEQUENCE: 1672
000

SEQ ID NO: 1673       moltype =    length =
SEQUENCE: 1673
000

SEQ ID NO: 1674       moltype =    length =
SEQUENCE: 1674
000

SEQ ID NO: 1675       moltype =    length =
SEQUENCE: 1675
000

SEQ ID NO: 1676       moltype =    length =

SEQUENCE: 1676
000

SEQ ID NO: 1677          moltype =    length =
SEQUENCE: 1677
000

SEQ ID NO: 1678          moltype =    length =
SEQUENCE: 1678
000

SEQ ID NO: 1679          moltype =    length =
SEQUENCE: 1679
000

SEQ ID NO: 1680          moltype =    length =
SEQUENCE: 1680
000

SEQ ID NO: 1681          moltype =    length =
SEQUENCE: 1681
000

SEQ ID NO: 1682          moltype =    length =
SEQUENCE: 1682
000

SEQ ID NO: 1683          moltype =    length =
SEQUENCE: 1683
000

SEQ ID NO: 1684          moltype =    length =
SEQUENCE: 1684
000

SEQ ID NO: 1685          moltype =    length =
SEQUENCE: 1685
000

SEQ ID NO: 1686          moltype =    length =
SEQUENCE: 1686
000

SEQ ID NO: 1687          moltype =    length =
SEQUENCE: 1687
000

SEQ ID NO: 1688          moltype =    length =
SEQUENCE: 1688
000

SEQ ID NO: 1689          moltype =    length =
SEQUENCE: 1689
000

SEQ ID NO: 1690          moltype =    length =
SEQUENCE: 1690
000

SEQ ID NO: 1691          moltype =    length =
SEQUENCE: 1691
000

SEQ ID NO: 1692          moltype =    length =
SEQUENCE: 1692
000

SEQ ID NO: 1693          moltype =    length =
SEQUENCE: 1693
000

SEQ ID NO: 1694          moltype =    length =
SEQUENCE: 1694
000

SEQ ID NO: 1695          moltype =    length =
SEQUENCE: 1695
000

| | | |
|---|---|---|
| SEQ ID NO: 1696 SEQUENCE: 1696 | moltype = | length = 000 |
| SEQ ID NO: 1697 SEQUENCE: 1697 | moltype = | length = 000 |
| SEQ ID NO: 1698 SEQUENCE: 1698 | moltype = | length = 000 |
| SEQ ID NO: 1699 SEQUENCE: 1699 | moltype = | length = 000 |
| SEQ ID NO: 1700 SEQUENCE: 1700 | moltype = | length = 000 |
| SEQ ID NO: 1701 SEQUENCE: 1701 | moltype = | length = 000 |
| SEQ ID NO: 1702 SEQUENCE: 1702 | moltype = | length = 000 |
| SEQ ID NO: 1703 SEQUENCE: 1703 | moltype = | length = 000 |
| SEQ ID NO: 1704 SEQUENCE: 1704 | moltype = | length = 000 |
| SEQ ID NO: 1705 SEQUENCE: 1705 | moltype = | length = 000 |
| SEQ ID NO: 1706 SEQUENCE: 1706 | moltype = | length = 000 |
| SEQ ID NO: 1707 SEQUENCE: 1707 | moltype = | length = 000 |
| SEQ ID NO: 1708 SEQUENCE: 1708 | moltype = | length = 000 |
| SEQ ID NO: 1709 SEQUENCE: 1709 | moltype = | length = 000 |
| SEQ ID NO: 1710 SEQUENCE: 1710 | moltype = | length = 000 |
| SEQ ID NO: 1711 SEQUENCE: 1711 | moltype = | length = 000 |
| SEQ ID NO: 1712 SEQUENCE: 1712 | moltype = | length = 000 |
| SEQ ID NO: 1713 SEQUENCE: 1713 | moltype = | length = 000 |
| SEQ ID NO: 1714 SEQUENCE: 1714 | moltype = | length = 000 |
| SEQ ID NO: 1715 SEQUENCE: 1715 | moltype = | length = 000 |

| | | |
|---|---|---|
| SEQ ID NO: 1716<br>SEQUENCE: 1716<br>000 | moltype = | length = |
| SEQ ID NO: 1717<br>SEQUENCE: 1717<br>000 | moltype = | length = |
| SEQ ID NO: 1718<br>SEQUENCE: 1718<br>000 | moltype = | length = |
| SEQ ID NO: 1719<br>SEQUENCE: 1719<br>000 | moltype = | length = |
| SEQ ID NO: 1720<br>SEQUENCE: 1720<br>000 | moltype = | length = |
| SEQ ID NO: 1721<br>SEQUENCE: 1721<br>000 | moltype = | length = |
| SEQ ID NO: 1722<br>SEQUENCE: 1722<br>000 | moltype = | length = |
| SEQ ID NO: 1723<br>SEQUENCE: 1723<br>000 | moltype = | length = |
| SEQ ID NO: 1724<br>SEQUENCE: 1724<br>000 | moltype = | length = |
| SEQ ID NO: 1725<br>SEQUENCE: 1725<br>000 | moltype = | length = |
| SEQ ID NO: 1726<br>SEQUENCE: 1726<br>000 | moltype = | length = |
| SEQ ID NO: 1727<br>SEQUENCE: 1727<br>000 | moltype = | length = |
| SEQ ID NO: 1728<br>SEQUENCE: 1728<br>000 | moltype = | length = |
| SEQ ID NO: 1729<br>SEQUENCE: 1729<br>000 | moltype = | length = |
| SEQ ID NO: 1730<br>SEQUENCE: 1730<br>000 | moltype = | length = |
| SEQ ID NO: 1731<br>SEQUENCE: 1731<br>000 | moltype = | length = |
| SEQ ID NO: 1732<br>SEQUENCE: 1732<br>000 | moltype = | length = |
| SEQ ID NO: 1733<br>SEQUENCE: 1733<br>000 | moltype = | length = |
| SEQ ID NO: 1734<br>SEQUENCE: 1734<br>000 | moltype = | length = |
| SEQ ID NO: 1735<br>SEQUENCE: 1735 | moltype = | length = |

```
SEQ ID NO: 1736        moltype =    length =
SEQUENCE: 1736
000

SEQ ID NO: 1737        moltype =    length =
SEQUENCE: 1737
000

SEQ ID NO: 1738        moltype =    length =
SEQUENCE: 1738
000

SEQ ID NO: 1739        moltype =    length =
SEQUENCE: 1739
000

SEQ ID NO: 1740        moltype =    length =
SEQUENCE: 1740
000

SEQ ID NO: 1741        moltype =    length =
SEQUENCE: 1741
000

SEQ ID NO: 1742        moltype =    length =
SEQUENCE: 1742
000

SEQ ID NO: 1743        moltype =    length =
SEQUENCE: 1743
000

SEQ ID NO: 1744        moltype =    length =
SEQUENCE: 1744
000

SEQ ID NO: 1745        moltype =    length =
SEQUENCE: 1745
000

SEQ ID NO: 1746        moltype =    length =
SEQUENCE: 1746
000

SEQ ID NO: 1747        moltype =    length =
SEQUENCE: 1747
000

SEQ ID NO: 1748        moltype =    length =
SEQUENCE: 1748
000

SEQ ID NO: 1749        moltype =    length =
SEQUENCE: 1749
000

SEQ ID NO: 1750        moltype =    length =
SEQUENCE: 1750
000

SEQ ID NO: 1751        moltype =    length =
SEQUENCE: 1751
000

SEQ ID NO: 1752        moltype =    length =
SEQUENCE: 1752
000

SEQ ID NO: 1753        moltype =    length =
SEQUENCE: 1753
000

SEQ ID NO: 1754        moltype =    length =
SEQUENCE: 1754
000

SEQ ID NO: 1755        moltype =    length =
```

| | | |
|---|---|---|
| SEQUENCE: 1755 000 | | |
| SEQ ID NO: 1756 SEQUENCE: 1756 000 | moltype = | length = |
| SEQ ID NO: 1757 SEQUENCE: 1757 000 | moltype = | length = |
| SEQ ID NO: 1758 SEQUENCE: 1758 000 | moltype = | length = |
| SEQ ID NO: 1759 SEQUENCE: 1759 000 | moltype = | length = |
| SEQ ID NO: 1760 SEQUENCE: 1760 000 | moltype = | length = |
| SEQ ID NO: 1761 SEQUENCE: 1761 000 | moltype = | length = |
| SEQ ID NO: 1762 SEQUENCE: 1762 000 | moltype = | length = |
| SEQ ID NO: 1763 SEQUENCE: 1763 000 | moltype = | length = |
| SEQ ID NO: 1764 SEQUENCE: 1764 000 | moltype = | length = |
| SEQ ID NO: 1765 SEQUENCE: 1765 000 | moltype = | length = |
| SEQ ID NO: 1766 SEQUENCE: 1766 000 | moltype = | length = |
| SEQ ID NO: 1767 SEQUENCE: 1767 000 | moltype = | length = |
| SEQ ID NO: 1768 SEQUENCE: 1768 000 | moltype = | length = |
| SEQ ID NO: 1769 SEQUENCE: 1769 000 | moltype = | length = |
| SEQ ID NO: 1770 SEQUENCE: 1770 000 | moltype = | length = |
| SEQ ID NO: 1771 SEQUENCE: 1771 000 | moltype = | length = |
| SEQ ID NO: 1772 SEQUENCE: 1772 000 | moltype = | length = |
| SEQ ID NO: 1773 SEQUENCE: 1773 000 | moltype = | length = |
| SEQ ID NO: 1774 SEQUENCE: 1774 000 | moltype = | length = |

| | | |
|---|---|---|
| SEQ ID NO: 1775<br>SEQUENCE: 1775 | moltype = | length = 000 |
| SEQ ID NO: 1776<br>SEQUENCE: 1776 | moltype = | length = 000 |
| SEQ ID NO: 1777<br>SEQUENCE: 1777 | moltype = | length = 000 |
| SEQ ID NO: 1778<br>SEQUENCE: 1778 | moltype = | length = 000 |
| SEQ ID NO: 1779<br>SEQUENCE: 1779 | moltype = | length = 000 |
| SEQ ID NO: 1780<br>SEQUENCE: 1780 | moltype = | length = 000 |
| SEQ ID NO: 1781<br>SEQUENCE: 1781 | moltype = | length = 000 |
| SEQ ID NO: 1782<br>SEQUENCE: 1782 | moltype = | length = 000 |
| SEQ ID NO: 1783<br>SEQUENCE: 1783 | moltype = | length = 000 |
| SEQ ID NO: 1784<br>SEQUENCE: 1784 | moltype = | length = 000 |
| SEQ ID NO: 1785<br>SEQUENCE: 1785 | moltype = | length = 000 |
| SEQ ID NO: 1786<br>SEQUENCE: 1786 | moltype = | length = 000 |
| SEQ ID NO: 1787<br>SEQUENCE: 1787 | moltype = | length = 000 |
| SEQ ID NO: 1788<br>SEQUENCE: 1788 | moltype = | length = 000 |
| SEQ ID NO: 1789<br>SEQUENCE: 1789 | moltype = | length = 000 |
| SEQ ID NO: 1790<br>SEQUENCE: 1790 | moltype = | length = 000 |
| SEQ ID NO: 1791<br>SEQUENCE: 1791 | moltype = | length = 000 |
| SEQ ID NO: 1792<br>SEQUENCE: 1792 | moltype = | length = 000 |
| SEQ ID NO: 1793<br>SEQUENCE: 1793 | moltype = | length = 000 |
| SEQ ID NO: 1794<br>SEQUENCE: 1794 | moltype = | length = 000 |

| | | |
|---|---|---|
| SEQ ID NO: 1795
SEQUENCE: 1795
000 | moltype = | length = |
| SEQ ID NO: 1796
SEQUENCE: 1796
000 | moltype = | length = |
| SEQ ID NO: 1797
SEQUENCE: 1797
000 | moltype = | length = |
| SEQ ID NO: 1798
SEQUENCE: 1798
000 | moltype = | length = |
| SEQ ID NO: 1799
SEQUENCE: 1799
000 | moltype = | length = |
| SEQ ID NO: 1800
SEQUENCE: 1800
000 | moltype = | length = |
| SEQ ID NO: 1801
SEQUENCE: 1801
000 | moltype = | length = |
| SEQ ID NO: 1802
SEQUENCE: 1802
000 | moltype = | length = |
| SEQ ID NO: 1803
SEQUENCE: 1803
000 | moltype = | length = |
| SEQ ID NO: 1804
SEQUENCE: 1804
000 | moltype = | length = |
| SEQ ID NO: 1805
SEQUENCE: 1805
000 | moltype = | length = |
| SEQ ID NO: 1806
SEQUENCE: 1806
000 | moltype = | length = |
| SEQ ID NO: 1807
SEQUENCE: 1807
000 | moltype = | length = |
| SEQ ID NO: 1808
SEQUENCE: 1808
000 | moltype = | length = |
| SEQ ID NO: 1809
SEQUENCE: 1809
000 | moltype = | length = |
| SEQ ID NO: 1810
SEQUENCE: 1810
000 | moltype = | length = |
| SEQ ID NO: 1811
SEQUENCE: 1811
000 | moltype = | length = |
| SEQ ID NO: 1812
SEQUENCE: 1812
000 | moltype = | length = |
| SEQ ID NO: 1813
SEQUENCE: 1813
000 | moltype = | length = |
| SEQ ID NO: 1814
SEQUENCE: 1814 | moltype = | length = |

000

SEQ ID NO: 1815    moltype =    length =
SEQUENCE: 1815
000

SEQ ID NO: 1816    moltype =    length =
SEQUENCE: 1816
000

SEQ ID NO: 1817    moltype =    length =
SEQUENCE: 1817
000

SEQ ID NO: 1818    moltype =    length =
SEQUENCE: 1818
000

SEQ ID NO: 1819    moltype =    length =
SEQUENCE: 1819
000

SEQ ID NO: 1820    moltype =    length =
SEQUENCE: 1820
000

SEQ ID NO: 1821    moltype =    length =
SEQUENCE: 1821
000

SEQ ID NO: 1822    moltype =    length =
SEQUENCE: 1822
000

SEQ ID NO: 1823    moltype =    length =
SEQUENCE: 1823
000

SEQ ID NO: 1824    moltype =    length =
SEQUENCE: 1824
000

SEQ ID NO: 1825    moltype =    length =
SEQUENCE: 1825
000

SEQ ID NO: 1826    moltype =    length =
SEQUENCE: 1826
000

SEQ ID NO: 1827    moltype =    length =
SEQUENCE: 1827
000

SEQ ID NO: 1828    moltype =    length =
SEQUENCE: 1828
000

SEQ ID NO: 1829    moltype =    length =
SEQUENCE: 1829
000

SEQ ID NO: 1830    moltype =    length =
SEQUENCE: 1830
000

SEQ ID NO: 1831    moltype =    length =
SEQUENCE: 1831
000

SEQ ID NO: 1832    moltype =    length =
SEQUENCE: 1832
000

SEQ ID NO: 1833    moltype =    length =
SEQUENCE: 1833
000

SEQ ID NO: 1834    moltype =    length =

| | | |
|---|---|---|
| SEQUENCE: 1834 000 | | |
| SEQ ID NO: 1835 SEQUENCE: 1835 000 | moltype = | length = |
| SEQ ID NO: 1836 SEQUENCE: 1836 000 | moltype = | length = |
| SEQ ID NO: 1837 SEQUENCE: 1837 000 | moltype = | length = |
| SEQ ID NO: 1838 SEQUENCE: 1838 000 | moltype = | length = |
| SEQ ID NO: 1839 SEQUENCE: 1839 000 | moltype = | length = |
| SEQ ID NO: 1840 SEQUENCE: 1840 000 | moltype = | length = |
| SEQ ID NO: 1841 SEQUENCE: 1841 000 | moltype = | length = |
| SEQ ID NO: 1842 SEQUENCE: 1842 000 | moltype = | length = |
| SEQ ID NO: 1843 SEQUENCE: 1843 000 | moltype = | length = |
| SEQ ID NO: 1844 SEQUENCE: 1844 000 | moltype = | length = |
| SEQ ID NO: 1845 SEQUENCE: 1845 000 | moltype = | length = |
| SEQ ID NO: 1846 SEQUENCE: 1846 000 | moltype = | length = |
| SEQ ID NO: 1847 SEQUENCE: 1847 000 | moltype = | length = |
| SEQ ID NO: 1848 SEQUENCE: 1848 000 | moltype = | length = |
| SEQ ID NO: 1849 SEQUENCE: 1849 000 | moltype = | length = |
| SEQ ID NO: 1850 SEQUENCE: 1850 000 | moltype = | length = |
| SEQ ID NO: 1851 SEQUENCE: 1851 000 | moltype = | length = |
| SEQ ID NO: 1852 SEQUENCE: 1852 000 | moltype = | length = |
| SEQ ID NO: 1853 SEQUENCE: 1853 000 | moltype = | length = |

-continued

| | | |
|---|---|---|
| SEQ ID NO: 1854<br>SEQUENCE: 1854<br>000 | moltype = | length = |
| SEQ ID NO: 1855<br>SEQUENCE: 1855<br>000 | moltype = | length = |
| SEQ ID NO: 1856<br>SEQUENCE: 1856<br>000 | moltype = | length = |
| SEQ ID NO: 1857<br>SEQUENCE: 1857<br>000 | moltype = | length = |
| SEQ ID NO: 1858<br>SEQUENCE: 1858<br>000 | moltype = | length = |
| SEQ ID NO: 1859<br>SEQUENCE: 1859<br>000 | moltype = | length = |
| SEQ ID NO: 1860<br>SEQUENCE: 1860<br>000 | moltype = | length = |
| SEQ ID NO: 1861<br>SEQUENCE: 1861<br>000 | moltype = | length = |
| SEQ ID NO: 1862<br>SEQUENCE: 1862<br>000 | moltype = | length = |
| SEQ ID NO: 1863<br>SEQUENCE: 1863<br>000 | moltype = | length = |
| SEQ ID NO: 1864<br>SEQUENCE: 1864<br>000 | moltype = | length = |
| SEQ ID NO: 1865<br>SEQUENCE: 1865<br>000 | moltype = | length = |
| SEQ ID NO: 1866<br>SEQUENCE: 1866<br>000 | moltype = | length = |
| SEQ ID NO: 1867<br>SEQUENCE: 1867<br>000 | moltype = | length = |
| SEQ ID NO: 1868<br>SEQUENCE: 1868<br>000 | moltype = | length = |
| SEQ ID NO: 1869<br>SEQUENCE: 1869<br>000 | moltype = | length = |
| SEQ ID NO: 1870<br>SEQUENCE: 1870<br>000 | moltype = | length = |
| SEQ ID NO: 1871<br>SEQUENCE: 1871<br>000 | moltype = | length = |
| SEQ ID NO: 1872<br>SEQUENCE: 1872<br>000 | moltype = | length = |
| SEQ ID NO: 1873<br>SEQUENCE: 1873<br>000 | moltype = | length = |

SEQ ID NO: 1874        moltype =        length =
SEQUENCE: 1874
000

SEQ ID NO: 1875        moltype =        length =
SEQUENCE: 1875
000

SEQ ID NO: 1876        moltype =        length =
SEQUENCE: 1876
000

SEQ ID NO: 1877        moltype =        length =
SEQUENCE: 1877
000

SEQ ID NO: 1878        moltype =        length =
SEQUENCE: 1878
000

SEQ ID NO: 1879        moltype =        length =
SEQUENCE: 1879
000

SEQ ID NO: 1880        moltype =        length =
SEQUENCE: 1880
000

SEQ ID NO: 1881        moltype =        length =
SEQUENCE: 1881
000

SEQ ID NO: 1882        moltype =        length =
SEQUENCE: 1882
000

SEQ ID NO: 1883        moltype =        length =
SEQUENCE: 1883
000

SEQ ID NO: 1884        moltype =        length =
SEQUENCE: 1884
000

SEQ ID NO: 1885        moltype =        length =
SEQUENCE: 1885
000

SEQ ID NO: 1886        moltype =        length =
SEQUENCE: 1886
000

SEQ ID NO: 1887        moltype =        length =
SEQUENCE: 1887
000

SEQ ID NO: 1888        moltype =        length =
SEQUENCE: 1888
000

SEQ ID NO: 1889        moltype =        length =
SEQUENCE: 1889
000

SEQ ID NO: 1890        moltype =        length =
SEQUENCE: 1890
000

SEQ ID NO: 1891        moltype =        length =
SEQUENCE: 1891
000

SEQ ID NO: 1892        moltype =        length =
SEQUENCE: 1892
000

SEQ ID NO: 1893        moltype =        length =
SEQUENCE: 1893

000

SEQ ID NO: 1894        moltype =    length =
SEQUENCE: 1894
000

SEQ ID NO: 1895        moltype =    length =
SEQUENCE: 1895
000

SEQ ID NO: 1896        moltype =    length =
SEQUENCE: 1896
000

SEQ ID NO: 1897        moltype =    length =
SEQUENCE: 1897
000

SEQ ID NO: 1898        moltype =    length =
SEQUENCE: 1898
000

SEQ ID NO: 1899        moltype =    length =
SEQUENCE: 1899
000

SEQ ID NO: 1900        moltype =    length =
SEQUENCE: 1900
000

SEQ ID NO: 1901        moltype =    length =
SEQUENCE: 1901
000

SEQ ID NO: 1902        moltype =    length =
SEQUENCE: 1902
000

SEQ ID NO: 1903        moltype =    length =
SEQUENCE: 1903
000

SEQ ID NO: 1904        moltype =    length =
SEQUENCE: 1904
000

SEQ ID NO: 1905        moltype =    length =
SEQUENCE: 1905
000

SEQ ID NO: 1906        moltype =    length =
SEQUENCE: 1906
000

SEQ ID NO: 1907        moltype =    length =
SEQUENCE: 1907
000

SEQ ID NO: 1908        moltype =    length =
SEQUENCE: 1908
000

SEQ ID NO: 1909        moltype =    length =
SEQUENCE: 1909
000

SEQ ID NO: 1910        moltype =    length =
SEQUENCE: 1910
000

SEQ ID NO: 1911        moltype =    length =
SEQUENCE: 1911
000

SEQ ID NO: 1912        moltype =    length =
SEQUENCE: 1912
000

SEQ ID NO: 1913        moltype =    length =

-continued

```
SEQUENCE: 1913
000

SEQ ID NO: 1914          moltype =     length =
SEQUENCE: 1914
000

SEQ ID NO: 1915          moltype =     length =
SEQUENCE: 1915
000

SEQ ID NO: 1916          moltype =     length =
SEQUENCE: 1916
000

SEQ ID NO: 1917          moltype =     length =
SEQUENCE: 1917
000

SEQ ID NO: 1918          moltype =     length =
SEQUENCE: 1918
000

SEQ ID NO: 1919          moltype =     length =
SEQUENCE: 1919
000

SEQ ID NO: 1920          moltype =     length =
SEQUENCE: 1920
000

SEQ ID NO: 1921          moltype =     length =
SEQUENCE: 1921
000

SEQ ID NO: 1922          moltype =     length =
SEQUENCE: 1922
000

SEQ ID NO: 1923          moltype =     length =
SEQUENCE: 1923
000

SEQ ID NO: 1924          moltype =     length =
SEQUENCE: 1924
000

SEQ ID NO: 1925          moltype =     length =
SEQUENCE: 1925
000

SEQ ID NO: 1926          moltype =     length =
SEQUENCE: 1926
000

SEQ ID NO: 1927          moltype =     length =
SEQUENCE: 1927
000

SEQ ID NO: 1928          moltype =     length =
SEQUENCE: 1928
000

SEQ ID NO: 1929          moltype =     length =
SEQUENCE: 1929
000

SEQ ID NO: 1930          moltype =     length =
SEQUENCE: 1930
000

SEQ ID NO: 1931          moltype =     length =
SEQUENCE: 1931
000

SEQ ID NO: 1932          moltype =     length =
SEQUENCE: 1932
000
```

| | | |
|---|---|---|
| SEQ ID NO: 1933<br>SEQUENCE: 1933 | moltype =<br>000 | length = |
| SEQ ID NO: 1934<br>SEQUENCE: 1934 | moltype =<br>000 | length = |
| SEQ ID NO: 1935<br>SEQUENCE: 1935 | moltype =<br>000 | length = |
| SEQ ID NO: 1936<br>SEQUENCE: 1936 | moltype =<br>000 | length = |
| SEQ ID NO: 1937<br>SEQUENCE: 1937 | moltype =<br>000 | length = |
| SEQ ID NO: 1938<br>SEQUENCE: 1938 | moltype =<br>000 | length = |
| SEQ ID NO: 1939<br>SEQUENCE: 1939 | moltype =<br>000 | length = |
| SEQ ID NO: 1940<br>SEQUENCE: 1940 | moltype =<br>000 | length = |
| SEQ ID NO: 1941<br>SEQUENCE: 1941 | moltype =<br>000 | length = |
| SEQ ID NO: 1942<br>SEQUENCE: 1942 | moltype =<br>000 | length = |
| SEQ ID NO: 1943<br>SEQUENCE: 1943 | moltype =<br>000 | length = |
| SEQ ID NO: 1944<br>SEQUENCE: 1944 | moltype =<br>000 | length = |
| SEQ ID NO: 1945<br>SEQUENCE: 1945 | moltype =<br>000 | length = |
| SEQ ID NO: 1946<br>SEQUENCE: 1946 | moltype =<br>000 | length = |
| SEQ ID NO: 1947<br>SEQUENCE: 1947 | moltype =<br>000 | length = |
| SEQ ID NO: 1948<br>SEQUENCE: 1948 | moltype =<br>000 | length = |
| SEQ ID NO: 1949<br>SEQUENCE: 1949 | moltype =<br>000 | length = |
| SEQ ID NO: 1950<br>SEQUENCE: 1950 | moltype =<br>000 | length = |
| SEQ ID NO: 1951<br>SEQUENCE: 1951 | moltype =<br>000 | length = |
| SEQ ID NO: 1952<br>SEQUENCE: 1952 | moltype =<br>000 | length = |

| | | |
|---|---|---|
| SEQ ID NO: 1953<br>SEQUENCE: 1953<br>000 | moltype = | length = |
| SEQ ID NO: 1954<br>SEQUENCE: 1954<br>000 | moltype = | length = |
| SEQ ID NO: 1955<br>SEQUENCE: 1955<br>000 | moltype = | length = |
| SEQ ID NO: 1956<br>SEQUENCE: 1956<br>000 | moltype = | length = |
| SEQ ID NO: 1957<br>SEQUENCE: 1957<br>000 | moltype = | length = |
| SEQ ID NO: 1958<br>SEQUENCE: 1958<br>000 | moltype = | length = |
| SEQ ID NO: 1959<br>SEQUENCE: 1959<br>000 | moltype = | length = |
| SEQ ID NO: 1960<br>SEQUENCE: 1960<br>000 | moltype = | length = |
| SEQ ID NO: 1961<br>SEQUENCE: 1961<br>000 | moltype = | length = |
| SEQ ID NO: 1962<br>SEQUENCE: 1962<br>000 | moltype = | length = |
| SEQ ID NO: 1963<br>SEQUENCE: 1963<br>000 | moltype = | length = |
| SEQ ID NO: 1964<br>SEQUENCE: 1964<br>000 | moltype = | length = |
| SEQ ID NO: 1965<br>SEQUENCE: 1965<br>000 | moltype = | length = |
| SEQ ID NO: 1966<br>SEQUENCE: 1966<br>000 | moltype = | length = |
| SEQ ID NO: 1967<br>SEQUENCE: 1967<br>000 | moltype = | length = |
| SEQ ID NO: 1968<br>SEQUENCE: 1968<br>000 | moltype = | length = |
| SEQ ID NO: 1969<br>SEQUENCE: 1969<br>000 | moltype = | length = |
| SEQ ID NO: 1970<br>SEQUENCE: 1970<br>000 | moltype = | length = |
| SEQ ID NO: 1971<br>SEQUENCE: 1971<br>000 | moltype = | length = |
| SEQ ID NO: 1972<br>SEQUENCE: 1972 | moltype = | length = |

```
SEQ ID NO: 1973       moltype =      length =
SEQUENCE: 1973
000

SEQ ID NO: 1974       moltype =      length =
SEQUENCE: 1974
000

SEQ ID NO: 1975       moltype =      length =
SEQUENCE: 1975
000

SEQ ID NO: 1976       moltype =      length =
SEQUENCE: 1976
000

SEQ ID NO: 1977       moltype =      length =
SEQUENCE: 1977
000

SEQ ID NO: 1978       moltype =      length =
SEQUENCE: 1978
000

SEQ ID NO: 1979       moltype =      length =
SEQUENCE: 1979
000

SEQ ID NO: 1980       moltype =      length =
SEQUENCE: 1980
000

SEQ ID NO: 1981       moltype =      length =
SEQUENCE: 1981
000

SEQ ID NO: 1982       moltype =      length =
SEQUENCE: 1982
000

SEQ ID NO: 1983       moltype =      length =
SEQUENCE: 1983
000

SEQ ID NO: 1984       moltype =      length =
SEQUENCE: 1984
000

SEQ ID NO: 1985       moltype =      length =
SEQUENCE: 1985
000

SEQ ID NO: 1986       moltype =      length =
SEQUENCE: 1986
000

SEQ ID NO: 1987       moltype =      length =
SEQUENCE: 1987
000

SEQ ID NO: 1988       moltype =      length =
SEQUENCE: 1988
000

SEQ ID NO: 1989       moltype =      length =
SEQUENCE: 1989
000

SEQ ID NO: 1990       moltype =      length =
SEQUENCE: 1990
000

SEQ ID NO: 1991       moltype =      length =
SEQUENCE: 1991
000

SEQ ID NO: 1992       moltype =      length =
```

| | | |
|---|---|---|
| SEQUENCE: 1992 000 | | |
| SEQ ID NO: 1993 SEQUENCE: 1993 000 | moltype = | length = |
| SEQ ID NO: 1994 SEQUENCE: 1994 000 | moltype = | length = |
| SEQ ID NO: 1995 SEQUENCE: 1995 000 | moltype = | length = |
| SEQ ID NO: 1996 SEQUENCE: 1996 000 | moltype = | length = |
| SEQ ID NO: 1997 SEQUENCE: 1997 000 | moltype = | length = |
| SEQ ID NO: 1998 SEQUENCE: 1998 000 | moltype = | length = |
| SEQ ID NO: 1999 SEQUENCE: 1999 000 | moltype = | length = |
| SEQ ID NO: 2000 SEQUENCE: 2000 000 | moltype = | length = |
| SEQ ID NO: 2001 SEQUENCE: 2001 000 | moltype = | length = |
| SEQ ID NO: 2002 SEQUENCE: 2002 000 | moltype = | length = |
| SEQ ID NO: 2003 SEQUENCE: 2003 000 | moltype = | length = |
| SEQ ID NO: 2004 SEQUENCE: 2004 000 | moltype = | length = |
| SEQ ID NO: 2005 SEQUENCE: 2005 000 | moltype = | length = |
| SEQ ID NO: 2006 SEQUENCE: 2006 000 | moltype = | length = |
| SEQ ID NO: 2007 SEQUENCE: 2007 000 | moltype = | length = |
| SEQ ID NO: 2008 SEQUENCE: 2008 000 | moltype = | length = |
| SEQ ID NO: 2009 SEQUENCE: 2009 000 | moltype = | length = |
| SEQ ID NO: 2010 SEQUENCE: 2010 000 | moltype = | length = |
| SEQ ID NO: 2011 SEQUENCE: 2011 000 | moltype = | length = |

| | | |
|---|---|---|
| SEQ ID NO: 2012<br>SEQUENCE: 2012 | moltype = | length = 000 |
| SEQ ID NO: 2013<br>SEQUENCE: 2013 | moltype = | length = 000 |
| SEQ ID NO: 2014<br>SEQUENCE: 2014 | moltype = | length = 000 |
| SEQ ID NO: 2015<br>SEQUENCE: 2015 | moltype = | length = 000 |
| SEQ ID NO: 2016<br>SEQUENCE: 2016 | moltype = | length = 000 |
| SEQ ID NO: 2017<br>SEQUENCE: 2017 | moltype = | length = 000 |
| SEQ ID NO: 2018<br>SEQUENCE: 2018 | moltype = | length = 000 |
| SEQ ID NO: 2019<br>SEQUENCE: 2019 | moltype = | length = 000 |
| SEQ ID NO: 2020<br>SEQUENCE: 2020 | moltype = | length = 000 |
| SEQ ID NO: 2021<br>SEQUENCE: 2021 | moltype = | length = 000 |
| SEQ ID NO: 2022<br>SEQUENCE: 2022 | moltype = | length = 000 |
| SEQ ID NO: 2023<br>SEQUENCE: 2023 | moltype = | length = 000 |
| SEQ ID NO: 2024<br>SEQUENCE: 2024 | moltype = | length = 000 |
| SEQ ID NO: 2025<br>SEQUENCE: 2025 | moltype = | length = 000 |
| SEQ ID NO: 2026<br>SEQUENCE: 2026 | moltype = | length = 000 |
| SEQ ID NO: 2027<br>SEQUENCE: 2027 | moltype = | length = 000 |
| SEQ ID NO: 2028<br>SEQUENCE: 2028 | moltype = | length = 000 |
| SEQ ID NO: 2029<br>SEQUENCE: 2029 | moltype = | length = 000 |
| SEQ ID NO: 2030<br>SEQUENCE: 2030 | moltype = | length = 000 |
| SEQ ID NO: 2031<br>SEQUENCE: 2031 | moltype = | length = 000 |

SEQ ID NO: 2032         moltype =    length =
SEQUENCE: 2032
000

SEQ ID NO: 2033         moltype =    length =
SEQUENCE: 2033
000

SEQ ID NO: 2034         moltype =    length =
SEQUENCE: 2034
000

SEQ ID NO: 2035         moltype =    length =
SEQUENCE: 2035
000

SEQ ID NO: 2036         moltype =    length =
SEQUENCE: 2036
000

SEQ ID NO: 2037         moltype =    length =
SEQUENCE: 2037
000

SEQ ID NO: 2038         moltype =    length =
SEQUENCE: 2038
000

SEQ ID NO: 2039         moltype =    length =
SEQUENCE: 2039
000

SEQ ID NO: 2040         moltype =    length =
SEQUENCE: 2040
000

SEQ ID NO: 2041         moltype =    length =
SEQUENCE: 2041
000

SEQ ID NO: 2042         moltype =    length =
SEQUENCE: 2042
000

SEQ ID NO: 2043         moltype =    length =
SEQUENCE: 2043
000

SEQ ID NO: 2044         moltype =    length =
SEQUENCE: 2044
000

SEQ ID NO: 2045         moltype =    length =
SEQUENCE: 2045
000

SEQ ID NO: 2046         moltype =    length =
SEQUENCE: 2046
000

SEQ ID NO: 2047         moltype =    length =
SEQUENCE: 2047
000

SEQ ID NO: 2048         moltype =    length =
SEQUENCE: 2048
000

SEQ ID NO: 2049         moltype =    length =
SEQUENCE: 2049
000

SEQ ID NO: 2050         moltype =    length =
SEQUENCE: 2050
000

SEQ ID NO: 2051         moltype =    length =
SEQUENCE: 2051

```
000

SEQ ID NO: 2052          moltype =     length =
SEQUENCE: 2052
000

SEQ ID NO: 2053          moltype =     length =
SEQUENCE: 2053
000

SEQ ID NO: 2054          moltype =     length =
SEQUENCE: 2054
000

SEQ ID NO: 2055          moltype =     length =
SEQUENCE: 2055
000

SEQ ID NO: 2056          moltype =     length =
SEQUENCE: 2056
000

SEQ ID NO: 2057          moltype =     length =
SEQUENCE: 2057
000

SEQ ID NO: 2058          moltype =     length =
SEQUENCE: 2058
000

SEQ ID NO: 2059          moltype =     length =
SEQUENCE: 2059
000

SEQ ID NO: 2060          moltype =     length =
SEQUENCE: 2060
000

SEQ ID NO: 2061          moltype =     length =
SEQUENCE: 2061
000

SEQ ID NO: 2062          moltype =     length =
SEQUENCE: 2062
000

SEQ ID NO: 2063          moltype =     length =
SEQUENCE: 2063
000

SEQ ID NO: 2064          moltype =     length =
SEQUENCE: 2064
000

SEQ ID NO: 2065          moltype =     length =
SEQUENCE: 2065
000

SEQ ID NO: 2066          moltype =     length =
SEQUENCE: 2066
000

SEQ ID NO: 2067          moltype =     length =
SEQUENCE: 2067
000

SEQ ID NO: 2068          moltype =     length =
SEQUENCE: 2068
000

SEQ ID NO: 2069          moltype =     length =
SEQUENCE: 2069
000

SEQ ID NO: 2070          moltype =     length =
SEQUENCE: 2070
000

SEQ ID NO: 2071          moltype =     length =
```

| | | |
|---|---|---|
| SEQUENCE: 2071 000 | | |
| SEQ ID NO: 2072 SEQUENCE: 2072 000 | moltype = | length = |
| SEQ ID NO: 2073 SEQUENCE: 2073 000 | moltype = | length = |
| SEQ ID NO: 2074 SEQUENCE: 2074 000 | moltype = | length = |
| SEQ ID NO: 2075 SEQUENCE: 2075 000 | moltype = | length = |
| SEQ ID NO: 2076 SEQUENCE: 2076 000 | moltype = | length = |
| SEQ ID NO: 2077 SEQUENCE: 2077 000 | moltype = | length = |
| SEQ ID NO: 2078 SEQUENCE: 2078 000 | moltype = | length = |
| SEQ ID NO: 2079 SEQUENCE: 2079 000 | moltype = | length = |
| SEQ ID NO: 2080 SEQUENCE: 2080 000 | moltype = | length = |
| SEQ ID NO: 2081 SEQUENCE: 2081 000 | moltype = | length = |
| SEQ ID NO: 2082 SEQUENCE: 2082 000 | moltype = | length = |
| SEQ ID NO: 2083 SEQUENCE: 2083 000 | moltype = | length = |
| SEQ ID NO: 2084 SEQUENCE: 2084 000 | moltype = | length = |
| SEQ ID NO: 2085 SEQUENCE: 2085 000 | moltype = | length = |
| SEQ ID NO: 2086 SEQUENCE: 2086 000 | moltype = | length = |
| SEQ ID NO: 2087 SEQUENCE: 2087 000 | moltype = | length = |
| SEQ ID NO: 2088 SEQUENCE: 2088 000 | moltype = | length = |
| SEQ ID NO: 2089 SEQUENCE: 2089 000 | moltype = | length = |
| SEQ ID NO: 2090 SEQUENCE: 2090 000 | moltype = | length = |

| | | |
|---|---|---|
| SEQ ID NO: 2091 SEQUENCE: 2091 | moltype = 000 | length = |
| SEQ ID NO: 2092 SEQUENCE: 2092 | moltype = 000 | length = |
| SEQ ID NO: 2093 SEQUENCE: 2093 | moltype = 000 | length = |
| SEQ ID NO: 2094 SEQUENCE: 2094 | moltype = 000 | length = |
| SEQ ID NO: 2095 SEQUENCE: 2095 | moltype = 000 | length = |
| SEQ ID NO: 2096 SEQUENCE: 2096 | moltype = 000 | length = |
| SEQ ID NO: 2097 SEQUENCE: 2097 | moltype = 000 | length = |
| SEQ ID NO: 2098 SEQUENCE: 2098 | moltype = 000 | length = |
| SEQ ID NO: 2099 SEQUENCE: 2099 | moltype = 000 | length = |
| SEQ ID NO: 2100 SEQUENCE: 2100 | moltype = 000 | length = |
| SEQ ID NO: 2101 SEQUENCE: 2101 | moltype = 000 | length = |
| SEQ ID NO: 2102 SEQUENCE: 2102 | moltype = 000 | length = |
| SEQ ID NO: 2103 SEQUENCE: 2103 | moltype = 000 | length = |
| SEQ ID NO: 2104 SEQUENCE: 2104 | moltype = 000 | length = |
| SEQ ID NO: 2105 SEQUENCE: 2105 | moltype = 000 | length = |
| SEQ ID NO: 2106 SEQUENCE: 2106 | moltype = 000 | length = |
| SEQ ID NO: 2107 SEQUENCE: 2107 | moltype = 000 | length = |
| SEQ ID NO: 2108 SEQUENCE: 2108 | moltype = 000 | length = |
| SEQ ID NO: 2109 SEQUENCE: 2109 | moltype = 000 | length = |
| SEQ ID NO: 2110 SEQUENCE: 2110 | moltype = 000 | length = |

| | | |
|---|---|---|
| SEQ ID NO: 2111<br>SEQUENCE: 2111<br>000 | moltype = | length = |
| SEQ ID NO: 2112<br>SEQUENCE: 2112<br>000 | moltype = | length = |
| SEQ ID NO: 2113<br>SEQUENCE: 2113<br>000 | moltype = | length = |
| SEQ ID NO: 2114<br>SEQUENCE: 2114<br>000 | moltype = | length = |
| SEQ ID NO: 2115<br>SEQUENCE: 2115<br>000 | moltype = | length = |
| SEQ ID NO: 2116<br>SEQUENCE: 2116<br>000 | moltype = | length = |
| SEQ ID NO: 2117<br>SEQUENCE: 2117<br>000 | moltype = | length = |
| SEQ ID NO: 2118<br>SEQUENCE: 2118<br>000 | moltype = | length = |
| SEQ ID NO: 2119<br>SEQUENCE: 2119<br>000 | moltype = | length = |
| SEQ ID NO: 2120<br>SEQUENCE: 2120<br>000 | moltype = | length = |
| SEQ ID NO: 2121<br>SEQUENCE: 2121<br>000 | moltype = | length = |
| SEQ ID NO: 2122<br>SEQUENCE: 2122<br>000 | moltype = | length = |
| SEQ ID NO: 2123<br>SEQUENCE: 2123<br>000 | moltype = | length = |
| SEQ ID NO: 2124<br>SEQUENCE: 2124<br>000 | moltype = | length = |
| SEQ ID NO: 2125<br>SEQUENCE: 2125<br>000 | moltype = | length = |
| SEQ ID NO: 2126<br>SEQUENCE: 2126<br>000 | moltype = | length = |
| SEQ ID NO: 2127<br>SEQUENCE: 2127<br>000 | moltype = | length = |
| SEQ ID NO: 2128<br>SEQUENCE: 2128<br>000 | moltype = | length = |
| SEQ ID NO: 2129<br>SEQUENCE: 2129<br>000 | moltype = | length = |
| SEQ ID NO: 2130<br>SEQUENCE: 2130 | moltype = | length = |

000

SEQ ID NO: 2131    moltype =    length =
SEQUENCE: 2131
000

SEQ ID NO: 2132    moltype =    length =
SEQUENCE: 2132
000

SEQ ID NO: 2133    moltype =    length =
SEQUENCE: 2133
000

SEQ ID NO: 2134    moltype =    length =
SEQUENCE: 2134
000

SEQ ID NO: 2135    moltype =    length =
SEQUENCE: 2135
000

SEQ ID NO: 2136    moltype =    length =
SEQUENCE: 2136
000

SEQ ID NO: 2137    moltype =    length =
SEQUENCE: 2137
000

SEQ ID NO: 2138    moltype =    length =
SEQUENCE: 2138
000

SEQ ID NO: 2139    moltype =    length =
SEQUENCE: 2139
000

SEQ ID NO: 2140    moltype =    length =
SEQUENCE: 2140
000

SEQ ID NO: 2141    moltype =    length =
SEQUENCE: 2141
000

SEQ ID NO: 2142    moltype =    length =
SEQUENCE: 2142
000

SEQ ID NO: 2143    moltype =    length =
SEQUENCE: 2143
000

SEQ ID NO: 2144    moltype =    length =
SEQUENCE: 2144
000

SEQ ID NO: 2145    moltype =    length =
SEQUENCE: 2145
000

SEQ ID NO: 2146    moltype =    length =
SEQUENCE: 2146
000

SEQ ID NO: 2147    moltype =    length =
SEQUENCE: 2147
000

SEQ ID NO: 2148    moltype =    length =
SEQUENCE: 2148
000

SEQ ID NO: 2149    moltype =    length =
SEQUENCE: 2149
000

SEQ ID NO: 2150    moltype =    length =

-continued

```
SEQUENCE: 2150
000

SEQ ID NO: 2151         moltype =    length =
SEQUENCE: 2151
000

SEQ ID NO: 2152         moltype =    length =
SEQUENCE: 2152
000

SEQ ID NO: 2153         moltype =    length =
SEQUENCE: 2153
000

SEQ ID NO: 2154         moltype =    length =
SEQUENCE: 2154
000

SEQ ID NO: 2155         moltype =    length =
SEQUENCE: 2155
000

SEQ ID NO: 2156         moltype =    length =
SEQUENCE: 2156
000

SEQ ID NO: 2157         moltype =    length =
SEQUENCE: 2157
000

SEQ ID NO: 2158         moltype =    length =
SEQUENCE: 2158
000

SEQ ID NO: 2159         moltype =    length =
SEQUENCE: 2159
000

SEQ ID NO: 2160         moltype =    length =
SEQUENCE: 2160
000

SEQ ID NO: 2161         moltype =    length =
SEQUENCE: 2161
000

SEQ ID NO: 2162         moltype =    length =
SEQUENCE: 2162
000

SEQ ID NO: 2163         moltype =    length =
SEQUENCE: 2163
000

SEQ ID NO: 2164         moltype =    length =
SEQUENCE: 2164
000

SEQ ID NO: 2165         moltype =    length =
SEQUENCE: 2165
000

SEQ ID NO: 2166         moltype =    length =
SEQUENCE: 2166
000

SEQ ID NO: 2167         moltype =    length =
SEQUENCE: 2167
000

SEQ ID NO: 2168         moltype =    length =
SEQUENCE: 2168
000

SEQ ID NO: 2169         moltype =    length =
SEQUENCE: 2169
000
```

-continued

| | | |
|---|---|---|
| SEQ ID NO: 2170 SEQUENCE: 2170 | moltype = | length = 000 |
| SEQ ID NO: 2171 SEQUENCE: 2171 | moltype = | length = 000 |
| SEQ ID NO: 2172 SEQUENCE: 2172 | moltype = | length = 000 |
| SEQ ID NO: 2173 SEQUENCE: 2173 | moltype = | length = 000 |
| SEQ ID NO: 2174 SEQUENCE: 2174 | moltype = | length = 000 |
| SEQ ID NO: 2175 SEQUENCE: 2175 | moltype = | length = 000 |
| SEQ ID NO: 2176 SEQUENCE: 2176 | moltype = | length = 000 |
| SEQ ID NO: 2177 SEQUENCE: 2177 | moltype = | length = 000 |
| SEQ ID NO: 2178 SEQUENCE: 2178 | moltype = | length = 000 |
| SEQ ID NO: 2179 SEQUENCE: 2179 | moltype = | length = 000 |
| SEQ ID NO: 2180 SEQUENCE: 2180 | moltype = | length = 000 |
| SEQ ID NO: 2181 SEQUENCE: 2181 | moltype = | length = 000 |
| SEQ ID NO: 2182 SEQUENCE: 2182 | moltype = | length = 000 |
| SEQ ID NO: 2183 SEQUENCE: 2183 | moltype = | length = 000 |
| SEQ ID NO: 2184 SEQUENCE: 2184 | moltype = | length = 000 |
| SEQ ID NO: 2185 SEQUENCE: 2185 | moltype = | length = 000 |
| SEQ ID NO: 2186 SEQUENCE: 2186 | moltype = | length = 000 |
| SEQ ID NO: 2187 SEQUENCE: 2187 | moltype = | length = 000 |
| SEQ ID NO: 2188 SEQUENCE: 2188 | moltype = | length = 000 |
| SEQ ID NO: 2189 SEQUENCE: 2189 | moltype = | length = 000 |

SEQ ID NO: 2190         moltype =         length =
SEQUENCE: 2190
000

SEQ ID NO: 2191         moltype =         length =
SEQUENCE: 2191
000

SEQ ID NO: 2192         moltype =         length =
SEQUENCE: 2192
000

SEQ ID NO: 2193         moltype =         length =
SEQUENCE: 2193
000

SEQ ID NO: 2194         moltype =         length =
SEQUENCE: 2194
000

SEQ ID NO: 2195         moltype =         length =
SEQUENCE: 2195
000

SEQ ID NO: 2196         moltype =         length =
SEQUENCE: 2196
000

SEQ ID NO: 2197         moltype =         length =
SEQUENCE: 2197
000

SEQ ID NO: 2198         moltype =         length =
SEQUENCE: 2198
000

SEQ ID NO: 2199         moltype =         length =
SEQUENCE: 2199
000

SEQ ID NO: 2200         moltype =         length =
SEQUENCE: 2200
000

SEQ ID NO: 2201         moltype =         length =
SEQUENCE: 2201
000

SEQ ID NO: 2202         moltype =         length =
SEQUENCE: 2202
000

SEQ ID NO: 2203         moltype =         length =
SEQUENCE: 2203
000

SEQ ID NO: 2204         moltype =         length =
SEQUENCE: 2204
000

SEQ ID NO: 2205         moltype =         length =
SEQUENCE: 2205
000

SEQ ID NO: 2206         moltype =         length =
SEQUENCE: 2206
000

SEQ ID NO: 2207         moltype =         length =
SEQUENCE: 2207
000

SEQ ID NO: 2208         moltype =         length =
SEQUENCE: 2208
000

SEQ ID NO: 2209         moltype =         length =
SEQUENCE: 2209

000

SEQ ID NO: 2210      moltype =      length =
SEQUENCE: 2210
000

SEQ ID NO: 2211      moltype =      length =
SEQUENCE: 2211
000

SEQ ID NO: 2212      moltype =      length =
SEQUENCE: 2212
000

SEQ ID NO: 2213      moltype =      length =
SEQUENCE: 2213
000

SEQ ID NO: 2214      moltype =      length =
SEQUENCE: 2214
000

SEQ ID NO: 2215      moltype =      length =
SEQUENCE: 2215
000

SEQ ID NO: 2216      moltype =      length =
SEQUENCE: 2216
000

SEQ ID NO: 2217      moltype =      length =
SEQUENCE: 2217
000

SEQ ID NO: 2218      moltype =      length =
SEQUENCE: 2218
000

SEQ ID NO: 2219      moltype =      length =
SEQUENCE: 2219
000

SEQ ID NO: 2220      moltype =      length =
SEQUENCE: 2220
000

SEQ ID NO: 2221      moltype =      length =
SEQUENCE: 2221
000

SEQ ID NO: 2222      moltype =      length =
SEQUENCE: 2222
000

SEQ ID NO: 2223      moltype =      length =
SEQUENCE: 2223
000

SEQ ID NO: 2224      moltype =      length =
SEQUENCE: 2224
000

SEQ ID NO: 2225      moltype =      length =
SEQUENCE: 2225
000

SEQ ID NO: 2226      moltype =      length =
SEQUENCE: 2226
000

SEQ ID NO: 2227      moltype =      length =
SEQUENCE: 2227
000

SEQ ID NO: 2228      moltype =      length =
SEQUENCE: 2228
000

SEQ ID NO: 2229      moltype =      length =

| | | |
|---|---|---|
| SEQUENCE: 2229 000 | | |
| SEQ ID NO: 2230 SEQUENCE: 2230 000 | moltype = | length = |
| SEQ ID NO: 2231 SEQUENCE: 2231 000 | moltype = | length = |
| SEQ ID NO: 2232 SEQUENCE: 2232 000 | moltype = | length = |
| SEQ ID NO: 2233 SEQUENCE: 2233 000 | moltype = | length = |
| SEQ ID NO: 2234 SEQUENCE: 2234 000 | moltype = | length = |
| SEQ ID NO: 2235 SEQUENCE: 2235 000 | moltype = | length = |
| SEQ ID NO: 2236 SEQUENCE: 2236 000 | moltype = | length = |
| SEQ ID NO: 2237 SEQUENCE: 2237 000 | moltype = | length = |
| SEQ ID NO: 2238 SEQUENCE: 2238 000 | moltype = | length = |
| SEQ ID NO: 2239 SEQUENCE: 2239 000 | moltype = | length = |
| SEQ ID NO: 2240 SEQUENCE: 2240 000 | moltype = | length = |
| SEQ ID NO: 2241 SEQUENCE: 2241 000 | moltype = | length = |
| SEQ ID NO: 2242 SEQUENCE: 2242 000 | moltype = | length = |
| SEQ ID NO: 2243 SEQUENCE: 2243 000 | moltype = | length = |
| SEQ ID NO: 2244 SEQUENCE: 2244 000 | moltype = | length = |
| SEQ ID NO: 2245 SEQUENCE: 2245 000 | moltype = | length = |
| SEQ ID NO: 2246 SEQUENCE: 2246 000 | moltype = | length = |
| SEQ ID NO: 2247 SEQUENCE: 2247 000 | moltype = | length = |
| SEQ ID NO: 2248 SEQUENCE: 2248 000 | moltype = | length = |

| | | |
|---|---|---|
| SEQ ID NO: 2249 SEQUENCE: 2249 | moltype = | length = 000 |
| SEQ ID NO: 2250 SEQUENCE: 2250 | moltype = | length = 000 |
| SEQ ID NO: 2251 SEQUENCE: 2251 | moltype = | length = 000 |
| SEQ ID NO: 2252 SEQUENCE: 2252 | moltype = | length = 000 |
| SEQ ID NO: 2253 SEQUENCE: 2253 | moltype = | length = 000 |
| SEQ ID NO: 2254 SEQUENCE: 2254 | moltype = | length = 000 |
| SEQ ID NO: 2255 SEQUENCE: 2255 | moltype = | length = 000 |
| SEQ ID NO: 2256 SEQUENCE: 2256 | moltype = | length = 000 |
| SEQ ID NO: 2257 SEQUENCE: 2257 | moltype = | length = 000 |
| SEQ ID NO: 2258 SEQUENCE: 2258 | moltype = | length = 000 |
| SEQ ID NO: 2259 SEQUENCE: 2259 | moltype = | length = 000 |
| SEQ ID NO: 2260 SEQUENCE: 2260 | moltype = | length = 000 |
| SEQ ID NO: 2261 SEQUENCE: 2261 | moltype = | length = 000 |
| SEQ ID NO: 2262 SEQUENCE: 2262 | moltype = | length = 000 |
| SEQ ID NO: 2263 SEQUENCE: 2263 | moltype = | length = 000 |
| SEQ ID NO: 2264 SEQUENCE: 2264 | moltype = | length = 000 |
| SEQ ID NO: 2265 SEQUENCE: 2265 | moltype = | length = 000 |
| SEQ ID NO: 2266 SEQUENCE: 2266 | moltype = | length = 000 |
| SEQ ID NO: 2267 SEQUENCE: 2267 | moltype = | length = 000 |
| SEQ ID NO: 2268 SEQUENCE: 2268 | moltype = | length = 000 |

SEQ ID NO: 2269            moltype =     length =
SEQUENCE: 2269
000

SEQ ID NO: 2270            moltype =     length =
SEQUENCE: 2270
000

SEQ ID NO: 2271            moltype =     length =
SEQUENCE: 2271
000

SEQ ID NO: 2272            moltype =     length =
SEQUENCE: 2272
000

SEQ ID NO: 2273            moltype =     length =
SEQUENCE: 2273
000

SEQ ID NO: 2274            moltype =     length =
SEQUENCE: 2274
000

SEQ ID NO: 2275            moltype =     length =
SEQUENCE: 2275
000

SEQ ID NO: 2276            moltype =     length =
SEQUENCE: 2276
000

SEQ ID NO: 2277            moltype =     length =
SEQUENCE: 2277
000

SEQ ID NO: 2278            moltype =     length =
SEQUENCE: 2278
000

SEQ ID NO: 2279            moltype =     length =
SEQUENCE: 2279
000

SEQ ID NO: 2280            moltype =     length =
SEQUENCE: 2280
000

SEQ ID NO: 2281            moltype =     length =
SEQUENCE: 2281
000

SEQ ID NO: 2282            moltype =     length =
SEQUENCE: 2282
000

SEQ ID NO: 2283            moltype =     length =
SEQUENCE: 2283
000

SEQ ID NO: 2284            moltype =     length =
SEQUENCE: 2284
000

SEQ ID NO: 2285            moltype =     length =
SEQUENCE: 2285
000

SEQ ID NO: 2286            moltype =     length =
SEQUENCE: 2286
000

SEQ ID NO: 2287            moltype =     length =
SEQUENCE: 2287
000

SEQ ID NO: 2288            moltype =     length =
SEQUENCE: 2288

-continued

000

SEQ ID NO: 2289         moltype =      length =
SEQUENCE: 2289
000

SEQ ID NO: 2290         moltype =      length =
SEQUENCE: 2290
000

SEQ ID NO: 2291         moltype =      length =
SEQUENCE: 2291
000

SEQ ID NO: 2292         moltype =      length =
SEQUENCE: 2292
000

SEQ ID NO: 2293         moltype =      length =
SEQUENCE: 2293
000

SEQ ID NO: 2294         moltype =      length =
SEQUENCE: 2294
000

SEQ ID NO: 2295         moltype =      length =
SEQUENCE: 2295
000

SEQ ID NO: 2296         moltype =      length =
SEQUENCE: 2296
000

SEQ ID NO: 2297         moltype =      length =
SEQUENCE: 2297
000

SEQ ID NO: 2298         moltype =      length =
SEQUENCE: 2298
000

SEQ ID NO: 2299         moltype =      length =
SEQUENCE: 2299
000

SEQ ID NO: 2300         moltype =      length =
SEQUENCE: 2300
000

SEQ ID NO: 2301         moltype =      length =
SEQUENCE: 2301
000

SEQ ID NO: 2302         moltype =      length =
SEQUENCE: 2302
000

SEQ ID NO: 2303         moltype =      length =
SEQUENCE: 2303
000

SEQ ID NO: 2304         moltype =      length =
SEQUENCE: 2304
000

SEQ ID NO: 2305         moltype =      length =
SEQUENCE: 2305
000

SEQ ID NO: 2306         moltype =      length =
SEQUENCE: 2306
000

SEQ ID NO: 2307         moltype =      length =
SEQUENCE: 2307
000

SEQ ID NO: 2308         moltype =      length =

-continued

| | | |
|---|---|---|
| SEQUENCE: 2308 000 | | |
| SEQ ID NO: 2309 SEQUENCE: 2309 000 | moltype = | length = |
| SEQ ID NO: 2310 SEQUENCE: 2310 000 | moltype = | length = |
| SEQ ID NO: 2311 SEQUENCE: 2311 000 | moltype = | length = |
| SEQ ID NO: 2312 SEQUENCE: 2312 000 | moltype = | length = |
| SEQ ID NO: 2313 SEQUENCE: 2313 000 | moltype = | length = |
| SEQ ID NO: 2314 SEQUENCE: 2314 000 | moltype = | length = |
| SEQ ID NO: 2315 SEQUENCE: 2315 000 | moltype = | length = |
| SEQ ID NO: 2316 SEQUENCE: 2316 000 | moltype = | length = |
| SEQ ID NO: 2317 SEQUENCE: 2317 000 | moltype = | length = |
| SEQ ID NO: 2318 SEQUENCE: 2318 000 | moltype = | length = |
| SEQ ID NO: 2319 SEQUENCE: 2319 000 | moltype = | length = |
| SEQ ID NO: 2320 SEQUENCE: 2320 000 | moltype = | length = |
| SEQ ID NO: 2321 SEQUENCE: 2321 000 | moltype = | length = |
| SEQ ID NO: 2322 SEQUENCE: 2322 000 | moltype = | length = |
| SEQ ID NO: 2323 SEQUENCE: 2323 000 | moltype = | length = |
| SEQ ID NO: 2324 SEQUENCE: 2324 000 | moltype = | length = |
| SEQ ID NO: 2325 SEQUENCE: 2325 000 | moltype = | length = |
| SEQ ID NO: 2326 SEQUENCE: 2326 000 | moltype = | length = |
| SEQ ID NO: 2327 SEQUENCE: 2327 000 | moltype = | length = |

| | | |
|---|---|---|
| SEQ ID NO: 2328<br>SEQUENCE: 2328<br>000 | moltype = | length = |
| SEQ ID NO: 2329<br>SEQUENCE: 2329<br>000 | moltype = | length = |
| SEQ ID NO: 2330<br>SEQUENCE: 2330<br>000 | moltype = | length = |
| SEQ ID NO: 2331<br>SEQUENCE: 2331<br>000 | moltype = | length = |
| SEQ ID NO: 2332<br>SEQUENCE: 2332<br>000 | moltype = | length = |
| SEQ ID NO: 2333<br>SEQUENCE: 2333<br>000 | moltype = | length = |
| SEQ ID NO: 2334<br>SEQUENCE: 2334<br>000 | moltype = | length = |
| SEQ ID NO: 2335<br>SEQUENCE: 2335<br>000 | moltype = | length = |
| SEQ ID NO: 2336<br>SEQUENCE: 2336<br>000 | moltype = | length = |
| SEQ ID NO: 2337<br>SEQUENCE: 2337<br>000 | moltype = | length = |
| SEQ ID NO: 2338<br>SEQUENCE: 2338<br>000 | moltype = | length = |
| SEQ ID NO: 2339<br>SEQUENCE: 2339<br>000 | moltype = | length = |
| SEQ ID NO: 2340<br>SEQUENCE: 2340<br>000 | moltype = | length = |
| SEQ ID NO: 2341<br>SEQUENCE: 2341<br>000 | moltype = | length = |
| SEQ ID NO: 2342<br>SEQUENCE: 2342<br>000 | moltype = | length = |
| SEQ ID NO: 2343<br>SEQUENCE: 2343<br>000 | moltype = | length = |
| SEQ ID NO: 2344<br>SEQUENCE: 2344<br>000 | moltype = | length = |
| SEQ ID NO: 2345<br>SEQUENCE: 2345<br>000 | moltype = | length = |
| SEQ ID NO: 2346<br>SEQUENCE: 2346<br>000 | moltype = | length = |
| SEQ ID NO: 2347<br>SEQUENCE: 2347<br>000 | moltype = | length = |

| | | |
|---|---|---|
| SEQ ID NO: 2348<br>SEQUENCE: 2348<br>000 | moltype = | length = |
| SEQ ID NO: 2349<br>SEQUENCE: 2349<br>000 | moltype = | length = |
| SEQ ID NO: 2350<br>SEQUENCE: 2350<br>000 | moltype = | length = |
| SEQ ID NO: 2351<br>SEQUENCE: 2351<br>000 | moltype = | length = |
| SEQ ID NO: 2352<br>SEQUENCE: 2352<br>000 | moltype = | length = |
| SEQ ID NO: 2353<br>SEQUENCE: 2353<br>000 | moltype = | length = |
| SEQ ID NO: 2354<br>SEQUENCE: 2354<br>000 | moltype = | length = |
| SEQ ID NO: 2355<br>SEQUENCE: 2355<br>000 | moltype = | length = |
| SEQ ID NO: 2356<br>SEQUENCE: 2356<br>000 | moltype = | length = |
| SEQ ID NO: 2357<br>SEQUENCE: 2357<br>000 | moltype = | length = |
| SEQ ID NO: 2358<br>SEQUENCE: 2358<br>000 | moltype = | length = |
| SEQ ID NO: 2359<br>SEQUENCE: 2359<br>000 | moltype = | length = |
| SEQ ID NO: 2360<br>SEQUENCE: 2360<br>000 | moltype = | length = |
| SEQ ID NO: 2361<br>SEQUENCE: 2361<br>000 | moltype = | length = |
| SEQ ID NO: 2362<br>SEQUENCE: 2362<br>000 | moltype = | length = |
| SEQ ID NO: 2363<br>SEQUENCE: 2363<br>000 | moltype = | length = |
| SEQ ID NO: 2364<br>SEQUENCE: 2364<br>000 | moltype = | length = |
| SEQ ID NO: 2365<br>SEQUENCE: 2365<br>000 | moltype = | length = |
| SEQ ID NO: 2366<br>SEQUENCE: 2366<br>000 | moltype = | length = |
| SEQ ID NO: 2367<br>SEQUENCE: 2367 | moltype = | length = |

000

SEQ ID NO: 2368          moltype =      length =
SEQUENCE: 2368
000

SEQ ID NO: 2369          moltype =      length =
SEQUENCE: 2369
000

SEQ ID NO: 2370          moltype =      length =
SEQUENCE: 2370
000

SEQ ID NO: 2371          moltype =      length =
SEQUENCE: 2371
000

SEQ ID NO: 2372          moltype =      length =
SEQUENCE: 2372
000

SEQ ID NO: 2373          moltype =      length =
SEQUENCE: 2373
000

SEQ ID NO: 2374          moltype =      length =
SEQUENCE: 2374
000

SEQ ID NO: 2375          moltype =      length =
SEQUENCE: 2375
000

SEQ ID NO: 2376          moltype =      length =
SEQUENCE: 2376
000

SEQ ID NO: 2377          moltype =      length =
SEQUENCE: 2377
000

SEQ ID NO: 2378          moltype =      length =
SEQUENCE: 2378
000

SEQ ID NO: 2379          moltype =      length =
SEQUENCE: 2379
000

SEQ ID NO: 2380          moltype =      length =
SEQUENCE: 2380
000

SEQ ID NO: 2381          moltype =      length =
SEQUENCE: 2381
000

SEQ ID NO: 2382          moltype =      length =
SEQUENCE: 2382
000

SEQ ID NO: 2383          moltype =      length =
SEQUENCE: 2383
000

SEQ ID NO: 2384          moltype =      length =
SEQUENCE: 2384
000

SEQ ID NO: 2385          moltype =      length =
SEQUENCE: 2385
000

SEQ ID NO: 2386          moltype =      length =
SEQUENCE: 2386
000

SEQ ID NO: 2387          moltype =      length =

| | | |
|---|---|---|
| SEQUENCE: 2387 000 | | |
| SEQ ID NO: 2388 SEQUENCE: 2388 000 | moltype = | length = |
| SEQ ID NO: 2389 SEQUENCE: 2389 000 | moltype = | length = |
| SEQ ID NO: 2390 SEQUENCE: 2390 000 | moltype = | length = |
| SEQ ID NO: 2391 SEQUENCE: 2391 000 | moltype = | length = |
| SEQ ID NO: 2392 SEQUENCE: 2392 000 | moltype = | length = |
| SEQ ID NO: 2393 SEQUENCE: 2393 000 | moltype = | length = |
| SEQ ID NO: 2394 SEQUENCE: 2394 000 | moltype = | length = |
| SEQ ID NO: 2395 SEQUENCE: 2395 000 | moltype = | length = |
| SEQ ID NO: 2396 SEQUENCE: 2396 000 | moltype = | length = |
| SEQ ID NO: 2397 SEQUENCE: 2397 000 | moltype = | length = |
| SEQ ID NO: 2398 SEQUENCE: 2398 000 | moltype = | length = |
| SEQ ID NO: 2399 SEQUENCE: 2399 000 | moltype = | length = |
| SEQ ID NO: 2400 SEQUENCE: 2400 000 | moltype = | length = |
| SEQ ID NO: 2401 SEQUENCE: 2401 000 | moltype = | length = |
| SEQ ID NO: 2402 SEQUENCE: 2402 000 | moltype = | length = |
| SEQ ID NO: 2403 SEQUENCE: 2403 000 | moltype = | length = |
| SEQ ID NO: 2404 SEQUENCE: 2404 000 | moltype = | length = |
| SEQ ID NO: 2405 SEQUENCE: 2405 000 | moltype = | length = |
| SEQ ID NO: 2406 SEQUENCE: 2406 000 | moltype = | length = |

| | | |
|---|---|---|
| SEQ ID NO: 2407 SEQUENCE: 2407 | moltype = | length = 000 |
| SEQ ID NO: 2408 SEQUENCE: 2408 | moltype = | length = 000 |
| SEQ ID NO: 2409 SEQUENCE: 2409 | moltype = | length = 000 |
| SEQ ID NO: 2410 SEQUENCE: 2410 | moltype = | length = 000 |
| SEQ ID NO: 2411 SEQUENCE: 2411 | moltype = | length = 000 |
| SEQ ID NO: 2412 SEQUENCE: 2412 | moltype = | length = 000 |
| SEQ ID NO: 2413 SEQUENCE: 2413 | moltype = | length = 000 |
| SEQ ID NO: 2414 SEQUENCE: 2414 | moltype = | length = 000 |
| SEQ ID NO: 2415 SEQUENCE: 2415 | moltype = | length = 000 |
| SEQ ID NO: 2416 SEQUENCE: 2416 | moltype = | length = 000 |
| SEQ ID NO: 2417 SEQUENCE: 2417 | moltype = | length = 000 |
| SEQ ID NO: 2418 SEQUENCE: 2418 | moltype = | length = 000 |
| SEQ ID NO: 2419 SEQUENCE: 2419 | moltype = | length = 000 |
| SEQ ID NO: 2420 SEQUENCE: 2420 | moltype = | length = 000 |
| SEQ ID NO: 2421 SEQUENCE: 2421 | moltype = | length = 000 |
| SEQ ID NO: 2422 SEQUENCE: 2422 | moltype = | length = 000 |
| SEQ ID NO: 2423 SEQUENCE: 2423 | moltype = | length = 000 |
| SEQ ID NO: 2424 SEQUENCE: 2424 | moltype = | length = 000 |
| SEQ ID NO: 2425 SEQUENCE: 2425 | moltype = | length = 000 |
| SEQ ID NO: 2426 SEQUENCE: 2426 | moltype = | length = 000 |

| | | |
|---|---|---|
| SEQ ID NO: 2427<br>SEQUENCE: 2427<br>000 | moltype = | length = |
| SEQ ID NO: 2428<br>SEQUENCE: 2428<br>000 | moltype = | length = |
| SEQ ID NO: 2429<br>SEQUENCE: 2429<br>000 | moltype = | length = |
| SEQ ID NO: 2430<br>SEQUENCE: 2430<br>000 | moltype = | length = |
| SEQ ID NO: 2431<br>SEQUENCE: 2431<br>000 | moltype = | length = |
| SEQ ID NO: 2432<br>SEQUENCE: 2432<br>000 | moltype = | length = |
| SEQ ID NO: 2433<br>SEQUENCE: 2433<br>000 | moltype = | length = |
| SEQ ID NO: 2434<br>SEQUENCE: 2434<br>000 | moltype = | length = |
| SEQ ID NO: 2435<br>SEQUENCE: 2435<br>000 | moltype = | length = |
| SEQ ID NO: 2436<br>SEQUENCE: 2436<br>000 | moltype = | length = |
| SEQ ID NO: 2437<br>SEQUENCE: 2437<br>000 | moltype = | length = |
| SEQ ID NO: 2438<br>SEQUENCE: 2438<br>000 | moltype = | length = |
| SEQ ID NO: 2439<br>SEQUENCE: 2439<br>000 | moltype = | length = |
| SEQ ID NO: 2440<br>SEQUENCE: 2440<br>000 | moltype = | length = |
| SEQ ID NO: 2441<br>SEQUENCE: 2441<br>000 | moltype = | length = |
| SEQ ID NO: 2442<br>SEQUENCE: 2442<br>000 | moltype = | length = |
| SEQ ID NO: 2443<br>SEQUENCE: 2443<br>000 | moltype = | length = |
| SEQ ID NO: 2444<br>SEQUENCE: 2444<br>000 | moltype = | length = |
| SEQ ID NO: 2445<br>SEQUENCE: 2445<br>000 | moltype = | length = |
| SEQ ID NO: 2446<br>SEQUENCE: 2446 | moltype = | length = |

-continued

000

SEQ ID NO: 2447        moltype =       length =
SEQUENCE: 2447
000

SEQ ID NO: 2448        moltype =       length =
SEQUENCE: 2448
000

SEQ ID NO: 2449        moltype =       length =
SEQUENCE: 2449
000

SEQ ID NO: 2450        moltype =       length =
SEQUENCE: 2450
000

SEQ ID NO: 2451        moltype =       length =
SEQUENCE: 2451
000

SEQ ID NO: 2452        moltype =       length =
SEQUENCE: 2452
000

SEQ ID NO: 2453        moltype =       length =
SEQUENCE: 2453
000

SEQ ID NO: 2454        moltype =       length =
SEQUENCE: 2454
000

SEQ ID NO: 2455        moltype =       length =
SEQUENCE: 2455
000

SEQ ID NO: 2456        moltype =       length =
SEQUENCE: 2456
000

SEQ ID NO: 2457        moltype =       length =
SEQUENCE: 2457
000

SEQ ID NO: 2458        moltype =       length =
SEQUENCE: 2458
000

SEQ ID NO: 2459        moltype =       length =
SEQUENCE: 2459
000

SEQ ID NO: 2460        moltype =       length =
SEQUENCE: 2460
000

SEQ ID NO: 2461        moltype =       length =
SEQUENCE: 2461
000

SEQ ID NO: 2462        moltype =       length =
SEQUENCE: 2462
000

SEQ ID NO: 2463        moltype =       length =
SEQUENCE: 2463
000

SEQ ID NO: 2464        moltype =       length =
SEQUENCE: 2464
000

SEQ ID NO: 2465        moltype =       length =
SEQUENCE: 2465
000

SEQ ID NO: 2466        moltype =       length =

| | | |
|---|---|---|
| SEQUENCE: 2466 000 | | |
| SEQ ID NO: 2467 SEQUENCE: 2467 000 | moltype = | length = |
| SEQ ID NO: 2468 SEQUENCE: 2468 000 | moltype = | length = |
| SEQ ID NO: 2469 SEQUENCE: 2469 000 | moltype = | length = |
| SEQ ID NO: 2470 SEQUENCE: 2470 000 | moltype = | length = |
| SEQ ID NO: 2471 SEQUENCE: 2471 000 | moltype = | length = |
| SEQ ID NO: 2472 SEQUENCE: 2472 000 | moltype = | length = |
| SEQ ID NO: 2473 SEQUENCE: 2473 000 | moltype = | length = |
| SEQ ID NO: 2474 SEQUENCE: 2474 000 | moltype = | length = |
| SEQ ID NO: 2475 SEQUENCE: 2475 000 | moltype = | length = |
| SEQ ID NO: 2476 SEQUENCE: 2476 000 | moltype = | length = |
| SEQ ID NO: 2477 SEQUENCE: 2477 000 | moltype = | length = |
| SEQ ID NO: 2478 SEQUENCE: 2478 000 | moltype = | length = |
| SEQ ID NO: 2479 SEQUENCE: 2479 000 | moltype = | length = |
| SEQ ID NO: 2480 SEQUENCE: 2480 000 | moltype = | length = |
| SEQ ID NO: 2481 SEQUENCE: 2481 000 | moltype = | length = |
| SEQ ID NO: 2482 SEQUENCE: 2482 000 | moltype = | length = |
| SEQ ID NO: 2483 SEQUENCE: 2483 000 | moltype = | length = |
| SEQ ID NO: 2484 SEQUENCE: 2484 000 | moltype = | length = |
| SEQ ID NO: 2485 SEQUENCE: 2485 000 | moltype = | length = |

| | | |
|---|---|---|
| SEQ ID NO: 2486 SEQUENCE: 2486 | moltype = | length = 000 |
| SEQ ID NO: 2487 SEQUENCE: 2487 | moltype = | length = 000 |
| SEQ ID NO: 2488 SEQUENCE: 2488 | moltype = | length = 000 |
| SEQ ID NO: 2489 SEQUENCE: 2489 | moltype = | length = 000 |
| SEQ ID NO: 2490 SEQUENCE: 2490 | moltype = | length = 000 |
| SEQ ID NO: 2491 SEQUENCE: 2491 | moltype = | length = 000 |
| SEQ ID NO: 2492 SEQUENCE: 2492 | moltype = | length = 000 |
| SEQ ID NO: 2493 SEQUENCE: 2493 | moltype = | length = 000 |
| SEQ ID NO: 2494 SEQUENCE: 2494 | moltype = | length = 000 |
| SEQ ID NO: 2495 SEQUENCE: 2495 | moltype = | length = 000 |
| SEQ ID NO: 2496 SEQUENCE: 2496 | moltype = | length = 000 |
| SEQ ID NO: 2497 SEQUENCE: 2497 | moltype = | length = 000 |
| SEQ ID NO: 2498 SEQUENCE: 2498 | moltype = | length = 000 |
| SEQ ID NO: 2499 SEQUENCE: 2499 | moltype = | length = 000 |
| SEQ ID NO: 2500 SEQUENCE: 2500 | moltype = | length = 000 |
| SEQ ID NO: 2501 SEQUENCE: 2501 | moltype = | length = 000 |
| SEQ ID NO: 2502 SEQUENCE: 2502 | moltype = | length = 000 |
| SEQ ID NO: 2503 SEQUENCE: 2503 | moltype = | length = 000 |
| SEQ ID NO: 2504 SEQUENCE: 2504 | moltype = | length = 000 |
| SEQ ID NO: 2505 SEQUENCE: 2505 | moltype = | length = 000 |

SEQ ID NO: 2506    moltype =    length =
SEQUENCE: 2506
000

SEQ ID NO: 2507    moltype =    length =
SEQUENCE: 2507
000

SEQ ID NO: 2508    moltype =    length =
SEQUENCE: 2508
000

SEQ ID NO: 2509    moltype =    length =
SEQUENCE: 2509
000

SEQ ID NO: 2510    moltype =    length =
SEQUENCE: 2510
000

SEQ ID NO: 2511    moltype =    length =
SEQUENCE: 2511
000

SEQ ID NO: 2512    moltype =    length =
SEQUENCE: 2512
000

SEQ ID NO: 2513    moltype =    length =
SEQUENCE: 2513
000

SEQ ID NO: 2514    moltype =    length =
SEQUENCE: 2514
000

SEQ ID NO: 2515    moltype =    length =
SEQUENCE: 2515
000

SEQ ID NO: 2516    moltype =    length =
SEQUENCE: 2516
000

SEQ ID NO: 2517    moltype =    length =
SEQUENCE: 2517
000

SEQ ID NO: 2518    moltype =    length =
SEQUENCE: 2518
000

SEQ ID NO: 2519    moltype =    length =
SEQUENCE: 2519
000

SEQ ID NO: 2520    moltype =    length =
SEQUENCE: 2520
000

SEQ ID NO: 2521    moltype =    length =
SEQUENCE: 2521
000

SEQ ID NO: 2522    moltype =    length =
SEQUENCE: 2522
000

SEQ ID NO: 2523    moltype =    length =
SEQUENCE: 2523
000

SEQ ID NO: 2524    moltype =    length =
SEQUENCE: 2524
000

SEQ ID NO: 2525    moltype =    length =
SEQUENCE: 2525

000

SEQ ID NO: 2526         moltype =      length =
SEQUENCE: 2526
000

SEQ ID NO: 2527         moltype =      length =
SEQUENCE: 2527
000

SEQ ID NO: 2528         moltype =      length =
SEQUENCE: 2528
000

SEQ ID NO: 2529         moltype =      length =
SEQUENCE: 2529
000

SEQ ID NO: 2530         moltype =      length =
SEQUENCE: 2530
000

SEQ ID NO: 2531         moltype =      length =
SEQUENCE: 2531
000

SEQ ID NO: 2532         moltype =      length =
SEQUENCE: 2532
000

SEQ ID NO: 2533         moltype =      length =
SEQUENCE: 2533
000

SEQ ID NO: 2534         moltype =      length =
SEQUENCE: 2534
000

SEQ ID NO: 2535         moltype =      length =
SEQUENCE: 2535
000

SEQ ID NO: 2536         moltype =      length =
SEQUENCE: 2536
000

SEQ ID NO: 2537         moltype =      length =
SEQUENCE: 2537
000

SEQ ID NO: 2538         moltype =      length =
SEQUENCE: 2538
000

SEQ ID NO: 2539         moltype =      length =
SEQUENCE: 2539
000

SEQ ID NO: 2540         moltype =      length =
SEQUENCE: 2540
000

SEQ ID NO: 2541         moltype =      length =
SEQUENCE: 2541
000

SEQ ID NO: 2542         moltype =      length =
SEQUENCE: 2542
000

SEQ ID NO: 2543         moltype =      length =
SEQUENCE: 2543
000

SEQ ID NO: 2544         moltype =      length =
SEQUENCE: 2544
000

SEQ ID NO: 2545         moltype =      length =

| | | |
|---|---|---|
| SEQUENCE: 2545 000 | | |
| SEQ ID NO: 2546 SEQUENCE: 2546 000 | moltype = | length = |
| SEQ ID NO: 2547 SEQUENCE: 2547 000 | moltype = | length = |
| SEQ ID NO: 2548 SEQUENCE: 2548 000 | moltype = | length = |
| SEQ ID NO: 2549 SEQUENCE: 2549 000 | moltype = | length = |
| SEQ ID NO: 2550 SEQUENCE: 2550 000 | moltype = | length = |
| SEQ ID NO: 2551 SEQUENCE: 2551 000 | moltype = | length = |
| SEQ ID NO: 2552 SEQUENCE: 2552 000 | moltype = | length = |
| SEQ ID NO: 2553 SEQUENCE: 2553 000 | moltype = | length = |
| SEQ ID NO: 2554 SEQUENCE: 2554 000 | moltype = | length = |
| SEQ ID NO: 2555 SEQUENCE: 2555 000 | moltype = | length = |
| SEQ ID NO: 2556 SEQUENCE: 2556 000 | moltype = | length = |
| SEQ ID NO: 2557 SEQUENCE: 2557 000 | moltype = | length = |
| SEQ ID NO: 2558 SEQUENCE: 2558 000 | moltype = | length = |
| SEQ ID NO: 2559 SEQUENCE: 2559 000 | moltype = | length = |
| SEQ ID NO: 2560 SEQUENCE: 2560 000 | moltype = | length = |
| SEQ ID NO: 2561 SEQUENCE: 2561 000 | moltype = | length = |
| SEQ ID NO: 2562 SEQUENCE: 2562 000 | moltype = | length = |
| SEQ ID NO: 2563 SEQUENCE: 2563 000 | moltype = | length = |
| SEQ ID NO: 2564 SEQUENCE: 2564 000 | moltype = | length = |

-continued

| | | |
|---|---|---|
| SEQ ID NO: 2565<br>SEQUENCE: 2565<br>000 | moltype = | length = |
| SEQ ID NO: 2566<br>SEQUENCE: 2566<br>000 | moltype = | length = |
| SEQ ID NO: 2567<br>SEQUENCE: 2567<br>000 | moltype = | length = |
| SEQ ID NO: 2568<br>SEQUENCE: 2568<br>000 | moltype = | length = |
| SEQ ID NO: 2569<br>SEQUENCE: 2569<br>000 | moltype = | length = |
| SEQ ID NO: 2570<br>SEQUENCE: 2570<br>000 | moltype = | length = |
| SEQ ID NO: 2571<br>SEQUENCE: 2571<br>000 | moltype = | length = |
| SEQ ID NO: 2572<br>SEQUENCE: 2572<br>000 | moltype = | length = |
| SEQ ID NO: 2573<br>SEQUENCE: 2573<br>000 | moltype = | length = |
| SEQ ID NO: 2574<br>SEQUENCE: 2574<br>000 | moltype = | length = |
| SEQ ID NO: 2575<br>SEQUENCE: 2575<br>000 | moltype = | length = |
| SEQ ID NO: 2576<br>SEQUENCE: 2576<br>000 | moltype = | length = |
| SEQ ID NO: 2577<br>SEQUENCE: 2577<br>000 | moltype = | length = |
| SEQ ID NO: 2578<br>SEQUENCE: 2578<br>000 | moltype = | length = |
| SEQ ID NO: 2579<br>SEQUENCE: 2579<br>000 | moltype = | length = |
| SEQ ID NO: 2580<br>SEQUENCE: 2580<br>000 | moltype = | length = |
| SEQ ID NO: 2581<br>SEQUENCE: 2581<br>000 | moltype = | length = |
| SEQ ID NO: 2582<br>SEQUENCE: 2582<br>000 | moltype = | length = |
| SEQ ID NO: 2583<br>SEQUENCE: 2583<br>000 | moltype = | length = |
| SEQ ID NO: 2584<br>SEQUENCE: 2584<br>000 | moltype = | length = |

| | | |
|---|---|---|
| SEQ ID NO: 2585 SEQUENCE: 2585 000 | moltype = | length = |
| SEQ ID NO: 2586 SEQUENCE: 2586 000 | moltype = | length = |
| SEQ ID NO: 2587 SEQUENCE: 2587 000 | moltype = | length = |
| SEQ ID NO: 2588 SEQUENCE: 2588 000 | moltype = | length = |
| SEQ ID NO: 2589 SEQUENCE: 2589 000 | moltype = | length = |
| SEQ ID NO: 2590 SEQUENCE: 2590 000 | moltype = | length = |
| SEQ ID NO: 2591 SEQUENCE: 2591 000 | moltype = | length = |
| SEQ ID NO: 2592 SEQUENCE: 2592 000 | moltype = | length = |
| SEQ ID NO: 2593 SEQUENCE: 2593 000 | moltype = | length = |
| SEQ ID NO: 2594 SEQUENCE: 2594 000 | moltype = | length = |
| SEQ ID NO: 2595 SEQUENCE: 2595 000 | moltype = | length = |
| SEQ ID NO: 2596 SEQUENCE: 2596 000 | moltype = | length = |
| SEQ ID NO: 2597 SEQUENCE: 2597 000 | moltype = | length = |
| SEQ ID NO: 2598 SEQUENCE: 2598 000 | moltype = | length = |
| SEQ ID NO: 2599 SEQUENCE: 2599 000 | moltype = | length = |
| SEQ ID NO: 2600 SEQUENCE: 2600 000 | moltype = | length = |
| SEQ ID NO: 2601 SEQUENCE: 2601 000 | moltype = | length = |
| SEQ ID NO: 2602 SEQUENCE: 2602 000 | moltype = | length = |
| SEQ ID NO: 2603 SEQUENCE: 2603 000 | moltype = | length = |
| SEQ ID NO: 2604 SEQUENCE: 2604 | moltype = | length = |

000

SEQ ID NO: 2605        moltype =     length =
SEQUENCE: 2605
000

SEQ ID NO: 2606        moltype =     length =
SEQUENCE: 2606
000

SEQ ID NO: 2607        moltype =     length =
SEQUENCE: 2607
000

SEQ ID NO: 2608        moltype =     length =
SEQUENCE: 2608
000

SEQ ID NO: 2609        moltype =     length =
SEQUENCE: 2609
000

SEQ ID NO: 2610        moltype =     length =
SEQUENCE: 2610
000

SEQ ID NO: 2611        moltype =     length =
SEQUENCE: 2611
000

SEQ ID NO: 2612        moltype =     length =
SEQUENCE: 2612
000

SEQ ID NO: 2613        moltype =     length =
SEQUENCE: 2613
000

SEQ ID NO: 2614        moltype =     length =
SEQUENCE: 2614
000

SEQ ID NO: 2615        moltype =     length =
SEQUENCE: 2615
000

SEQ ID NO: 2616        moltype =     length =
SEQUENCE: 2616
000

SEQ ID NO: 2617        moltype =     length =
SEQUENCE: 2617
000

SEQ ID NO: 2618        moltype =     length =
SEQUENCE: 2618
000

SEQ ID NO: 2619        moltype =     length =
SEQUENCE: 2619
000

SEQ ID NO: 2620        moltype =     length =
SEQUENCE: 2620
000

SEQ ID NO: 2621        moltype =     length =
SEQUENCE: 2621
000

SEQ ID NO: 2622        moltype =     length =
SEQUENCE: 2622
000

SEQ ID NO: 2623        moltype =     length =
SEQUENCE: 2623
000

SEQ ID NO: 2624        moltype =     length =

-continued

| | | |
|---|---|---|
| SEQUENCE: 2624 000 | | |
| SEQ ID NO: 2625 SEQUENCE: 2625 000 | moltype = | length = |
| SEQ ID NO: 2626 SEQUENCE: 2626 000 | moltype = | length = |
| SEQ ID NO: 2627 SEQUENCE: 2627 000 | moltype = | length = |
| SEQ ID NO: 2628 SEQUENCE: 2628 000 | moltype = | length = |
| SEQ ID NO: 2629 SEQUENCE: 2629 000 | moltype = | length = |
| SEQ ID NO: 2630 SEQUENCE: 2630 000 | moltype = | length = |
| SEQ ID NO: 2631 SEQUENCE: 2631 000 | moltype = | length = |
| SEQ ID NO: 2632 SEQUENCE: 2632 000 | moltype = | length = |
| SEQ ID NO: 2633 SEQUENCE: 2633 000 | moltype = | length = |
| SEQ ID NO: 2634 SEQUENCE: 2634 000 | moltype = | length = |
| SEQ ID NO: 2635 SEQUENCE: 2635 000 | moltype = | length = |
| SEQ ID NO: 2636 SEQUENCE: 2636 000 | moltype = | length = |
| SEQ ID NO: 2637 SEQUENCE: 2637 000 | moltype = | length = |
| SEQ ID NO: 2638 SEQUENCE: 2638 000 | moltype = | length = |
| SEQ ID NO: 2639 SEQUENCE: 2639 000 | moltype = | length = |
| SEQ ID NO: 2640 SEQUENCE: 2640 000 | moltype = | length = |
| SEQ ID NO: 2641 SEQUENCE: 2641 000 | moltype = | length = |
| SEQ ID NO: 2642 SEQUENCE: 2642 000 | moltype = | length = |
| SEQ ID NO: 2643 SEQUENCE: 2643 000 | moltype = | length = |

| | | |
|---|---|---|
| SEQ ID NO: 2644<br>SEQUENCE: 2644 | moltype = | length = 000 |
| SEQ ID NO: 2645<br>SEQUENCE: 2645 | moltype = | length = 000 |
| SEQ ID NO: 2646<br>SEQUENCE: 2646 | moltype = | length = 000 |
| SEQ ID NO: 2647<br>SEQUENCE: 2647 | moltype = | length = 000 |
| SEQ ID NO: 2648<br>SEQUENCE: 2648 | moltype = | length = 000 |
| SEQ ID NO: 2649<br>SEQUENCE: 2649 | moltype = | length = 000 |
| SEQ ID NO: 2650<br>SEQUENCE: 2650 | moltype = | length = 000 |
| SEQ ID NO: 2651<br>SEQUENCE: 2651 | moltype = | length = 000 |
| SEQ ID NO: 2652<br>SEQUENCE: 2652 | moltype = | length = 000 |
| SEQ ID NO: 2653<br>SEQUENCE: 2653 | moltype = | length = 000 |
| SEQ ID NO: 2654<br>SEQUENCE: 2654 | moltype = | length = 000 |
| SEQ ID NO: 2655<br>SEQUENCE: 2655 | moltype = | length = 000 |
| SEQ ID NO: 2656<br>SEQUENCE: 2656 | moltype = | length = 000 |
| SEQ ID NO: 2657<br>SEQUENCE: 2657 | moltype = | length = 000 |
| SEQ ID NO: 2658<br>SEQUENCE: 2658 | moltype = | length = 000 |
| SEQ ID NO: 2659<br>SEQUENCE: 2659 | moltype = | length = 000 |
| SEQ ID NO: 2660<br>SEQUENCE: 2660 | moltype = | length = 000 |
| SEQ ID NO: 2661<br>SEQUENCE: 2661 | moltype = | length = 000 |
| SEQ ID NO: 2662<br>SEQUENCE: 2662 | moltype = | length = 000 |
| SEQ ID NO: 2663<br>SEQUENCE: 2663 | moltype = | length = 000 |

SEQ ID NO: 2664        moltype =    length =
SEQUENCE: 2664
000

SEQ ID NO: 2665        moltype =    length =
SEQUENCE: 2665
000

SEQ ID NO: 2666        moltype =    length =
SEQUENCE: 2666
000

SEQ ID NO: 2667        moltype =    length =
SEQUENCE: 2667
000

SEQ ID NO: 2668        moltype =    length =
SEQUENCE: 2668
000

SEQ ID NO: 2669        moltype =    length =
SEQUENCE: 2669
000

SEQ ID NO: 2670        moltype =    length =
SEQUENCE: 2670
000

SEQ ID NO: 2671        moltype =    length =
SEQUENCE: 2671
000

SEQ ID NO: 2672        moltype =    length =
SEQUENCE: 2672
000

SEQ ID NO: 2673        moltype =    length =
SEQUENCE: 2673
000

SEQ ID NO: 2674        moltype =    length =
SEQUENCE: 2674
000

SEQ ID NO: 2675        moltype =    length =
SEQUENCE: 2675
000

SEQ ID NO: 2676        moltype =    length =
SEQUENCE: 2676
000

SEQ ID NO: 2677        moltype =    length =
SEQUENCE: 2677
000

SEQ ID NO: 2678        moltype =    length =
SEQUENCE: 2678
000

SEQ ID NO: 2679        moltype =    length =
SEQUENCE: 2679
000

SEQ ID NO: 2680        moltype =    length =
SEQUENCE: 2680
000

SEQ ID NO: 2681        moltype =    length =
SEQUENCE: 2681
000

SEQ ID NO: 2682        moltype =    length =
SEQUENCE: 2682
000

SEQ ID NO: 2683        moltype =    length =
SEQUENCE: 2683

000

SEQ ID NO: 2684        moltype =     length =
SEQUENCE: 2684
000

SEQ ID NO: 2685        moltype =     length =
SEQUENCE: 2685
000

SEQ ID NO: 2686        moltype =     length =
SEQUENCE: 2686
000

SEQ ID NO: 2687        moltype =     length =
SEQUENCE: 2687
000

SEQ ID NO: 2688        moltype =     length =
SEQUENCE: 2688
000

SEQ ID NO: 2689        moltype =     length =
SEQUENCE: 2689
000

SEQ ID NO: 2690        moltype =     length =
SEQUENCE: 2690
000

SEQ ID NO: 2691        moltype =     length =
SEQUENCE: 2691
000

SEQ ID NO: 2692        moltype =     length =
SEQUENCE: 2692
000

SEQ ID NO: 2693        moltype =     length =
SEQUENCE: 2693
000

SEQ ID NO: 2694        moltype =     length =
SEQUENCE: 2694
000

SEQ ID NO: 2695        moltype =     length =
SEQUENCE: 2695
000

SEQ ID NO: 2696        moltype =     length =
SEQUENCE: 2696
000

SEQ ID NO: 2697        moltype =     length =
SEQUENCE: 2697
000

SEQ ID NO: 2698        moltype =     length =
SEQUENCE: 2698
000

SEQ ID NO: 2699        moltype =     length =
SEQUENCE: 2699
000

SEQ ID NO: 2700        moltype =     length =
SEQUENCE: 2700
000

SEQ ID NO: 2701        moltype =     length =
SEQUENCE: 2701
000

SEQ ID NO: 2702        moltype =     length =
SEQUENCE: 2702
000

SEQ ID NO: 2703        moltype =     length =

-continued

SEQUENCE: 2703
000

SEQ ID NO: 2704        moltype =    length =
SEQUENCE: 2704
000

SEQ ID NO: 2705        moltype =    length =
SEQUENCE: 2705
000

SEQ ID NO: 2706        moltype =    length =
SEQUENCE: 2706
000

SEQ ID NO: 2707        moltype =    length =
SEQUENCE: 2707
000

SEQ ID NO: 2708        moltype =    length =
SEQUENCE: 2708
000

SEQ ID NO: 2709        moltype =    length =
SEQUENCE: 2709
000

SEQ ID NO: 2710        moltype =    length =
SEQUENCE: 2710
000

SEQ ID NO: 2711        moltype =    length =
SEQUENCE: 2711
000

SEQ ID NO: 2712        moltype =    length =
SEQUENCE: 2712
000

SEQ ID NO: 2713        moltype =    length =
SEQUENCE: 2713
000

SEQ ID NO: 2714        moltype =    length =
SEQUENCE: 2714
000

SEQ ID NO: 2715        moltype =    length =
SEQUENCE: 2715
000

SEQ ID NO: 2716        moltype =    length =
SEQUENCE: 2716
000

SEQ ID NO: 2717        moltype =    length =
SEQUENCE: 2717
000

SEQ ID NO: 2718        moltype =    length =
SEQUENCE: 2718
000

SEQ ID NO: 2719        moltype =    length =
SEQUENCE: 2719
000

SEQ ID NO: 2720        moltype =    length =
SEQUENCE: 2720
000

SEQ ID NO: 2721        moltype =    length =
SEQUENCE: 2721
000

SEQ ID NO: 2722        moltype =    length =
SEQUENCE: 2722
000

| | | |
|---|---|---|
| SEQ ID NO: 2723  SEQUENCE: 2723 | moltype = 000 | length = |
| SEQ ID NO: 2724  SEQUENCE: 2724 | moltype = 000 | length = |
| SEQ ID NO: 2725  SEQUENCE: 2725 | moltype = 000 | length = |
| SEQ ID NO: 2726  SEQUENCE: 2726 | moltype = 000 | length = |
| SEQ ID NO: 2727  SEQUENCE: 2727 | moltype = 000 | length = |
| SEQ ID NO: 2728  SEQUENCE: 2728 | moltype = 000 | length = |
| SEQ ID NO: 2729  SEQUENCE: 2729 | moltype = 000 | length = |
| SEQ ID NO: 2730  SEQUENCE: 2730 | moltype = 000 | length = |
| SEQ ID NO: 2731  SEQUENCE: 2731 | moltype = 000 | length = |
| SEQ ID NO: 2732  SEQUENCE: 2732 | moltype = 000 | length = |
| SEQ ID NO: 2733  SEQUENCE: 2733 | moltype = 000 | length = |
| SEQ ID NO: 2734  SEQUENCE: 2734 | moltype = 000 | length = |
| SEQ ID NO: 2735  SEQUENCE: 2735 | moltype = 000 | length = |
| SEQ ID NO: 2736  SEQUENCE: 2736 | moltype = 000 | length = |
| SEQ ID NO: 2737  SEQUENCE: 2737 | moltype = 000 | length = |
| SEQ ID NO: 2738  SEQUENCE: 2738 | moltype = 000 | length = |
| SEQ ID NO: 2739  SEQUENCE: 2739 | moltype = 000 | length = |
| SEQ ID NO: 2740  SEQUENCE: 2740 | moltype = 000 | length = |
| SEQ ID NO: 2741  SEQUENCE: 2741 | moltype = 000 | length = |
| SEQ ID NO: 2742  SEQUENCE: 2742 | moltype = 000 | length = |

-continued

SEQ ID NO: 2743    moltype =    length =
SEQUENCE: 2743
000

SEQ ID NO: 2744    moltype =    length =
SEQUENCE: 2744
000

SEQ ID NO: 2745    moltype =    length =
SEQUENCE: 2745
000

SEQ ID NO: 2746    moltype =    length =
SEQUENCE: 2746
000

SEQ ID NO: 2747    moltype =    length =
SEQUENCE: 2747
000

SEQ ID NO: 2748    moltype =    length =
SEQUENCE: 2748
000

SEQ ID NO: 2749    moltype =    length =
SEQUENCE: 2749
000

SEQ ID NO: 2750    moltype =    length =
SEQUENCE: 2750
000

SEQ ID NO: 2751    moltype =    length =
SEQUENCE: 2751
000

SEQ ID NO: 2752    moltype =    length =
SEQUENCE: 2752
000

SEQ ID NO: 2753    moltype =    length =
SEQUENCE: 2753
000

SEQ ID NO: 2754    moltype =    length =
SEQUENCE: 2754
000

SEQ ID NO: 2755    moltype =    length =
SEQUENCE: 2755
000

SEQ ID NO: 2756    moltype =    length =
SEQUENCE: 2756
000

SEQ ID NO: 2757    moltype =    length =
SEQUENCE: 2757
000

SEQ ID NO: 2758    moltype =    length =
SEQUENCE: 2758
000

SEQ ID NO: 2759    moltype =    length =
SEQUENCE: 2759
000

SEQ ID NO: 2760    moltype =    length =
SEQUENCE: 2760
000

SEQ ID NO: 2761    moltype =    length =
SEQUENCE: 2761
000

SEQ ID NO: 2762    moltype =    length =
SEQUENCE: 2762

000

SEQ ID NO: 2763         moltype =     length =
SEQUENCE: 2763
000

SEQ ID NO: 2764         moltype =     length =
SEQUENCE: 2764
000

SEQ ID NO: 2765         moltype =     length =
SEQUENCE: 2765
000

SEQ ID NO: 2766         moltype =     length =
SEQUENCE: 2766
000

SEQ ID NO: 2767         moltype =     length =
SEQUENCE: 2767
000

SEQ ID NO: 2768         moltype =     length =
SEQUENCE: 2768
000

SEQ ID NO: 2769         moltype =     length =
SEQUENCE: 2769
000

SEQ ID NO: 2770         moltype =     length =
SEQUENCE: 2770
000

SEQ ID NO: 2771         moltype =     length =
SEQUENCE: 2771
000

SEQ ID NO: 2772         moltype =     length =
SEQUENCE: 2772
000

SEQ ID NO: 2773         moltype =     length =
SEQUENCE: 2773
000

SEQ ID NO: 2774         moltype =     length =
SEQUENCE: 2774
000

SEQ ID NO: 2775         moltype =     length =
SEQUENCE: 2775
000

SEQ ID NO: 2776         moltype =     length =
SEQUENCE: 2776
000

SEQ ID NO: 2777         moltype =     length =
SEQUENCE: 2777
000

SEQ ID NO: 2778         moltype =     length =
SEQUENCE: 2778
000

SEQ ID NO: 2779         moltype =     length =
SEQUENCE: 2779
000

SEQ ID NO: 2780         moltype =     length =
SEQUENCE: 2780
000

SEQ ID NO: 2781         moltype =     length =
SEQUENCE: 2781
000

SEQ ID NO: 2782         moltype =     length =

| | | |
|---|---|---|
| SEQUENCE: 2782 000 | | |
| SEQ ID NO: 2783 SEQUENCE: 2783 000 | moltype = | length = |
| SEQ ID NO: 2784 SEQUENCE: 2784 000 | moltype = | length = |
| SEQ ID NO: 2785 SEQUENCE: 2785 000 | moltype = | length = |
| SEQ ID NO: 2786 SEQUENCE: 2786 000 | moltype = | length = |
| SEQ ID NO: 2787 SEQUENCE: 2787 000 | moltype = | length = |
| SEQ ID NO: 2788 SEQUENCE: 2788 000 | moltype = | length = |
| SEQ ID NO: 2789 SEQUENCE: 2789 000 | moltype = | length = |
| SEQ ID NO: 2790 SEQUENCE: 2790 000 | moltype = | length = |
| SEQ ID NO: 2791 SEQUENCE: 2791 000 | moltype = | length = |
| SEQ ID NO: 2792 SEQUENCE: 2792 000 | moltype = | length = |
| SEQ ID NO: 2793 SEQUENCE: 2793 000 | moltype = | length = |
| SEQ ID NO: 2794 SEQUENCE: 2794 000 | moltype = | length = |
| SEQ ID NO: 2795 SEQUENCE: 2795 000 | moltype = | length = |
| SEQ ID NO: 2796 SEQUENCE: 2796 000 | moltype = | length = |
| SEQ ID NO: 2797 SEQUENCE: 2797 000 | moltype = | length = |
| SEQ ID NO: 2798 SEQUENCE: 2798 000 | moltype = | length = |
| SEQ ID NO: 2799 SEQUENCE: 2799 000 | moltype = | length = |
| SEQ ID NO: 2800 SEQUENCE: 2800 000 | moltype = | length = |
| SEQ ID NO: 2801 SEQUENCE: 2801 000 | moltype = | length = |

| | | |
|---|---|---|
| SEQ ID NO: 2802<br>SEQUENCE: 2802<br>000 | moltype = | length = |
| SEQ ID NO: 2803<br>SEQUENCE: 2803<br>000 | moltype = | length = |
| SEQ ID NO: 2804<br>SEQUENCE: 2804<br>000 | moltype = | length = |
| SEQ ID NO: 2805<br>SEQUENCE: 2805<br>000 | moltype = | length = |
| SEQ ID NO: 2806<br>SEQUENCE: 2806<br>000 | moltype = | length = |
| SEQ ID NO: 2807<br>SEQUENCE: 2807<br>000 | moltype = | length = |
| SEQ ID NO: 2808<br>SEQUENCE: 2808<br>000 | moltype = | length = |
| SEQ ID NO: 2809<br>SEQUENCE: 2809<br>000 | moltype = | length = |
| SEQ ID NO: 2810<br>SEQUENCE: 2810<br>000 | moltype = | length = |
| SEQ ID NO: 2811<br>SEQUENCE: 2811<br>000 | moltype = | length = |
| SEQ ID NO: 2812<br>SEQUENCE: 2812<br>000 | moltype = | length = |
| SEQ ID NO: 2813<br>SEQUENCE: 2813<br>000 | moltype = | length = |
| SEQ ID NO: 2814<br>SEQUENCE: 2814<br>000 | moltype = | length = |
| SEQ ID NO: 2815<br>SEQUENCE: 2815<br>000 | moltype = | length = |
| SEQ ID NO: 2816<br>SEQUENCE: 2816<br>000 | moltype = | length = |
| SEQ ID NO: 2817<br>SEQUENCE: 2817<br>000 | moltype = | length = |
| SEQ ID NO: 2818<br>SEQUENCE: 2818<br>000 | moltype = | length = |
| SEQ ID NO: 2819<br>SEQUENCE: 2819<br>000 | moltype = | length = |
| SEQ ID NO: 2820<br>SEQUENCE: 2820<br>000 | moltype = | length = |
| SEQ ID NO: 2821<br>SEQUENCE: 2821<br>000 | moltype = | length = |

| | | |
|---|---|---|
| SEQ ID NO: 2822 SEQUENCE: 2822 | moltype = 000 | length = |
| SEQ ID NO: 2823 SEQUENCE: 2823 | moltype = 000 | length = |
| SEQ ID NO: 2824 SEQUENCE: 2824 | moltype = 000 | length = |
| SEQ ID NO: 2825 SEQUENCE: 2825 | moltype = 000 | length = |
| SEQ ID NO: 2826 SEQUENCE: 2826 | moltype = 000 | length = |
| SEQ ID NO: 2827 SEQUENCE: 2827 | moltype = 000 | length = |
| SEQ ID NO: 2828 SEQUENCE: 2828 | moltype = 000 | length = |
| SEQ ID NO: 2829 SEQUENCE: 2829 | moltype = 000 | length = |
| SEQ ID NO: 2830 SEQUENCE: 2830 | moltype = 000 | length = |
| SEQ ID NO: 2831 SEQUENCE: 2831 | moltype = 000 | length = |
| SEQ ID NO: 2832 SEQUENCE: 2832 | moltype = 000 | length = |
| SEQ ID NO: 2833 SEQUENCE: 2833 | moltype = 000 | length = |
| SEQ ID NO: 2834 SEQUENCE: 2834 | moltype = 000 | length = |
| SEQ ID NO: 2835 SEQUENCE: 2835 | moltype = 000 | length = |
| SEQ ID NO: 2836 SEQUENCE: 2836 | moltype = 000 | length = |
| SEQ ID NO: 2837 SEQUENCE: 2837 | moltype = 000 | length = |
| SEQ ID NO: 2838 SEQUENCE: 2838 | moltype = 000 | length = |
| SEQ ID NO: 2839 SEQUENCE: 2839 | moltype = 000 | length = |
| SEQ ID NO: 2840 SEQUENCE: 2840 | moltype = 000 | length = |
| SEQ ID NO: 2841 SEQUENCE: 2841 | moltype = | length = |

000

SEQ ID NO: 2842    moltype =    length =
SEQUENCE: 2842
000

SEQ ID NO: 2843    moltype =    length =
SEQUENCE: 2843
000

SEQ ID NO: 2844    moltype =    length =
SEQUENCE: 2844
000

SEQ ID NO: 2845    moltype =    length =
SEQUENCE: 2845
000

SEQ ID NO: 2846    moltype =    length =
SEQUENCE: 2846
000

SEQ ID NO: 2847    moltype =    length =
SEQUENCE: 2847
000

SEQ ID NO: 2848    moltype =    length =
SEQUENCE: 2848
000

SEQ ID NO: 2849    moltype =    length =
SEQUENCE: 2849
000

SEQ ID NO: 2850    moltype =    length =
SEQUENCE: 2850
000

SEQ ID NO: 2851    moltype =    length =
SEQUENCE: 2851
000

SEQ ID NO: 2852    moltype =    length =
SEQUENCE: 2852
000

SEQ ID NO: 2853    moltype =    length =
SEQUENCE: 2853
000

SEQ ID NO: 2854    moltype =    length =
SEQUENCE: 2854
000

SEQ ID NO: 2855    moltype =    length =
SEQUENCE: 2855
000

SEQ ID NO: 2856    moltype =    length =
SEQUENCE: 2856
000

SEQ ID NO: 2857    moltype =    length =
SEQUENCE: 2857
000

SEQ ID NO: 2858    moltype =    length =
SEQUENCE: 2858
000

SEQ ID NO: 2859    moltype =    length =
SEQUENCE: 2859
000

SEQ ID NO: 2860    moltype =    length =
SEQUENCE: 2860
000

SEQ ID NO: 2861    moltype =    length =

| | | |
|---|---|---|
| SEQUENCE: 2861 000 | | |
| SEQ ID NO: 2862 SEQUENCE: 2862 000 | moltype = | length = |
| SEQ ID NO: 2863 SEQUENCE: 2863 000 | moltype = | length = |
| SEQ ID NO: 2864 SEQUENCE: 2864 000 | moltype = | length = |
| SEQ ID NO: 2865 SEQUENCE: 2865 000 | moltype = | length = |
| SEQ ID NO: 2866 SEQUENCE: 2866 000 | moltype = | length = |
| SEQ ID NO: 2867 SEQUENCE: 2867 000 | moltype = | length = |
| SEQ ID NO: 2868 SEQUENCE: 2868 000 | moltype = | length = |
| SEQ ID NO: 2869 SEQUENCE: 2869 000 | moltype = | length = |
| SEQ ID NO: 2870 SEQUENCE: 2870 000 | moltype = | length = |
| SEQ ID NO: 2871 SEQUENCE: 2871 000 | moltype = | length = |
| SEQ ID NO: 2872 SEQUENCE: 2872 000 | moltype = | length = |
| SEQ ID NO: 2873 SEQUENCE: 2873 000 | moltype = | length = |
| SEQ ID NO: 2874 SEQUENCE: 2874 000 | moltype = | length = |
| SEQ ID NO: 2875 SEQUENCE: 2875 000 | moltype = | length = |
| SEQ ID NO: 2876 SEQUENCE: 2876 000 | moltype = | length = |
| SEQ ID NO: 2877 SEQUENCE: 2877 000 | moltype = | length = |
| SEQ ID NO: 2878 SEQUENCE: 2878 000 | moltype = | length = |
| SEQ ID NO: 2879 SEQUENCE: 2879 000 | moltype = | length = |
| SEQ ID NO: 2880 SEQUENCE: 2880 000 | moltype = | length = |

| | | |
|---|---|---|
| SEQ ID NO: 2881<br>SEQUENCE: 2881<br>000 | moltype = | length = |
| SEQ ID NO: 2882<br>SEQUENCE: 2882<br>000 | moltype = | length = |
| SEQ ID NO: 2883<br>SEQUENCE: 2883<br>000 | moltype = | length = |
| SEQ ID NO: 2884<br>SEQUENCE: 2884<br>000 | moltype = | length = |
| SEQ ID NO: 2885<br>SEQUENCE: 2885<br>000 | moltype = | length = |
| SEQ ID NO: 2886<br>SEQUENCE: 2886<br>000 | moltype = | length = |
| SEQ ID NO: 2887<br>SEQUENCE: 2887<br>000 | moltype = | length = |
| SEQ ID NO: 2888<br>SEQUENCE: 2888<br>000 | moltype = | length = |
| SEQ ID NO: 2889<br>SEQUENCE: 2889<br>000 | moltype = | length = |
| SEQ ID NO: 2890<br>SEQUENCE: 2890<br>000 | moltype = | length = |
| SEQ ID NO: 2891<br>SEQUENCE: 2891<br>000 | moltype = | length = |
| SEQ ID NO: 2892<br>SEQUENCE: 2892<br>000 | moltype = | length = |
| SEQ ID NO: 2893<br>SEQUENCE: 2893<br>000 | moltype = | length = |
| SEQ ID NO: 2894<br>SEQUENCE: 2894<br>000 | moltype = | length = |
| SEQ ID NO: 2895<br>SEQUENCE: 2895<br>000 | moltype = | length = |
| SEQ ID NO: 2896<br>SEQUENCE: 2896<br>000 | moltype = | length = |
| SEQ ID NO: 2897<br>SEQUENCE: 2897<br>000 | moltype = | length = |
| SEQ ID NO: 2898<br>SEQUENCE: 2898<br>000 | moltype = | length = |
| SEQ ID NO: 2899<br>SEQUENCE: 2899<br>000 | moltype = | length = |
| SEQ ID NO: 2900<br>SEQUENCE: 2900<br>000 | moltype = | length = |

-continued

SEQ ID NO: 2901      moltype =     length =
SEQUENCE: 2901
000

SEQ ID NO: 2902      moltype =     length =
SEQUENCE: 2902
000

SEQ ID NO: 2903      moltype =     length =
SEQUENCE: 2903
000

SEQ ID NO: 2904      moltype =     length =
SEQUENCE: 2904
000

SEQ ID NO: 2905      moltype =     length =
SEQUENCE: 2905
000

SEQ ID NO: 2906      moltype =     length =
SEQUENCE: 2906
000

SEQ ID NO: 2907      moltype =     length =
SEQUENCE: 2907
000

SEQ ID NO: 2908      moltype =     length =
SEQUENCE: 2908
000

SEQ ID NO: 2909      moltype =     length =
SEQUENCE: 2909
000

SEQ ID NO: 2910      moltype =     length =
SEQUENCE: 2910
000

SEQ ID NO: 2911      moltype =     length =
SEQUENCE: 2911
000

SEQ ID NO: 2912      moltype =     length =
SEQUENCE: 2912
000

SEQ ID NO: 2913      moltype =     length =
SEQUENCE: 2913
000

SEQ ID NO: 2914      moltype =     length =
SEQUENCE: 2914
000

SEQ ID NO: 2915      moltype =     length =
SEQUENCE: 2915
000

SEQ ID NO: 2916      moltype =     length =
SEQUENCE: 2916
000

SEQ ID NO: 2917      moltype =     length =
SEQUENCE: 2917
000

SEQ ID NO: 2918      moltype =     length =
SEQUENCE: 2918
000

SEQ ID NO: 2919      moltype =     length =
SEQUENCE: 2919
000

SEQ ID NO: 2920      moltype =     length =
SEQUENCE: 2920

000

SEQ ID NO: 2921      moltype =    length =
SEQUENCE: 2921
000

SEQ ID NO: 2922      moltype =    length =
SEQUENCE: 2922
000

SEQ ID NO: 2923      moltype =    length =
SEQUENCE: 2923
000

SEQ ID NO: 2924      moltype =    length =
SEQUENCE: 2924
000

SEQ ID NO: 2925      moltype =    length =
SEQUENCE: 2925
000

SEQ ID NO: 2926      moltype =    length =
SEQUENCE: 2926
000

SEQ ID NO: 2927      moltype =    length =
SEQUENCE: 2927
000

SEQ ID NO: 2928      moltype =    length =
SEQUENCE: 2928
000

SEQ ID NO: 2929      moltype =    length =
SEQUENCE: 2929
000

SEQ ID NO: 2930      moltype =    length =
SEQUENCE: 2930
000

SEQ ID NO: 2931      moltype =    length =
SEQUENCE: 2931
000

SEQ ID NO: 2932      moltype =    length =
SEQUENCE: 2932
000

SEQ ID NO: 2933      moltype =    length =
SEQUENCE: 2933
000

SEQ ID NO: 2934      moltype =    length =
SEQUENCE: 2934
000

SEQ ID NO: 2935      moltype =    length =
SEQUENCE: 2935
000

SEQ ID NO: 2936      moltype =    length =
SEQUENCE: 2936
000

SEQ ID NO: 2937      moltype =    length =
SEQUENCE: 2937
000

SEQ ID NO: 2938      moltype =    length =
SEQUENCE: 2938
000

SEQ ID NO: 2939      moltype =    length =
SEQUENCE: 2939
000

SEQ ID NO: 2940      moltype =    length =

SEQUENCE: 2940
000

SEQ ID NO: 2941      moltype =    length =
SEQUENCE: 2941
000

SEQ ID NO: 2942      moltype =    length =
SEQUENCE: 2942
000

SEQ ID NO: 2943      moltype =    length =
SEQUENCE: 2943
000

SEQ ID NO: 2944      moltype =    length =
SEQUENCE: 2944
000

SEQ ID NO: 2945      moltype =    length =
SEQUENCE: 2945
000

SEQ ID NO: 2946      moltype =    length =
SEQUENCE: 2946
000

SEQ ID NO: 2947      moltype =    length =
SEQUENCE: 2947
000

SEQ ID NO: 2948      moltype =    length =
SEQUENCE: 2948
000

SEQ ID NO: 2949      moltype =    length =
SEQUENCE: 2949
000

SEQ ID NO: 2950      moltype =    length =
SEQUENCE: 2950
000

SEQ ID NO: 2951      moltype =    length =
SEQUENCE: 2951
000

SEQ ID NO: 2952      moltype =    length =
SEQUENCE: 2952
000

SEQ ID NO: 2953      moltype =    length =
SEQUENCE: 2953
000

SEQ ID NO: 2954      moltype =    length =
SEQUENCE: 2954
000

SEQ ID NO: 2955      moltype =    length =
SEQUENCE: 2955
000

SEQ ID NO: 2956      moltype =    length =
SEQUENCE: 2956
000

SEQ ID NO: 2957      moltype =    length =
SEQUENCE: 2957
000

SEQ ID NO: 2958      moltype =    length =
SEQUENCE: 2958
000

SEQ ID NO: 2959      moltype =    length =
SEQUENCE: 2959
000

| | | |
|---|---|---|
| SEQ ID NO: 2960
SEQUENCE: 2960
000 | moltype = | length = |
| SEQ ID NO: 2961
SEQUENCE: 2961
000 | moltype = | length = |
| SEQ ID NO: 2962
SEQUENCE: 2962
000 | moltype = | length = |
| SEQ ID NO: 2963
SEQUENCE: 2963
000 | moltype = | length = |
| SEQ ID NO: 2964
SEQUENCE: 2964
000 | moltype = | length = |
| SEQ ID NO: 2965
SEQUENCE: 2965
000 | moltype = | length = |
| SEQ ID NO: 2966
SEQUENCE: 2966
000 | moltype = | length = |
| SEQ ID NO: 2967
SEQUENCE: 2967
000 | moltype = | length = |
| SEQ ID NO: 2968
SEQUENCE: 2968
000 | moltype = | length = |
| SEQ ID NO: 2969
SEQUENCE: 2969
000 | moltype = | length = |
| SEQ ID NO: 2970
SEQUENCE: 2970
000 | moltype = | length = |
| SEQ ID NO: 2971
SEQUENCE: 2971
000 | moltype = | length = |
| SEQ ID NO: 2972
SEQUENCE: 2972
000 | moltype = | length = |
| SEQ ID NO: 2973
SEQUENCE: 2973
000 | moltype = | length = |
| SEQ ID NO: 2974
SEQUENCE: 2974
000 | moltype = | length = |
| SEQ ID NO: 2975
SEQUENCE: 2975
000 | moltype = | length = |
| SEQ ID NO: 2976
SEQUENCE: 2976
000 | moltype = | length = |
| SEQ ID NO: 2977
SEQUENCE: 2977
000 | moltype = | length = |
| SEQ ID NO: 2978
SEQUENCE: 2978
000 | moltype = | length = |
| SEQ ID NO: 2979
SEQUENCE: 2979
000 | moltype = | length = |

| | | |
|---|---|---|
| SEQ ID NO: 2980 SEQUENCE: 2980 000 | moltype = | length = |
| SEQ ID NO: 2981 SEQUENCE: 2981 000 | moltype = | length = |
| SEQ ID NO: 2982 SEQUENCE: 2982 000 | moltype = | length = |
| SEQ ID NO: 2983 SEQUENCE: 2983 000 | moltype = | length = |
| SEQ ID NO: 2984 SEQUENCE: 2984 000 | moltype = | length = |
| SEQ ID NO: 2985 SEQUENCE: 2985 000 | moltype = | length = |
| SEQ ID NO: 2986 SEQUENCE: 2986 000 | moltype = | length = |
| SEQ ID NO: 2987 SEQUENCE: 2987 000 | moltype = | length = |
| SEQ ID NO: 2988 SEQUENCE: 2988 000 | moltype = | length = |
| SEQ ID NO: 2989 SEQUENCE: 2989 000 | moltype = | length = |
| SEQ ID NO: 2990 SEQUENCE: 2990 000 | moltype = | length = |
| SEQ ID NO: 2991 SEQUENCE: 2991 000 | moltype = | length = |
| SEQ ID NO: 2992 SEQUENCE: 2992 000 | moltype = | length = |
| SEQ ID NO: 2993 SEQUENCE: 2993 000 | moltype = | length = |
| SEQ ID NO: 2994 SEQUENCE: 2994 000 | moltype = | length = |
| SEQ ID NO: 2995 SEQUENCE: 2995 000 | moltype = | length = |
| SEQ ID NO: 2996 SEQUENCE: 2996 000 | moltype = | length = |
| SEQ ID NO: 2997 SEQUENCE: 2997 000 | moltype = | length = |
| SEQ ID NO: 2998 SEQUENCE: 2998 000 | moltype = | length = |
| SEQ ID NO: 2999 SEQUENCE: 2999 | moltype = | length = |

-continued

000

SEQ ID NO: 3000      moltype =    length =
SEQUENCE: 3000
000

SEQ ID NO: 3001      moltype =    length =
SEQUENCE: 3001
000

SEQ ID NO: 3002      moltype =    length =
SEQUENCE: 3002
000

SEQ ID NO: 3003      moltype =    length =
SEQUENCE: 3003
000

SEQ ID NO: 3004      moltype =    length =
SEQUENCE: 3004
000

SEQ ID NO: 3005      moltype =    length =
SEQUENCE: 3005
000

SEQ ID NO: 3006      moltype =    length =
SEQUENCE: 3006
000

SEQ ID NO: 3007      moltype =    length =
SEQUENCE: 3007
000

SEQ ID NO: 3008      moltype =    length =
SEQUENCE: 3008
000

SEQ ID NO: 3009      moltype =    length =
SEQUENCE: 3009
000

SEQ ID NO: 3010      moltype =    length =
SEQUENCE: 3010
000

SEQ ID NO: 3011      moltype =    length =
SEQUENCE: 3011
000

SEQ ID NO: 3012      moltype =    length =
SEQUENCE: 3012
000

SEQ ID NO: 3013      moltype =    length =
SEQUENCE: 3013
000

SEQ ID NO: 3014      moltype =    length =
SEQUENCE: 3014
000

SEQ ID NO: 3015      moltype =    length =
SEQUENCE: 3015
000

SEQ ID NO: 3016      moltype =    length =
SEQUENCE: 3016
000

SEQ ID NO: 3017      moltype =    length =
SEQUENCE: 3017
000

SEQ ID NO: 3018      moltype =    length =
SEQUENCE: 3018
000

SEQ ID NO: 3019      moltype =    length =

| | | |
|---|---|---|
| SEQUENCE: 3019 000 | | |
| SEQ ID NO: 3020 SEQUENCE: 3020 000 | moltype = | length = |
| SEQ ID NO: 3021 SEQUENCE: 3021 000 | moltype = | length = |
| SEQ ID NO: 3022 SEQUENCE: 3022 000 | moltype = | length = |
| SEQ ID NO: 3023 SEQUENCE: 3023 000 | moltype = | length = |
| SEQ ID NO: 3024 SEQUENCE: 3024 000 | moltype = | length = |
| SEQ ID NO: 3025 SEQUENCE: 3025 000 | moltype = | length = |
| SEQ ID NO: 3026 SEQUENCE: 3026 000 | moltype = | length = |
| SEQ ID NO: 3027 SEQUENCE: 3027 000 | moltype = | length = |
| SEQ ID NO: 3028 SEQUENCE: 3028 000 | moltype = | length = |
| SEQ ID NO: 3029 SEQUENCE: 3029 000 | moltype = | length = |
| SEQ ID NO: 3030 SEQUENCE: 3030 000 | moltype = | length = |
| SEQ ID NO: 3031 SEQUENCE: 3031 000 | moltype = | length = |
| SEQ ID NO: 3032 SEQUENCE: 3032 000 | moltype = | length = |
| SEQ ID NO: 3033 SEQUENCE: 3033 000 | moltype = | length = |
| SEQ ID NO: 3034 SEQUENCE: 3034 000 | moltype = | length = |
| SEQ ID NO: 3035 SEQUENCE: 3035 000 | moltype = | length = |
| SEQ ID NO: 3036 SEQUENCE: 3036 000 | moltype = | length = |
| SEQ ID NO: 3037 SEQUENCE: 3037 000 | moltype = | length = |
| SEQ ID NO: 3038 SEQUENCE: 3038 000 | moltype = | length = |

| | | |
|---|---|---|
| SEQ ID NO: 3039<br>SEQUENCE: 3039<br>000 | moltype = | length = |
| SEQ ID NO: 3040<br>SEQUENCE: 3040<br>000 | moltype = | length = |
| SEQ ID NO: 3041<br>SEQUENCE: 3041<br>000 | moltype = | length = |
| SEQ ID NO: 3042<br>SEQUENCE: 3042<br>000 | moltype = | length = |
| SEQ ID NO: 3043<br>SEQUENCE: 3043<br>000 | moltype = | length = |
| SEQ ID NO: 3044<br>SEQUENCE: 3044<br>000 | moltype = | length = |
| SEQ ID NO: 3045<br>SEQUENCE: 3045<br>000 | moltype = | length = |
| SEQ ID NO: 3046<br>SEQUENCE: 3046<br>000 | moltype = | length = |
| SEQ ID NO: 3047<br>SEQUENCE: 3047<br>000 | moltype = | length = |
| SEQ ID NO: 3048<br>SEQUENCE: 3048<br>000 | moltype = | length = |
| SEQ ID NO: 3049<br>SEQUENCE: 3049<br>000 | moltype = | length = |
| SEQ ID NO: 3050<br>SEQUENCE: 3050<br>000 | moltype = | length = |
| SEQ ID NO: 3051<br>SEQUENCE: 3051<br>000 | moltype = | length = |
| SEQ ID NO: 3052<br>SEQUENCE: 3052<br>000 | moltype = | length = |
| SEQ ID NO: 3053<br>SEQUENCE: 3053<br>000 | moltype = | length = |
| SEQ ID NO: 3054<br>SEQUENCE: 3054<br>000 | moltype = | length = |
| SEQ ID NO: 3055<br>SEQUENCE: 3055<br>000 | moltype = | length = |
| SEQ ID NO: 3056<br>SEQUENCE: 3056<br>000 | moltype = | length = |
| SEQ ID NO: 3057<br>SEQUENCE: 3057<br>000 | moltype = | length = |
| SEQ ID NO: 3058<br>SEQUENCE: 3058<br>000 | moltype = | length = |

| | | |
|---|---|---|
| SEQ ID NO: 3059 SEQUENCE: 3059 000 | moltype = | length = |
| SEQ ID NO: 3060 SEQUENCE: 3060 000 | moltype = | length = |
| SEQ ID NO: 3061 SEQUENCE: 3061 000 | moltype = | length = |
| SEQ ID NO: 3062 SEQUENCE: 3062 000 | moltype = | length = |
| SEQ ID NO: 3063 SEQUENCE: 3063 000 | moltype = | length = |
| SEQ ID NO: 3064 SEQUENCE: 3064 000 | moltype = | length = |
| SEQ ID NO: 3065 SEQUENCE: 3065 000 | moltype = | length = |
| SEQ ID NO: 3066 SEQUENCE: 3066 000 | moltype = | length = |
| SEQ ID NO: 3067 SEQUENCE: 3067 000 | moltype = | length = |
| SEQ ID NO: 3068 SEQUENCE: 3068 000 | moltype = | length = |
| SEQ ID NO: 3069 SEQUENCE: 3069 000 | moltype = | length = |
| SEQ ID NO: 3070 SEQUENCE: 3070 000 | moltype = | length = |
| SEQ ID NO: 3071 SEQUENCE: 3071 000 | moltype = | length = |
| SEQ ID NO: 3072 SEQUENCE: 3072 000 | moltype = | length = |
| SEQ ID NO: 3073 SEQUENCE: 3073 000 | moltype = | length = |
| SEQ ID NO: 3074 SEQUENCE: 3074 000 | moltype = | length = |
| SEQ ID NO: 3075 SEQUENCE: 3075 000 | moltype = | length = |
| SEQ ID NO: 3076 SEQUENCE: 3076 000 | moltype = | length = |
| SEQ ID NO: 3077 SEQUENCE: 3077 000 | moltype = | length = |
| SEQ ID NO: 3078 SEQUENCE: 3078 | moltype = | length = |

000

SEQ ID NO: 3079     moltype =     length =
SEQUENCE: 3079
000

SEQ ID NO: 3080     moltype =     length =
SEQUENCE: 3080
000

SEQ ID NO: 3081     moltype =     length =
SEQUENCE: 3081
000

SEQ ID NO: 3082     moltype =     length =
SEQUENCE: 3082
000

SEQ ID NO: 3083     moltype =     length =
SEQUENCE: 3083
000

SEQ ID NO: 3084     moltype =     length =
SEQUENCE: 3084
000

SEQ ID NO: 3085     moltype =     length =
SEQUENCE: 3085
000

SEQ ID NO: 3086     moltype =     length =
SEQUENCE: 3086
000

SEQ ID NO: 3087     moltype =     length =
SEQUENCE: 3087
000

SEQ ID NO: 3088     moltype =     length =
SEQUENCE: 3088
000

SEQ ID NO: 3089     moltype =     length =
SEQUENCE: 3089
000

SEQ ID NO: 3090     moltype =     length =
SEQUENCE: 3090
000

SEQ ID NO: 3091     moltype =     length =
SEQUENCE: 3091
000

SEQ ID NO: 3092     moltype =     length =
SEQUENCE: 3092
000

SEQ ID NO: 3093     moltype =     length =
SEQUENCE: 3093
000

SEQ ID NO: 3094     moltype =     length =
SEQUENCE: 3094
000

SEQ ID NO: 3095     moltype =     length =
SEQUENCE: 3095
000

SEQ ID NO: 3096     moltype =     length =
SEQUENCE: 3096
000

SEQ ID NO: 3097     moltype =     length =
SEQUENCE: 3097
000

SEQ ID NO: 3098     moltype =     length =

```
SEQUENCE: 3098
000

SEQ ID NO: 3099         moltype =    length =
SEQUENCE: 3099
000

SEQ ID NO: 3100         moltype = AA  length = 225
FEATURE                 Location/Qualifiers
source                  1..225
                        mol_type = protein
                        organism = Homo sapiens
SEQUENCE: 3100
THTCPPCPAP ELLGGPSVFL FPPKPKDTLM ISRTPEVTCV VVDVSHEDPE VKFNWYVDGV    60
EVHNAKTKPR EEQYNSTYRV VSVLTVLHQD WLNGKEYKCK VSNKALPAPI EKTISKAKGQ   120
PREPQVYTLP PSREEMTKNQ VSLTCLVKGF YPSDIAVEWE SNGQPENNYK TTPPVLDSDG   180
SFFLYSKLTV DKSRWQQGNV FSCSVMHEAL HNHYTQKSLS LSPGK                   225

SEQ ID NO: 3101         moltype =    length =
SEQUENCE: 3101
000

SEQ ID NO: 3102         moltype =    length =
SEQUENCE: 3102
000

SEQ ID NO: 3103         moltype =    length =
SEQUENCE: 3103
000

SEQ ID NO: 3104         moltype =    length =
SEQUENCE: 3104
000

SEQ ID NO: 3105         moltype =    length =
SEQUENCE: 3105
000

SEQ ID NO: 3106         moltype =    length =
SEQUENCE: 3106
000

SEQ ID NO: 3107         moltype =    length =
SEQUENCE: 3107
000

SEQ ID NO: 3108         moltype =    length =
SEQUENCE: 3108
000

SEQ ID NO: 3109         moltype =    length =
SEQUENCE: 3109
000

SEQ ID NO: 3110         moltype =    length =
SEQUENCE: 3110
000

SEQ ID NO: 3111         moltype =    length =
SEQUENCE: 3111
000

SEQ ID NO: 3112         moltype =    length =
SEQUENCE: 3112
000

SEQ ID NO: 3113         moltype =    length =
SEQUENCE: 3113
000

SEQ ID NO: 3114         moltype =    length =
SEQUENCE: 3114
000

SEQ ID NO: 3115         moltype =    length =
SEQUENCE: 3115
000

SEQ ID NO: 3116         moltype =    length =
```

```
SEQUENCE: 3116
000

SEQ ID NO: 3117           moltype =      length =
SEQUENCE: 3117
000

SEQ ID NO: 3118           moltype =      length =
SEQUENCE: 3118
000

SEQ ID NO: 3119           moltype =      length =
SEQUENCE: 3119
000

SEQ ID NO: 3120           moltype =      length =
SEQUENCE: 3120
000

SEQ ID NO: 3121           moltype =      length =
SEQUENCE: 3121
000

SEQ ID NO: 3122           moltype =      length =
SEQUENCE: 3122
000

SEQ ID NO: 3123           moltype =      length =
SEQUENCE: 3123
000

SEQ ID NO: 3124           moltype =      length =
SEQUENCE: 3124
000

SEQ ID NO: 3125           moltype =      length =
SEQUENCE: 3125
000

SEQ ID NO: 3126           moltype =      length =
SEQUENCE: 3126
000

SEQ ID NO: 3127           moltype =      length =
SEQUENCE: 3127
000

SEQ ID NO: 3128           moltype =      length =
SEQUENCE: 3128
000

SEQ ID NO: 3129           moltype =      length =
SEQUENCE: 3129
000

SEQ ID NO: 3130           moltype =      length =
SEQUENCE: 3130
000

SEQ ID NO: 3131           moltype =      length =
SEQUENCE: 3131
000

SEQ ID NO: 3132           moltype =      length =
SEQUENCE: 3132
000

SEQ ID NO: 3133           moltype =      length =
SEQUENCE: 3133
000

SEQ ID NO: 3134           moltype =      length =
SEQUENCE: 3134
000

SEQ ID NO: 3135           moltype =      length =
SEQUENCE: 3135
000
```

-continued

SEQ ID NO: 3136        moltype =    length =
SEQUENCE: 3136
000

SEQ ID NO: 3137        moltype =    length =
SEQUENCE: 3137
000

SEQ ID NO: 3138        moltype =    length =
SEQUENCE: 3138
000

SEQ ID NO: 3139        moltype =    length =
SEQUENCE: 3139
000

SEQ ID NO: 3140        moltype =    length =
SEQUENCE: 3140
000

SEQ ID NO: 3141        moltype =    length =
SEQUENCE: 3141
000

SEQ ID NO: 3142        moltype =    length =
SEQUENCE: 3142
000

SEQ ID NO: 3143        moltype =    length =
SEQUENCE: 3143
000

SEQ ID NO: 3144        moltype =    length =
SEQUENCE: 3144
000

SEQ ID NO: 3145        moltype =    length =
SEQUENCE: 3145
000

SEQ ID NO: 3146        moltype =    length =
SEQUENCE: 3146
000

SEQ ID NO: 3147        moltype =    length =
SEQUENCE: 3147
000

SEQ ID NO: 3148        moltype =    length =
SEQUENCE: 3148
000

SEQ ID NO: 3149        moltype =    length =
SEQUENCE: 3149
000

SEQ ID NO: 3150        moltype =    length =
SEQUENCE: 3150
000

SEQ ID NO: 3151        moltype =    length =
SEQUENCE: 3151
000

SEQ ID NO: 3152        moltype =    length =
SEQUENCE: 3152
000

SEQ ID NO: 3153        moltype =    length =
SEQUENCE: 3153
000

SEQ ID NO: 3154        moltype =    length =
SEQUENCE: 3154
000

SEQ ID NO: 3155        moltype =    length =
SEQUENCE: 3155
000

SEQ ID NO: 3156        moltype =   length =
SEQUENCE: 3156
000

SEQ ID NO: 3157        moltype =   length =
SEQUENCE: 3157
000

SEQ ID NO: 3158        moltype =   length =
SEQUENCE: 3158
000

SEQ ID NO: 3159        moltype =   length =
SEQUENCE: 3159
000

SEQ ID NO: 3160        moltype =   length =
SEQUENCE: 3160
000

SEQ ID NO: 3161        moltype =   length =
SEQUENCE: 3161
000

SEQ ID NO: 3162        moltype =   length =
SEQUENCE: 3162
000

SEQ ID NO: 3163        moltype =   length =
SEQUENCE: 3163
000

SEQ ID NO: 3164        moltype =   length =
SEQUENCE: 3164
000

SEQ ID NO: 3165        moltype =   length =
SEQUENCE: 3165
000

SEQ ID NO: 3166        moltype =   length =
SEQUENCE: 3166
000

SEQ ID NO: 3167        moltype =   length =
SEQUENCE: 3167
000

SEQ ID NO: 3168        moltype =   length =
SEQUENCE: 3168
000

SEQ ID NO: 3169        moltype =   length =
SEQUENCE: 3169
000

SEQ ID NO: 3170        moltype =   length =
SEQUENCE: 3170
000

SEQ ID NO: 3171        moltype =   length =
SEQUENCE: 3171
000

SEQ ID NO: 3172        moltype =   length =
SEQUENCE: 3172
000

SEQ ID NO: 3173        moltype =   length =
SEQUENCE: 3173
000

SEQ ID NO: 3174        moltype =   length =
SEQUENCE: 3174
000

SEQ ID NO: 3175        moltype =   length =
SEQUENCE: 3175

-continued

000

SEQ ID NO: 3176      moltype =      length =
SEQUENCE: 3176
000

SEQ ID NO: 3177      moltype =      length =
SEQUENCE: 3177
000

SEQ ID NO: 3178      moltype =      length =
SEQUENCE: 3178
000

SEQ ID NO: 3179      moltype =      length =
SEQUENCE: 3179
000

SEQ ID NO: 3180      moltype =      length =
SEQUENCE: 3180
000

SEQ ID NO: 3181      moltype =      length =
SEQUENCE: 3181
000

SEQ ID NO: 3182      moltype =      length =
SEQUENCE: 3182
000

SEQ ID NO: 3183      moltype =      length =
SEQUENCE: 3183
000

SEQ ID NO: 3184      moltype =      length =
SEQUENCE: 3184
000

SEQ ID NO: 3185      moltype =      length =
SEQUENCE: 3185
000

SEQ ID NO: 3186      moltype =      length =
SEQUENCE: 3186
000

SEQ ID NO: 3187      moltype =      length =
SEQUENCE: 3187
000

SEQ ID NO: 3188      moltype =      length =
SEQUENCE: 3188
000

SEQ ID NO: 3189      moltype =      length =
SEQUENCE: 3189
000

SEQ ID NO: 3190      moltype =      length =
SEQUENCE: 3190
000

SEQ ID NO: 3191      moltype =      length =
SEQUENCE: 3191
000

SEQ ID NO: 3192      moltype =      length =
SEQUENCE: 3192
000

SEQ ID NO: 3193      moltype =      length =
SEQUENCE: 3193
000

SEQ ID NO: 3194      moltype =      length =
SEQUENCE: 3194
000

SEQ ID NO: 3195      moltype =      length =

```
SEQUENCE: 3195
000

SEQ ID NO: 3196          moltype =    length =
SEQUENCE: 3196
000

SEQ ID NO: 3197          moltype =    length =
SEQUENCE: 3197
000

SEQ ID NO: 3198          moltype =    length =
SEQUENCE: 3198
000

SEQ ID NO: 3199          moltype =    length =
SEQUENCE: 3199
000

SEQ ID NO: 3200          moltype = AA  length = 223
FEATURE                  Location/Qualifiers
source                   1..223
                         mol_type = protein
                         organism = Homo sapiens
SEQUENCE: 3200
VECPPCPAPP VAGPSVFLFP PKPKDTLMIS RTPEVTCVVV DVSHEDPEVQ FNWYVDGVEV    60
HNAKTKPREE QFNSTFRVVS VLTVVHQDWL NGKEYKCKVS NKGLPAPIEK TISKTKGQPR   120
EPQVYTLPPS REEMTKNQVS LTCLVKGFYP SDIAVEWESN GQPENNYKTT PPMLDSDGSF   180
FLYSKLTVDK SRWQQGNVFS CSVMHEALHN HYTQKSLSLS PGK                     223

SEQ ID NO: 3201          moltype =    length =
SEQUENCE: 3201
000

SEQ ID NO: 3202          moltype =    length =
SEQUENCE: 3202
000

SEQ ID NO: 3203          moltype =    length =
SEQUENCE: 3203
000

SEQ ID NO: 3204          moltype =    length =
SEQUENCE: 3204
000

SEQ ID NO: 3205          moltype =    length =
SEQUENCE: 3205
000

SEQ ID NO: 3206          moltype =    length =
SEQUENCE: 3206
000

SEQ ID NO: 3207          moltype =    length =
SEQUENCE: 3207
000

SEQ ID NO: 3208          moltype =    length =
SEQUENCE: 3208
000

SEQ ID NO: 3209          moltype =    length =
SEQUENCE: 3209
000

SEQ ID NO: 3210          moltype =    length =
SEQUENCE: 3210
000

SEQ ID NO: 3211          moltype =    length =
SEQUENCE: 3211
000

SEQ ID NO: 3212          moltype =    length =
SEQUENCE: 3212
000

SEQ ID NO: 3213          moltype =    length =
```

| | | |
|---|---|---|
| SEQUENCE: 3213 000 | | |
| SEQ ID NO: 3214 SEQUENCE: 3214 000 | moltype = | length = |
| SEQ ID NO: 3215 SEQUENCE: 3215 000 | moltype = | length = |
| SEQ ID NO: 3216 SEQUENCE: 3216 000 | moltype = | length = |
| SEQ ID NO: 3217 SEQUENCE: 3217 000 | moltype = | length = |
| SEQ ID NO: 3218 SEQUENCE: 3218 000 | moltype = | length = |
| SEQ ID NO: 3219 SEQUENCE: 3219 000 | moltype = | length = |
| SEQ ID NO: 3220 SEQUENCE: 3220 000 | moltype = | length = |
| SEQ ID NO: 3221 SEQUENCE: 3221 000 | moltype = | length = |
| SEQ ID NO: 3222 SEQUENCE: 3222 000 | moltype = | length = |
| SEQ ID NO: 3223 SEQUENCE: 3223 000 | moltype = | length = |
| SEQ ID NO: 3224 SEQUENCE: 3224 000 | moltype = | length = |
| SEQ ID NO: 3225 SEQUENCE: 3225 000 | moltype = | length = |
| SEQ ID NO: 3226 SEQUENCE: 3226 000 | moltype = | length = |
| SEQ ID NO: 3227 SEQUENCE: 3227 000 | moltype = | length = |
| SEQ ID NO: 3228 SEQUENCE: 3228 000 | moltype = | length = |
| SEQ ID NO: 3229 SEQUENCE: 3229 000 | moltype = | length = |
| SEQ ID NO: 3230 SEQUENCE: 3230 000 | moltype = | length = |
| SEQ ID NO: 3231 SEQUENCE: 3231 000 | moltype = | length = |
| SEQ ID NO: 3232 SEQUENCE: 3232 000 | moltype = | length = |

-continued

SEQ ID NO: 3233  moltype =  length =
SEQUENCE: 3233
000

SEQ ID NO: 3234  moltype =  length =
SEQUENCE: 3234
000

SEQ ID NO: 3235  moltype =  length =
SEQUENCE: 3235
000

SEQ ID NO: 3236  moltype =  length =
SEQUENCE: 3236
000

SEQ ID NO: 3237  moltype =  length =
SEQUENCE: 3237
000

SEQ ID NO: 3238  moltype =  length =
SEQUENCE: 3238
000

SEQ ID NO: 3239  moltype =  length =
SEQUENCE: 3239
000

SEQ ID NO: 3240  moltype =  length =
SEQUENCE: 3240
000

SEQ ID NO: 3241  moltype =  length =
SEQUENCE: 3241
000

SEQ ID NO: 3242  moltype =  length =
SEQUENCE: 3242
000

SEQ ID NO: 3243  moltype =  length =
SEQUENCE: 3243
000

SEQ ID NO: 3244  moltype =  length =
SEQUENCE: 3244
000

SEQ ID NO: 3245  moltype =  length =
SEQUENCE: 3245
000

SEQ ID NO: 3246  moltype =  length =
SEQUENCE: 3246
000

SEQ ID NO: 3247  moltype =  length =
SEQUENCE: 3247
000

SEQ ID NO: 3248  moltype =  length =
SEQUENCE: 3248
000

SEQ ID NO: 3249  moltype =  length =
SEQUENCE: 3249
000

SEQ ID NO: 3250  moltype =  length =
SEQUENCE: 3250
000

SEQ ID NO: 3251  moltype =  length =
SEQUENCE: 3251
000

SEQ ID NO: 3252  moltype =  length =
SEQUENCE: 3252
000

| | | |
|---|---|---|
| SEQ ID NO: 3253 SEQUENCE: 3253 | moltype = 000 | length = |
| SEQ ID NO: 3254 SEQUENCE: 3254 | moltype = 000 | length = |
| SEQ ID NO: 3255 SEQUENCE: 3255 | moltype = 000 | length = |
| SEQ ID NO: 3256 SEQUENCE: 3256 | moltype = 000 | length = |
| SEQ ID NO: 3257 SEQUENCE: 3257 | moltype = 000 | length = |
| SEQ ID NO: 3258 SEQUENCE: 3258 | moltype = 000 | length = |
| SEQ ID NO: 3259 SEQUENCE: 3259 | moltype = 000 | length = |
| SEQ ID NO: 3260 SEQUENCE: 3260 | moltype = 000 | length = |
| SEQ ID NO: 3261 SEQUENCE: 3261 | moltype = 000 | length = |
| SEQ ID NO: 3262 SEQUENCE: 3262 | moltype = 000 | length = |
| SEQ ID NO: 3263 SEQUENCE: 3263 | moltype = 000 | length = |
| SEQ ID NO: 3264 SEQUENCE: 3264 | moltype = 000 | length = |
| SEQ ID NO: 3265 SEQUENCE: 3265 | moltype = 000 | length = |
| SEQ ID NO: 3266 SEQUENCE: 3266 | moltype = 000 | length = |
| SEQ ID NO: 3267 SEQUENCE: 3267 | moltype = 000 | length = |
| SEQ ID NO: 3268 SEQUENCE: 3268 | moltype = 000 | length = |
| SEQ ID NO: 3269 SEQUENCE: 3269 | moltype = 000 | length = |
| SEQ ID NO: 3270 SEQUENCE: 3270 | moltype = 000 | length = |
| SEQ ID NO: 3271 SEQUENCE: 3271 | moltype = 000 | length = |
| SEQ ID NO: 3272 SEQUENCE: 3272 | moltype = | length = |

```
SEQ ID NO: 3273       moltype =   length =
SEQUENCE: 3273
000

SEQ ID NO: 3274       moltype =   length =
SEQUENCE: 3274
000

SEQ ID NO: 3275       moltype =   length =
SEQUENCE: 3275
000

SEQ ID NO: 3276       moltype =   length =
SEQUENCE: 3276
000

SEQ ID NO: 3277       moltype =   length =
SEQUENCE: 3277
000

SEQ ID NO: 3278       moltype =   length =
SEQUENCE: 3278
000

SEQ ID NO: 3279       moltype =   length =
SEQUENCE: 3279
000

SEQ ID NO: 3280       moltype =   length =
SEQUENCE: 3280
000

SEQ ID NO: 3281       moltype =   length =
SEQUENCE: 3281
000

SEQ ID NO: 3282       moltype =   length =
SEQUENCE: 3282
000

SEQ ID NO: 3283       moltype =   length =
SEQUENCE: 3283
000

SEQ ID NO: 3284       moltype =   length =
SEQUENCE: 3284
000

SEQ ID NO: 3285       moltype =   length =
SEQUENCE: 3285
000

SEQ ID NO: 3286       moltype =   length =
SEQUENCE: 3286
000

SEQ ID NO: 3287       moltype =   length =
SEQUENCE: 3287
000

SEQ ID NO: 3288       moltype =   length =
SEQUENCE: 3288
000

SEQ ID NO: 3289       moltype =   length =
SEQUENCE: 3289
000

SEQ ID NO: 3290       moltype =   length =
SEQUENCE: 3290
000

SEQ ID NO: 3291       moltype =   length =
SEQUENCE: 3291
000

SEQ ID NO: 3292       moltype =   length =
```

-continued

```
SEQUENCE: 3292
000

SEQ ID NO: 3293          moltype =    length =
SEQUENCE: 3293
000

SEQ ID NO: 3294          moltype =    length =
SEQUENCE: 3294
000

SEQ ID NO: 3295          moltype =    length =
SEQUENCE: 3295
000

SEQ ID NO: 3296          moltype =    length =
SEQUENCE: 3296
000

SEQ ID NO: 3297          moltype =    length =
SEQUENCE: 3297
000

SEQ ID NO: 3298          moltype =    length =
SEQUENCE: 3298
000

SEQ ID NO: 3299          moltype =    length =
SEQUENCE: 3299
000

SEQ ID NO: 3300          moltype = AA  length = 232
FEATURE                  Location/Qualifiers
source                   1..232
                         mol_type = protein
                         organism = Homo sapiens
SEQUENCE: 3300
EPKSCDTPPP CPRCPAPELL GGPSVFLFPP KPKDTLMISR TPEVTCVVVD VSHEDPEVQF   60
KWYVDGVEVH NAKTKPREEQ YNSTFRVVSV LTVLHQDWLN GKEYKCKVSN KALPAPIEKT  120
ISKTKGQPRE PQVYTLPPSR EEMTKNQVSL TCLVKGFYPS DIAVEWESSG QPENNYNTTP  180
PMLDSDGSFF LYSKLTVDKS RWQQGNIFSC SVMHEALHNR FTQKSLSLSP GK          232

SEQ ID NO: 3301          moltype =    length =
SEQUENCE: 3301
000

SEQ ID NO: 3302          moltype =    length =
SEQUENCE: 3302
000

SEQ ID NO: 3303          moltype =    length =
SEQUENCE: 3303
000

SEQ ID NO: 3304          moltype =    length =
SEQUENCE: 3304
000

SEQ ID NO: 3305          moltype =    length =
SEQUENCE: 3305
000

SEQ ID NO: 3306          moltype =    length =
SEQUENCE: 3306
000

SEQ ID NO: 3307          moltype =    length =
SEQUENCE: 3307
000

SEQ ID NO: 3308          moltype =    length =
SEQUENCE: 3308
000

SEQ ID NO: 3309          moltype =    length =
SEQUENCE: 3309
000

SEQ ID NO: 3310          moltype =    length =
```

SEQUENCE: 3310
000

SEQ ID NO: 3311    moltype =    length =
SEQUENCE: 3311
000

SEQ ID NO: 3312    moltype =    length =
SEQUENCE: 3312
000

SEQ ID NO: 3313    moltype =    length =
SEQUENCE: 3313
000

SEQ ID NO: 3314    moltype =    length =
SEQUENCE: 3314
000

SEQ ID NO: 3315    moltype =    length =
SEQUENCE: 3315
000

SEQ ID NO: 3316    moltype =    length =
SEQUENCE: 3316
000

SEQ ID NO: 3317    moltype =    length =
SEQUENCE: 3317
000

SEQ ID NO: 3318    moltype =    length =
SEQUENCE: 3318
000

SEQ ID NO: 3319    moltype =    length =
SEQUENCE: 3319
000

SEQ ID NO: 3320    moltype =    length =
SEQUENCE: 3320
000

SEQ ID NO: 3321    moltype =    length =
SEQUENCE: 3321
000

SEQ ID NO: 3322    moltype =    length =
SEQUENCE: 3322
000

SEQ ID NO: 3323    moltype =    length =
SEQUENCE: 3323
000

SEQ ID NO: 3324    moltype =    length =
SEQUENCE: 3324
000

SEQ ID NO: 3325    moltype =    length =
SEQUENCE: 3325
000

SEQ ID NO: 3326    moltype =    length =
SEQUENCE: 3326
000

SEQ ID NO: 3327    moltype =    length =
SEQUENCE: 3327
000

SEQ ID NO: 3328    moltype =    length =
SEQUENCE: 3328
000

SEQ ID NO: 3329    moltype =    length =
SEQUENCE: 3329
000

| | | |
|---|---|---|
| SEQ ID NO: 3330<br>SEQUENCE: 3330<br>000 | moltype = | length = |
| SEQ ID NO: 3331<br>SEQUENCE: 3331<br>000 | moltype = | length = |
| SEQ ID NO: 3332<br>SEQUENCE: 3332<br>000 | moltype = | length = |
| SEQ ID NO: 3333<br>SEQUENCE: 3333<br>000 | moltype = | length = |
| SEQ ID NO: 3334<br>SEQUENCE: 3334<br>000 | moltype = | length = |
| SEQ ID NO: 3335<br>SEQUENCE: 3335<br>000 | moltype = | length = |
| SEQ ID NO: 3336<br>SEQUENCE: 3336<br>000 | moltype = | length = |
| SEQ ID NO: 3337<br>SEQUENCE: 3337<br>000 | moltype = | length = |
| SEQ ID NO: 3338<br>SEQUENCE: 3338<br>000 | moltype = | length = |
| SEQ ID NO: 3339<br>SEQUENCE: 3339<br>000 | moltype = | length = |
| SEQ ID NO: 3340<br>SEQUENCE: 3340<br>000 | moltype = | length = |
| SEQ ID NO: 3341<br>SEQUENCE: 3341<br>000 | moltype = | length = |
| SEQ ID NO: 3342<br>SEQUENCE: 3342<br>000 | moltype = | length = |
| SEQ ID NO: 3343<br>SEQUENCE: 3343<br>000 | moltype = | length = |
| SEQ ID NO: 3344<br>SEQUENCE: 3344<br>000 | moltype = | length = |
| SEQ ID NO: 3345<br>SEQUENCE: 3345<br>000 | moltype = | length = |
| SEQ ID NO: 3346<br>SEQUENCE: 3346<br>000 | moltype = | length = |
| SEQ ID NO: 3347<br>SEQUENCE: 3347<br>000 | moltype = | length = |
| SEQ ID NO: 3348<br>SEQUENCE: 3348<br>000 | moltype = | length = |
| SEQ ID NO: 3349<br>SEQUENCE: 3349<br>000 | moltype = | length = |

| | | |
|---|---|---|
| SEQ ID NO: 3350 SEQUENCE: 3350 | moltype = 000 | length = |
| SEQ ID NO: 3351 SEQUENCE: 3351 | moltype = 000 | length = |
| SEQ ID NO: 3352 SEQUENCE: 3352 | moltype = 000 | length = |
| SEQ ID NO: 3353 SEQUENCE: 3353 | moltype = 000 | length = |
| SEQ ID NO: 3354 SEQUENCE: 3354 | moltype = 000 | length = |
| SEQ ID NO: 3355 SEQUENCE: 3355 | moltype = 000 | length = |
| SEQ ID NO: 3356 SEQUENCE: 3356 | moltype = 000 | length = |
| SEQ ID NO: 3357 SEQUENCE: 3357 | moltype = 000 | length = |
| SEQ ID NO: 3358 SEQUENCE: 3358 | moltype = 000 | length = |
| SEQ ID NO: 3359 SEQUENCE: 3359 | moltype = 000 | length = |
| SEQ ID NO: 3360 SEQUENCE: 3360 | moltype = 000 | length = |
| SEQ ID NO: 3361 SEQUENCE: 3361 | moltype = 000 | length = |
| SEQ ID NO: 3362 SEQUENCE: 3362 | moltype = 000 | length = |
| SEQ ID NO: 3363 SEQUENCE: 3363 | moltype = 000 | length = |
| SEQ ID NO: 3364 SEQUENCE: 3364 | moltype = 000 | length = |
| SEQ ID NO: 3365 SEQUENCE: 3365 | moltype = 000 | length = |
| SEQ ID NO: 3366 SEQUENCE: 3366 | moltype = 000 | length = |
| SEQ ID NO: 3367 SEQUENCE: 3367 | moltype = 000 | length = |
| SEQ ID NO: 3368 SEQUENCE: 3368 | moltype = 000 | length = |
| SEQ ID NO: 3369 SEQUENCE: 3369 | moltype = | length = |

-continued

000

SEQ ID NO: 3370  moltype =  length =
SEQUENCE: 3370
000

SEQ ID NO: 3371  moltype =  length =
SEQUENCE: 3371
000

SEQ ID NO: 3372  moltype =  length =
SEQUENCE: 3372
000

SEQ ID NO: 3373  moltype =  length =
SEQUENCE: 3373
000

SEQ ID NO: 3374  moltype =  length =
SEQUENCE: 3374
000

SEQ ID NO: 3375  moltype =  length =
SEQUENCE: 3375
000

SEQ ID NO: 3376  moltype =  length =
SEQUENCE: 3376
000

SEQ ID NO: 3377  moltype =  length =
SEQUENCE: 3377
000

SEQ ID NO: 3378  moltype =  length =
SEQUENCE: 3378
000

SEQ ID NO: 3379  moltype =  length =
SEQUENCE: 3379
000

SEQ ID NO: 3380  moltype =  length =
SEQUENCE: 3380
000

SEQ ID NO: 3381  moltype =  length =
SEQUENCE: 3381
000

SEQ ID NO: 3382  moltype =  length =
SEQUENCE: 3382
000

SEQ ID NO: 3383  moltype =  length =
SEQUENCE: 3383
000

SEQ ID NO: 3384  moltype =  length =
SEQUENCE: 3384
000

SEQ ID NO: 3385  moltype =  length =
SEQUENCE: 3385
000

SEQ ID NO: 3386  moltype =  length =
SEQUENCE: 3386
000

SEQ ID NO: 3387  moltype =  length =
SEQUENCE: 3387
000

SEQ ID NO: 3388  moltype =  length =
SEQUENCE: 3388
000

SEQ ID NO: 3389  moltype =  length =

```
SEQUENCE: 3389
000

SEQ ID NO: 3390         moltype =    length =
SEQUENCE: 3390
000

SEQ ID NO: 3391         moltype =    length =
SEQUENCE: 3391
000

SEQ ID NO: 3392         moltype =    length =
SEQUENCE: 3392
000

SEQ ID NO: 3393         moltype =    length =
SEQUENCE: 3393
000

SEQ ID NO: 3394         moltype =    length =
SEQUENCE: 3394
000

SEQ ID NO: 3395         moltype =    length =
SEQUENCE: 3395
000

SEQ ID NO: 3396         moltype =    length =
SEQUENCE: 3396
000

SEQ ID NO: 3397         moltype =    length =
SEQUENCE: 3397
000

SEQ ID NO: 3398         moltype =    length =
SEQUENCE: 3398
000

SEQ ID NO: 3399         moltype =    length =
SEQUENCE: 3399
000

SEQ ID NO: 3400         moltype = AA  length = 279
FEATURE                 Location/Qualifiers
source                  1..279
                        mol_type = protein
                        organism = Homo sapiens
SEQUENCE: 3400
ELKTPLGDTT HTCPRCPEPK SCDTPPPCPR CPEPKSCDTP PPCPRCPEPK SCDTPPPCPR    60
CPAPELLGGP SVFLFPPKPK DTLMISRTPE VTCVVVDVSH EDPEVQFKWY VDGVEVHNAK   120
TKPREEQYNS TFRVVSVLTV LHQDWLNGKE YKCKVSNKAL PAPIEKTISK TKGQPREPQV   180
YTLPPSREEM TKNQVSLTCL VKGFYPSDIA VEWESSGQPE NNYNTTPPML DSDGSFFLYS   240
KLTVDKSRWQ QGNIFSCSVM HEALHNRFTQ KSLSLSPGK                         279

SEQ ID NO: 3401         moltype =    length =
SEQUENCE: 3401
000

SEQ ID NO: 3402         moltype =    length =
SEQUENCE: 3402
000

SEQ ID NO: 3403         moltype =    length =
SEQUENCE: 3403
000

SEQ ID NO: 3404         moltype =    length =
SEQUENCE: 3404
000

SEQ ID NO: 3405         moltype =    length =
SEQUENCE: 3405
000

SEQ ID NO: 3406         moltype =    length =
SEQUENCE: 3406
000
```

| | | |
|---|---|---|
| SEQ ID NO: 3407<br>SEQUENCE: 3407<br>000 | moltype = | length = |
| SEQ ID NO: 3408<br>SEQUENCE: 3408<br>000 | moltype = | length = |
| SEQ ID NO: 3409<br>SEQUENCE: 3409<br>000 | moltype = | length = |
| SEQ ID NO: 3410<br>SEQUENCE: 3410<br>000 | moltype = | length = |
| SEQ ID NO: 3411<br>SEQUENCE: 3411<br>000 | moltype = | length = |
| SEQ ID NO: 3412<br>SEQUENCE: 3412<br>000 | moltype = | length = |
| SEQ ID NO: 3413<br>SEQUENCE: 3413<br>000 | moltype = | length = |
| SEQ ID NO: 3414<br>SEQUENCE: 3414<br>000 | moltype = | length = |
| SEQ ID NO: 3415<br>SEQUENCE: 3415<br>000 | moltype = | length = |
| SEQ ID NO: 3416<br>SEQUENCE: 3416<br>000 | moltype = | length = |
| SEQ ID NO: 3417<br>SEQUENCE: 3417<br>000 | moltype = | length = |
| SEQ ID NO: 3418<br>SEQUENCE: 3418<br>000 | moltype = | length = |
| SEQ ID NO: 3419<br>SEQUENCE: 3419<br>000 | moltype = | length = |
| SEQ ID NO: 3420<br>SEQUENCE: 3420<br>000 | moltype = | length = |
| SEQ ID NO: 3421<br>SEQUENCE: 3421<br>000 | moltype = | length = |
| SEQ ID NO: 3422<br>SEQUENCE: 3422<br>000 | moltype = | length = |
| SEQ ID NO: 3423<br>SEQUENCE: 3423<br>000 | moltype = | length = |
| SEQ ID NO: 3424<br>SEQUENCE: 3424<br>000 | moltype = | length = |
| SEQ ID NO: 3425<br>SEQUENCE: 3425<br>000 | moltype = | length = |
| SEQ ID NO: 3426<br>SEQUENCE: 3426<br>000 | moltype = | length = |

| | | |
|---|---|---|
| SEQ ID NO: 3427<br>SEQUENCE: 3427<br>000 | moltype = | length = |
| SEQ ID NO: 3428<br>SEQUENCE: 3428<br>000 | moltype = | length = |
| SEQ ID NO: 3429<br>SEQUENCE: 3429<br>000 | moltype = | length = |
| SEQ ID NO: 3430<br>SEQUENCE: 3430<br>000 | moltype = | length = |
| SEQ ID NO: 3431<br>SEQUENCE: 3431<br>000 | moltype = | length = |
| SEQ ID NO: 3432<br>SEQUENCE: 3432<br>000 | moltype = | length = |
| SEQ ID NO: 3433<br>SEQUENCE: 3433<br>000 | moltype = | length = |
| SEQ ID NO: 3434<br>SEQUENCE: 3434<br>000 | moltype = | length = |
| SEQ ID NO: 3435<br>SEQUENCE: 3435<br>000 | moltype = | length = |
| SEQ ID NO: 3436<br>SEQUENCE: 3436<br>000 | moltype = | length = |
| SEQ ID NO: 3437<br>SEQUENCE: 3437<br>000 | moltype = | length = |
| SEQ ID NO: 3438<br>SEQUENCE: 3438<br>000 | moltype = | length = |
| SEQ ID NO: 3439<br>SEQUENCE: 3439<br>000 | moltype = | length = |
| SEQ ID NO: 3440<br>SEQUENCE: 3440<br>000 | moltype = | length = |
| SEQ ID NO: 3441<br>SEQUENCE: 3441<br>000 | moltype = | length = |
| SEQ ID NO: 3442<br>SEQUENCE: 3442<br>000 | moltype = | length = |
| SEQ ID NO: 3443<br>SEQUENCE: 3443<br>000 | moltype = | length = |
| SEQ ID NO: 3444<br>SEQUENCE: 3444<br>000 | moltype = | length = |
| SEQ ID NO: 3445<br>SEQUENCE: 3445<br>000 | moltype = | length = |
| SEQ ID NO: 3446<br>SEQUENCE: 3446 | moltype = | length = |

-continued

000

SEQ ID NO: 3447       moltype =    length =
SEQUENCE: 3447
000

SEQ ID NO: 3448       moltype =    length =
SEQUENCE: 3448
000

SEQ ID NO: 3449       moltype =    length =
SEQUENCE: 3449
000

SEQ ID NO: 3450       moltype =    length =
SEQUENCE: 3450
000

SEQ ID NO: 3451       moltype =    length =
SEQUENCE: 3451
000

SEQ ID NO: 3452       moltype =    length =
SEQUENCE: 3452
000

SEQ ID NO: 3453       moltype =    length =
SEQUENCE: 3453
000

SEQ ID NO: 3454       moltype =    length =
SEQUENCE: 3454
000

SEQ ID NO: 3455       moltype =    length =
SEQUENCE: 3455
000

SEQ ID NO: 3456       moltype =    length =
SEQUENCE: 3456
000

SEQ ID NO: 3457       moltype =    length =
SEQUENCE: 3457
000

SEQ ID NO: 3458       moltype =    length =
SEQUENCE: 3458
000

SEQ ID NO: 3459       moltype =    length =
SEQUENCE: 3459
000

SEQ ID NO: 3460       moltype =    length =
SEQUENCE: 3460
000

SEQ ID NO: 3461       moltype =    length =
SEQUENCE: 3461
000

SEQ ID NO: 3462       moltype =    length =
SEQUENCE: 3462
000

SEQ ID NO: 3463       moltype =    length =
SEQUENCE: 3463
000

SEQ ID NO: 3464       moltype =    length =
SEQUENCE: 3464
000

SEQ ID NO: 3465       moltype =    length =
SEQUENCE: 3465
000

SEQ ID NO: 3466       moltype =    length =

| | | |
|---|---|---|
| SEQUENCE: 3466 000 | | |
| SEQ ID NO: 3467 SEQUENCE: 3467 000 | moltype = | length = |
| SEQ ID NO: 3468 SEQUENCE: 3468 000 | moltype = | length = |
| SEQ ID NO: 3469 SEQUENCE: 3469 000 | moltype = | length = |
| SEQ ID NO: 3470 SEQUENCE: 3470 000 | moltype = | length = |
| SEQ ID NO: 3471 SEQUENCE: 3471 000 | moltype = | length = |
| SEQ ID NO: 3472 SEQUENCE: 3472 000 | moltype = | length = |
| SEQ ID NO: 3473 SEQUENCE: 3473 000 | moltype = | length = |
| SEQ ID NO: 3474 SEQUENCE: 3474 000 | moltype = | length = |
| SEQ ID NO: 3475 SEQUENCE: 3475 000 | moltype = | length = |
| SEQ ID NO: 3476 SEQUENCE: 3476 000 | moltype = | length = |
| SEQ ID NO: 3477 SEQUENCE: 3477 000 | moltype = | length = |
| SEQ ID NO: 3478 SEQUENCE: 3478 000 | moltype = | length = |
| SEQ ID NO: 3479 SEQUENCE: 3479 000 | moltype = | length = |
| SEQ ID NO: 3480 SEQUENCE: 3480 000 | moltype = | length = |
| SEQ ID NO: 3481 SEQUENCE: 3481 000 | moltype = | length = |
| SEQ ID NO: 3482 SEQUENCE: 3482 000 | moltype = | length = |
| SEQ ID NO: 3483 SEQUENCE: 3483 000 | moltype = | length = |
| SEQ ID NO: 3484 SEQUENCE: 3484 000 | moltype = | length = |
| SEQ ID NO: 3485 SEQUENCE: 3485 000 | moltype = | length = |

| | | |
|---|---|---|
| SEQ ID NO: 3486 SEQUENCE: 3486 | moltype = length = 000 | |
| SEQ ID NO: 3487 SEQUENCE: 3487 | moltype = length = 000 | |
| SEQ ID NO: 3488 SEQUENCE: 3488 | moltype = length = 000 | |
| SEQ ID NO: 3489 SEQUENCE: 3489 | moltype = length = 000 | |
| SEQ ID NO: 3490 SEQUENCE: 3490 | moltype = length = 000 | |
| SEQ ID NO: 3491 SEQUENCE: 3491 | moltype = length = 000 | |
| SEQ ID NO: 3492 SEQUENCE: 3492 | moltype = length = 000 | |
| SEQ ID NO: 3493 SEQUENCE: 3493 | moltype = length = 000 | |
| SEQ ID NO: 3494 SEQUENCE: 3494 | moltype = length = 000 | |
| SEQ ID NO: 3495 SEQUENCE: 3495 | moltype = length = 000 | |
| SEQ ID NO: 3496 SEQUENCE: 3496 | moltype = length = 000 | |
| SEQ ID NO: 3497 SEQUENCE: 3497 | moltype = length = 000 | |
| SEQ ID NO: 3498 SEQUENCE: 3498 | moltype = length = 000 | |
| SEQ ID NO: 3499 SEQUENCE: 3499 | moltype = length = 000 | |
| SEQ ID NO: 3500 FEATURE source | moltype = AA length = 229 Location/Qualifiers 1..229 mol_type = protein organism = Homo sapiens | |
| SEQUENCE: 3500 ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK | | 60 120 180 229 |
| SEQ ID NO: 3501 FEATURE REGION source | moltype = AA length = 6 Location/Qualifiers 1..6 note = Description of Artificial Sequence: Synthetic 6xHis tag 1..6 mol_type = protein organism = synthetic construct | |
| SEQUENCE: 3501 HHHHHH | | 6 |
| SEQ ID NO: 3502 | moltype = AA length = 5 | |

| FEATURE | Location/Qualifiers |
|---|---|
| REGION | 1..5 |
| | note = Description of Artificial Sequence: Synthetic peptide |
| source | 1..5 |
| | mol_type = protein |
| | organism = synthetic construct |

SEQUENCE: 3502

GGGGS                                                                 5

We claim:

1. A recombinant heteromultimer comprising an ALK7-Fc fusion protein and an ActRIIB-Fc fusion protein,
(a) wherein the ALK7-Fc fusion protein comprises:
(1) an ALK7 domain comprising an amino acid sequence that is at least 90% identical to amino acids 21-113 of SEQ ID NO: 38, and
(2) an Fc domain; wherein the Fc domain comprises a cysteine substitution at the position corresponding to S132 of SEQ ID NO: 3100 (S132C) and a tryptophan substitution at the position corresponding to T144 of SEQ ID NO: 3100 (T144W); and
(b) wherein the ActRIIB-Fc fusion protein comprises:
(1) an ActRIIB domain comprising an amino acid sequence that is at least 90% identical to amino acids 29-109 of SEQ ID NO: 1, and
(2) an Fc domain that is an IgG1 Fc domain, and wherein the IgG1 Fc domain comprises one or more amino acid modifications that alter the pI of the ActRIIB-Fc fusion protein; and
wherein the recombinant heteromultimer binds to one or more of activin B, activin C, and activin AC.

2. The heteromultimer of claim 1, wherein the ALK7-Fc fusion protein and the ActRIIB-Fc fusion protein Fc domain is an IgG1 Fc domain comprising an amino acid sequence that is at least 90% identical to the amino acid sequence of SEQ ID NO: 3100.

3. The heteromultimer of claim 2, wherein the ActRIIB-Fc fusion protein IgG1 Fc domain comprises a cysteine substitution at the position corresponding to Y127 of SEQ ID NO: 3100 (Y127C), a serine substitution at the position corresponding to T144 of SEQ ID NO: 3100 (T144S), an alanine substitution at the position corresponding to L146 of SEQ ID NO: 3100 (L146A), and a valine substitution at the position corresponding to Y185 of SEQ ID NO: 3100 (Y185V).

4. The heteromultimer of claim 2, wherein the ActRIIB-Fc fusion protein IgG1 Fc domain comprises a cysteine substitution at the position corresponding to S132 of SEQ ID NO: 3100 (S132C) and a tryptophan substitution at the position corresponding to T144 of SEQ ID NO: 3100 (T144W).

5. The heteromultimer of claim 1, wherein:
a) the ActRIIB-Fc fusion protein comprises one or more amino acid modifications that increase the pI of the ActRIIB-Fc fusion protein; and
b) the ALK7-Fc fusion protein comprises one or more amino acid modifications that decrease the pI of the ALK7-Fc fusion protein.

6. The heteromultimer of claim 1, wherein the ALK7-Fc fusion protein comprises an ALK7 domain comprising an amino acid sequence that is at least 90% identical to an amino acid sequence selected from the group consisting of:
a) an amino acid sequence that:
i) begins at any one of amino acids 21-28 of SEQ ID NO: 305 or 309, and
ii) ends at any one of amino acids 92-113 of SEQ ID NO: 305 or 309;
b) an amino acid sequence comprising amino acids 28-92 of SEQ ID NOs: 38, 305, or 309;
c) an amino acid sequence comprising amino acids 21-113 of SEQ ID NOs: 305 or 309; or
d) an amino acid sequence comprising the amino acid sequence of any one of SEQ ID NOs: 38, 39, 301, 302, 305, 306, 309, 310, 313, 112, 114, 405, and 406.

7. The heteromultimer of claim 1, wherein the ActRIIB-Fc fusion protein comprises an ActRIIB domain comprising an amino acid sequence that is at least 90% identical to an amino acid sequence selected from the group consisting of:
a) an amino acid sequence that:
i) begins at any one of amino acids of 20-29 SEQ ID NO: 1, and
ii) ends at any one of amino acids 109-134 of SEQ ID NO: 1;
b) an amino acid sequence comprising amino acids 20-134 of SEQ ID NO: 1;
d) an amino acid sequence comprising amino acids 25-131 of SEQ ID NO: 1; or
e) an amino acid sequence according to one of SEQ ID Nos: 1, 2, 3, 4, 5, 6, 100, 102, 401, and 402.

8. The heteromultimer of claim 1, wherein the ALK7-Fc fusion protein further comprises a linker domain positioned between the ALK7 domain and the Fc domain; and wherein the ActRIIB-Fc fusion protein further comprises a linker domain positioned between the ActRIIB domain and the Fc domain.

9. The heteromultimer of claim 8, wherein the linker domain is selected from: TGGG (SEQ ID NO: 62), TGGGG (SEQ ID NO: 60), SGGGG (SEQ ID NO: 61), GGGGS, GGG (SEQ ID NO: 58), GGGG (SEQ ID NO: 59), and SGGG (SEQ ID NO: 18).

10. The heteromultimer of claim 1, wherein the heteromultimer is a heterodimer.

11. A pharmaceutical preparation comprising the heteromultimer of claim 1, and a pharmaceutically acceptable carrier.

\* \* \* \* \*